(12) United States Patent
Park et al.

(10) Patent No.: US 12,404,280 B2
(45) Date of Patent: Sep. 2, 2025

(54) HETEROCYCLIC COMPOUND, AND ORGANIC LIGHT-EMITTING ELEMENT USING SAME

(71) Applicant: LT MATERIALS CO., LTD., Yongin (KR)

(72) Inventors: Seong-Jong Park, Yongin-si (KR); Hyun-Ju La, Yongin-si (KR); Won-Jang Jeong, Yongin-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 802 days.

(21) Appl. No.: 17/637,342

(22) PCT Filed: Aug. 19, 2020

(86) PCT No.: PCT/KR2020/011019
§ 371 (c)(1),
(2) Date: Feb. 22, 2022

(87) PCT Pub. No.: WO2021/040310
PCT Pub. Date: Mar. 4, 2021

(65) Prior Publication Data
US 2022/0324877 A1    Oct. 13, 2022

(30) Foreign Application Priority Data
Aug. 23, 2019  (KR) .................. 10-2019-0103655

(51) Int. Cl.
*H01L 51/54* (2006.01)
*C07D 498/04* (2006.01)
*H10K 85/60* (2023.01)
*H10K 50/18* (2023.01)

(52) U.S. Cl.
CPC ......... *C07D 498/04* (2013.01); *H10K 85/621* (2023.02); *H10K 85/654* (2023.02); *H10K 85/6572* (2023.02); *H10K 85/6574* (2023.02); *H10K 85/6576* (2023.02); *H10K 50/18* (2023.02)

(58) Field of Classification Search
None
See application file for complete search history.

(56) References Cited

U.S. PATENT DOCUMENTS

| | | | |
|---|---|---|---|
| 6,551,723 | B1 | 4/2003 | Okada et al. |
| 2015/0243895 | A1 | 8/2015 | Lim et al. |
| 2016/0380208 | A1 | 12/2016 | La et al. |
| 2018/0282295 | A1 | 10/2018 | Parham et al. |
| 2019/0288218 | A1 | 9/2019 | La et al. |
| 2020/0066996 | A1 | 2/2020 | La et al. |
| 2020/0339513 | A1 | 10/2020 | Heo et al. |

FOREIGN PATENT DOCUMENTS

| | | |
|---|---|---|
| CN | 105358533 A1 | 2/2016 |
| CN | 109384786 A | 2/2019 |
| JP | 2000-63818 A | 2/2000 |
| JP | 6479770 B2 | 3/2019 |
| KR | 10-2017-0084190 A | 7/2017 |
| KR | 10-2018-0062343 A | 6/2018 |
| KR | 10-2018-0075398 A | 7/2018 |
| KR | 10-2019-0078139 A | 7/2019 |

OTHER PUBLICATIONS

International Search Report (PCT/ISA/210) issued in PCT/KR2020/011019 mailed on Dec. 1, 2020.

*Primary Examiner* — Andrew K Bohaty
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device using the same.

15 Claims, 3 Drawing Sheets

[FIG. 1]
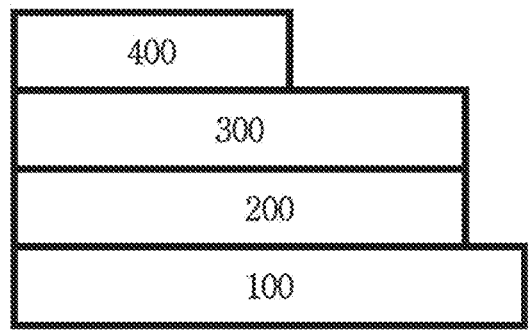
[FIG. 2]
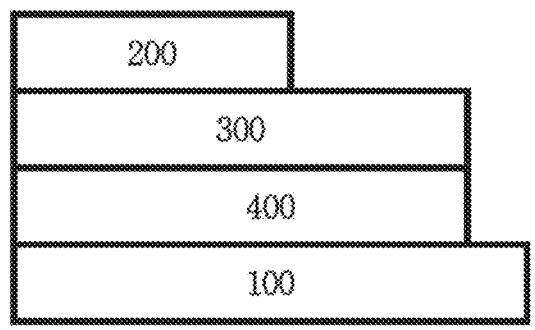
[FIG. 3]
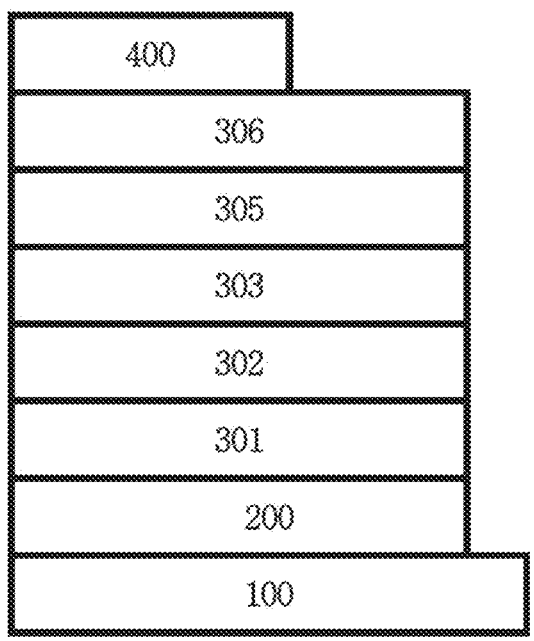

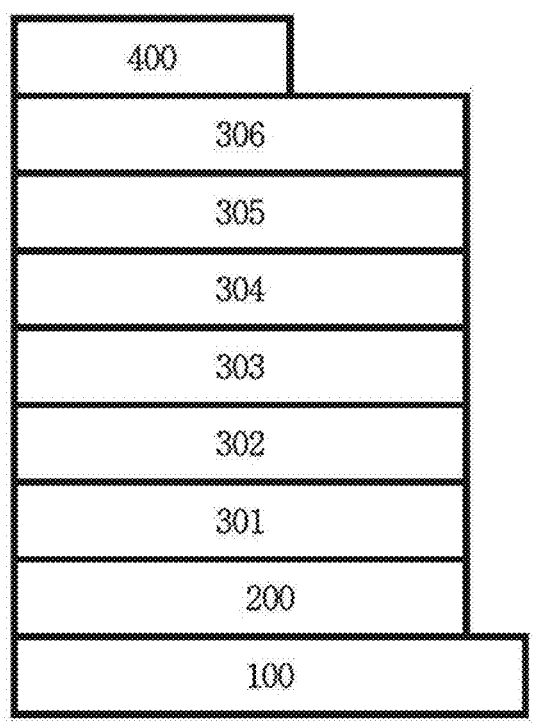
[FIG. 4]

[FIG. 5]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND, AND ORGANIC LIGHT-EMITTING ELEMENT USING SAME

TECHNICAL FIELD

The present specification relates to a heterocyclic compound, and an organic light emitting device using the same.

This application claims priority to and the benefits of Korean Patent Application No. 10-2019-0103655, filed with the Korean Intellectual Property Office on Aug. 23, 2019, the entire contents of which are incorporated herein by reference.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device using the same.

Technical Solution

One embodiment of the present specification provides a heterocyclic compound represented by the following Chemical Formula 1.

[Chemical Formula 1]

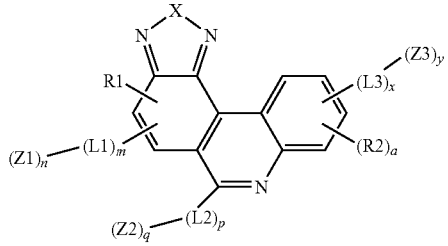

In Chemical Formula 1,

X is O; S; or NR,

L1 to L3 are the same as or different from each other, and each independently a direct bond; a substituted or unsubstituted arylene group having 6 to 60 carbon atoms; or a substituted or unsubstituted heteroarylene group having 2 to 60 carbon atoms, Z1 to Z3 are the same as or different from each other, and each independently selected from the group consisting of hydrogen; deuterium; a halogen group; a cyano group; —P(=O)(R104)(R105); —N(R106)(R107); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms, R1 and R2 are the same as or different from each other, and each independently selected from the group consisting of hydrogen; deuterium; a halogen group; a cyano group; —P(=O)(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms, or adjacent two or more groups bond to each other to form a substituted or unsubstituted aliphatic hydrocarbon ring; a substituted or unsubstituted aromatic hydrocarbon ring; a substituted or unsubstituted aliphatic heteroring; or a substituted or unsubstituted aromatic heteroring, R is hydrogen; deuterium; a halogen group; a cyano group; a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; or a substituted or unsubstituted heteroaryl group having 2 to 60 carbon atoms, R104 to R107 and R104' to R107' are each independently hydrogen; deuterium; a halogen group; an alkyl group; an alkenyl group; an alkoxy group; a cycloalkyl group; an aryl group; or a heteroaryl group, m, p, x, n, q and y are each an integer of 1 to 5, a is an integer of 1 to 3, and when m, p, x, n, q, y and a are each an integer of 2 or greater, substituents in the parentheses are the same as or different from each other.

Another embodiment of the present application provides an organic light emitting device including a first electrode; a second electrode provided opposite to the first electrode; and one or more organic material layers provided between the first electrode and the second electrode, wherein one or more layers of the organic material layers include the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as an electron transfer layer material or a charge generation material of the organic light emitting device.

Specifically, when using the compound represented by Chemical Formula 1 in an organic material layer, a driving voltage of the device can be lowered, light efficiency can be enhanced, and lifetime properties of the device can be enhanced.

DESCRIPTION OF DRAWINGS

FIG. 1 to FIG. 5 are diagrams each illustrating a lamination structure of an organic light emitting device according to One embodiment of the present specification.
100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Hereinafter, the present specification will be described in more detail.

In the present specification, a certain part "including" certain constituents means capable of further including other constituents, and does not exclude other constituents unless particularly stated on the contrary.

In the present specification, "substituted or unsubstituted" means being substituted with one or more substituents selected from the group consisting of deuterium; a halogen group; a cyano group; a linear or branched alkyl group having 1 to 60 carbon atoms; a linear or branched alkenyl group having 2 to 60 carbon atoms; a linear or branched alkynyl group having 2 to 60 carbon atoms; a monocyclic or polycyclic cycloalkyl group having 3 to 60 carbon atoms; a monocyclic or polycyclic heterocycloalkyl group having 2 to 60 carbon atoms; a monocyclic or polycyclic aryl group having 6 to 60 carbon atoms; a monocyclic or polycyclic heteroaryl group having 2 to 60 carbon atoms; a silyl group; a phosphine oxide group; an alkylamine group having 1 to 20 carbon atoms; a monocyclic or polycyclic arylamine group having 6 to 60 carbon atoms; and a monocyclic or polycyclic heteroarylamine group having 2 to 60 carbon atoms, or being unsubstituted, or being substituted with a substituent linking two or more substituents selected from among the substituents illustrated above, or being unsubstituted.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, a "case of a substituent being not indicated in a chemical formula or compound structure" means that a hydrogen atom bonds to a carbon atom. However, since deuterium ($^2$H) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0%, a hydrogen content being 100' or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or $^2$H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

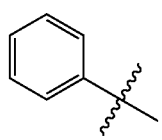 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

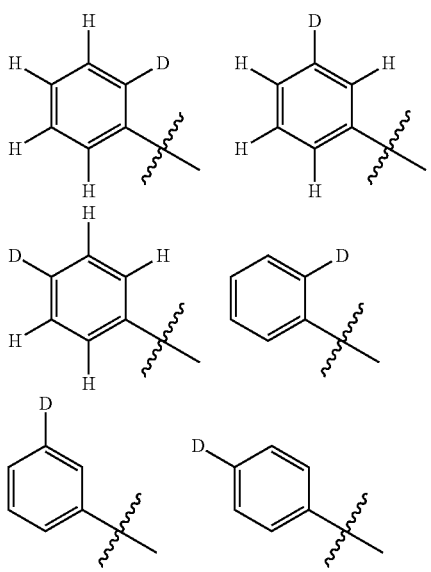

In addition, in one embodiment of the present application, "a phenyl group having a deuterium content of 0%" may mean a phenyl group that doe s not include a deuterium atom, that is, a phenyl group that has 5 hydrogen atoms.

In the present specification, the halogen may be fluorine, chlorine, bromine or iodine.

In the present specification, the alkyl group includes linear or branched having 1 to 60 carbon to atoms, and may be further substituted with other substituents. The number of carbon atoms of the alkyl group may be from 1 to 60, specifically from 1 to 40 an more specifically from 1 to 20. Specific examples thereof may include methyl group, an ethyl group, a propyl group, an n-propyl group, an isopropyl group, a butyl group, an n-butyl group, an isobutyl group, a tert-butyl group, a sec-butyl group, a 1-methy-butyl group, a 1-ethylbutyl group, a pentyl group, an n-pentyl group, a isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is from 1 to 60 and preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon atoms of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent including Si, having the Si atom directly linked as a radical, and is represented by —Si(R101)(R102)(R103). R101 to R103 are the same as or different from each other, and may be each independently a substituent formed with at least one of hydrogen; deuterium; a halogen group; an alkyl group; an alkenyl group; an alkoxy group; a cycloalkyl group; an aryl group; and a heteroaryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

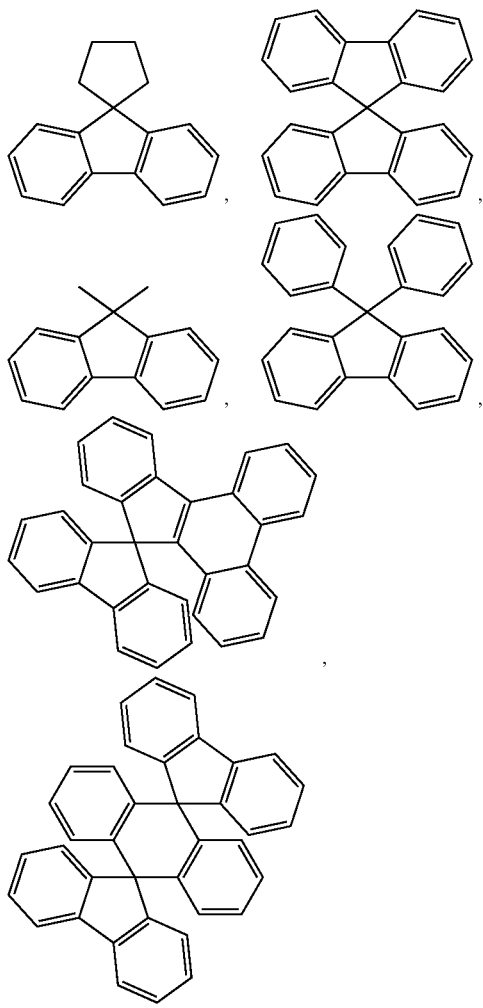

and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, examples of the aryl group and the heteroaryl group described above may be respectively applied to the arylene group and the heteroarylene group except that they are a divalent group.

In the present specification, the phosphine oxide group is represented by —P(=O)(R104)(R105), and R104 and R105 are the same as or different from each other and may be each independently a substituent formed with at least one of hydrogen; deuterium; a halogen group; an alkyl group; an alkenyl group; an alkoxy group; a cycloalkyl group; an aryl group; and a heteroaryl group. Specifically, the phosphine oxide group may be substituted with an aryl group, and as the aryl group, the examples described above may be applied. Examples of the phosphine oxide group may include a diphenylphosphine oxide group, a dinaphthylphosphine oxide group and the like, but are not limited thereto.

In the present specification, the amine group is represented by —N(R106)(R107), and R106 and R107 are the same as or different from each other and may be each independently a substituent formed with at least one of hydrogen; deuterium; a halogen group; an alkyl group; an alkenyl group; an alkoxy group; a cycloalkyl group; an aryl group; and a heteroaryl group. The amine group may be selected from the group consisting of —NH$_2$; a monoalkylamine group; a monoarylamine group; a monoheteroarylamine group; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic hydrocarbon ring, the aromatic hydrocarbon ring, the aliphatic heteroring or the aromatic heteroring that the adjacent groups may form, the structures illustrated as the cycloalkyl group, the aryl group, the cycloheteroalkyl group and the heteroaryl group described above may be applied except for those that are not a monovalent group.

One embodiment of the present specification provides a compound represented by Chemical Formula 1.

Chemical Formula 1 has a structure in which thiadiazole, oxadiazole or triazole is fused to phenanthridine, and has a wide band gap and a high T1 value by disconnecting electron distribution of HOMO (Highest Occupied Molecular Orbital) and LUMO (Lowest Unoccupied Molecular Orbital) by the thiadiazole, the oxadiazole or the triazole.

When having a low T1, excitons generated in a light emitting layer pass over to an electron transfer layer and resultantly emit light in the electron transfer layer or at an interface of the electron transfer layer by causing charge unbalance in the light emitting layer, and as a result, an organic electric device has a decrease in color purity, and decreases in efficiency and lifetime. By having a wide band gap, holes passing from the light emitting layer may be prevented due to a low HOMO level, and a high LUMO level may readily take over electrons in an electron injection layer and readily transfer the electrons to the light emitting layer.

In one embodiment of the present specification, X may be O; S; or NR.

In another embodiment, X may be O.

In another embodiment, X may be S.

In another embodiment, X may be NR.

In one embodiment of the present specification, R may be hydrogen; deuterium; a halogen group; a cyano group; a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; or a substituted or unsubstituted heteroaryl group having 2 to 60 carbon atoms.

In another embodiment, R may be a substituted or unsubstituted aryl group having 6 to 60 carbon atoms.

In another embodiment, R may be a substituted or unsubstituted aryl group having 6 to 40 carbon atoms.

In another embodiment, R may be a substituted or unsubstituted aryl group having 6 to 20 carbon atoms.

In another embodiment, R may be a phenyl group.

In one embodiment of the present specification, L1 to L3 are the same as or different from each other, and may be each independently a direct bond; a substituted or unsubstituted arylene group having 6 to 60 carbon atoms; or a substituted or unsubstituted heteroarylene group having 2 to 60 carbon atoms.

In another embodiment, L1 to L3 are the same as or different from each other, and may be each independently a direct bond; a substituted or unsubstituted arylene group having 6 to 40 carbon atoms; or a substituted or unsubstituted heteroarylene group having 2 to 40 carbon atoms.

In another embodiment, L1 to L3 are the same as or different from each other, and may be each independently a direct bond; or a substituted or unsubstituted arylene group having 6 to 20 carbon atoms.

In another embodiment, L1 to L3 are the same as or different from each other, and may be each independently a direct bond; or an arylene group having 6 to 20 carbon atoms unsubstituted or substituted with a halogen group.

In another embodiment, L1 to L3 are the same as or different from each other, and may be each independently a direct bond; a phenylene group unsubstituted or substituted with a halogen group; a biphenylene group; or a terphenylene group.

In one embodiment of the present specification, Z1 to Z3 are the same as or different from each other, and may be each independently selected from the group consisting of hydrogen; deuterium; a halogen group; a cyano group; —P(=O)(R104)(R105); —N(R106)(R107); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms.

In another embodiment, Z1 to Z3 are the same as or different from each other, and may be each independently hydrogen; deuterium; a cyano group; —P(=O)(R104)(R105); a substituted or unsubstituted aryl group having 6 to 60 carbon atoms; or a substituted or unsubstituted heteroaryl group having 2 to 60 carbon atoms.

In another embodiment, Z1 to Z3 are the same as or different from each other, and may be each independently hydrogen; deuterium; a cyano group; —P(=O)(R104)(R105); a substituted or unsubstituted aryl group having 6 to 40 carbon atoms; or a substituted or unsubstituted heteroaryl group having 2 to 40 carbon atoms. R104 and R105 may be each independently an alkyl group or an aryl group.

In another embodiment, Z1 to Z3 are the same as or different from each other, and may be each independently hydrogen; deuterium; a cyano group; —P(=O)(R104)(R105); a substituted or unsubstituted phenyl group; a biphenyl group; a naphthyl group; a substituted or unsubstituted pyridine group; a substituted or unsubstituted pyrimidine group; a substituted or unsubstituted triazine group; a substituted or unsubstituted quinoline group; a substituted or unsubstituted benzimidazolyl group; a benzoxazolyl group; a benzothiazolyl group; a carbazolyl group;

a dibenzofuran group; a dibenzothiophene group; a phenanthrenyl group; a phenanthrolinyl group; a 9,9-dimethyl-9H-fluorenyl group; or a benzo[4,5]thieno[3,2-d]pyrimidine group. R104 and R105 may be each independently an alkyl group or an aryl group.

In another embodiment, Z1 to Z3 are the same as or different from each other, and may be each independently hydrogen; deuterium; a cyano group; —P(=O)(R104)(R105); a phenyl group unsubstituted or substituted with one or more substituents selected from the group consisting of a halogen group, a cyano group, a phenyl group, a methyl group and a carbazole group; a biphenyl group; a naphthyl group; a pyridine group unsubstituted or substituted with a phenyl group or a pyridine group; a pyrimidine group unsubstituted or substituted with one or more substituents selected from the group consisting of a phenyl group, a biphenyl group, a naphthyl group, a phenanthrenyl group and toluene; a triazine group unsubstituted or substituted with one or more substituents selected from the group consisting of a phenyl group, a biphenyl group, a naphthyl group, a phenanthrenyl group and toluene; a quinoline group unsubstituted or substituted with a phenyl group; a benzimidazolyl group unsubstituted or substituted with one or more substituents selected from the group consisting of a phenyl group and an ethyl group; a benzoxazolyl group; a benzothiazolyl group; a carbazolyl group; a dibenzofuran group; a dibenzothiophene group; a phenanthrenyl group; a phenanthrolinyl group; a 9,9-dimethyl-9H-fluorenyl group; or a benzo[4,5]thieno[3,2-d]pyrimidine group, and R104 and R105 may be each independently a methyl group or a phenyl group.

In one embodiment of the present specification, R1 and R2 are the same as or different from each other, and may be each independently selected from the group consisting of hydrogen; deuterium; a halogen group; a cyano group; —P(=O)(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms, or adjacent two or more groups may bond to each other to form a substituted or unsubstituted aliphatic hydrocarbon ring; a substituted or unsubstituted aromatic hydrocarbon ring; a substituted or unsubstituted aliphatic heteroring; or a substituted or unsubstituted aromatic heteroring.

In another embodiment, R1 and R2 may each be hydrogen; or deuterium.

In the heterocyclic compound provided in one embodiment of the present specification, Chemical Formula 1 is represented by any one of the following Chemical Formulae 2 to 5.

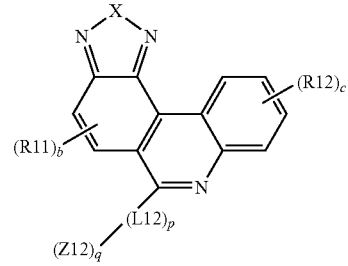

[Chemical Formula 2]

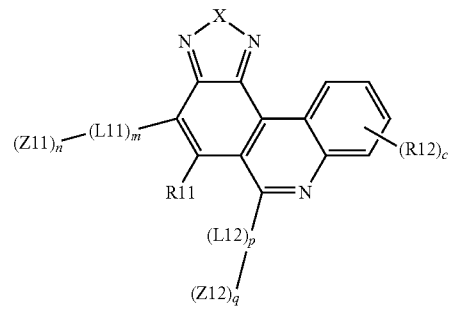

[Chemical Formula 3]

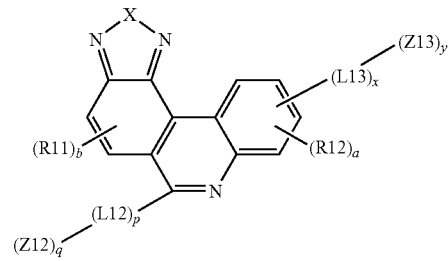

[Chemical Formula 4]

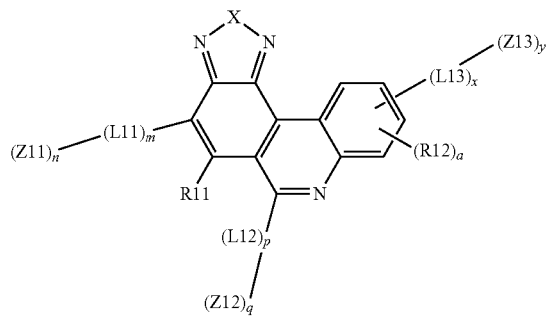

[Chemical Formula 5]

In Chemical Formula 2 to Chemical Formula 5,
X, m, p, x, n, q, y and a have the same definitions as in Chemical Formula 1,
L11 to L13 are the same as or different from each other, and each independently a direct bond; a substituted or unsubstituted arylene group having 6 to 60 carbon atoms; or a substituted or unsubstituted heteroarylene group having 2 to 60 carbon atoms,
Z11 to Z13 are the same as or different from each other, and each independently selected from the group consisting oft a cyano group; —P(=O)(R104)(R105); a substituted or unsubstituted aryl group having 6 to 60 carbon atoms; and a substituted or unsubstituted heteroaryl group having 2 to 60 carbon atoms,
R11 and R12 are the same as or different from each other, and each independently selected from the group consisting of hydrogen; deuterium; a halogen group; a cyano group; —P(=O(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; and a substituted or unsubstituted heterocycloalkyl group having 2 to 60 carbon atoms, R104, R105 and R104' to R107' are each independently hydrogen; deuterium; a halogen group; an alkyl group; an alkenyl group; an alkoxy group; a cycloalkyl group; an aryl group; or a heteroaryl group, b is 1 or 2, c is an integer of 1 to 4, when b is 2, two R11s are the same as or different from each other, and when c is 2 or greater, a plurality of R12s are the same as or different from each other.

In another embodiment, L11 to L13 are the same as or different from each other, and may be each independently a direct bond; a substituted or unsubstituted arylene group having 6 to 60 carbon atoms; or a substituted or unsubstituted heteroarylene group having 2 to 60 carbon atoms.

In another embodiment, L11 to L13 are the same as or different from each other, and may be each independently a direct bond; a substituted or unsubstituted arylene group having 6 to 40 carbon atoms; or a substituted or unsubstituted heteroarylene group having 2 to 40 carbon atoms.

In another embodiment, L11 to L13 are the same as or different from each other, and may be each independently a direct bond; or a substituted or unsubstituted arylene group having 6 to 20 carbon atoms.

In another embodiment, L11 to L13 are the same as or different from each other, and may be each independently a direct bond; or an arylene group having 6 to 20 carbon atoms unsubstituted or substituted with a halogen group.

In another embodiment, L11 to L13 are the same as or different from each other, and may be each independently a direct bond; a phenylene group unsubstituted or substituted with a halogen group; a biphenylene group; or a terphenylene group.

In another embodiment, Z11 to Z13 are the same as or different from each other, and may be each independently a cyano group; —P(=O)(R104)(R105); a substituted or unsubstituted aryl group having 6 to 60 carbon atoms; or a substituted or unsubstituted heteroaryl group having 2 to 60 carbon atoms.

In another embodiment, Z11 to Z13 are the same as or different from each other, and may be each independently a cyano group; —P(=O)(R104)(R105); a substituted or unsubstituted aryl group having 6 to 40 carbon atoms; or a substituted or unsubstituted heteroaryl group having 2 to 40 carbon atoms. R104 and R105 may be each independently an alkyl group or an aryl group.

In another embodiment, Z11 to Z13 are the same as or different from each other, and may be each independently a cyano group; —P(=O)(R104)(R105); a substituted or unsubstituted phenyl group; a biphenyl group; a naphthyl group; a substituted or unsubstituted pyridine group; a substituted or unsubstituted pyrimidine group; a substituted or unsubstituted triazine group; a substituted or unsubstituted quinoline group; a substituted or unsubstituted benzimidazolyl group; a benzoxazolyl group; a benzothiazolyl group; a carbazolyl group; a dibenzofuran group; a dibenzothiophene group; a phenanthrenyl group; a phenanthrolinyl group; a 9,9-dimethyl-9H-fluorenyl group; or a benzo[4,5]thieno[3,2-d]pyrimidine group. R104 and R105 may be each independently an alkyl group or an aryl group.

In another embodiment, Z11 to Z13 are the same as or different from each other, and may be each independently a cyano group; —P(=O)(R104)(R105); a phenyl group unsubstituted or substituted with one or more substituents selected from the group consisting of a halogen group, a cyano group, a phenyl group, a methyl group and a carbazole group; a biphenyl group; a naphthyl group; a pyridine group unsubstituted or substituted with a phenyl group or a pyridine group; a pyrimidine group unsubstituted or substituted with one or more substituents selected from the group consisting of a phenyl group, a biphenyl group, a naphthyl group, a phenanthrenyl group and toluene; a triazine group unsubstituted or substituted with one or more substituents selected from the group consisting of a phenyl group, a biphenyl group, a naphthyl group, a phenanthrenyl group and toluene; a quinoline group unsubstituted or substituted with a phenyl group; a benzimidazolyl group unsubstituted or substituted with one or more substituents selected from the group consisting of a phenyl group and an ethyl group; a benzoxazolyl group; a benzothiazolyl group; a carbazolyl group; a dibenzofuran group; a dibenzothiophene group; a phenanthrenyl group; a phenanthrolinyl group; a 9,9-dimethyl-9H-fluorenyl group; or a benzo[4,5]thieno[3,2-d]pyrimidine group, and R104 and R105 may be each independently a methyl group or a phenyl group.

In one embodiment of the present specification, R11 and R12 are the same as or different from each other, and may be each independently selected from the group consisting of hydrogen; deuterium; a halogen group; a cyano group; —P(=O)(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; and a substituted or unsubstituted heterocycloalkyl group having 2 to 60 carbon atoms.

In one embodiment of the present specification, R11 and R12 are the same as or different from each other, and may be each independently hydrogen; deuterium; or a substituted or unsubstituted alkyl group having 1 to 60 carbon atoms.

In one embodiment of the present specification, R11 and R12 are the same as or different from each other, and may be each independently hydrogen; or deuterium.

In one embodiment of the present specification, R11 and R12 may be hydrogen.

In the heterocyclic compound provided in one embodiment of the present specification, Chemical Formula 1 is represented by any one of the following compounds.

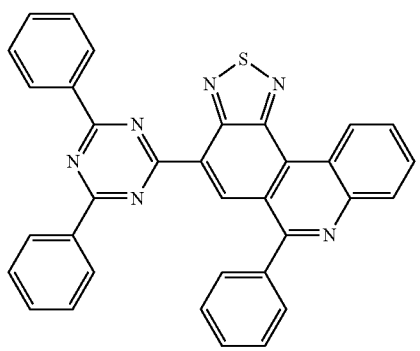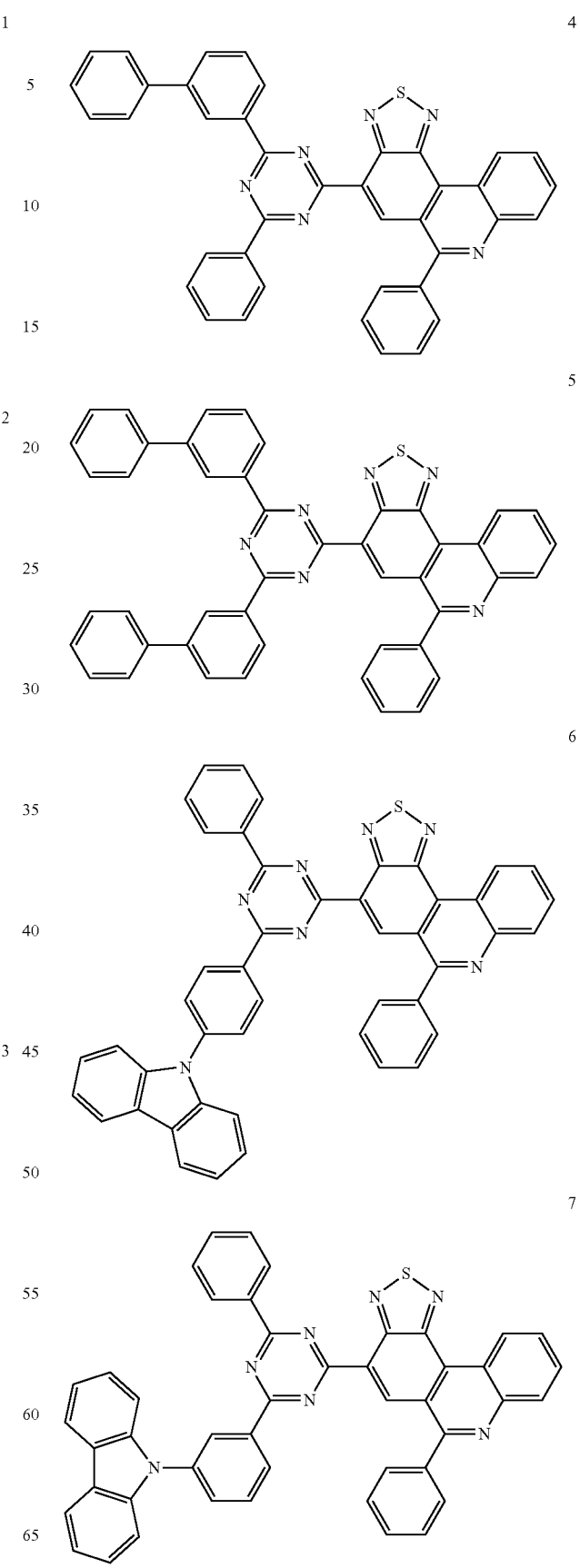

-continued
8
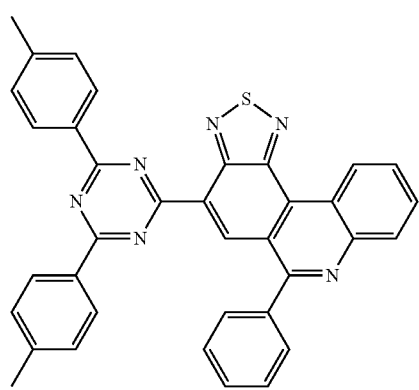
9
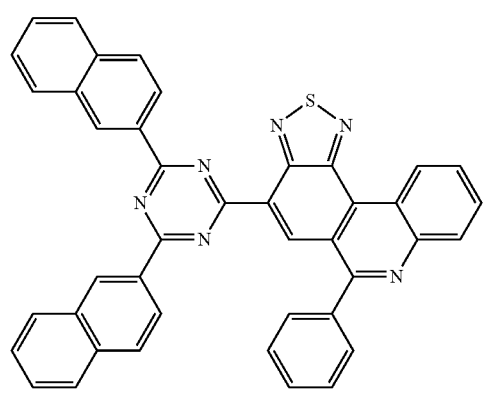
10
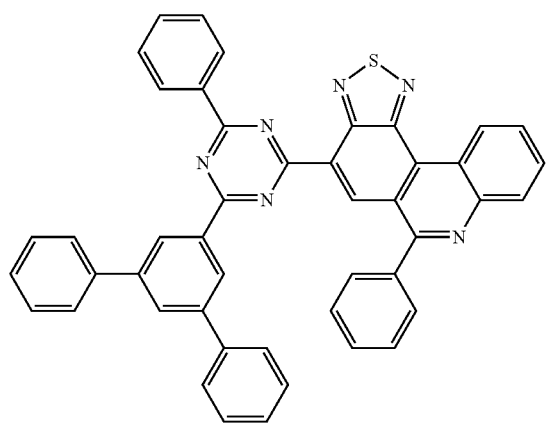
-continued
11
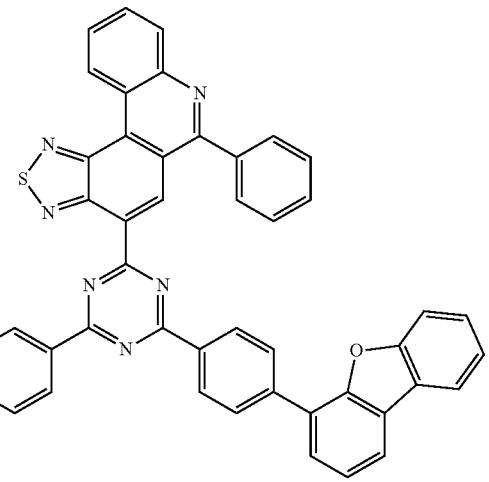
12
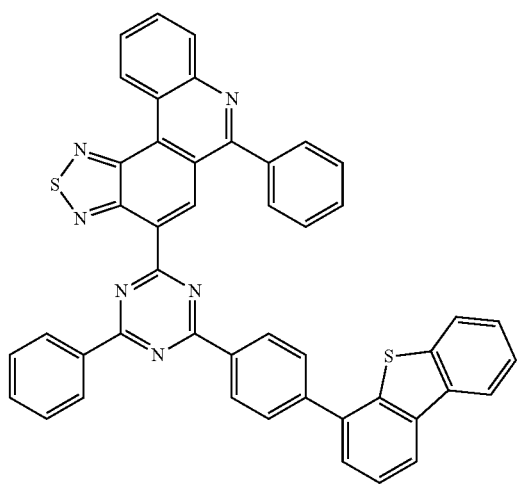
13
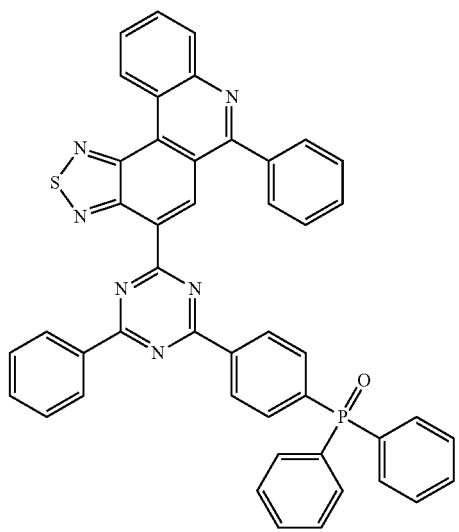

14
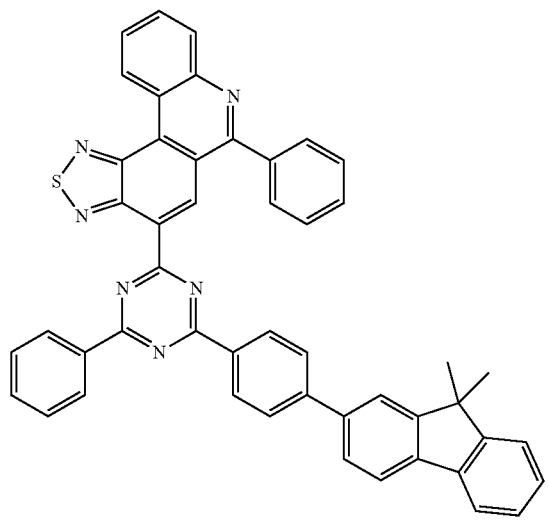
15
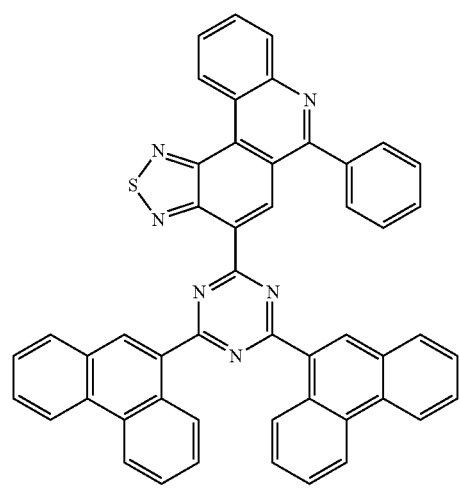
16
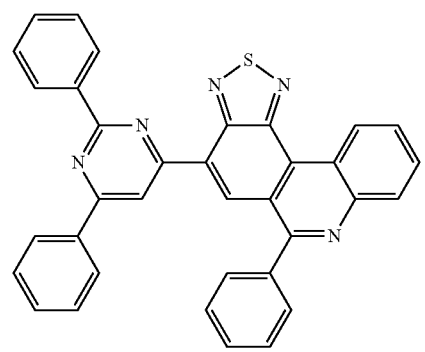
17
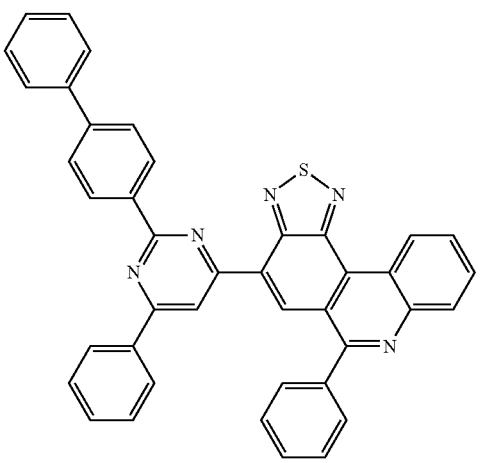
18
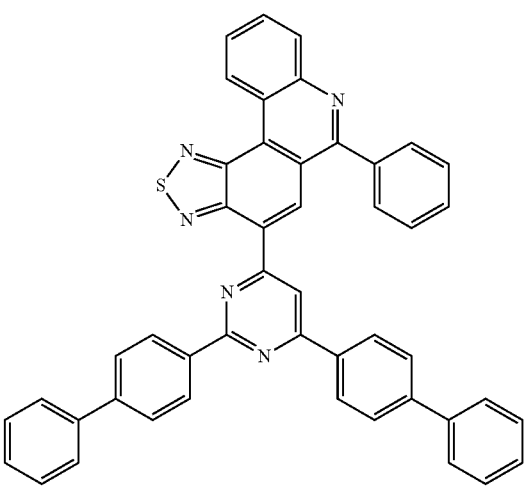
19
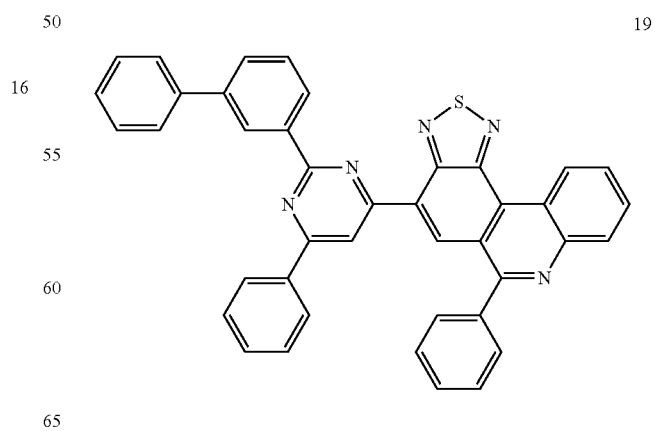

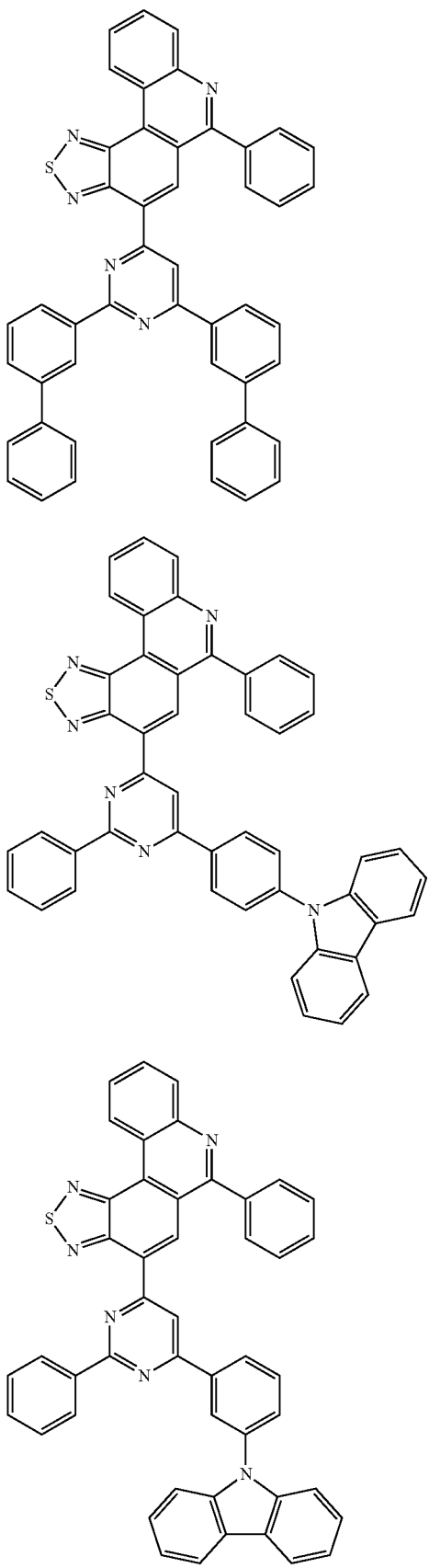
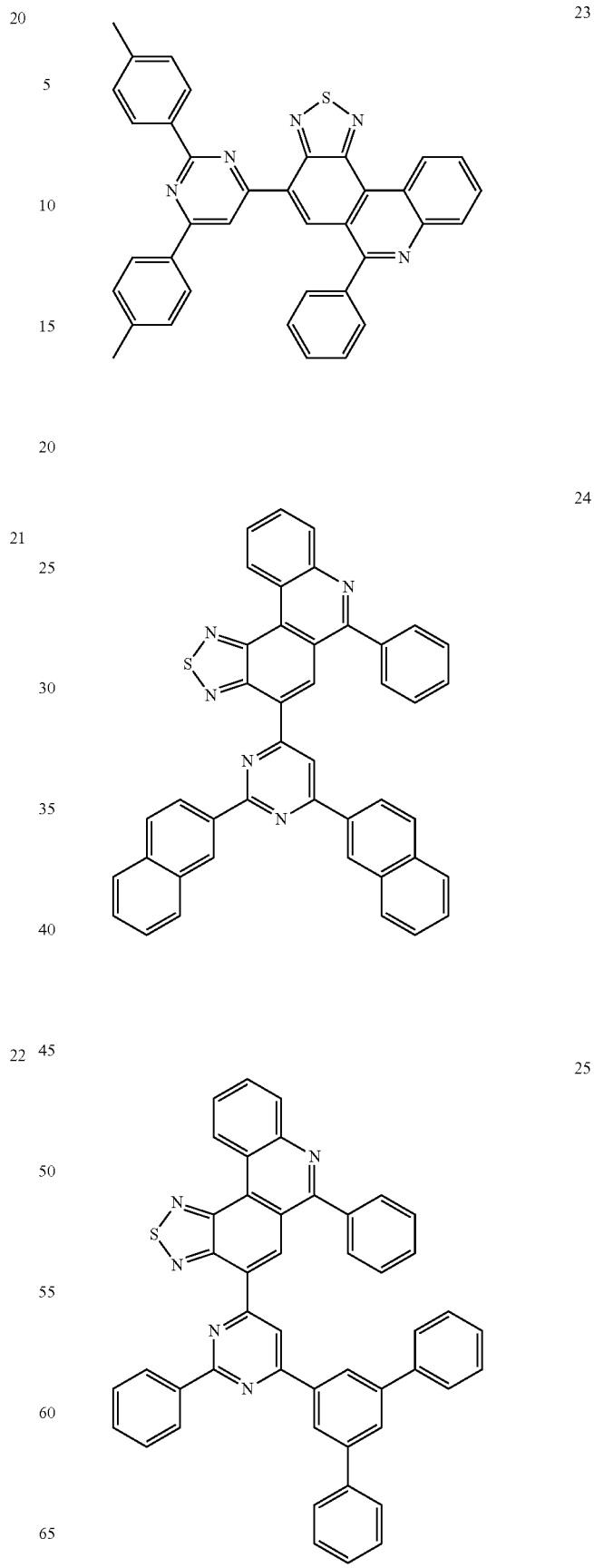

26
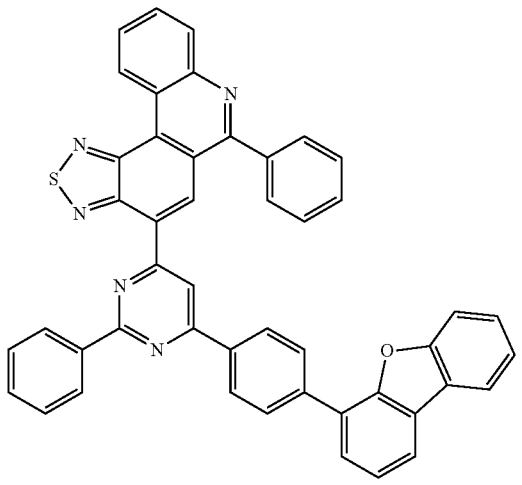
27
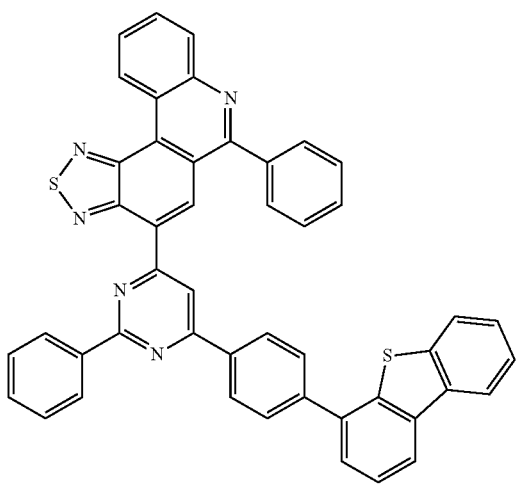
28
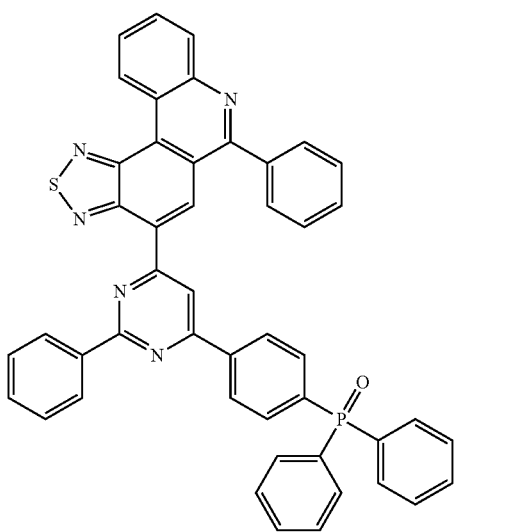
29
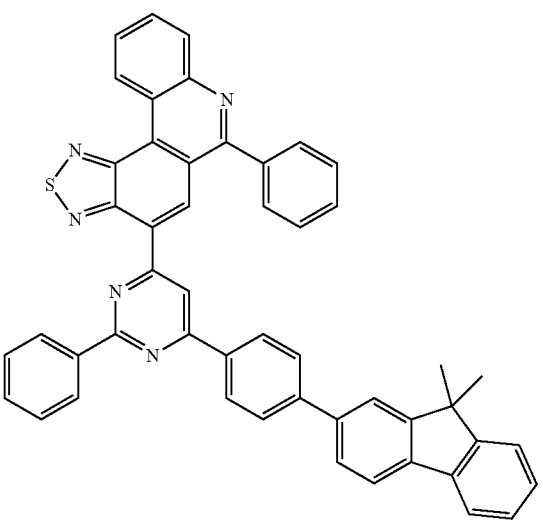
30
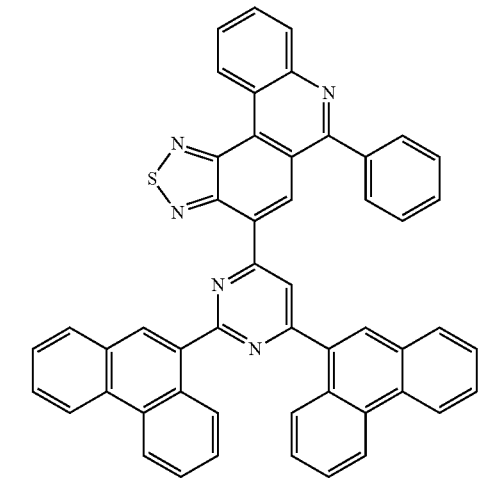
31
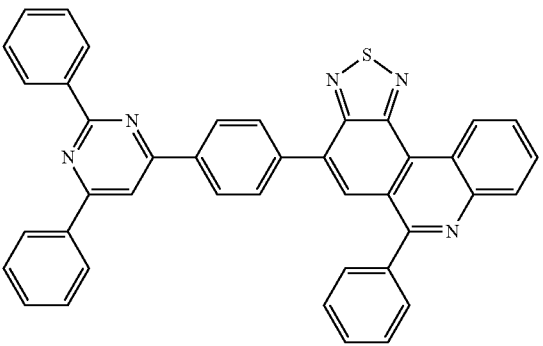

32
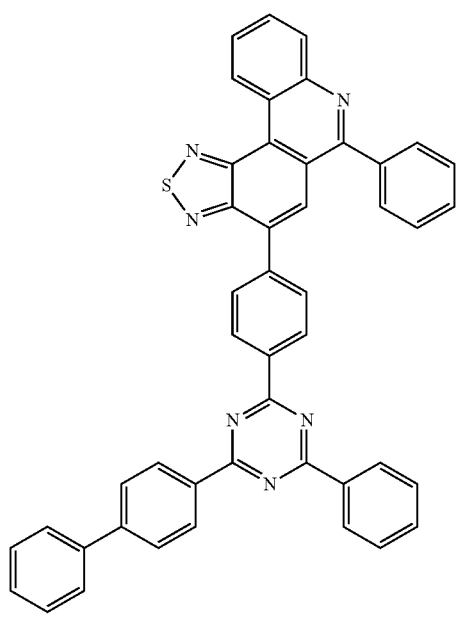
33
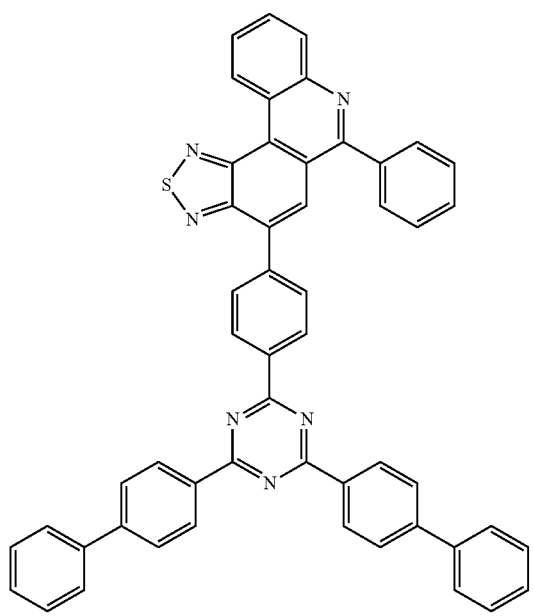
34
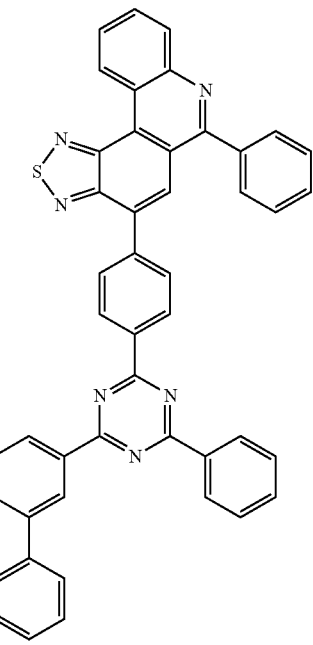
35
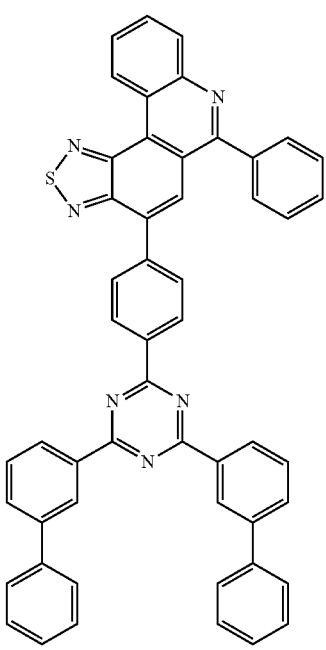

36
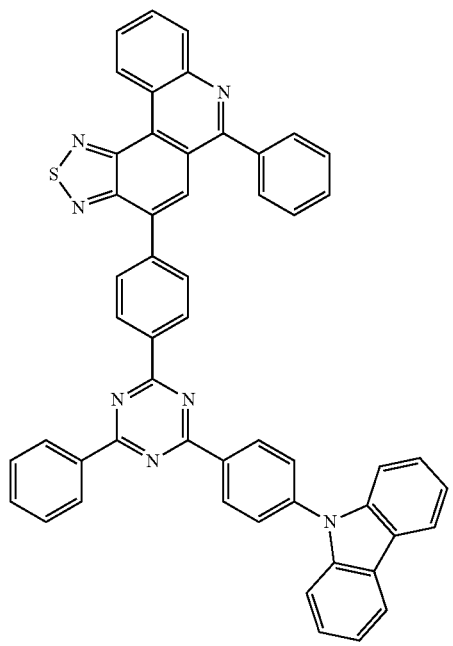
37
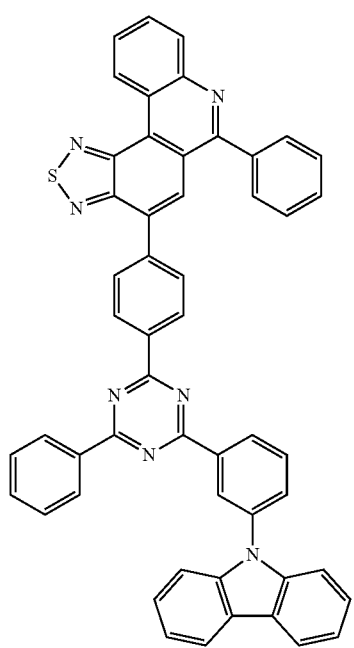
38
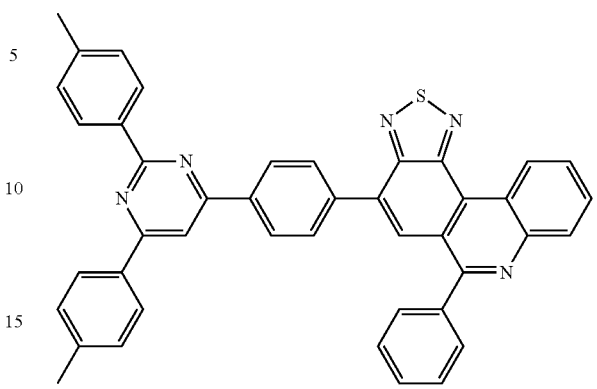
39
40

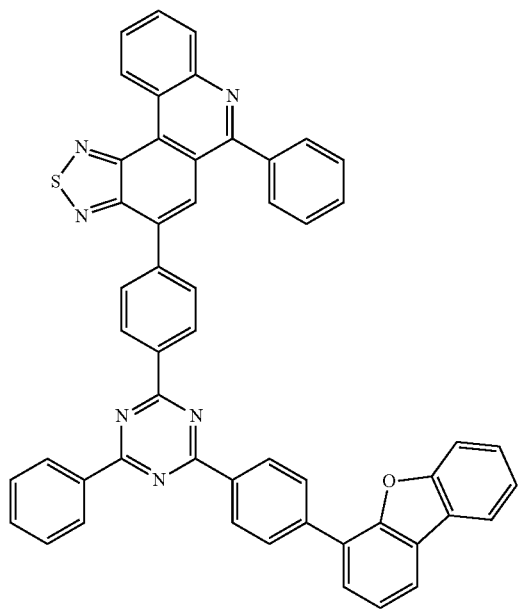
41
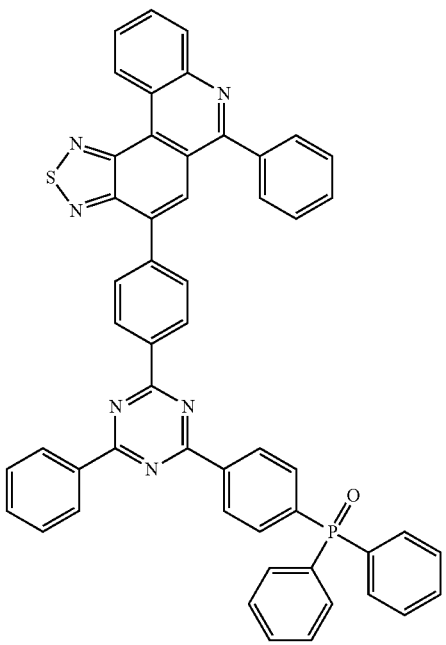
43
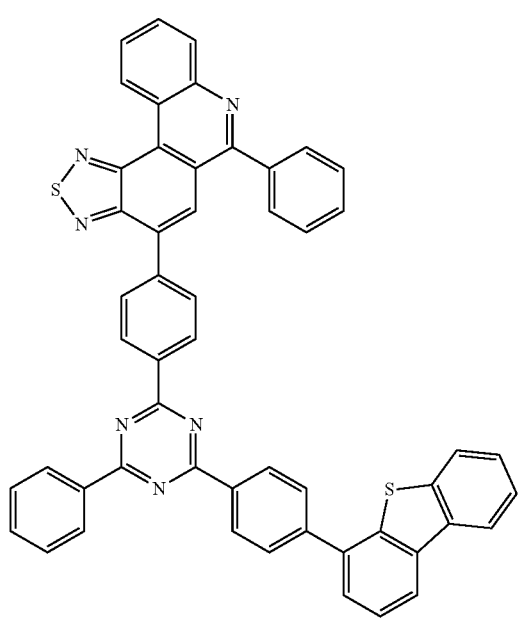
42
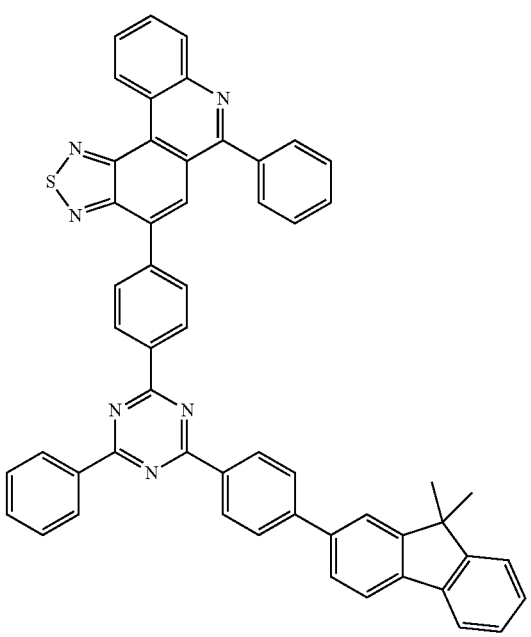
44

45
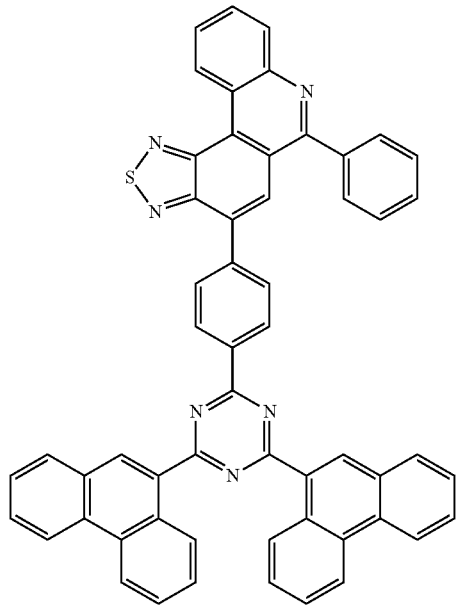
46
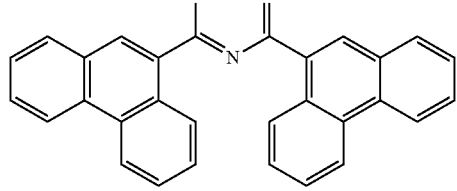
47
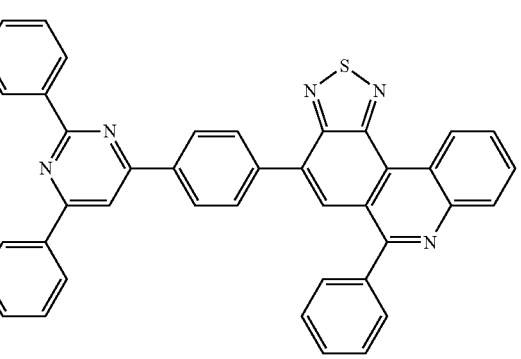
48
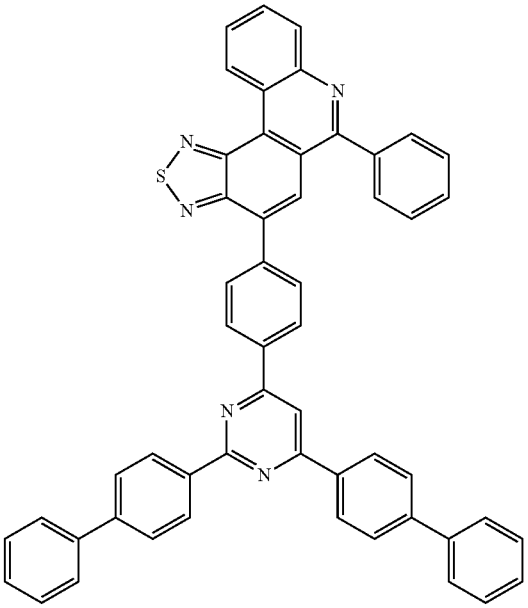
49

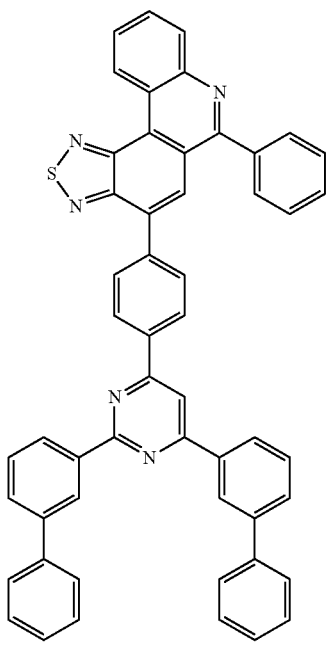
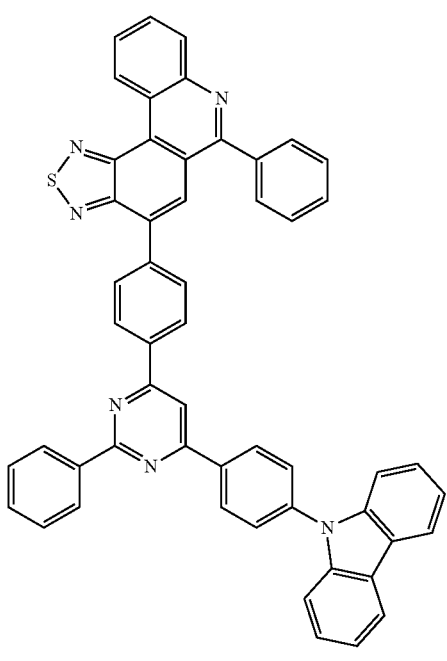
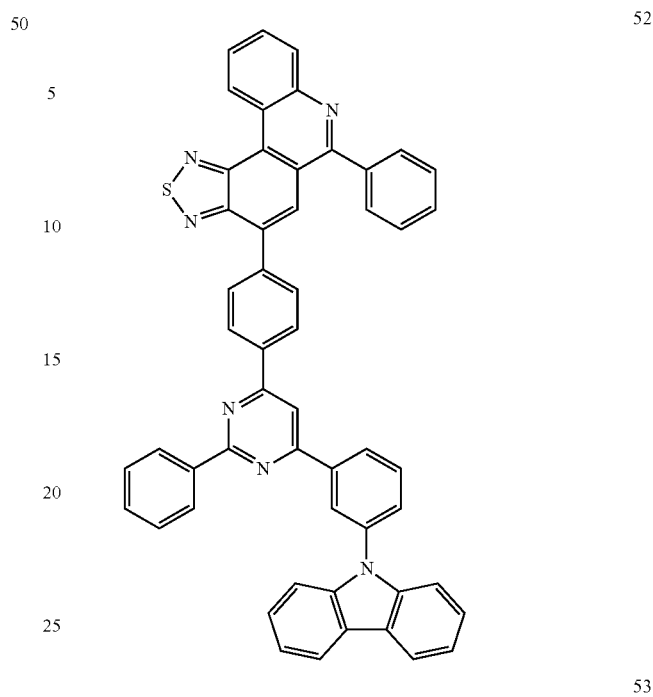
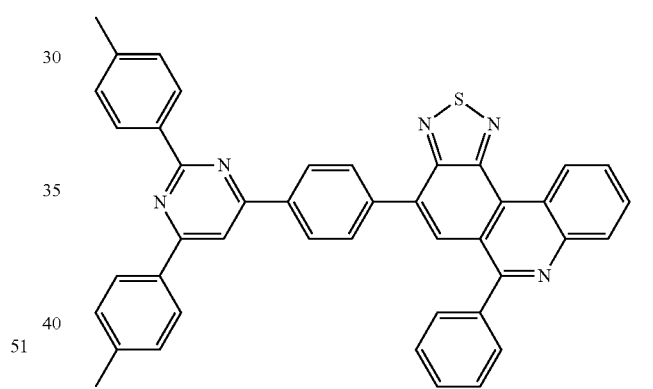
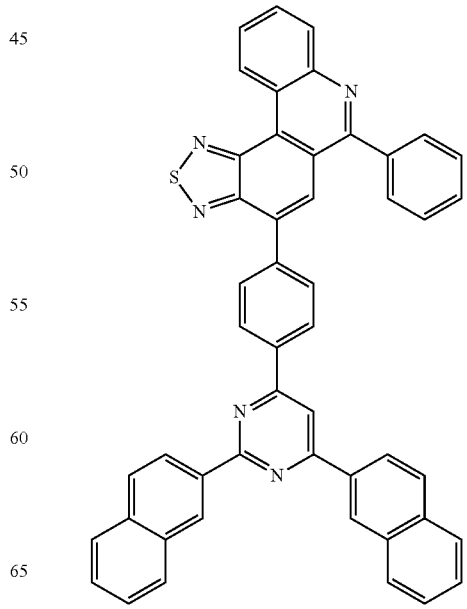

55
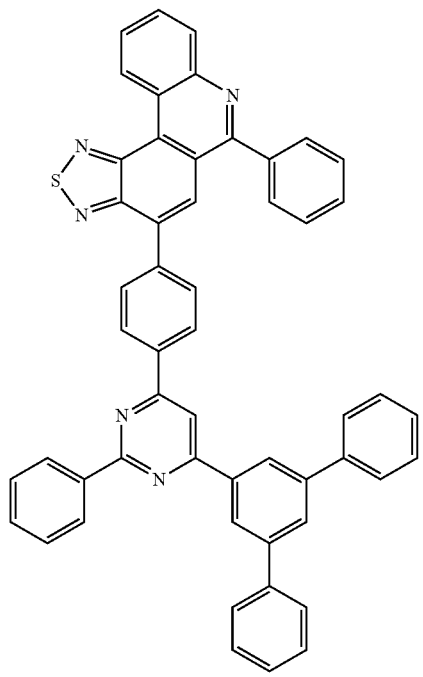
56
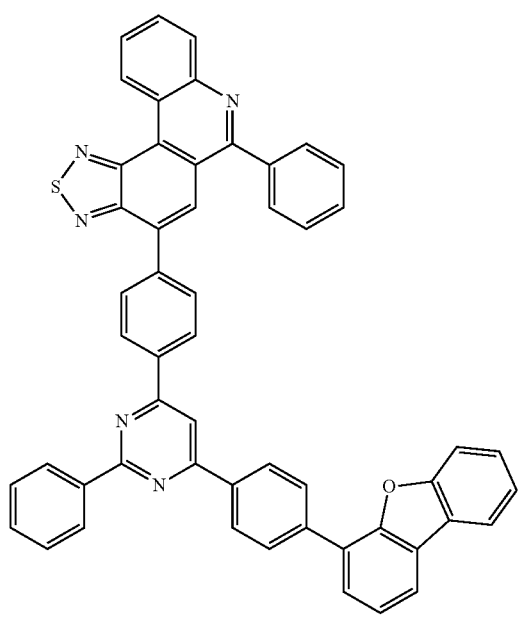
57
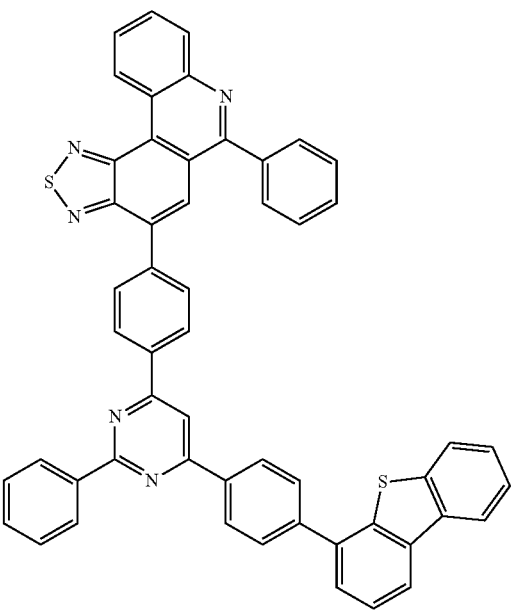
58
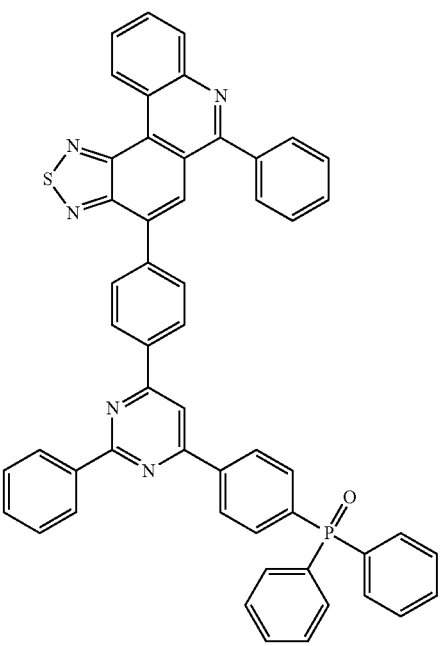

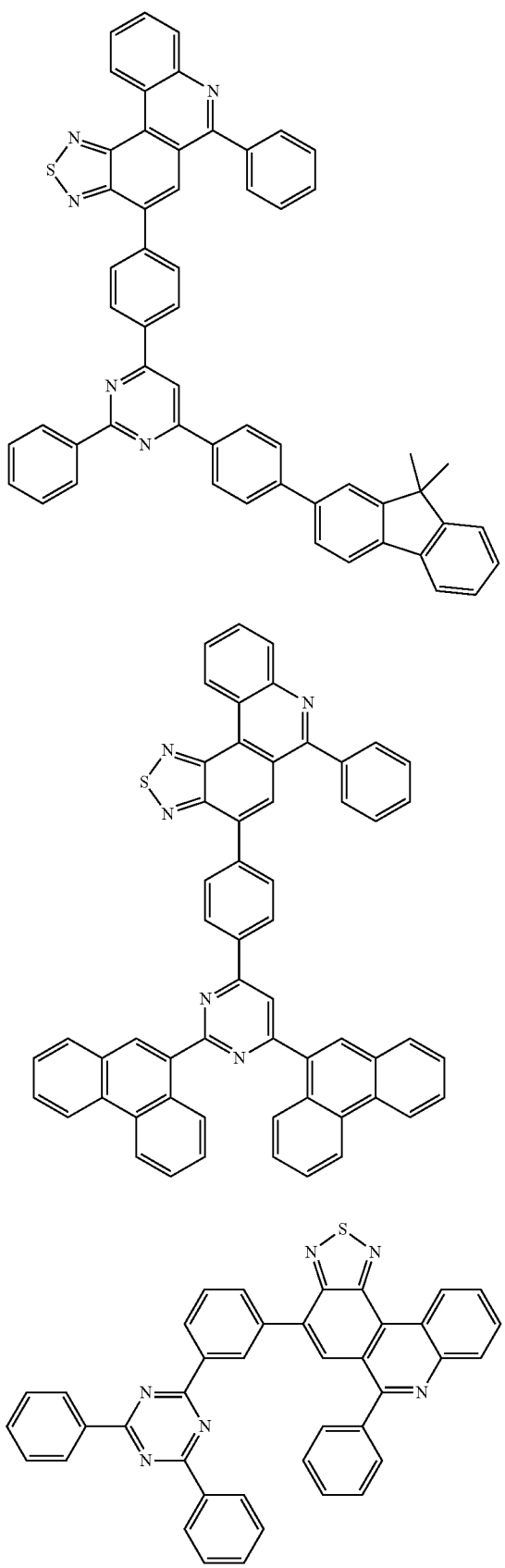
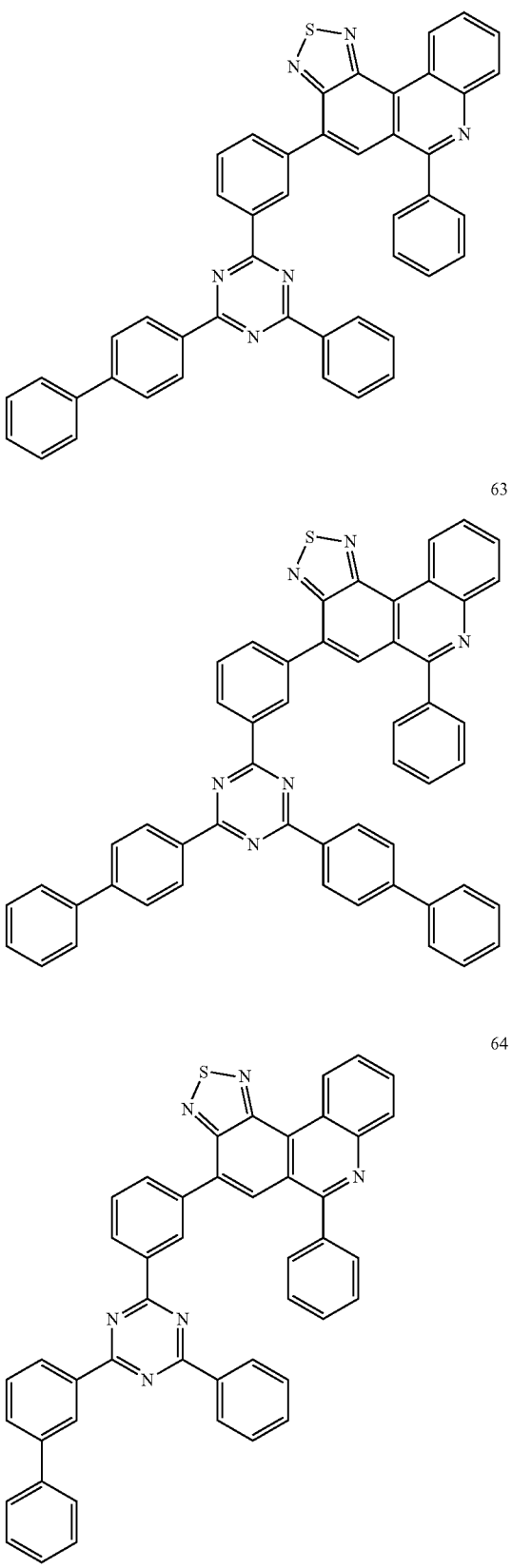

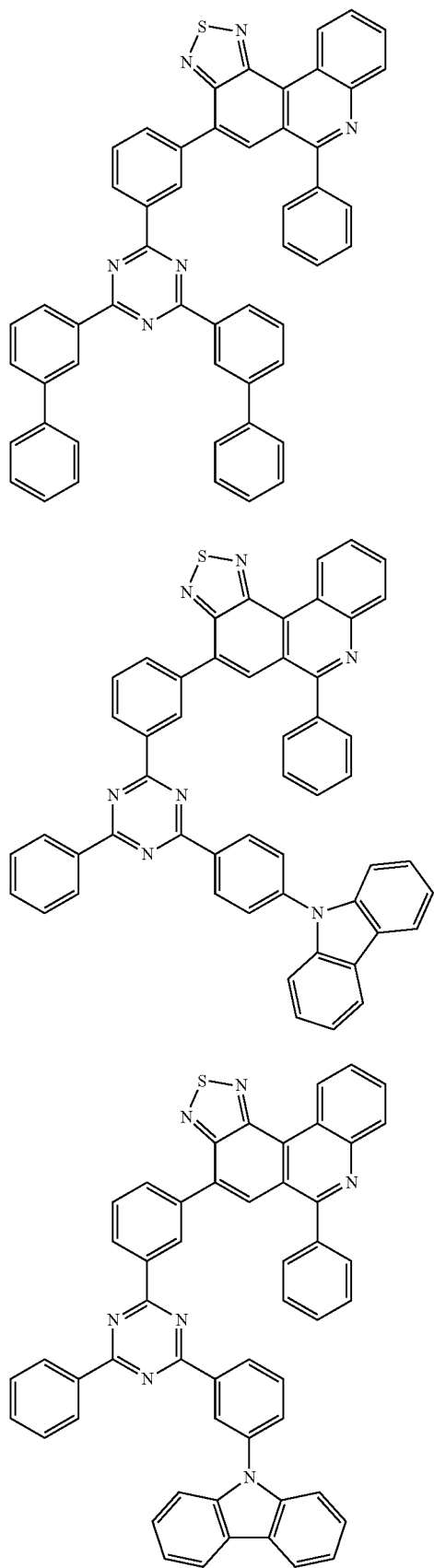
65
66
67
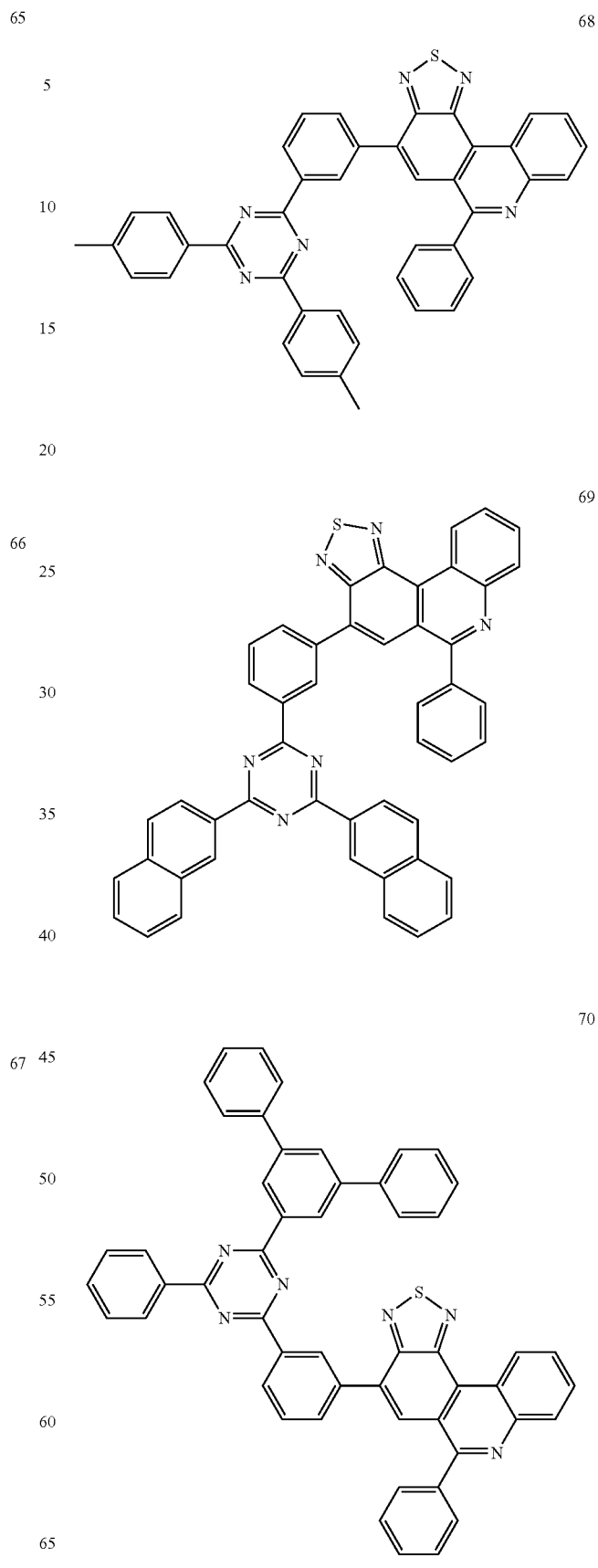
68
69
70

71
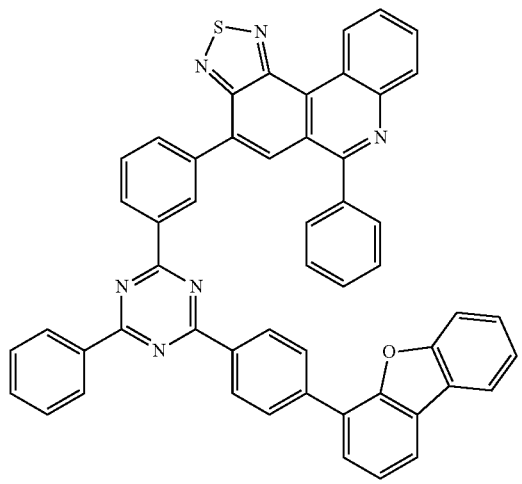
72
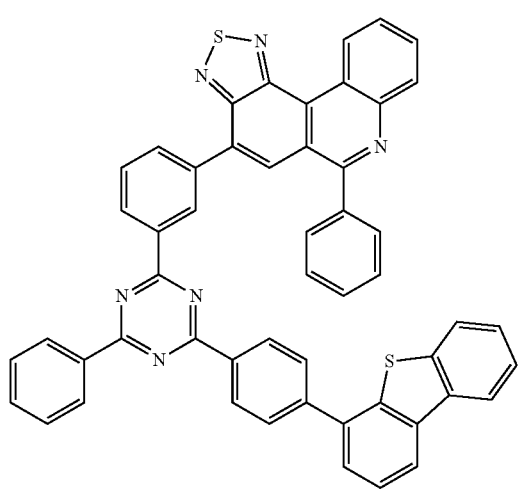
73
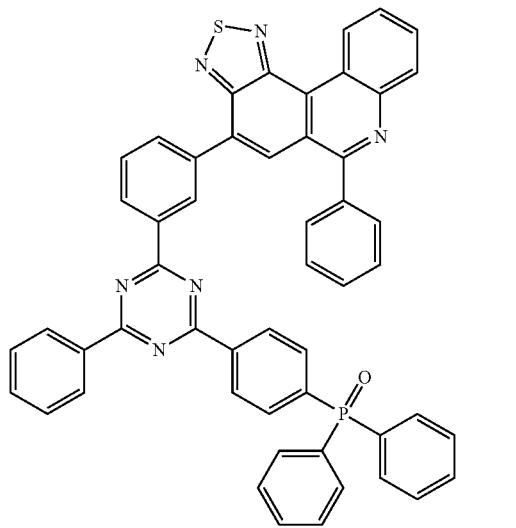
74
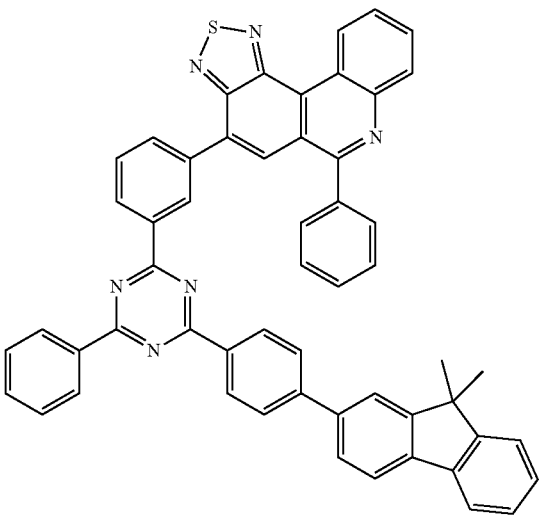
75
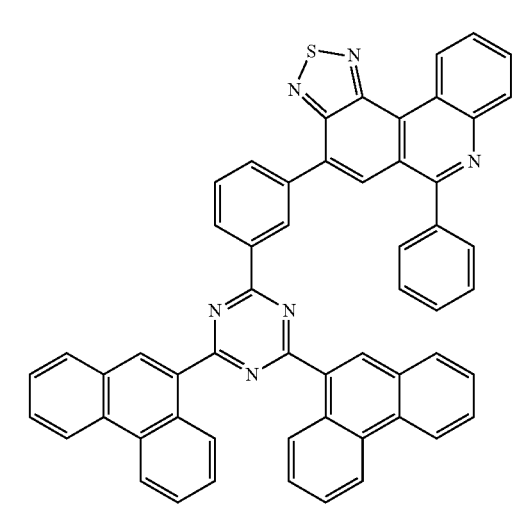
76
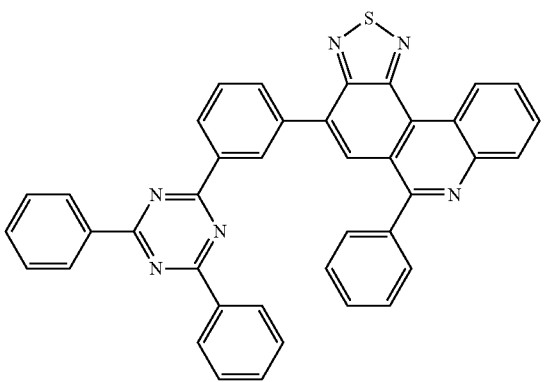

-continued
77
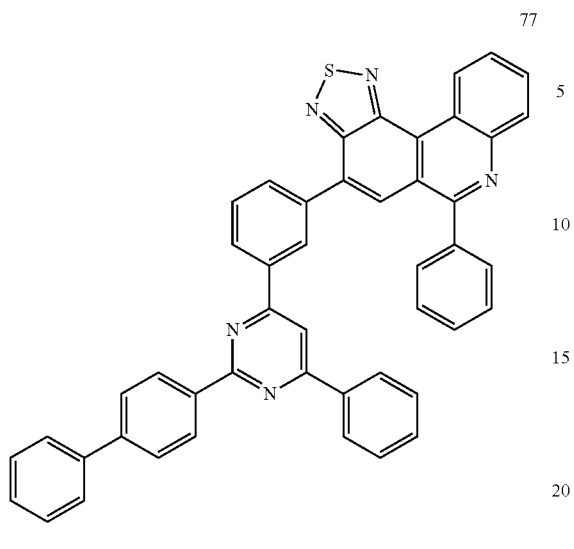
78
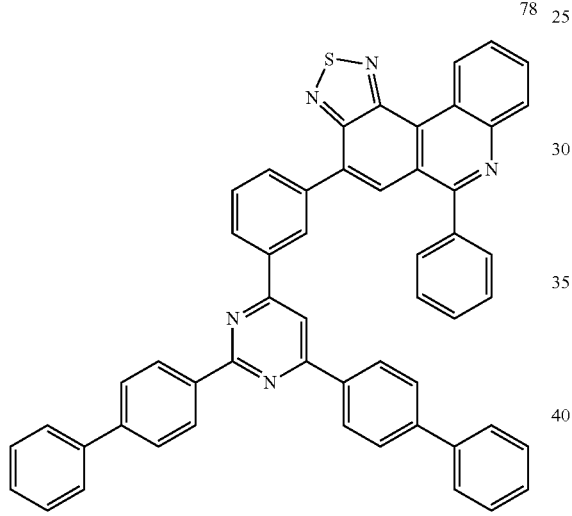
79
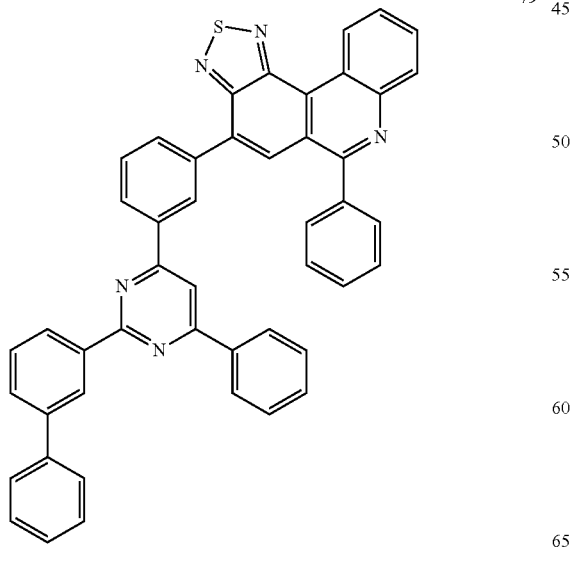
80
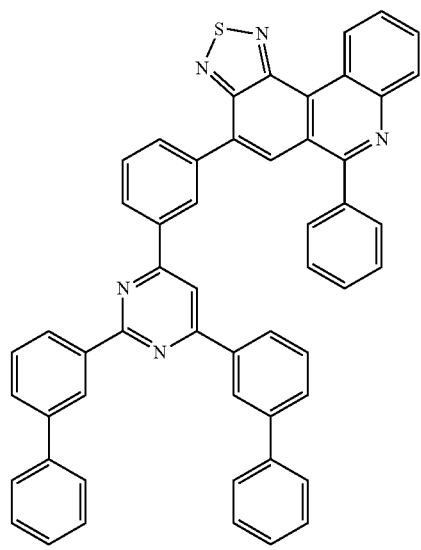
81
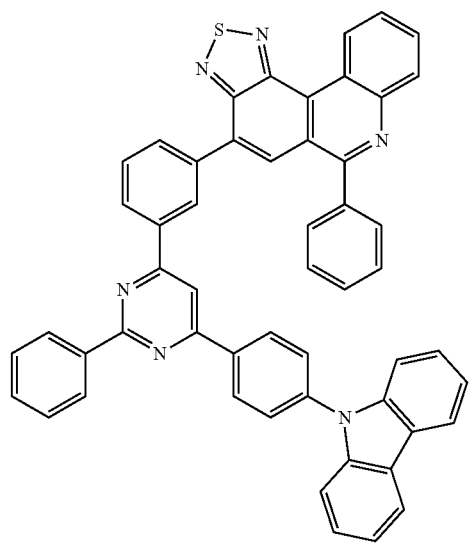
82
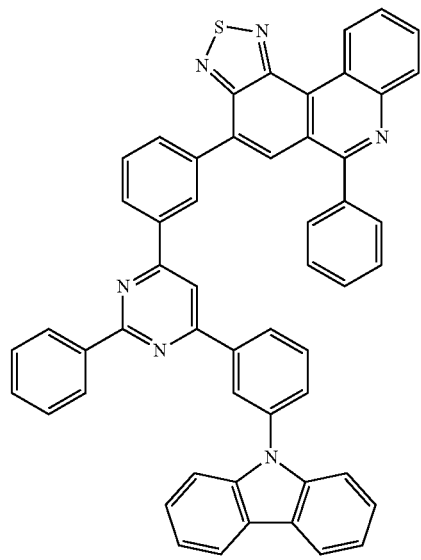

-continued
83
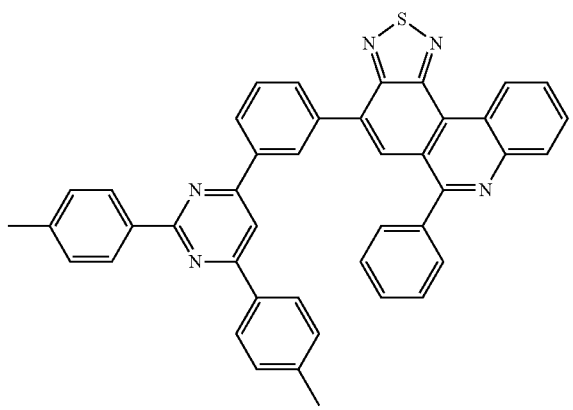
84
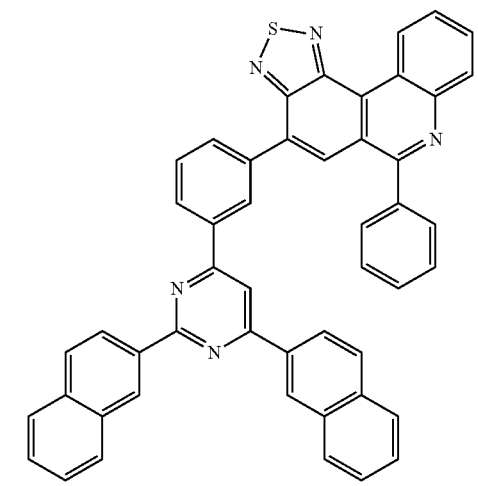
85
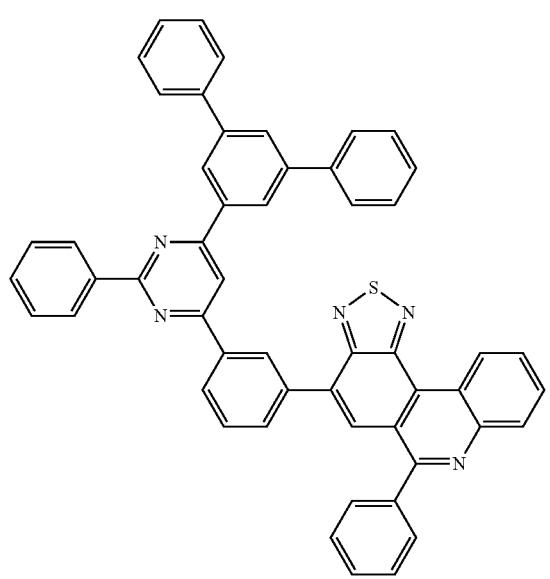
-continued
86
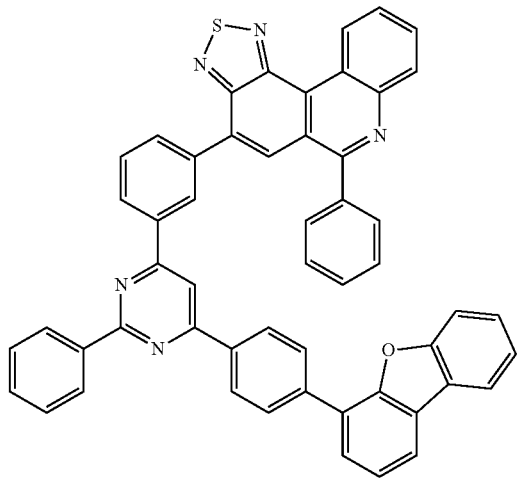
87
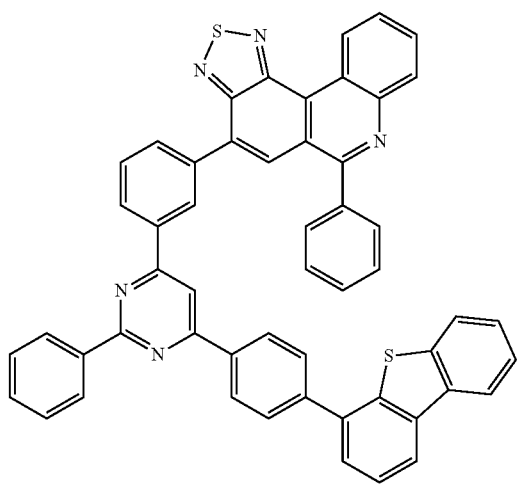
88
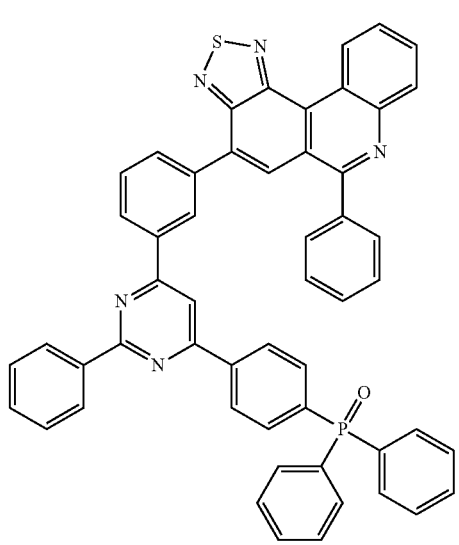

89
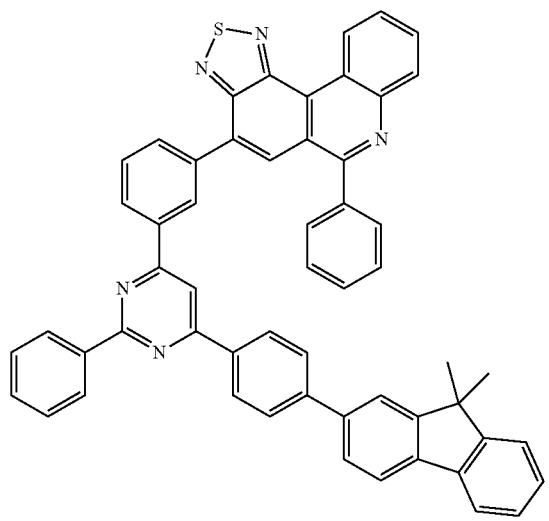
90
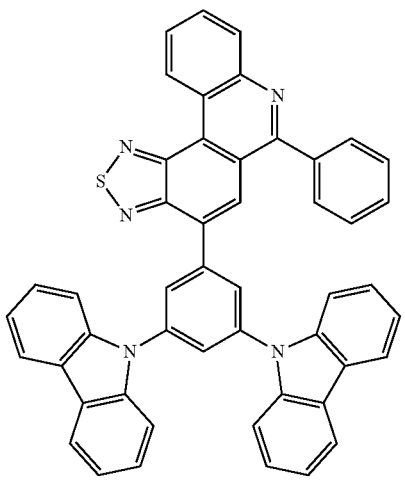
91
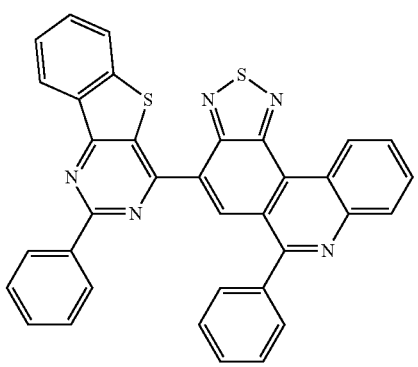
92
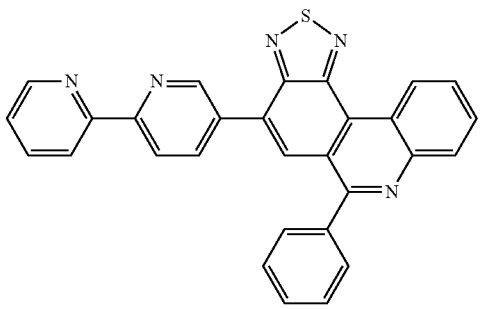
93
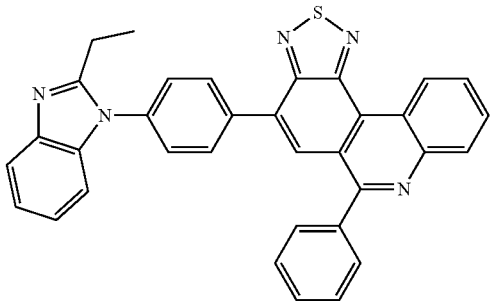
94
95

96
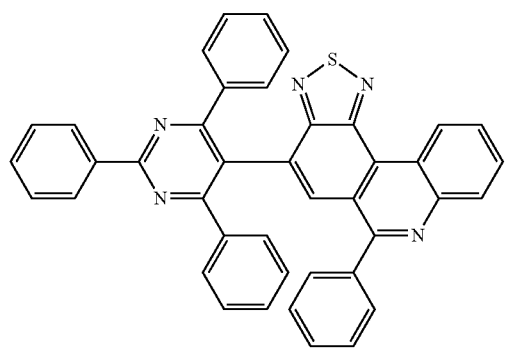
97
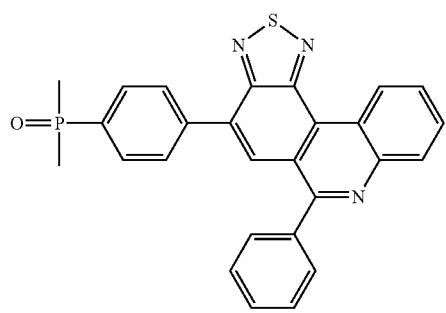
98
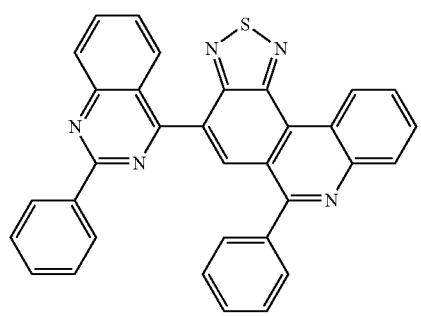
99
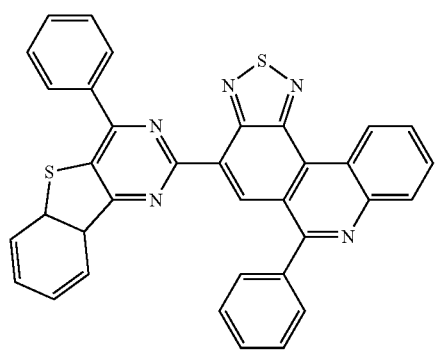
100
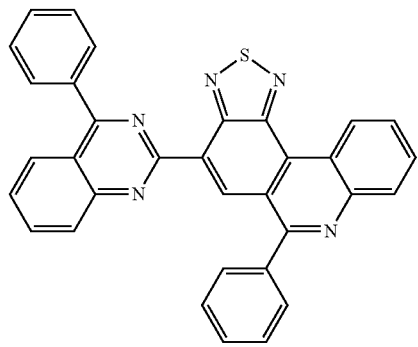
101
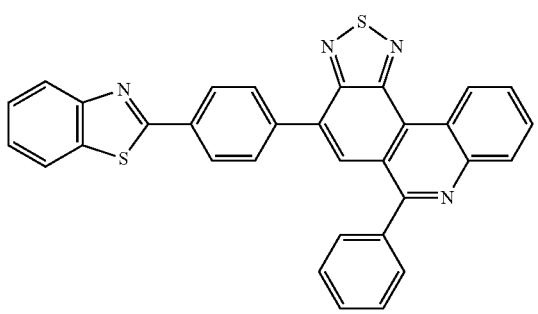
102
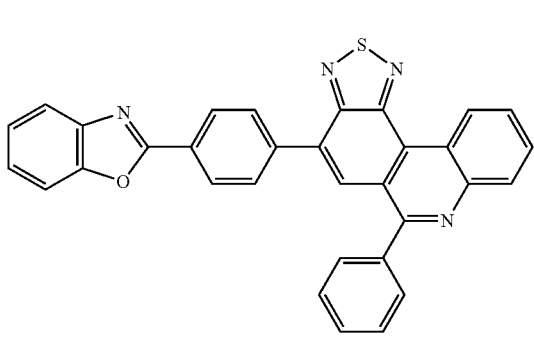
103
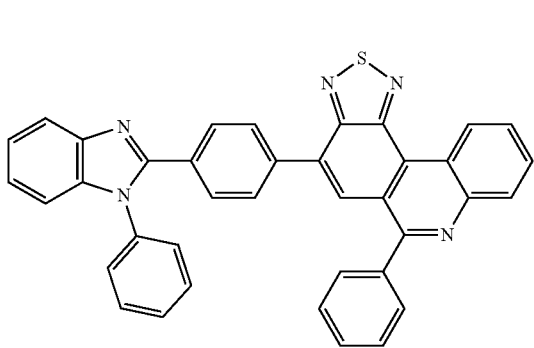

104
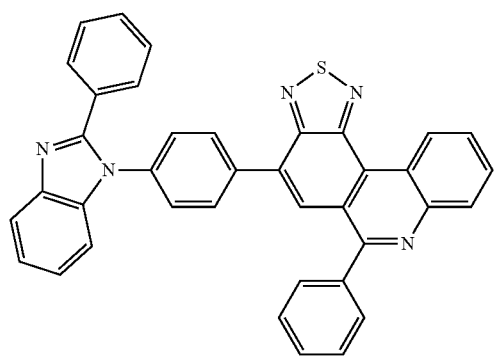
105
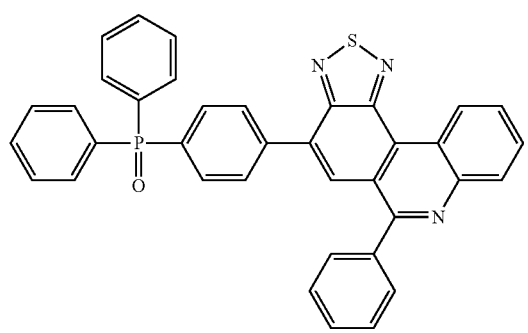
106
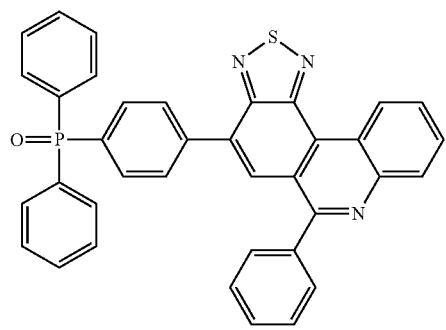
107
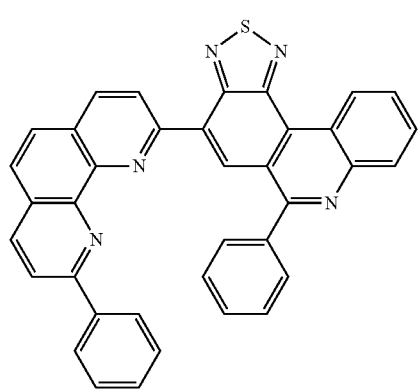
108
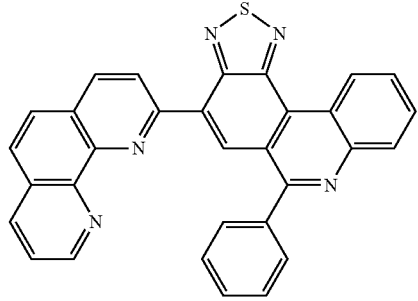
109
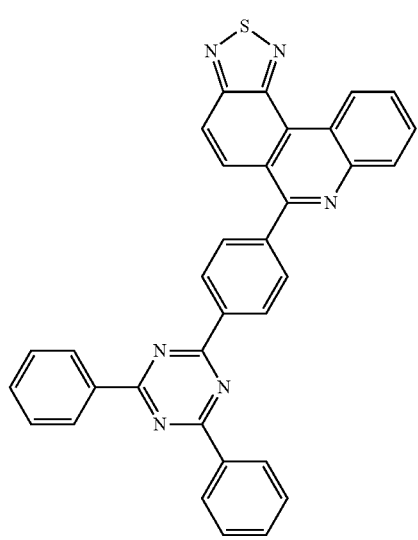
110
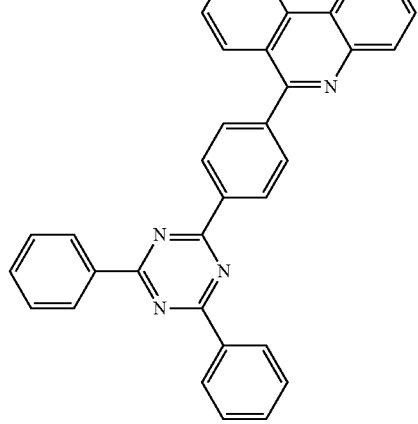

111
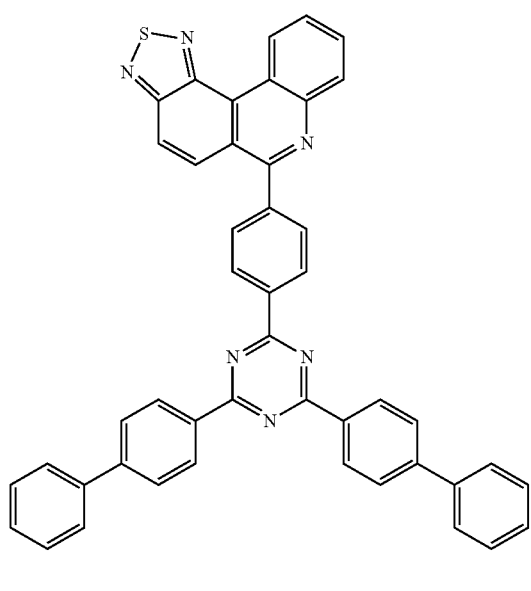
113
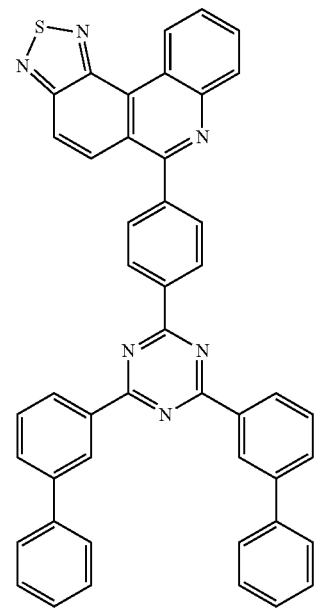
112
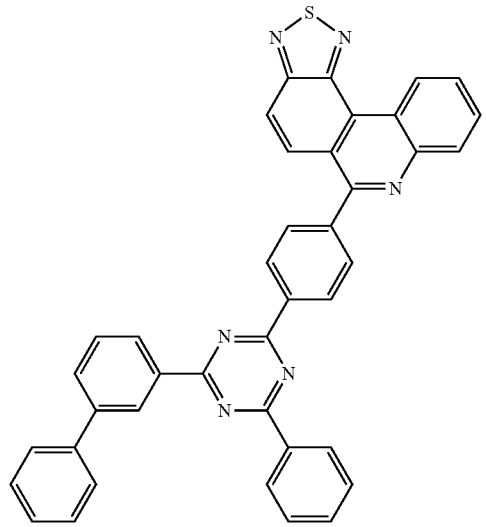
114
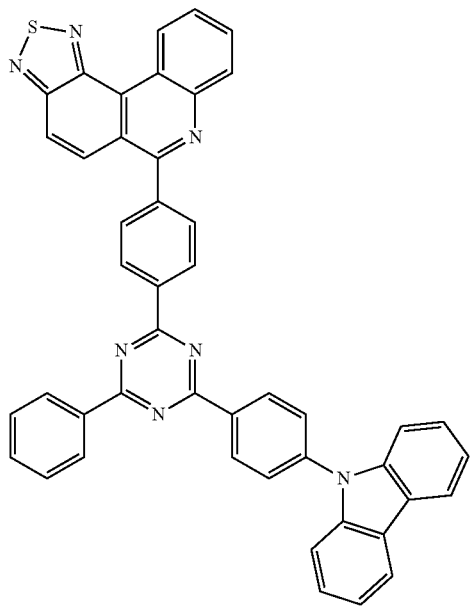

115
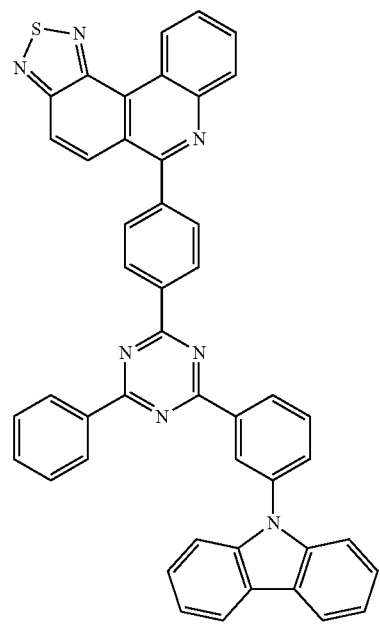
116
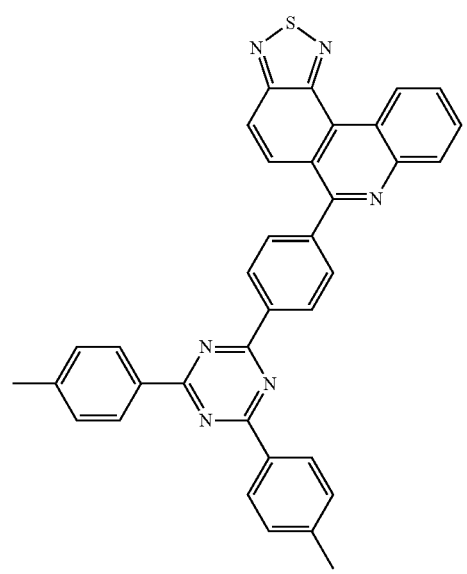
117
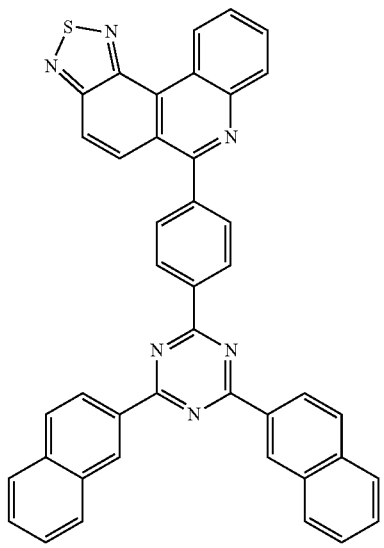
118
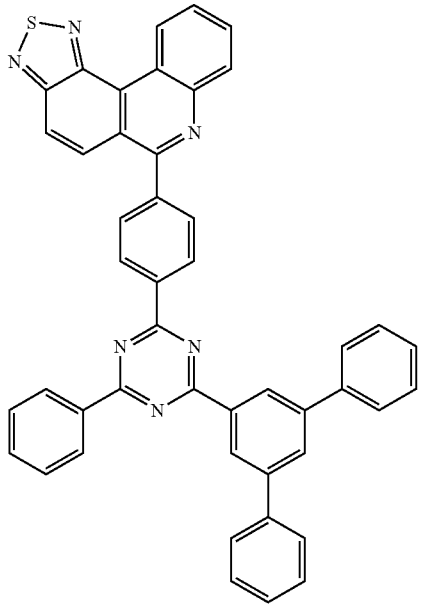

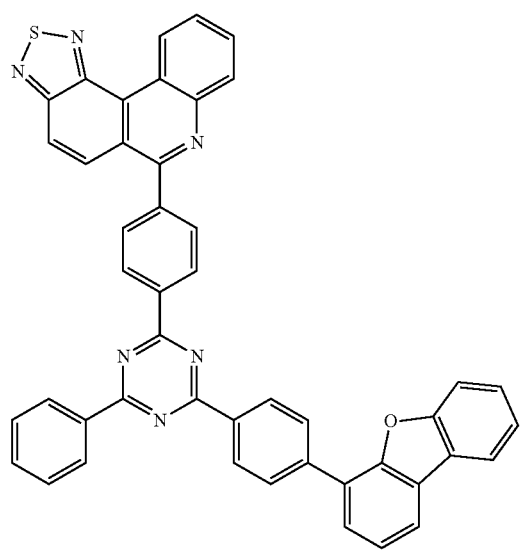
119
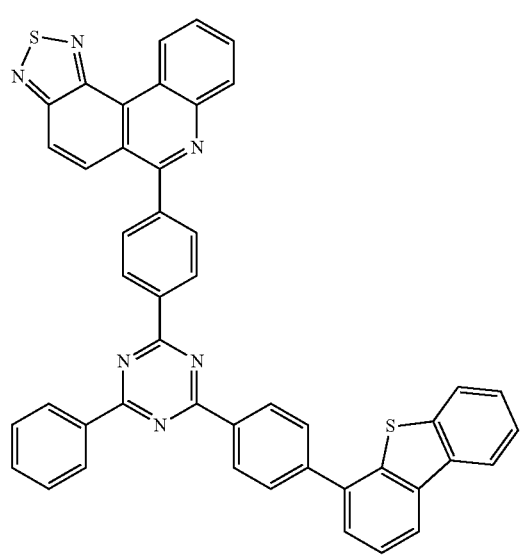
120
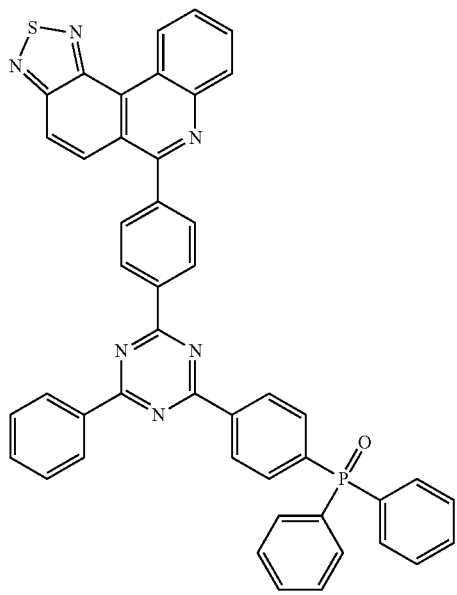
121
122

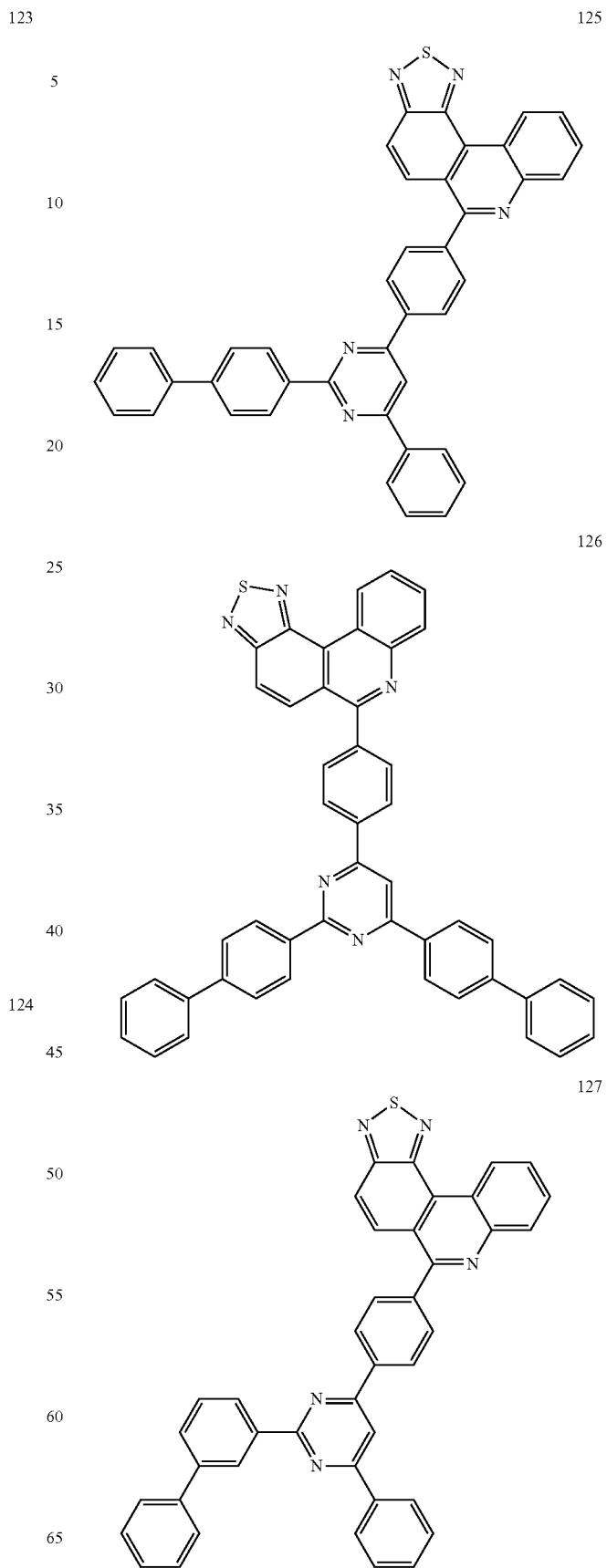

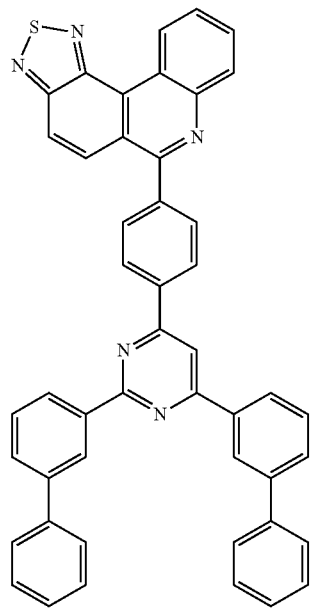
128
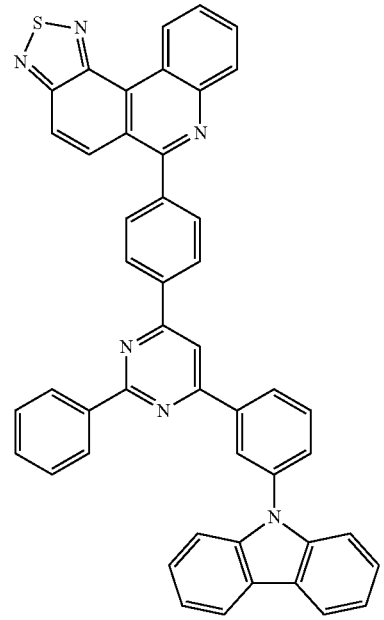
130
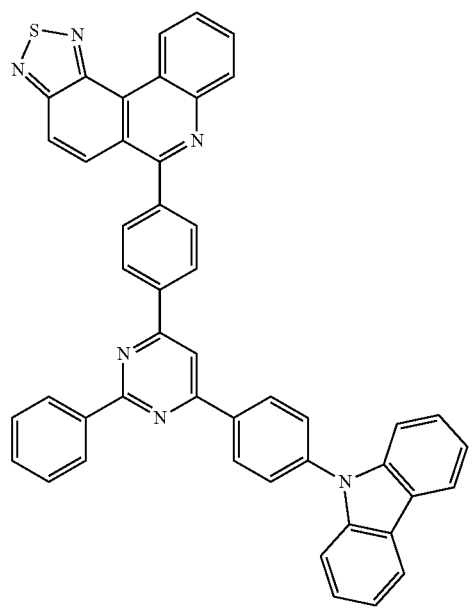
129
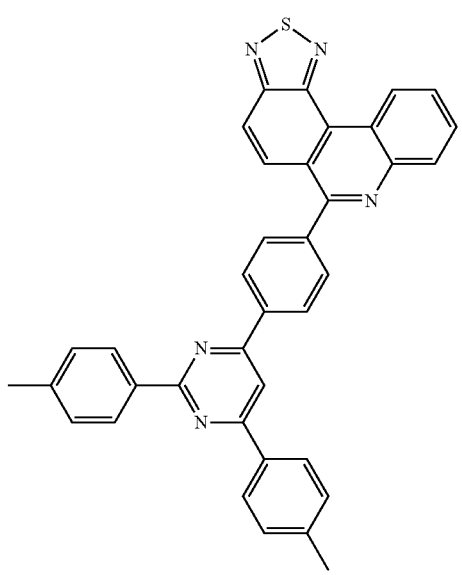
131

132
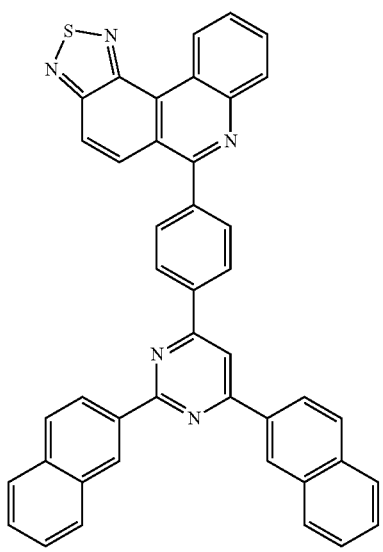
134
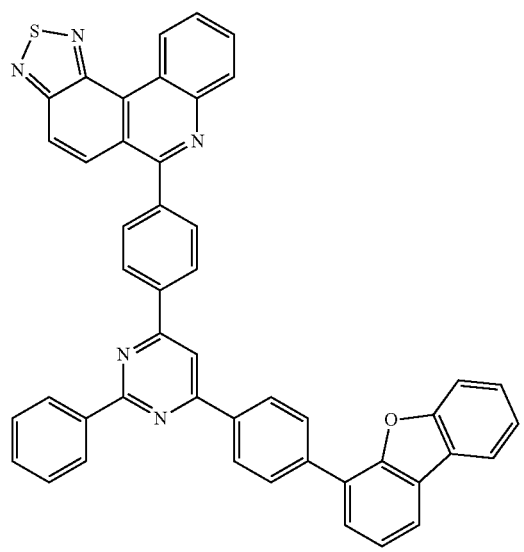
133
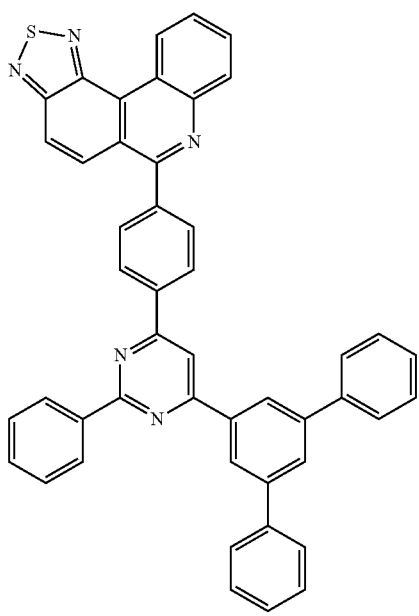
135
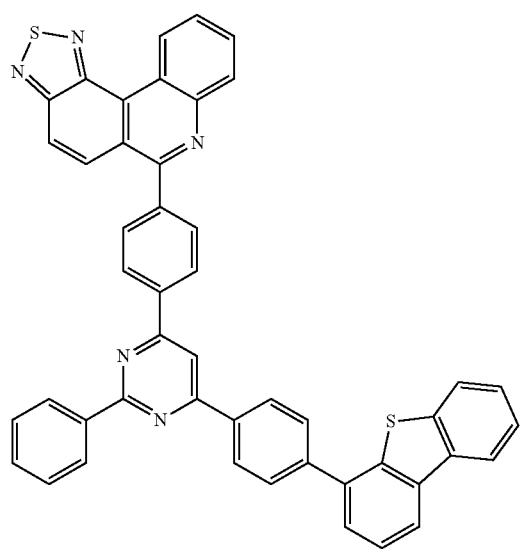

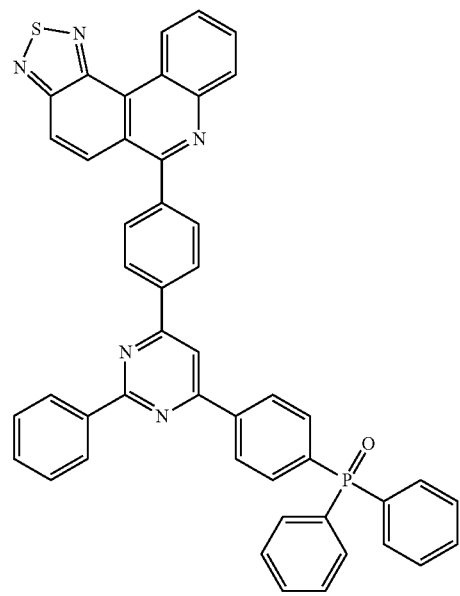
136
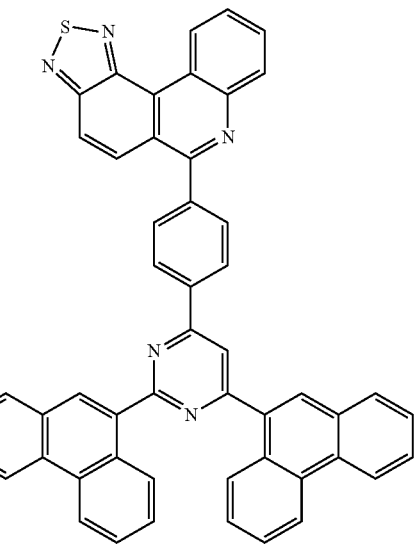
138
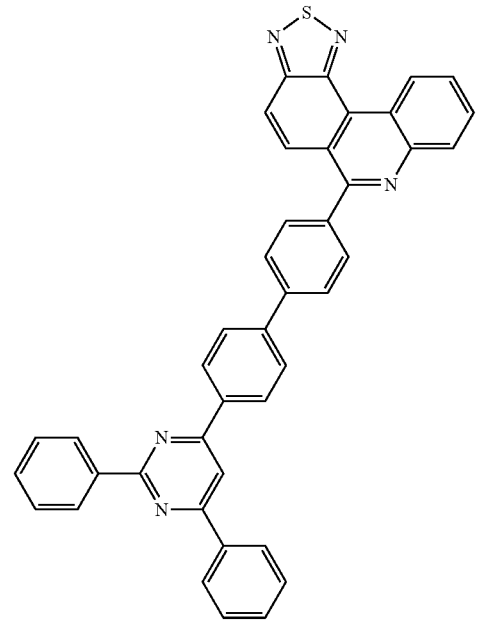
139

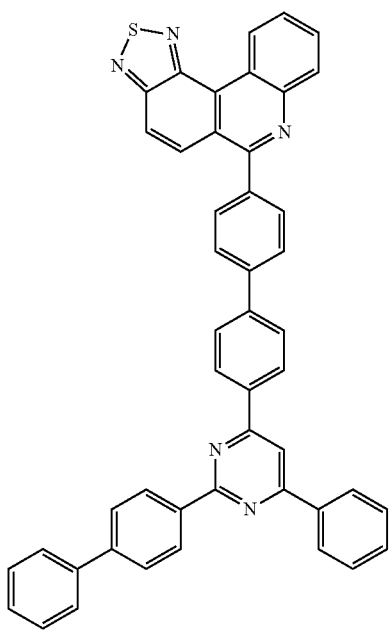
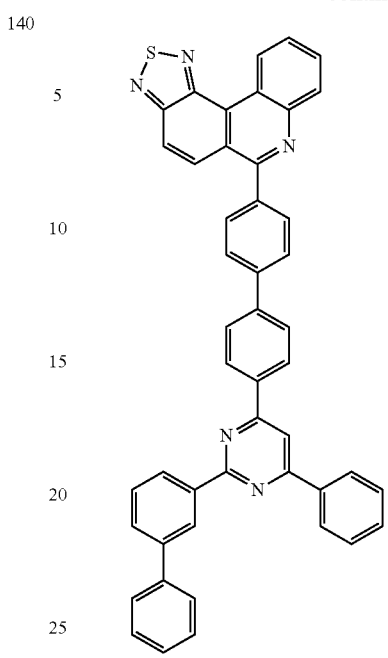

144
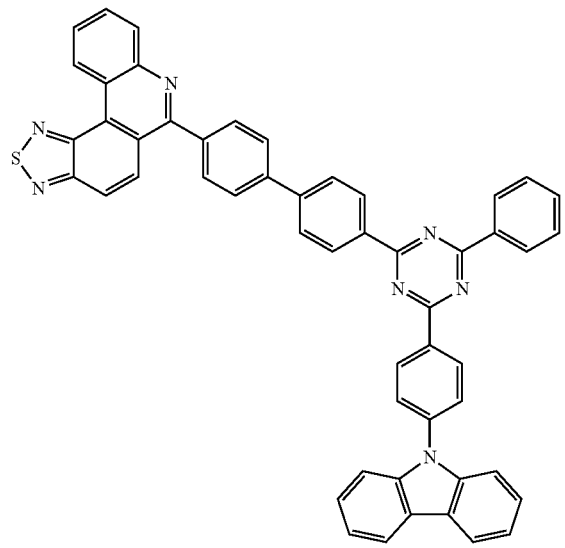
145
147
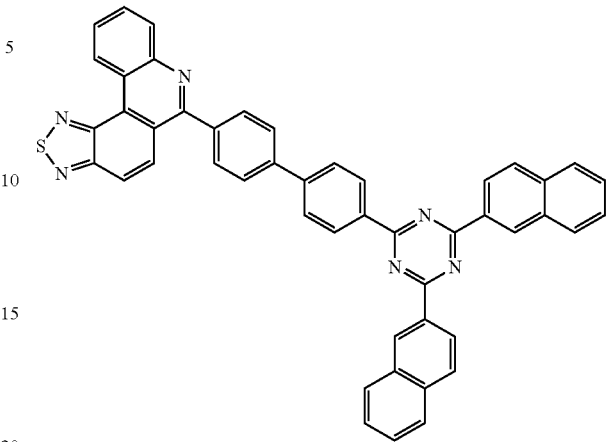
148
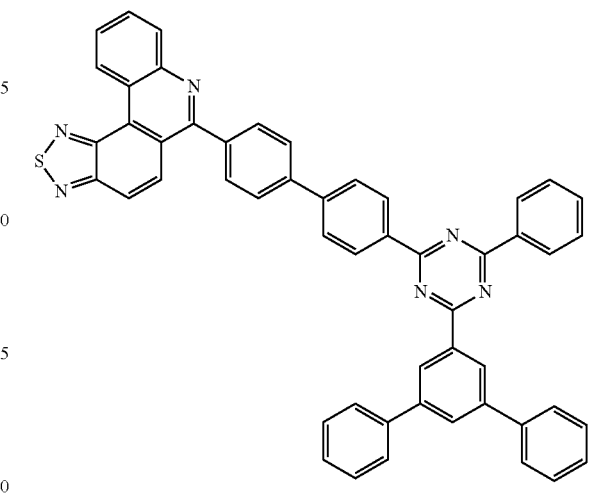
149
146
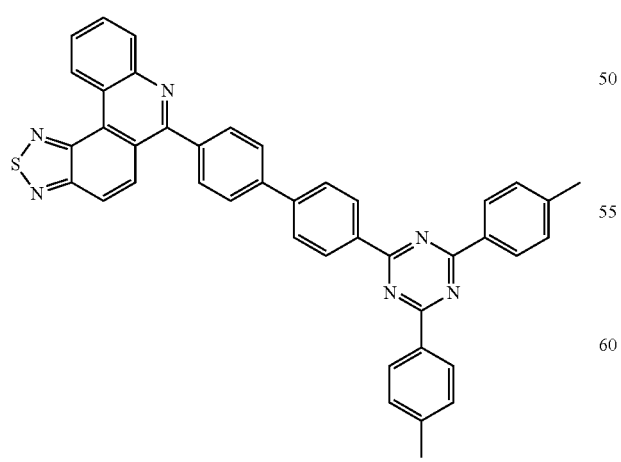 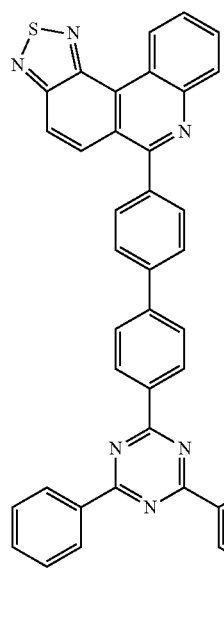

150
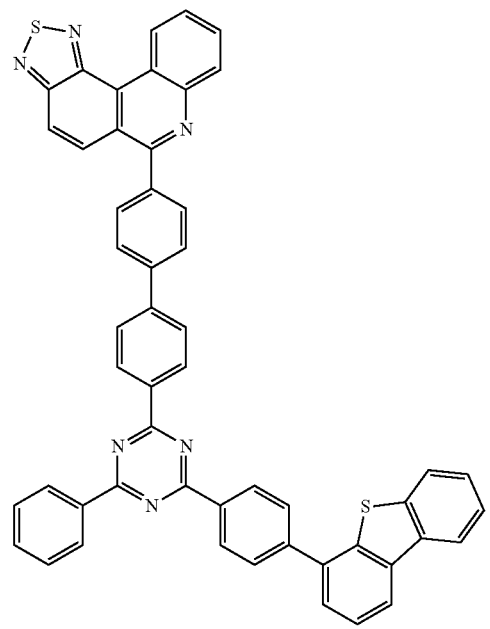
151
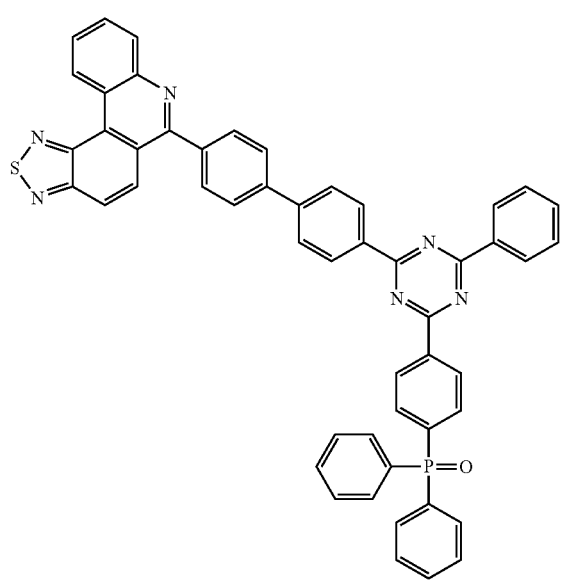
152
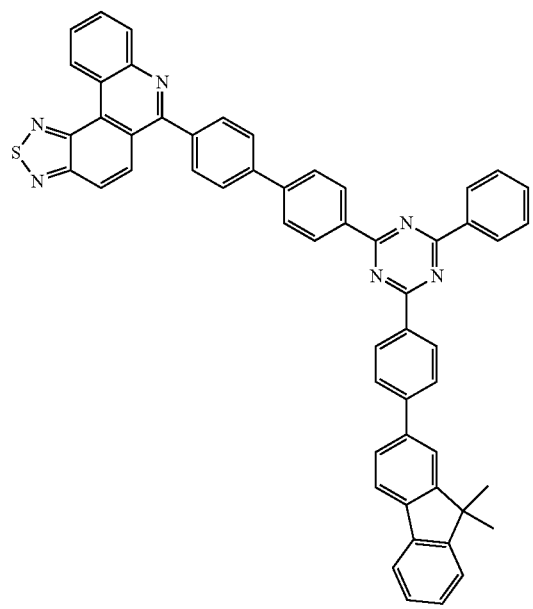
153
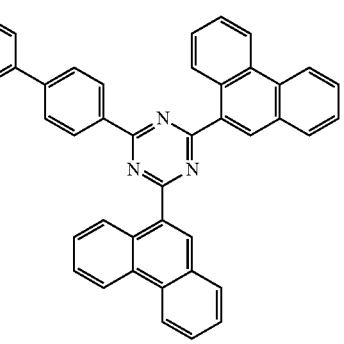
154
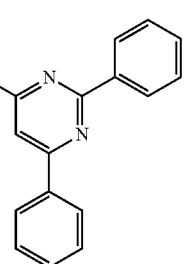

155
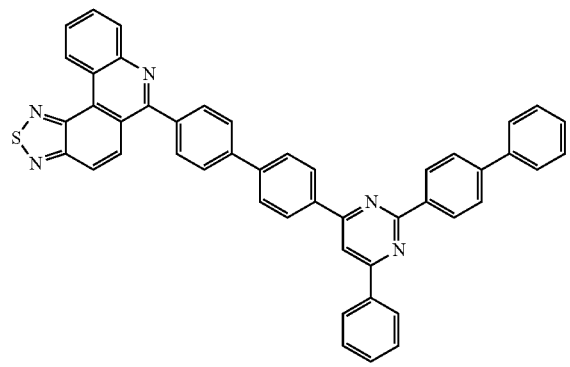
156
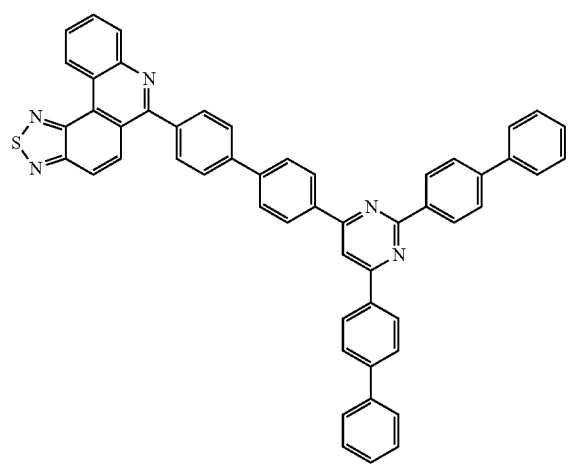
157
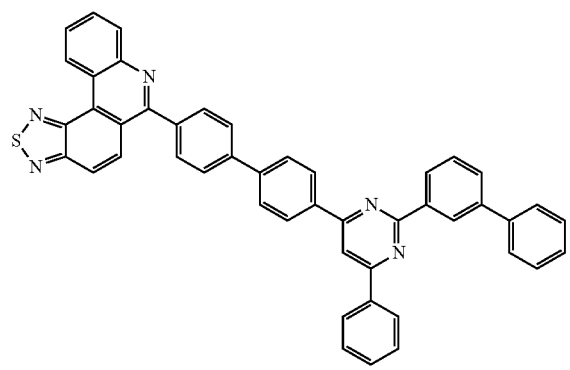
158
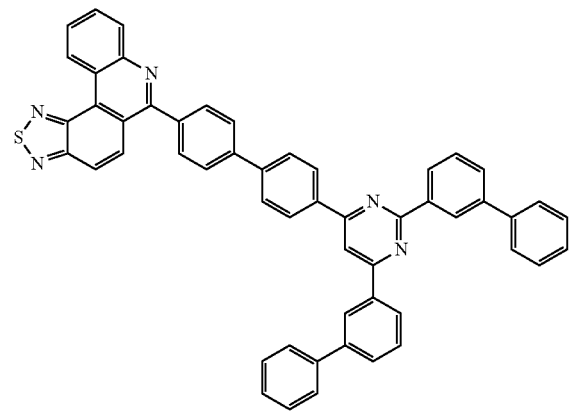
159
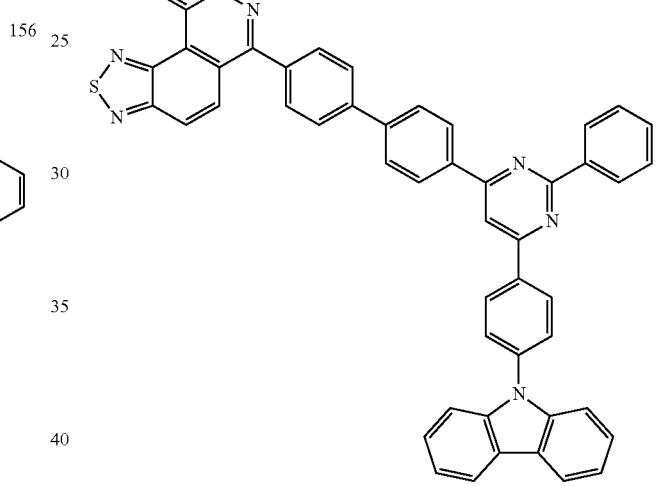
160
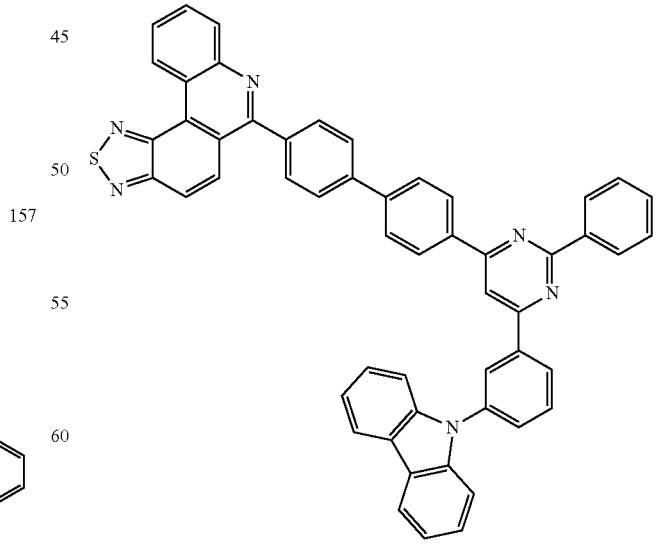

75
-continued
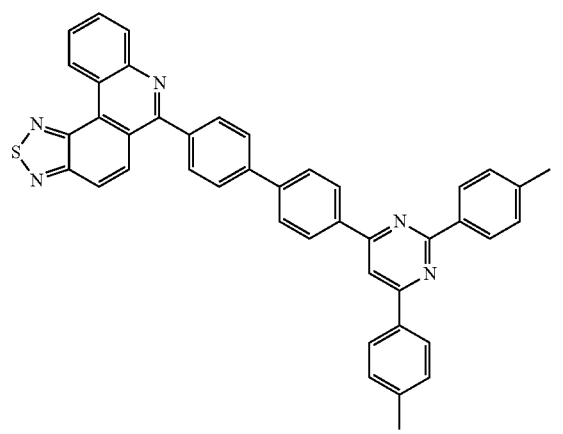
161
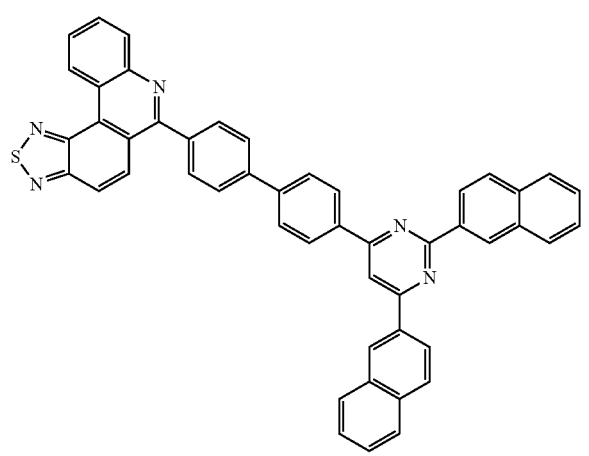
162
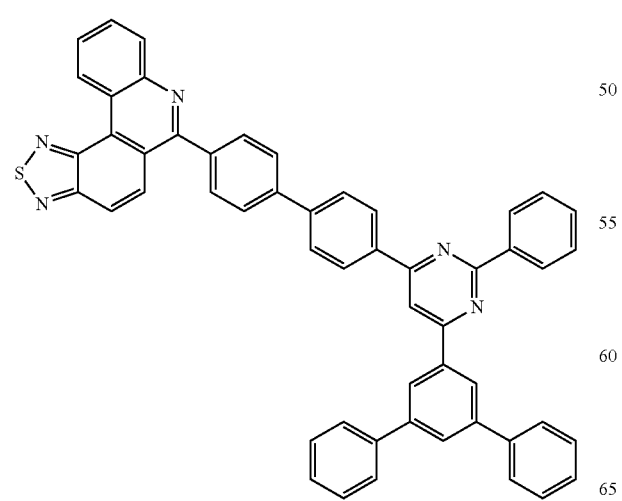
163
76
-continued
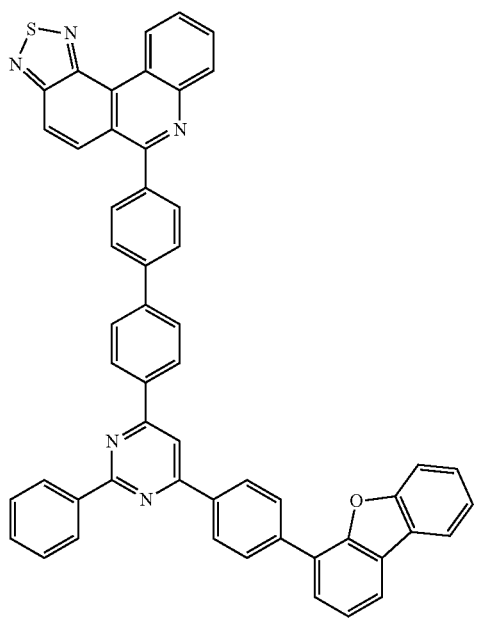
164
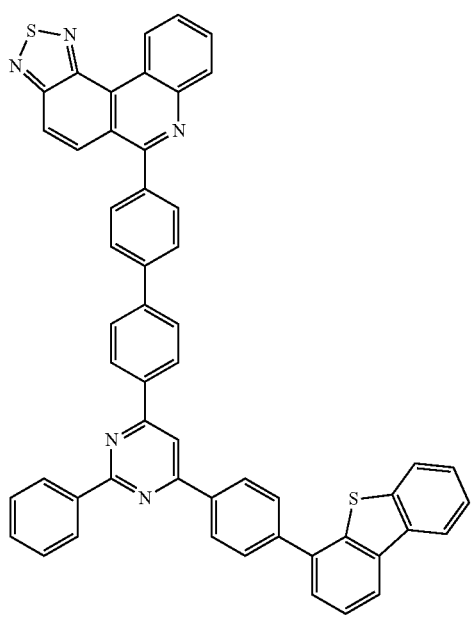
165

166
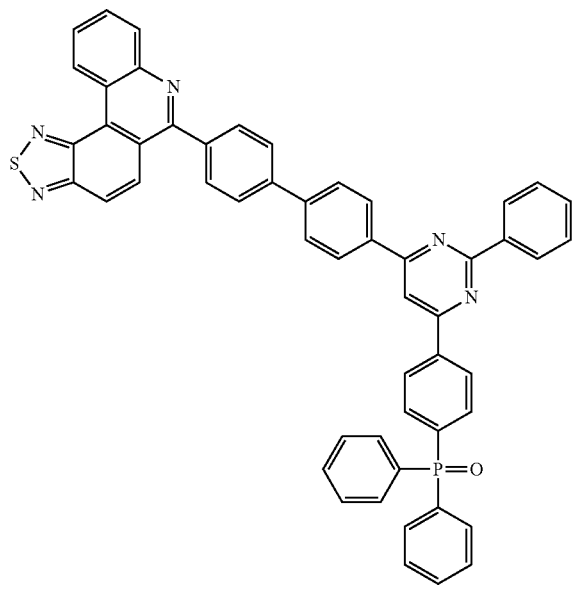
168
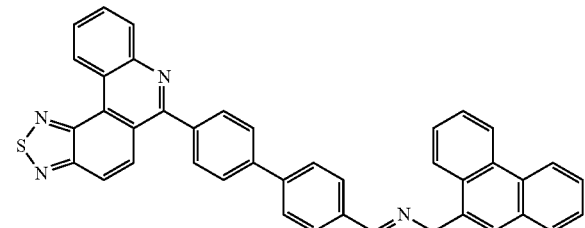
169
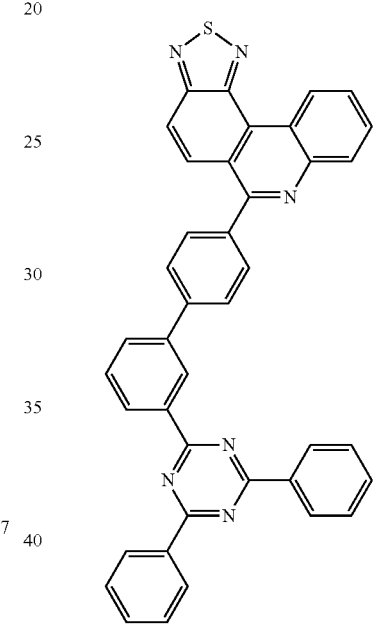
167
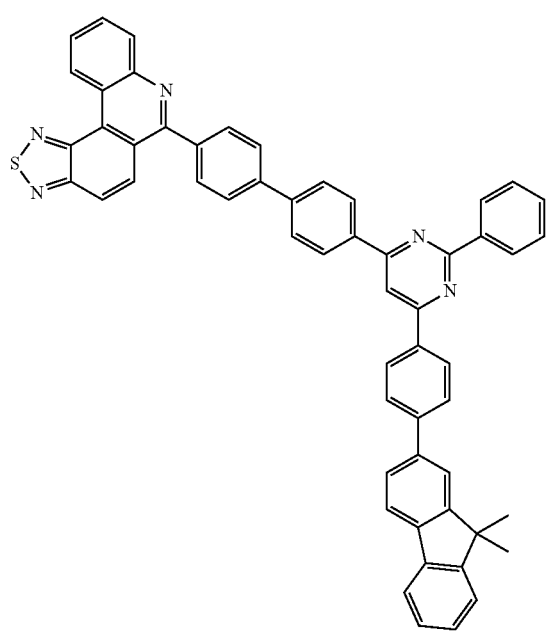
170
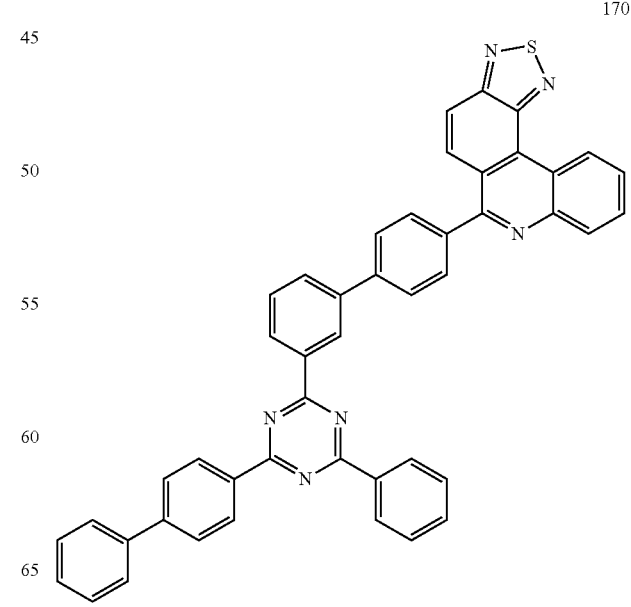

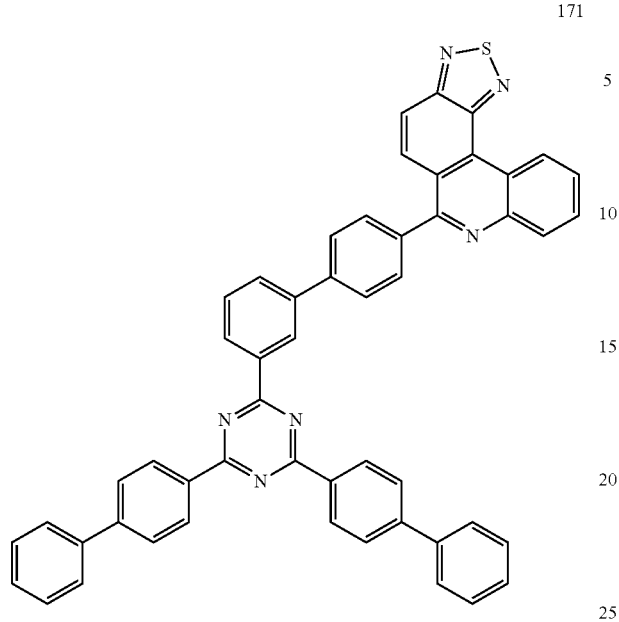
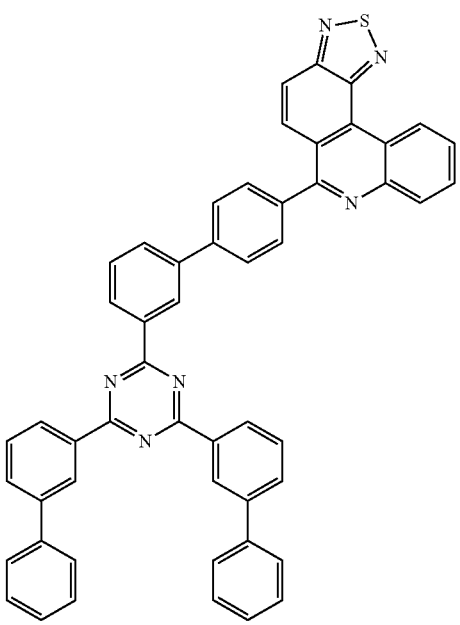

-continued
81
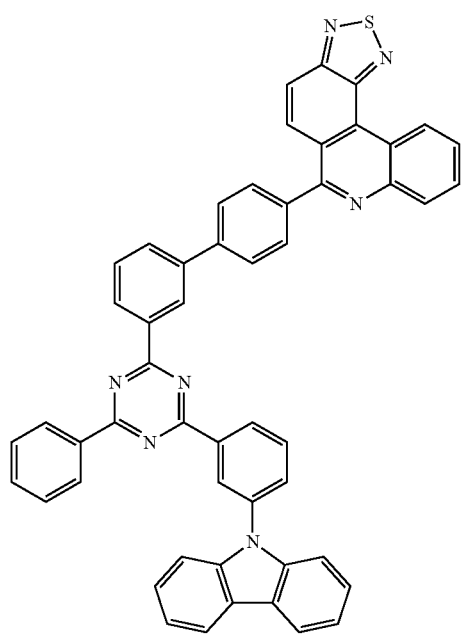
175
82
-continued
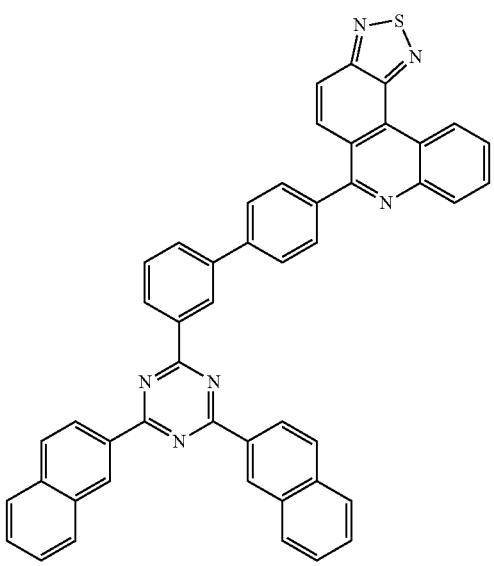
177
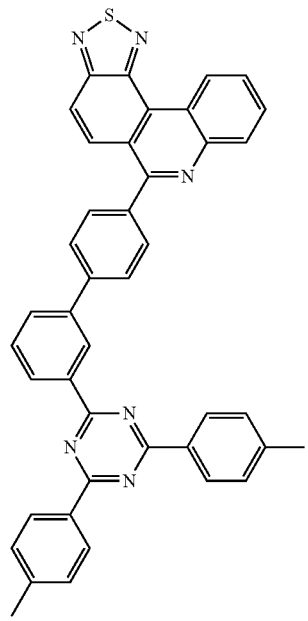
176
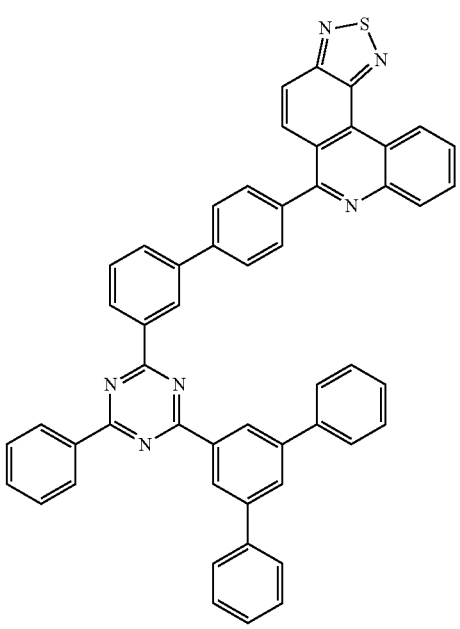
178

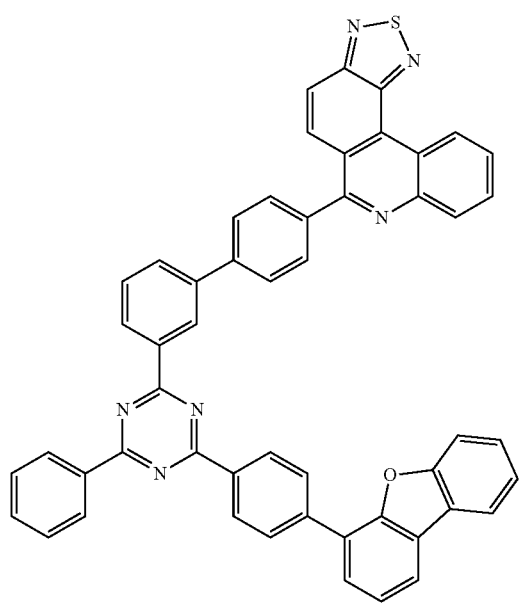
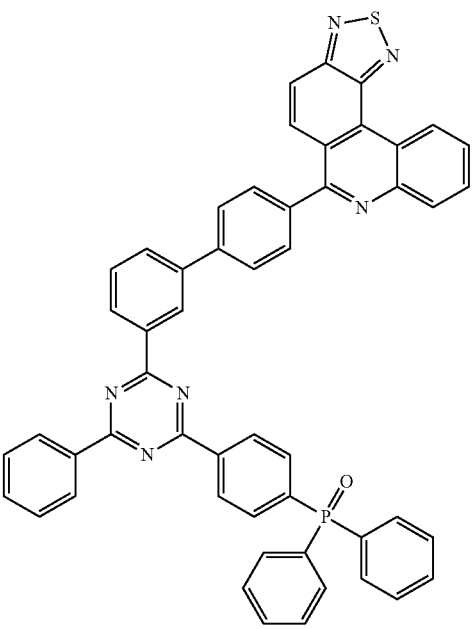

183
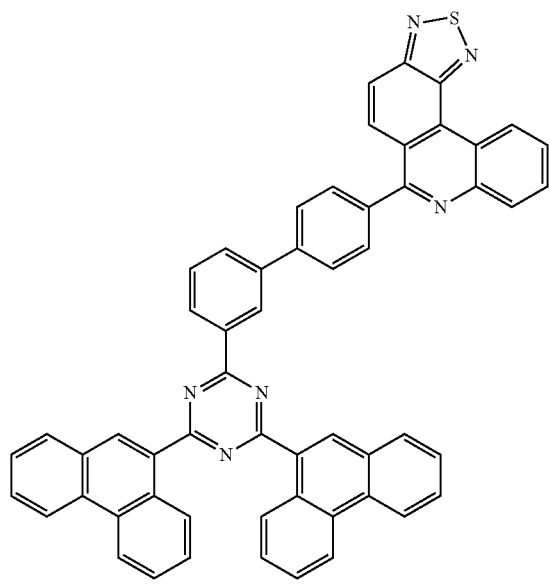
184
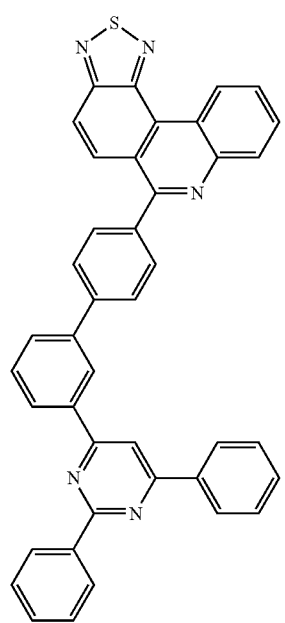
185
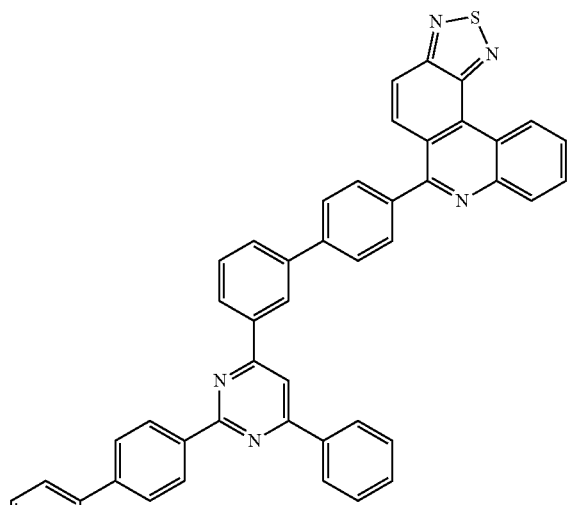
186
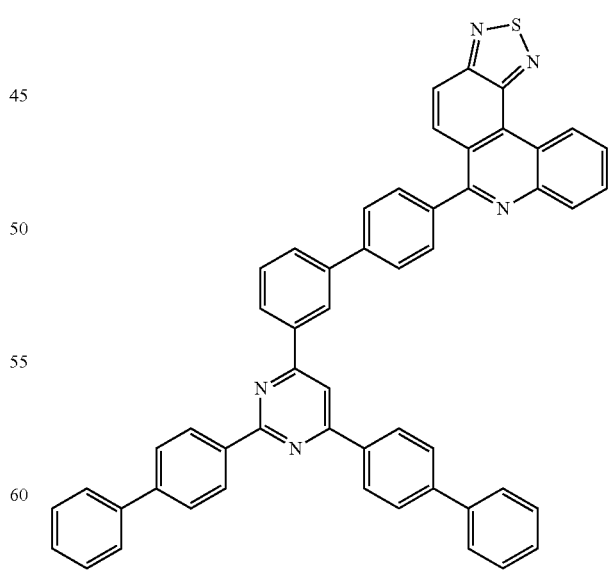

187 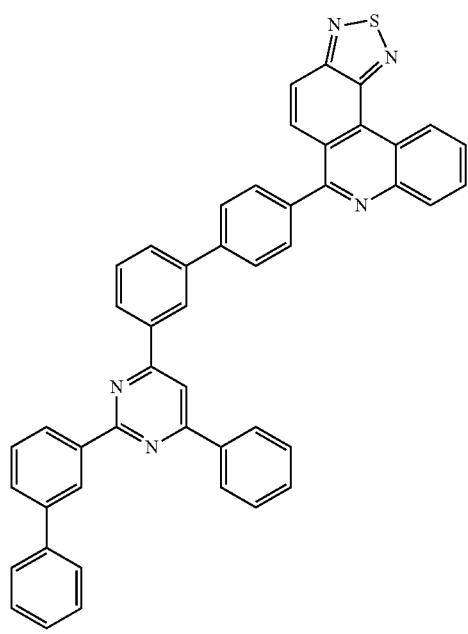
188 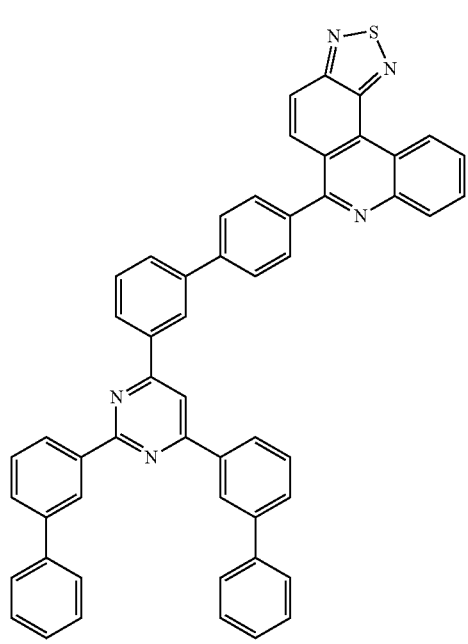
189 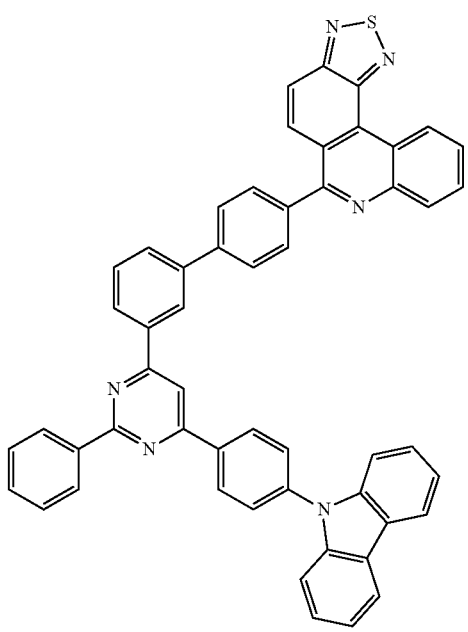
190 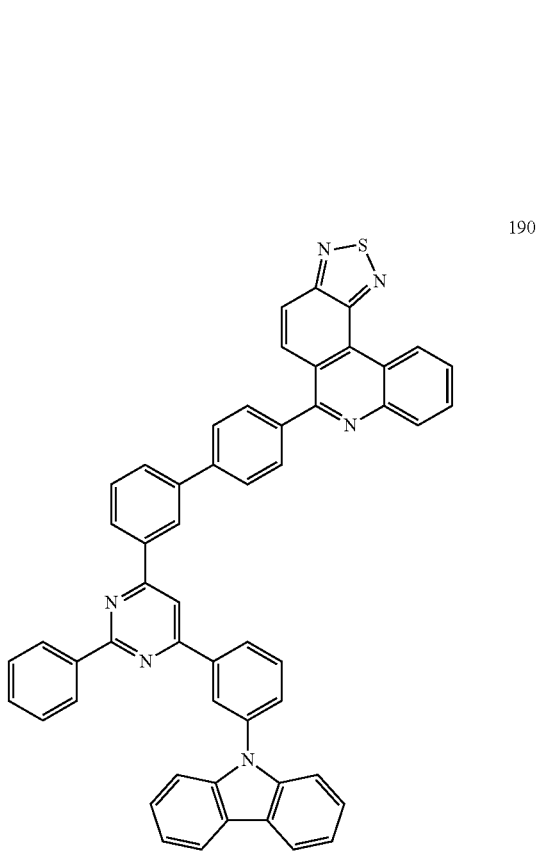

191 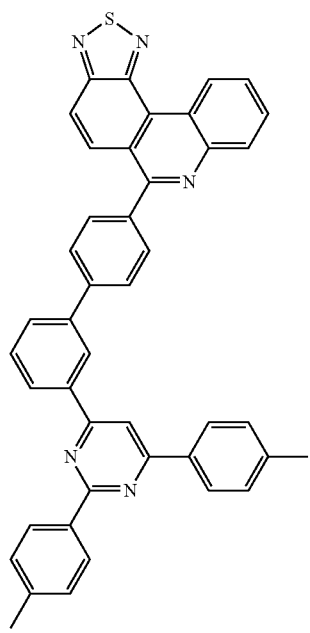
193 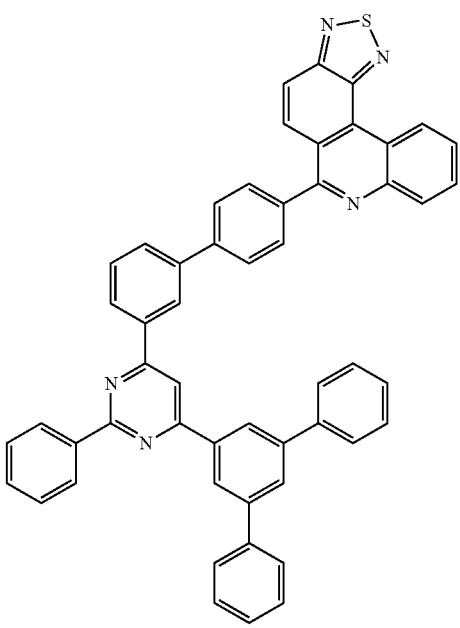
192
194 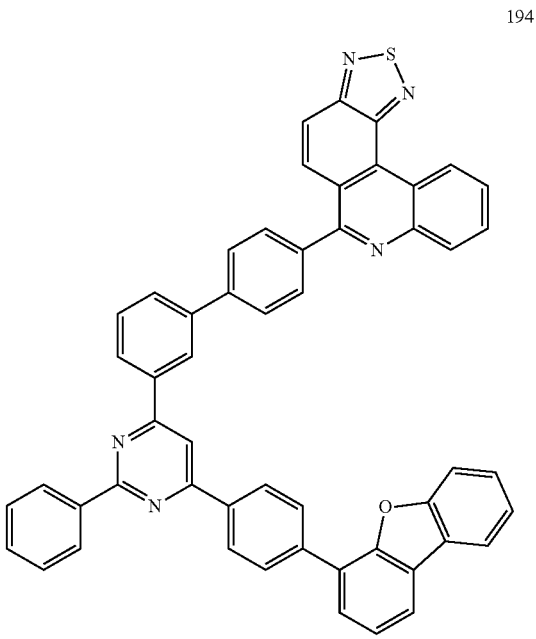

-continued
195
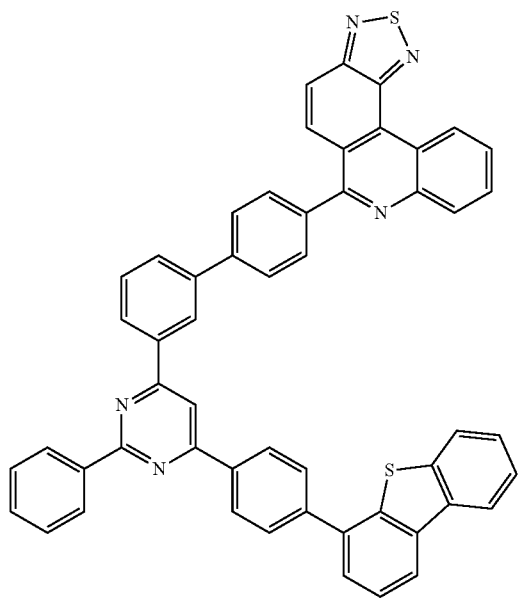
197
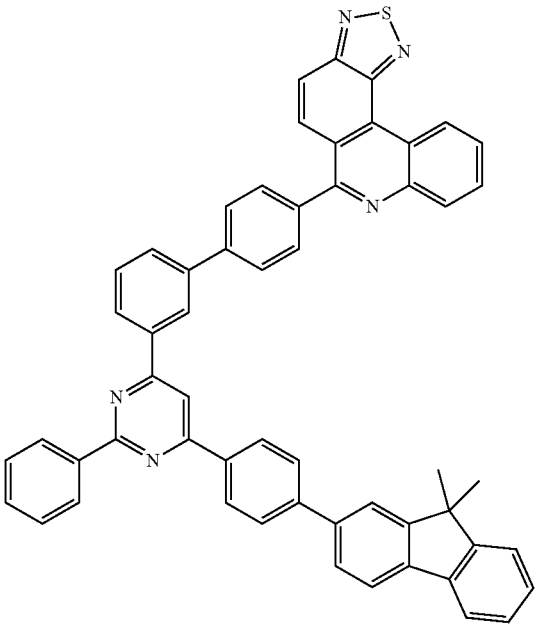
196
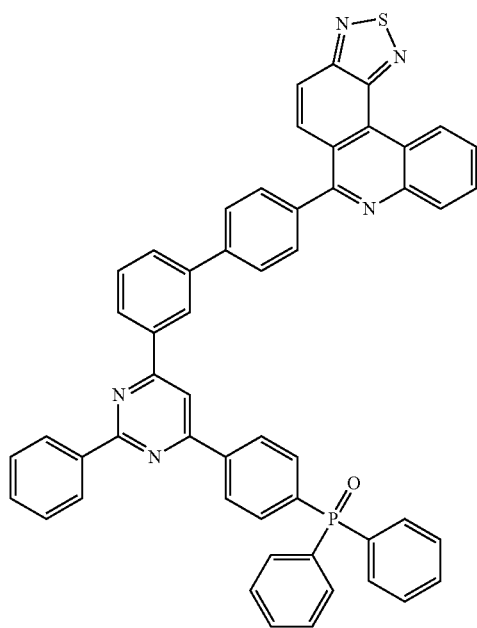
198
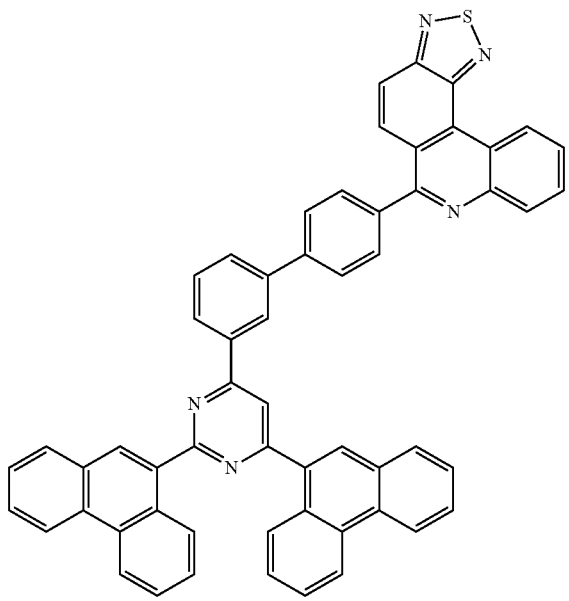

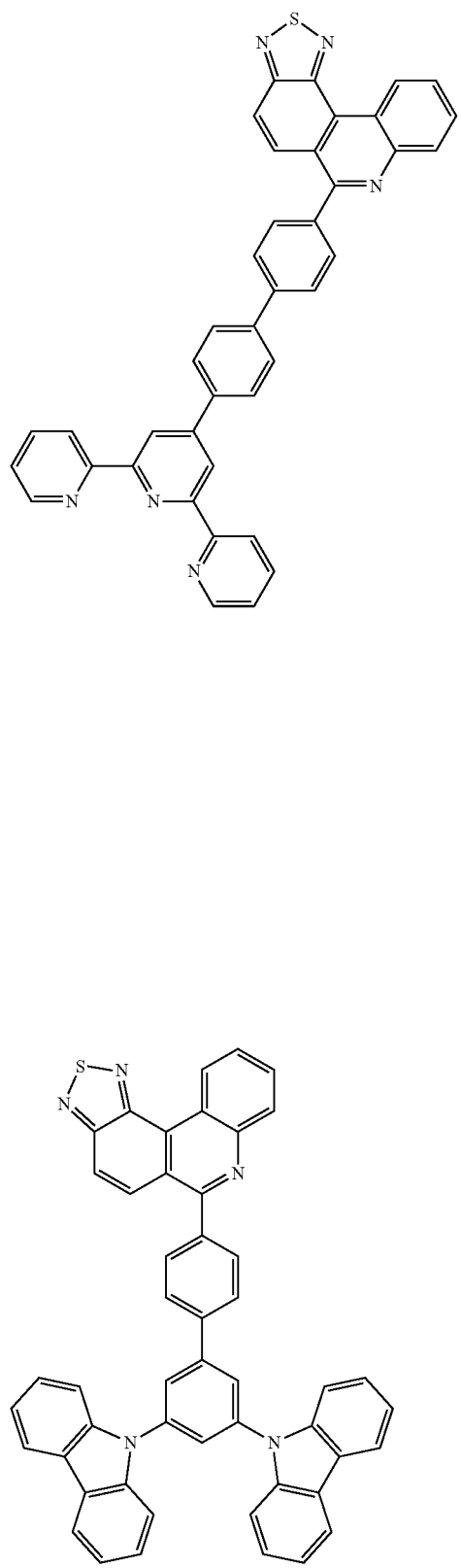
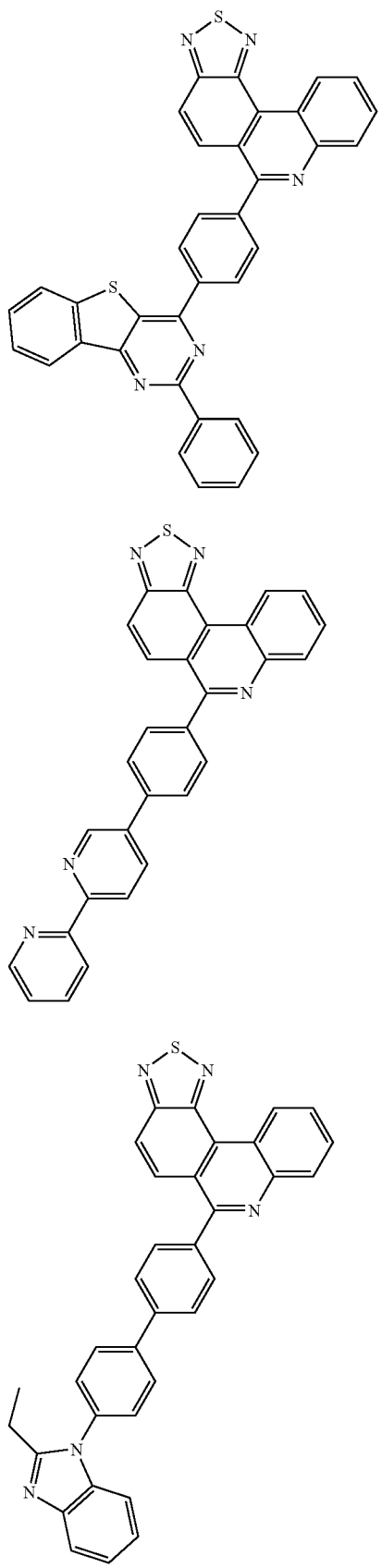

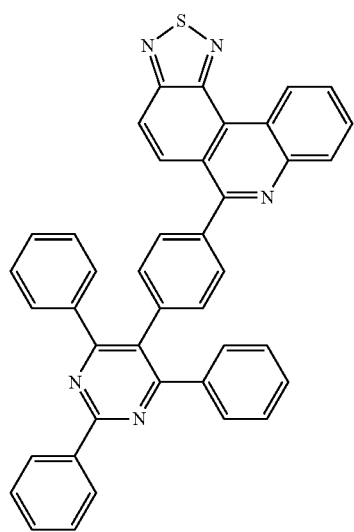 204
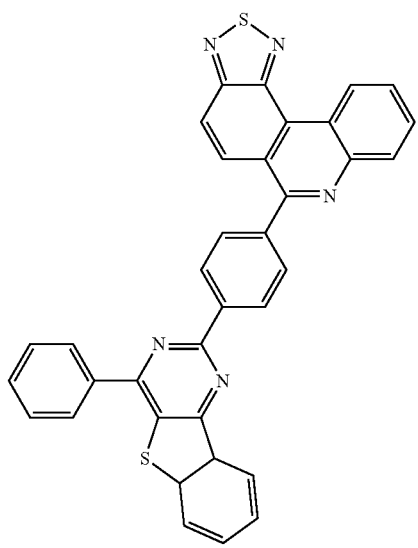 207
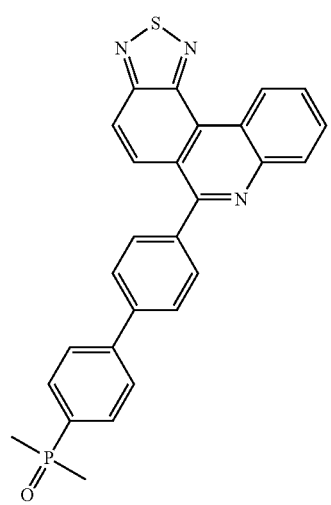 205
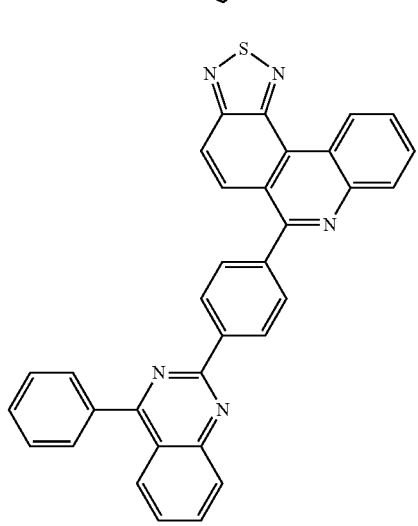 208
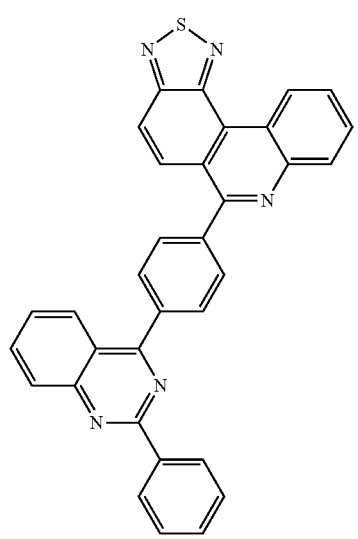 206
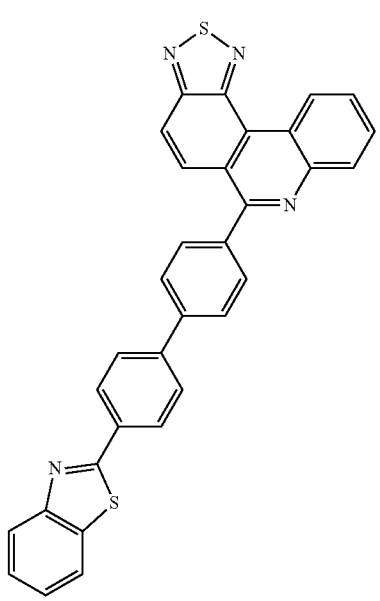 209

97
-continued
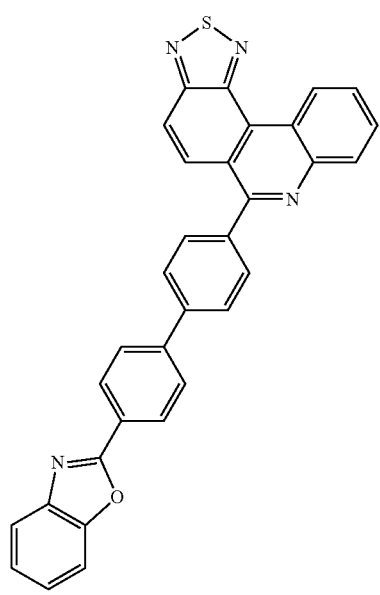
210
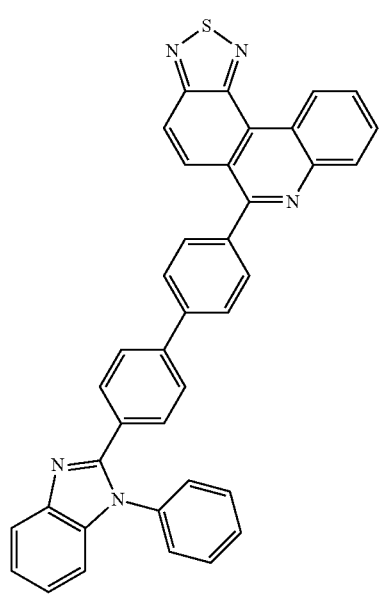
211
98
-continued
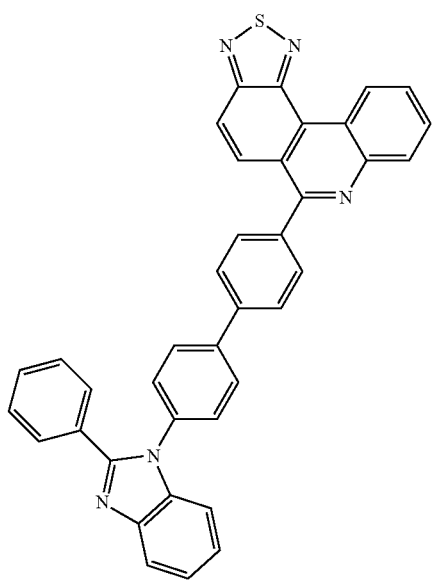
212
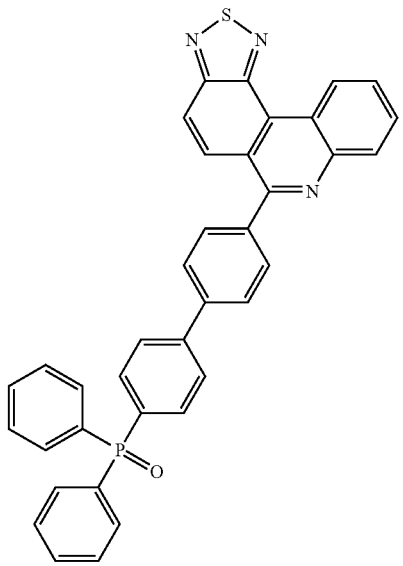
213

-continued
214
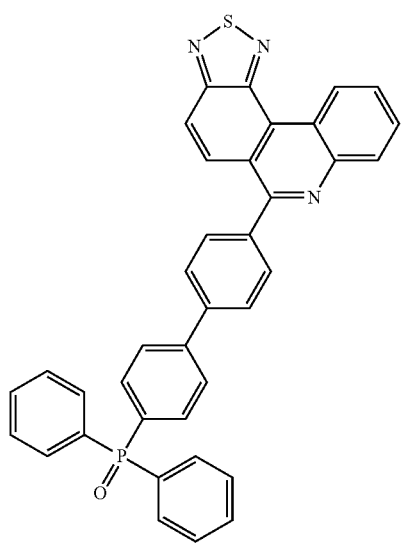
215
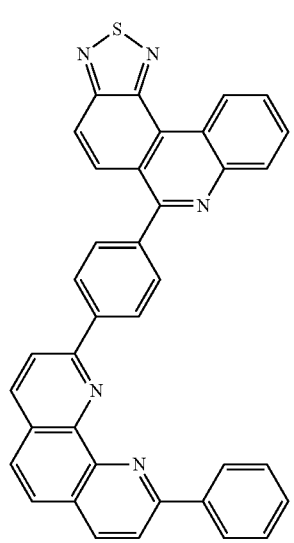
216
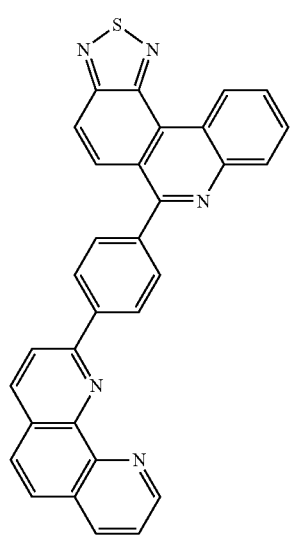
-continued
217
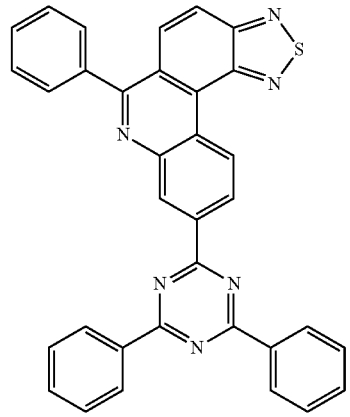
218
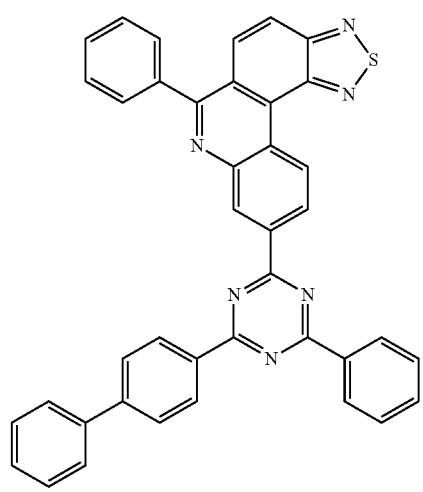
219
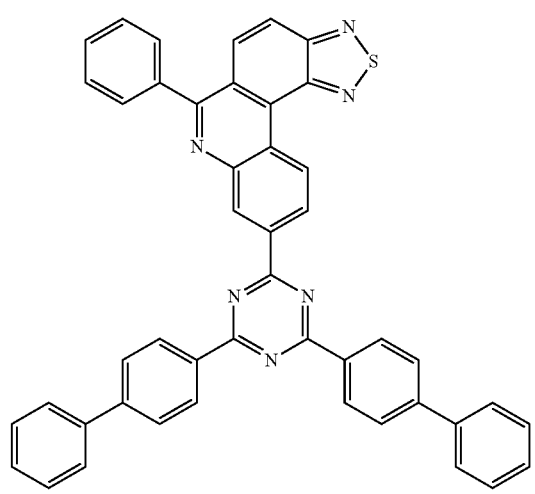

101
-continued
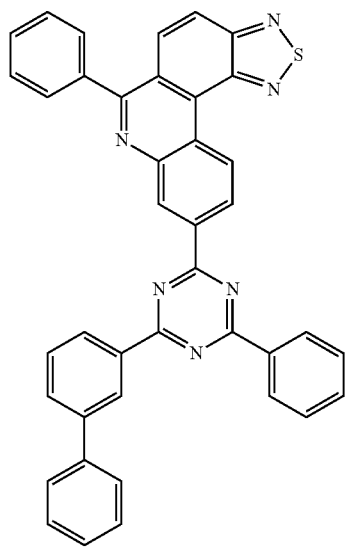
220
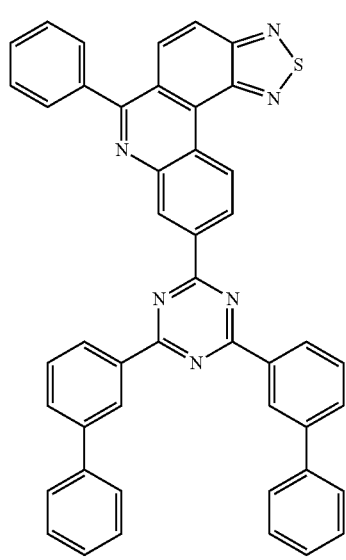
221
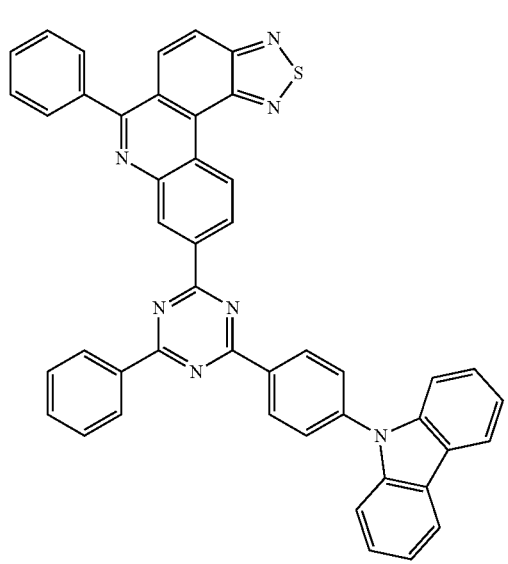
222
102
-continued
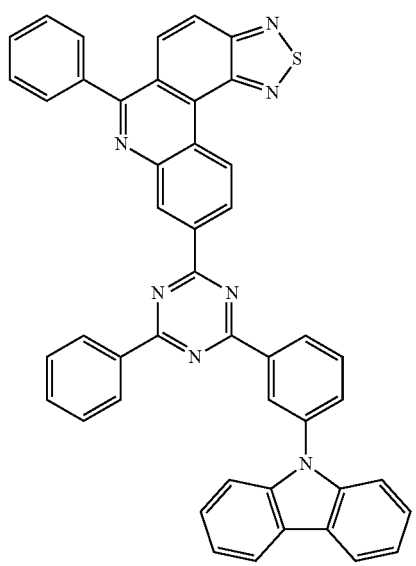
223
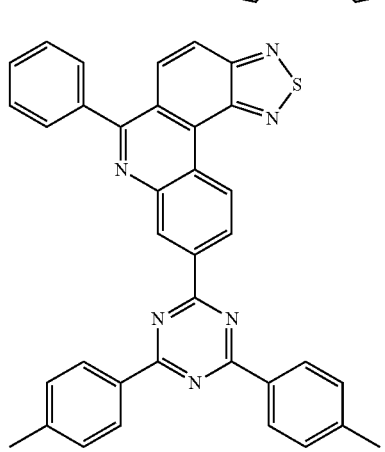
224
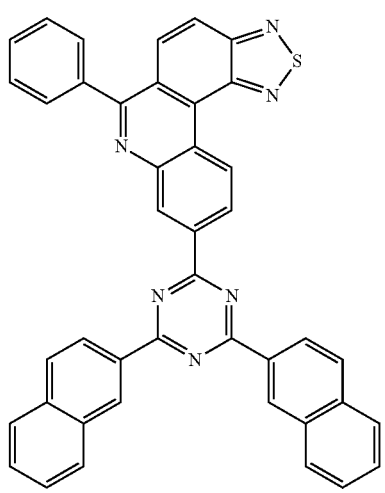
225

226
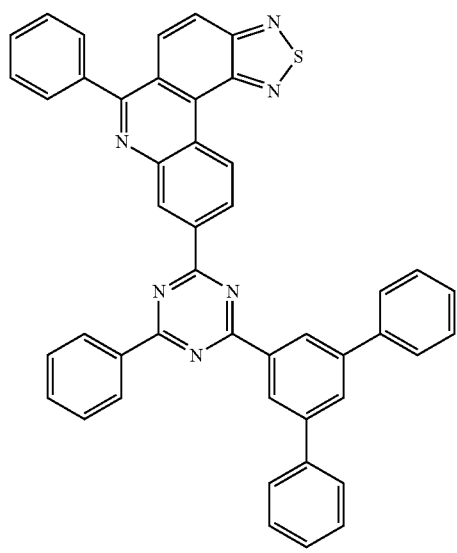
227
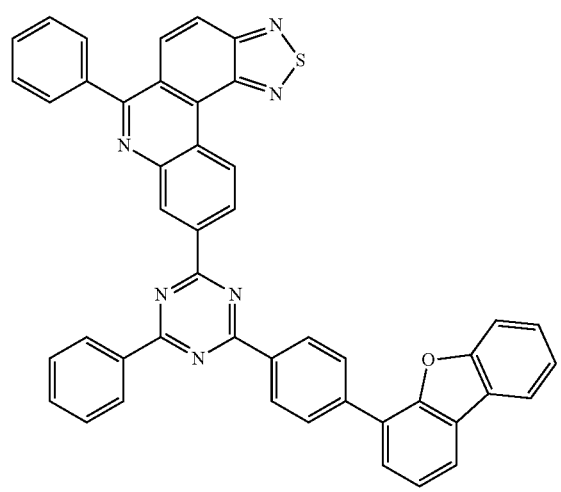
228
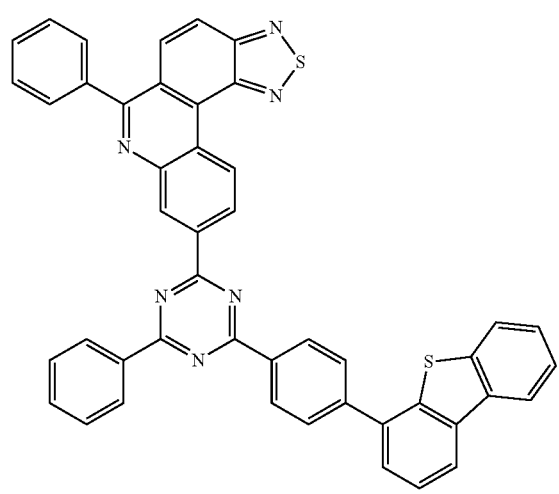
229
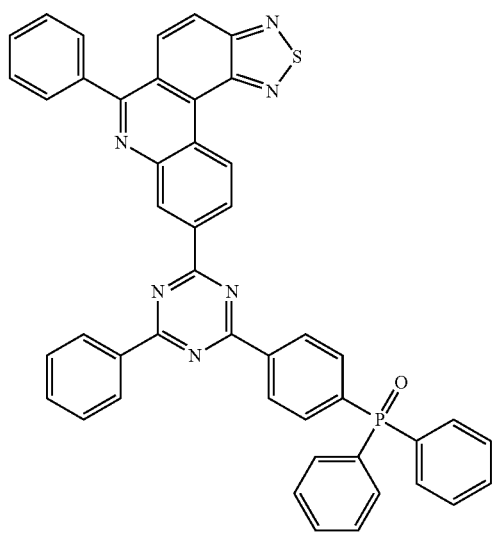
230
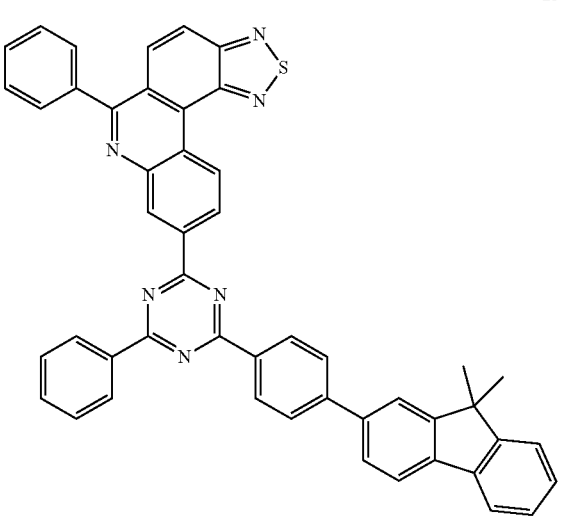
231
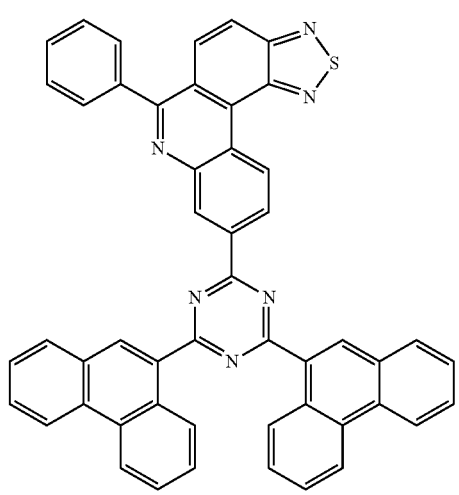

232 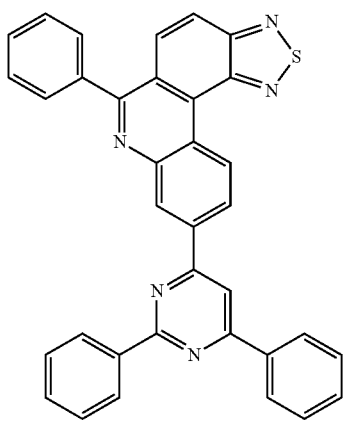
233 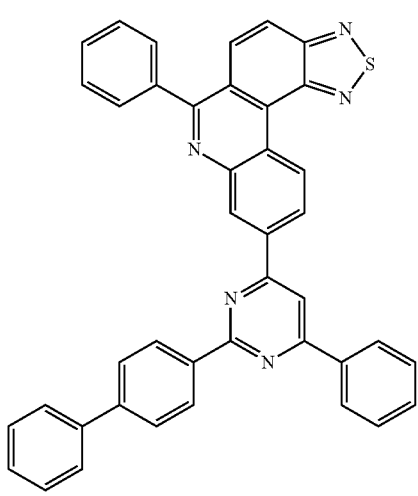
234 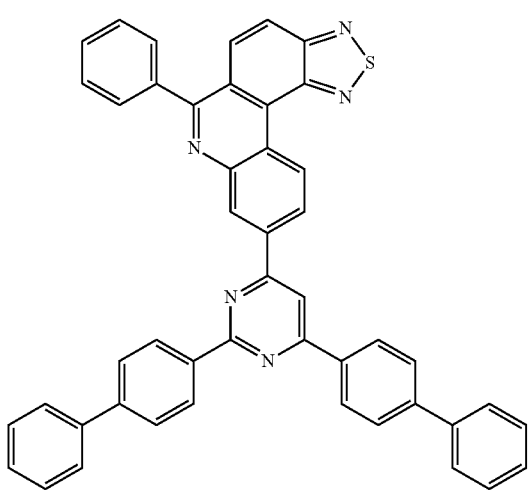
235 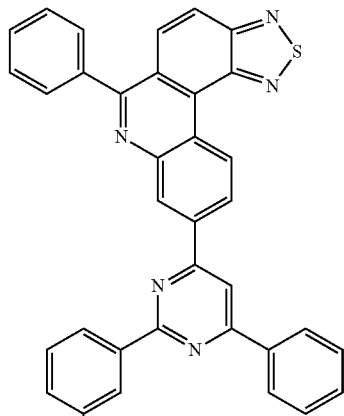
236 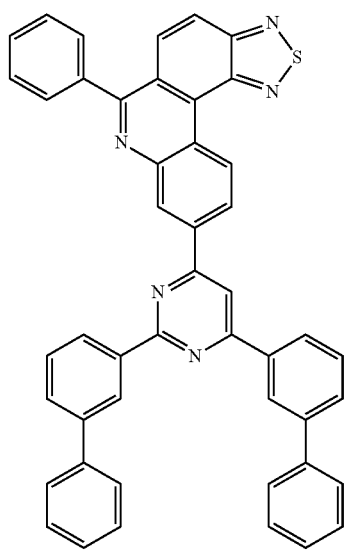
237 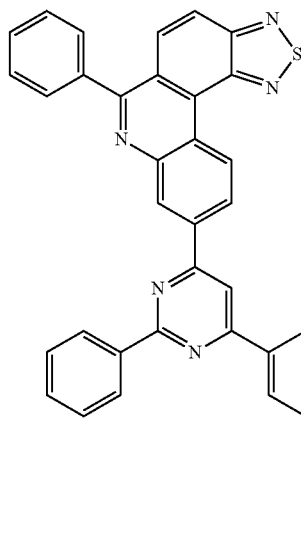

238 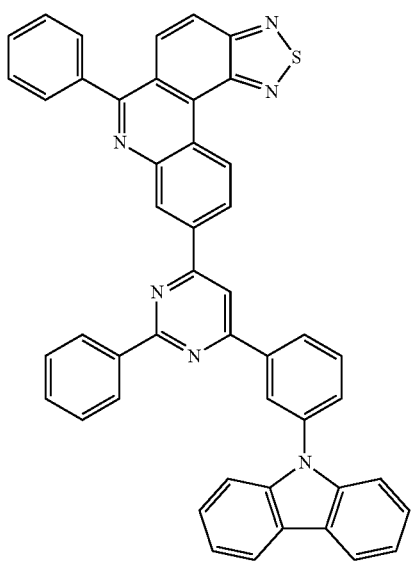
239 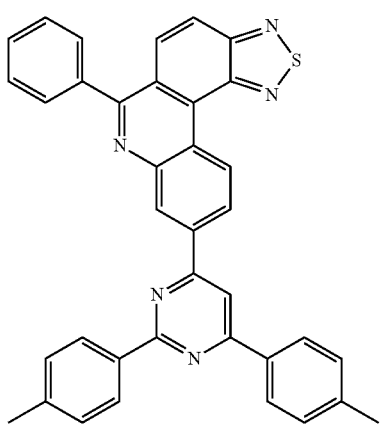
240 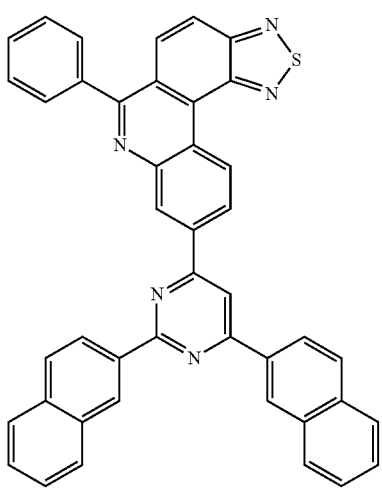
241 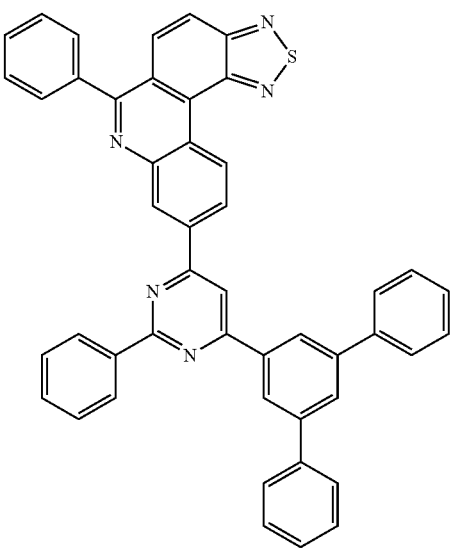
242 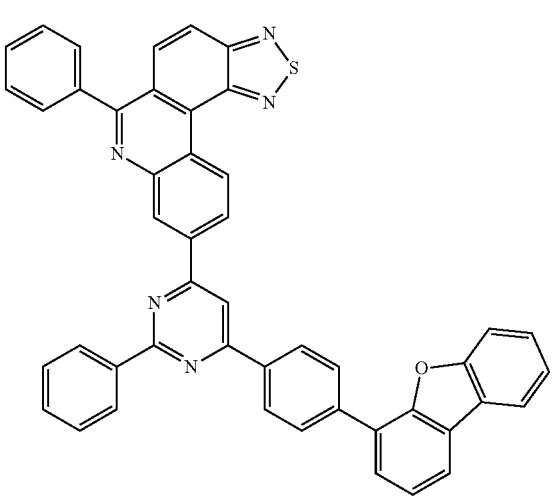
243 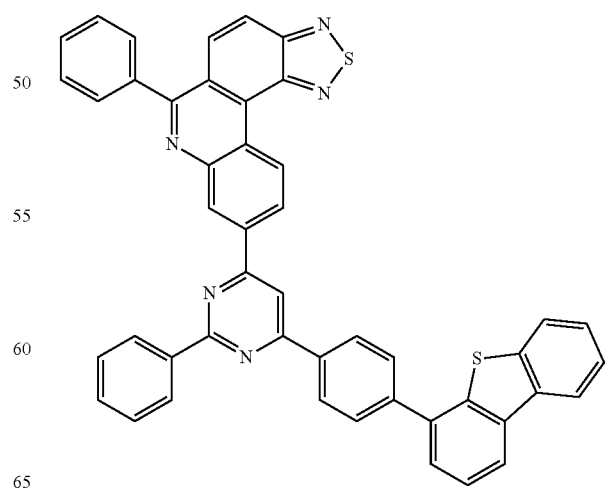

244
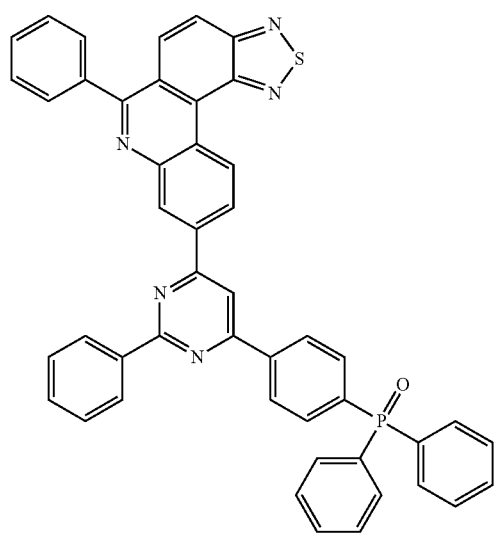
245
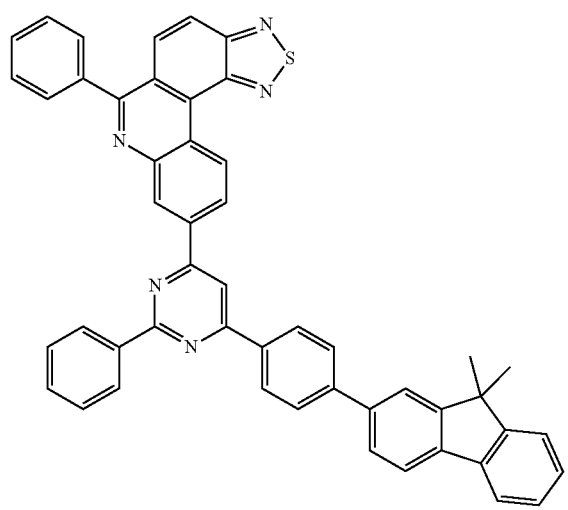
246
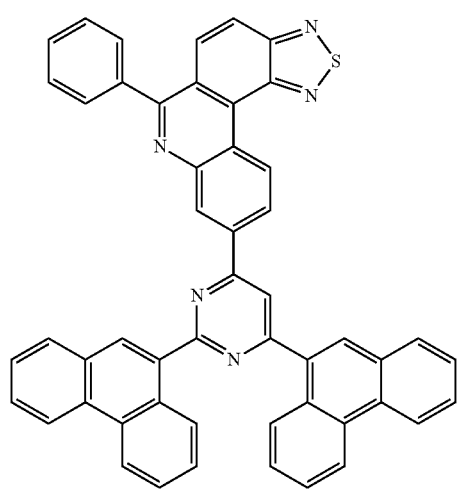
247
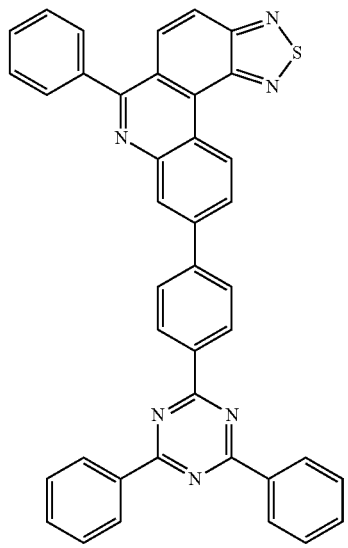
248
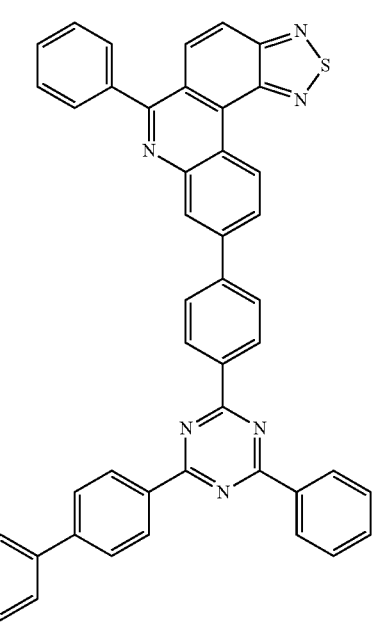

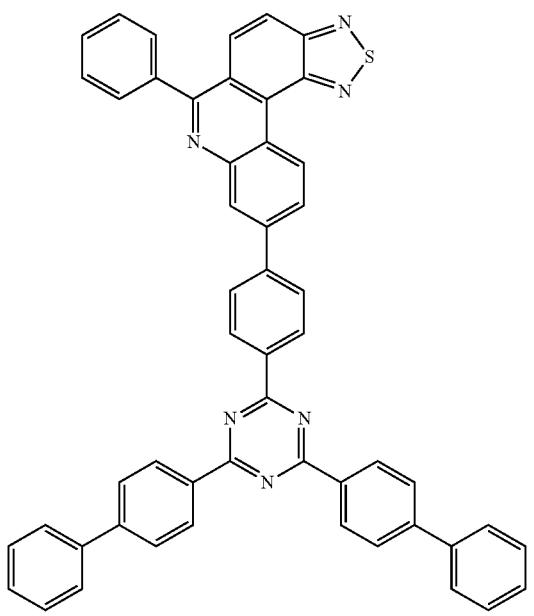
249
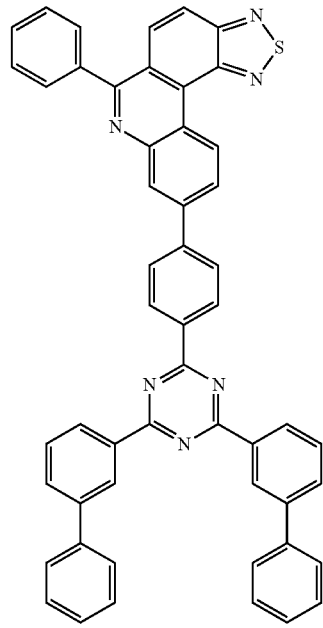
251
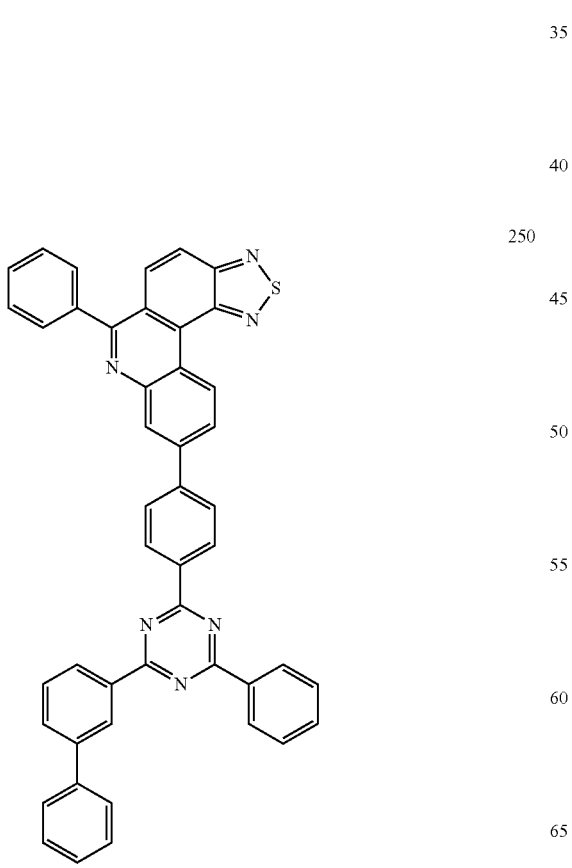
250
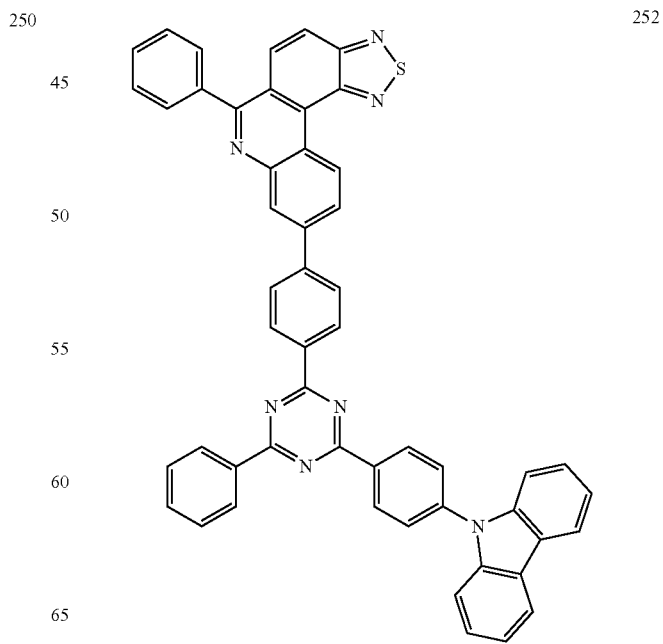
252

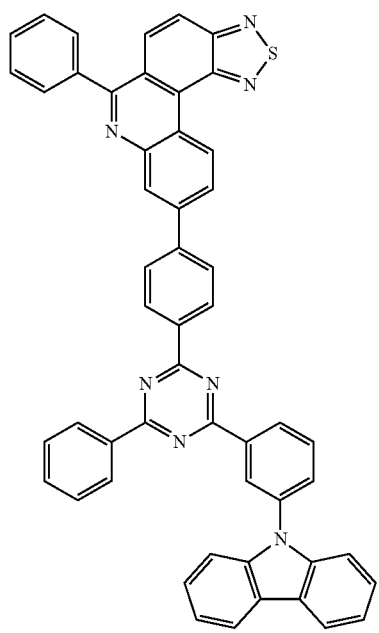
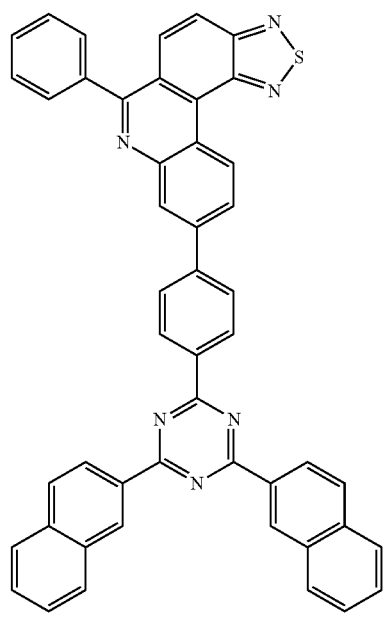

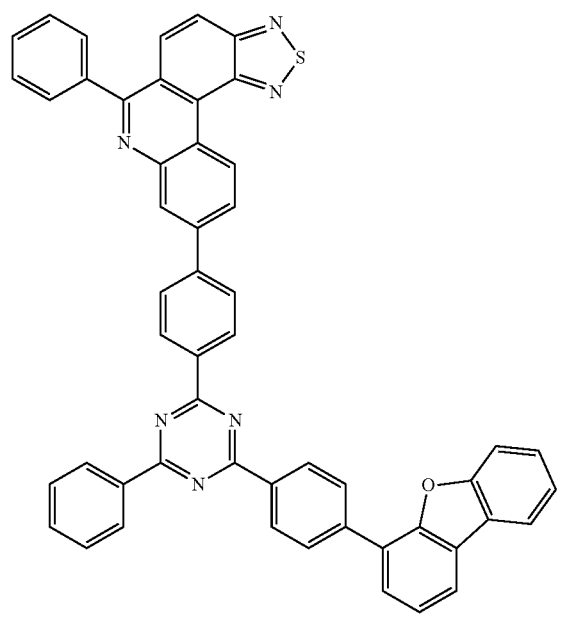
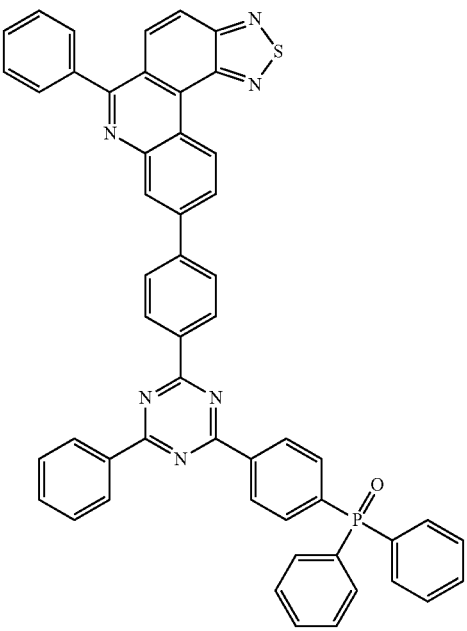

117
-continued
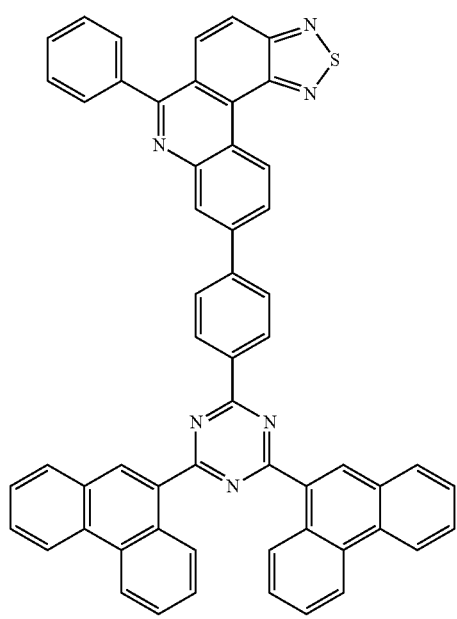
261
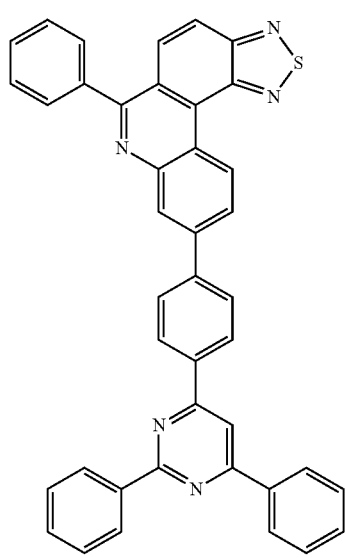
262
118
-continued
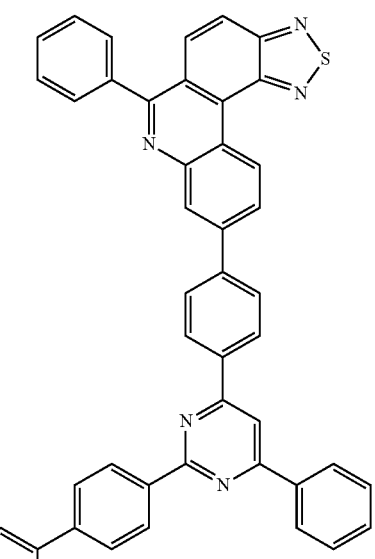
263
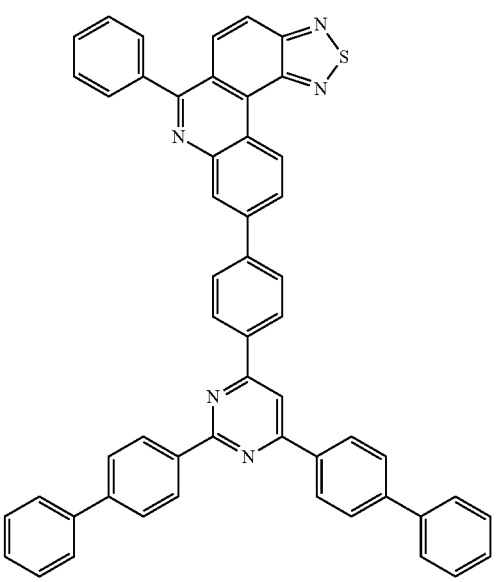
264

119
-continued
265
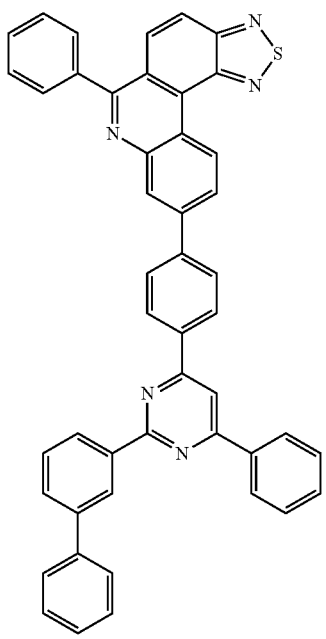
266
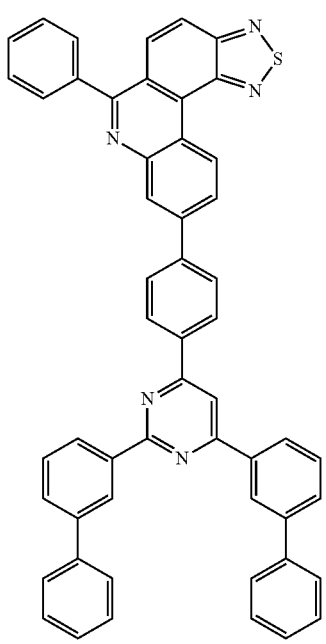
120
-continued
267
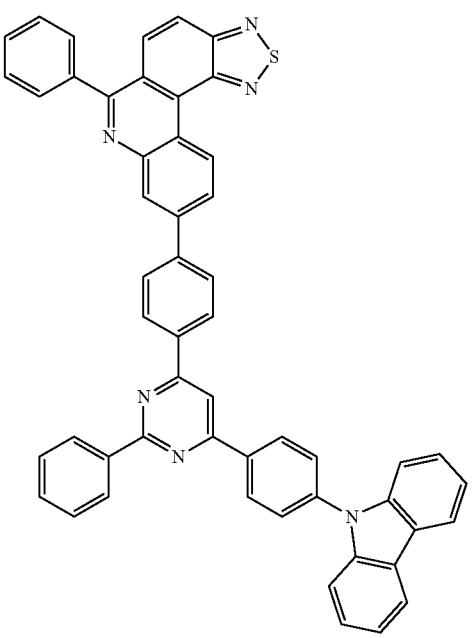
268
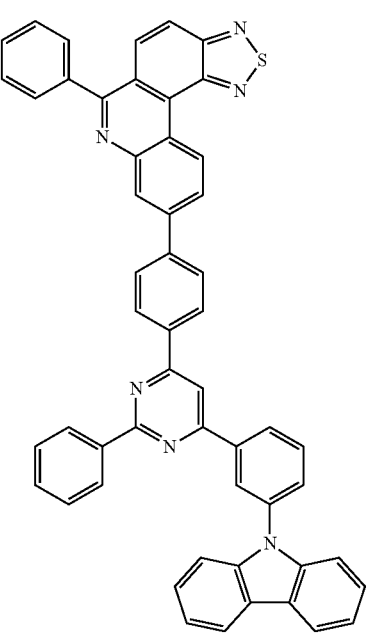

121
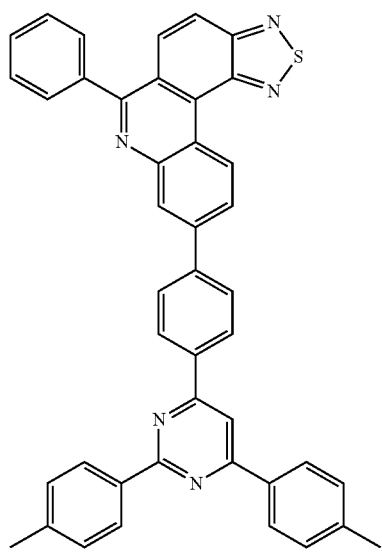
269
122
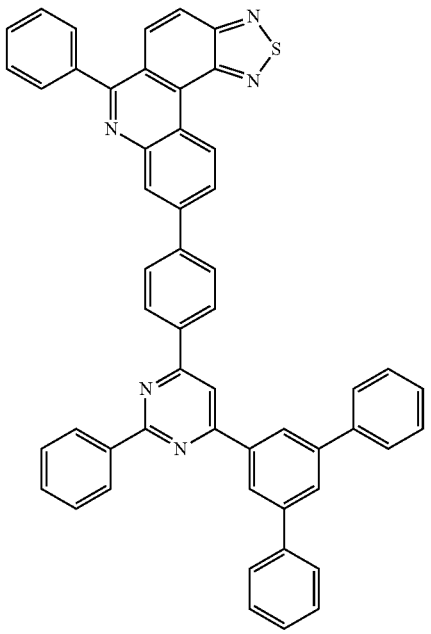
271
270
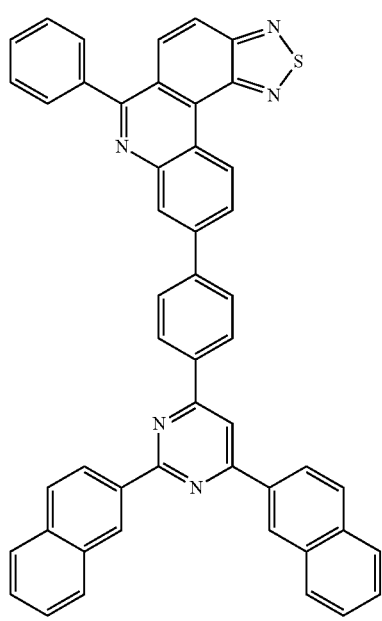
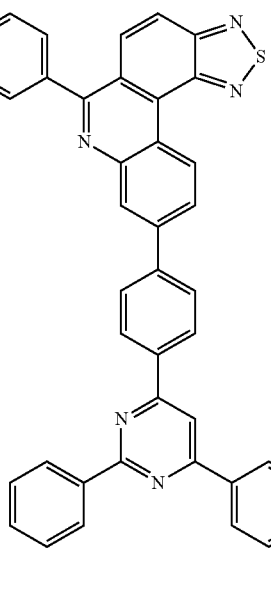
272

123 -continued
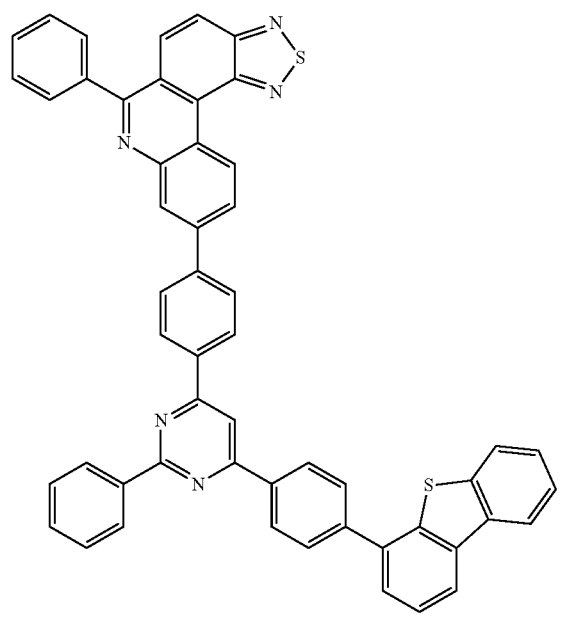
273
124 -continued
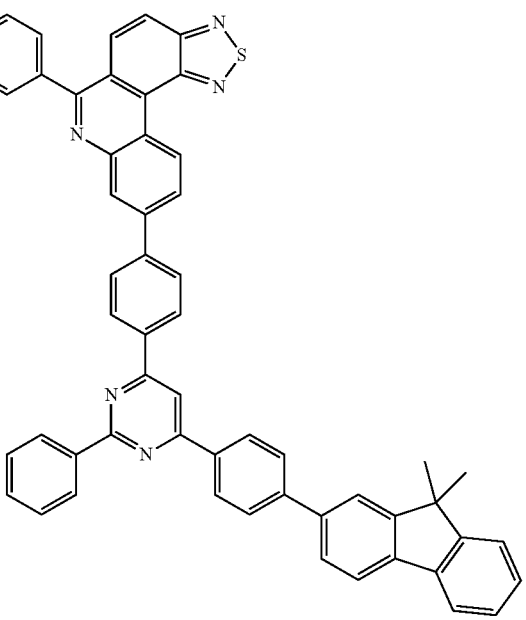
275
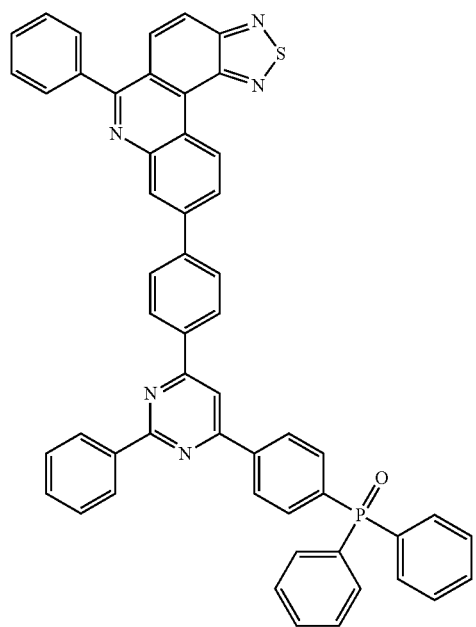
274
276

125
-continued
277
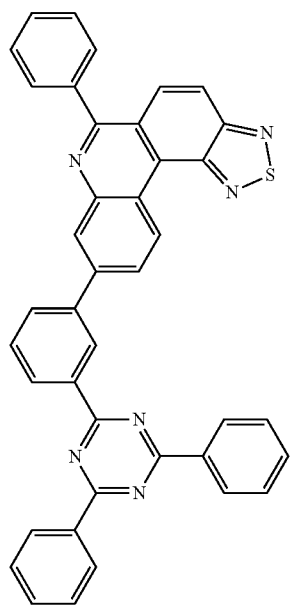
126
-continued
279
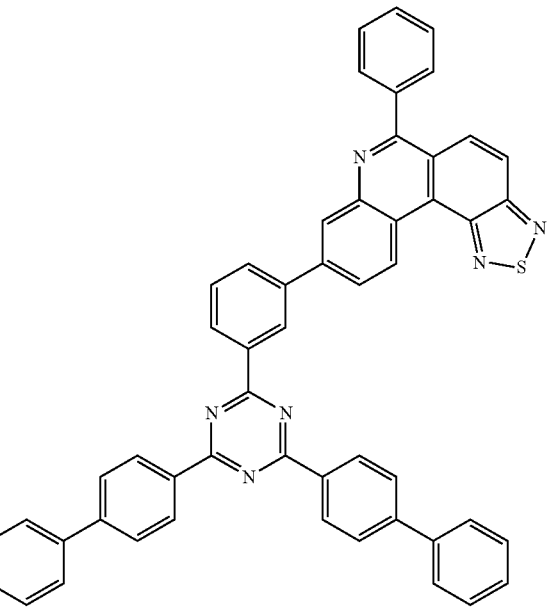
278
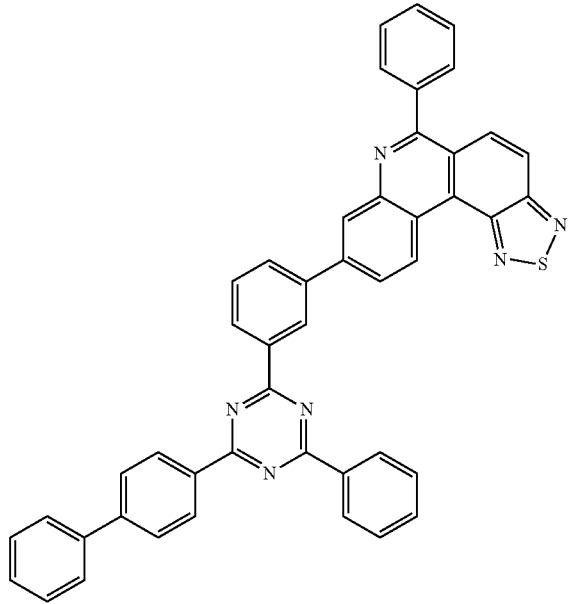
280

281
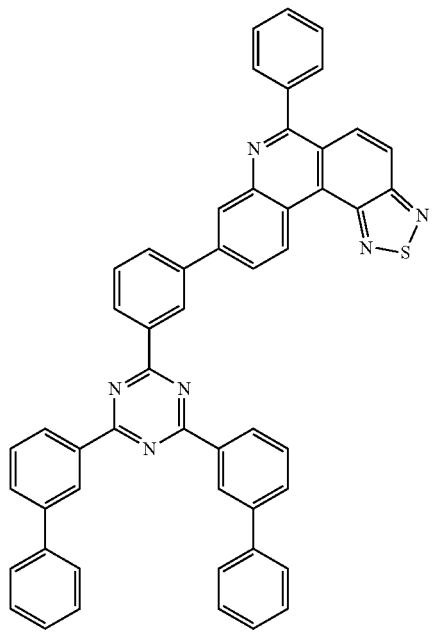
282
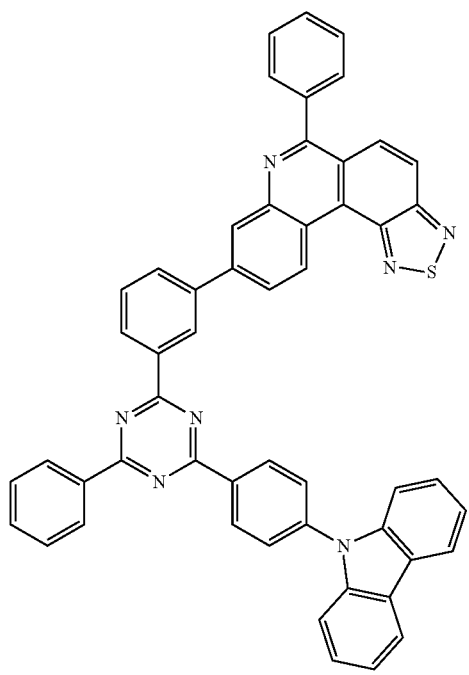
283
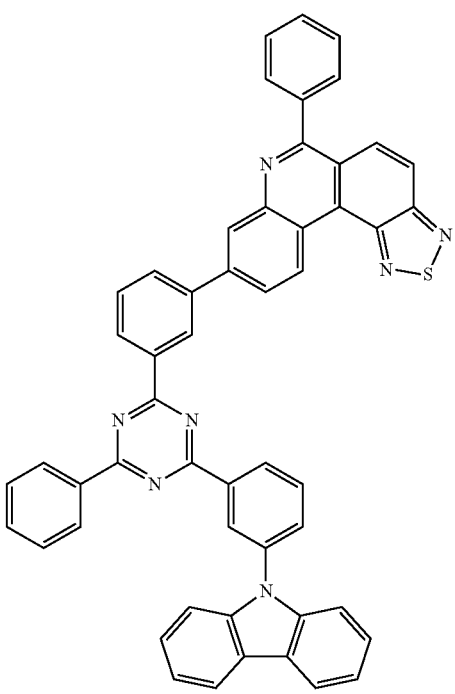
284
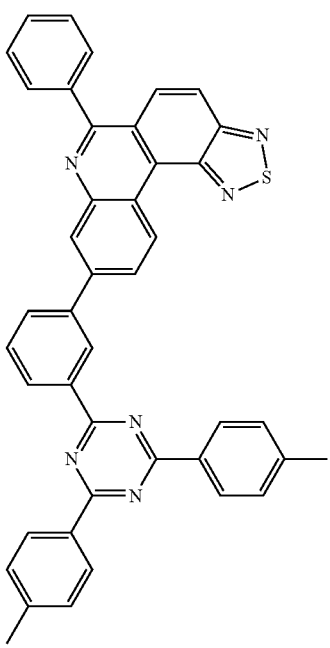

285
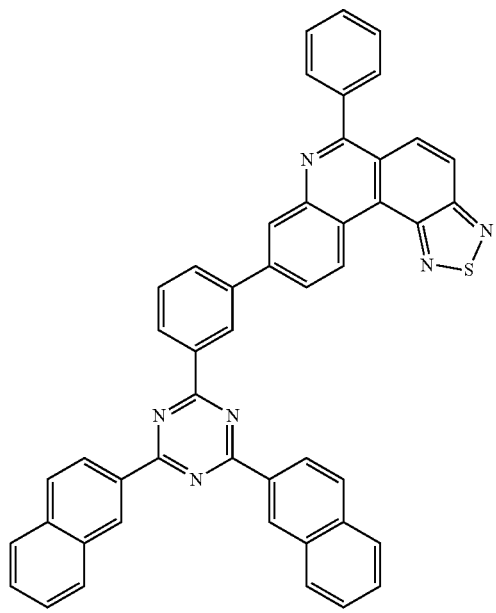
286
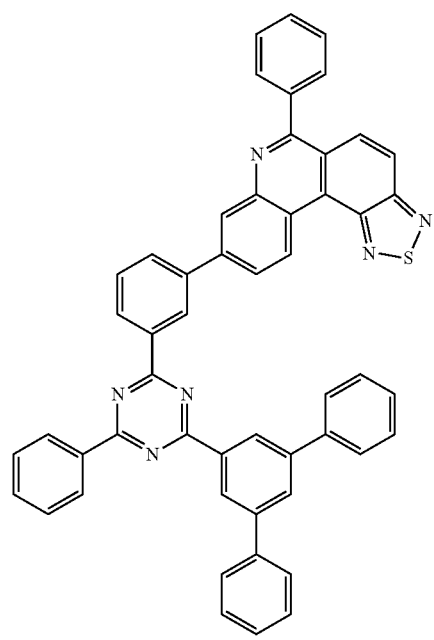
287
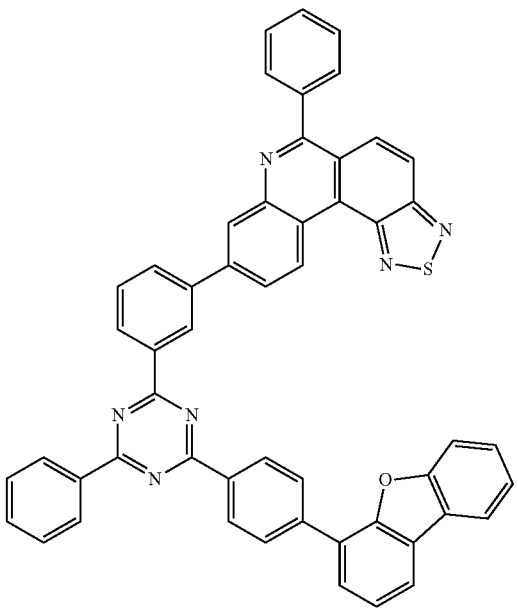
288
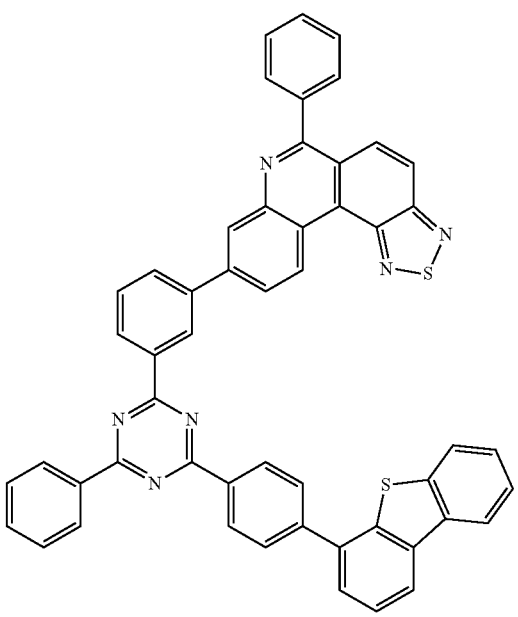

131
-continued
289
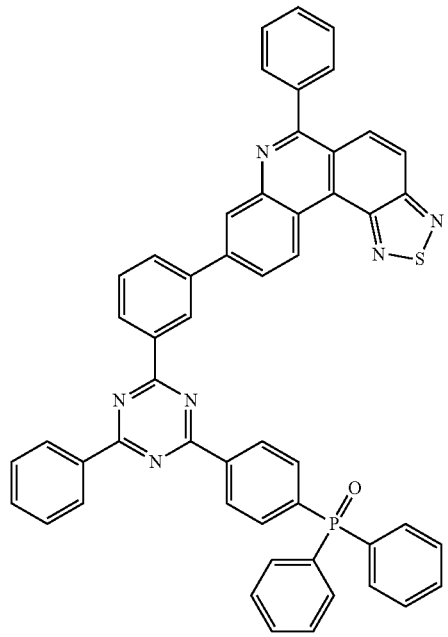
290
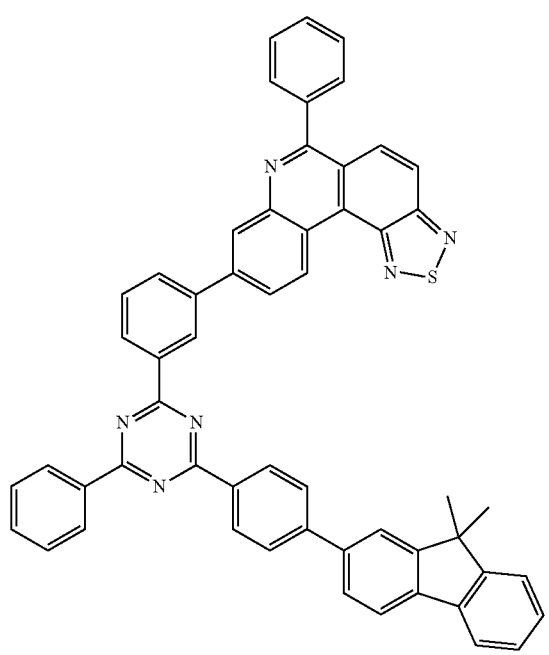
132
-continued
291
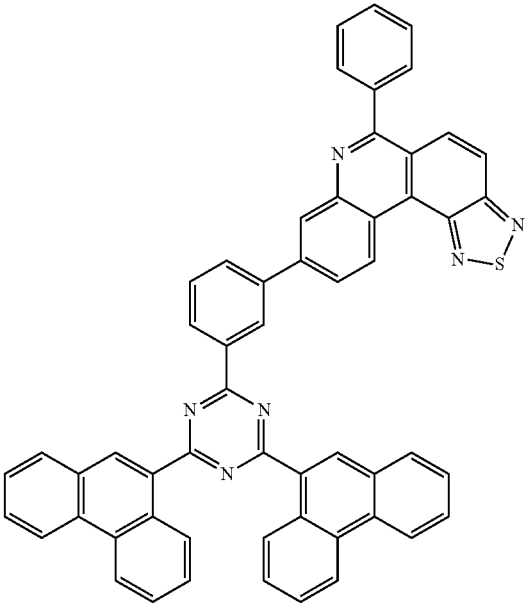
292
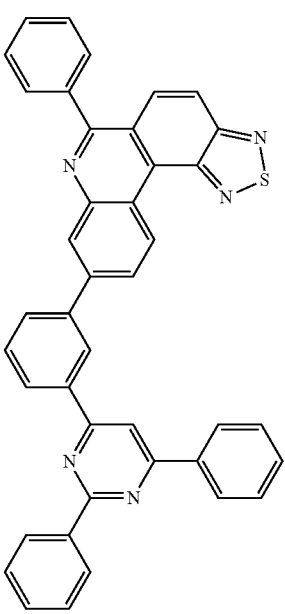

293
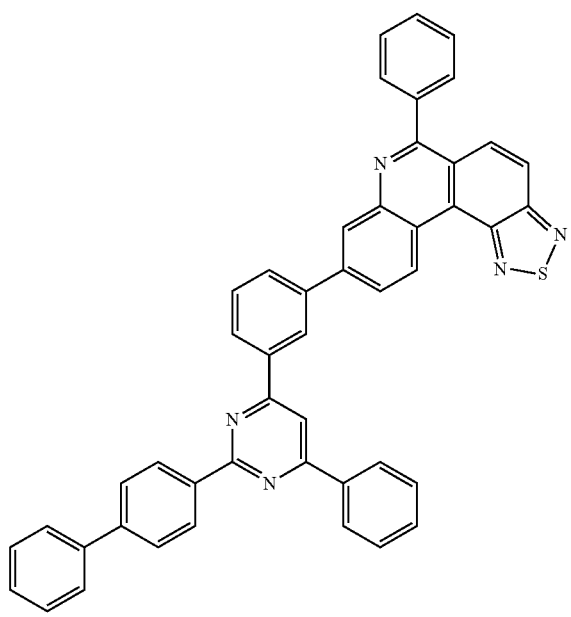
295
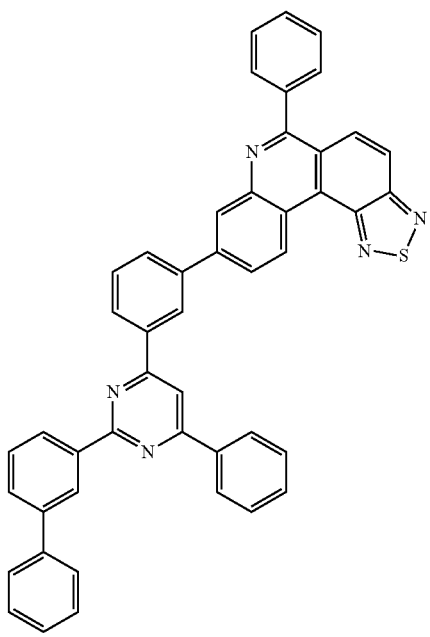
294
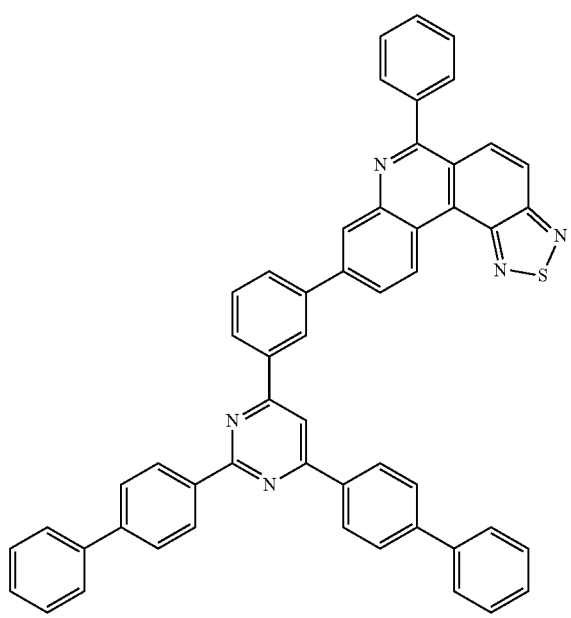
296
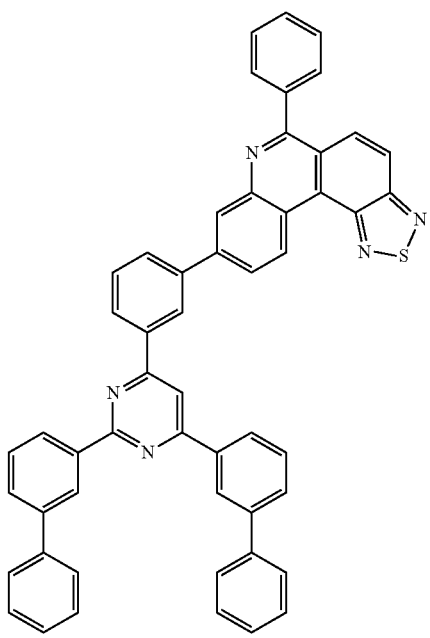

297
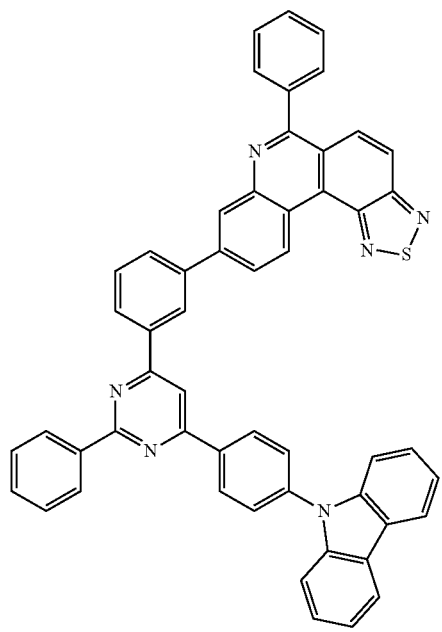
298
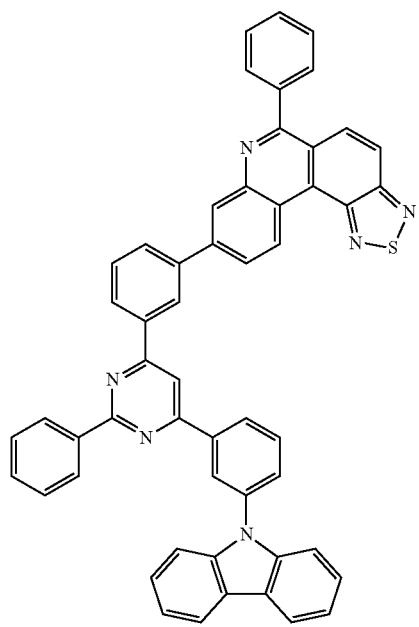
299
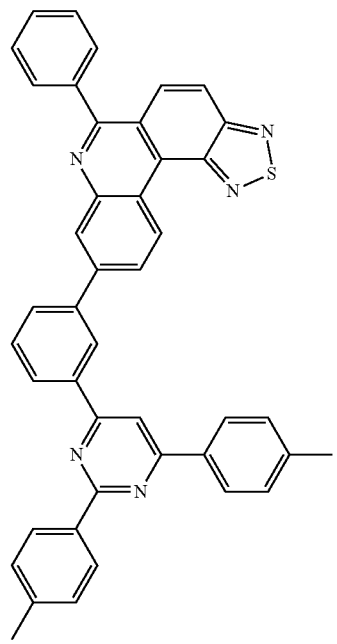
300
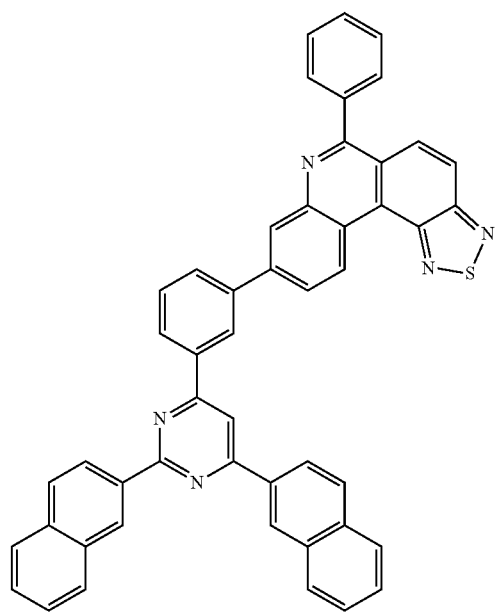

-continued
301
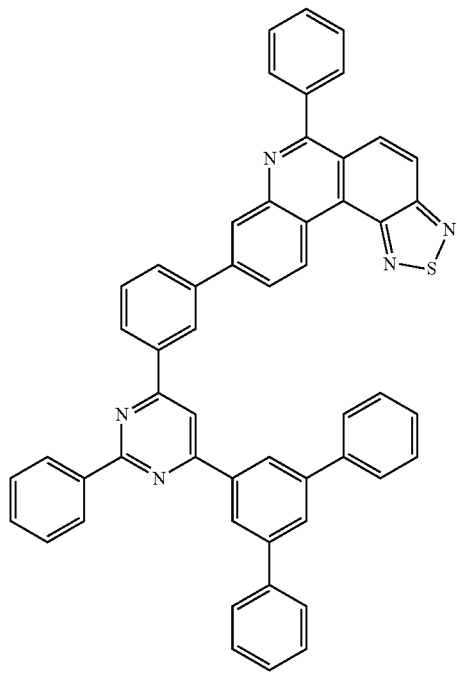
302
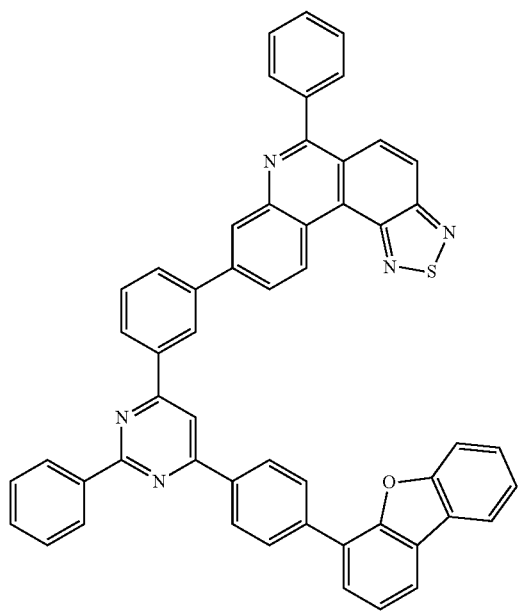
-continued
303
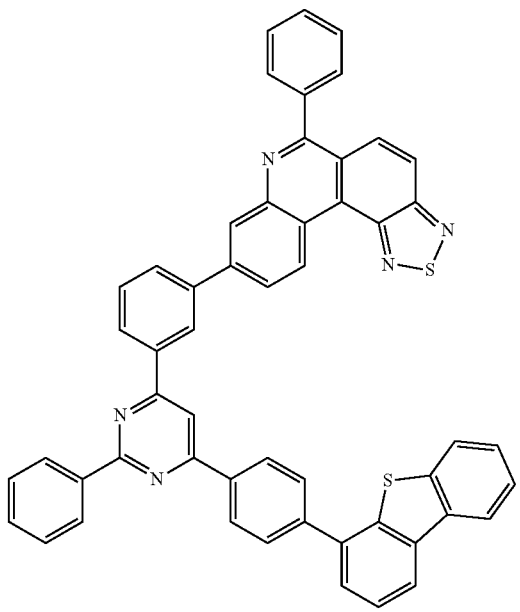
304
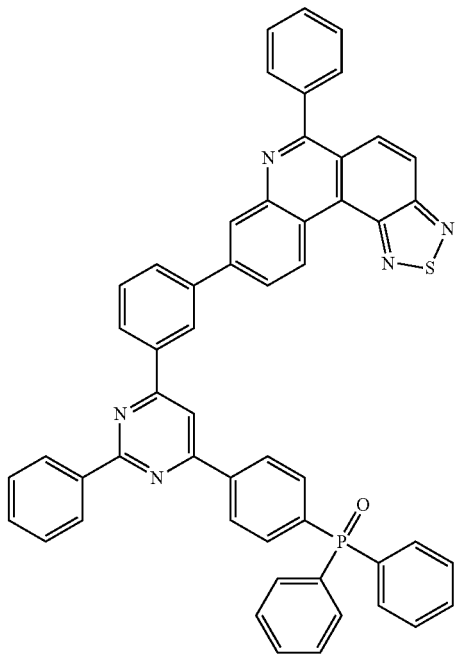

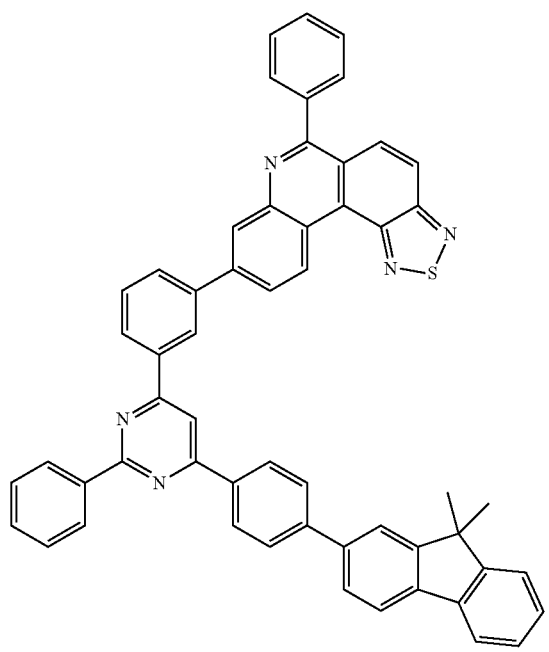
305
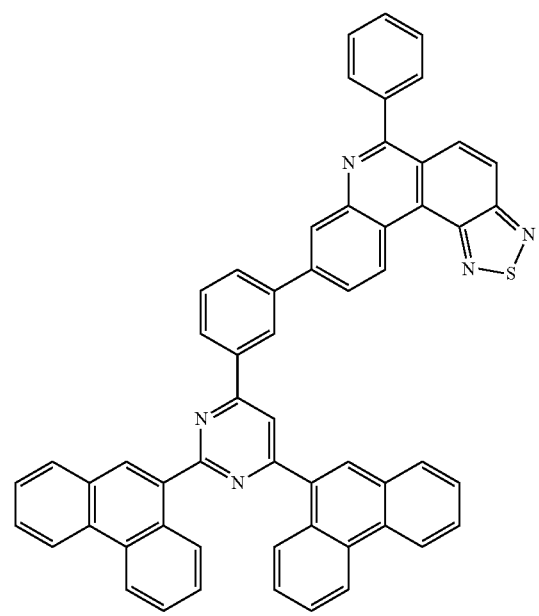
306
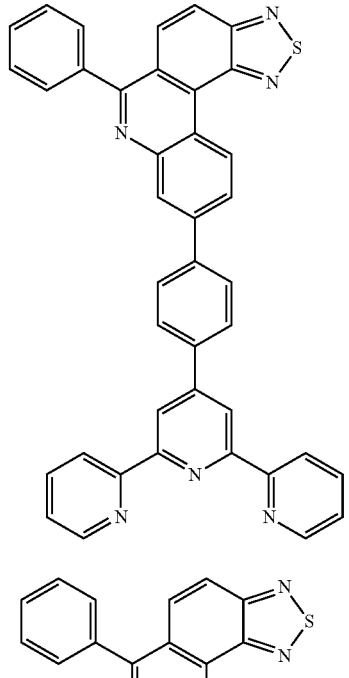
307
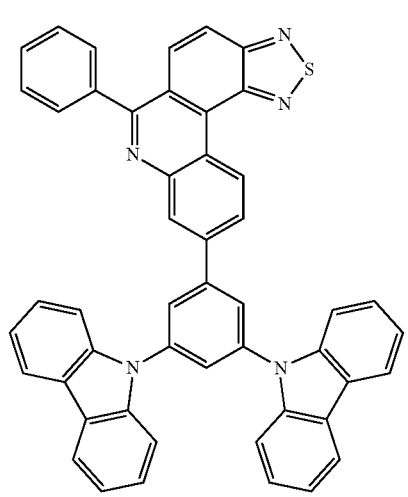
308
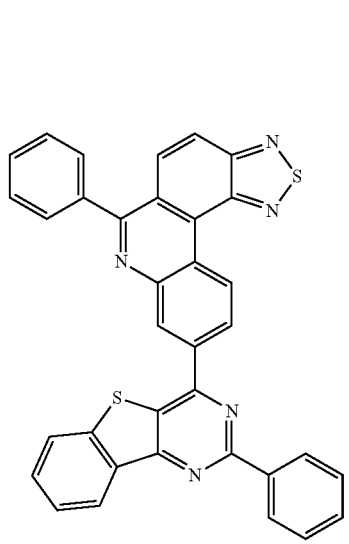
309

141
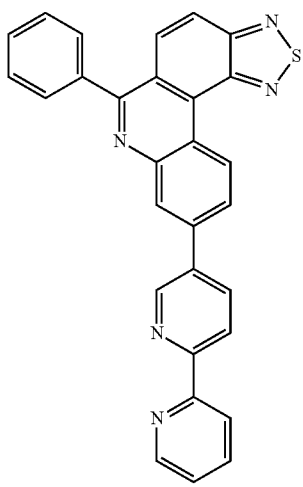
310
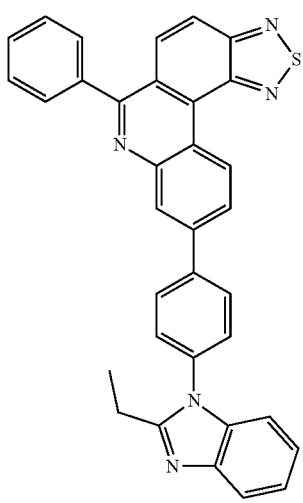
311
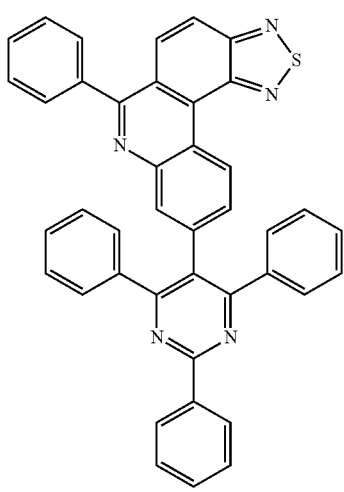
312
142
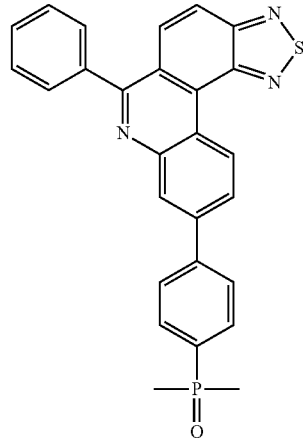
313
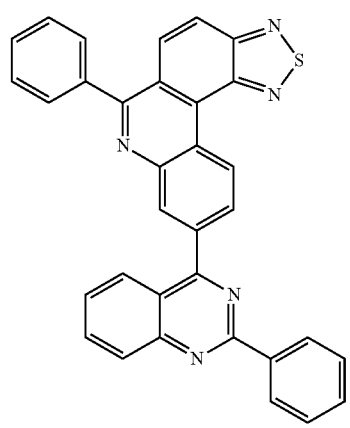
314
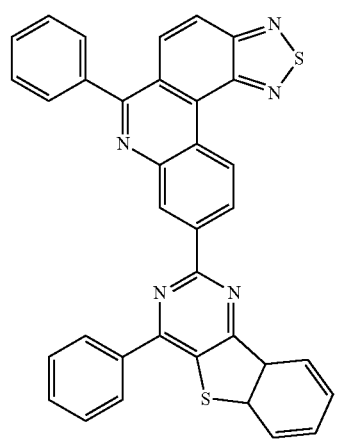
315

316
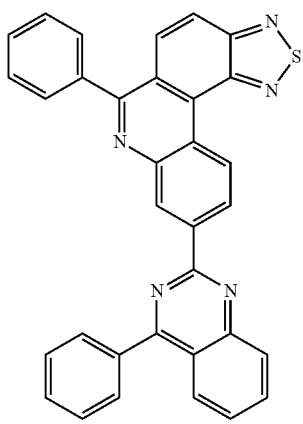
317
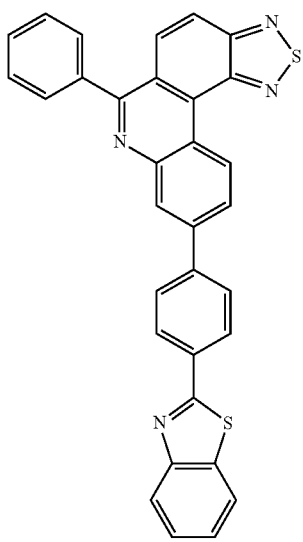
318
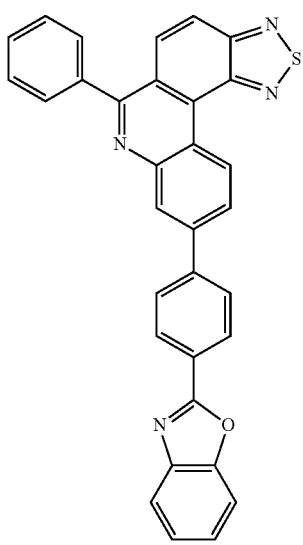
319
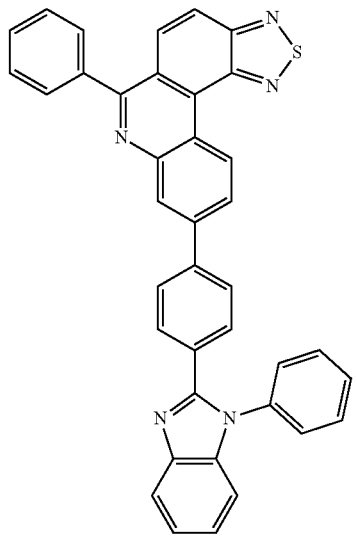
320
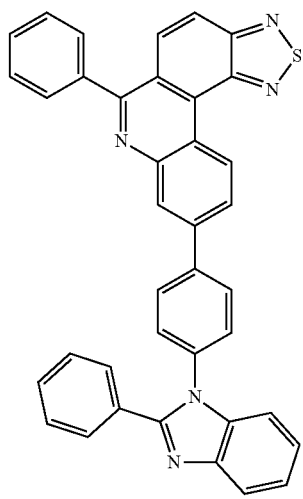
321
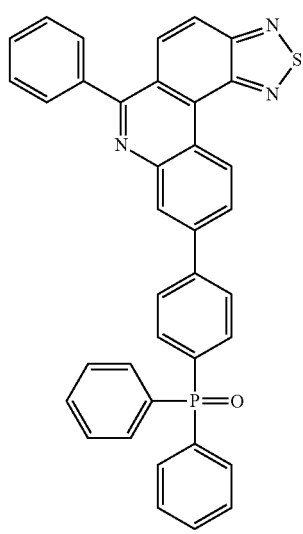

322
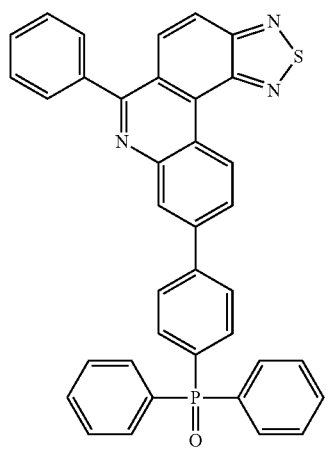
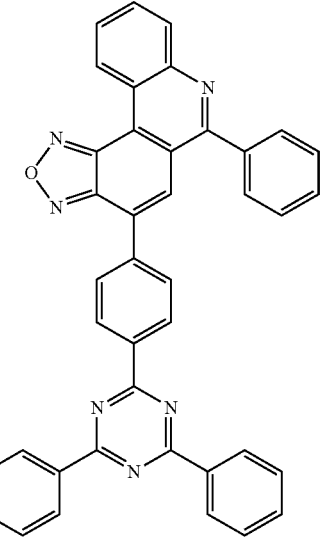
325
323
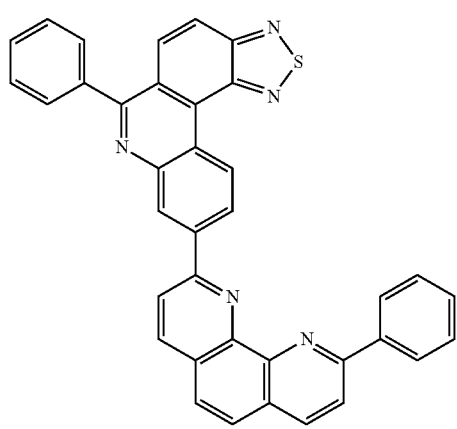
326
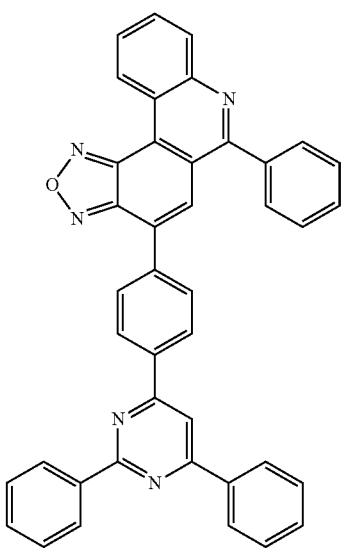
324
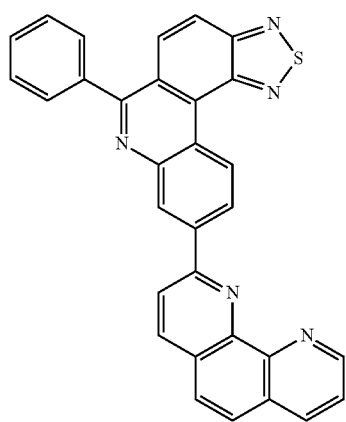
327
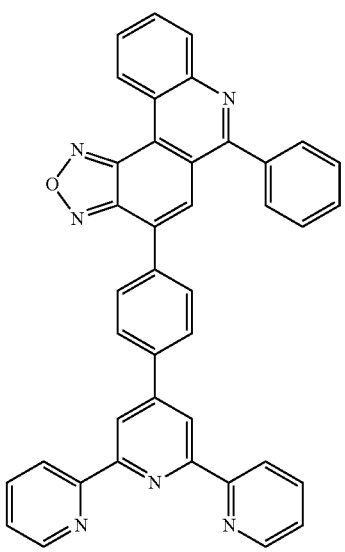

328
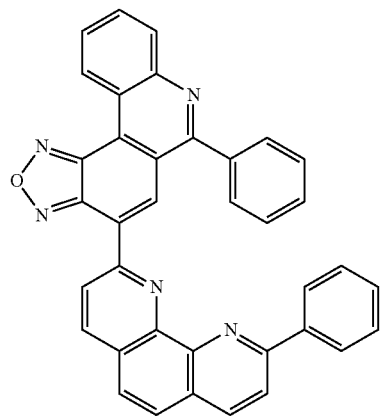
329
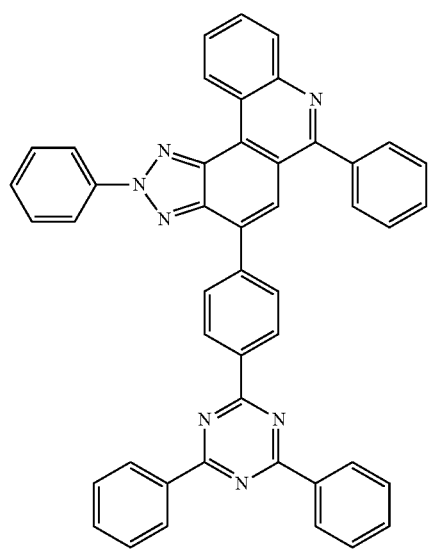
330
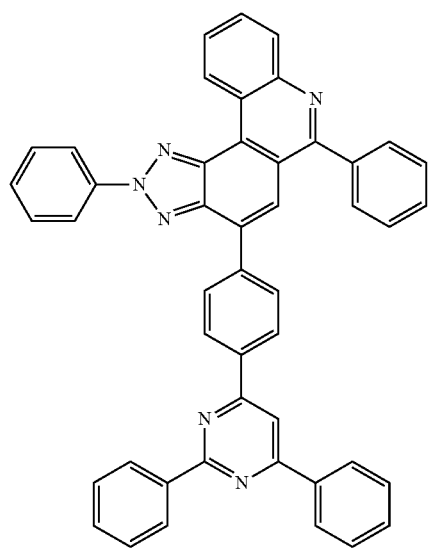
331
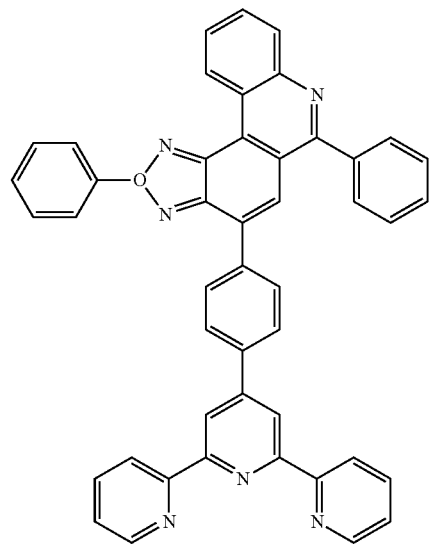
332
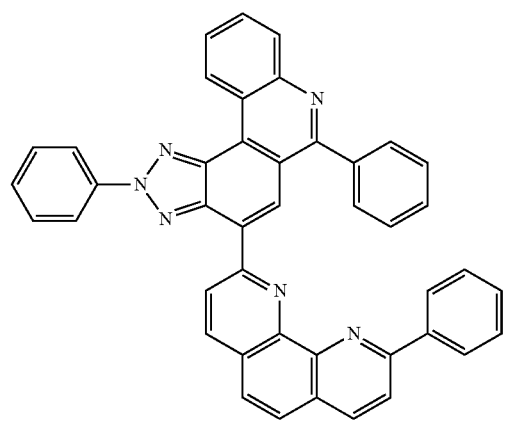
333
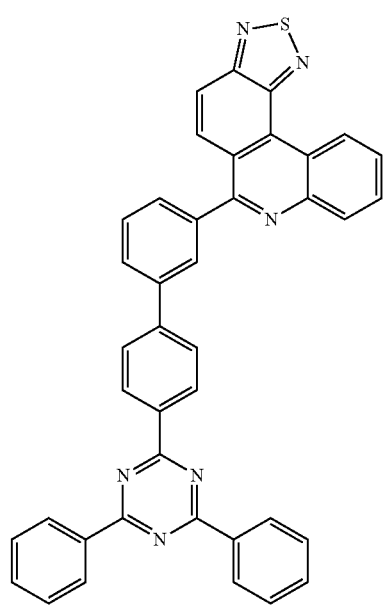

334
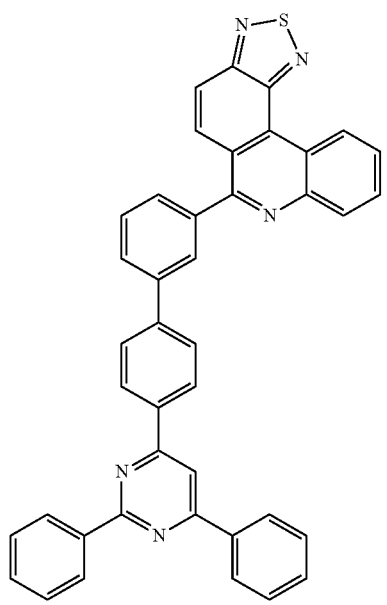
335
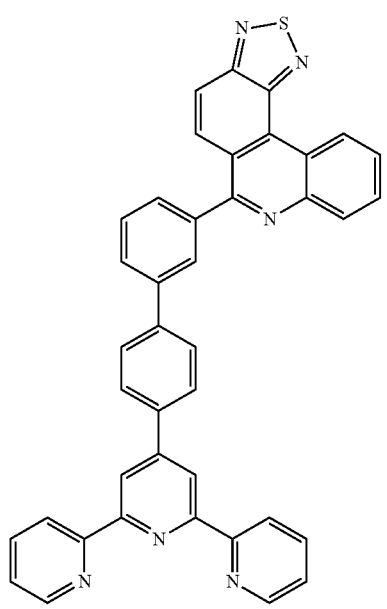
336
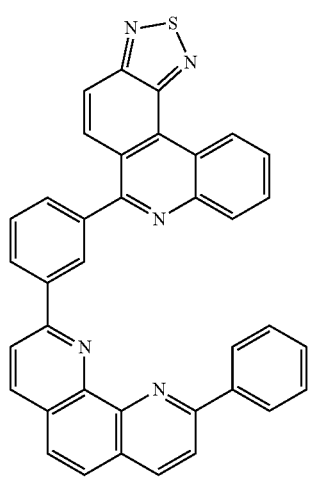
337
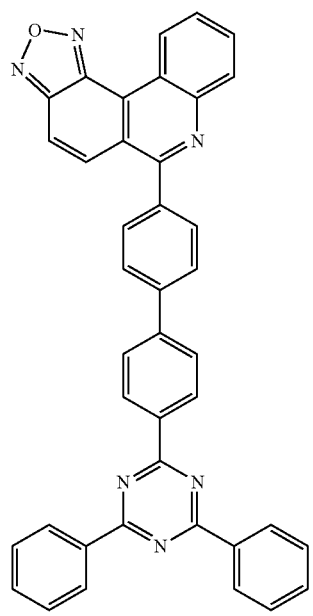
338
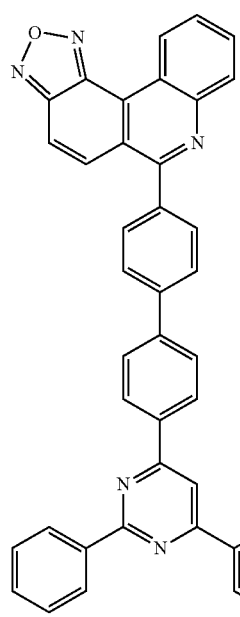

339
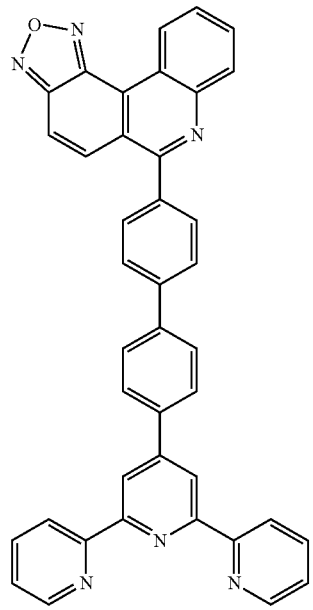
340
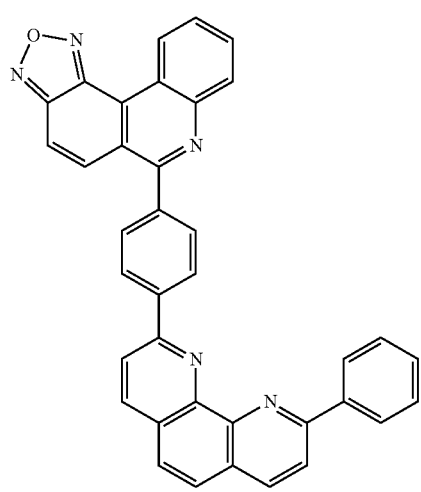
341
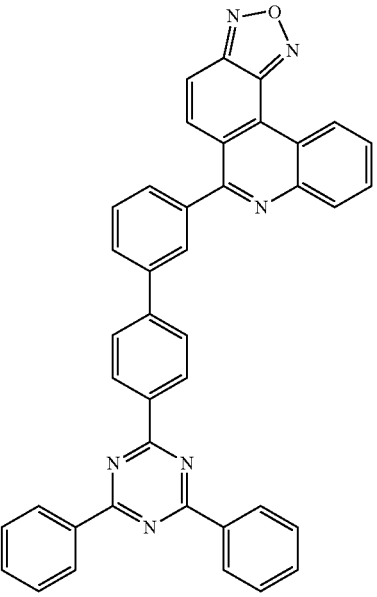
342
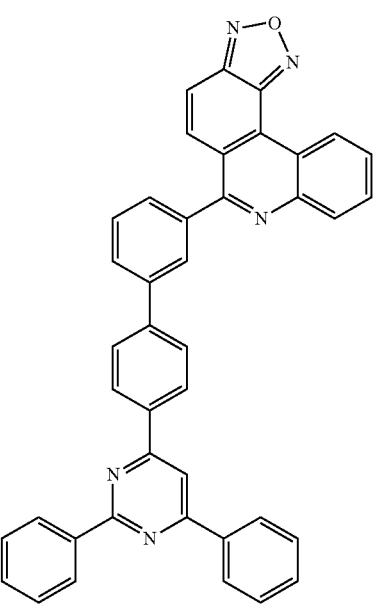

343
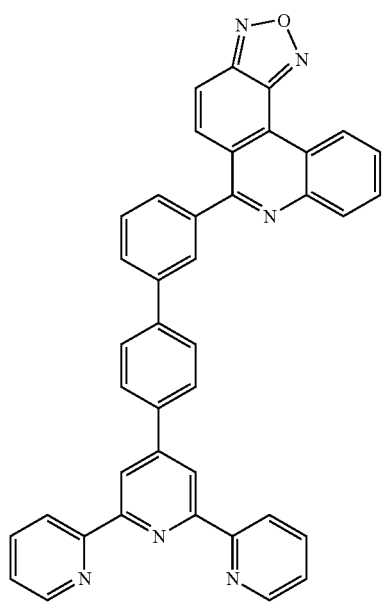
345
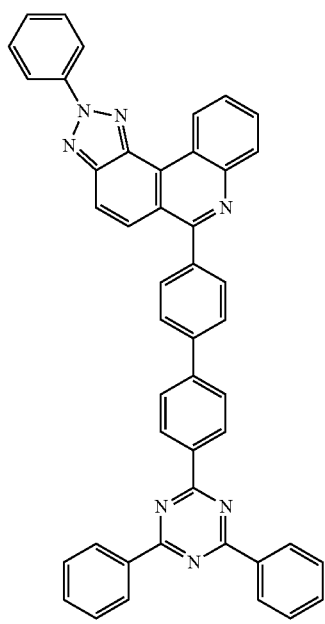
344
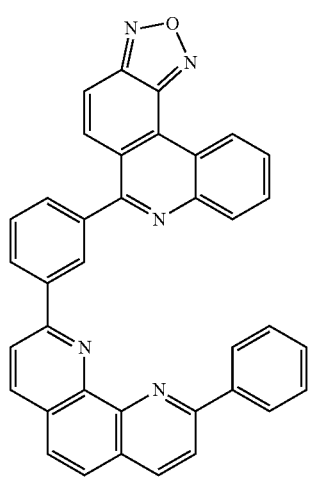
346
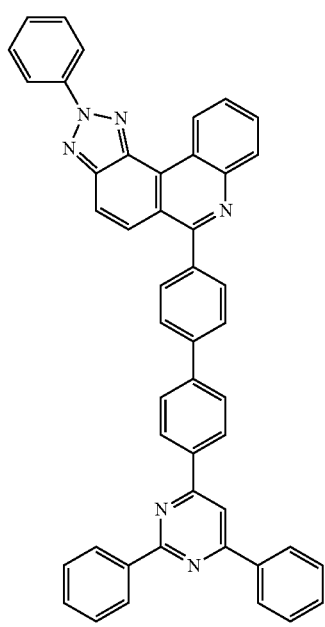

155
-continued
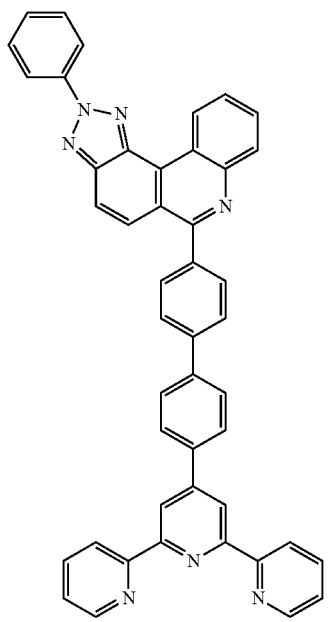
347
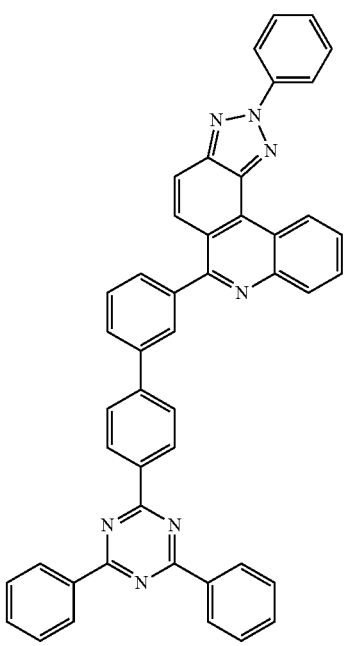
156
-continued
349
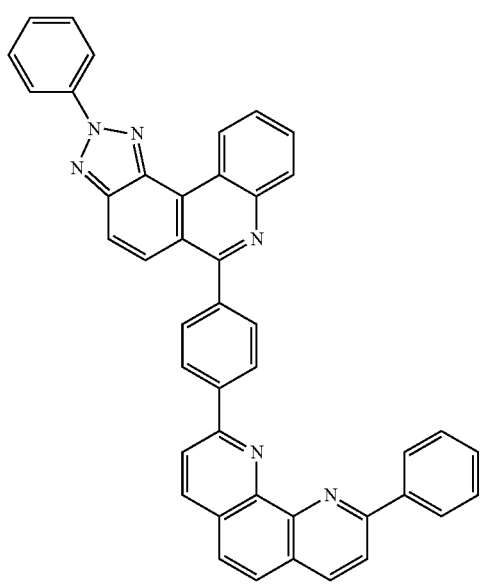
348
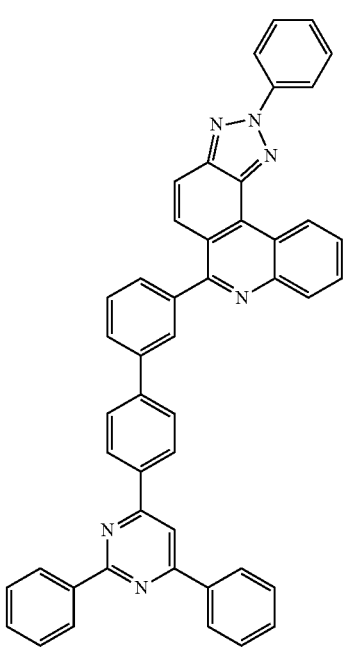
350

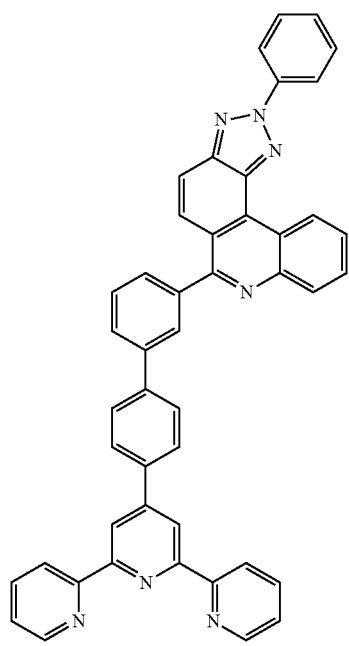
351
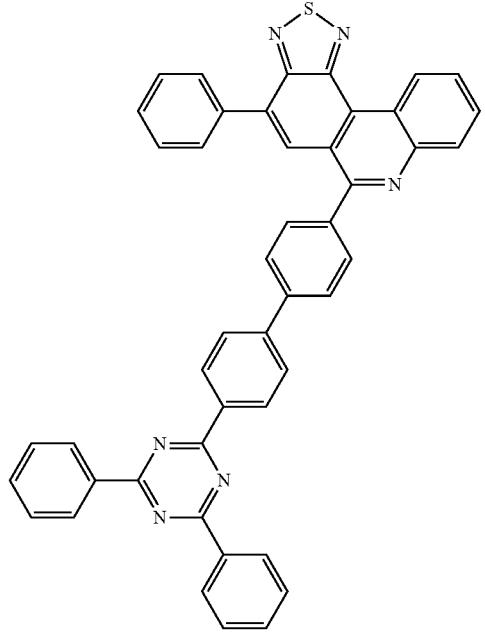
353
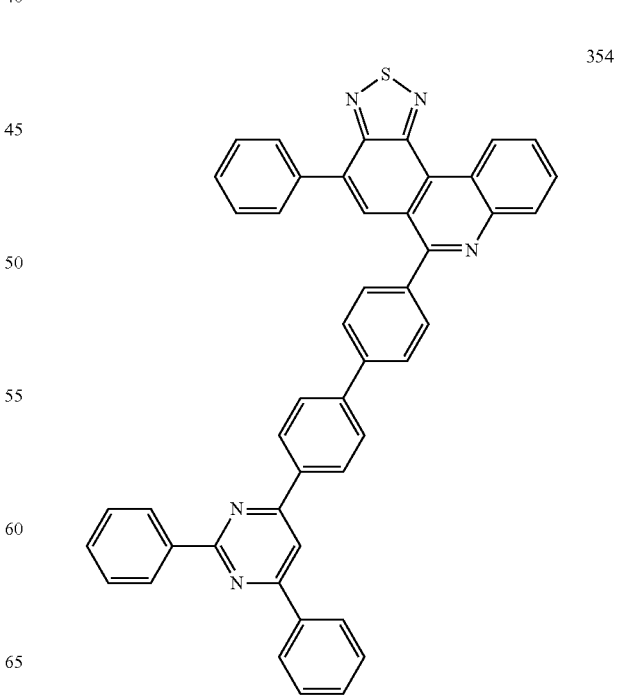
354
352

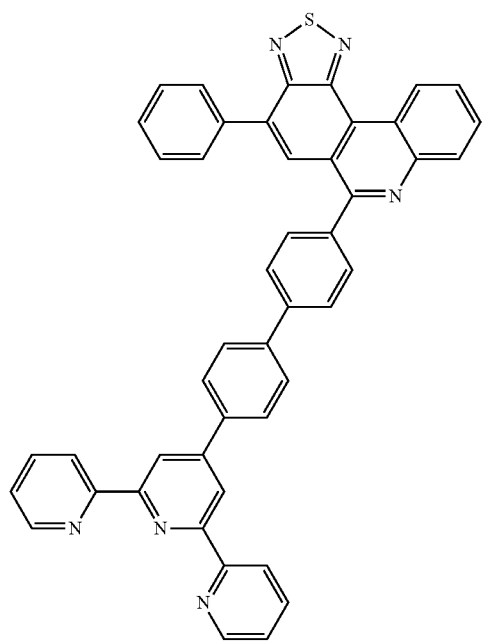
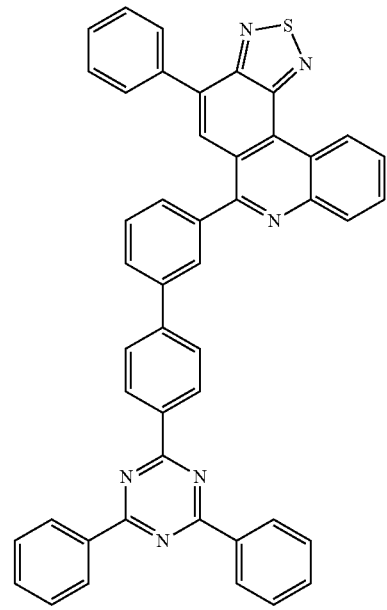

161
-continued
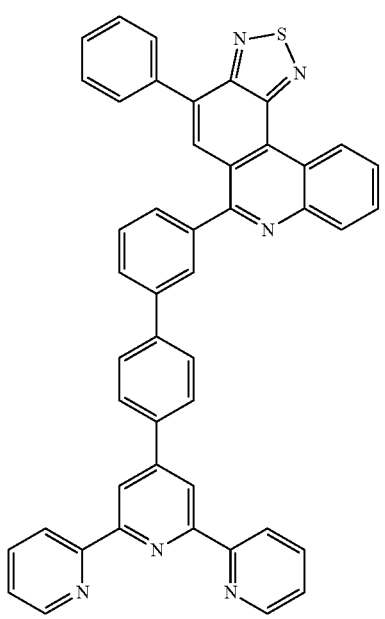
359
162
-continued
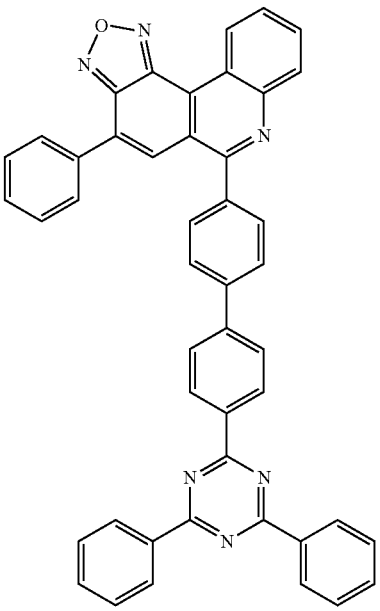
361
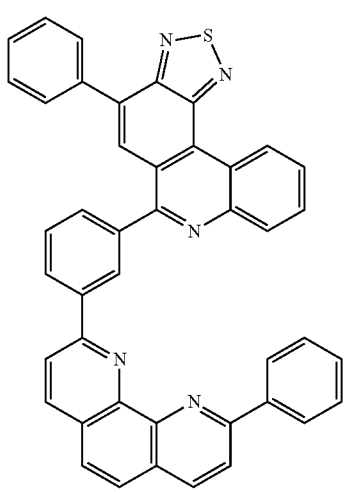
360
362

363
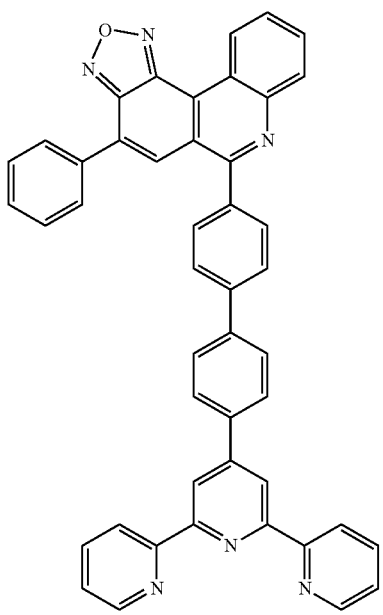
364
365
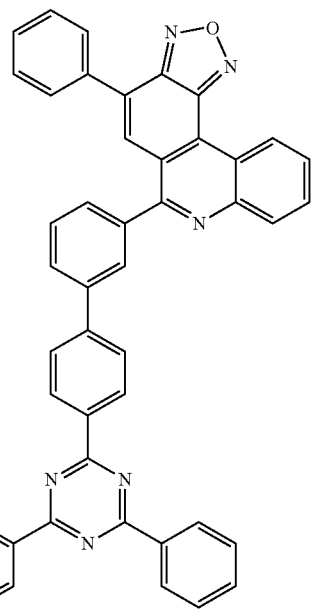
366

367
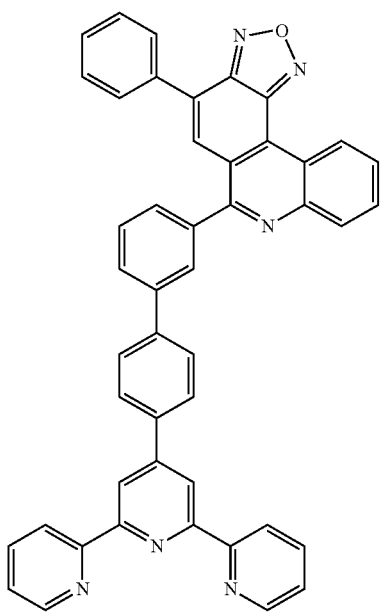
368
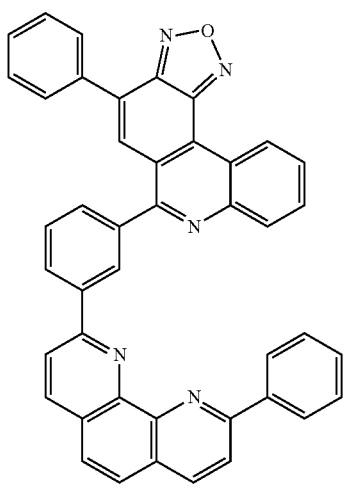
369
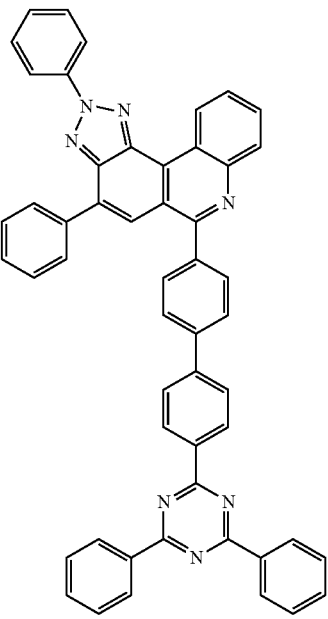
370
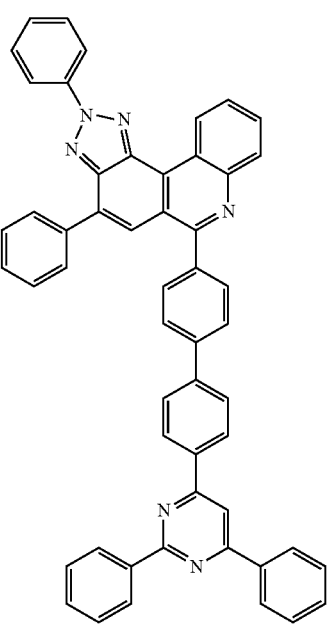

167
-continued
371
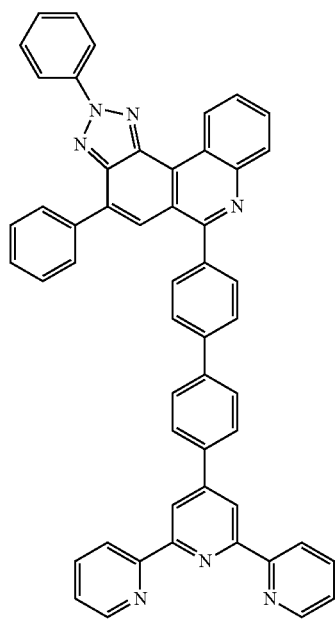
372
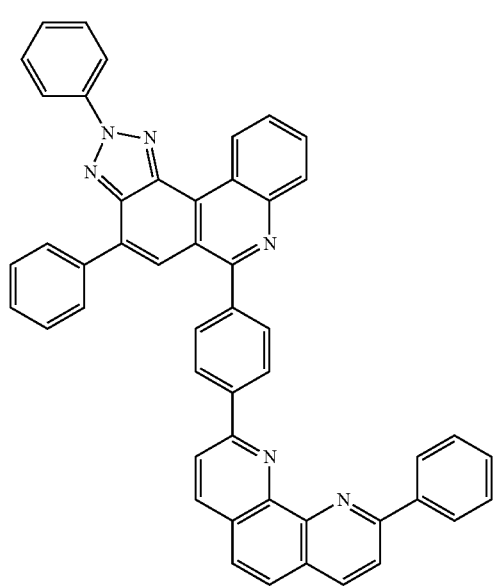
168
-continued
373
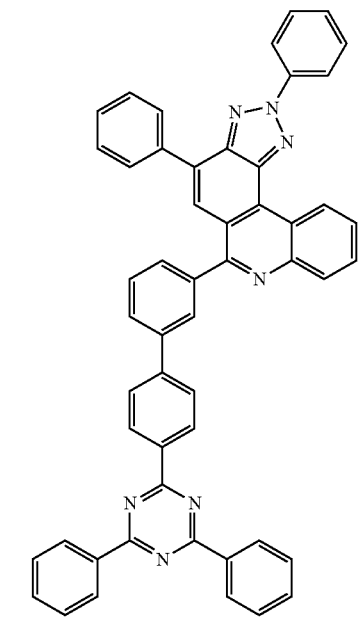
374
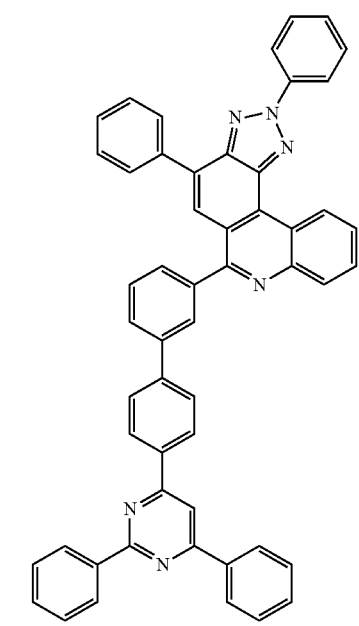

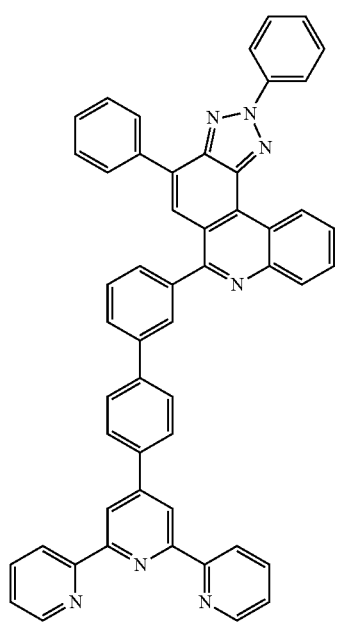
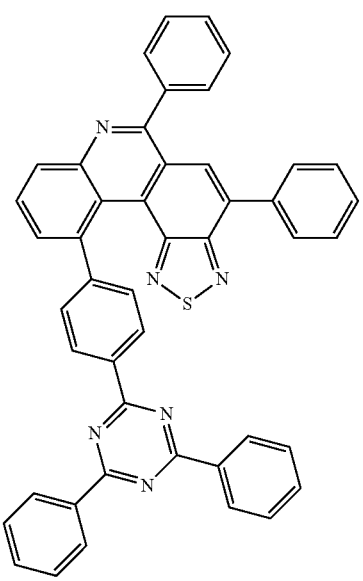
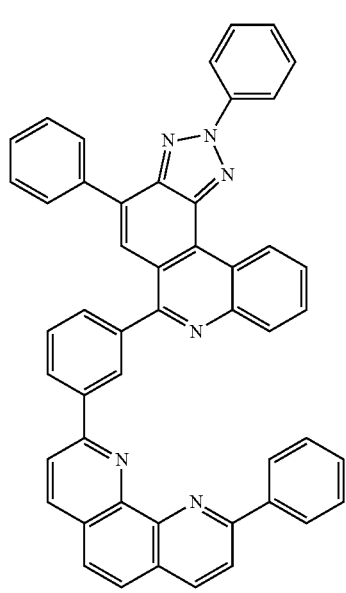
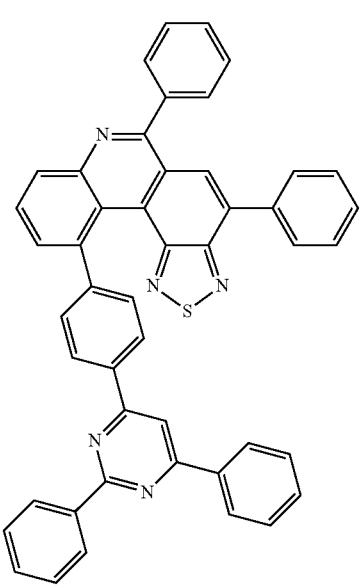

379
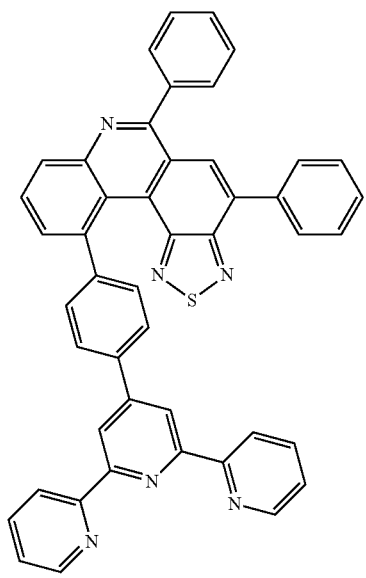
380
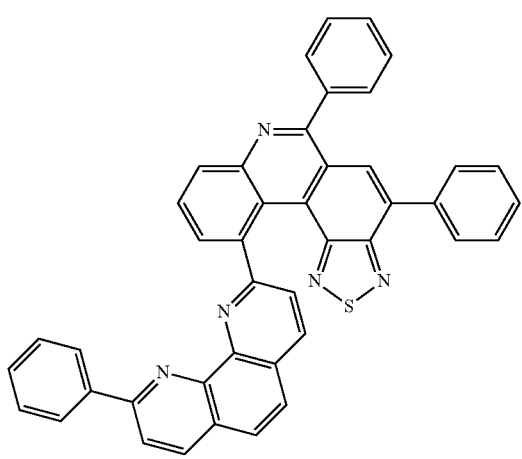
381
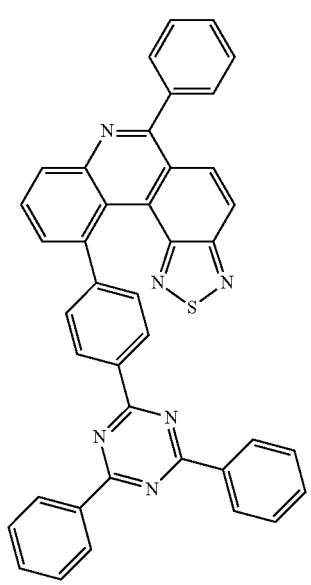
382
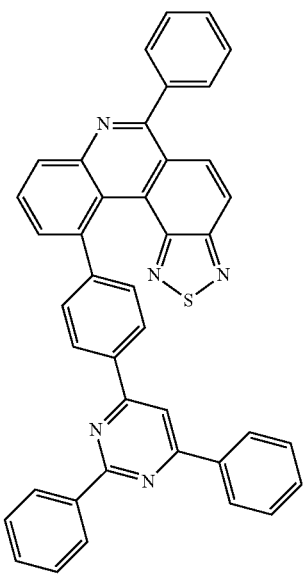
383
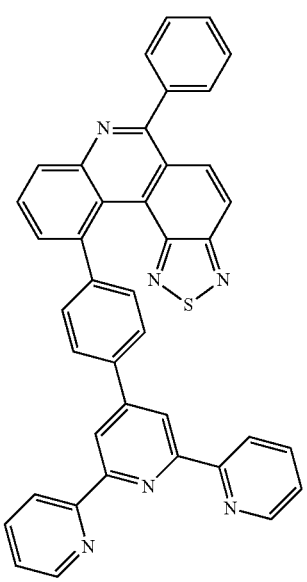
384
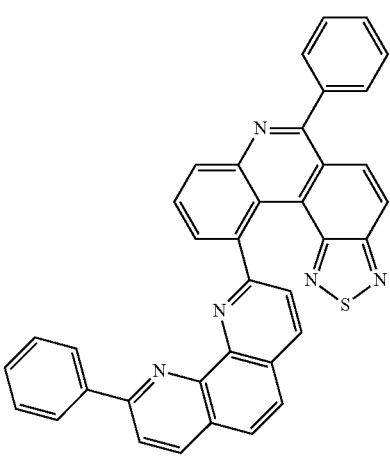

385
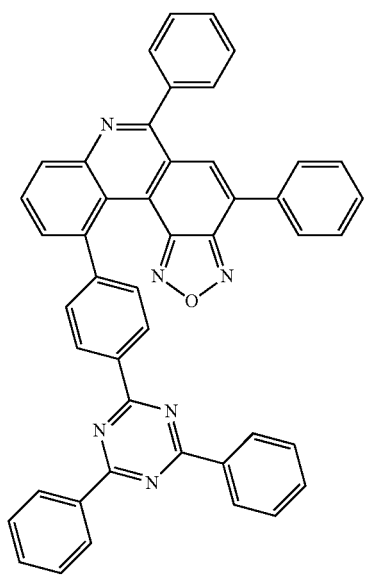
386
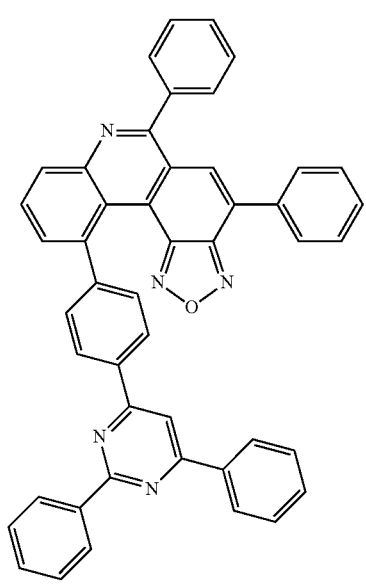
387
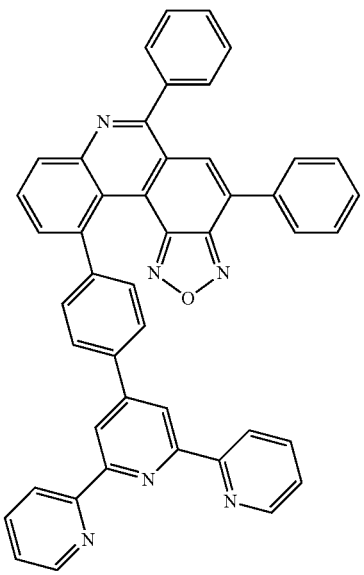
388
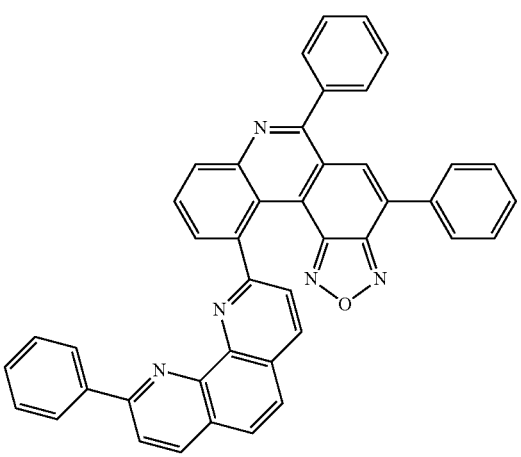
389
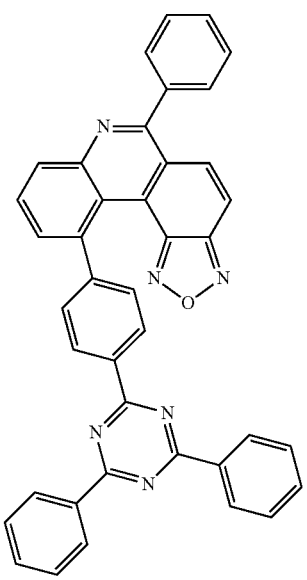

175
-continued
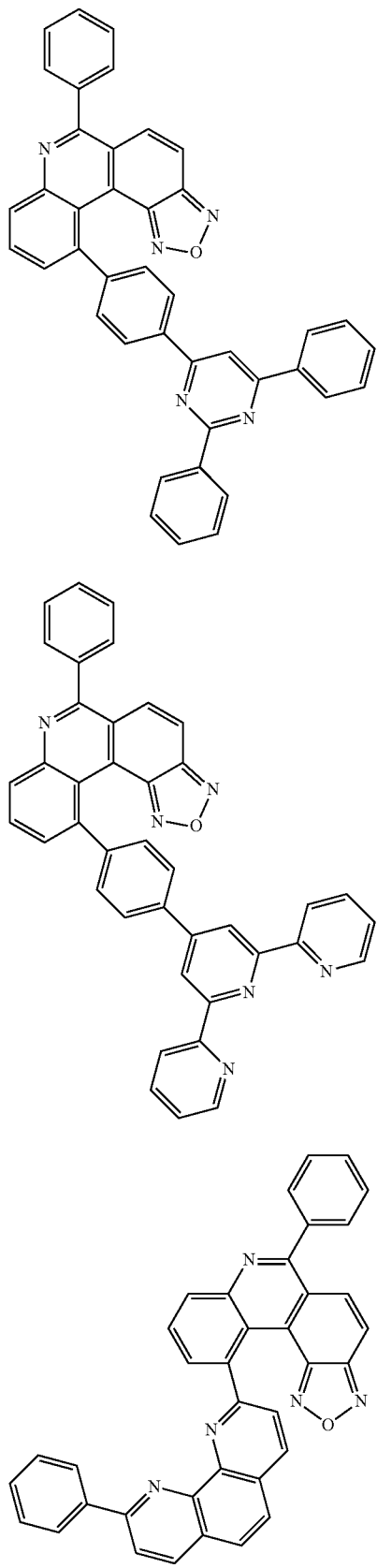
176
-continued
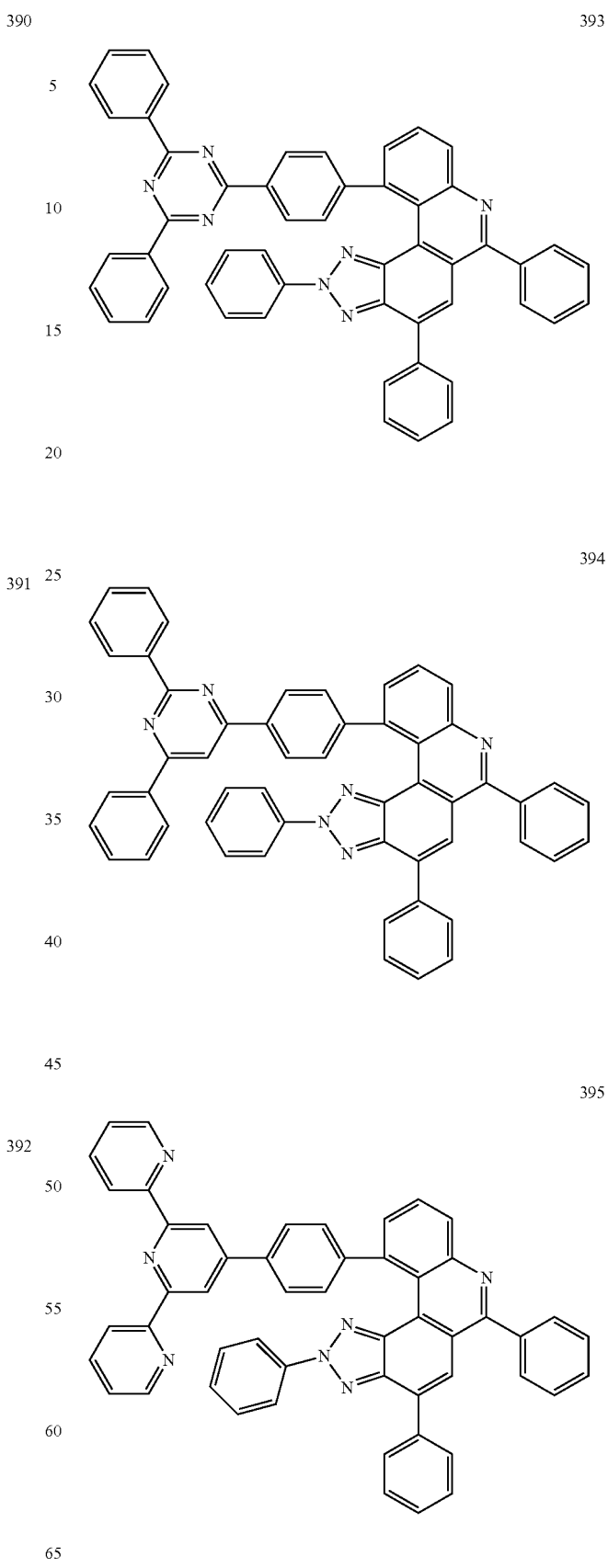

396
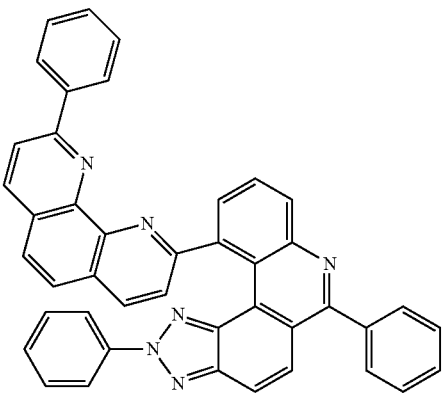
400
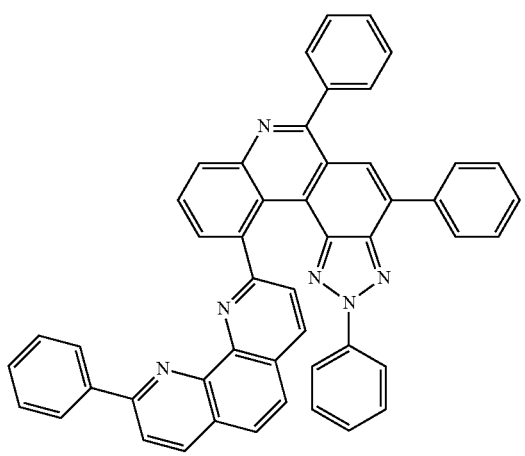
397
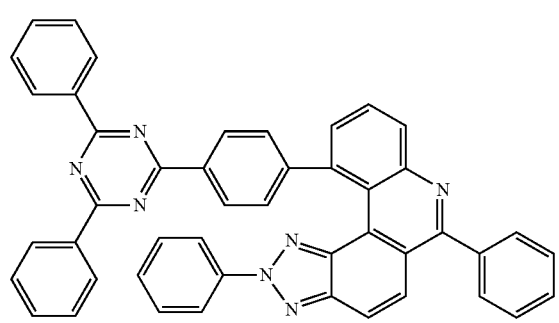
401
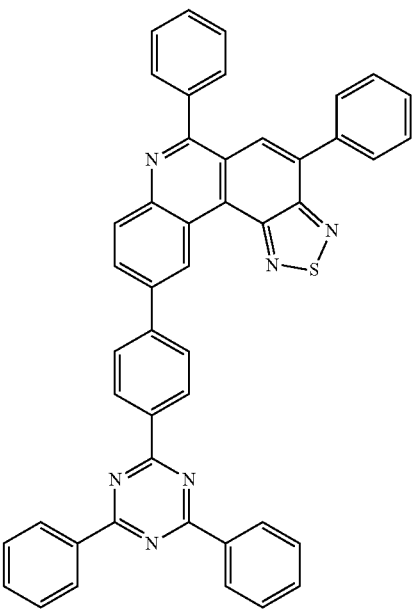
398
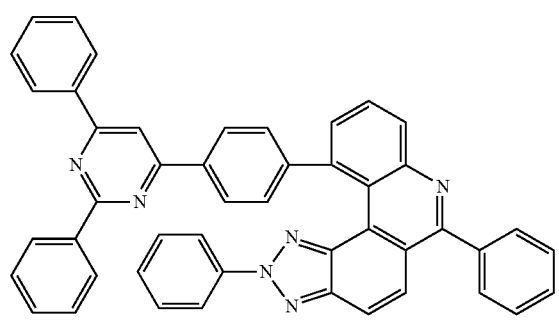
399
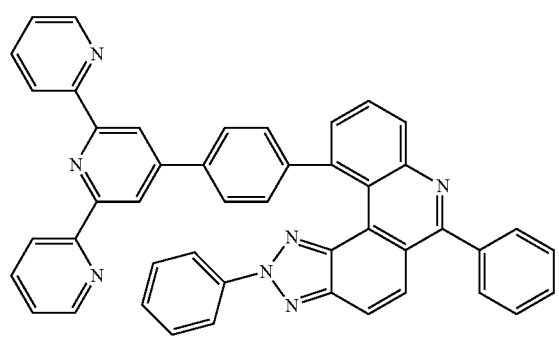
402
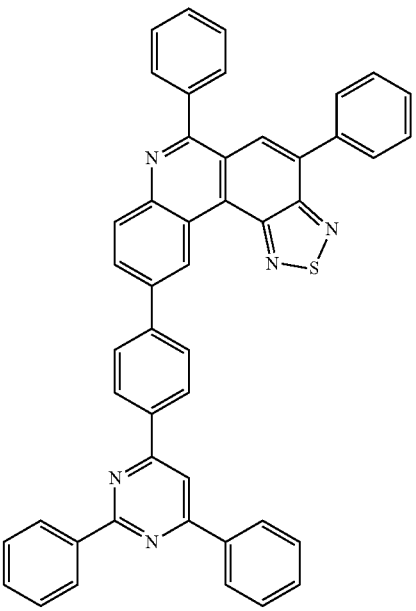

179
-continued
403
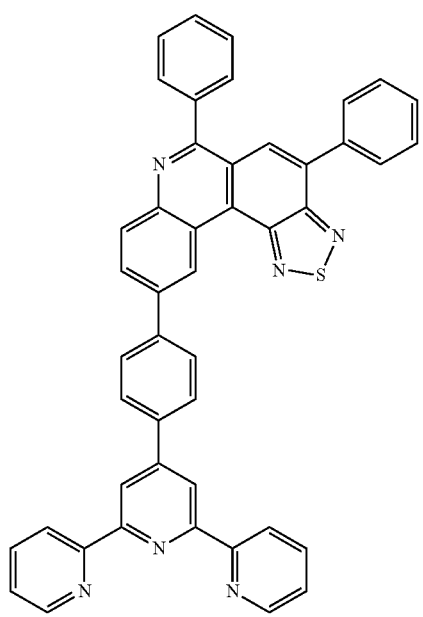
404
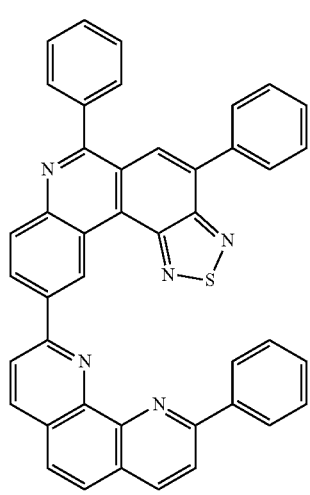
180
-continued
405
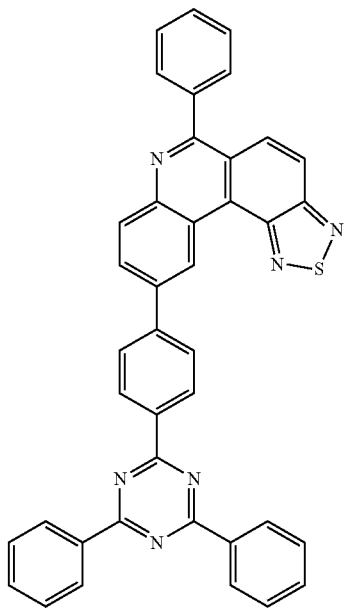
406
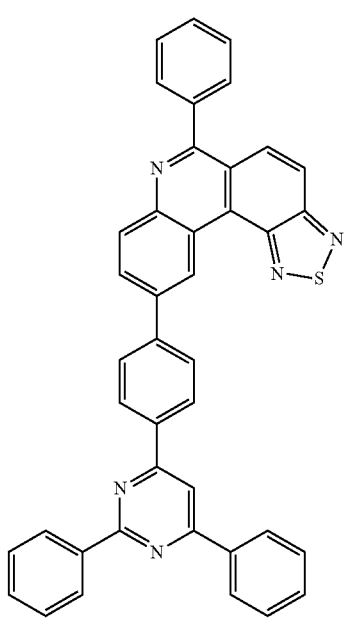

181
-continued
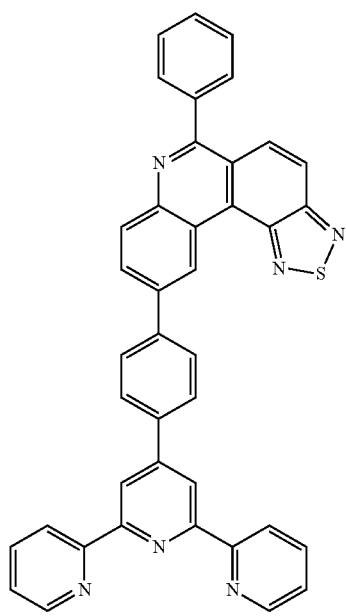
407
182
-continued
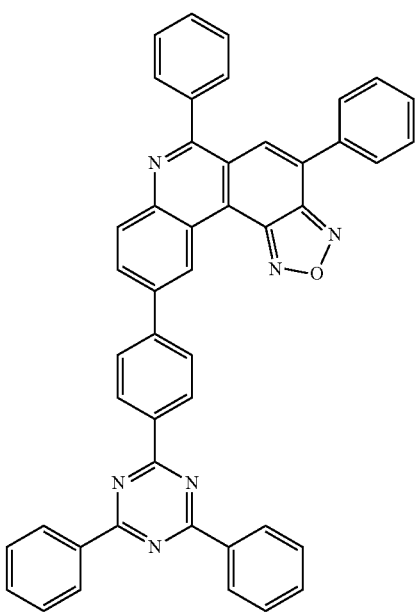
409
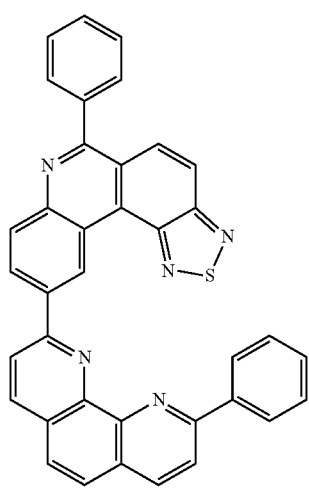
408
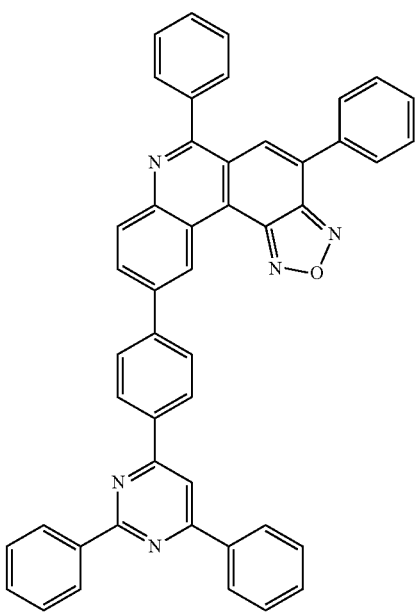
410

411
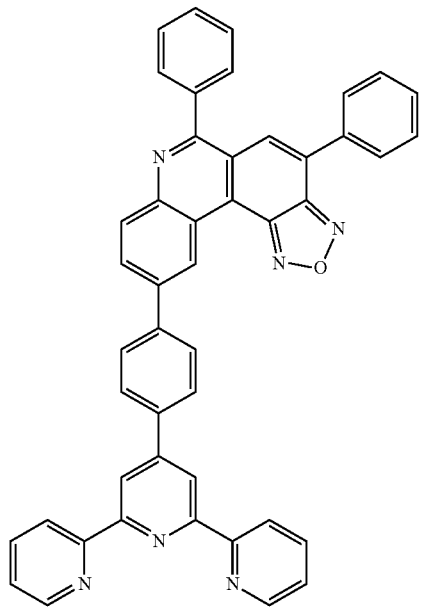
412
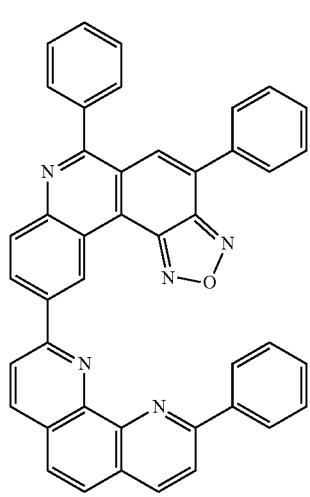
413
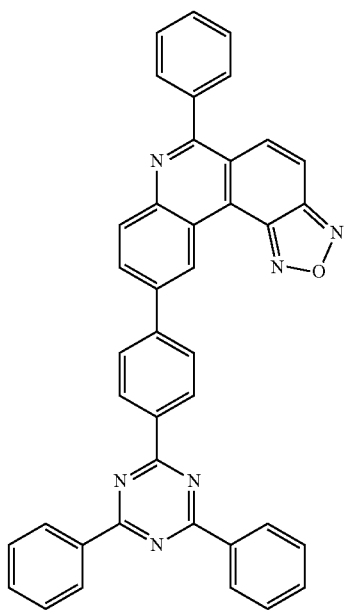
414
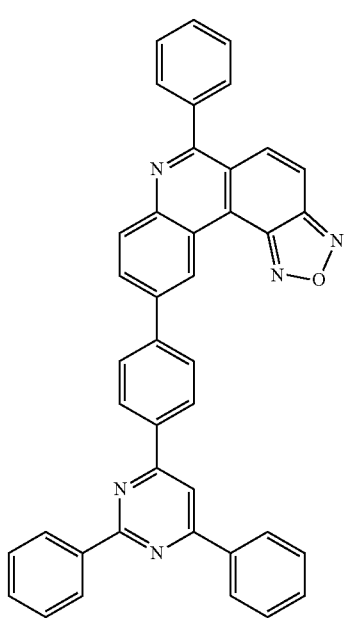

185
-continued
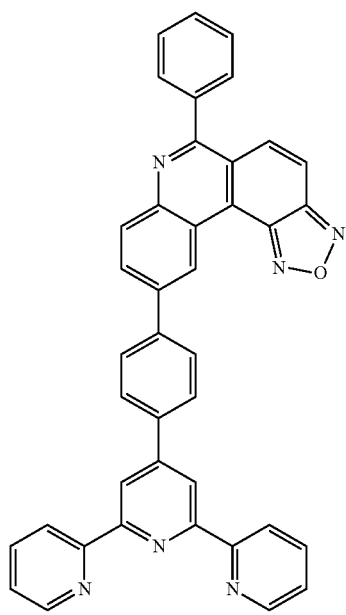
186
-continued
415
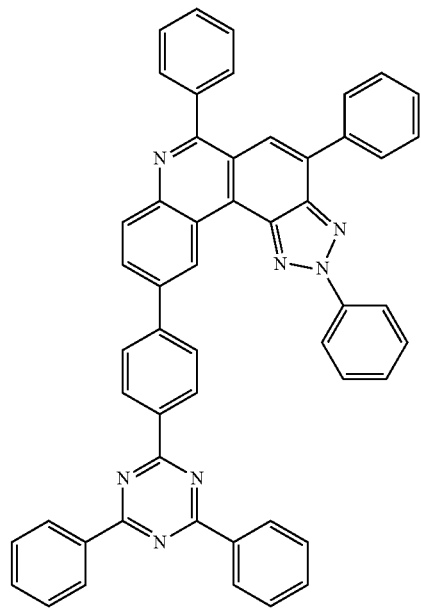
416
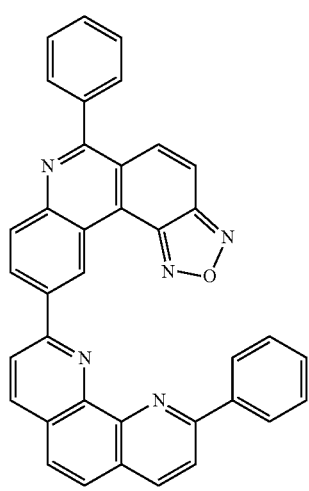
417
418
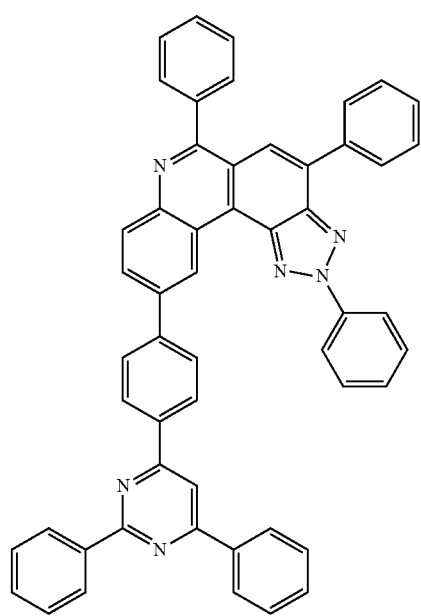

419
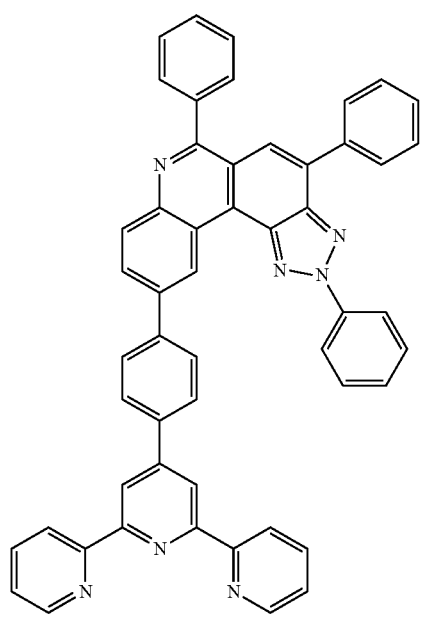
421
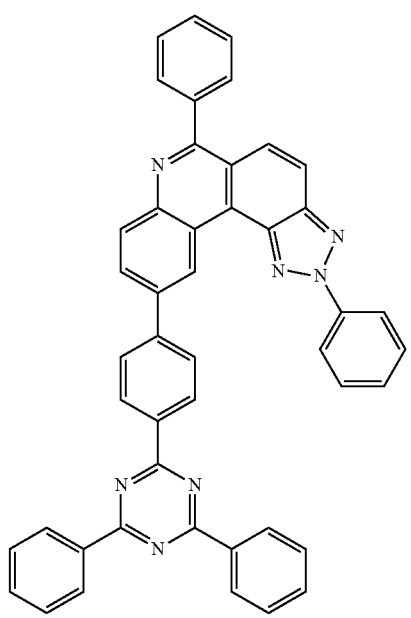
420
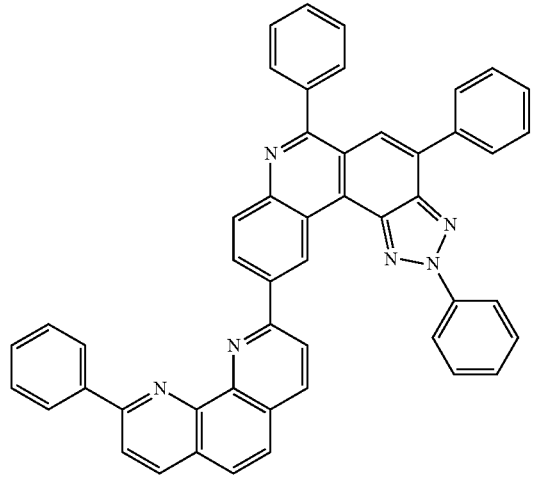
422
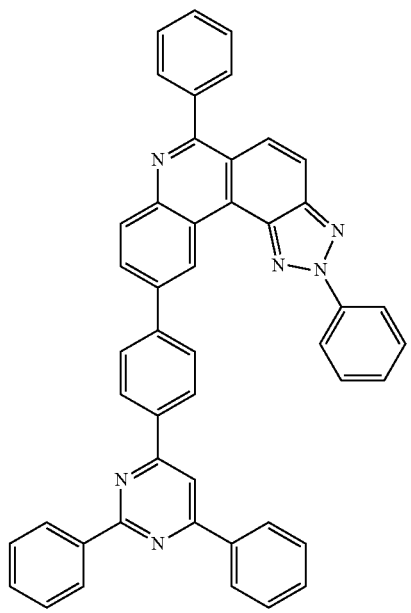

423
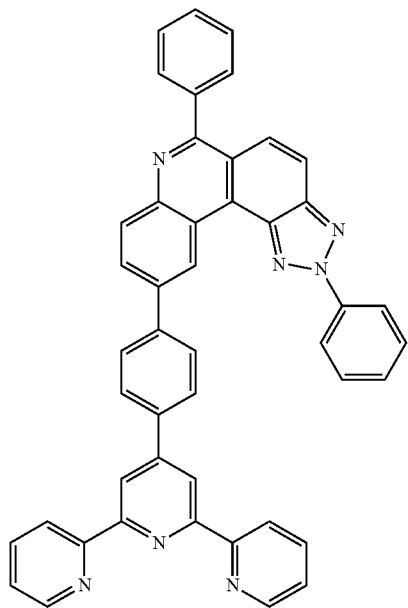
424
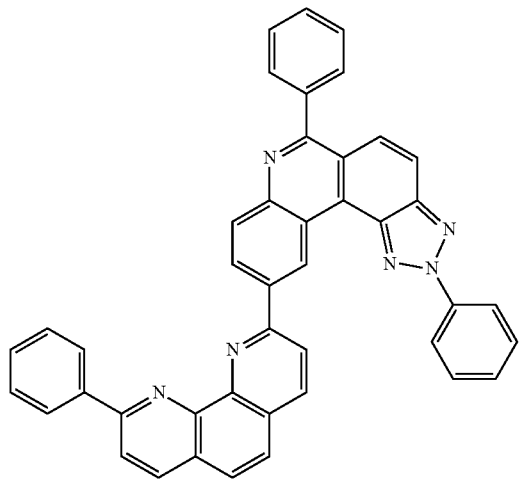
425
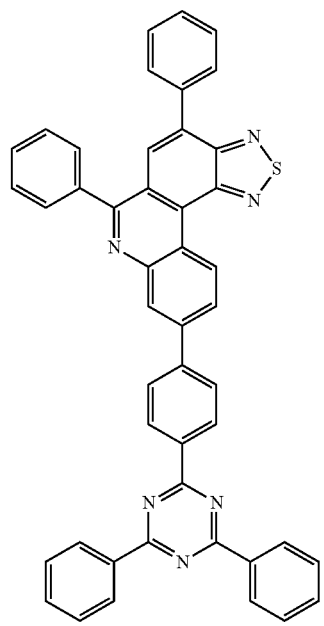
426
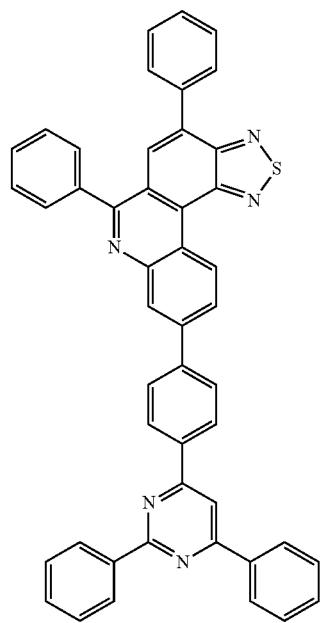

191
-continued
427
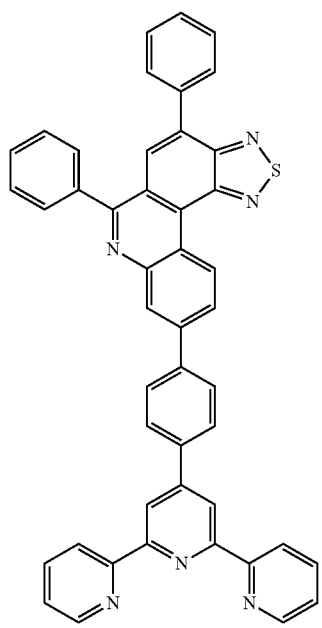
192
-continued
429
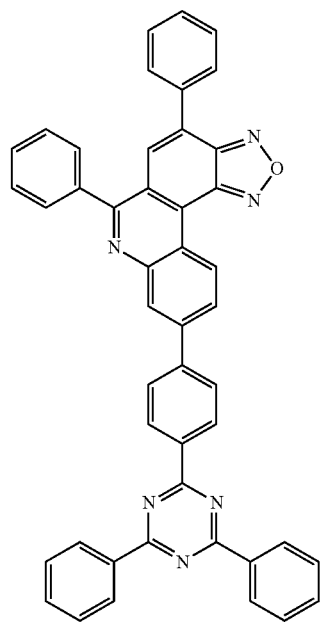
428
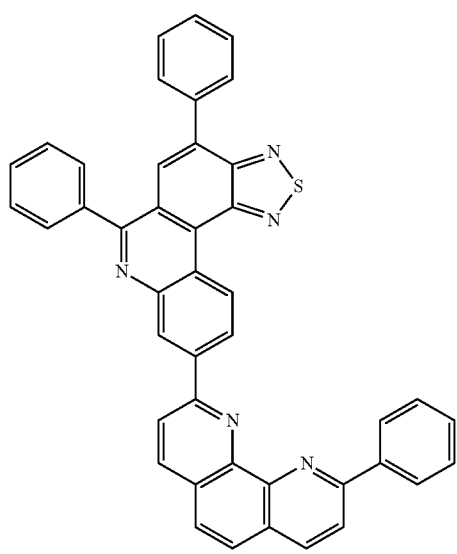
430
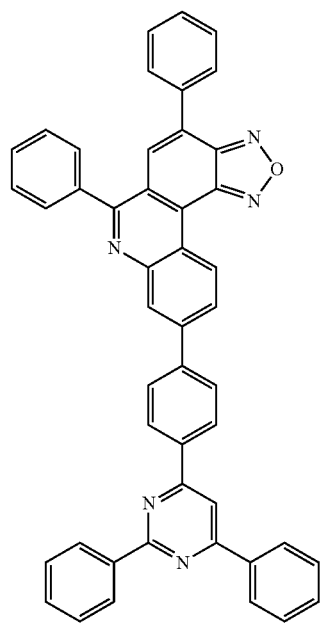

-continued
431
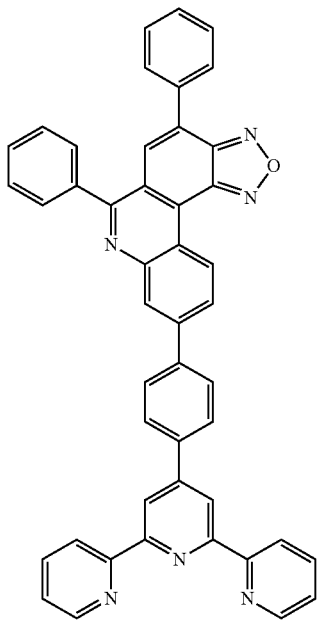
432
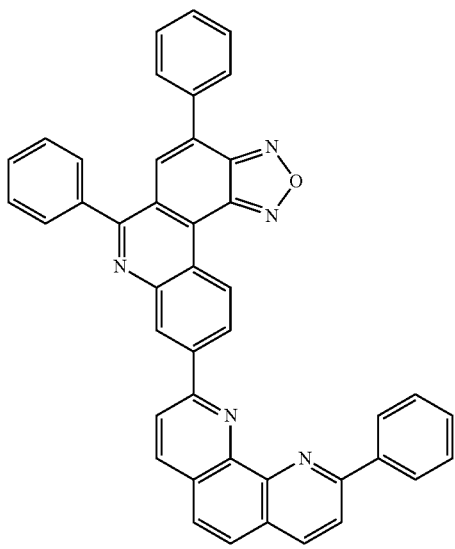
-continued
433
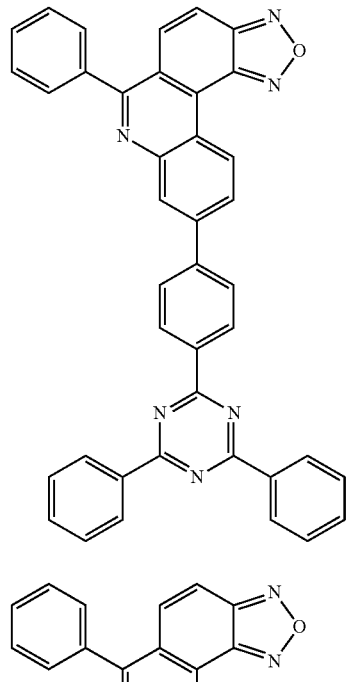
434
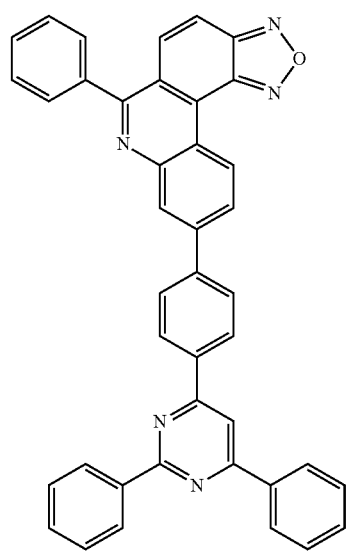
435
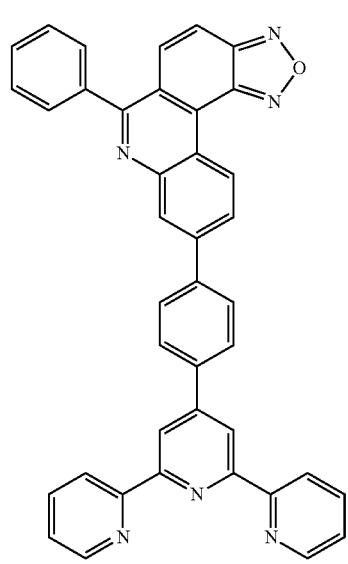

-continued
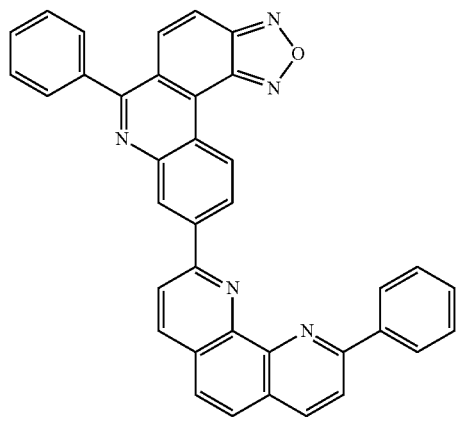
436
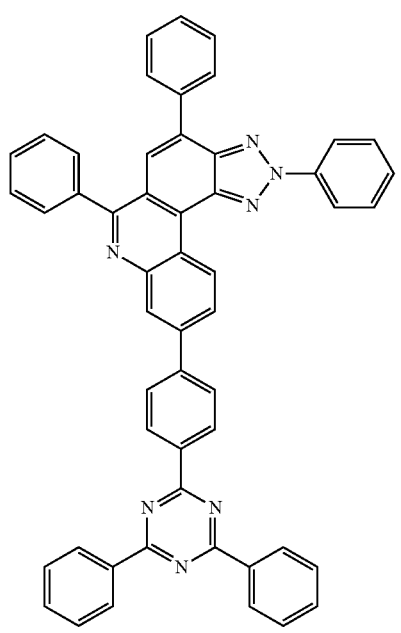
437
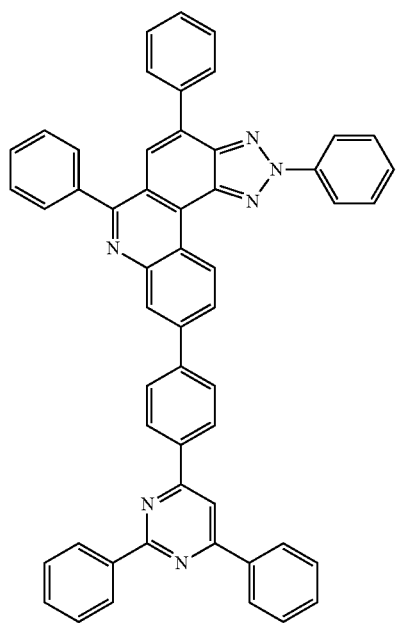
438
-continued
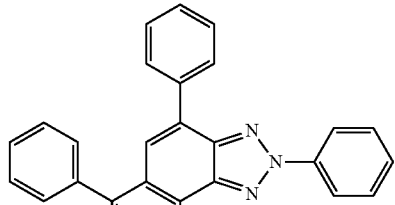
439
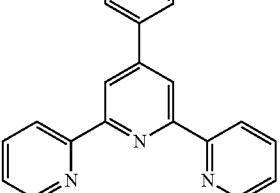
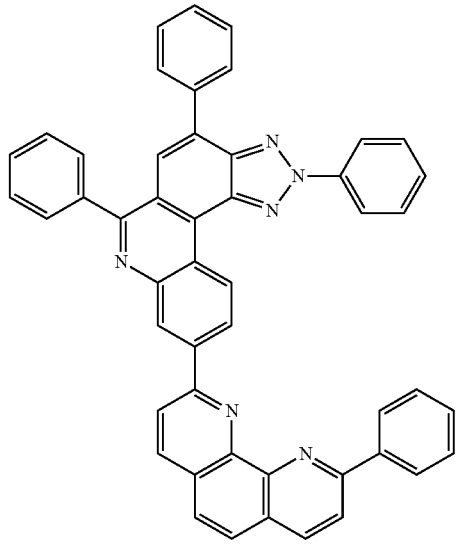
440

197
-continued
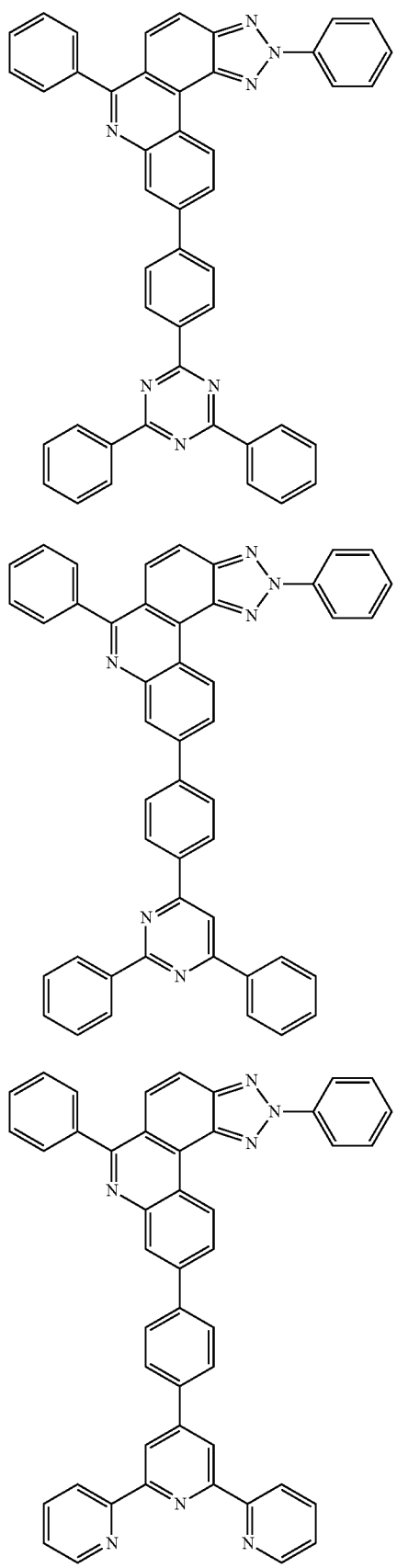
441
442
443
198
-continued
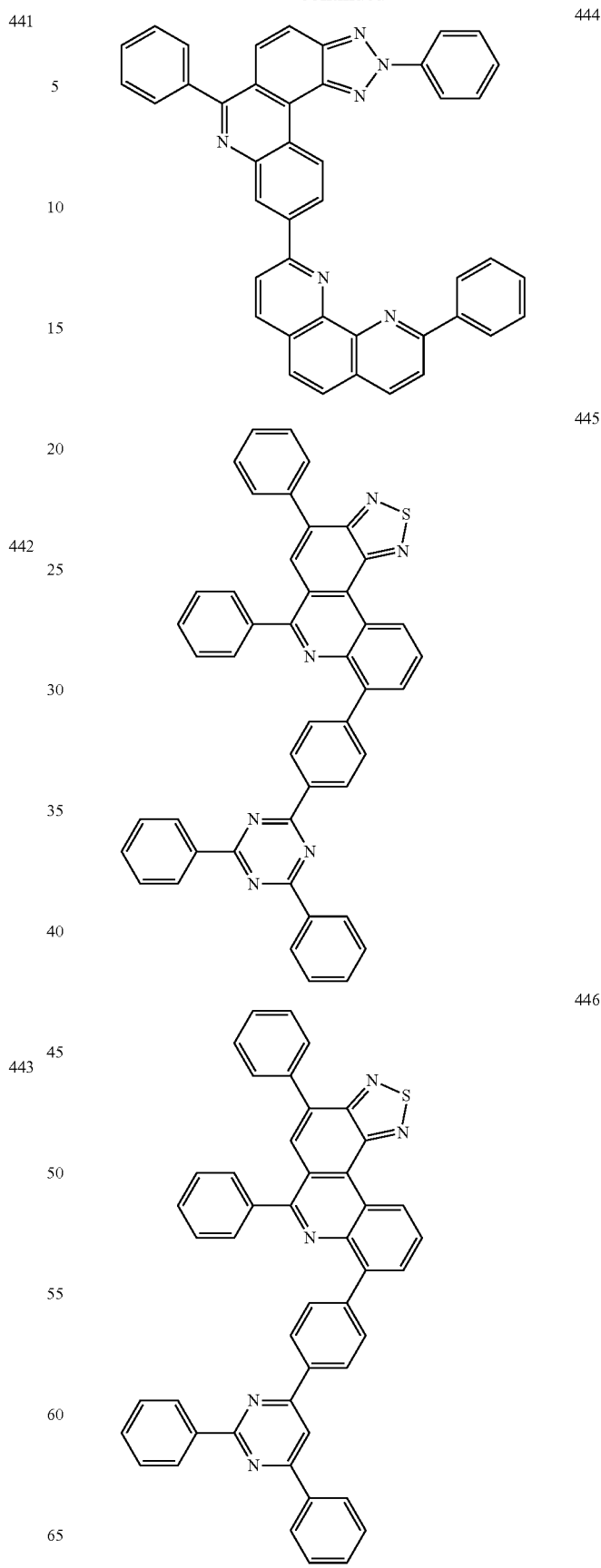
444
445
446

199
-continued
447
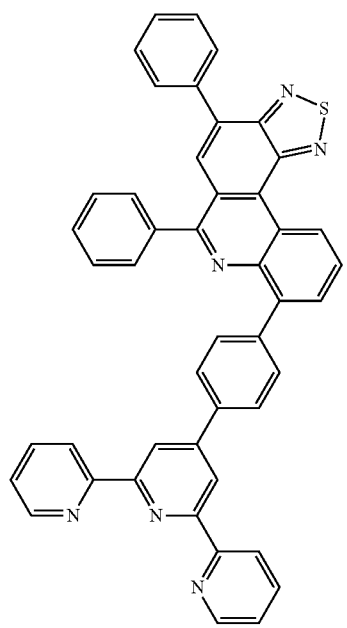
448
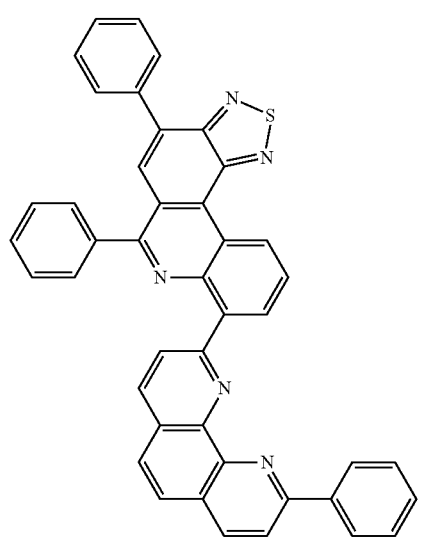
200
-continued
449
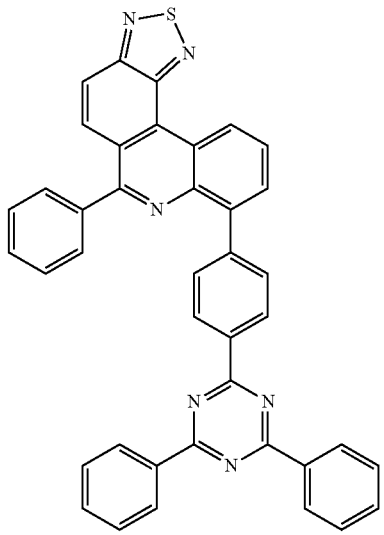
450
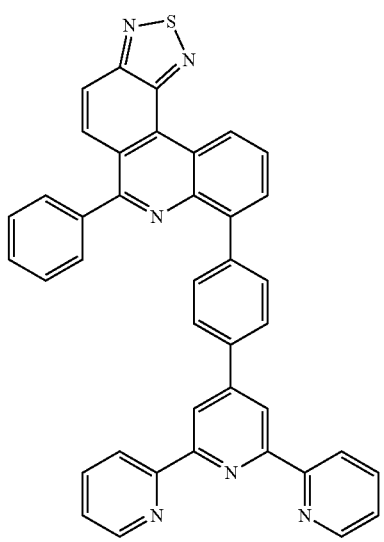
451

201
-continued
452
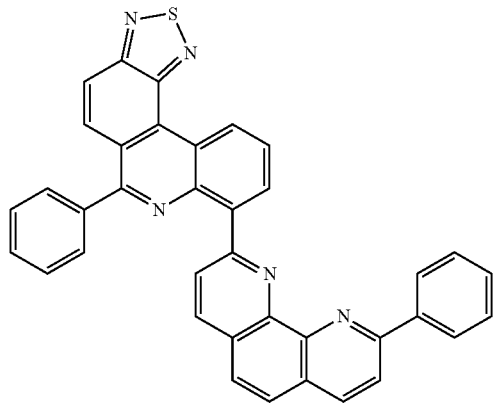
453
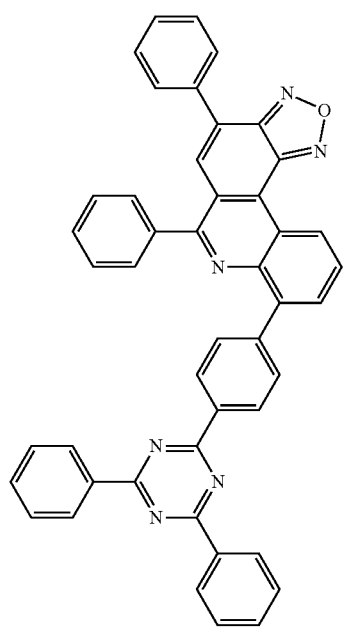
454
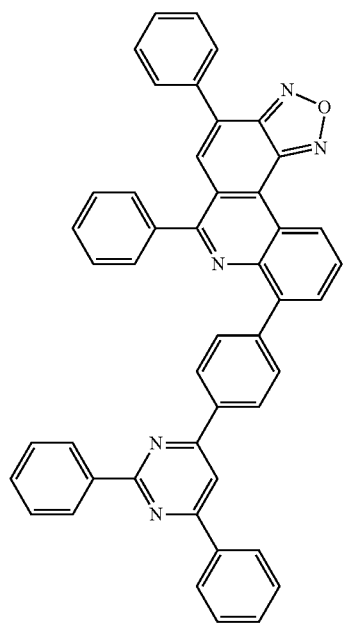
202
-continued
455
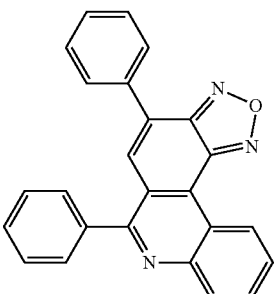
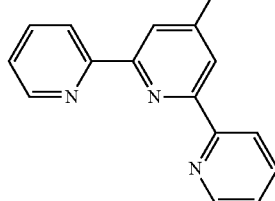
456
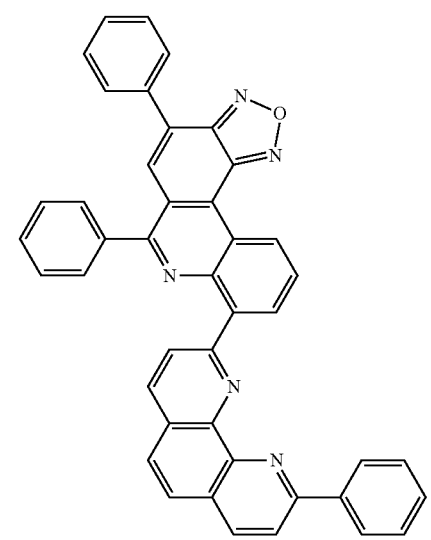

203
-continued
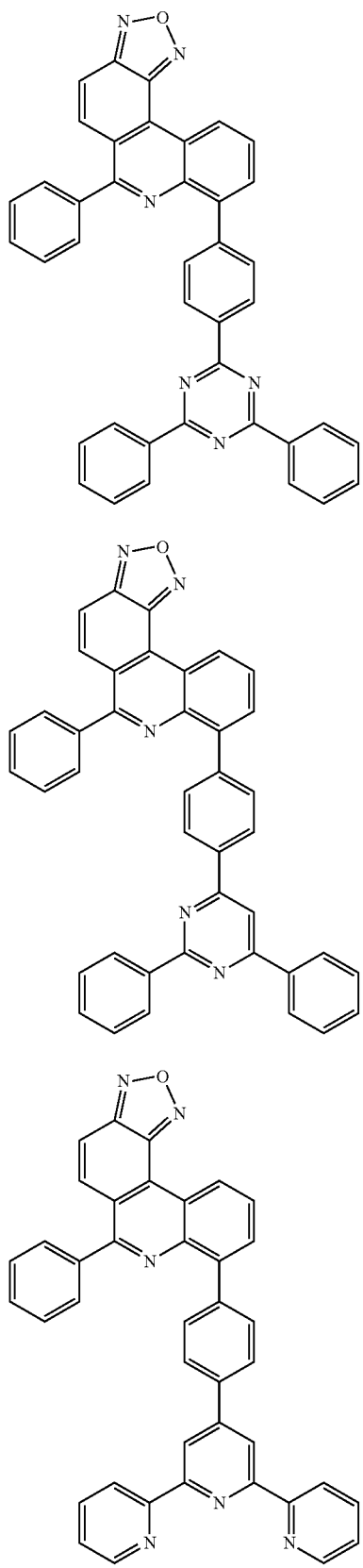
204
-continued
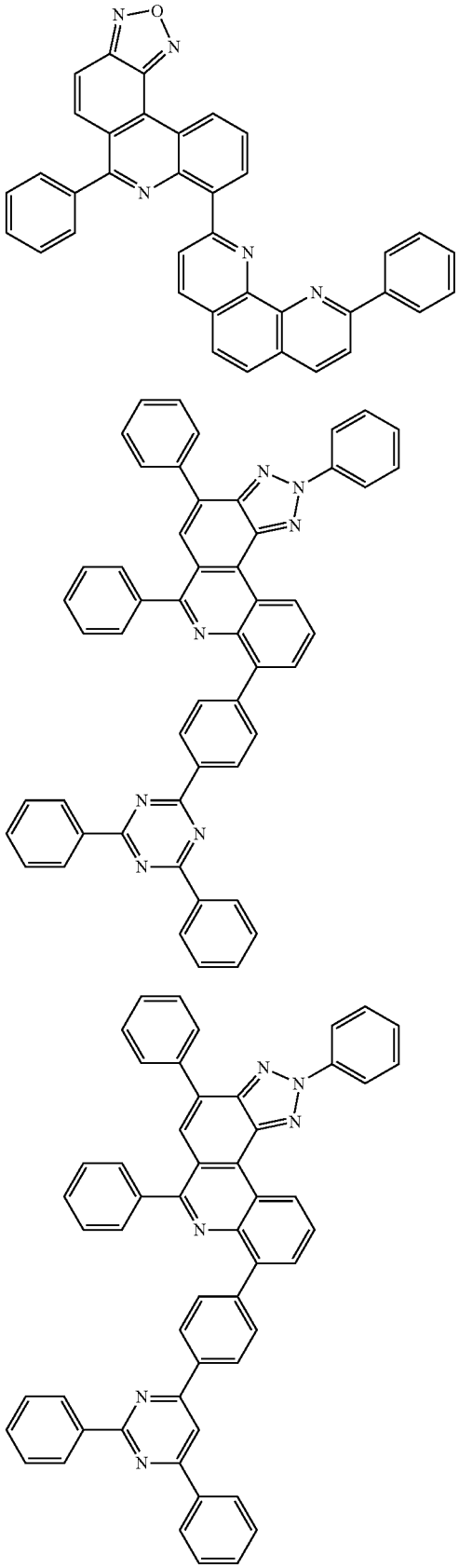

205
-continued
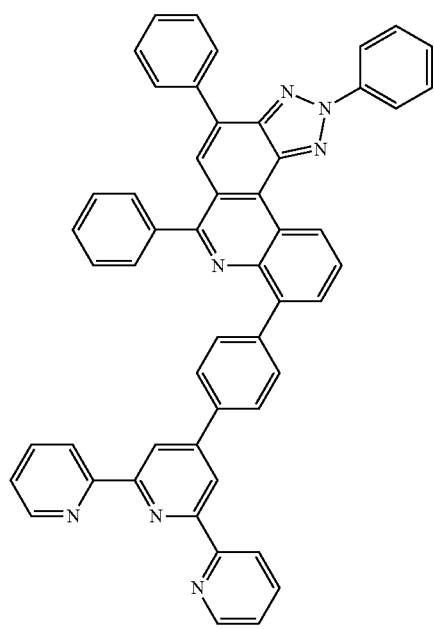
463
206
-continued
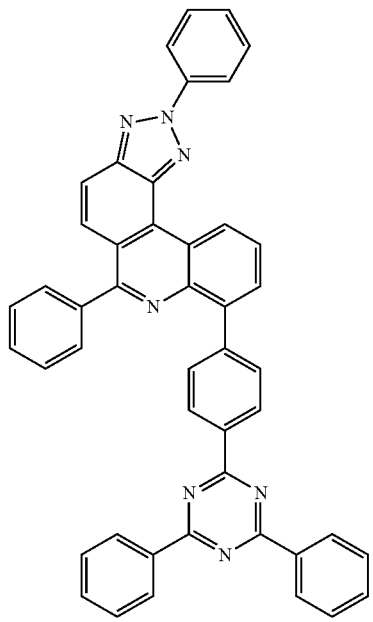
465
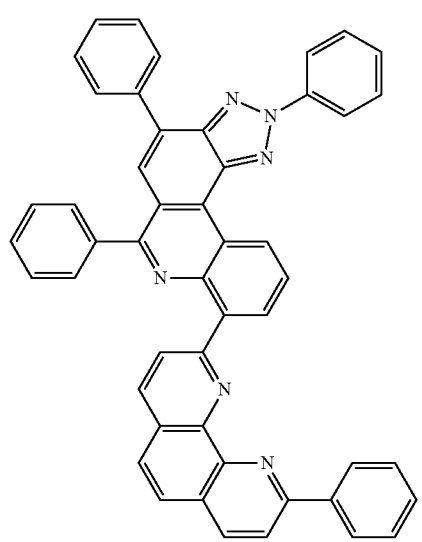
464
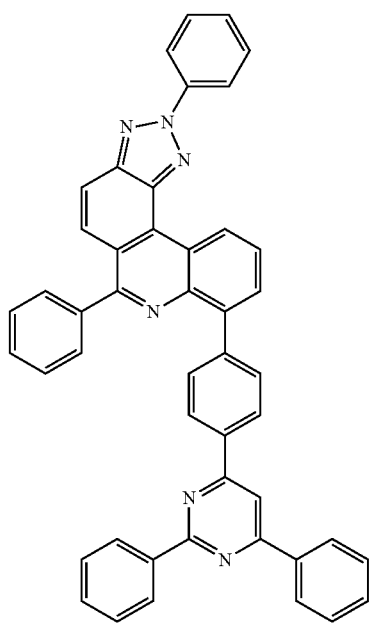
466

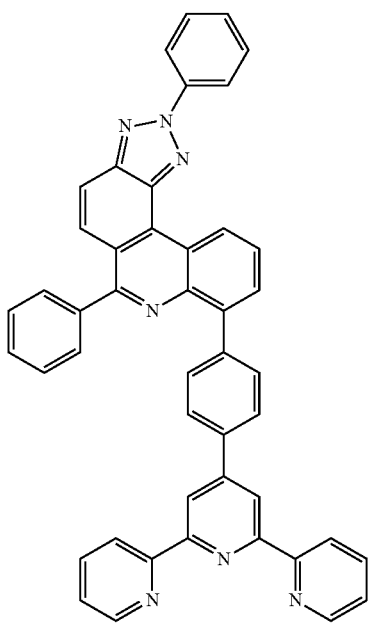
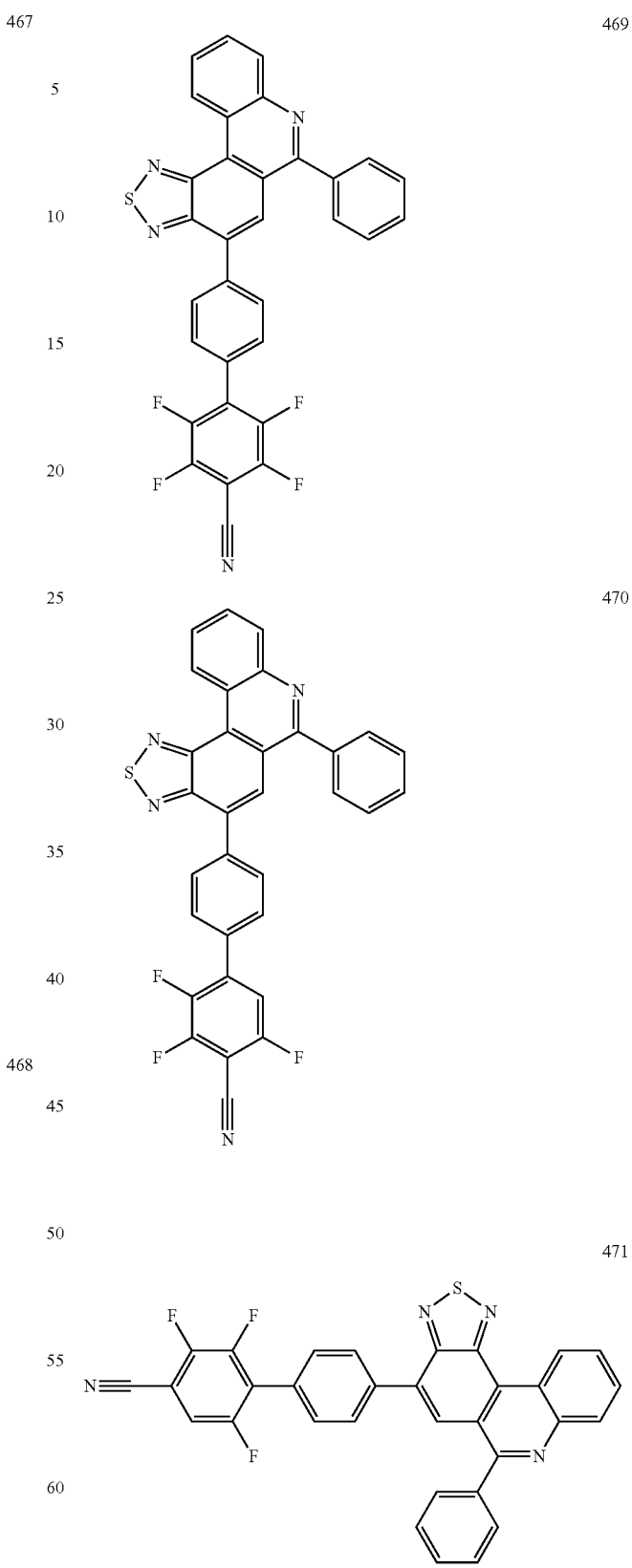

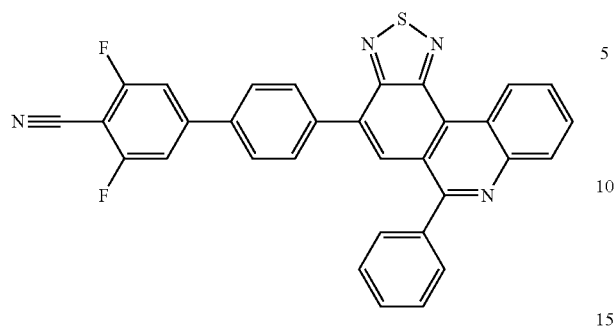
472
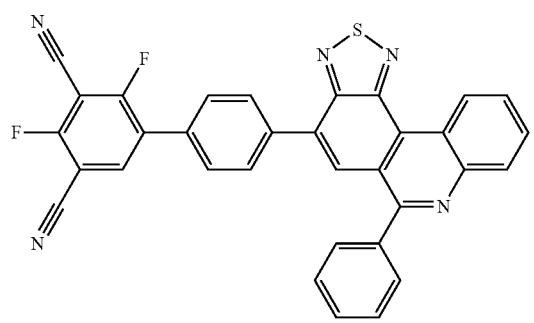
476
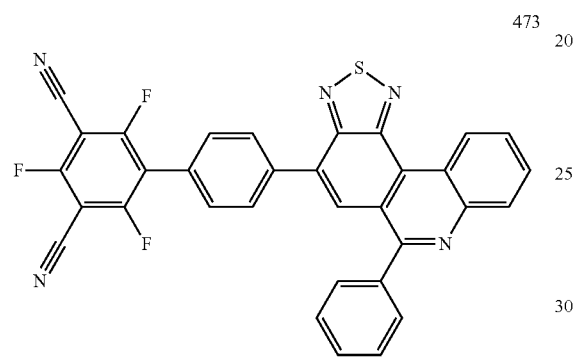
473
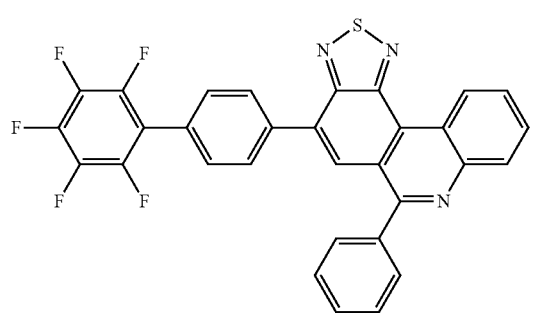
477
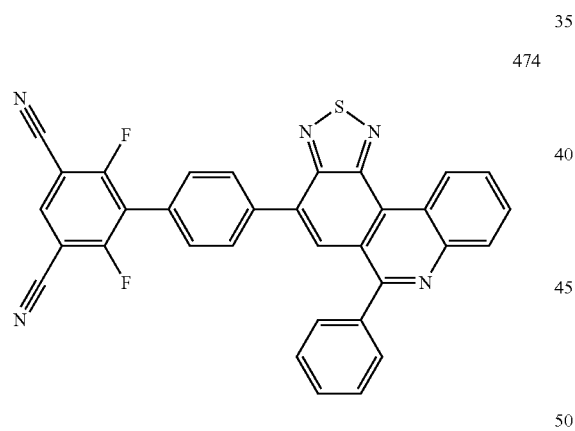
474
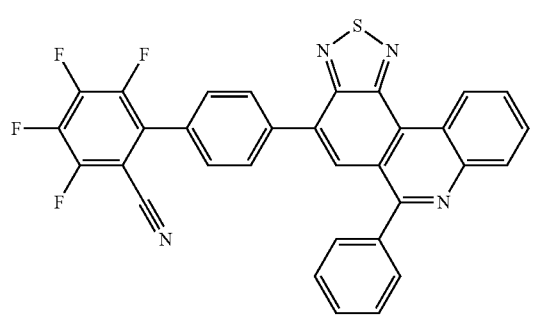
478
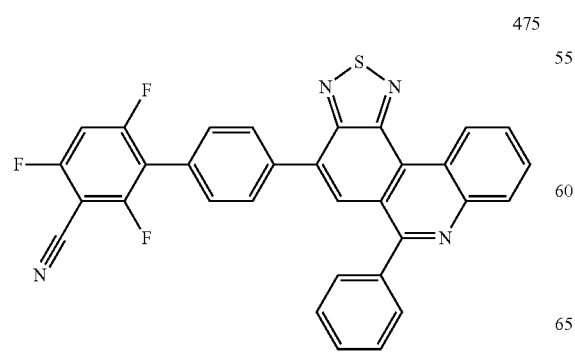
475
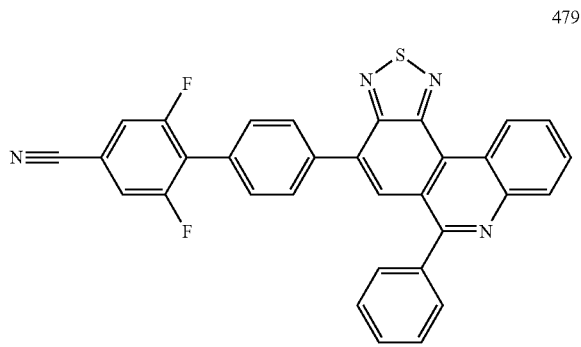
479

211
-continued
480
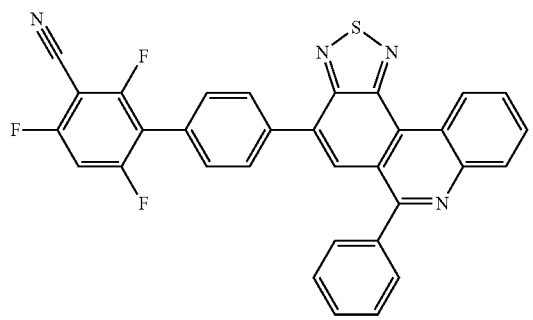
481
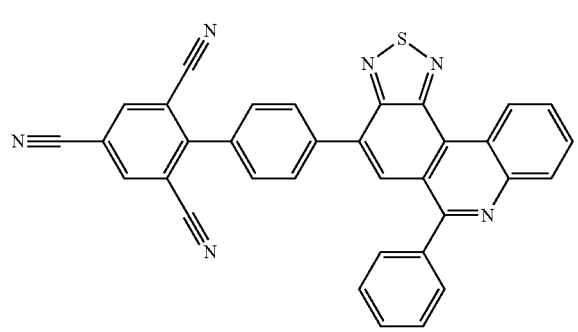
482
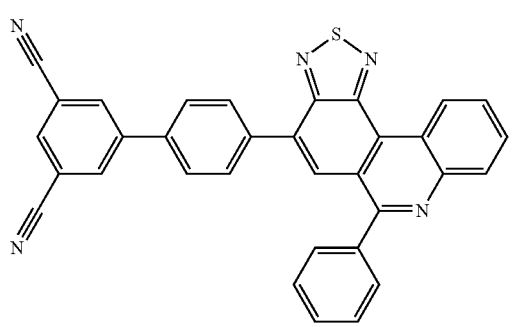
483
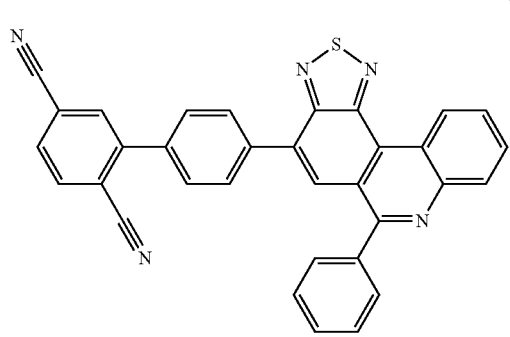
212
-continued
484
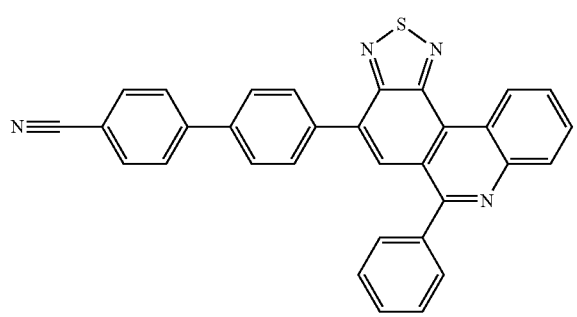
485
486
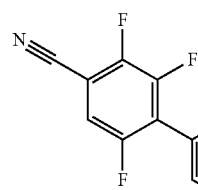
487
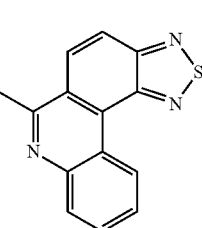

488
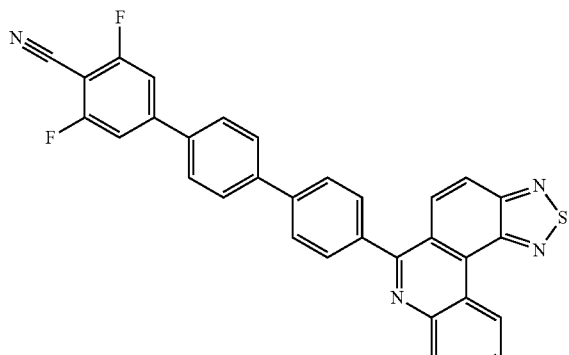
489
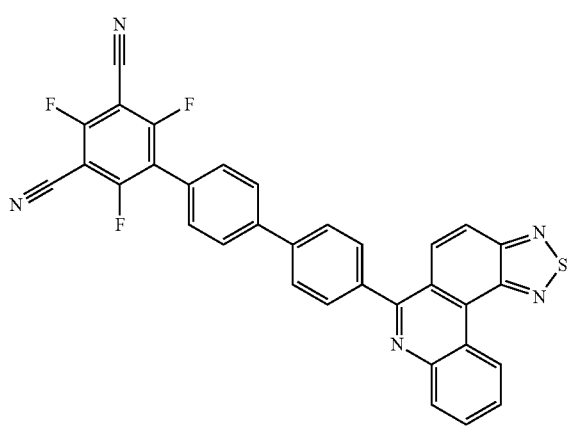
490
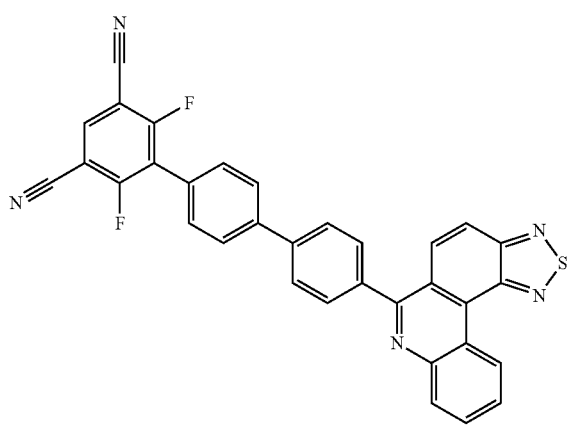
491
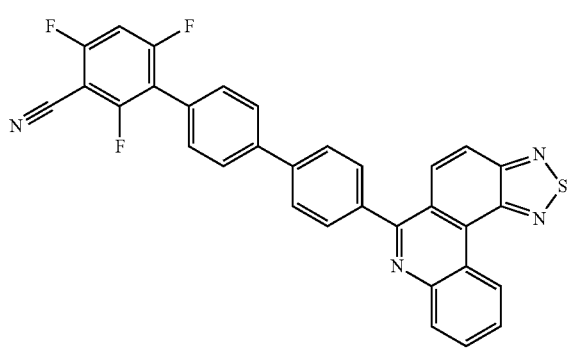
492
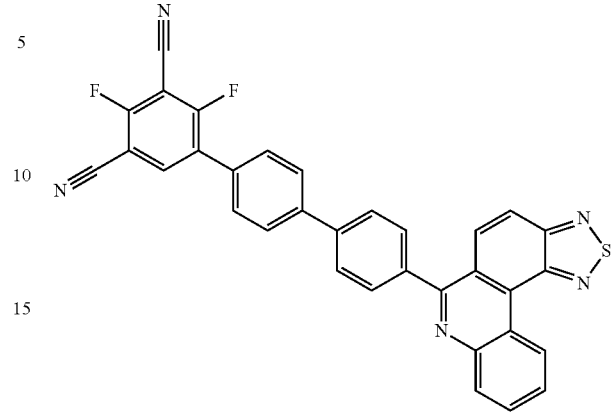
493
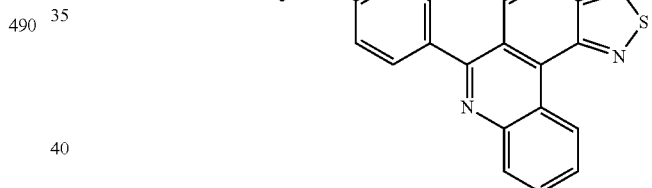
494

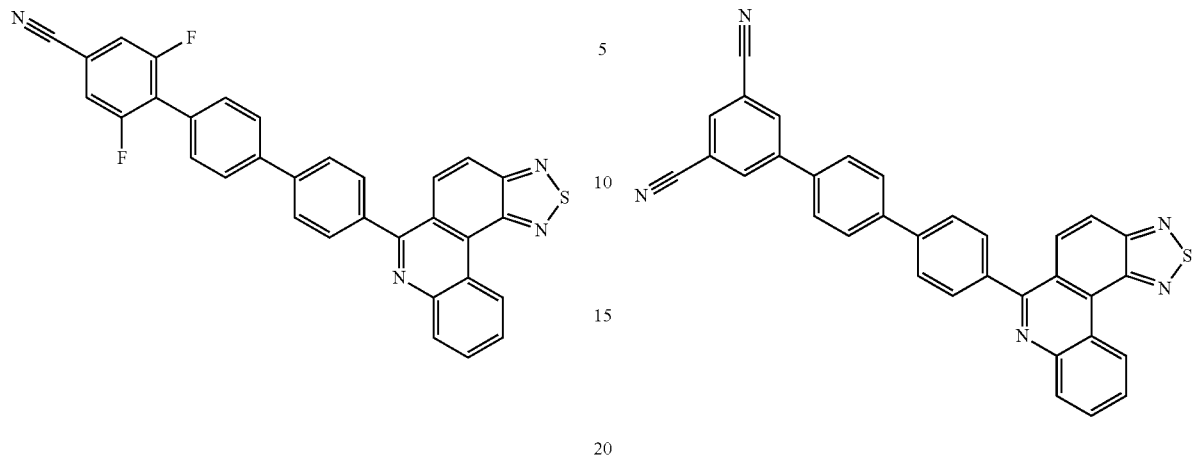
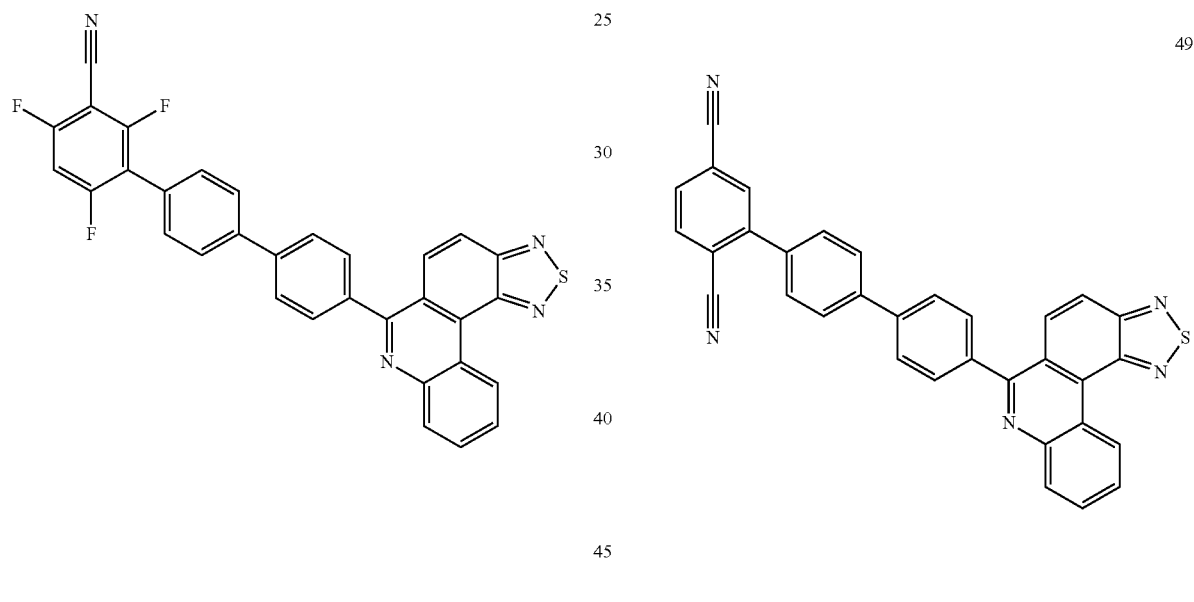
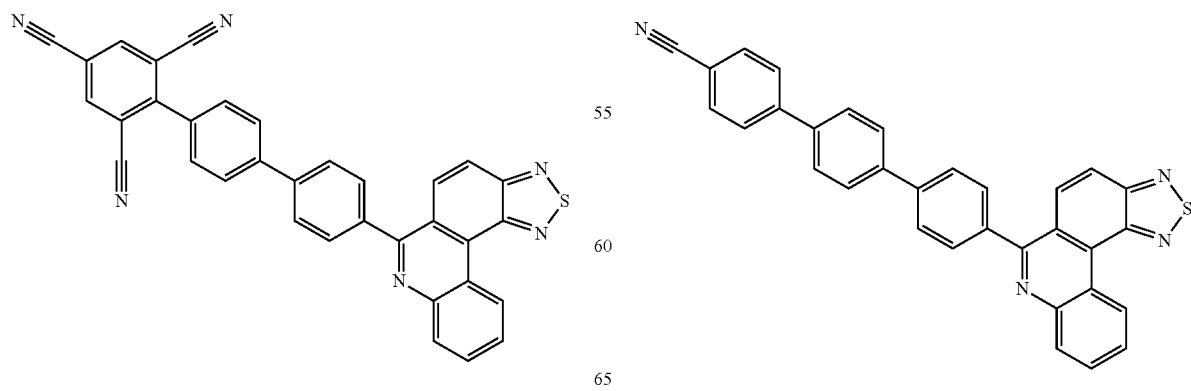

217
-continued
501
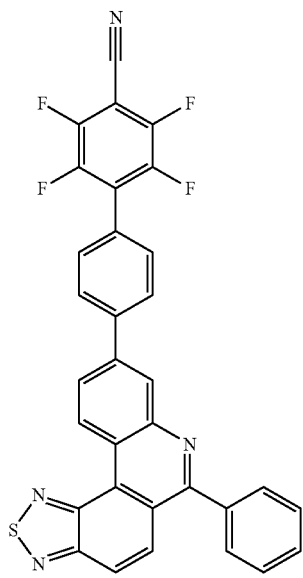
502
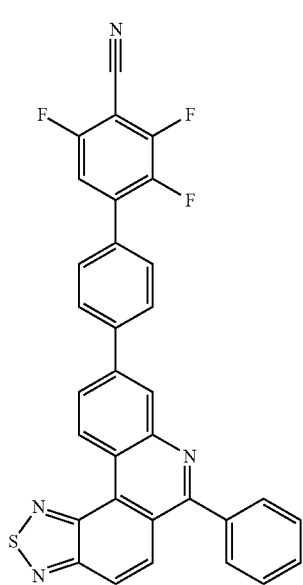
218
-continued
503
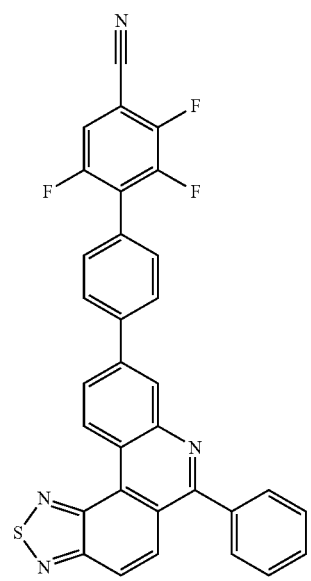
504
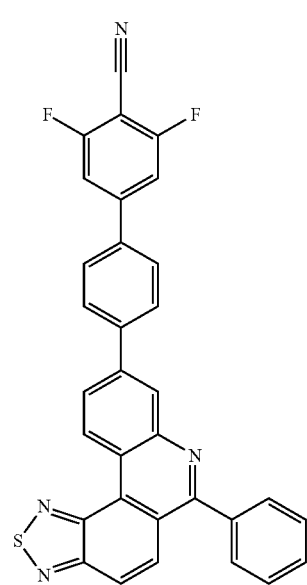

-continued
505
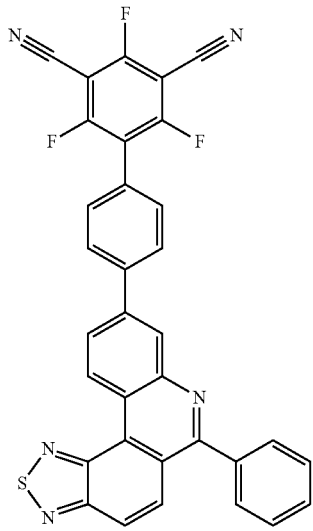
506
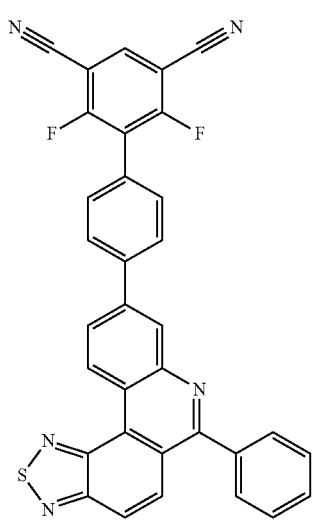
507
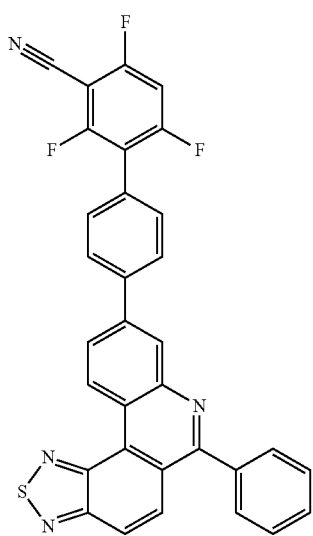
-continued
508
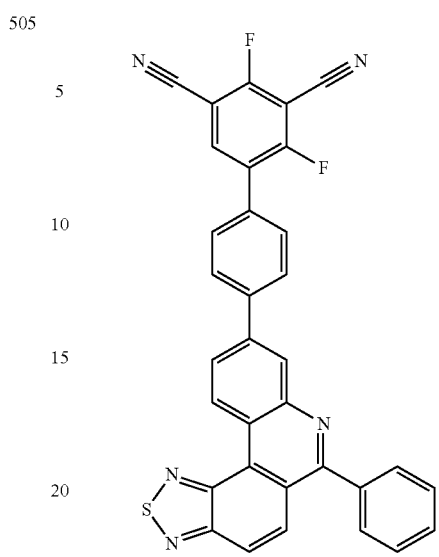
509
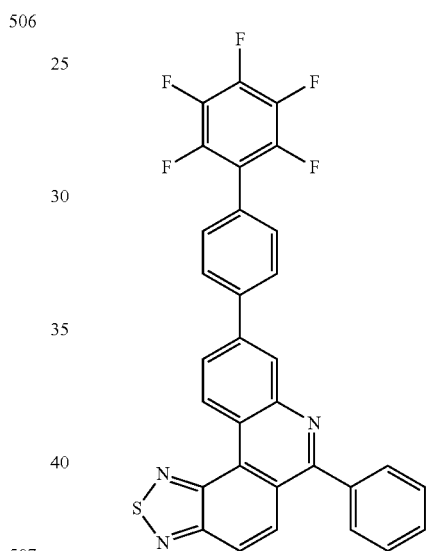
510
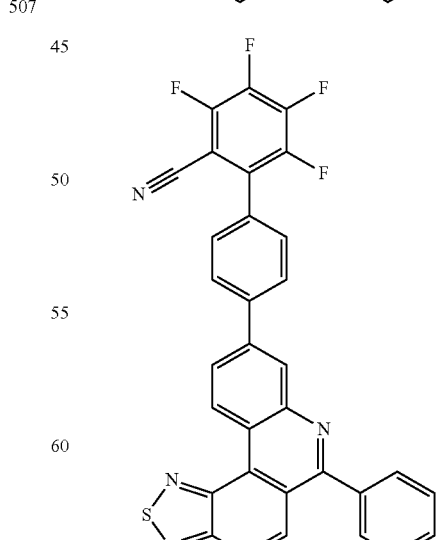

221
-continued
222
-continued
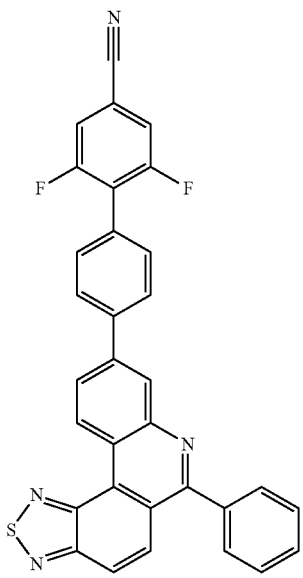
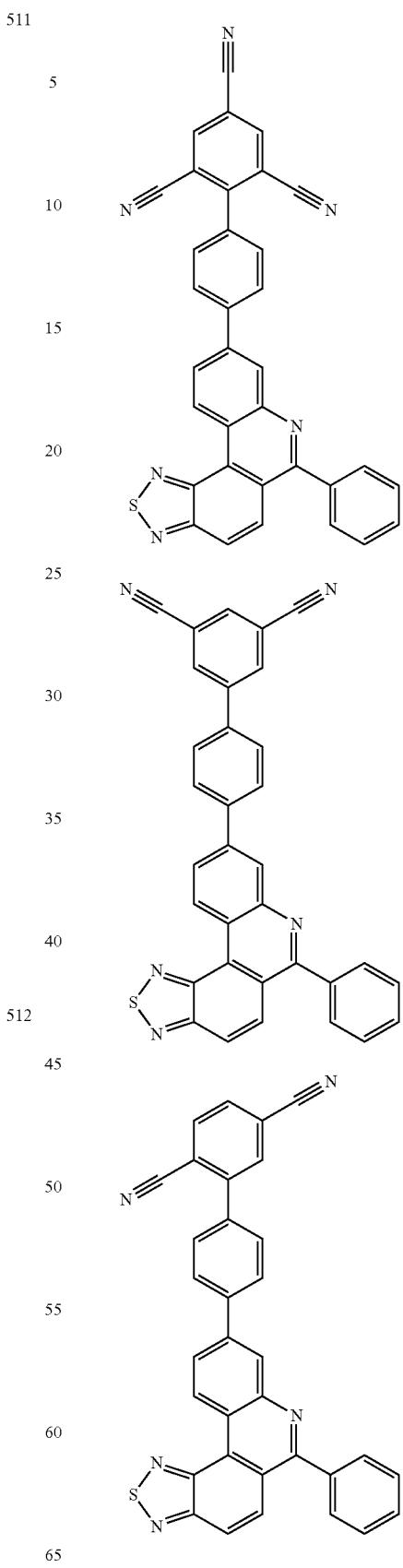

-continued
516
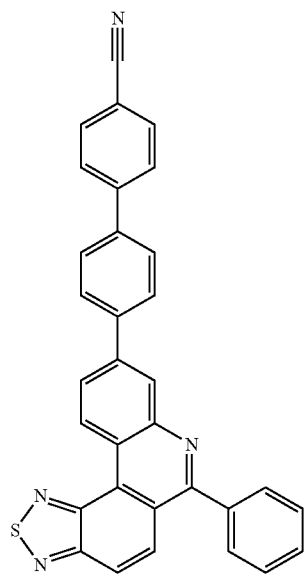
517
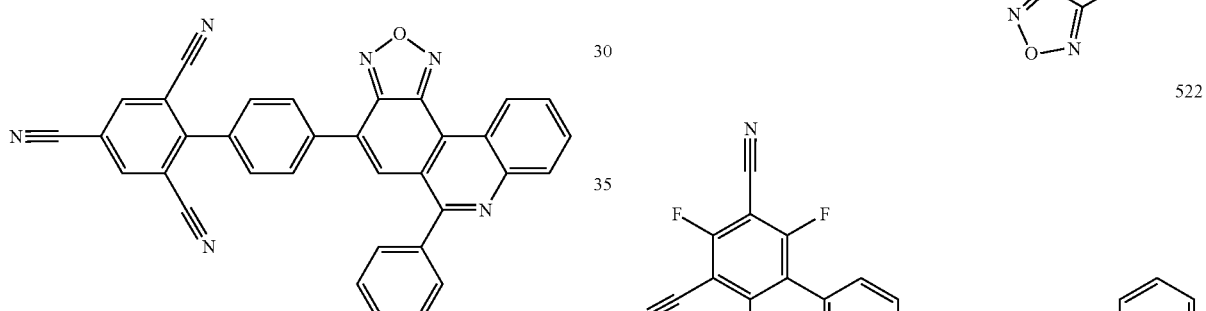
518
519
-continued
520
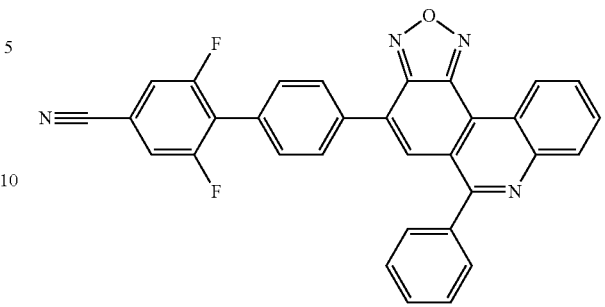
521
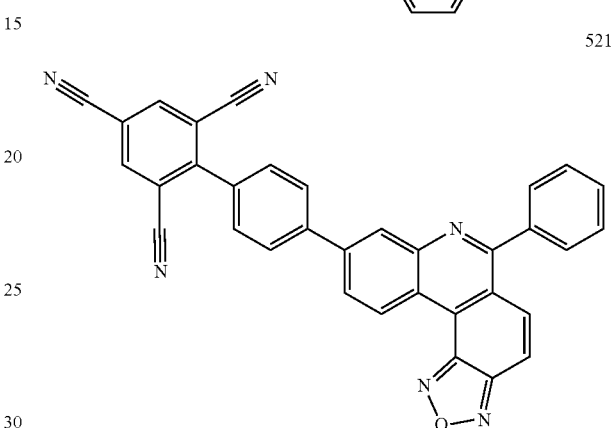
522
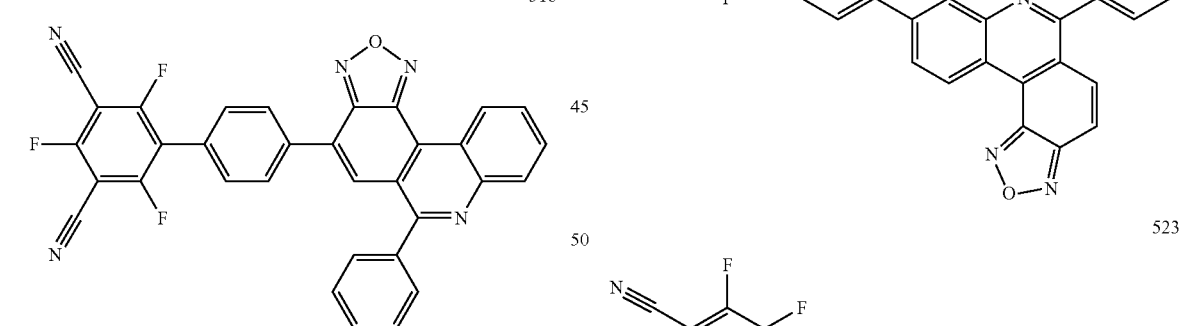
523
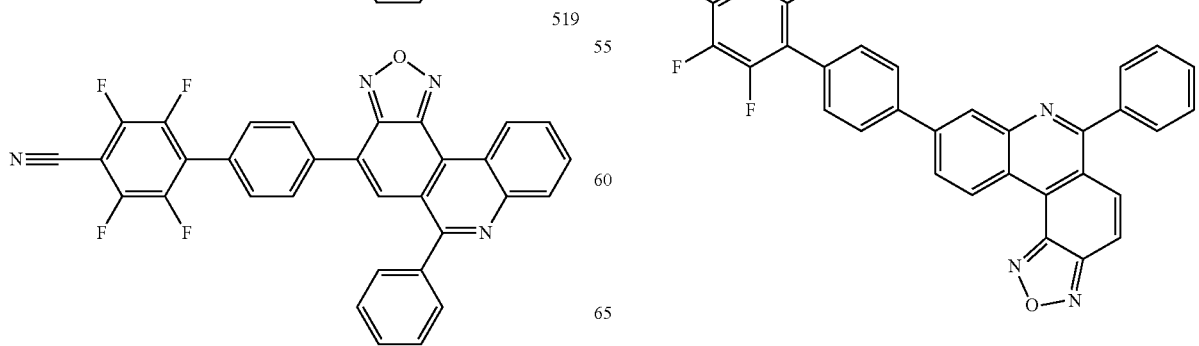

225
-continued
524
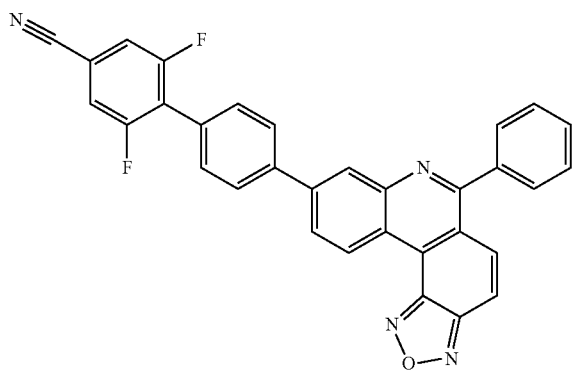
525
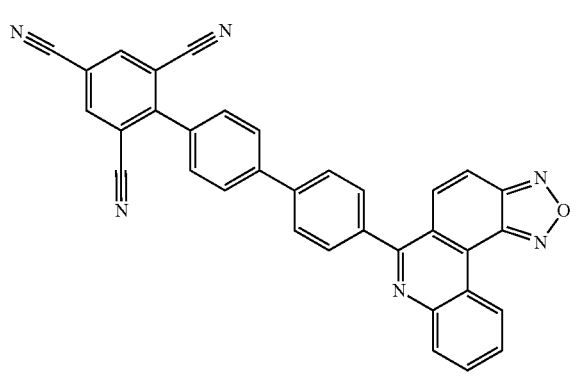
526
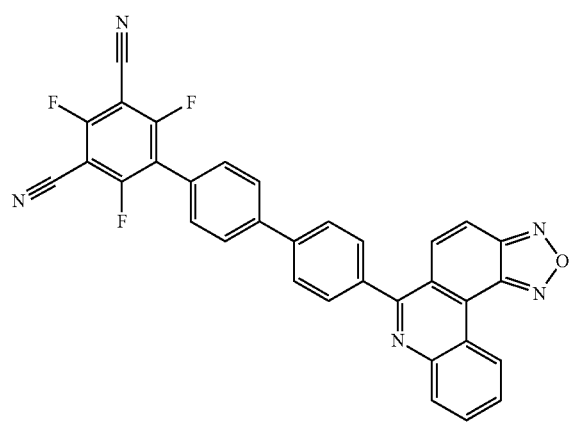
527
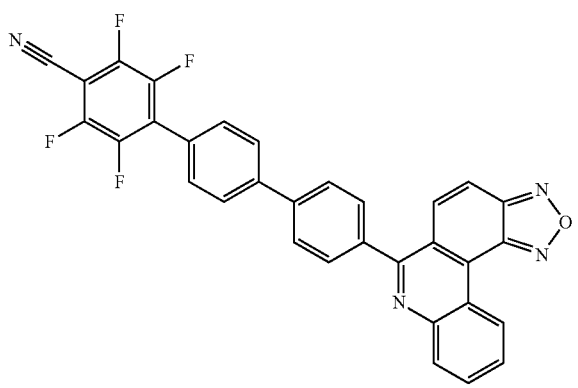
226
-continued
528
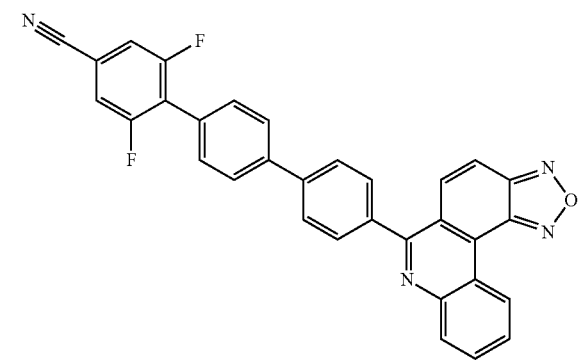
529
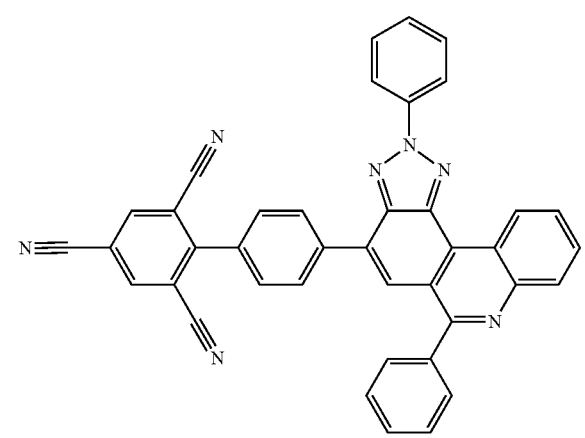
530
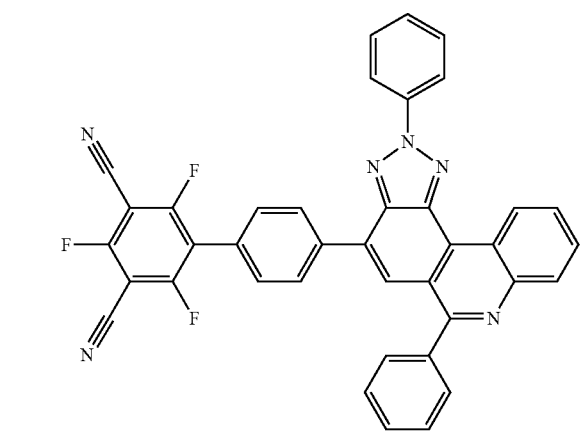

227
-continued
531
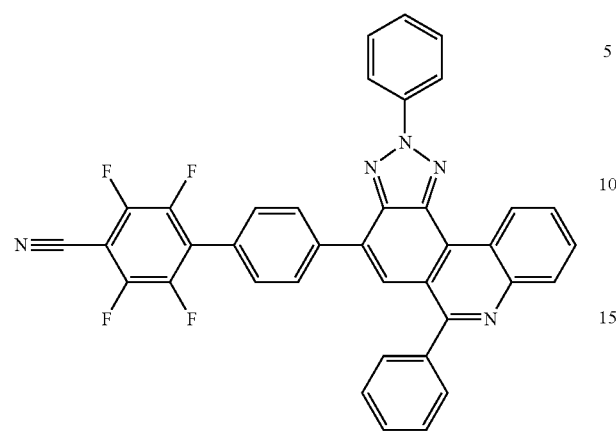
532
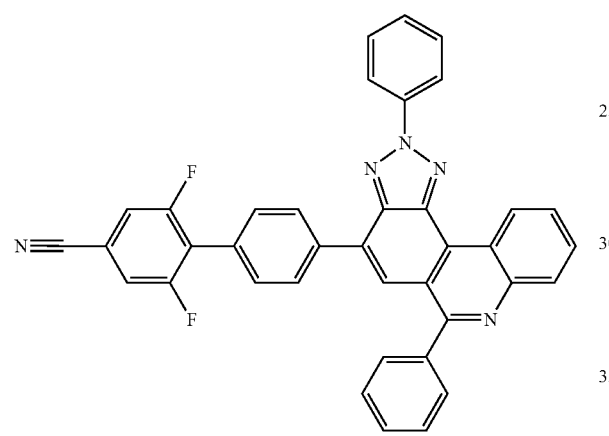
533
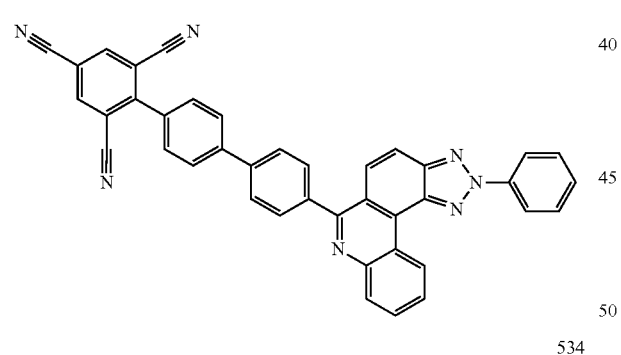
534
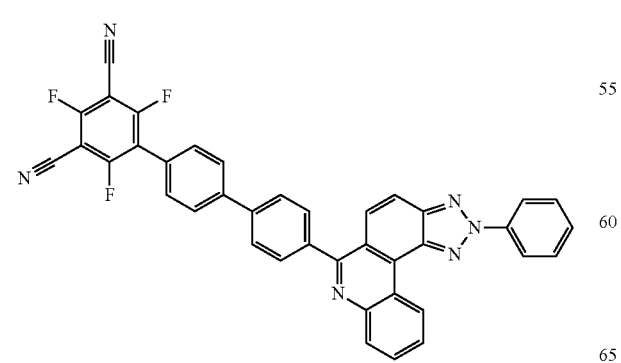
228
-continued
535
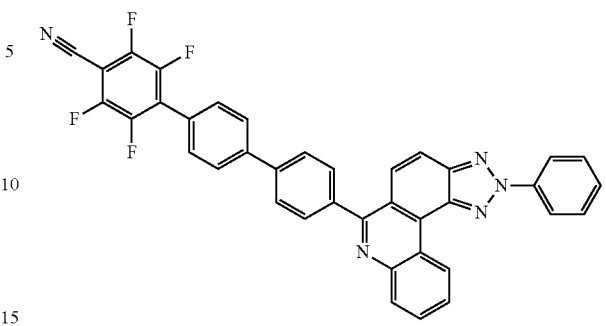
536
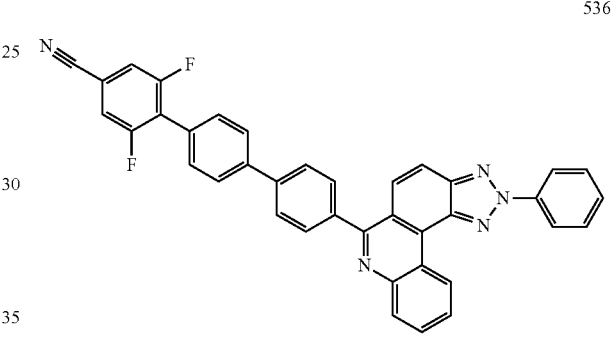
537
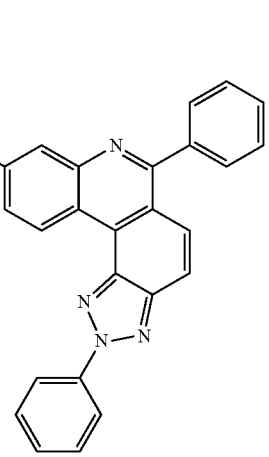

-continued
538
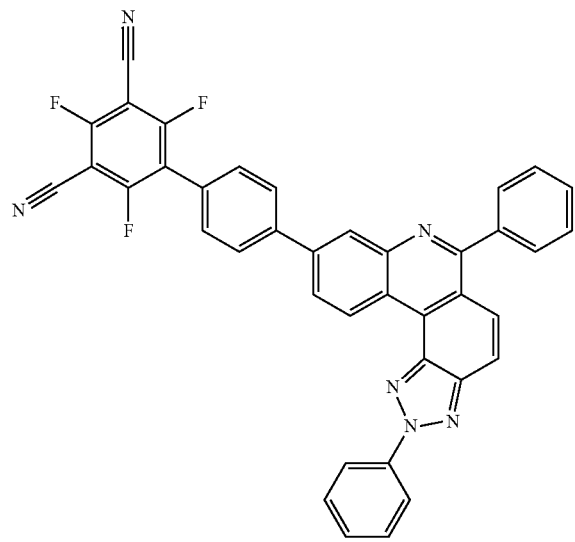
539
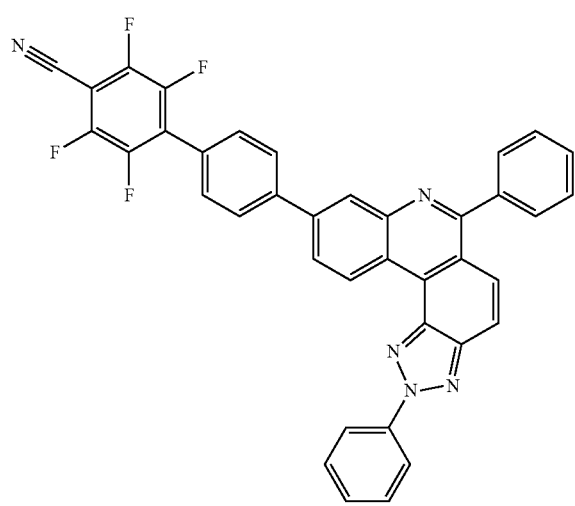
540
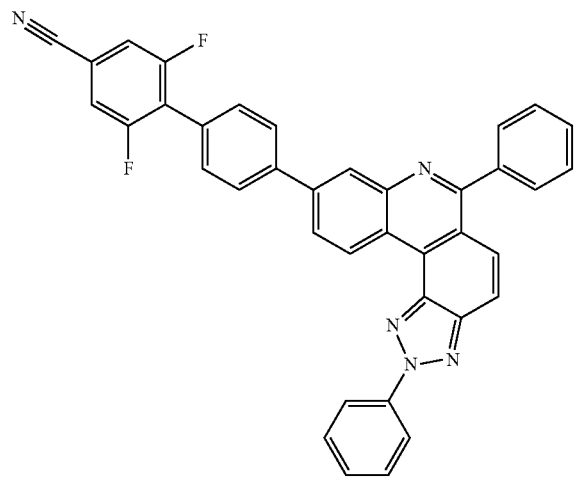
-continued
541
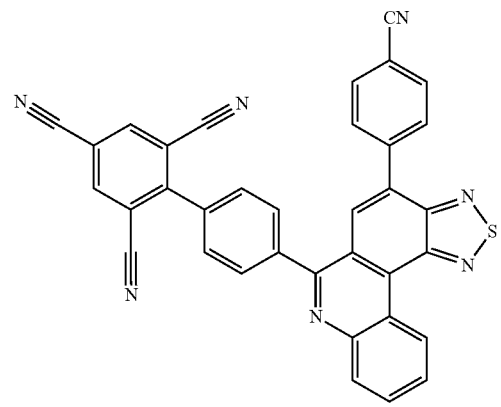
542
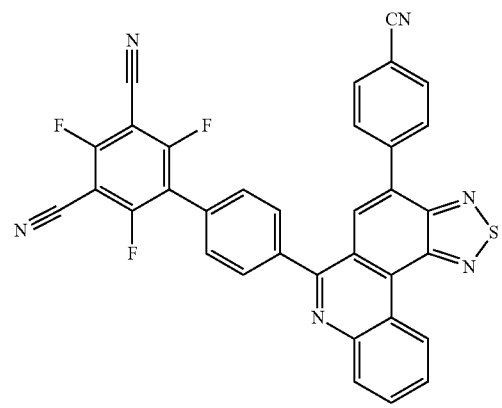
543
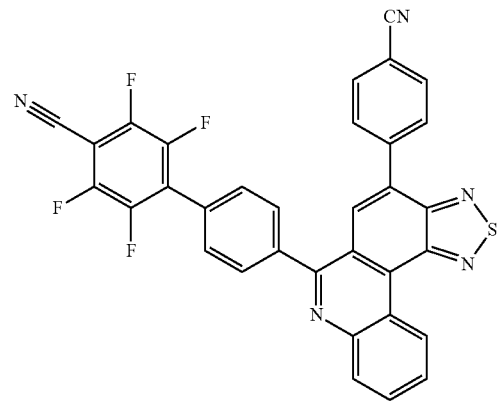

-continued
544
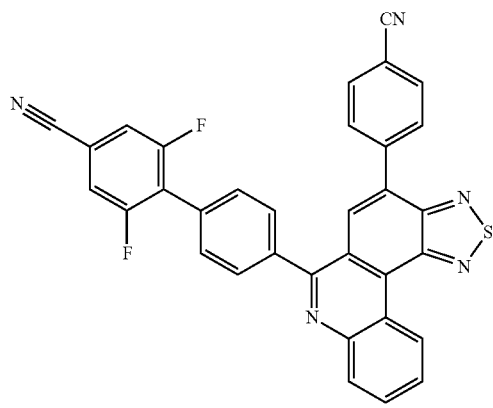
545
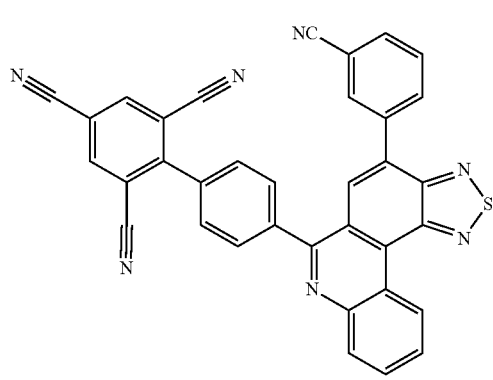
546
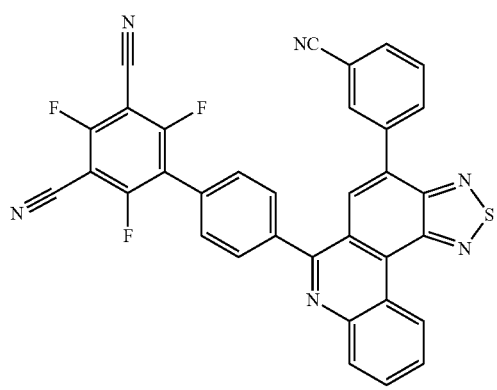
547
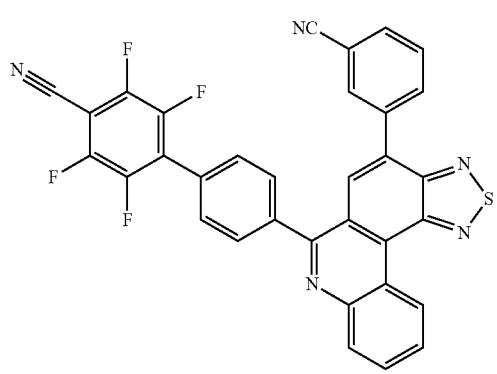
-continued
548
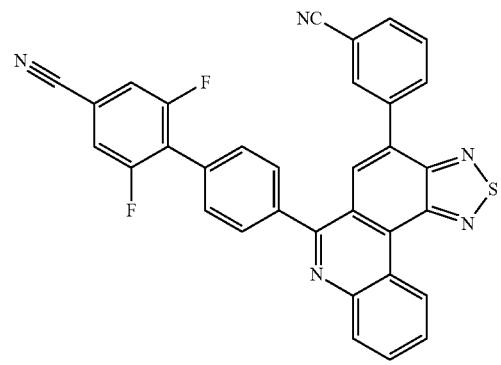
549
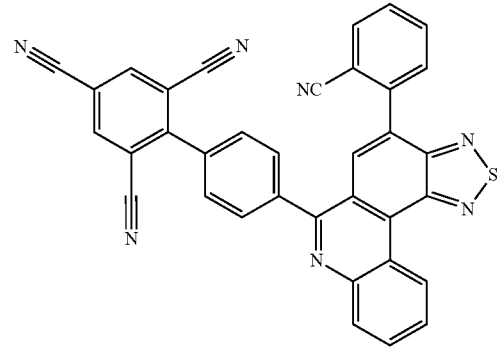
550
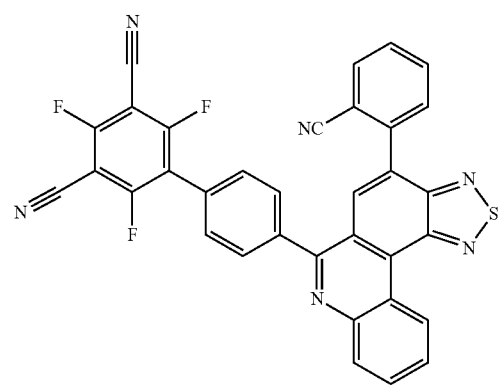
551
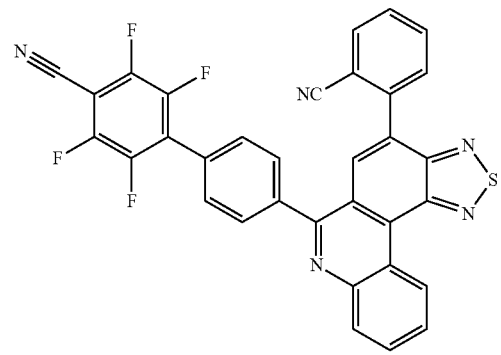

552
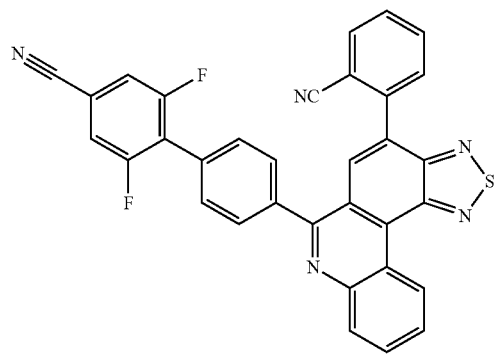
553
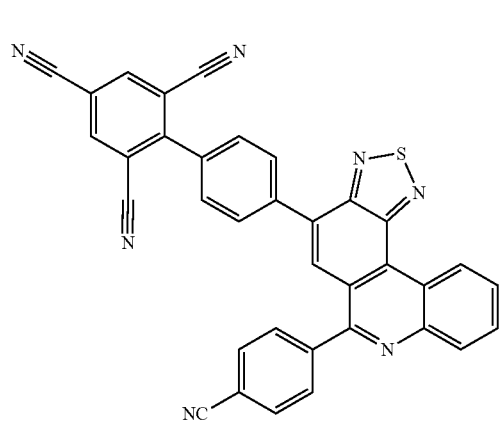
554
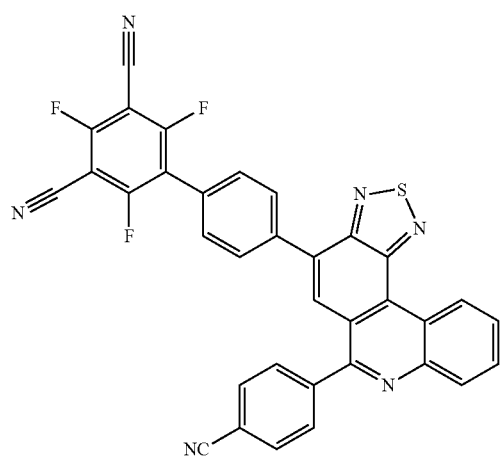
555
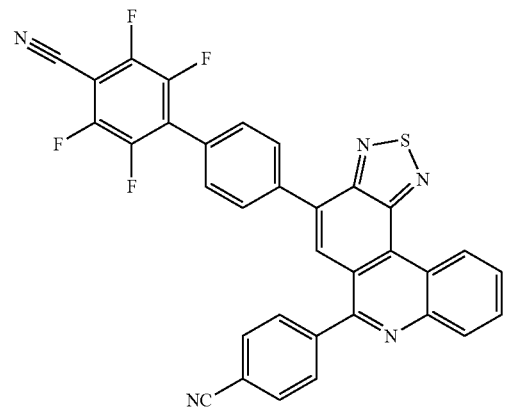
556
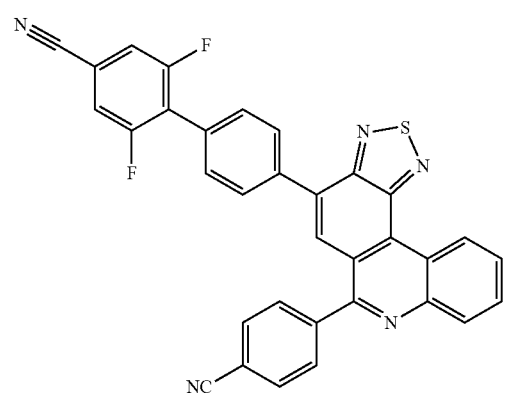
557
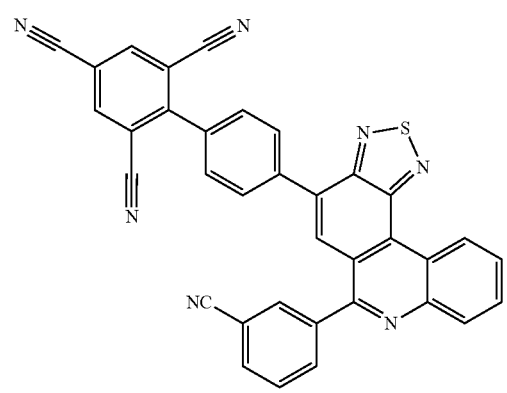

558
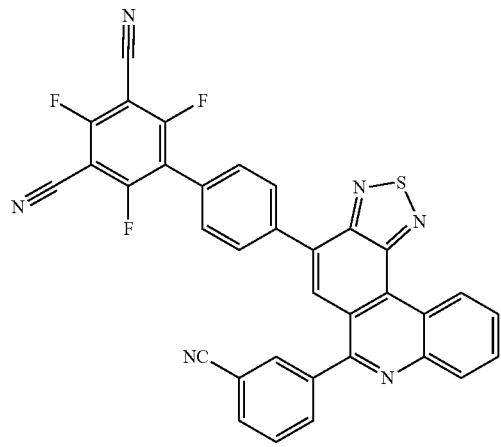
559
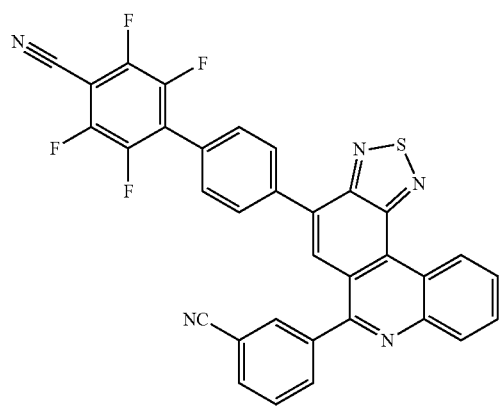
560
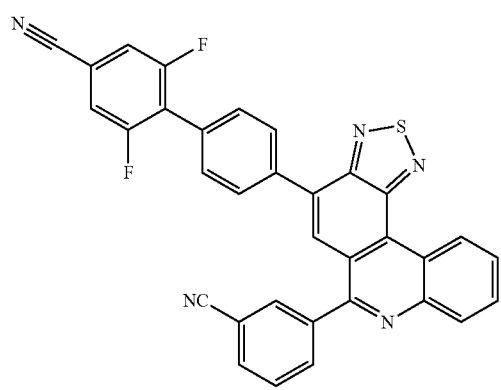
561
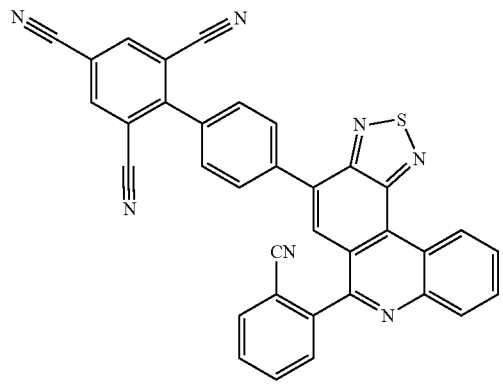
562
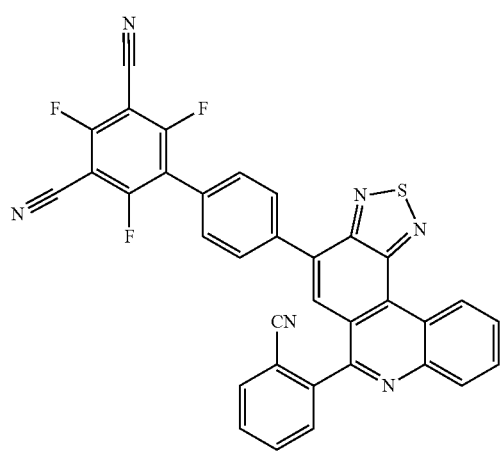
563
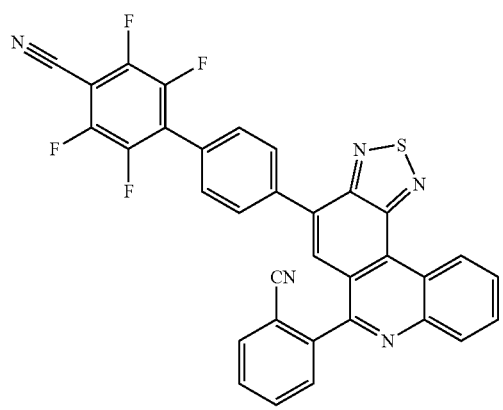

564
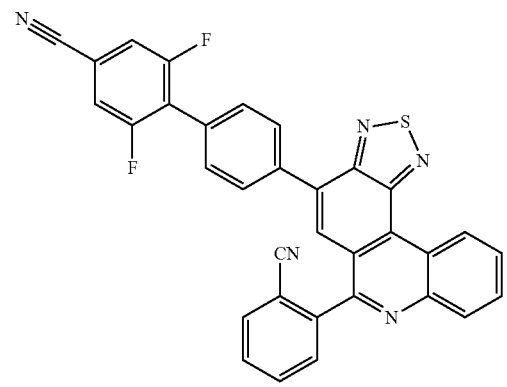
565
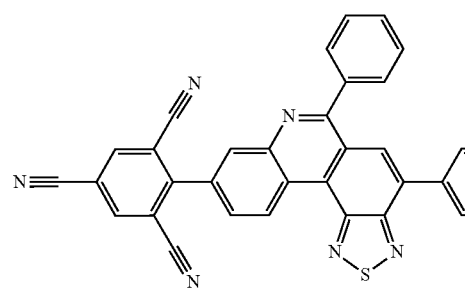
566
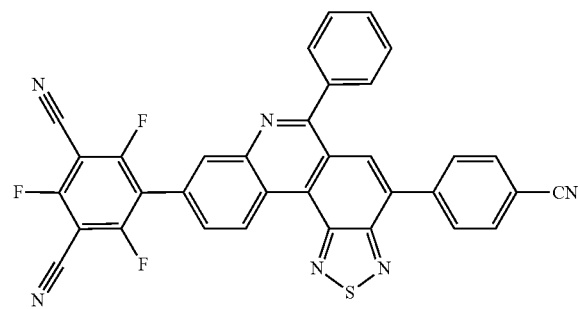
567
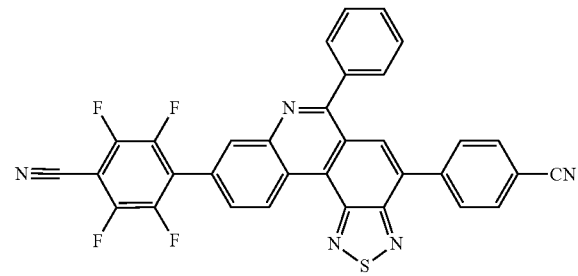
568
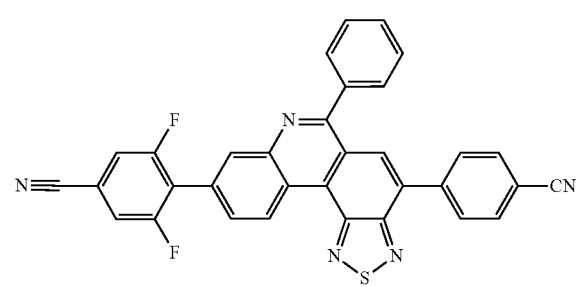
569
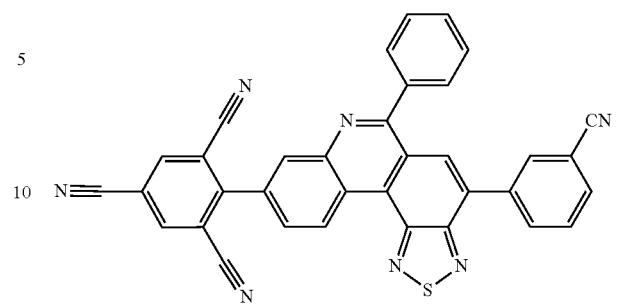
570
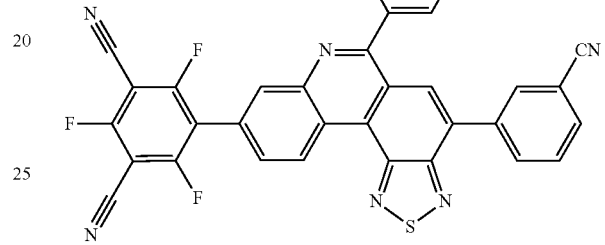
571
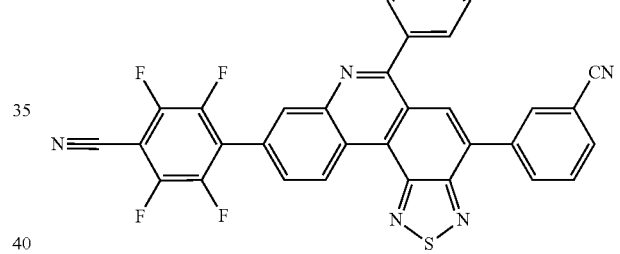
572
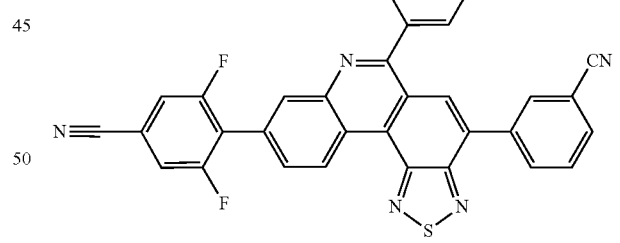
573
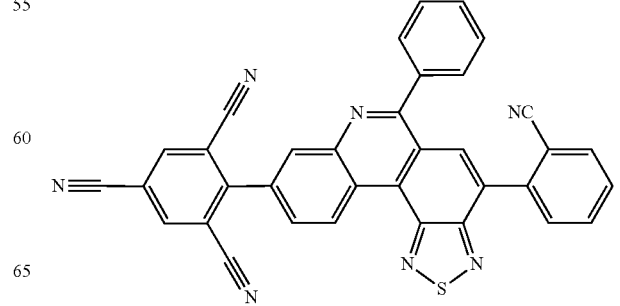

-continued
574
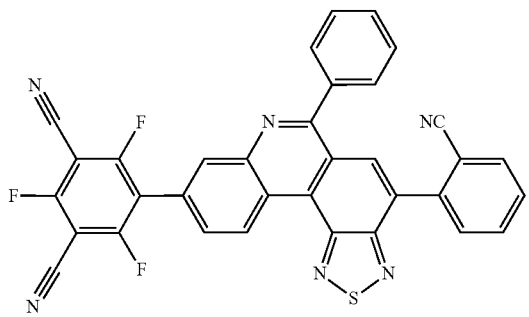
575
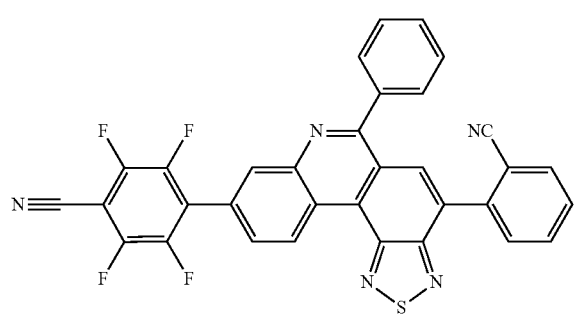
576
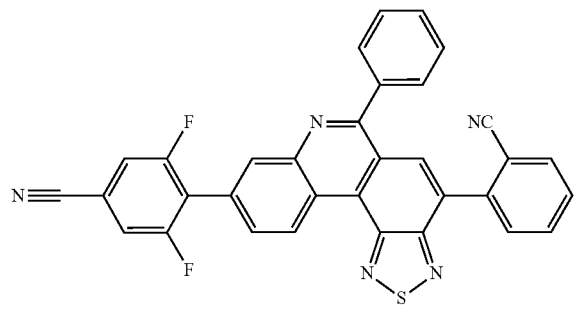
577
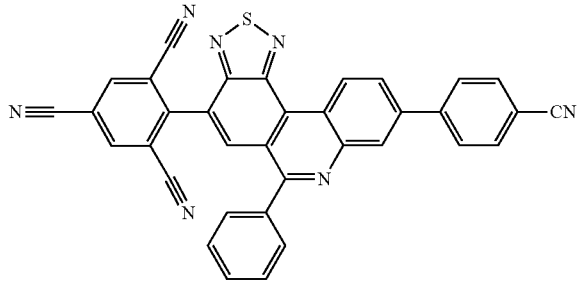
578
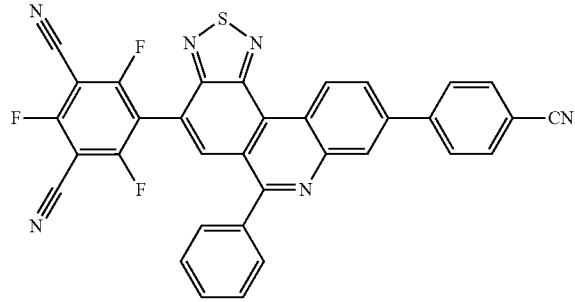
-continued
579
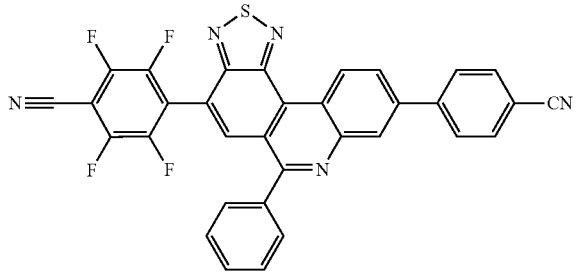
580
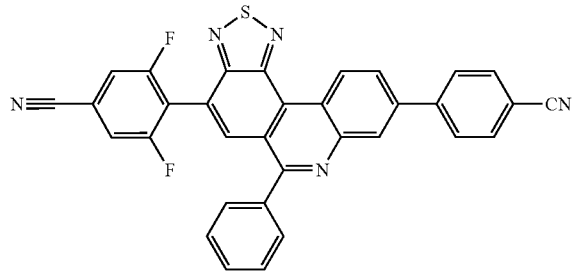
581
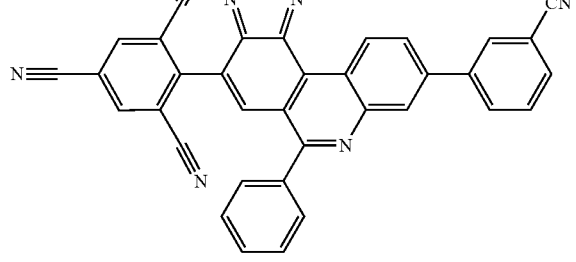
582
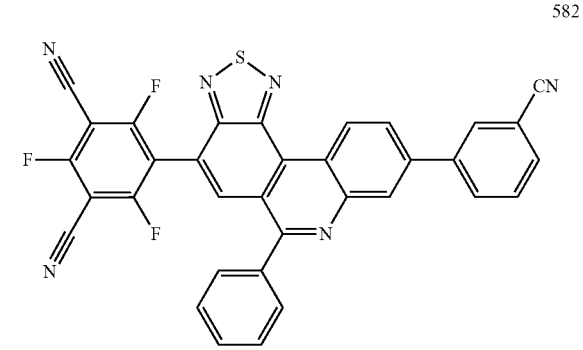
583
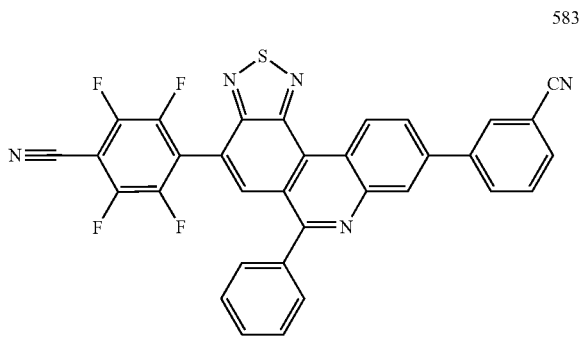

584
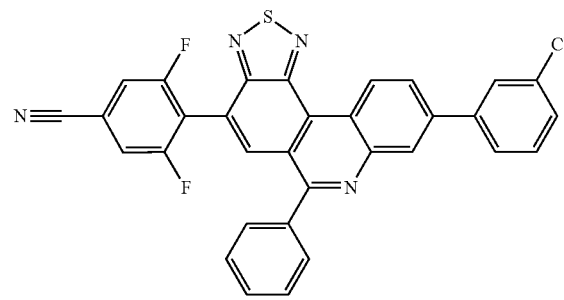
585
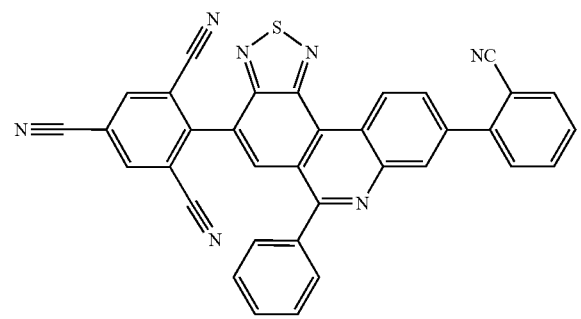
586
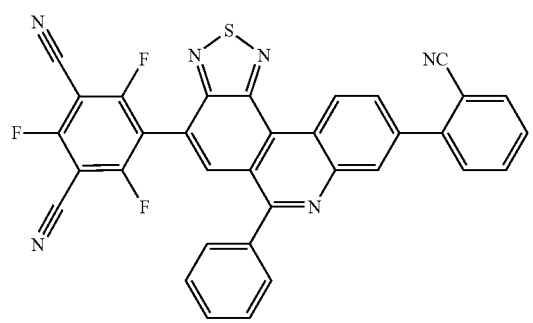
587
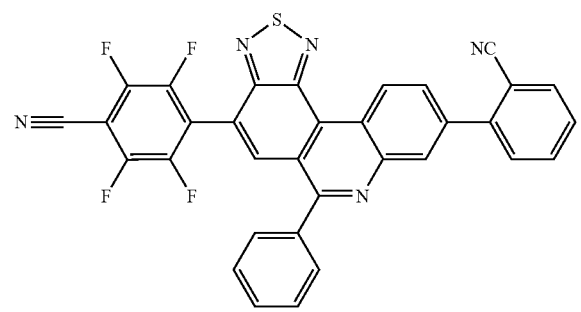
588
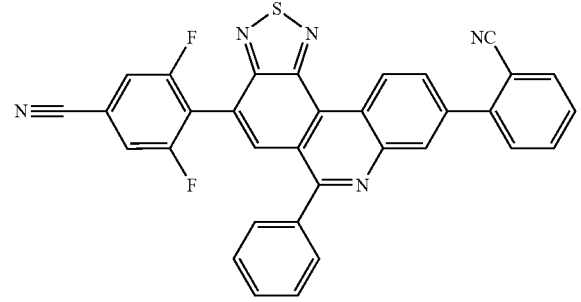
589
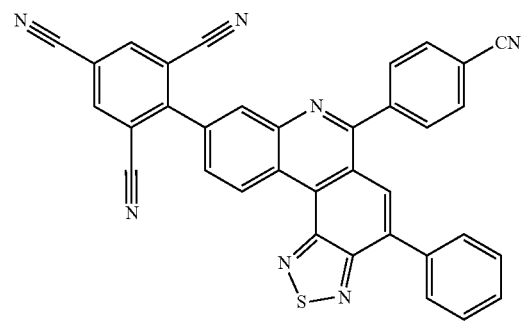
590
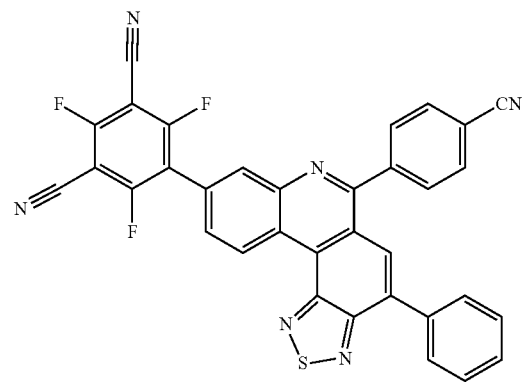
591
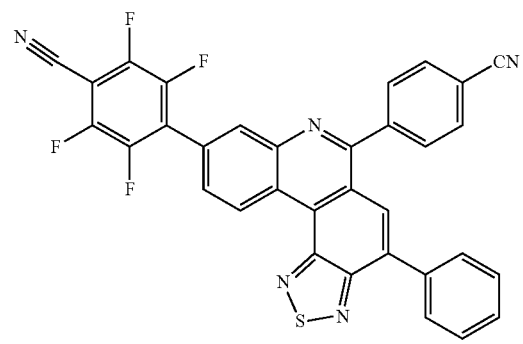
592
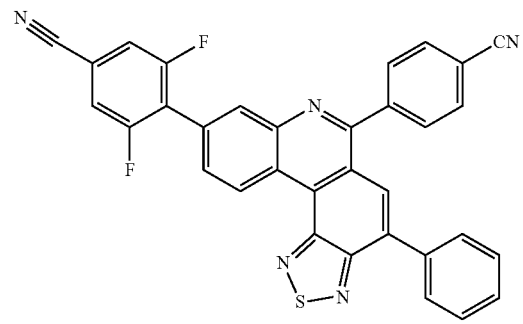

593
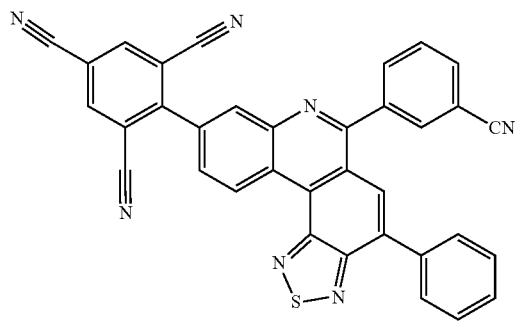
594
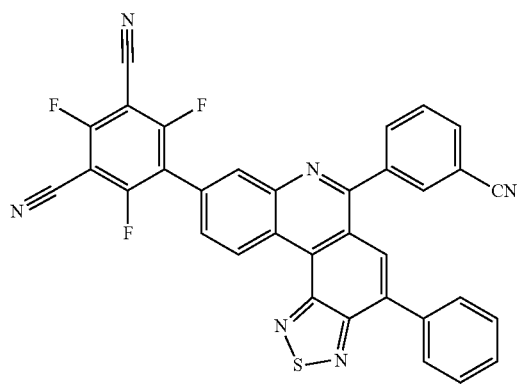
595
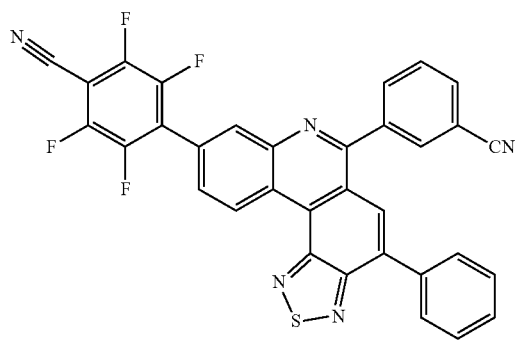
596
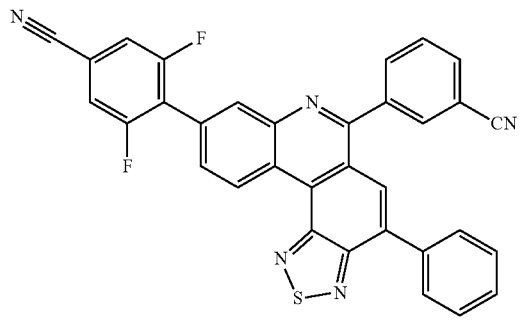
597
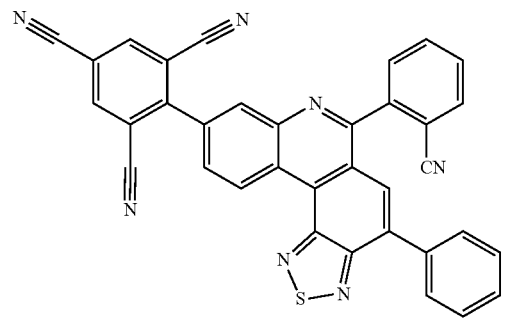
598
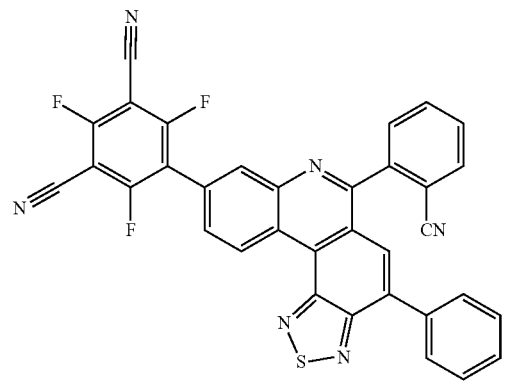
599
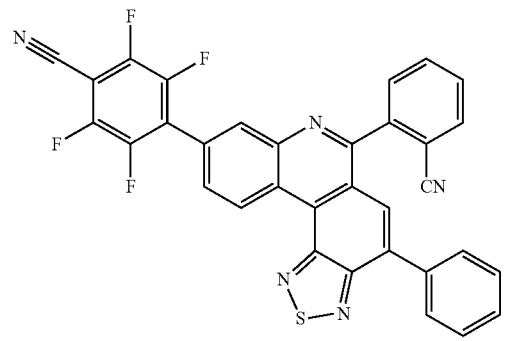
600
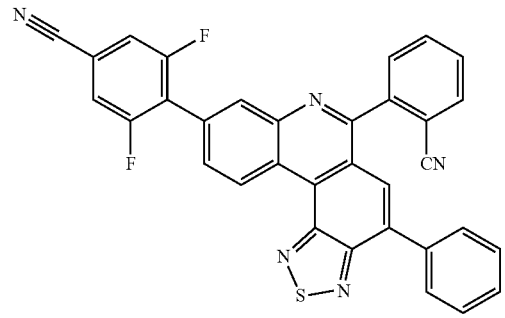

-continued
601
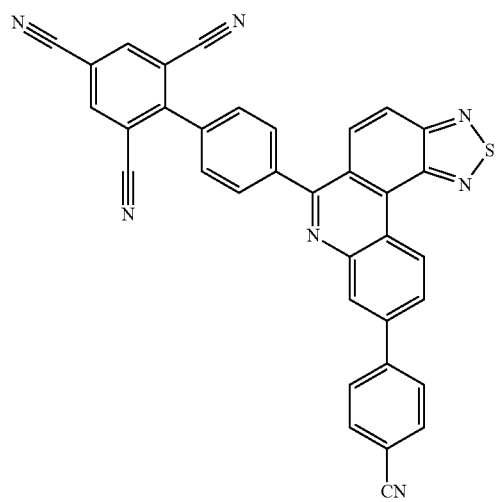
602
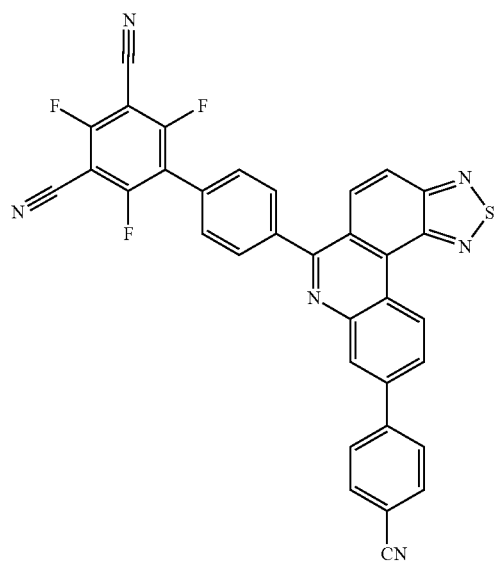
603
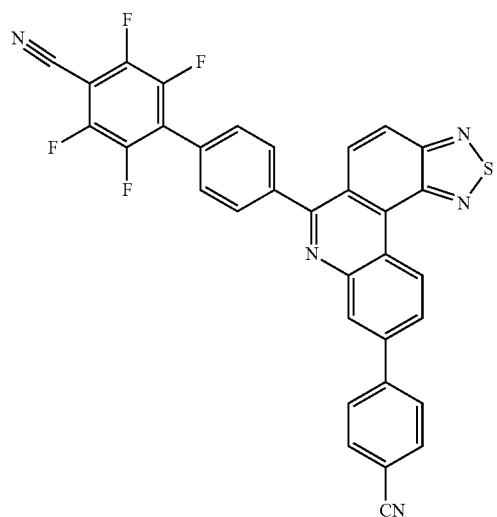
604
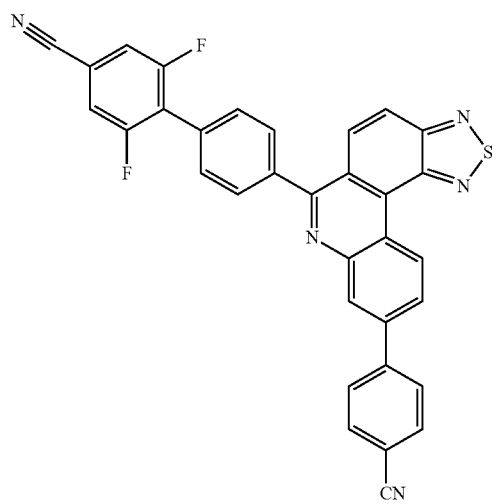
605
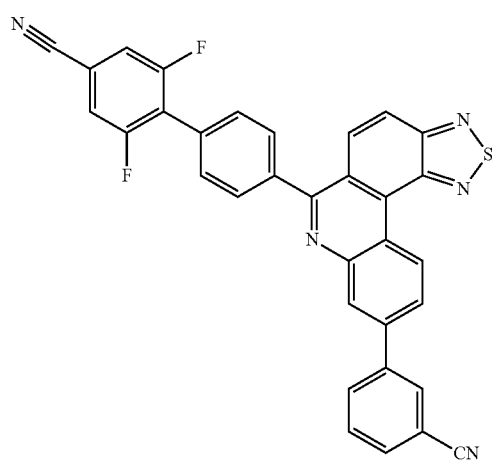
606
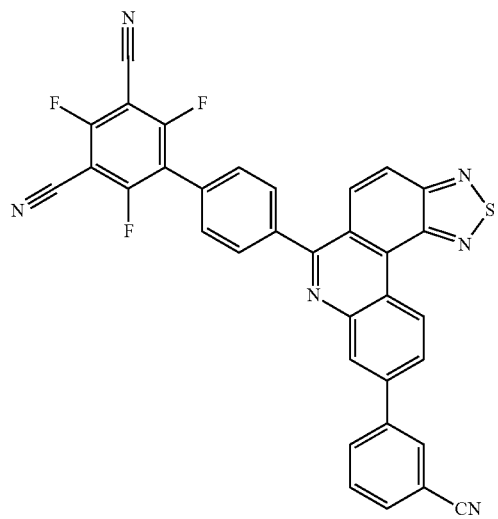

607
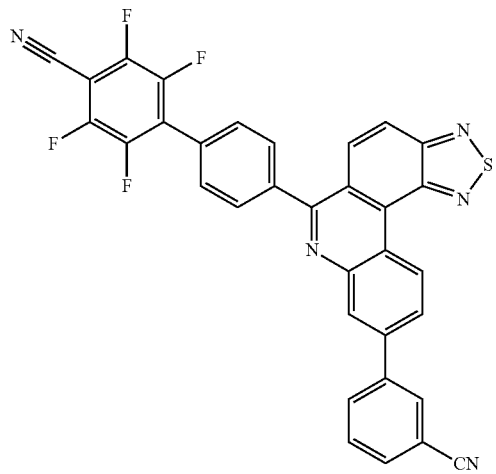
608
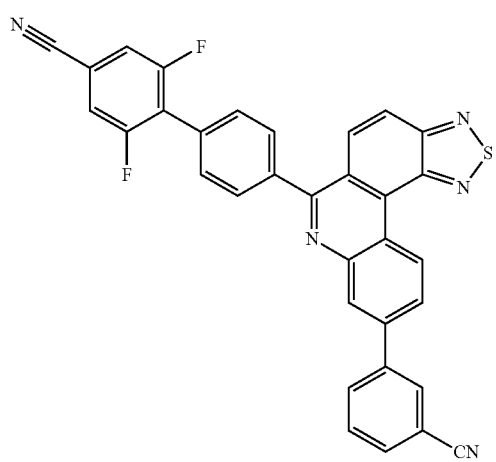
609
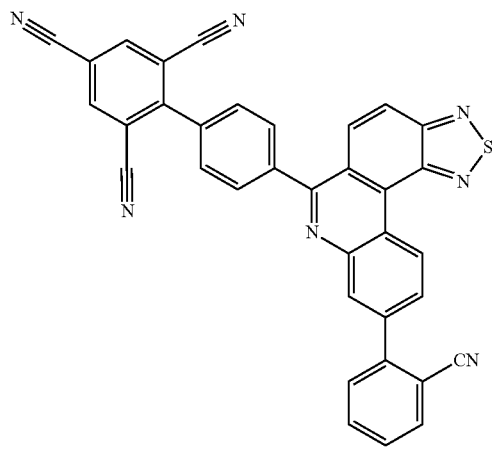
610
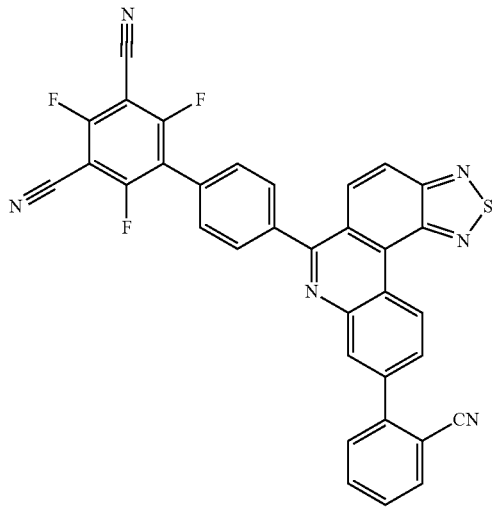
611
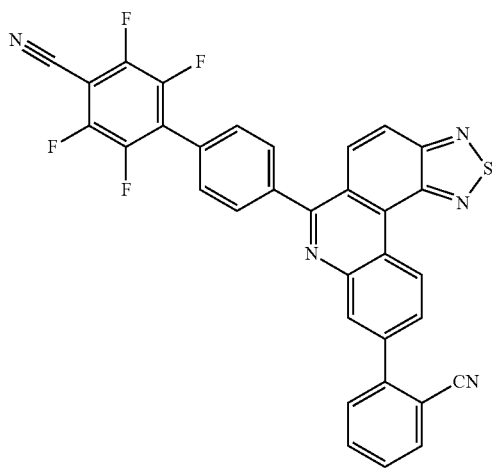
612
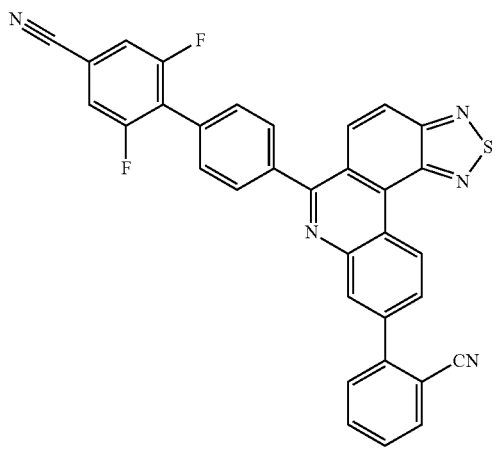

-continued
613
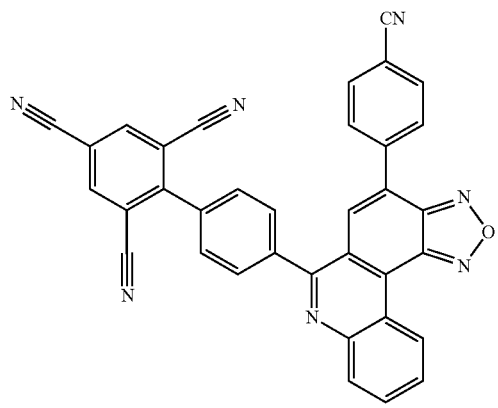
614
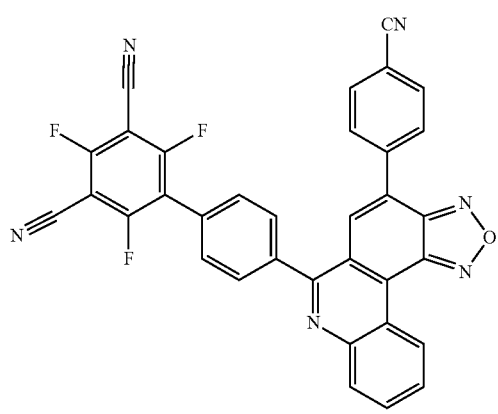
615
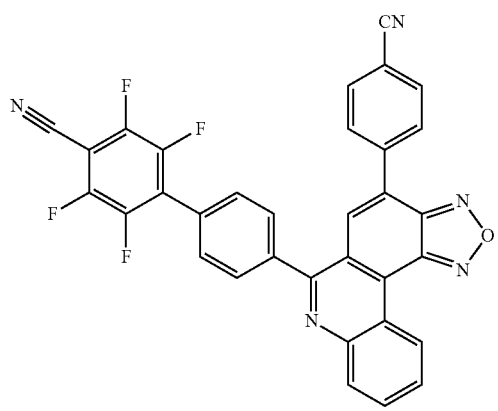
-continued
616
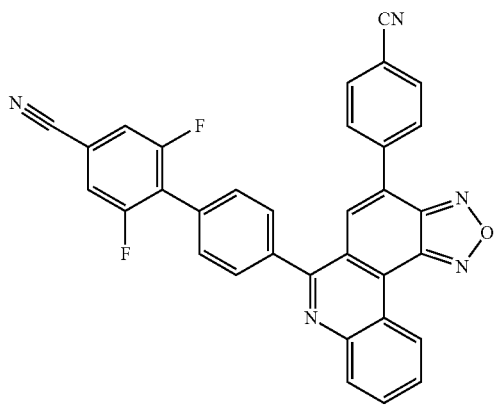
617
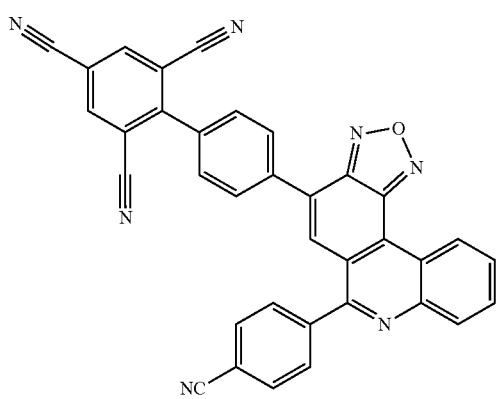
618
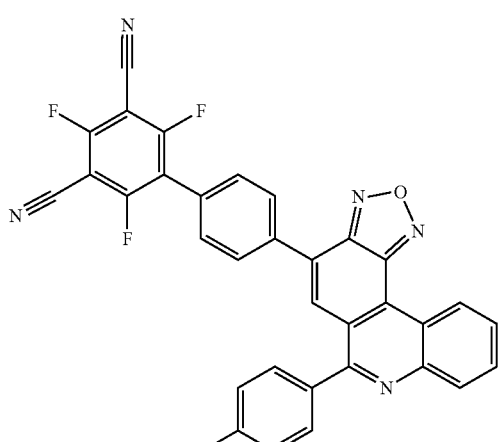

251
-continued
619
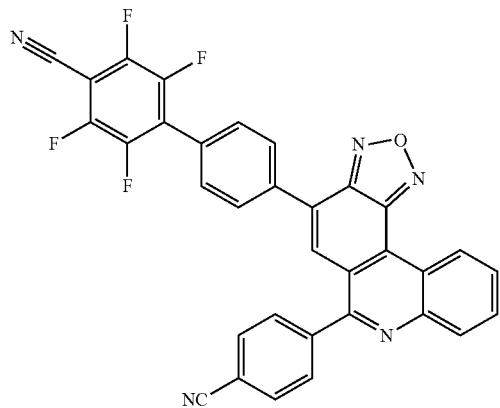
620
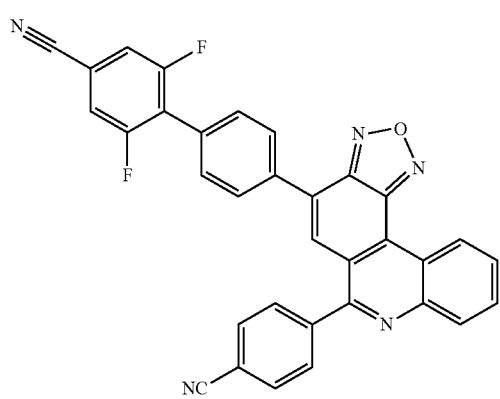
621
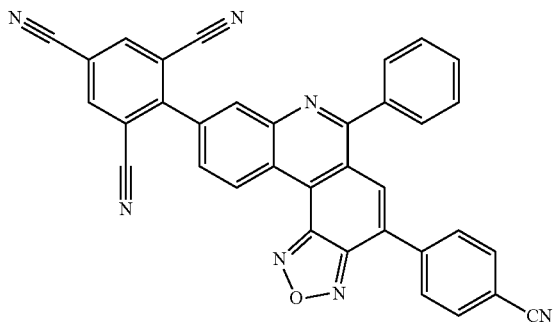
622
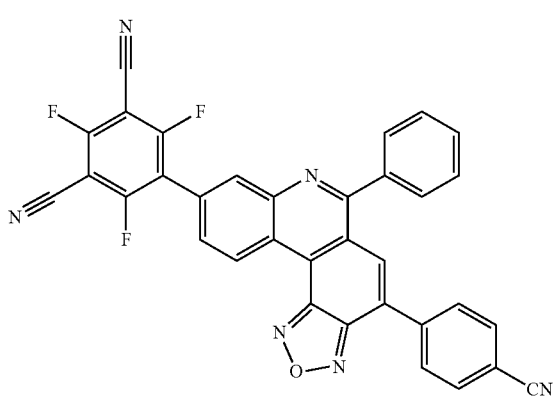
252
-continued
623
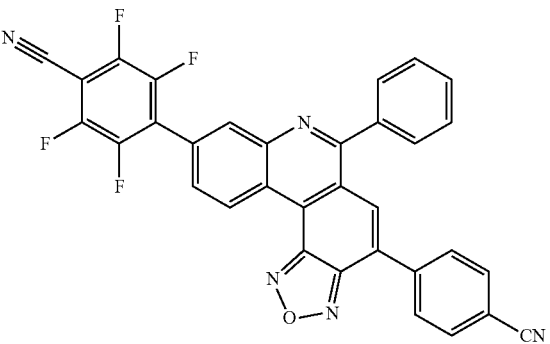
624
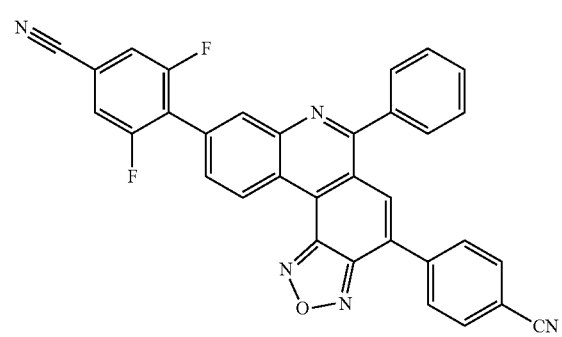
625
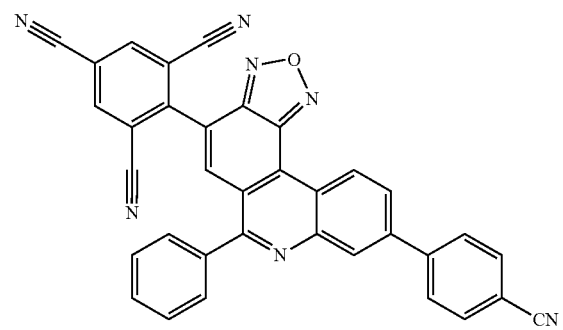
626
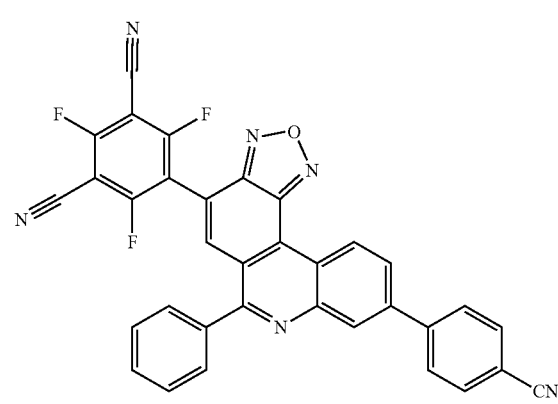

253
-continued
627
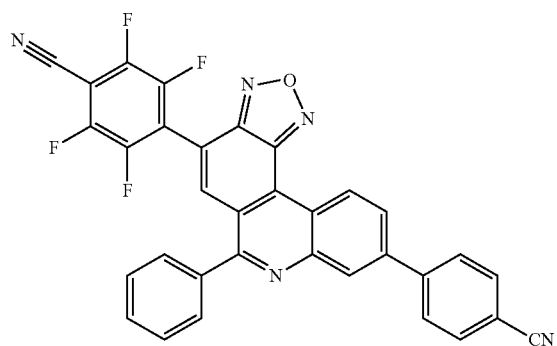
628
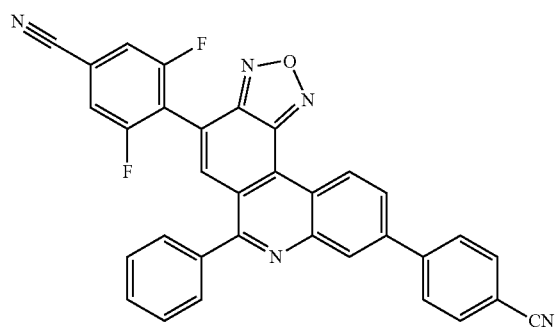
629
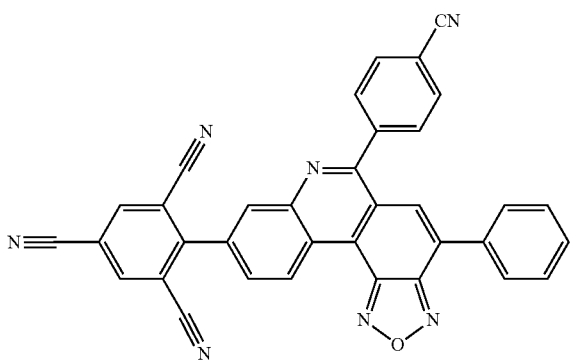
630
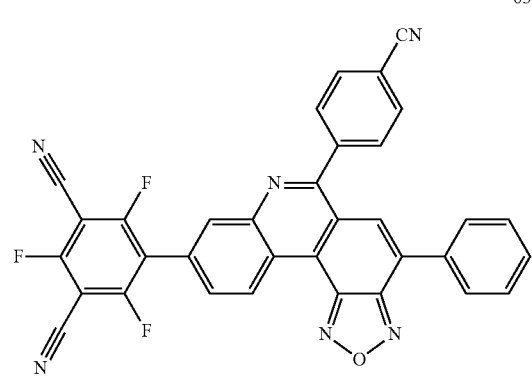
254
-continued
631
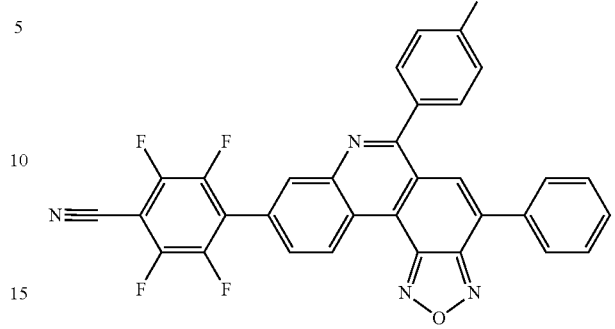
632
633
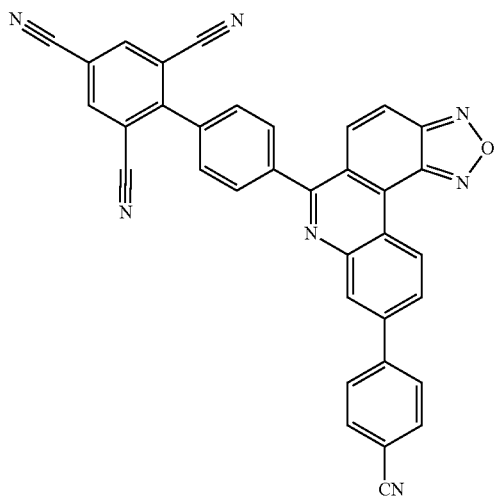

255
-continued
634
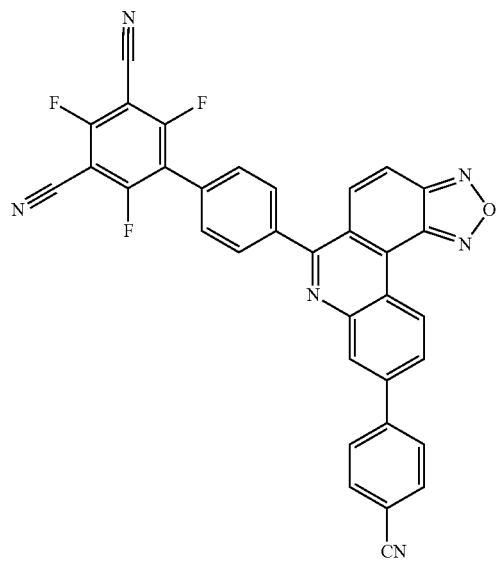
635
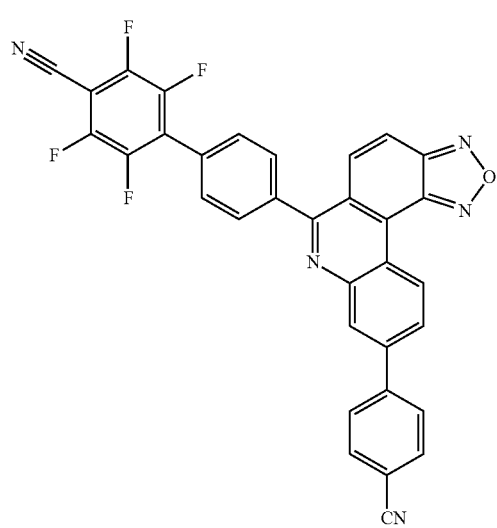
636
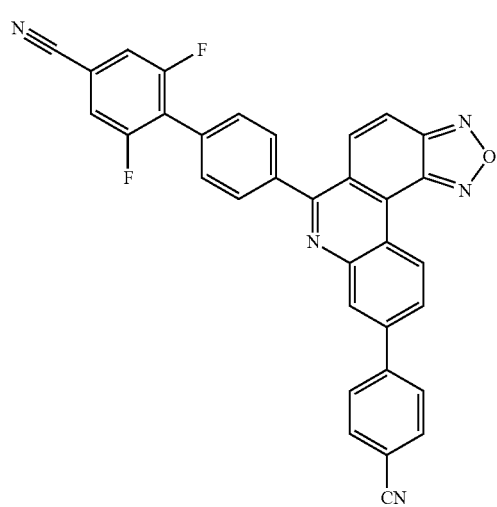
256
-continued
637
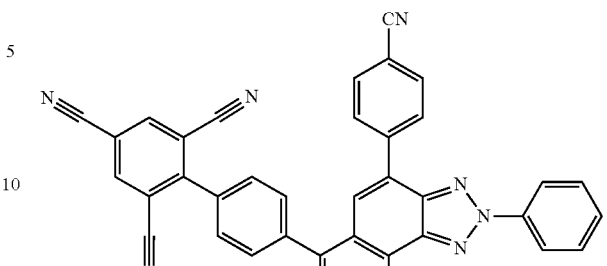
638
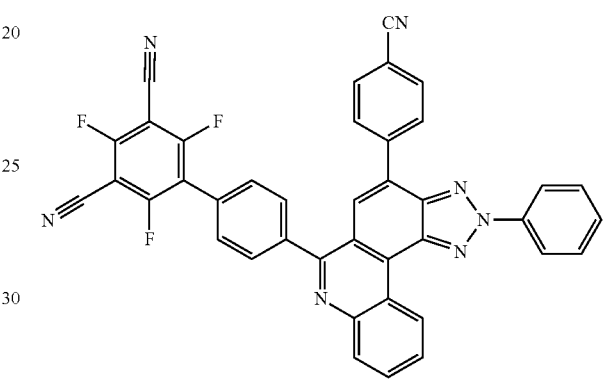
639
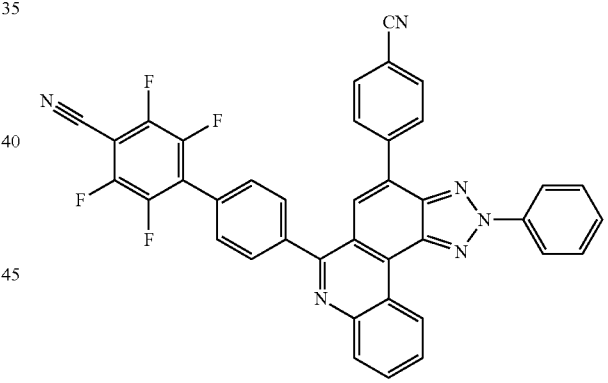
640
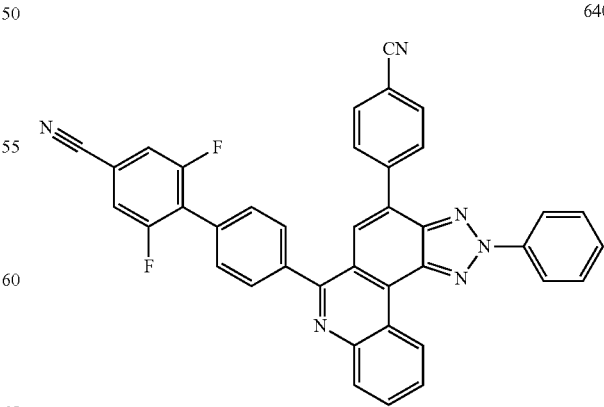

641
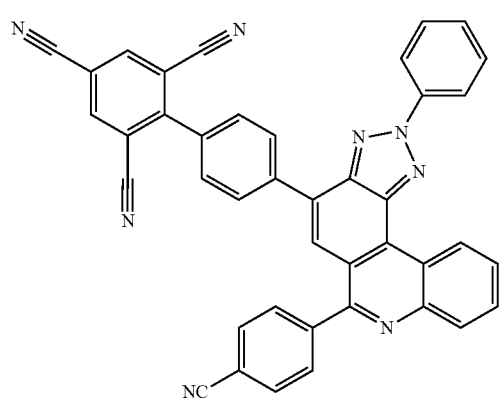
642
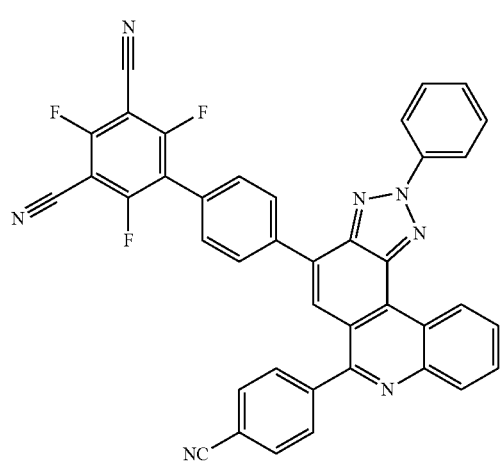
643
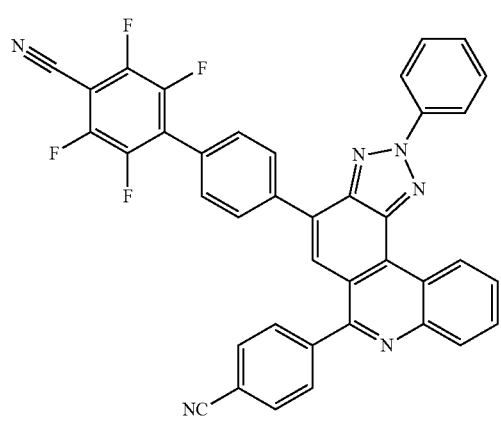
644
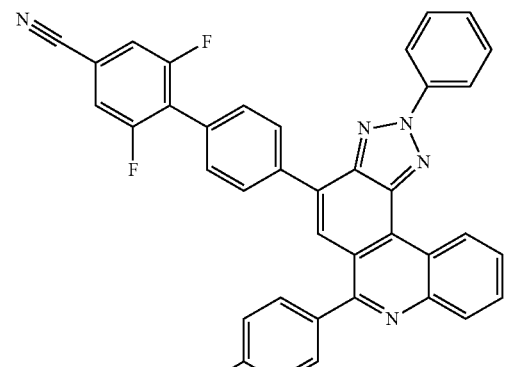
645
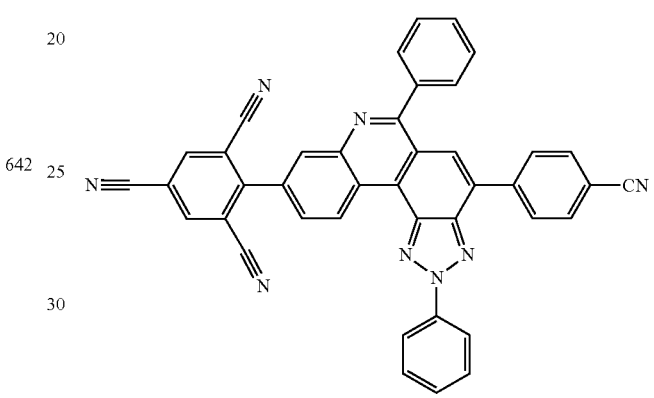
646
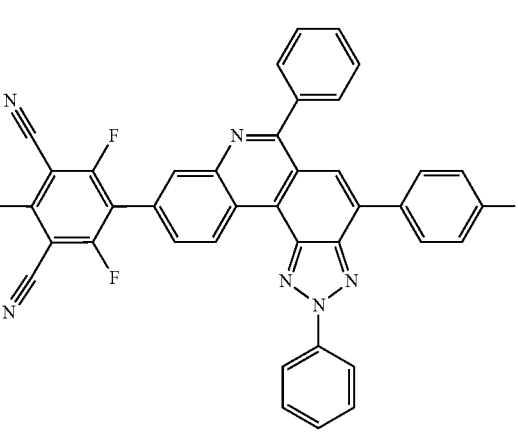
647
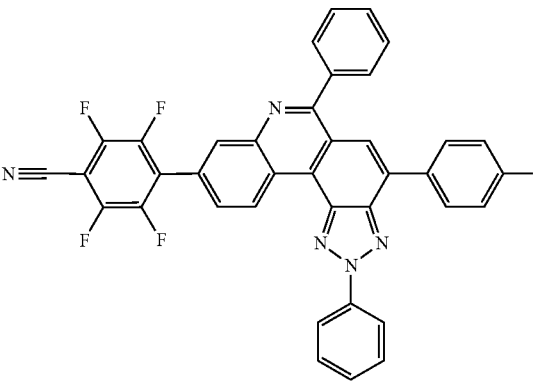

-continued
648
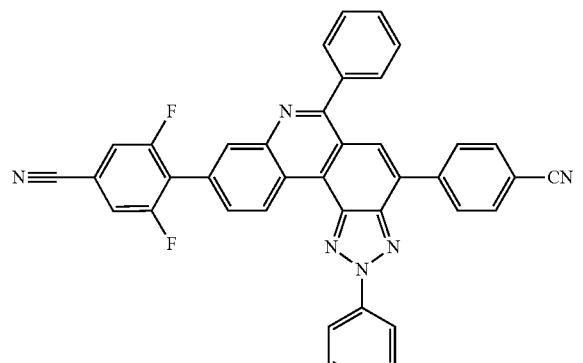
649
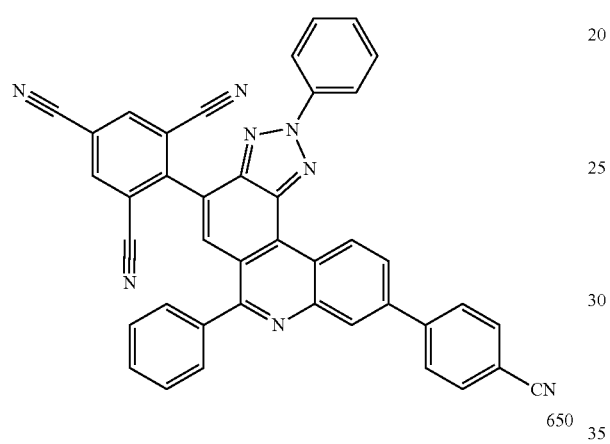
650
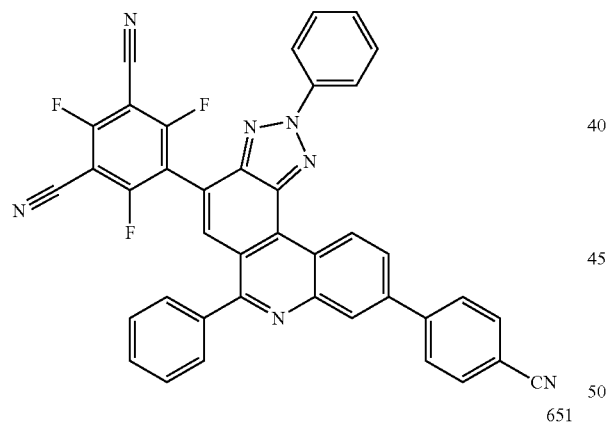
651
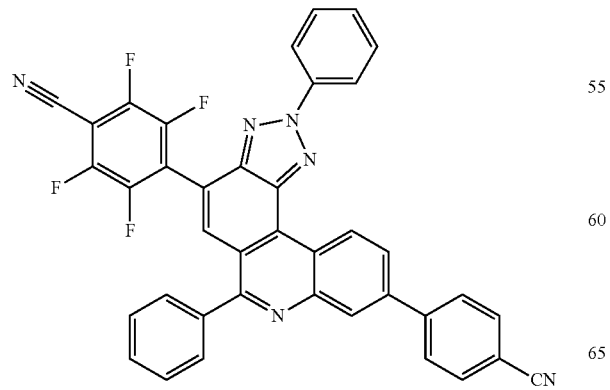
-continued
652
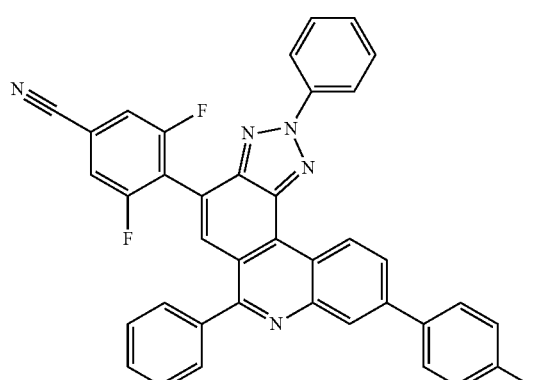
653
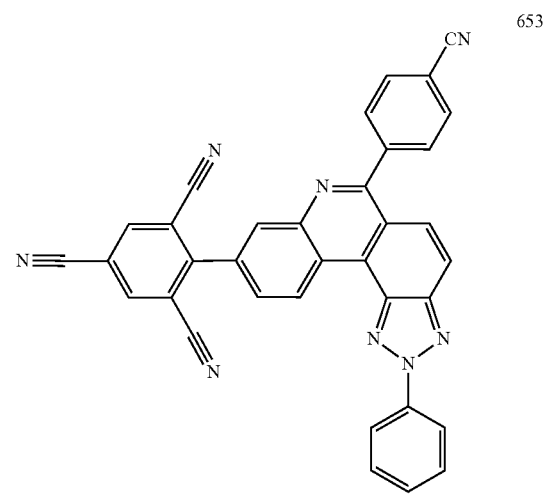
654
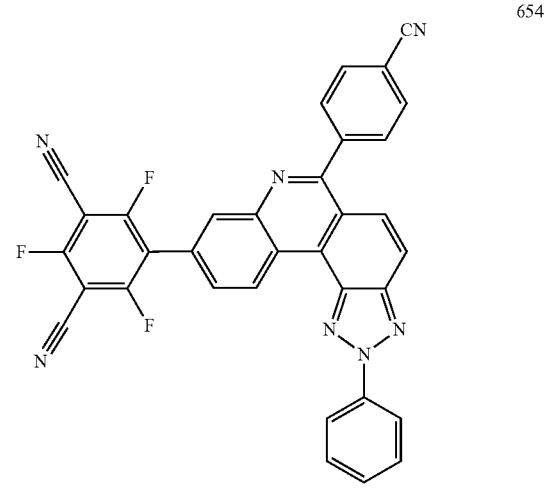

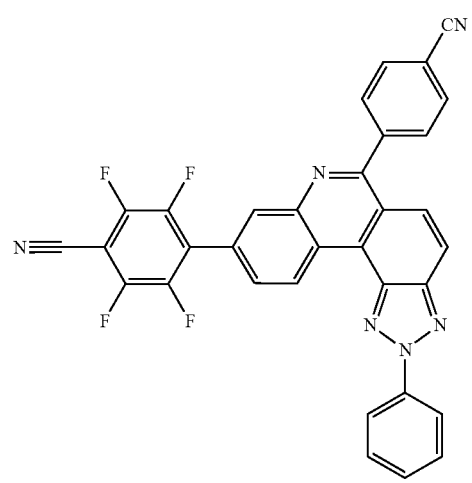
655
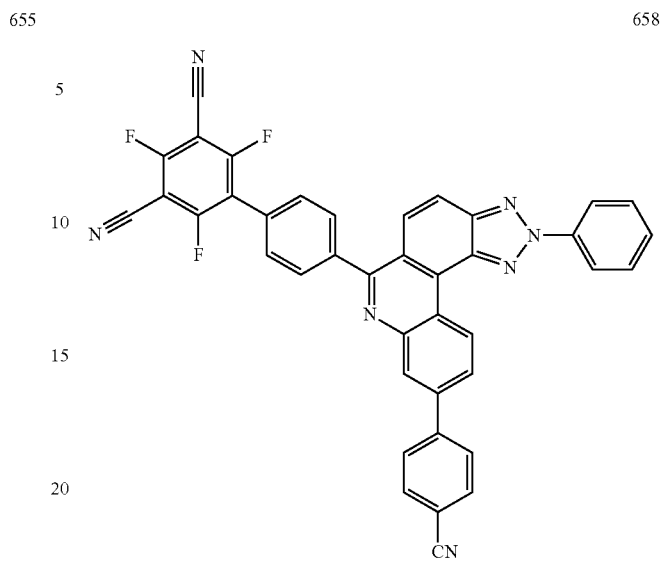
658
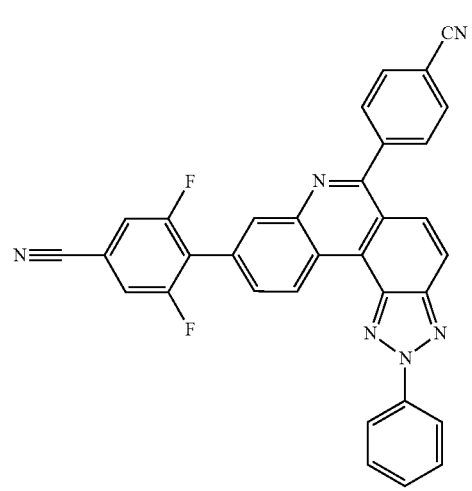
656
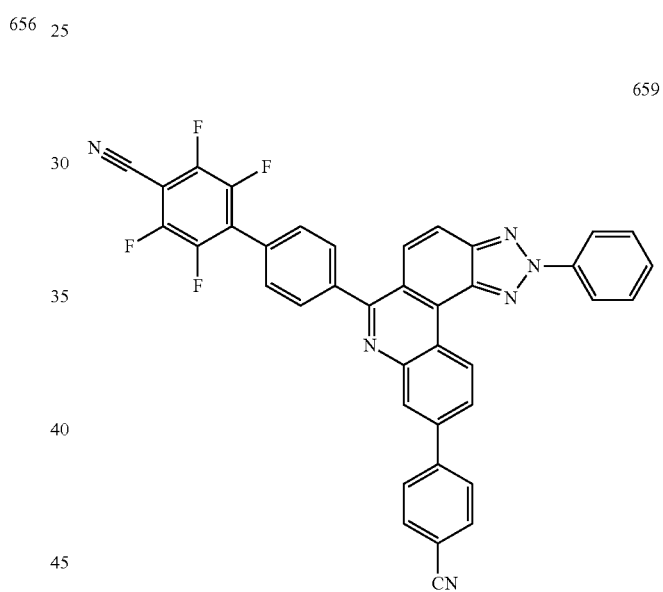
659
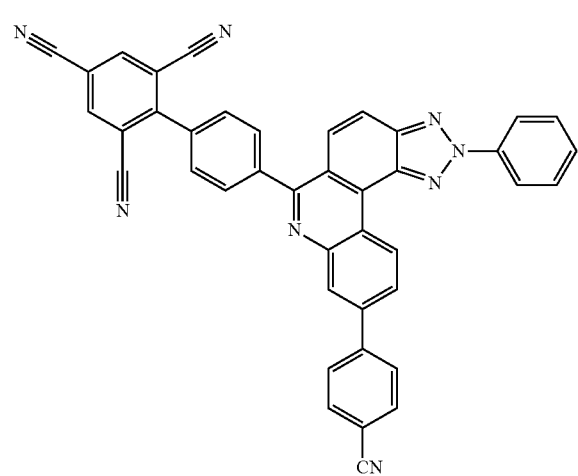
657
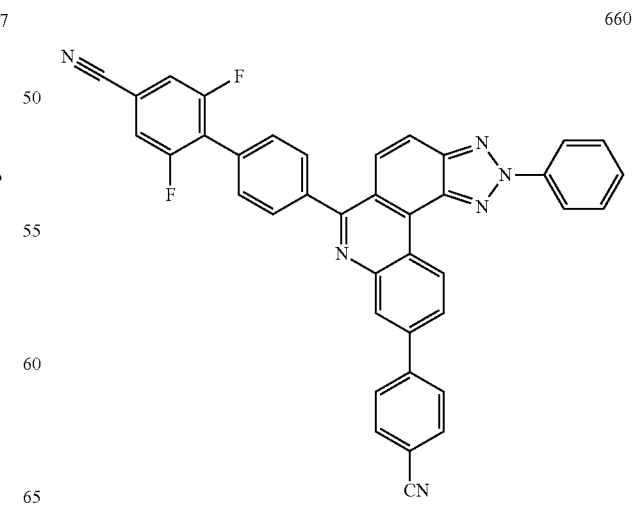
660

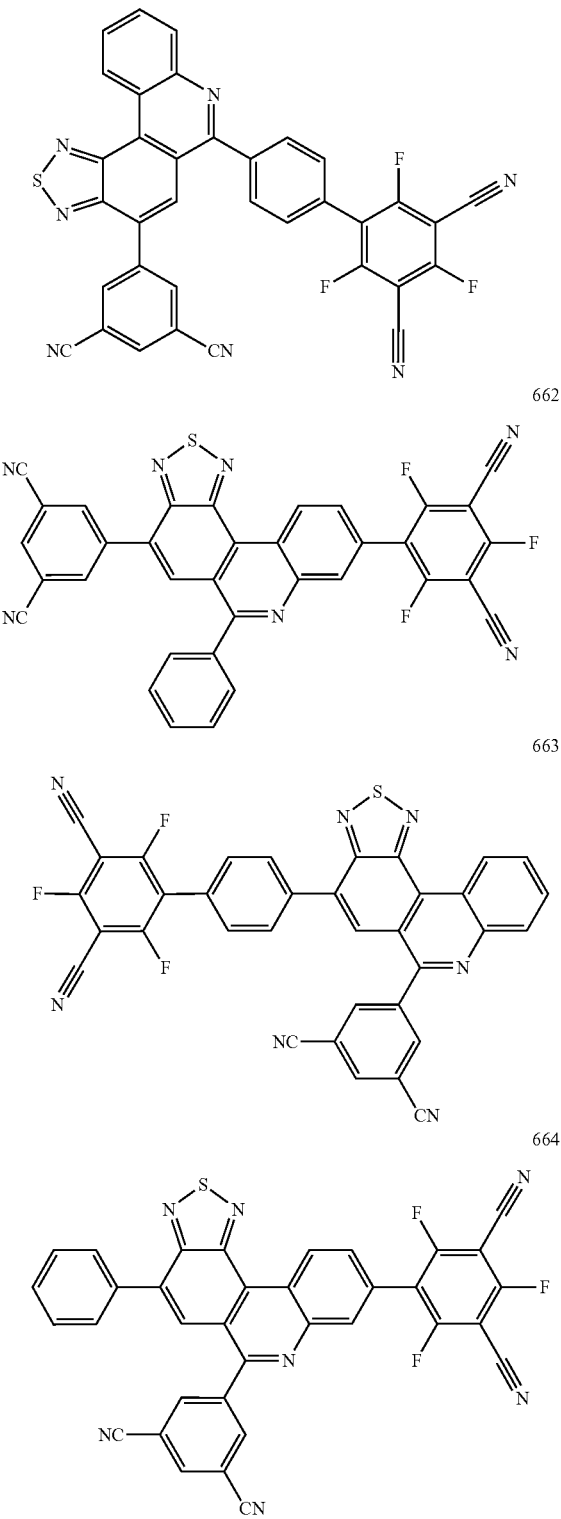

layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

One embodiment of the present specification provides an organic light emitting device including a first electrode; a second electrode; and one or more organic material layers provided between the first electrode and the second electrode, wherein one or more layers of the organic material layers include the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device.

In another embodiment of the present specification, the organic light emitting device may be a green organic light emitting device, and the heterocyclic compound according to Chemical Formula 1 may be used as a material of the green organic light emitting device.

In another embodiment of the present specification, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present specification may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes an electron transfer layer, and the electron transfer layer may include the heterocyclic compound.

In the organic light emitting device of the present specification, the organic material layer includes a hole blocking layer, and the hole blocking layer may include the heterocyclic compound.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 4 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 and FIG. 4 illustrate cases of the organic material layer being a multilayer. The organic light emitting device according to FIG. 3 includes a hole injection layer (301), a hole transfer layer (302), a light emitting layer (303), an electron transfer layer (305) and an electron injection layer (306), and the organic light emitting device according to FIG. 4 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer including Chemical Formula 1 may further include other materials as necessary.

In addition, the organic light emitting device according to one embodiment of the present specification includes an anode, a cathode, and two or more stacks provided between the anode and the cathode, the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present specification includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1. In addition, the first stack and the second stack may each independently further include one or more types of the hole injection layer, the hole transfer layer, the hole blocking layer, the electron transfer layer, the electron injection layer and the like described above.

The organic light emitting device according to one embodiment of the present specification includes a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes two or more stacks, and the two or more stacks each independently include a light emitting layer, a charge generation layer is included between the two or more stacks, and the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes a first stack including a first light emitting layer; a charge generation layer provided on the first stack; and a second stack provided on the charge generation layer and including a second light emitting layer, and the charge generation layer may include the heterocyclic compound represented by Chemical Formula 1.

The charge generation layer may be an N-type charge generation layer or a P-type charge generation layer, and the charge generation layer may further include a dopant known in the art in addition to the heterocyclic compound represented by Chemical Formula 1.

The charge generation layer may be an N-type charge generation layer, and the N-type charge generation layer may include the heterocyclic compound represented by Chemical Formula 1.

In the organic light emitting device according to one embodiment of the present specification, the second stack further includes a hole injection layer, and the hole injection layer includes the heterocyclic compound represented by Chemical Formula 1.

As the organic light emitting device according to one embodiment of the present specification, an organic light emitting device having a 2-stack tandem structure is illustrated in FIG. 5.

Herein, the first electron blocking layer, the first hole blocking layer, the second hole blocking layer and the like described in FIG. 5 may not be included in some cases.

In the organic light emitting device according to one embodiment of the present specification, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO₂/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

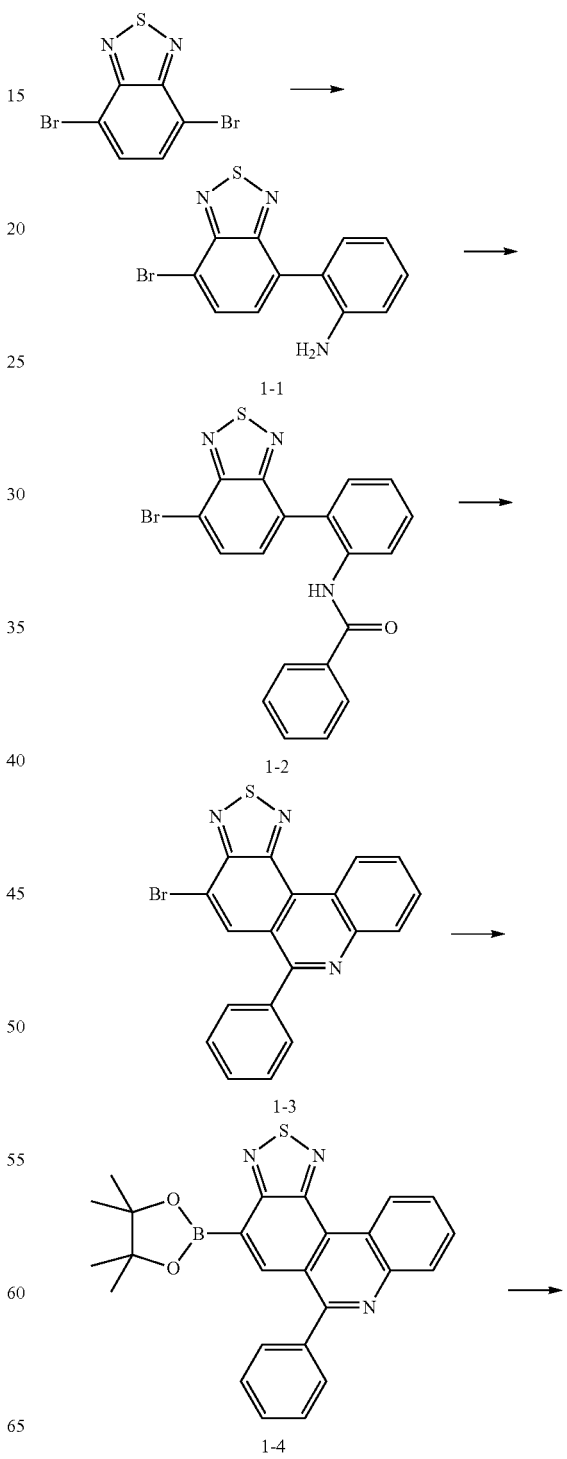

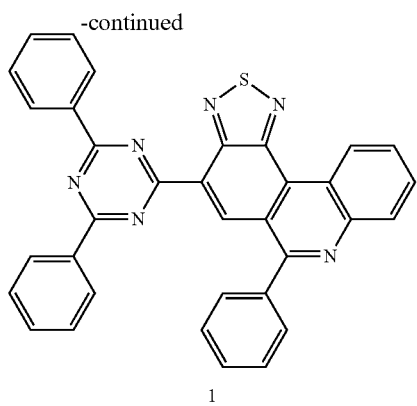

1

1) Preparation of Compound 1-1

After dissolving 4,7-dibromobenzo[c][1,2,5]thiadiazole (49 g, 166.6 mmol) and 2-(4,4,5,5-tetramethyl-1,3,2-dioxaborolan-2-yl)aniline (30 g, 136.9 mmol) in a mixed solution of toluene (1000 mL), ethanol (200 mL) and $H_2O$ (200 mL), $Pd(PPh_3)_4$ (tetrakis(triphenylphosphine)palladium(0)) (7.9 g, 6.845 mmol) and $K_3PO_4$ (87.1 g, 410.7 mmol) were introduced thereto, and the result was stirred for 5 hours under reflux. After the reaction was completed, the result was extracted with methylene chloride and distilled water, and the organic layer was dried with anhydrous $MgSO_4$. Subsequently, the solvent was removed using a rotary evaporator, and then the result was purified by column chromatography using dichloromethane and hexane as a developing solvent to obtain Compound 1-1 (39 g, yield 90%).

2) Preparation of Compound 1-2

After dissolving Compound 1-1 (39 g, 127.3 mmol) in methylene chloride (500 mL), triethylamine (18 mL, 127.3 mmol) was introduced thereto. After lowering the temperature from room temperature to 0° C., benzoyl chloride (19.8 g, 137.74 mmol) dissolved in methylene chloride was slowly added dropwise thereto. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 1-2 (45 g, yield 86%).

3) Preparation of Compound 1-3

After dissolving Compound 1-2 (45 g, 109.6 mmol) in nitrobenzene (500 mL), $POCl_3$ (25 g, 164.4 mmol) was slowly added dropwise thereto, and then the result was stirred for 4 hours at 150° C. After the reaction was completed, the result was neutralized with an aqueous $NaHCO_3$ solution and then extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 1-3 (40 g, yield 92%).

4) Preparation of Compound 1-4

After dissolving Compound 1-3 (40 g, 101.9 mmol) and bis(pinacolato)diboron (32.63 g, 128.48 mmol) in 1,4-dioxane (400 mL), $Pd(dppf)Cl_2$ ([1,1'-bis(diphenylphosphino)ferrocene]dichloropalladium (II)) (2.51 g, 3.43 mmol) and KOAc (potassium acetate) (25.22 g, 256.96 mmol) were introduced thereto, and the result was stirred for 5 hours under reflux. After the reaction was completed, the result was extracted with ethyl acetate and $H_2O$. The organic layer was dried with anhydrous $MgSO_4$, and after removing the solvent using a rotary evaporator, the result was passed through silica gel to obtain Compound 1-4 (40 g, yield 89%).

5) Preparation of Compound 1

After adding 2-chloro-4,6-diphenyl-1,3,5-triazine (6.1 g, 22.76 mnol), $Pd(PPh_3)_4$ (1.25 g, 1.09 mmol), $K_2CO_3$ (25.0 g, 65.4 mnol) and toluene/ethanol/$H_2O$ to Compound 1-4 (10.0 g, 22.76 mnol), the result was stirred for 6 hours at 110° C. After the reaction was completed, the result was cooled to room temperature, and extracted with distilled water and dichloromethane. The organic layer was dried with anhydrous $MgSO_4$, and after removing the solvent using a rotary evaporator, the result was purified by column chromatography using dichloromethane and hexane as a developing solvent to obtain Compound 1 (9.3 g, yield 76%).

[Preparation Example 2] Preparation of Compound 16

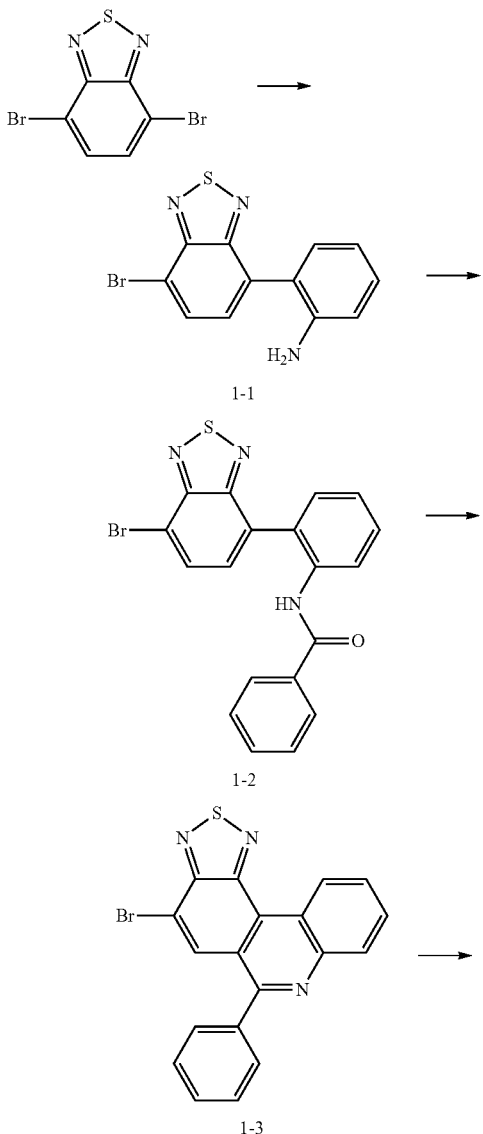

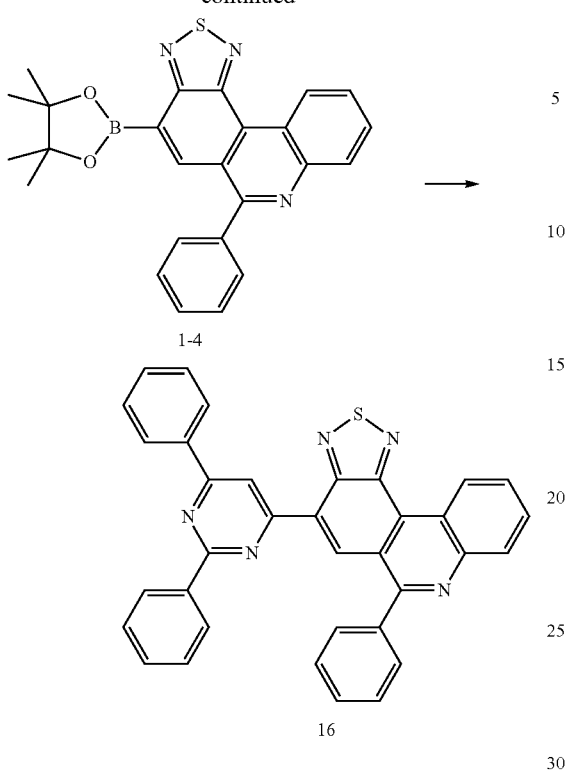

16

After adding 4-chloro-2,6-diphenylpyrimidine (6.1 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 16 (9.4 g, yield 76%).

[Preparation Example 3] Preparation of Compound 31

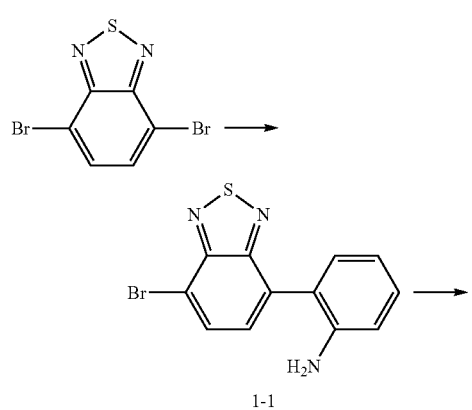

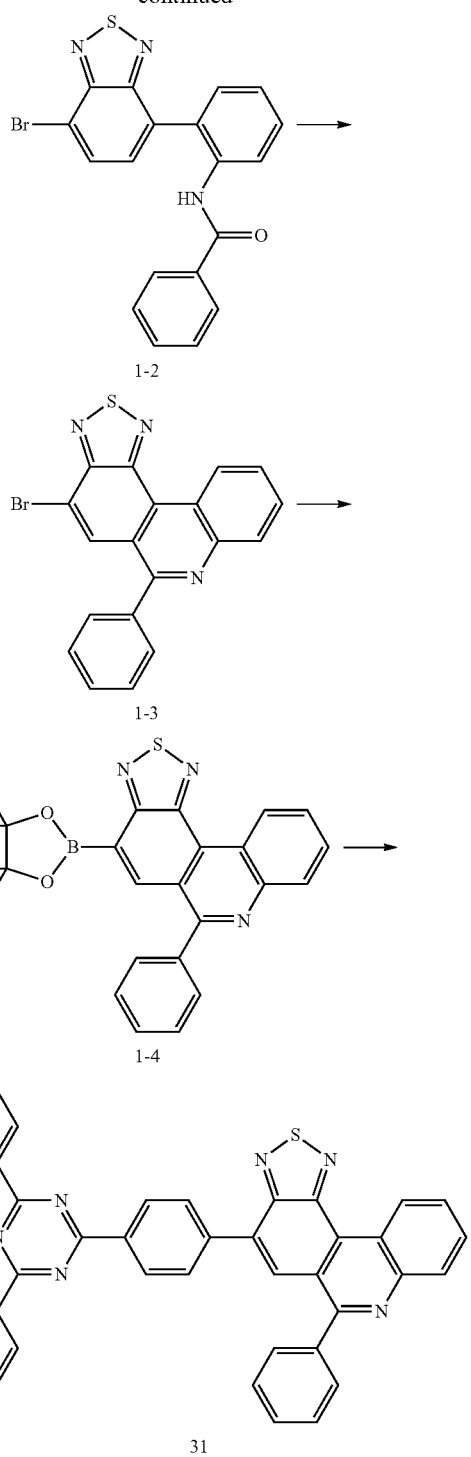

After adding 2-(4-bromophenyl)-4,6-diphenyl-1,3,5-triazine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 31 (10.1 g, yield 72%).

[Preparation Example 4] Preparation of Compound 46

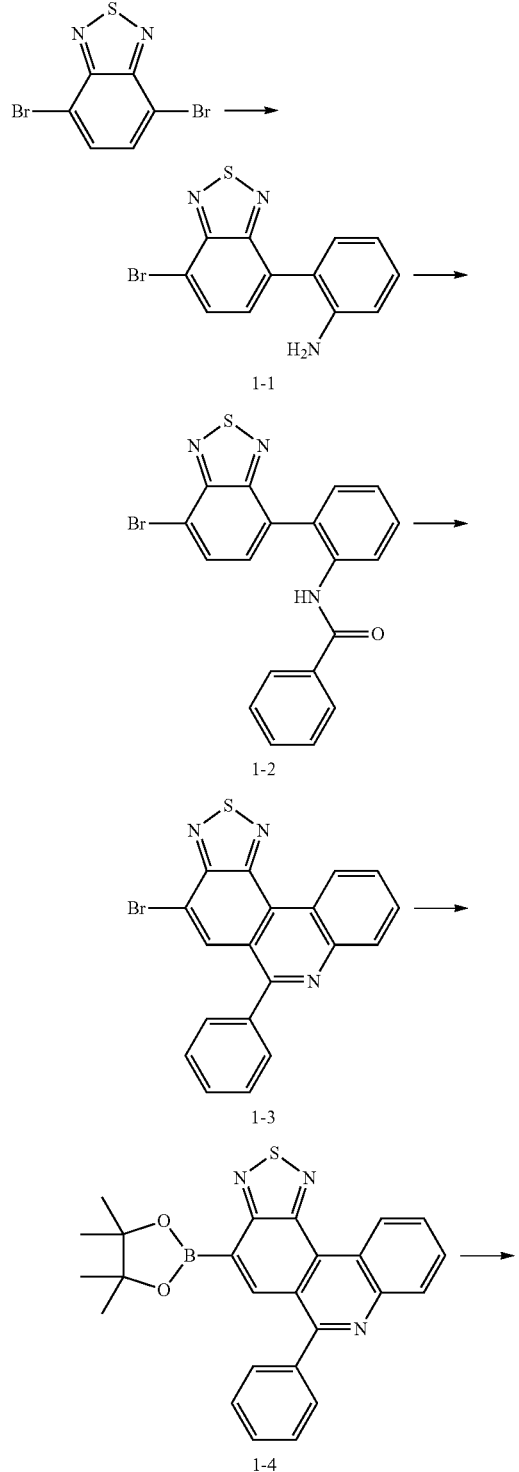 [SMILES: Brc1ccc(Br)c2nsnc12 ; Nc1ccccc1-c1ccc(Br)c2nsnc12 ; O=C(Nc1ccccc1-c1ccc(Br)c2nsnc12)c1ccccc1 ; Brc1cc2c(-c3ccccc3)nc3ccccc3c2c2nsnc12 ; CC1(C)OB(c2cc3c(-c4ccccc4)nc4ccccc4c3c3nsnc23)OC1(C)C]

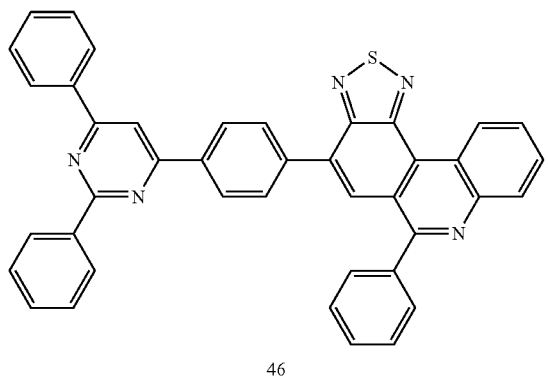 [SMILES: c1ccc(-c2cc(-c3ccc(-c4cc5c(-c6ccccc6)nc6ccccc6c5c5nsnc45)cc3)nc(-c3ccccc3)n2)cc1]

After adding 4-(4-bromophenyl)-2,6-diphenylpyrimidine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 46 (10.2 g, yield 72%).

[Preparation Example 5] Preparation of Compound 61

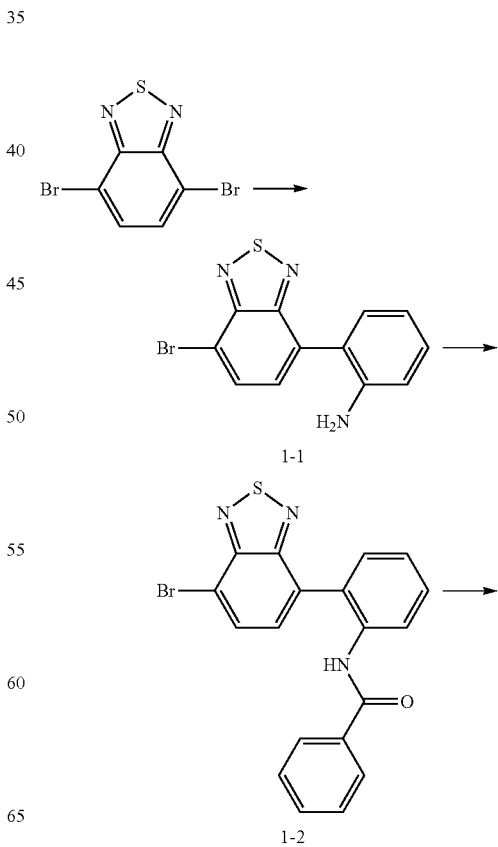

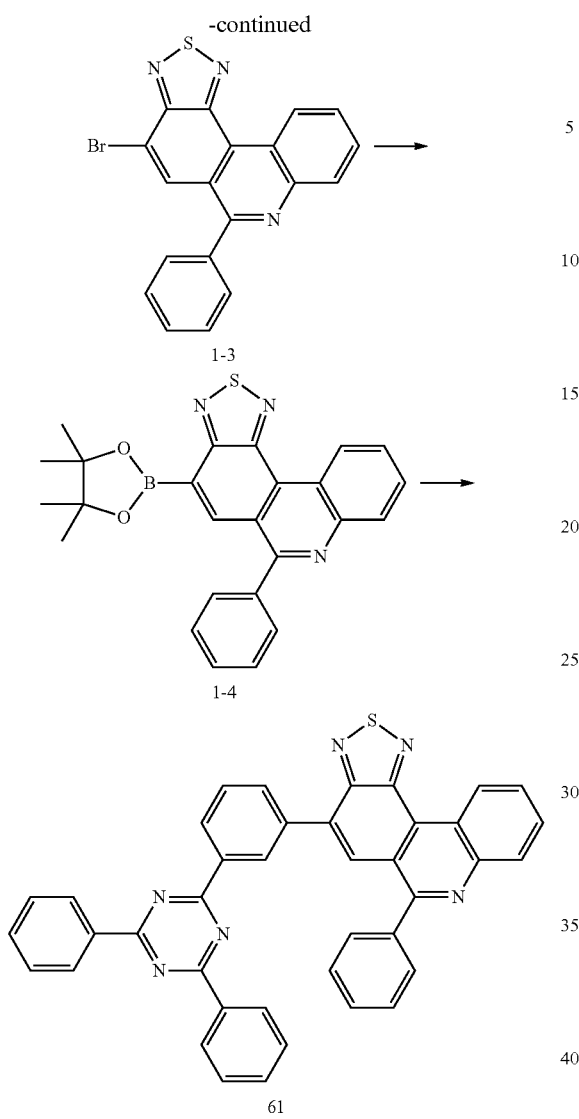

After adding 2-(3-bromophenyl)-4,6-diphenyl-1,3,5-triazine (8.8 g, 22.76 mmol), Pd(PPh₃)₄ (1.25 g, 1.09 mmol), K₂CO₃ (25.0 g, 65.4 mmol) and toluene/ethanol/H₂O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 61 (10.9 g, yield 77%).

[Preparation Example 6] Preparation of Compound 76

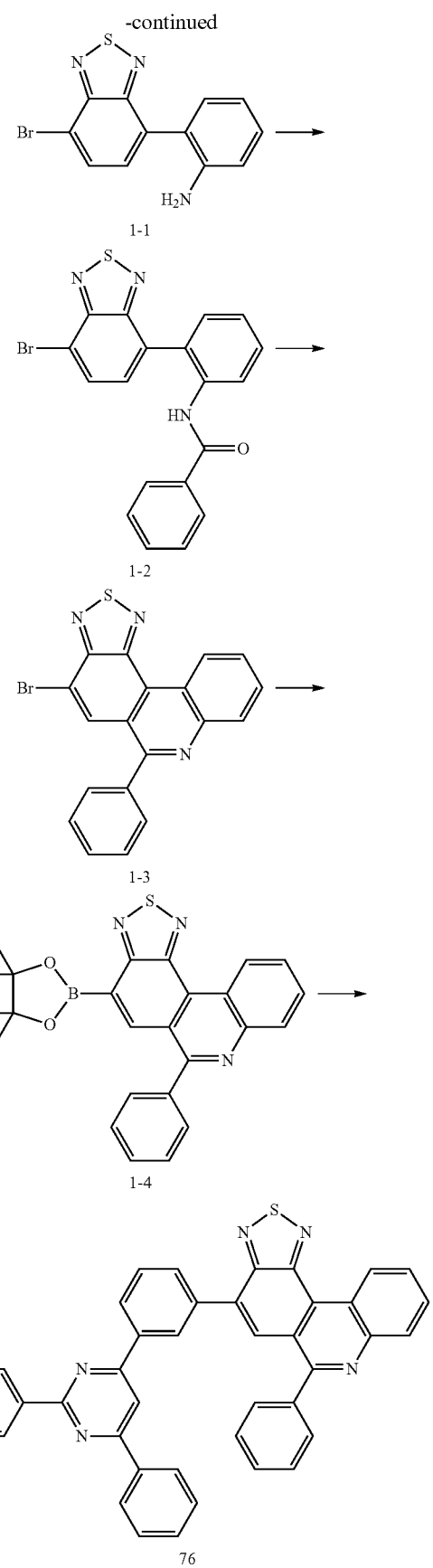

After adding 4-(3-bromophenyl)-2,6-diphenylpryimdine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 76 (10.5 g, yield 74%).

[Preparation Example 7] Preparation of Compound 91

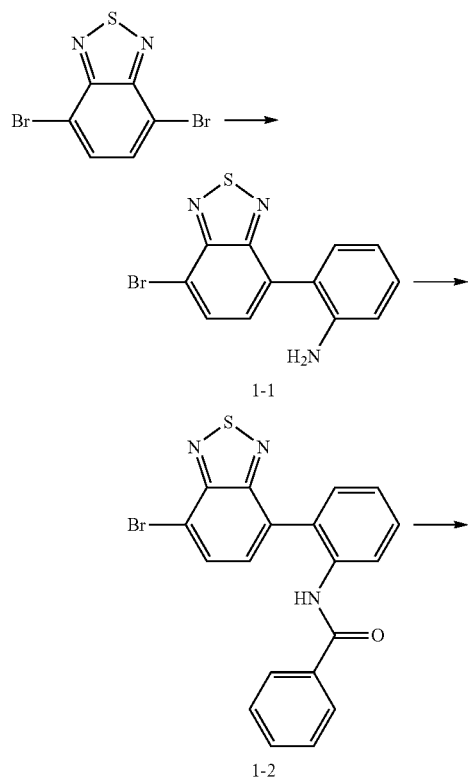

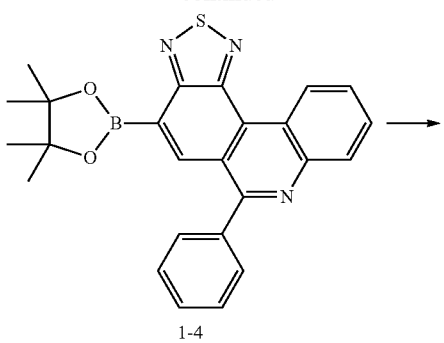

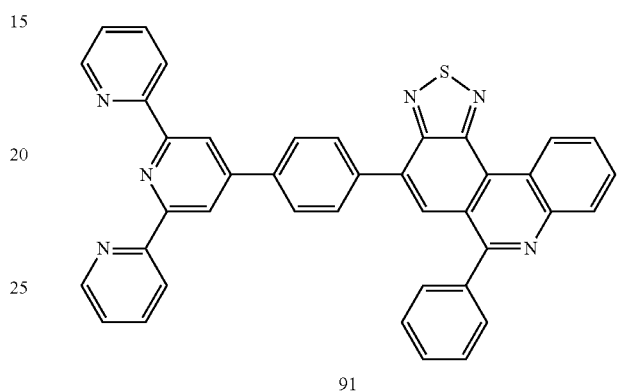

After adding 4'-(4-bromophenyl)-2,2':6',2"-terpyridine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 91 (10.7 g, yield 76%.

[Preparation Example 8] Preparation of Compound 107

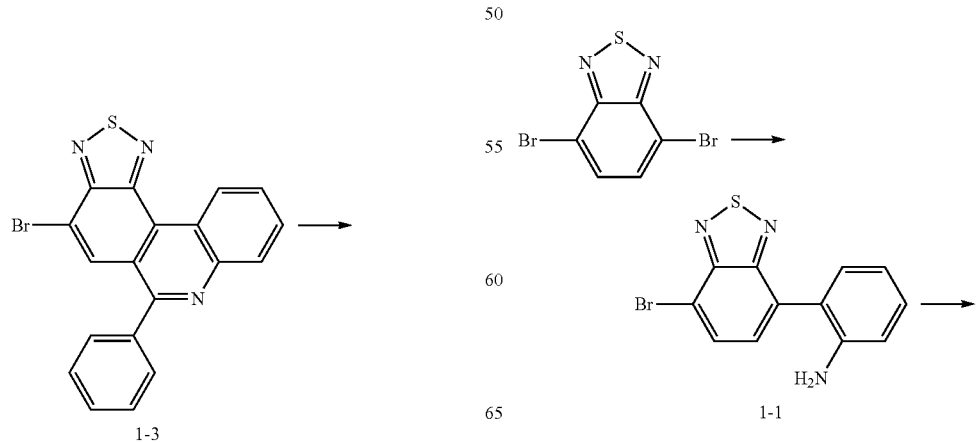

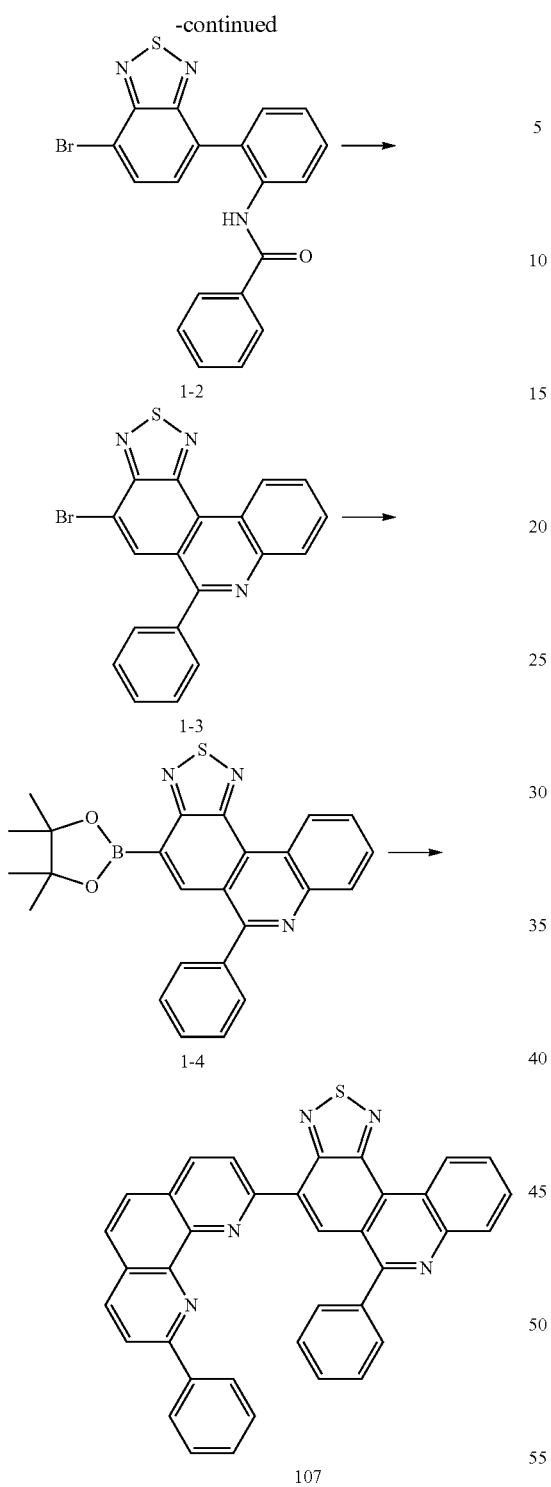

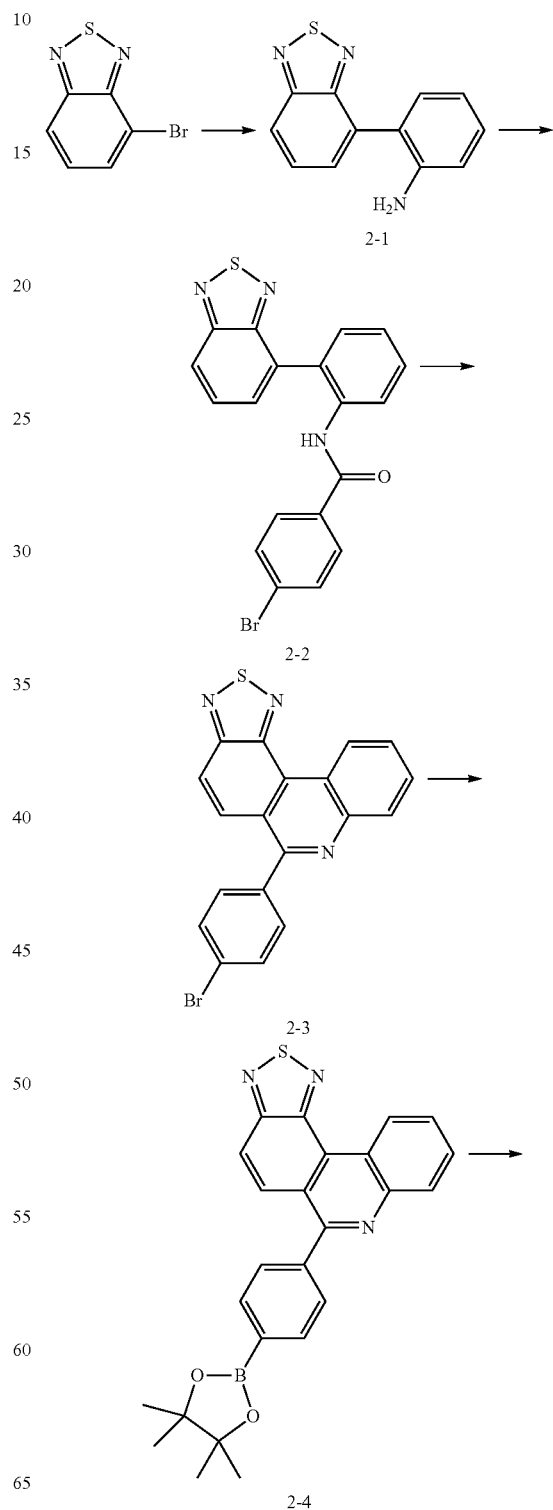

chromatography using dichloromethane and hexane as a developing solvent to obtain Compound 107 (10.0 g, yield 77%).

[Preparation Example 9] Preparation of Compound 109

After adding 2-bromo-9-phenyl-1,10-phenanthroline (7.6 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column -continued

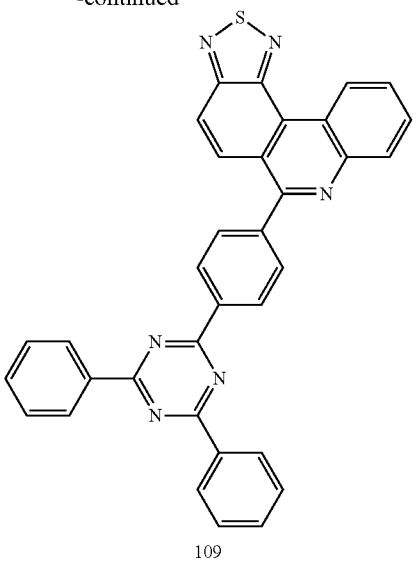

109

1) Preparation of Compound 2-1

After dissolving 4-bromobenzo[c][1,2,5]thiadiazole (50 g, 232.5 mmol) and 2-(4,4,5,5-tetramethyl-1,3,2-dioxaborolan-2-yl)aniline (50.9 g, 232.5 mmol) in toluene (1000 mL), ethanol (200 mL) and $H_2O$ (200 mL), $Pd(PPh_3)_4$ (13.4 g, 11.62 mmol) and $K_3PO_4$ (148.1 g, 697.5 mmol) were introduced thereto, and the result was stirred for 5 hours under reflux. After the reaction was completed, the result was extracted with methylene chloride and distilled water, and the organic layer was dried with anhydrous $MgSO_4$. Subsequently, the solvent was removed using a rotary evaporator, and then the result was purified by column chromatography using dichloromethane and hexane as a developing solvent to obtain Compound 2-1 (45 g, yield 85%).

2) Preparation of Compound 2-2

After dissolving Compound 2-1 (45 g, 197.9 mmol) in methylene chloride (450 mL), triethylamine (27 mL, 197.9 mmol) was introduced thereto. After lowering the temperature from room temperature to 0° C., 4-bromobenzoyl chloride (47.7 g, 217.6 mmol) dissolved in methylene chloride was slowly added dropwise thereto. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 2-2 (70 g, yield 85%).

3) Preparation of Compound 2-3

After dissolving Compound 2-2 (70 g, 170.6 mmol) in nitrobenzene (700 mL), $POCl_3$ (39.2 g, 255.9 mmol) was slowly added dropwise thereto, and then the result was stirred for 4 hours at 150° C. After the reaction was completed, the result was neutralized with an aqueous $NaHCO_3$ solution and then extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 2-3 (60 g, yield 90%).

4) Preparation of Compound 2-4

After dissolving Compound 2-3 (60 g, 152.9 mmol) and bis(pinacolato)diboron (48.95 g, 192.7 mmol) in 1,4-dioxane (600 mL), $Pd(dppf)Cl_2$ (3.76 g, 5.15 mmol) and KOAc (37.8 g, 385.4 mmol) were introduced thereto, and the result was stirred for 5 hours under reflux. After the reaction was completed, the result was extracted with ethyl acetate and $H_2O$. The organic layer was dried with anhydrous $MgSO_4$, and after removing the solvent using a rotary evaporator, the result was passed through silica gel to obtain Compound 2-4 (60 g, yield 89%).

5) Preparation of Compound 109

After adding 2-chloro-4,6-diphenyl-1,3,5-triazine (6.1 g, 22.76 mmol), $Pd(PPh_3)_4$ (1.25 g, 1.09 mmol), $K_2CO_3$ (25.0 g, 65.4 mmol) and toluene/ethanol/$H_2O$ to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous $MgSO_4$, and after removing the solvent using a rotary evaporator, the result was purified by column chromatography using dichloromethane and hexane as a developing solvent to obtain Compound 109 (9.3 g, yield 76%).

[Preparation Example 10] Preparation of Compound 124

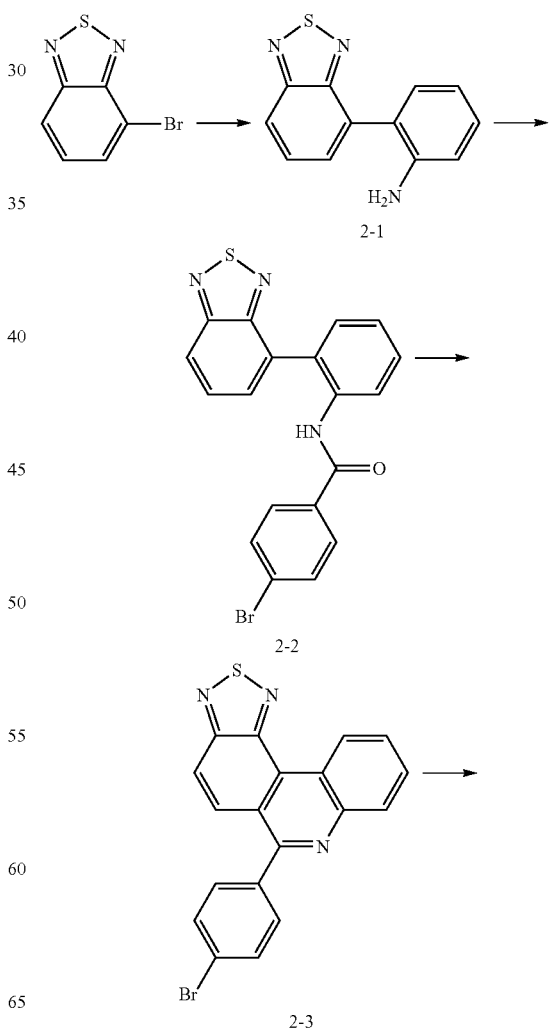

-continued

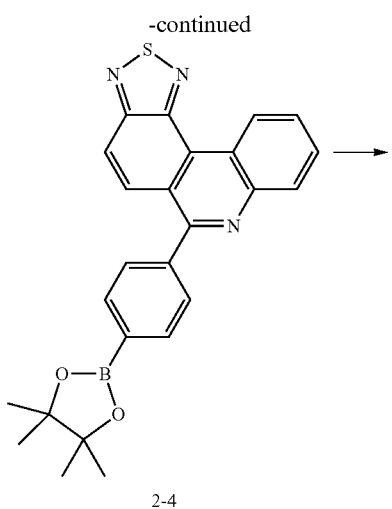

2-4

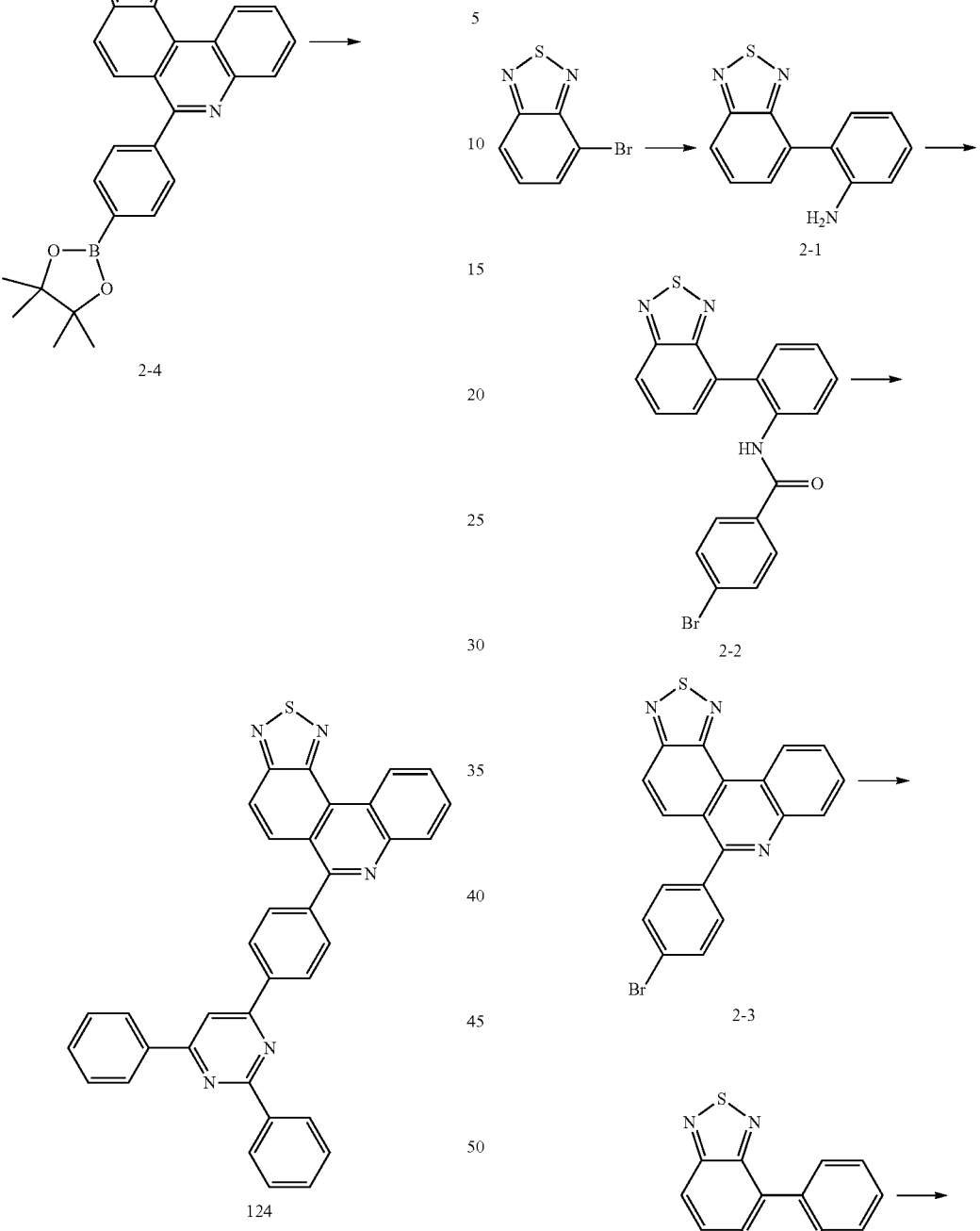

124

After adding 4-chloro-2,6-diphenylpryimidine (6.1 g, 22.76 mmol), Pd(PPh$_3$)$_4$ (1.25 g, 1.09 mmol), K$_2$CO$_3$ (25.0 g, 65.4 mmol), and toluene/ethanol/H$_2$O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 124 (9.7 g, yield 78%).

[Preparation Example 11] Preparation of Compound 139

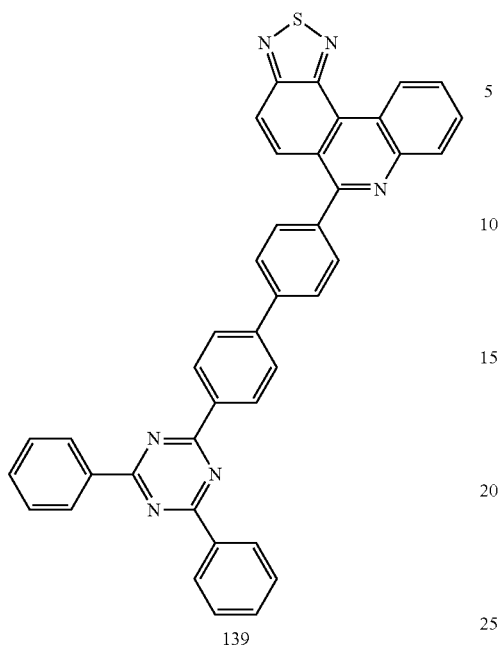

139

After adding 2-(4-bromophenyl)-4,6-diphenyl-1,3,5-triazine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 139 (11.0 g, yield 78%).

[Preparation Example 12] Preparation of Compound 144

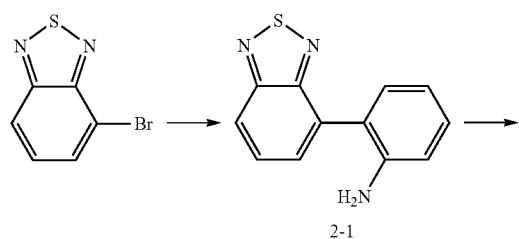

2-1

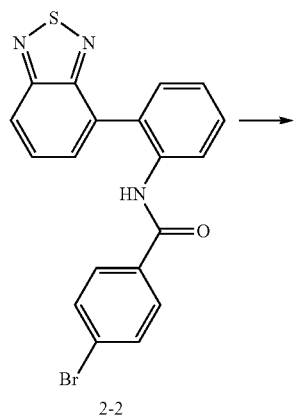

2-2

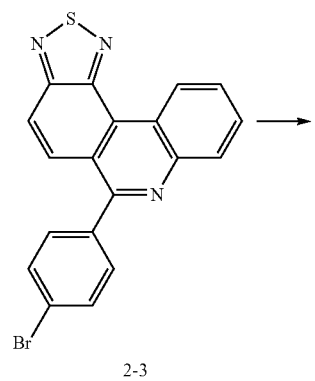

2-3

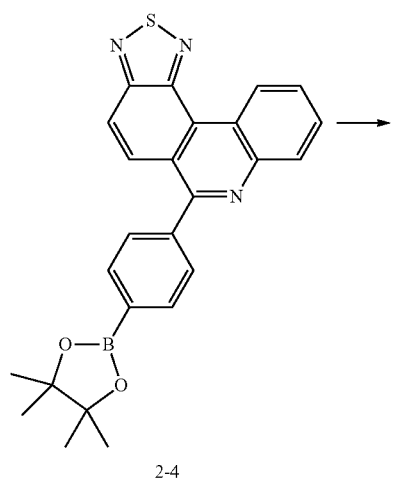

2-4

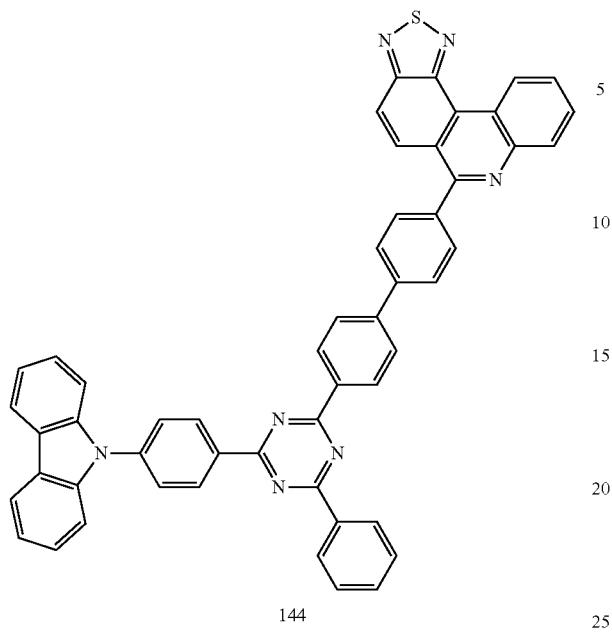

144

After adding 9-(4-(4-(4-bromophenyl)-6-phenyl-1,3,5-triazin-2-yl)phenyl)-9H-carbazole (12.6 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 144 (14.0 g, yield 78%).

[Preparation Example 13] Preparation of Compound 154

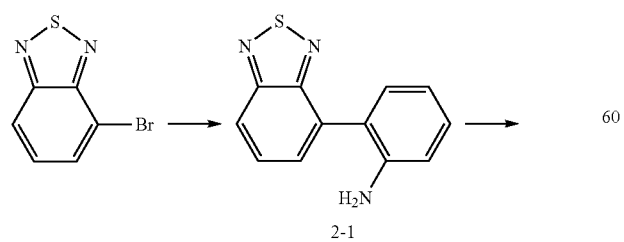

2-1

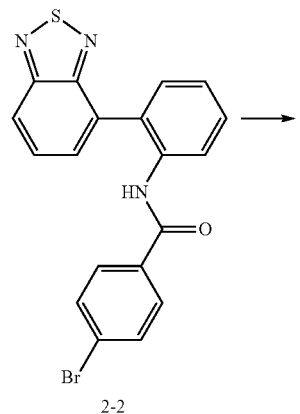

2-2

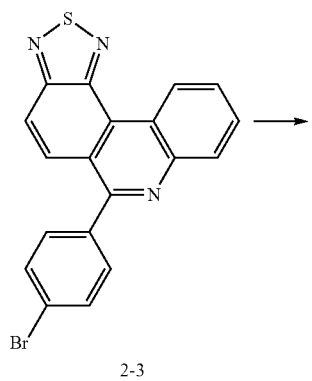

2-3

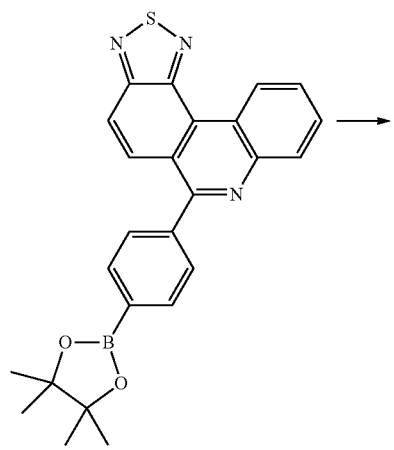

2-4

-continued

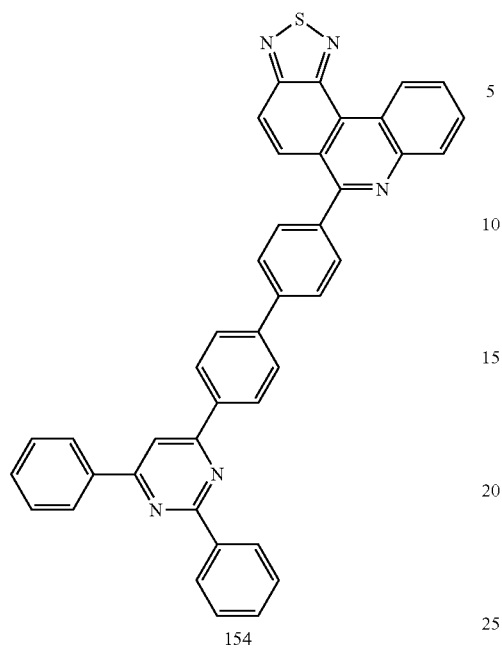
154

After adding 4-(4-bromophenyl)-2,6-diphenylpyrimidine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 154 (11.2 g, yield 79%).

[Preparation Example 14] Preparation of Compound 174

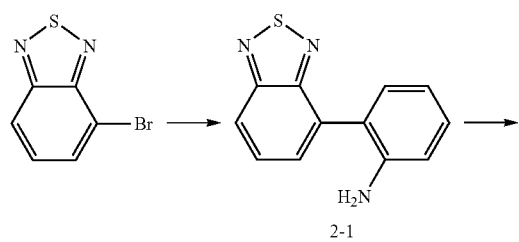
2-1

-continued

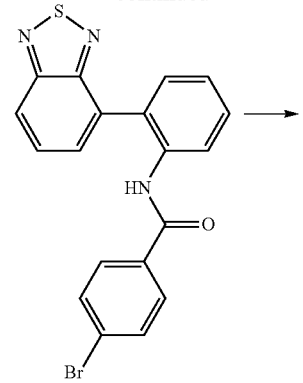
2-2

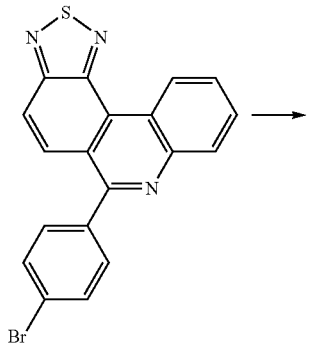
2-3

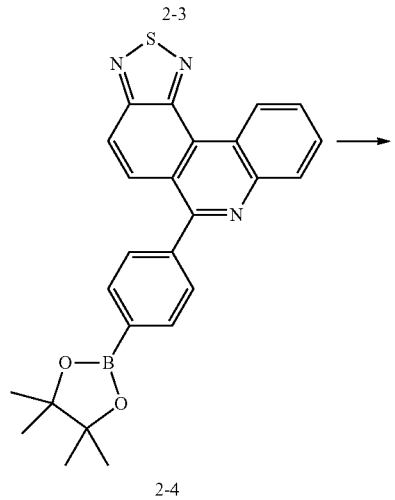
2-4

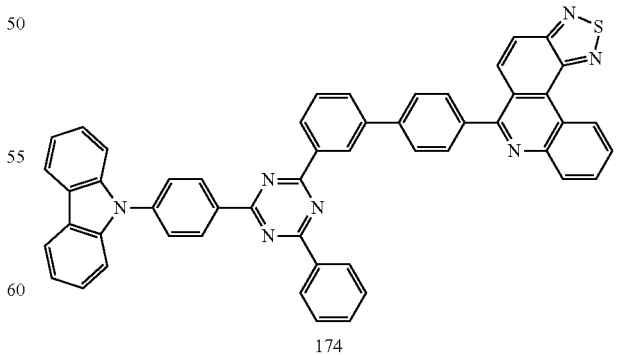
174

After adding 9-(4-(4-(3-bromophenyl)-6-phenyl-1,3,5-triazin-2-yl)phenyl)-9H-carbazole (12.6 g, 22.76 mmol), Pd(PPh$_3$)$_4$ (1.25 g, 1.09 mmol), K$_2$CO$_3$ (25.0 g, 65.4 mmol)

and toluene/ethanol/H₂O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 174 (14.0 g, 78%).

[Preparation Example 15] Preparation of Compound 199

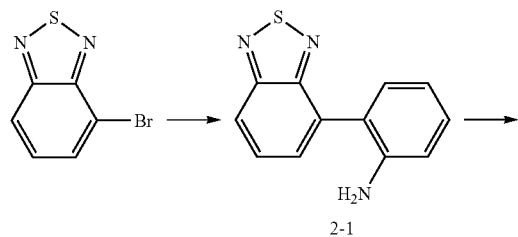
2-1

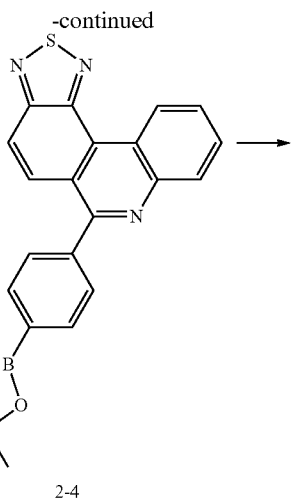
2-4

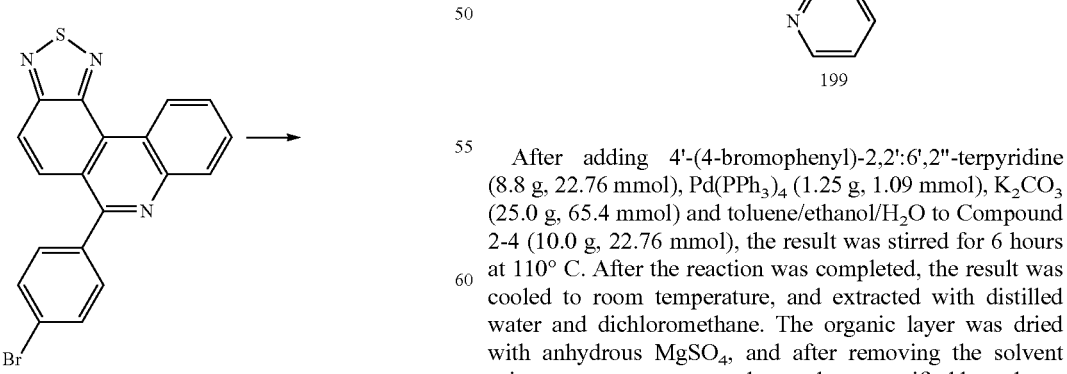
2-3

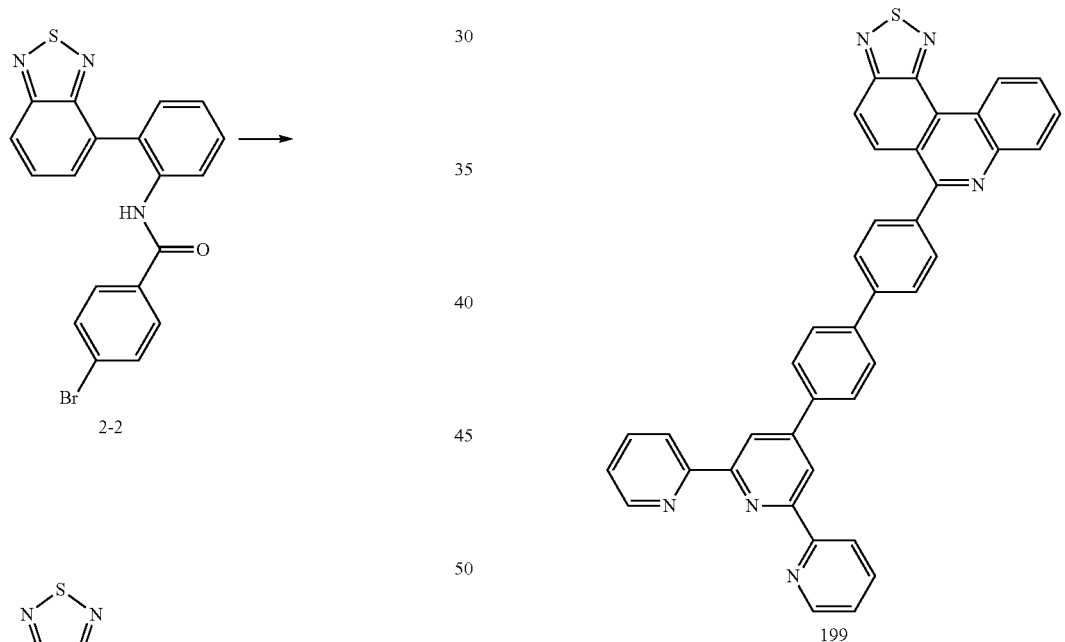
199

After adding 4'-(4-bromophenyl)-2,2':6',2"-terpyridine (8.8 g, 22.76 mmol), Pd(PPh₃)₄ (1.25 g, 1.09 mmol), K₂CO₃ (25.0 g, 65.4 mmol) and toluene/ethanol/H₂O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 199 (10.7 g, yield 76%).

[Preparation Example 16] Preparation of Compound 213

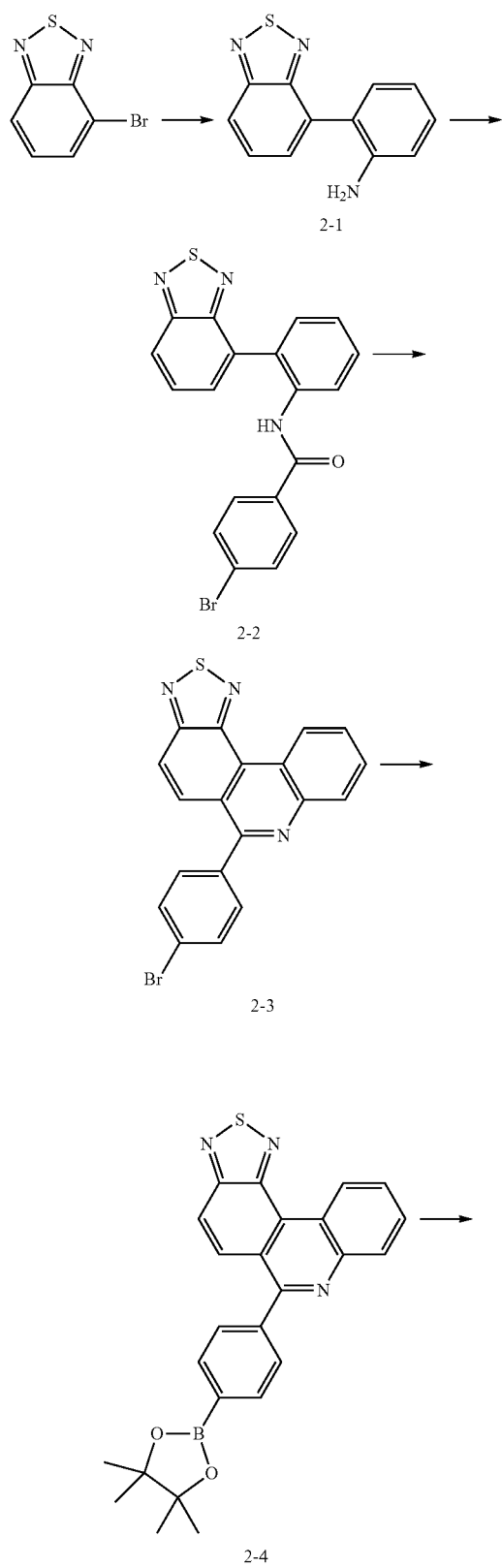

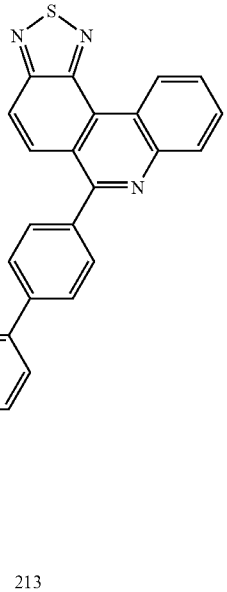

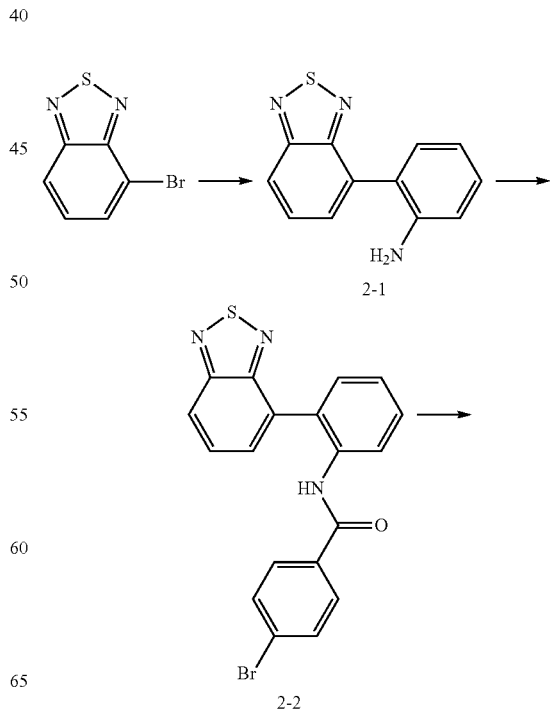

After adding (4-bromophenyl)diphenylphosphine oxide (8.1 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 213 (10.7 g, yield 79%).

[Preparation Example 17] Preparation of Compound 215

295

-continued

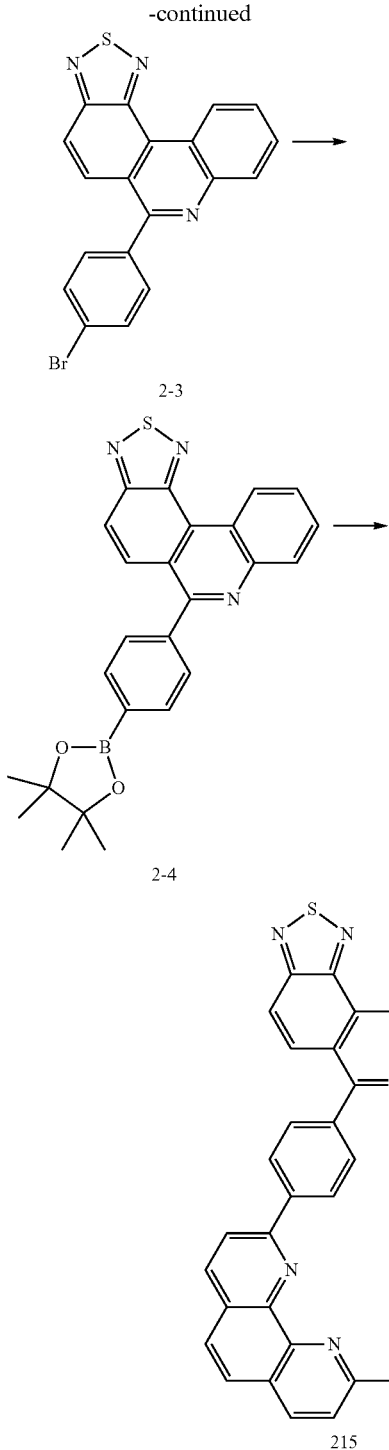

2-3

2-4

215

After adding 2-bromo-9-phenyl-1,10-phenanthroline (7.6 g, 22.76 mmol), Pd(PPh₃)₄ (1.25 g, 1.09 mmol), K₂CO₃ (25.0 g, 65.4 mmol) and toluene/ethanol/H₂O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 215 (10.5 g, yield 81%).

[Preparation Example 18] Preparation of Compound 217

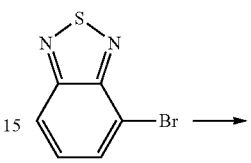

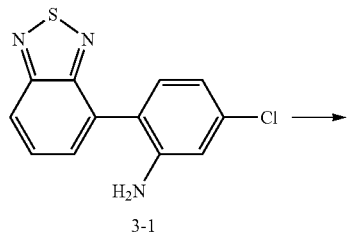

3-1

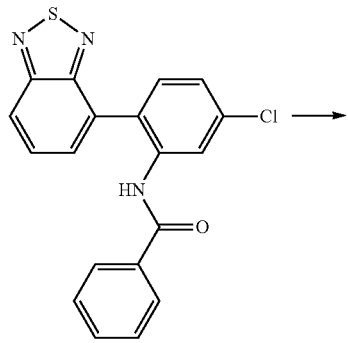

3-2

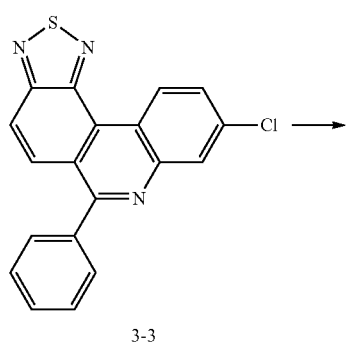

3-3

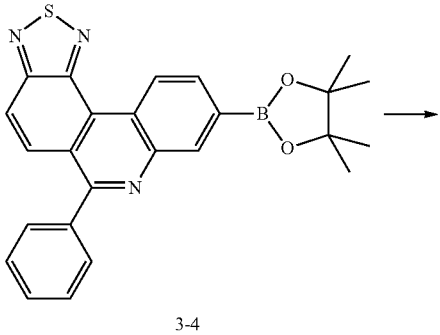

3-4

-continued

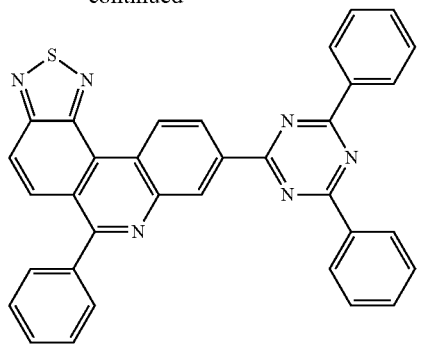

217

1) Preparation of Compound 3-1

After dissolving 4-bromobenzo[c][1,2,5]thiadiazole (50 g, 232.5 mmol) and 5-chloro-2-(4,4,5,5-tetramethyl-1,3,2-dioxaborolan-2-yl) aniline (58.9 g, 232.5 mmol) in toluene (1000 mL), ethanol (200 mL) and H$_2$O (200 mL), Pd(PPh$_3$)$_4$ (13.4 g, 11.63 mmol) and K$_3$PO$_4$ (148 g, 97.5 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 3-1 (50 g, yield 82%).

2) Preparation of Compound 3-2

After dissolving Compound 3-1 (50 g, 191 mmol) in methylene chloride (500 mL), triethylamine (26.6 mL, 191 mmol) was introduced thereto. After lowering the temperature from room temperature to 0° C., benzoyl chloride (29.5 g, 210.1 mmol) dissolved in methylene chloride was slowly added dropwise thereto. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 3-2 (60 g, yield 86%).

3) Preparation of Compound 3-3

After dissolving Compound 3-2 (60 g, 164 mmol) in nitrobenzene (600 mL), POCl$_3$ (37.7 g, 246 mmol) was slowly added dropwise thereto, and then the result was stirred for 4 hours at 150° C. After the reaction was completed, the result was neutralized with an aqueous NaHCO$_3$ solution and then extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 3-3 (50 g, yield 87%).

4) Preparation of Compound 3-4

After dissolving Compound 3-3 (50 g, 143.7 mmol) and bis(pinacolato)diboron (54.7 g, 215.6 mmol) in 1,4-dioxane (500 mL), Pd(dppf)Cl$_2$ (5.02 g, 6.86 mmol) and KOAc (42.3 g, 431.1 mmol) were introduced thereto, and the result was stirred for 5 hours under reflux. After the reaction was completed, the result was extracted with ethyl acetate and H$_2$O. The organic layer was dried with anhydrous MgSO$_4$, and after removing the solvent using a rotary evaporator, the result was passed through silica gel to obtain Compound 3-4 (50 g, yield 79%).

5) Preparation of Compound 217

After adding 2-chloro-4,6-diphenyl-1,3,5-triazine (6.1 g, 22.76 mnol), Pd(PPh$_3$)$_4$ (1.25 g, 1.09 mmol), K$_2$CO$_3$ (25.0 g, 65.4 mmol) and toluene/ethanol/H$_2$O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 217 (9.3 g, yield 76%).

[Preparation Example 19] Preparation of Compound 232

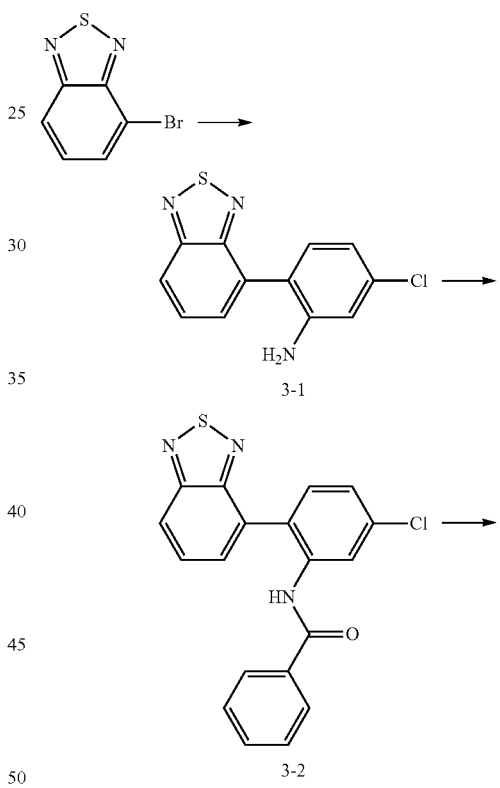

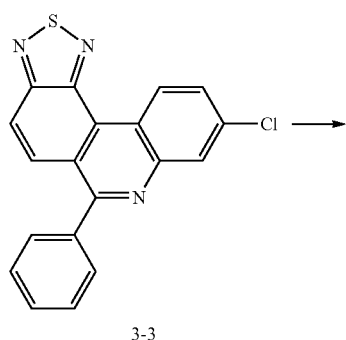

3-3

-continued

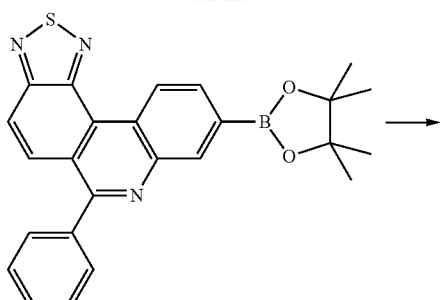

3-4

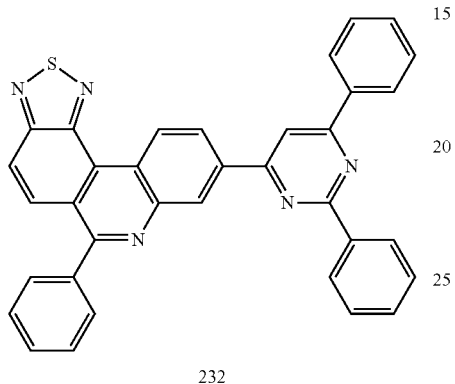

232

After adding 4-chloro-2,6-diphenylpyrimidine (6.1 g, 22.76 mmol), Pd(PPh₃)₄ (1.25 g, 1.09 mmol), K₂CO₃ (25.0 g, 65.4 mmol) and toluene/ethanol/H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 232 (9.7 g, 78%).

[Preparation Example 20] Preparation of Compound 247

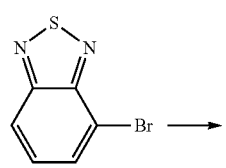

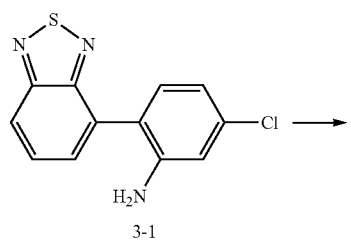

3-1

-continued

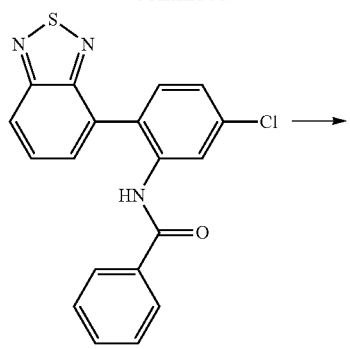

3-2

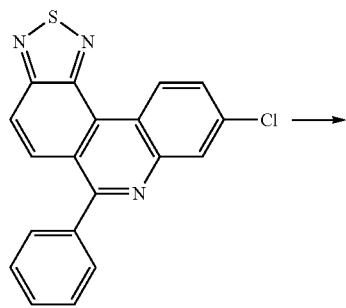

3-3

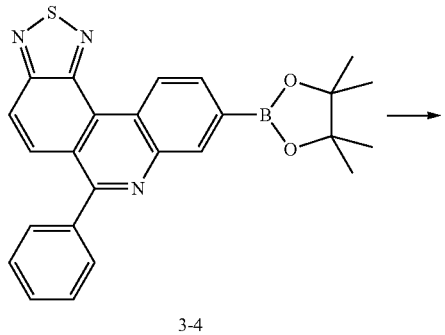

3-4

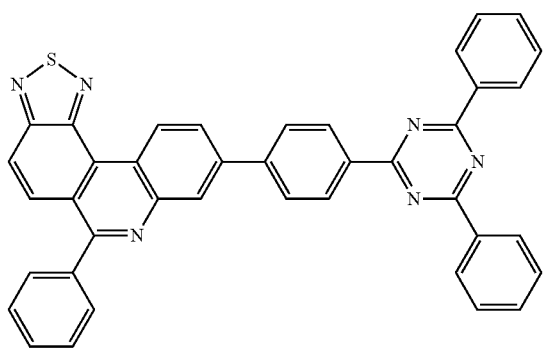

247

After adding 2-(4-bromophenyl)-4,6-diphenyl-1,3,5-triazine (8.8 g, 22.76 mmol), Pd(PPh₃)₄ (1.25 g, 1.09 mmol), K₂CO₃ (25.0 g, 65.4 mmol) and toluene/ethanol/H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 247 (11.1 g, yield 78%).

[Preparation Example 21] Preparation of Compound 253

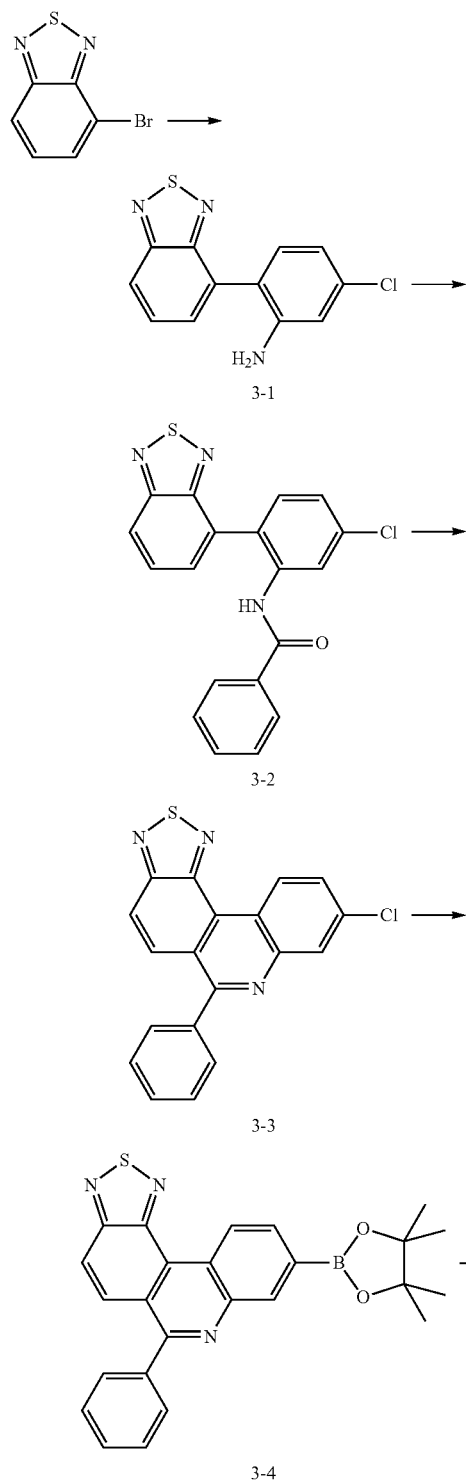

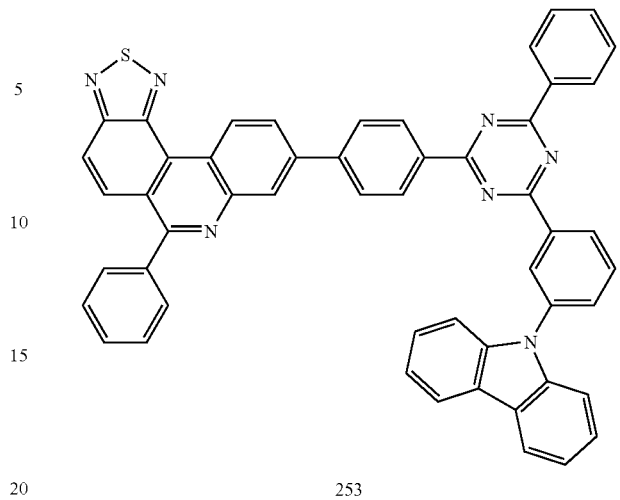

After adding 9-(3-(4-(4-bromophenyl)-6-phenyl-1,3,5-triazin-2-yl)phenyl)-9H-carbazole (12.6 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 253 (13.0 g, yield 73%).

[Preparation Example 22] Preparation of Compound 262

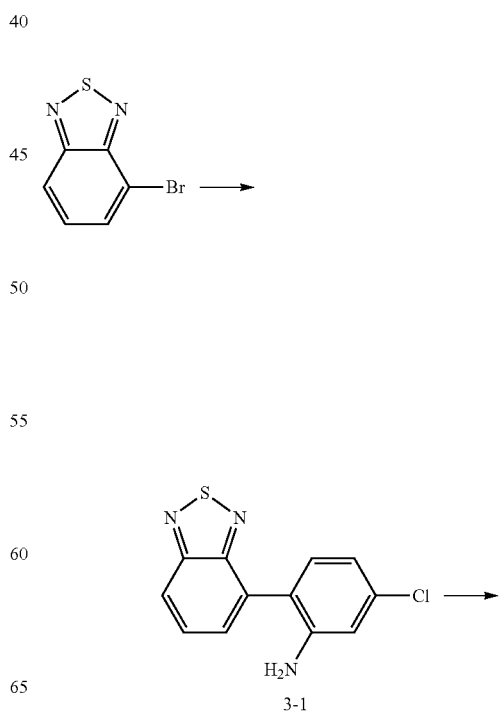

-continued

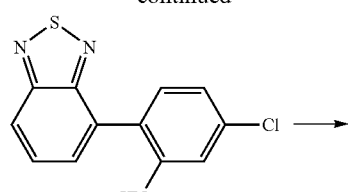

3-2

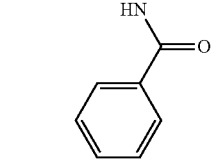

3-3

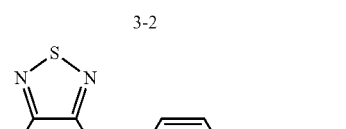

3-4

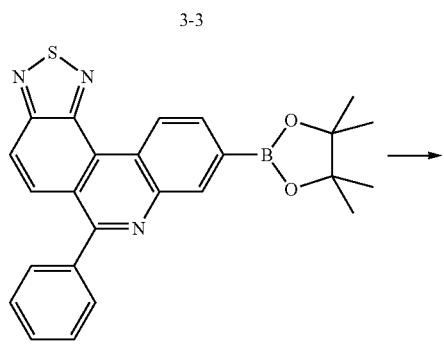

262

After adding 4-(4-bromophenyl)-2,6-diphenylpyrimidine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 262 (10.9 g, yield 77%).

[Preparation Example 23] Preparation of Compound 268

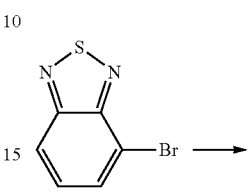

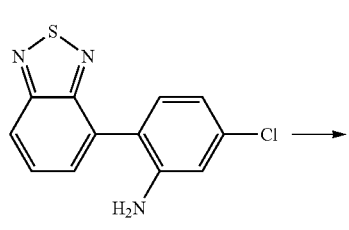

3-1

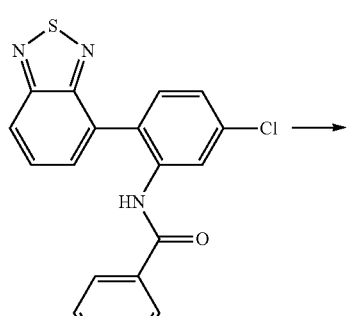

3-2

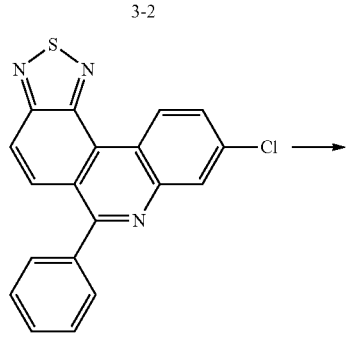

3-3

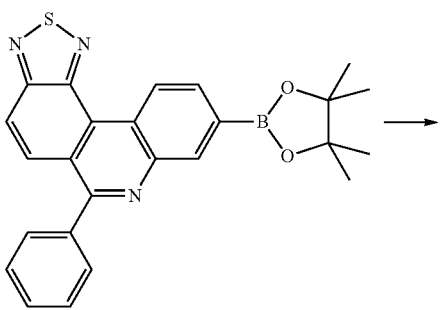

3-4

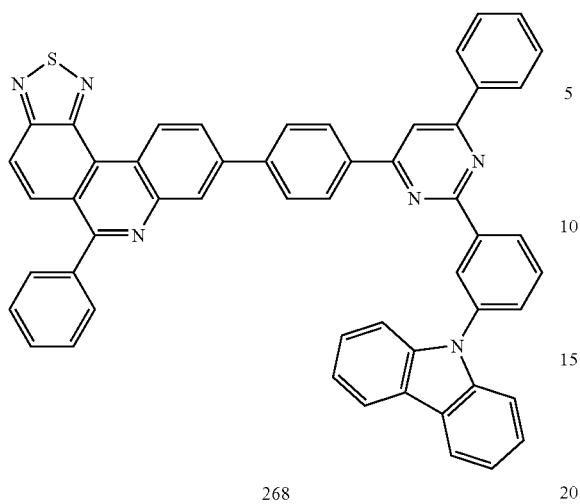

268

After adding 9-(3-(4-(4-bromophenyl)-6-phenylpyrimidin-2-yl)phenyl)-9H-carbazole (12.6 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 268 (13.5 g, yield 75%).

[Preparation Example 24] Preparation of Compound 283

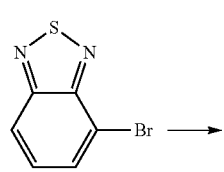

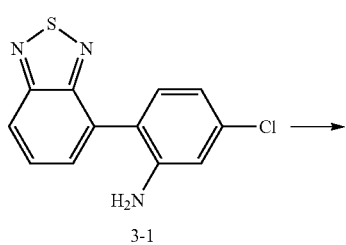

3-1

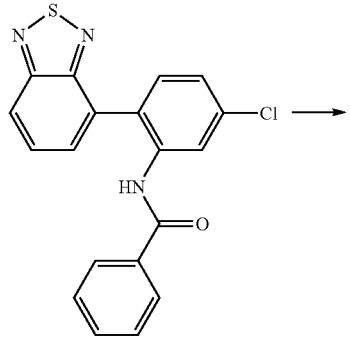

3-2

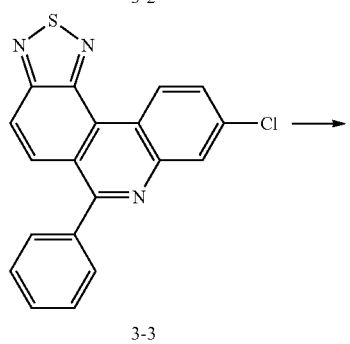

3-3

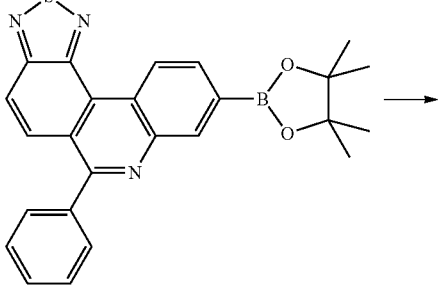

3-4

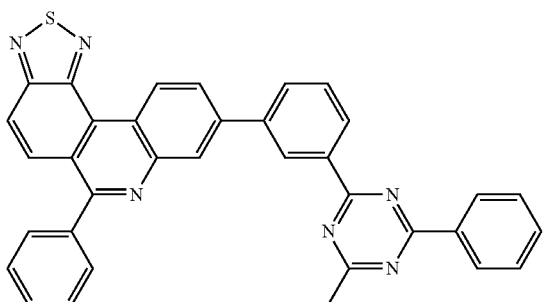

283

After adding 9-(3-(4-(3-bromophenyl)-6-phenyl-1,3,5-triazin-2-yl)phenyl)-9H-carbazole (12.6 g, 22.76 mmol), Pd(PPh$_3$)$_4$ (1.25 g, 1.09 mmol), K$_2$CO$_3$ (25.0 g, 65.4 mmol)

and toluene/ethanol/H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 283 (13.1 g, yield 73%).

[Preparation Example 25] Preparation of Compound 298

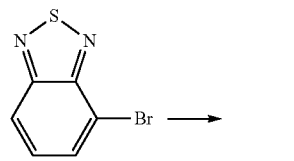

3-1

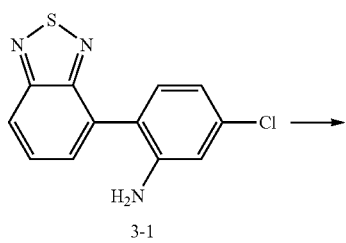

3-2

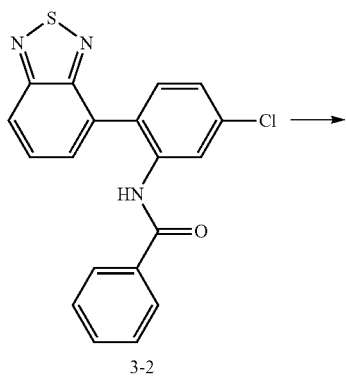

3-3

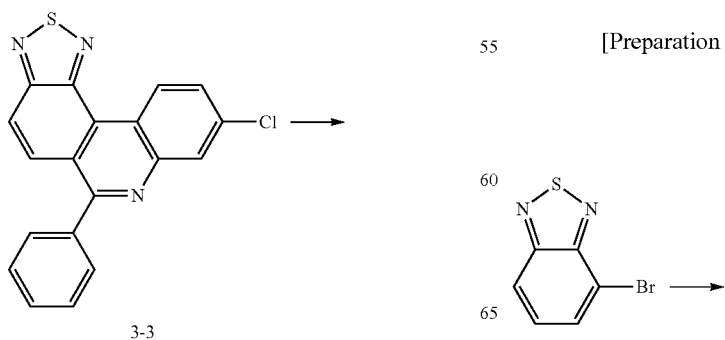

3-4

298

After adding 9-(3-(4-(3-bromophenyl)-6-phenylpyrimidin-2-yl)phenyl)-9H-carbazole (12.6 g, 22.76 mmol), Pd(PPh₃)₄ (1.25 g, 1.09 mmol), K₂CO₃ (25.0 g, 65.4 mmol) and toluene/ethanol/H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 298 (13.7 g, yield 73%).

[Preparation Example 26] Preparation of Compound 307

-continued

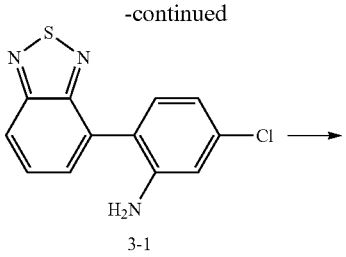

3-1

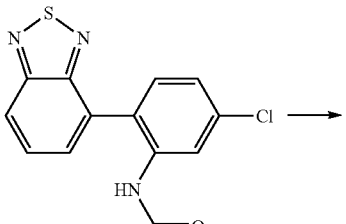

3-2

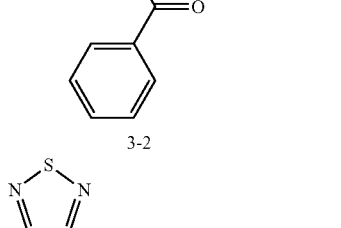

3-3

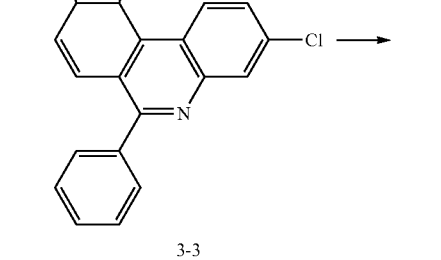

3-4

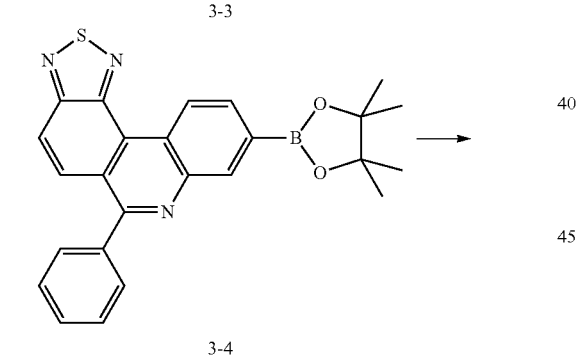

307

After adding 4'-(4-bromophenyl)-2,2':6',2"-terpyridine (8.8 g, 22.76 mmol), Pd(PPh$_3$)$_4$ (1.25 g, 1.09 mmol), K$_2$CO$_3$ (25.0 g, 65.4 mmol) and toluene/ethanol/H$_2$O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 307 (10.9 g, yield 77%).

[Preparation Example 27] Preparation of Compound 323

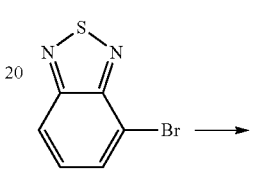

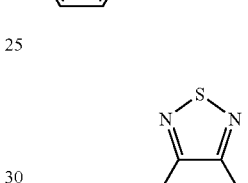

3-1

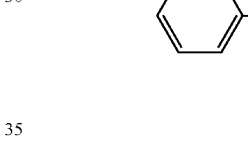

3-2

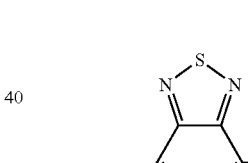

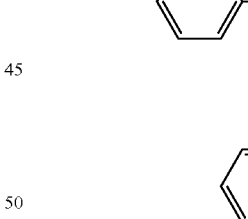

3-3

-continued

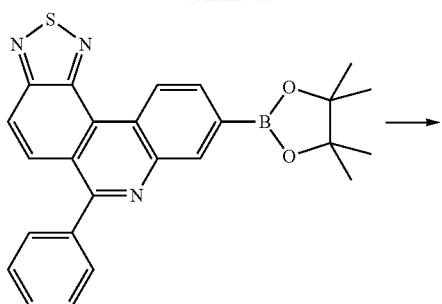

3-4

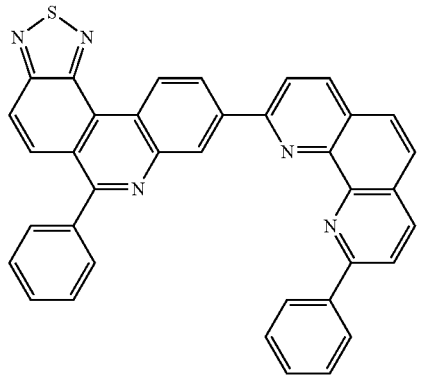

323

After adding 2-bromo-9-phenyl-1,10-phenanthroline (7.6 g, 22.76 mmol), Pd(PPh₃)₄ (1.25 g, 1.09 mmol), K₂CO₃ (25.0 g, 65.4 mmol) and toluene/ethanol/H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 323 (9.9 g, yield 76%).

[Preparation Example 28] Preparation of Compound 325

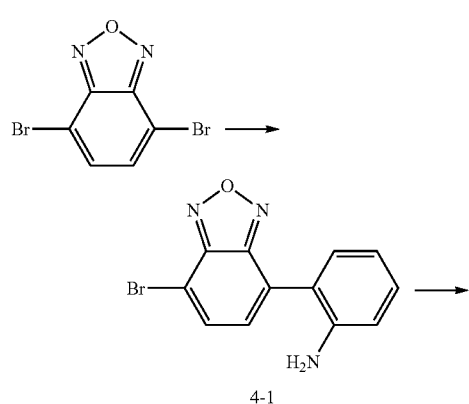

-continued

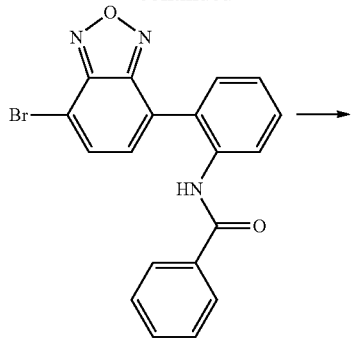

4-2

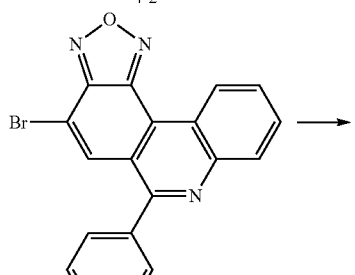

4-3

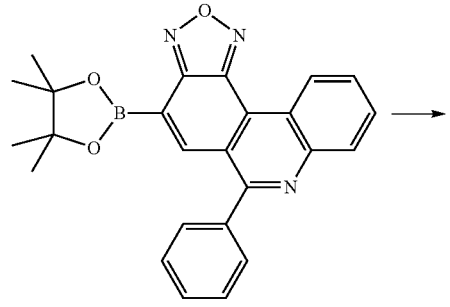

4-4

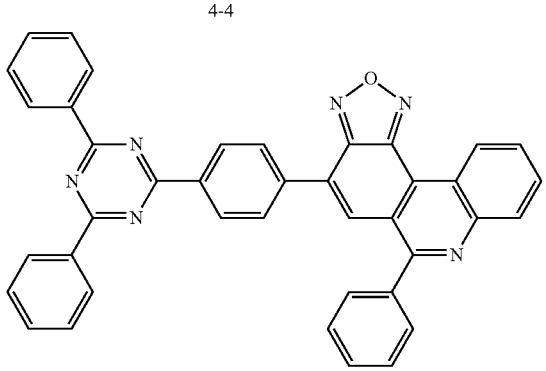

325

1) Preparation of Compound 4-1

After dissolving 4,7-dibromobenzo[c][1,2,5]oxadiazole (50 g, 179.9 mmol) and 2-(4,4,5,5-tetramethyl-1,3,2-dioxaborolan-2-yl)aniline (39.4 g, 179.9 mmol) in toluene (1000 mL), ethanol (200 mL) and H₂O (200 mL), Pd(PPh₃)₄ (10.4 g, 8.995 mmol) and K₃PO₄ (114.5 g, 539.7 mmol) were introduced thereto, and the result was stirred for 5 hours under reflux. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 4-1 (45 g, yield 86%).

2) Preparation of Compound 4-2

After dissolving Compound 4-1 (45 g, 155.1 mmol) in methylene chloride (500 mL), triethylamine (21.6 mL, 155.1 mmol) was introduced thereto. After lowering the temperature from room temperature to 0° C., benzoyl chloride (23.9 g, 170.61 mmol) dissolved in methylene chloride was slowly added dropwise thereto. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 4-2 (50 g, yield 82%).

3) Preparation of Compound 4-3

After dissolving Compound 4-2 (50 g, 126.8 mmol) in nitrobenzene (500 mL), $POCl_3$ (25 g, 164.4 mmol) was slowly added dropwise thereto, and then the result was stirred for 4 hours at 150° C. After the reaction was completed, the result was neutralized with an aqueous $NaHCO_3$ solution and then extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 4-3 (40 g, yield 83%).

4) Preparation of Compound 4-4

After dissolving Compound 4-3 (40 g, 106.3 mmol) and bis(pinacolato)diboron (40.4 g, 159.4 mmol) in 1,4-dioxane (400 mL), $Pd(dppf)Cl_2$ (4.3 g, 5.31 mmol) and KOAc (31.2 g, 318.9 mmol) were introduced thereto, and the result was stirred for 5 hours under reflux. After the reaction was completed, the result was extracted with ethyl acetate and $H_2O$. The organic layer was dried with anhydrous $MgSO_4$, and after removing the solvent using a rotary evaporator, the result was passed through silica gel to obtain Compound 4-4 (40 g, yield 88%).

5) Preparation of Compound 325

After adding 2-(4-bromophenyl)-4,6-diphenyl-1,3,5-triazine (9.1 g, 23.62 mmol), $Pd(PPh_3)_4$ (1.25 g, 1.09 mmol), $K_2CO_3$ (25.0 g, 65.4 mmol) and toluene/ethanol/$H_2O$ to Compound 4-4 (10.0 g, 23.62 mmol), the result was stirred for 6 hours at 110° C. After the reaction was completed, the result was cooled to room temperature, and extracted with distilled water and dichloromethane. The organic layer was dried with anhydrous $MgSO_4$, and after removing the solvent using a rotary evaporator, the result was purified by column chromatography using dichloromethane and hexane as a developing solvent to obtain Compound 325 (11 g, yield 76%).

[Preparation Example 29] Preparation of Compound 326

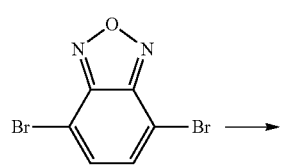

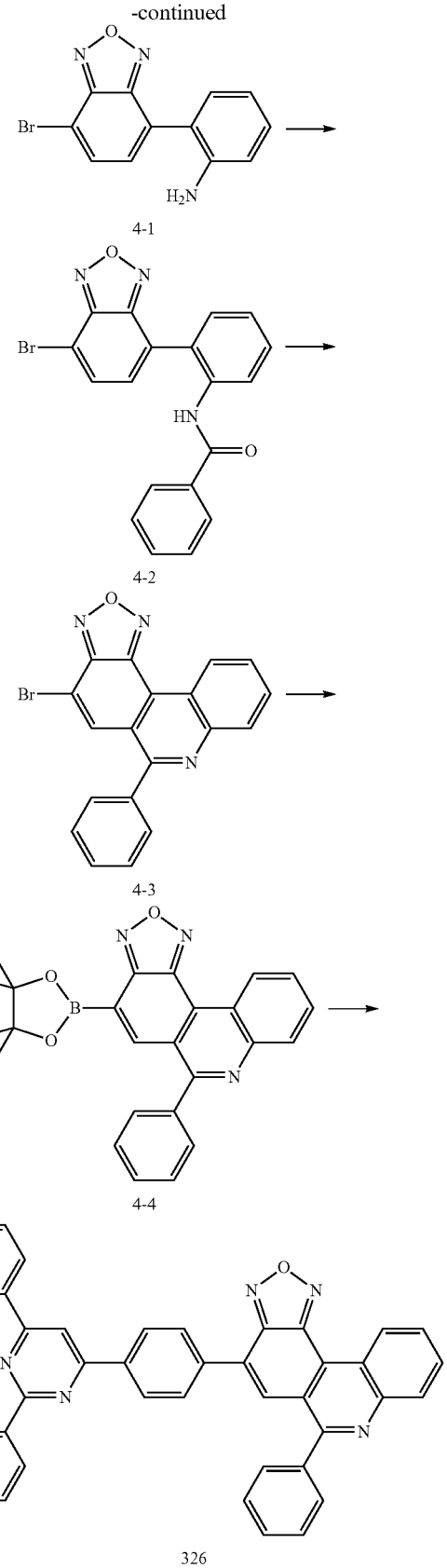

After adding 4-(4-bromophenyl)-2,6-diphenylpyrimidine (9.1 g, 23.62 mmol), $Pd(PPh_3)_4$ (1.25 g, 1.09 mmol), $K_2CO_3$ (25.0 g, 65.4 mmol) and toluene/ethanol/H₂O to Compound 4-4 (10.0 g, 23.62 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 326 (11.5 g, yield 80%).

[Preparation Example 30] Preparation of Compound 337

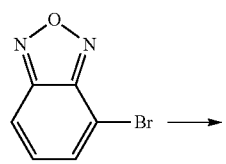

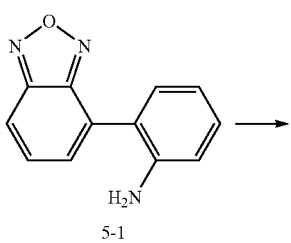
5-1

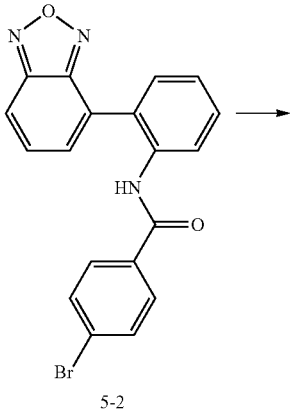
5-2

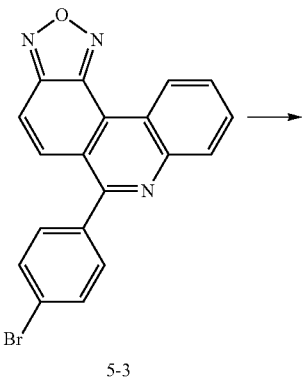
5-3

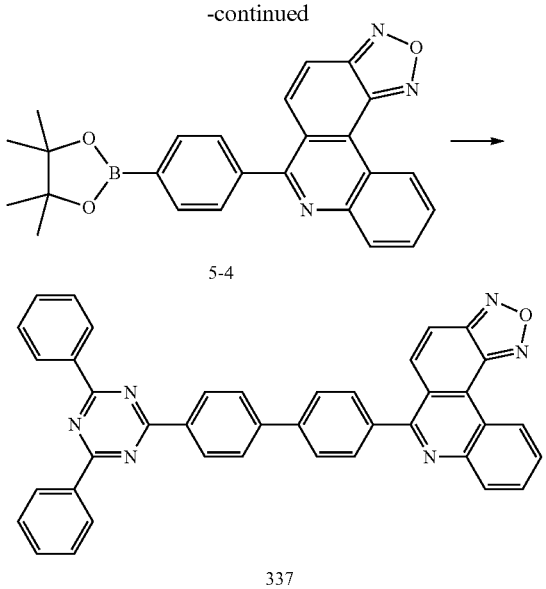
5-4

337

1) Preparation of Compound 5-1

After dissolving 4-bromobenzo[c][1,2,5]oxadiazole (50 g, 251.2 mmol) and 2-(4,4,5,5-tetramethyl-1,3,2-dioxaborolan-2-yl)aniline (55 g, 251.2 mnol) in toluene (1000 mL), ethanol (200 mL) and H₂O (200 mL), Pd(PPh₃)₄ (14.5 g, 12.56 mmol) and K₃PO₄ (159.9 g, 753.6 mmol) were introduced thereto, and the result was stirred for 5 hours under reflux. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 5-1 (45 g, yield 85%).

2) Preparation of Compound 5-2

After dissolving Compound 5-1 (45 g, 213.0 mmol) in methylene chloride (500 mL), triethylamine (29.7 mL, 213.0 mmol) was introduced thereto. After lowering the temperature from room temperature to 0° C., 4-bromobenzoyl chloride (51.4 g, 234.3 mmol) dissolved in methylene chloride was slowly added dropwise thereto. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 5-2 (70 g, yield 83%).

3) Preparation of Compound 5-3

After dissolving Compound 5-2 (50 g, 126.8 mmol) in nitrobenzene (500 mL), POCl₃ (25 g, 164.4 mmol) was slowly added dropwise thereto, and then the result was stirred for 4 hours at 150° C. After the reaction was completed, the result was neutralized with an aqueous NaHCO₃ solution and then extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 5-3 (42 g, yield 87%).

4) Preparation of Compound 5-4

After dissolving Compound 5-3 (40 g, 106.3 mmol) and bis(pinacolato)diboron (40.4 g, 159.4 mmol) in 1,4-dioxane (400 mL), Pd(dppf)Cl₂ (4.3 g, 5.31 mmol) and KOAc (31.2 g, 318.9 mmol) were introduced thereto, and the result was stirred for 5 hours under reflux. After the reaction was completed, the result was extracted with ethyl acetate and H₂O. The organic layer was dried with anhydrous MgSO₄, and after removing the solvent using a rotary evaporator, the result was passed through silica gel to obtain Compound 5-4 (41 g, yield 90%).

5) Preparation of Compound 337

After adding 2-(4-bromophenyl)-4,6-diphenyl-1,3,5-triazine (9.1 g, 23.62 mmol), Pd(PPh₃)₄ (1.25 g, 1.09 mmol), K₂CO₃ (25.0 g, 65.4 mmol) and toluene/ethanol/H₂O to Compound 5-4 (10.0 g, 23.62 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 337 (10 g, yield 70%).

[Preparation Example 31] Preparation of Compound 338

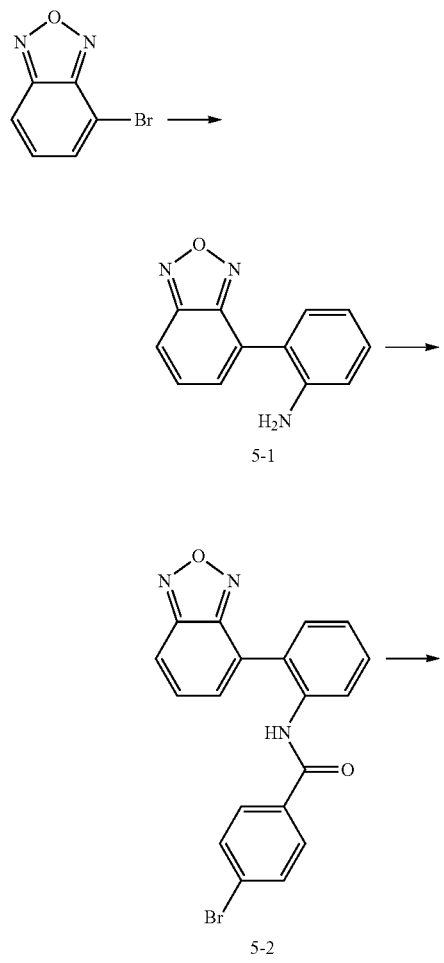

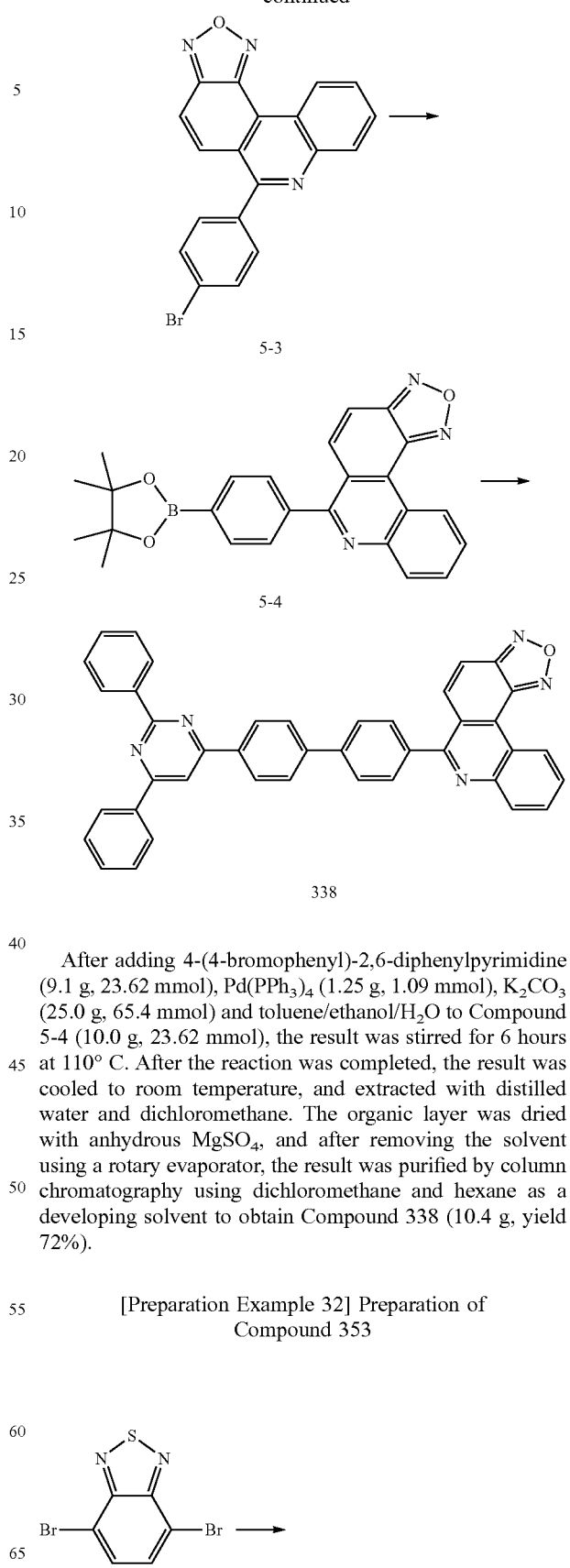

After adding 4-(4-bromophenyl)-2,6-diphenylpyrimidine (9.1 g, 23.62 mmol), Pd(PPh₃)₄ (1.25 g, 1.09 mmol), K₂CO₃ (25.0 g, 65.4 mmol) and toluene/ethanol/H₂O to Compound 5-4 (10.0 g, 23.62 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 338 (10.4 g, yield 72%).

[Preparation Example 32] Preparation of Compound 353

-continued

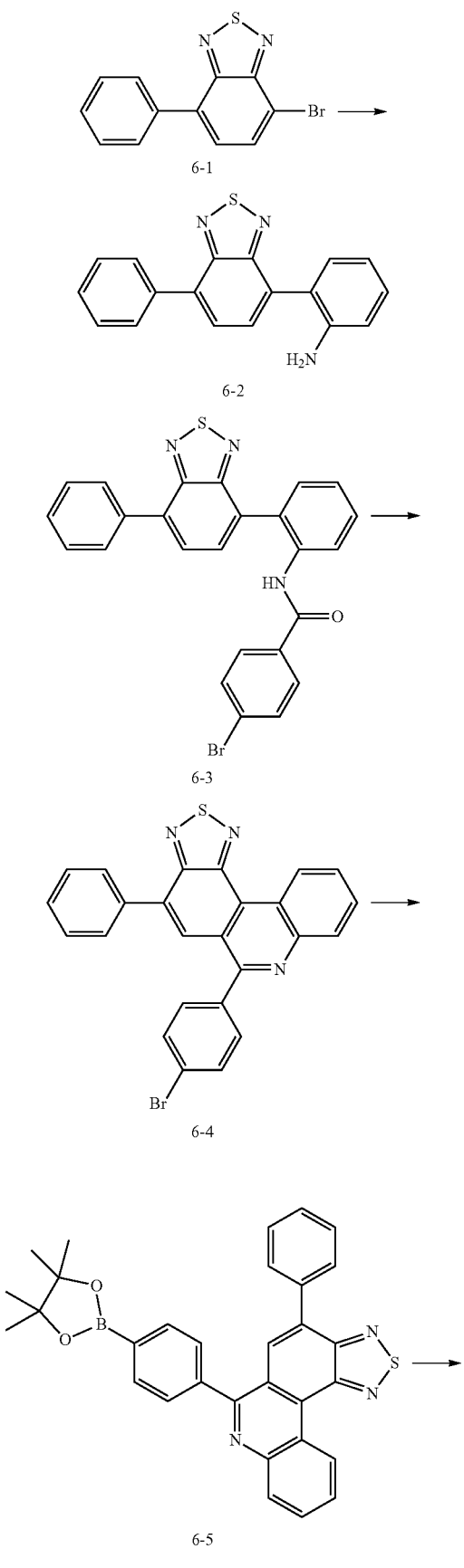

6-1

6-2

6-3

6-4

6-5

-continued

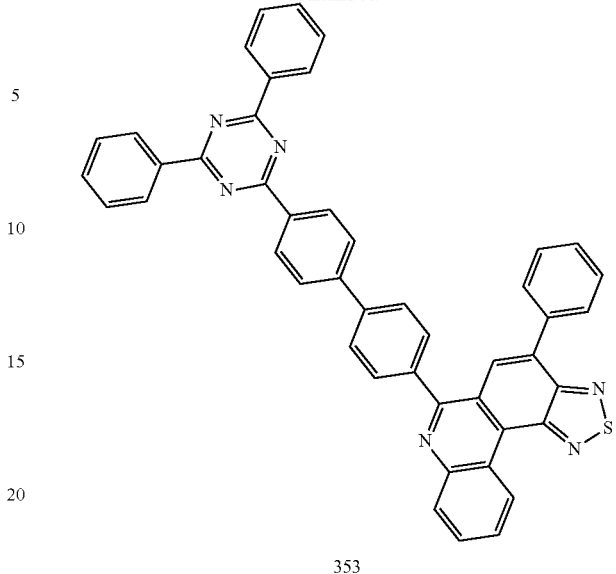

353

After dissolving 4,7-dibromobenzo[c][1,2,5]thiadiazole (50 g, 170.1 mmol) and phenylboronic acid (20.7 g, 170.1 mmol) in toluene (1000 mL), ethanol (200 mL) and $H_2O$ (200 mL), Pd(PPh$_3$)$_4$ (7.9 g, 6.845 mmol) and K$_3$PO$_4$ (87.1 g, 410.7 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 6-1 (45 g, yield 91%).

2) Preparation of Compound 6-2

After dissolving Compound 6-1 (45 g, 154.5 mmol) and 2-(4,4,5,5-tetramethyl-1,3,2-dioxaborolan-2-yl) aniline (33.8 g, 154.5 mmol) in toluene (900 mL), ethanol (180 mL) and $H_2O$ (180 mL), Pd(PPh$_3$)$_4$ (8.9 g, 7.72 mmol) and K$_3$PO$_4$ (63.9 g, 463.5 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 6-2 (38.7 g, yield 83%).

3) Preparation of Compound 6-3

After dissolving Compound 6-2 (38.7 g, 127.3 mmol) in methylene chloride (387 mL), triethylamine (18 mL, 127.3 mmol) was introduced thereto. After lowering the temperature from room temperature to 0° C., 4-bromobenzoyl chloride (27.9 g, 137.74 mmol) dissolved in methylene chloride was slowly added dropwise thereto. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 6-3 (52 g, yield 84%).

4) Preparation of Compound 6-4

After dissolving Compound 6-3 (52 g, 106.9 mmol) in nitrobenzene (520 mL), $POCl_3$ (24.5 g, 160.3 mmol) was slowly added dropwise thereto, and then the result was stirred for 4 hours at 150° C. After the reaction was completed, The result was neutralized with an aqueous $NaHCO_3$ solution and then extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 6-4 (45 g, yield 90%).

5) Preparation of Compound 6-5

After dissolving Compound 6-4 (40 g, 85.4 mmol) and bis(pinacolato)diboron (32.63 g, 128.48 mmol) in 1,4-dioxane (400 mL), $Pd(dppf)Cl_2$ (3.48 g, 4.27 mmol) and KOAc (25.22 g, 256.96 mmol) were introduced thereto, and the result was stirred for 5 hours under reflux. After the reaction was completed, the result was extracted with ethyl acetate and $H_2O$. The organic layer was dried with anhydrous $MgSO_4$, and after removing the solvent using a rotary evaporator, the result was passed through silica gel to obtain Compound 6-5 (40 g, yield 90%).

6) Preparation of Compound 353

After adding 2-(4-bromophenyl)-4,6-diphenyl-1,3,5-triazine (7.5 g, 19.4 mmol), $Pd(PPh_3)_4$ (1.25 g, 1.09 mmol), $K_2CO_3$ (25.0 g, 65.4 mnol) and toluene/ethanol/$H_2O$ to Compound 6-5 (10.0 g, 19.4 mmol), the result was stirred for 6 hours at 110° C. After the reaction was completed, the result was cooled to room temperature, and extracted with distilled water and dichloromethane. The organic layer was dried with anhydrous $MgSO_4$, and after removing the solvent using a rotary evaporator, the result was purified by column chromatography using dichloromethane and hexane as a developing solvent to obtain Compound 353 (10 g, yield 74%).

[Preparation Example 33] Preparation of Compound 354

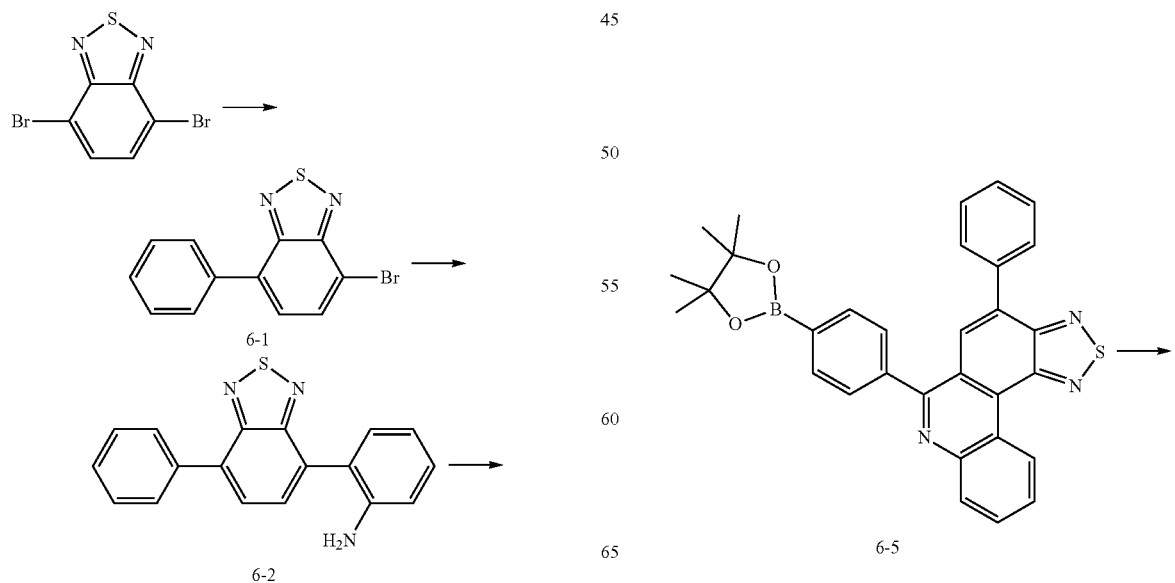

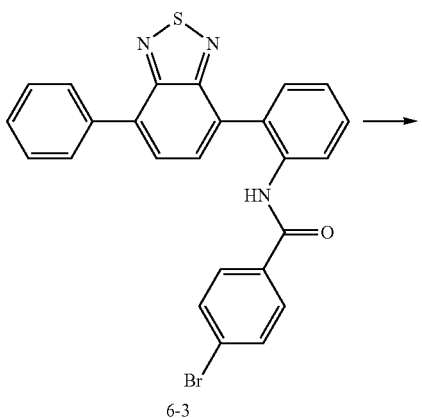

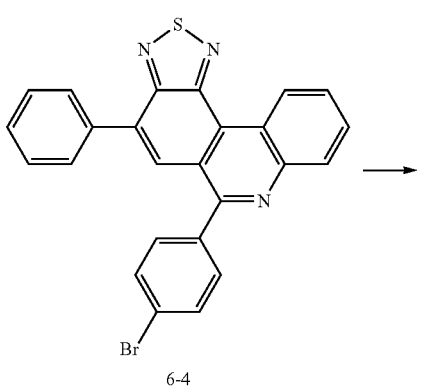

323

-continued

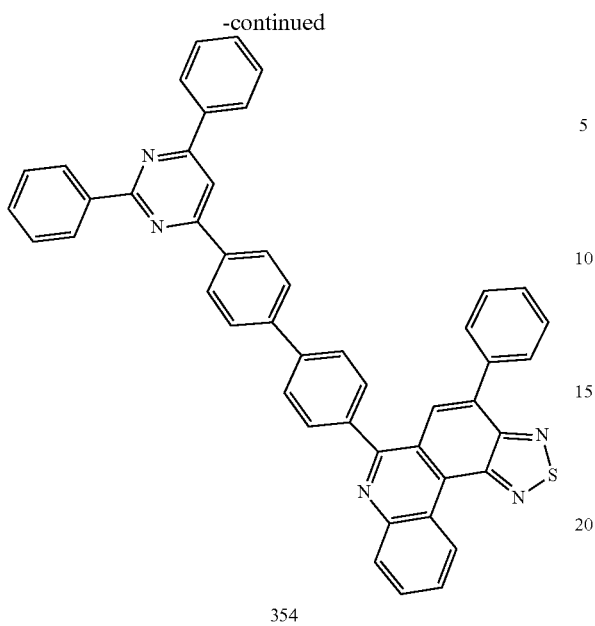

354

After adding 4-(4-bromophenyl)-2,6-diphenylpyrimidine (7.5 g, 19.4 mmol), Pd(PPh$_3$)$_4$ (1.25 g, 1.09 mmol), K$_2$CO$_3$ (25.0 g, 65.4 mmol) and toluene/ethanol/H$_2$O to Compound 6-5 (10.0 g, 19.4 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 354 (10.5 g, yield 77%).

[Preparation Example 34] Preparation of Compound 361

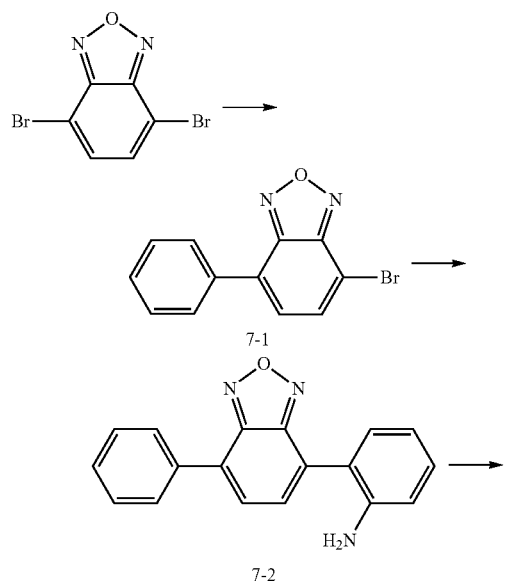

324

-continued

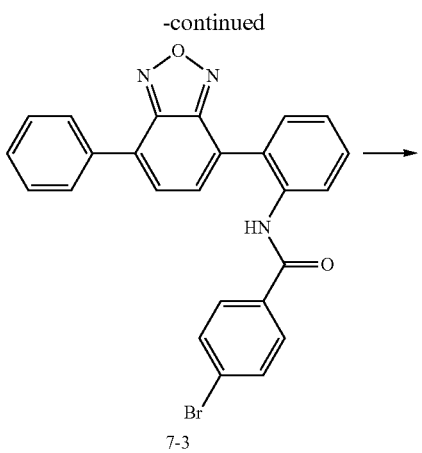

7-3

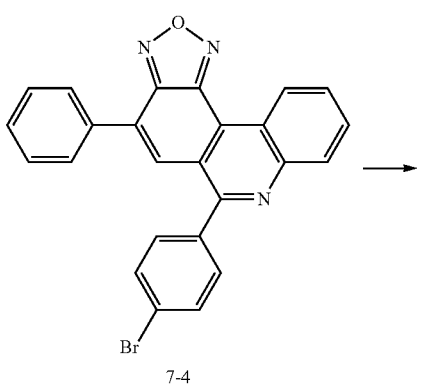

7-4

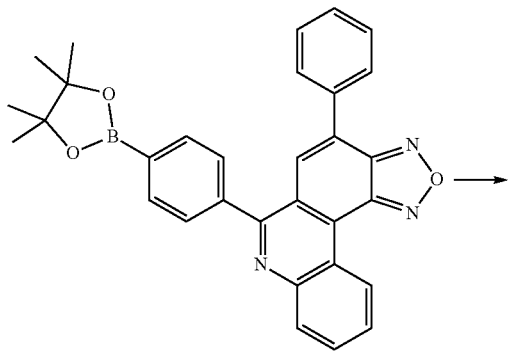

7-5

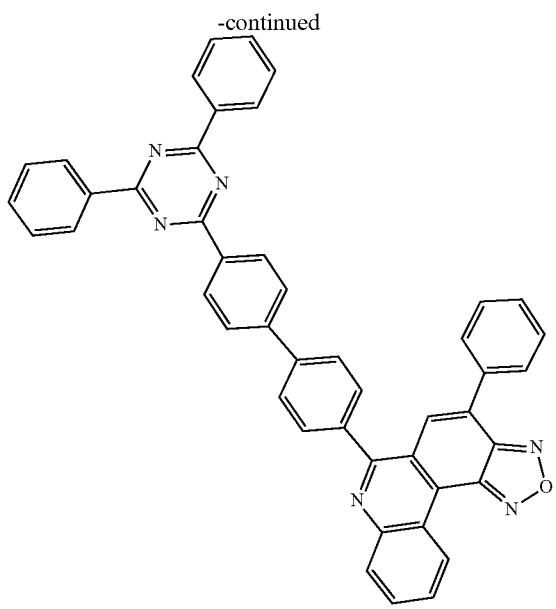

361

1) Preparation of Compound 7-1

After dissolving 4,7-dibromobenzo[c][1,2,5]oxadiazole (55.5 g, 200 mmol) and phenylboronic acid (24.4 g, 200 mmol) in toluene (1000 mL), ethanol (200 mL) and H₂O (200 mL), Pd(PPh₃)₄ (11.5 g, 10 mmol) and K₃PO₄ (127.3 g, 600 mmol) were introduced thereto, and the result was stirred for 5 hours under reflux. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 7-1 (49 g, yield 89%).

2) Preparation of Compound 7-2

After dissolving Compound 7-1 (42.5 g, 154.5 mmol) and 2-(4,4,5,5-tetramethyl-1,3,2-dioxaborolan-2-yl)aniline
(33.8 g, 154.5 mmol) in toluene (1000 mL), ethanol (200 mL) and H₂O (200 mL), Pd(PPh₃)₄ (8.9 g, 7.72 mmol) and K₃PO₄ (63.9 g, 463.5 mmol) were introduced thereto, and the result was stirred for 5 hours under reflux. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 7-2 (37.7 g, yield 83%).

3) Preparation of Compound 7-3

After dissolving Compound 7-2 (36.6 g, 127.3 mmol) in methylene chloride (450 mL), triethylamine (18 mL, 127.3 mmol) was introduced thereto. After lowering the temperature from room temperature to 0° C., 4-bromobenzoyl chloride (27.9 g, 137.74 mmol) dissolved in methylene chloride was slowly added dropwise thereto. After the reaction was completed, the result was extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 7-3 (50.3 g, yield 84%).

4) Preparation of Compound 7-4

After dissolving Compound 7-3 (50.2 g, 106.9 mmol) in nitrobenzene (502 mL), POCl₃ (24.5 g, 160.3 mmol) was slowly added dropwise thereto, and then the result was stirred for 4 hours at 150° C. After the reaction was completed, the result was neutralized with an aqueous NaHCO₃ solution and then extracted with methylene chloride and distilled water, and the organic layer was dried with anhydrous MgSO₄. After removing the solvent using a rotary evaporator, the result was purified by column chromatography using dichloromethane and hexane as a developing solvent to obtain Compound 7-4 (40 g, yield 83%).

5) Preparation of Compound 7-5

After dissolving Compound 7-4 (38.6 g, 85.4 mmol) and bis(pinacolato)diboron (32.63 g, 128.48 mmol) in 1,4-dioxane (400 mL), Pd(dppf)Cl₂ (3.48 g, 4.27 mmol) and KOAc (25.22 g, 256.96 mmol) were introduced thereto, and the result was stirred for 5 hours under reflux. After the reaction was completed, the result was extracted with ethyl acetate and H₂O. The organic layer was dried with anhydrous MgSO₄, and after removing the solvent using a rotary evaporator, the result was passed through silica gel to obtain Compound 7-5 (39 g, yield 91%).

6) Preparation of Compound 361

After adding 2-(4-bromophenyl)-4,6-diphenyl-1,3,5-triazine (7.76 g, 20.0 mmol), Pd(PPh₃)₄ (1.15 g, 1.00 mmol), K₂CO₃ (8.29 g, 60.0 mmol) and toluene/ethanol/H₂O to Compound 7-5 (10.0 g, 20.0 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 361 (10.4 g, yield 76%).

[Preparation Example 35] Preparation of Compound 362

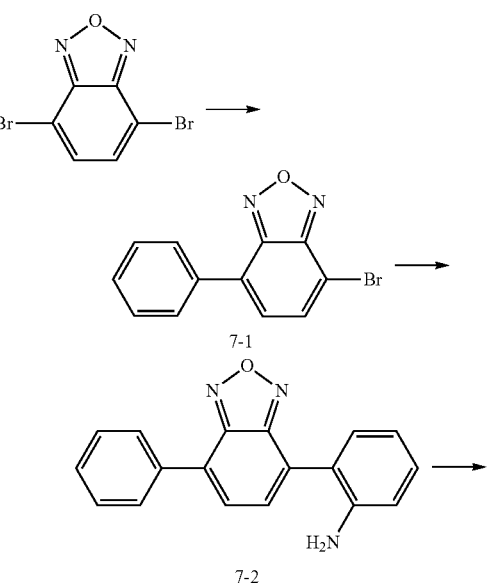

327
-continued

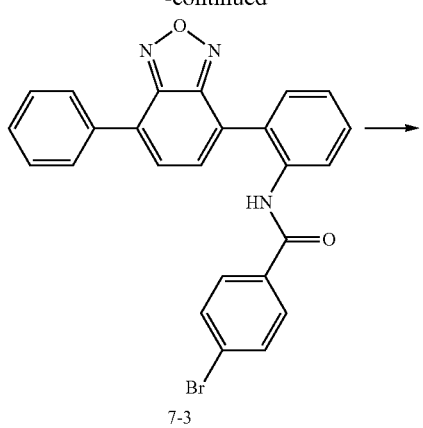

7-3

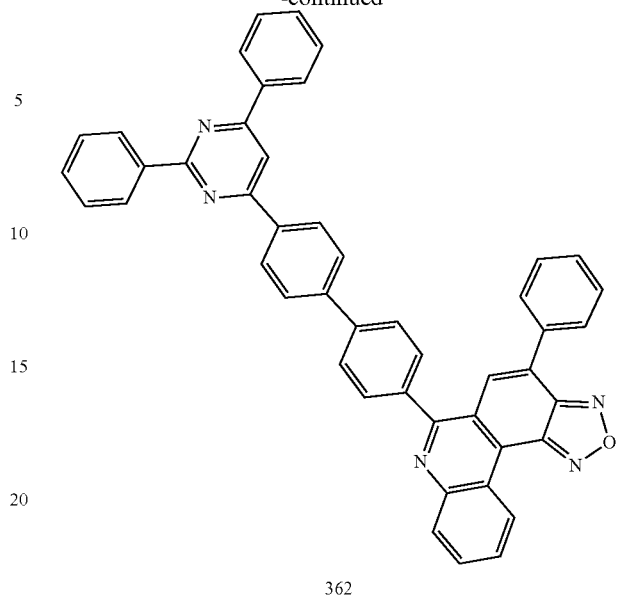

328
-continued

362

After adding 4-(4-bromophenyl)-2,6-diphenylpyrimidine (7.71 g, 20.0 mmol), Pd(PPh$_3$)$_4$ (1.15 g, 1.00 mmol), K$_2$CO$_3$ (8.29 g, 60.0 mmol) and toluene/ethanol/H$_2$O to Compound 7-5 (10.0 g, 20.0 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 362 (10.7 g, yield 78%).

[Preparation Example 36] Preparation of Compound 409

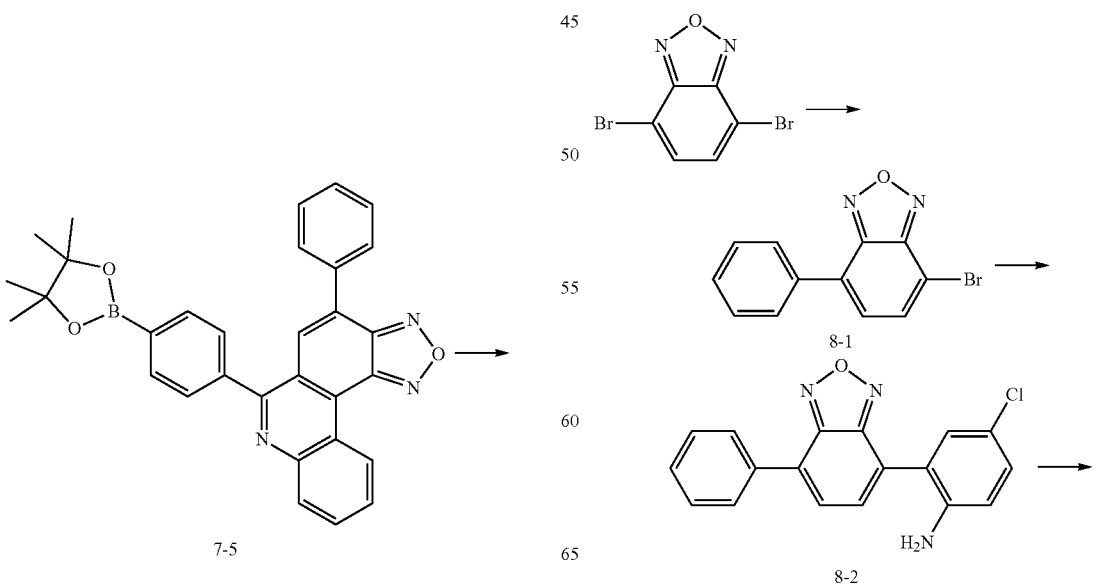

-continued

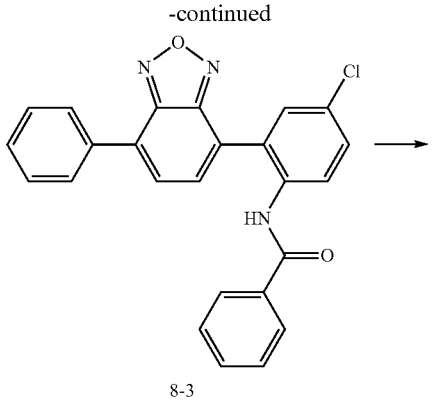

8-3

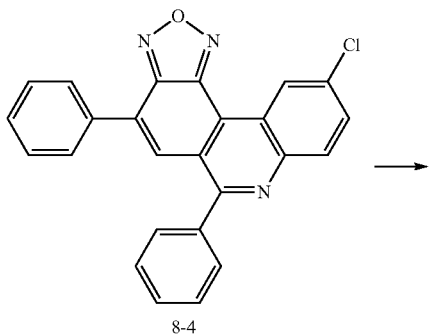

8-4

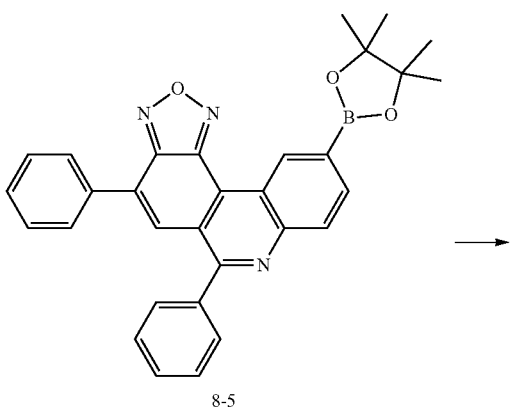

8-5

-continued

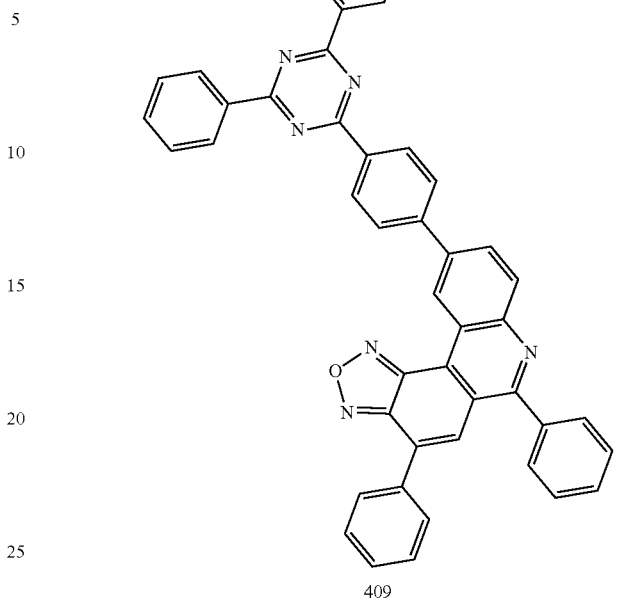

409

1) Preparation of Compound 8-1

After dissolving 4,7-dibromobenzo[c][1,2,5]oxadiazole (55.5 g, 200 mmol) and phenylboronic acid (24.4 g, 200 mmol) in toluene (1000 mL), ethanol (200 mL) and $H_2O$ (200 mL), $Pd(PPh_3)_4$ (11.5 g, 10 mmol) and $K_3PO_4$ (127.3 g, 600 mmol) were introduced thereto, and the result was stirred for 5 hours under reflux. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 8-1 (49 g, yield 89%).

2) Preparation of Compound 8-2

After dissolving Compound 8-1 (42.5 g, 154.5 mmol) and 4-chloro-2-(4,4,5,5-tetramethyl-1,3,2-dioxaborolan-2-yl) aniline (39.2 g, 154.5 mmol) in toluene (1000 mL), ethanol (200 mL) and $H_2O$ (200 mL), $Pd(PPh_3)_4$ (8.9 g, 7.72 mmol) and $K_3PO_4$ (63.9 g, 463.5 mmol) were introduced thereto, and the result was stirred for 5 hours under reflux. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 8-2 (41.2 g, yield 83%).

3) Preparation of Compound 8-3

After dissolving Compound 8-2 (40.9 g, 127.3 mmol) in methylene chloride (480 mL), triethylamine (18 mL, 127.3 mmol) was introduced thereto. After lowering the temperature from room temperature to 0° C., 4-bromobenzoyl chloride (27.9 g, 137.74 mmol) dissolved in methylene chloride was slowly added dropwise thereto. After the reaction was completed, the result was extracted with methylene chloride and distilled water, and the organic layer was dried with anhydrous $MgSO_4$. After removing the solvent using a rotary evaporator, the result was purified by column chromatography using dichloromethane and hexane as a developing solvent to obtain Compound 8-3 (49 g, yield 90%).

4) Preparation of Compound 8-4

After dissolving Compound 8-3 (45.5 g, 106.9 mmol) in nitrobenzene (455 mL), POCl$_3$ (24.5 g, 160.3 mmol) was slowly added dropwise thereto, and then the result was stirred for 4 hours at 150° C. After the reaction was completed, the result was neutralized with an aqueous NaHCO$_3$ solution and then extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 8-4 (38 g, yield 87%).

5) Preparation of Compound 8-5

After dissolving Compound 8-4 (34.8 g, 85.4 mmol) and bis(pinacolato)diboron (32.63 g, 128.48 mmol) in 1,4-dioxane (400 mL), Pd(dppf)Cl$_2$ (3.48 g, 4.27 mmol) and KOAc (25.22 g, 256.96 mmol) were introduced thereto, and the result was stirred for 5 hours under reflux. After the reaction was completed, the result was extracted with ethyl acetate and H$_2$O. The organic layer was dried with anhydrous MgSO$_4$, and after removing the solvent using a rotary evaporator, the result was passed through silica gel to obtain Compound 8-5 (36 g, yield 84%).

6) Preparation of Compound 409

After adding 2-(4-bromophenyl)-4,6-diphenyl-1,3,5-triazine (7.76 g, 20.0 mmol), Pd(PPh$_3$)$_4$ (1.15 g, 1.00 mmol), K$_2$CO$_3$ (8.29 g, 60.0 mmol) and toluene/ethanol/H$_2$O to Compound 8-5 (10.0 g, 20.0 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 409 (9.9 g, yield 72%).

[Preparation Example 37] Preparation of Compound 411

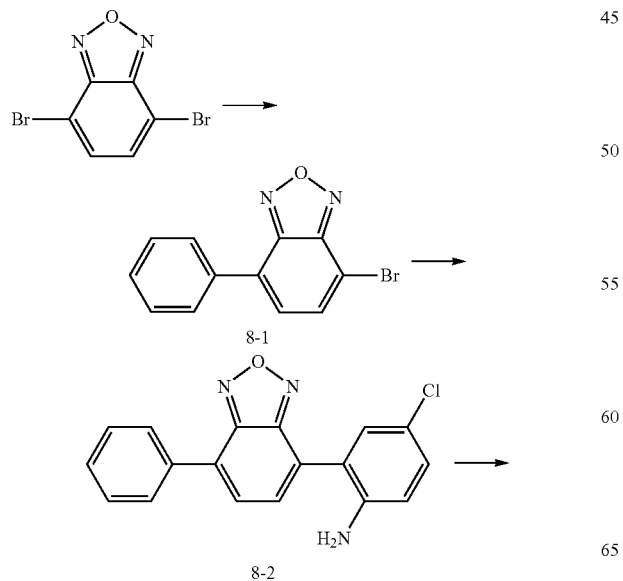

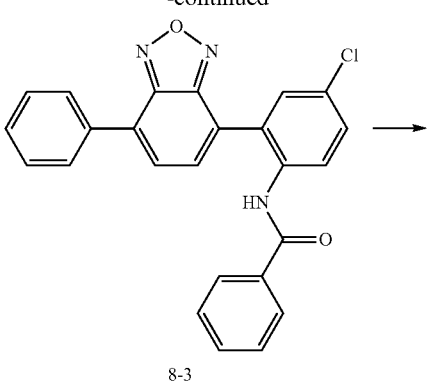

8-3

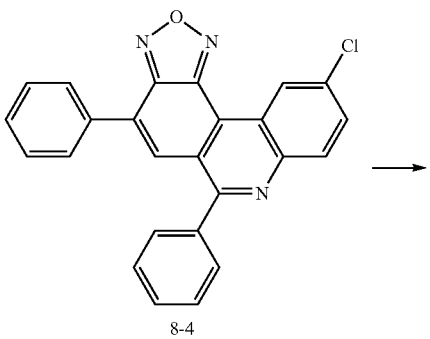

8-4

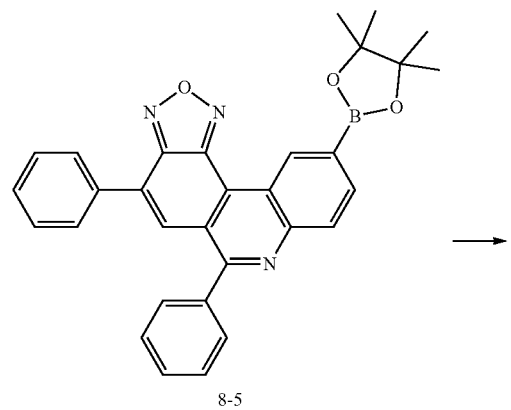

8-5

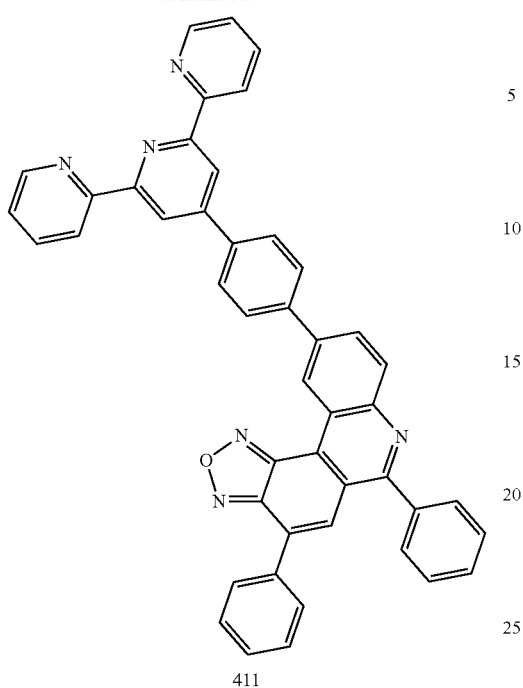

411

After adding 4'-(4-bromophenyl)-2,2':6',2"-terpyridine (7.76 g, 20.0 mmol), Pd(PPh$_3$)$_4$ (1.15 g, 1.00 mmol), K$_2$CO$_3$ (8.29 g, 60.0 mmol) and toluene/ethanol/H$_2$O to Compound 8-5 (10.0 g, 20.0 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 411 (10.2 g, yield 75%).

[Preparation Example 38] Preparation of Compound 412

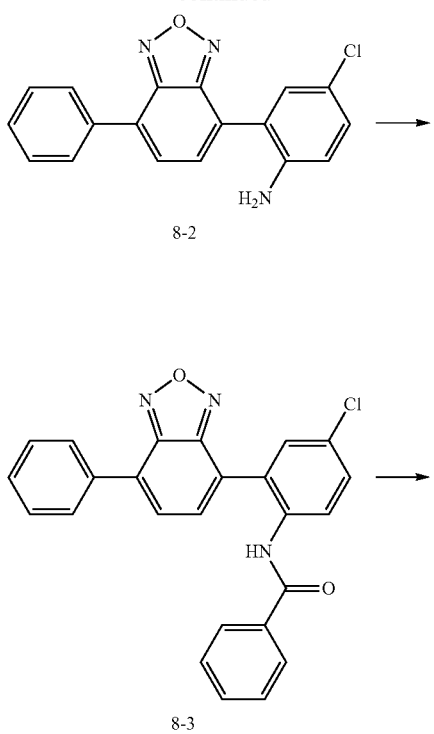

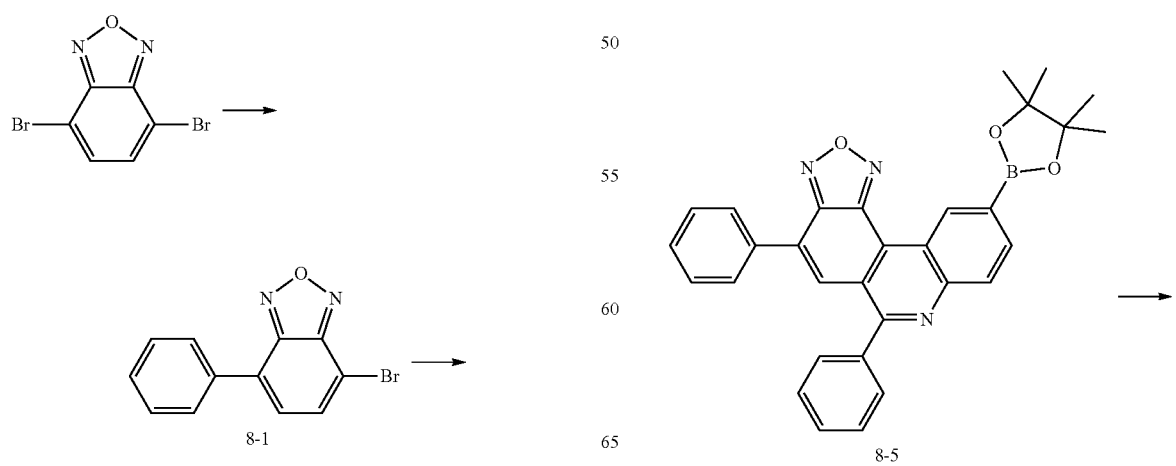

-continued

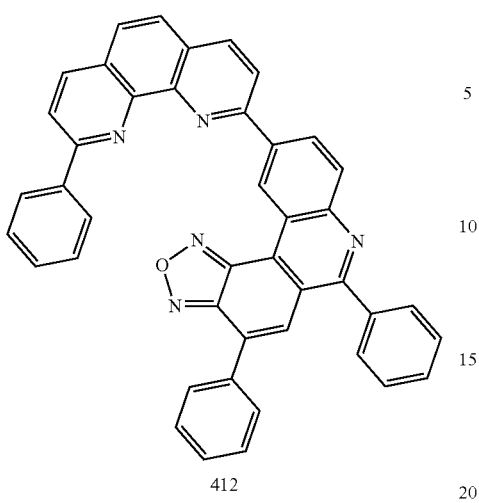

412

After adding 2-bromo-9-phenyl-1,10-phenanthroline (6.7 g, 20.0 mmol), Pd(PPh$_3$)$_4$ (1.15 g, 1.00 mmol), K$_2$CO$_3$ (8.29 g, 60.0 mmol) and toluene/ethanol/H$_2$O to Compound 8-5 (10.0 g, 20.0 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain red Compound 412 (10.1 g, yield 80%).

[Preparation Example 39] Preparation of Compound 417

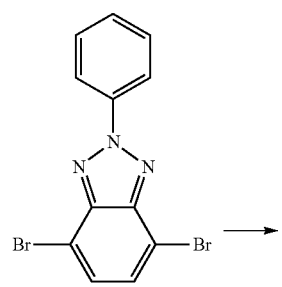

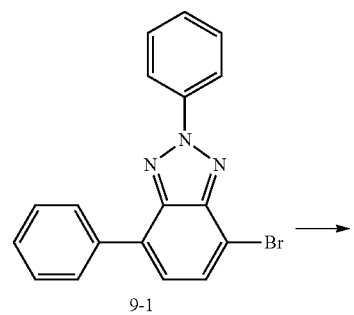

9-1

-continued

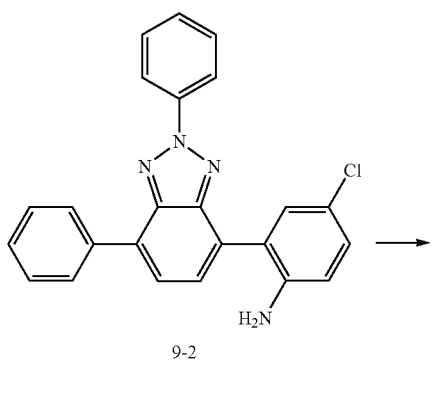

9-2

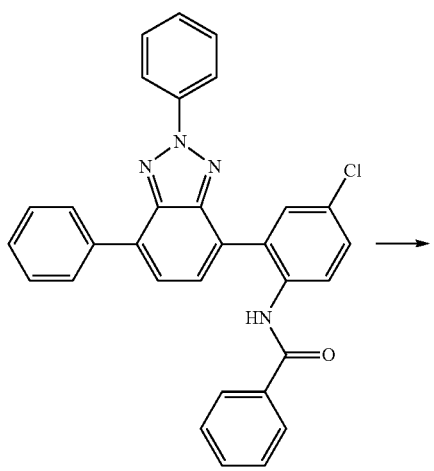

9-3

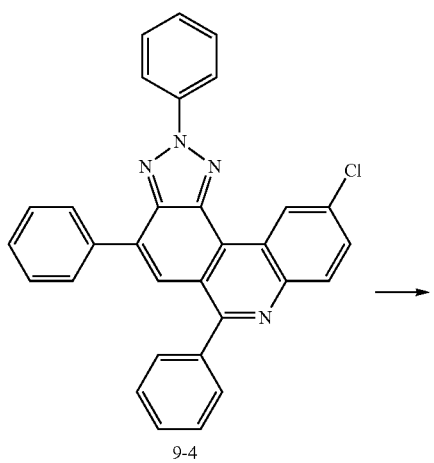

9-4

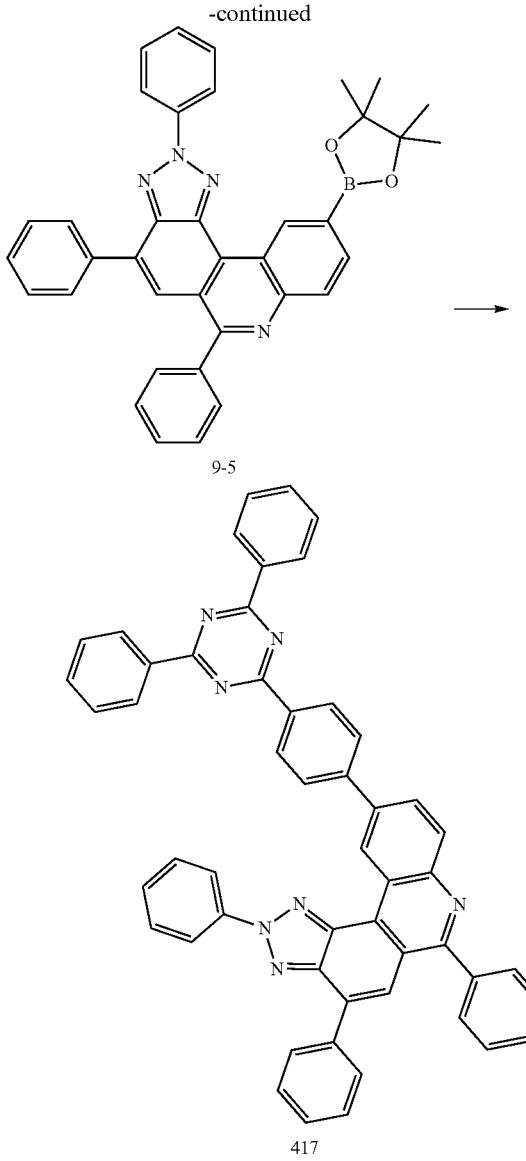

9-5

417

1) Preparation of Compound 9-1

After dissolving 4,7-dibromo-2-phenyl-2H-benzo[d][1,2,3]triazole (35.3 g, 100 mmol) and phenylboronic acid (12.2 g, 100 mmol) in toluene (700 mL), ethanol (14 mL) and H$_2$O (14 mL), Pd(PPh$_3$)$_4$ (5.75 g, 5 mmol) and K$_3$PO$_4$ (65.7 g, 300 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 9-1 (30 g, yield 85%).

2) Preparation of Compound 9-2

After dissolving Compound 9-1 (27.05 g, 77.25 mmol) and 4-chloro-2-(4,4,5,5-tetramethyl-1,3,2-dioxaborolan-2-yl) aniline (39.2 g, 77.25 mmol) in toluene (770 mL), ethanol (154 mL) and H$_2$O (154 mL), Pd(PPh$_3$)$_4$ (4.45 g, 3.86 mmol) and K$_3$PO$_4$ (63.9 g, 231.75 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 9-2 (26 g, yield 84%).

3) Preparation of Compound 9-3

After dissolving Compound 9-2 (25.3 g, 63.65 mmol) in methylene chloride (300 mL), triethylamine (9 mL, 63.65 mmol) was introduced thereto. After lowering the temperature from room temperature to 0° C., 4-bromobenzoyl chloride (13.95 g, 68.87 mmol) dissolved in methylene chloride was slowly added dropwise thereto. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 9-3 (49 g, yield 90%).

4) Preparation of Compound 9-4

After dissolving Compound 9-3 (26.7 g, 53.45 mmol) in nitrobenzene (267 mL), POCl$_3$ (12.25 g, 80.15 mmol) was slowly added dropwise thereto, and then the result was stirred for 4 hours at 150° C. After the reaction was completed, the result was neutralized with an aqueous NaHCO$_3$ solution and then extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 9-4 (22.8 g, yield 88%).

5) Preparation of Compound 9-5

After dissolving Compound 9-4 (20.6 g, 42.7 mmol) and bis(pinacolato)diboron (16.3 g, 64.24 mmol) in 1,4-dioxane (210 mL), Pd(dppf)Cl$_2$ (1.74 g, 2.13 mmol) and KOAc (12.56 g, 128.4 mmol) were introduced thereto, and the result was stirred for 5 hours under reflux. After the reaction was completed, the result was extracted with ethyl acetate and H$_2$O. The organic layer was dried with anhydrous MgSO$_4$, and after removing the solvent using a rotary evaporator, the result was passed through silica gel to obtain Compound 9-5 (20.1 g, yield 82%).

6) Preparation of Compound 417

After adding 2-(4-bromophenyl)-4,6-diphenyl-1,3,5-triazine (6.75 g, 17.4 mmol), Pd(PPh$_3$)$_4$ (1.00 g, 0.87 mmol), K$_2$CO$_3$ (7.2 g, 52.2 mnol) and toluene/ethanol/H$_2$O to Compound 9-5 (10.0 g, 17.4 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 417 (10 g, yield 76%).

[Preparation Example 40] Preparation of Compound 425

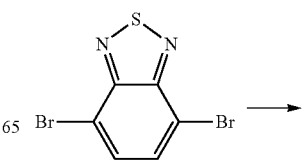

-continued

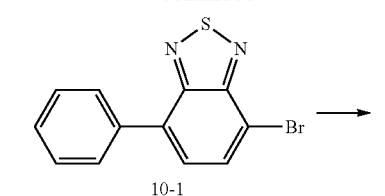

10-1

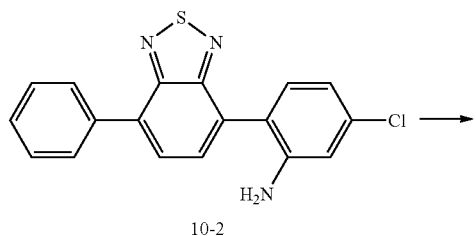

10-2

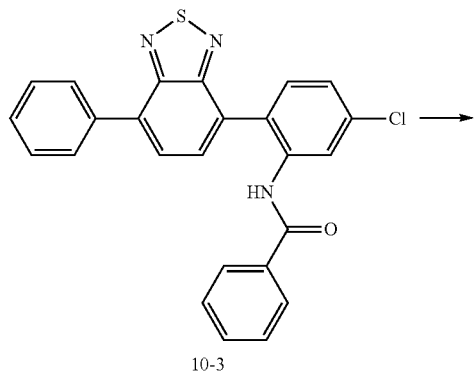

10-3

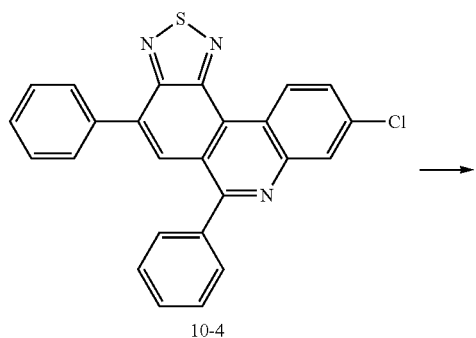

10-4

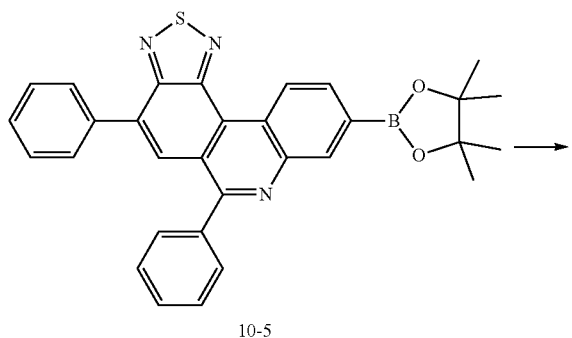

10-5

-continued

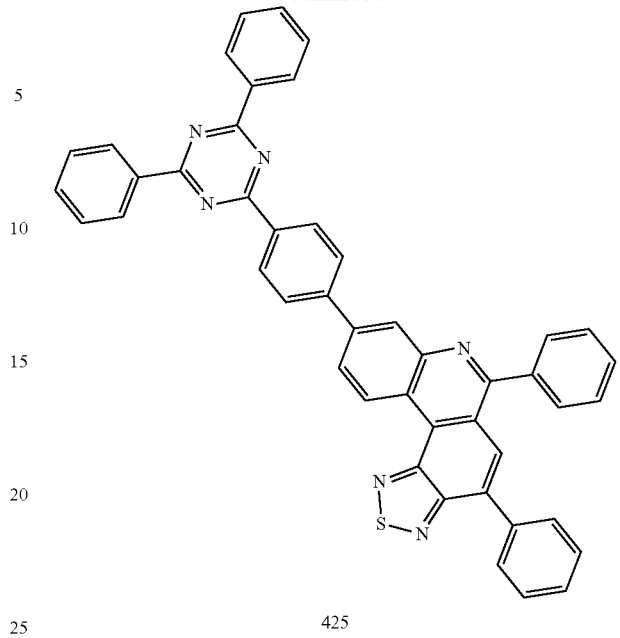

425

1) Preparation of Compound 10-1

After dissolving 4,7-dibromobenzo[c][1,2,5]thiadiazole (58.8 g, 200 mmol) and phenylboronic acid (24.4 g, 200 mmol) in toluene (1000 mL), ethanol (200 mL) and H$_2$O (200 mL), Pd(PPh$_3$)$_4$ (11.5 g, 10 mmol) and K$_3$PO$_4$ (127.3 g, 600 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 10-1 (52 g, yield 89%).

2) Preparation of Compound 10-2

After dissolving Compound 10-1 (45 g, 154.5 mmol) and 5-chloro-2-(4,4,5,5-tetramethyl-1,3,2-dioxaborolan-2-yl)aniline (39.2 g, 154.5 mmol) in toluene (1000 mL), ethanol (200 mL) and H$_2$O (200 mL), Pd(PPh$_3$)$_4$ (8.9 g, 7.72 mmol) and K$_3$PO$_4$ (63.9 g, 463.5 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 10-2 (43.4 g, yield 83%).

3) Preparation of Compound 10-3

After dissolving Compound 10-2 (43.0 g, 127.3 mmol) in methylene chloride (430 mL), triethylamine (18 mL, 127.3 mmol) was introduced thereto. After lowering the temperature from room temperature to 0° C., 4-bromobenzoyl chloride (27.9 g, 137.74 mmol) dissolved in methylene chloride was slowly added dropwise thereto. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 10-3 (50.58 g, 90%).

4) Preparation of Compound 10-4

After dissolving Compound 10-3 (47.2 g, 106.9 mmol) in nitrobenzene (455 mL), POCl$_3$ (24.5 g, 160.3 mmol) was slowly added dropwise thereto, and then the result was stirred for 4 hours at 150° C. After the reaction was completed, the result was neutralized with an aqueous NaHCO$_3$ solution and then extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 10-4 (39.5 g, yield 87%).

5) Preparation of Compound 10-5

After dissolving Compound 10-4 (36.2 g, 85.4 mmol) and bis(pinacolato)diboron (32.63 g, 128.48 mmol) in 1,4-dioxane (362 mL), Pd(dppf)Cl$_2$ (3.48 g, 4.27 mmol) and KOAc (25.22 g, 256.96 mmol) were introduced thereto, and the result was stirred for 5 hours under reflux. After the reaction was completed, the result was extracted with ethyl acetate and H$_2$O. The organic layer was dried with anhydrous MgSO$_4$, and after removing the solvent using a rotary evaporator, the result was passed through silica gel to obtain Compound 10-5 (38 g, yield 86%).

6) Preparation of Compound 425

After adding 2-(4-bromophenyl)-4,6-diphenyl-1,3,5-triazine (7.52 g, 19.4 mmol), Pd(PPh$_3$)$_4$ (1.12 g, 0.97 mmol), K$_2$CO$_3$ (8.04 g, 58.2 mmol) and toluene/ethanol/H$_2$O to Compound 10-5 (10.0 g, 19.4 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 425 (10.2 g, yield 75%).

[Preparation Example 41] Preparation of Compound 426

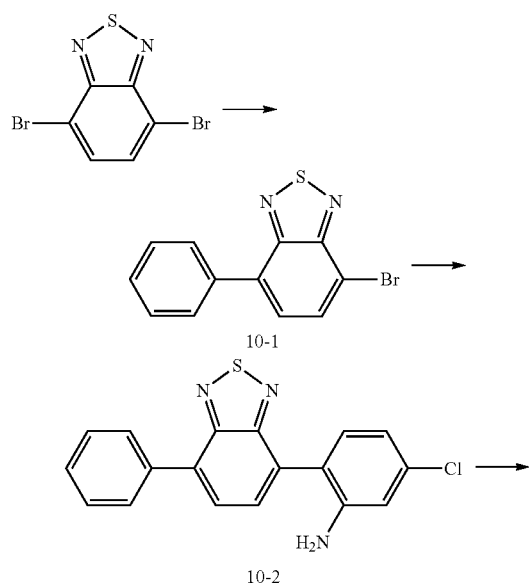

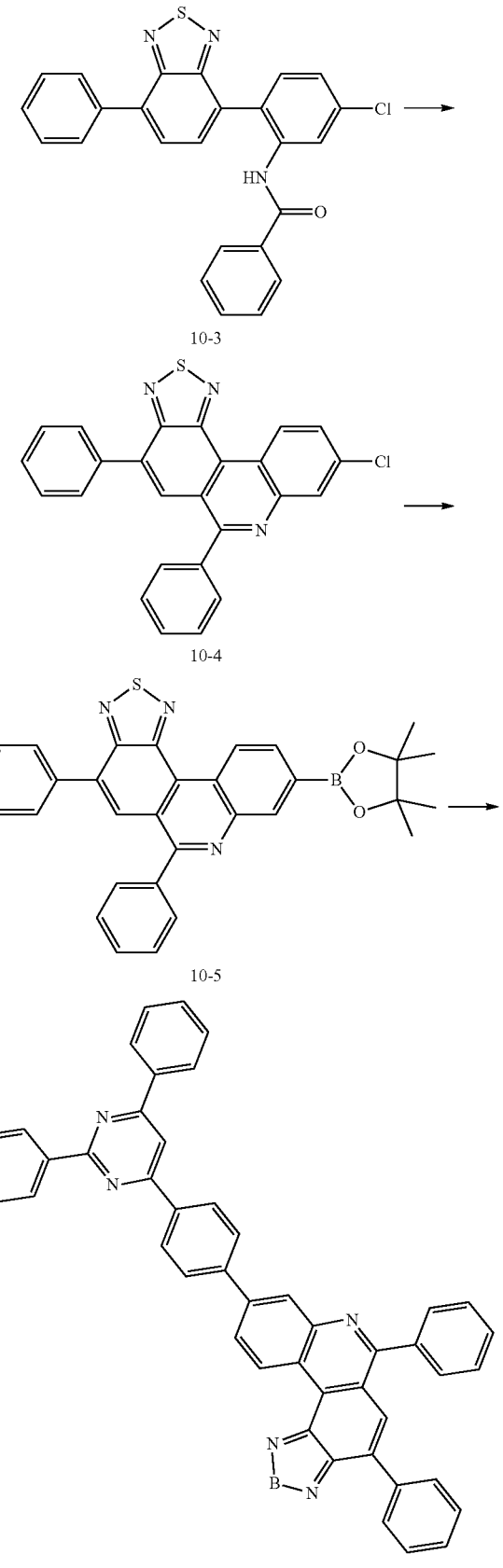

After adding 4-(4-bromophenyl)-2,6-diphenylpyrimidine (7.51 g, 19.4 mmol), Pd(PPh$_3$)$_4$ (1.12 g, 0.97 mmol), K$_2$CO$_3$ (8.04 g, 58.2 mmol) and toluene/ethanol/H$_2$O to Compound 10-5 (10.0 g, 19.4 mmol), the result was stirred for 6 hours at 110° C. After the reaction was completed, the result was cooled to room temperature, and extracted with distilled water and dichloromethane. The organic layer was dried with anhydrous MgSO$_4$, and after removing the solvent using a rotary evaporator, the result was purified by column chromatography using dichloromethane and hexane as a developing solvent to obtain Compound 426 (10.4 g, yield 77%).

[Preparation Example 42] Preparation of Compound 449

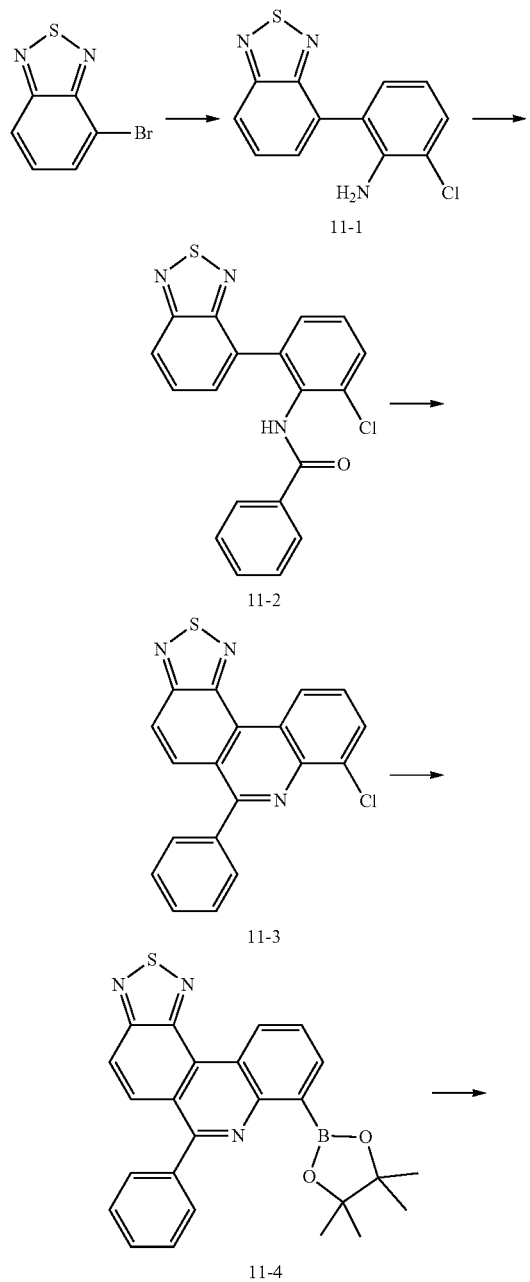

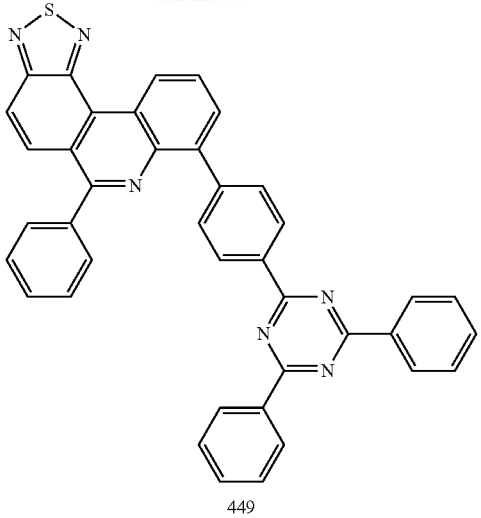

1) Preparation of Compound 11-1

After dissolving 4-bromobenzo[c][1,2,5]thiadiazole (45 g, 154.5 mmol) and 2-chloro-6-(4,4,5,5-tetramethyl-1,3,2-dioxaborolan-2-yl) aniline (39.2 g, 154.5 mmol) in toluene (1000 mL), ethanol (200 mL) and H$_2$O (200 mL), Pd(PPh$_3$)$_4$ (8.9 g, 7.72 mmol) and K$_3$PO$_4$ (63.9 g, 463.5 mmol) were introduced thereto, and the result was stirred for 5 hours under reflux. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 11-1 (43.4 g, yield 83%).

2) Preparation of Compound 11-2

After dissolving Compound 11-1 (43.0 g, 127.3 mnol) in methylene chlor ide (430 mL), triethylamine (18 mL, 127.3 mmol) was introduced thereto. After lowering the temperature from room temperature to 0° C., 4-bromobenzoyl chloride (27.9 g, 137.74 mmol) dissolved in methylene chloride was slowly added dropwise thereto. After the reaction was completed, the result was extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 11-2 (50.58 g, yield 90%).

3) Preparation of Compound 11-3

After dissolving Compound 11-2 (47.2 g, 106.9 mmol) in nitrobenzene (455 mL), POCl$_3$ (24.5 g, 160.3 mmol) was slowly added dropwise thereto, and then the result was stirred for 4 hours at 150° C. After the reaction was completed, the result was neutralized with an aqueous NaHCO$_3$ solution and then extracted with methylene chloride and distilled water, and the organic layer was dried with anhydrous MgSO$_4$. After removing the solvent using a rotary evaporator, the result was purified by column chromatography using dichloromethane and hexane as a developing solvent to obtain Compound 11-3 (39.5 g, yield 87%).

4) Preparation of Compound 11-4

After dissolving Compound 11-3 (36.2 g, 85.4 mmol) and bis(pinacolato)diboron (32.63 g, 128.48 mmol) in 1,4-dioxane (362 mL), Pd(dppf)Cl$_2$ (3.48 g, 4.27 mmol) and KOAc (25.22 g, 256.96 mmol) were introduced thereto, and the result was stirred for 5 hours under reflux. After the reaction was completed, the result was extracted with ethyl acetate and H₂O. The organic layer was dried with anhydrous MgSO₄, and after removing the solvent using a rotary evaporator, the result was passed through silica gel to obtain Compound 11-4 (38 g, yield 86%).

5) Preparation of Compound 449

After adding 2-(4-bromophenyl)-4,6-diphenyl-1,3,5-triazine (7.52 g, 19.4 mmol), Pd(PPh₃)₄ (1.12 g, 0.97 mmol), K₂CO₃ (8.04 g, 58.2 mmol) and toluene/ethanol/H₂O to Compound 11-4 (10.0 g, 19.4 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 449 (10 g, yield 74%).

[Preparation Example 43] Preparation of Compound 450

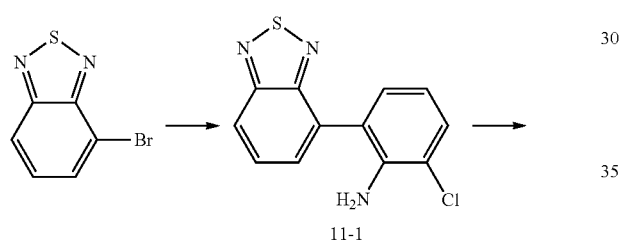
11-1

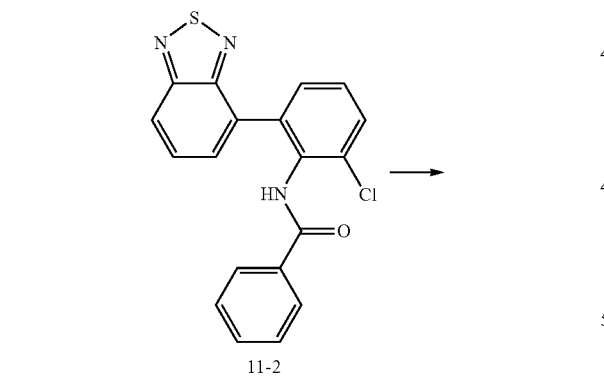
11-2

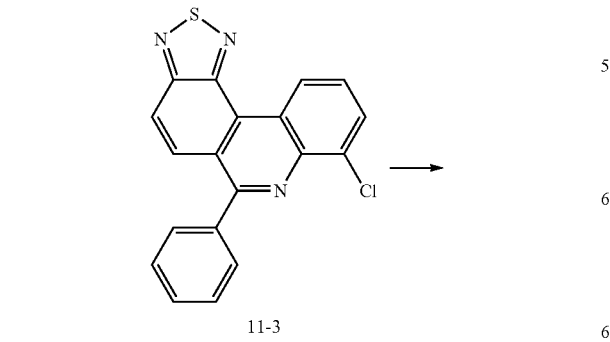
11-3

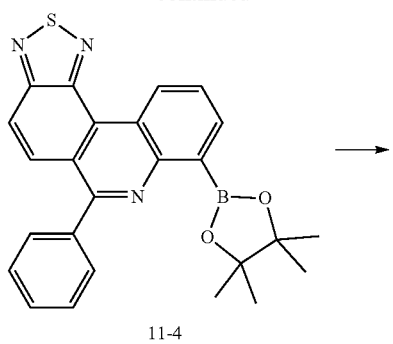
11-4

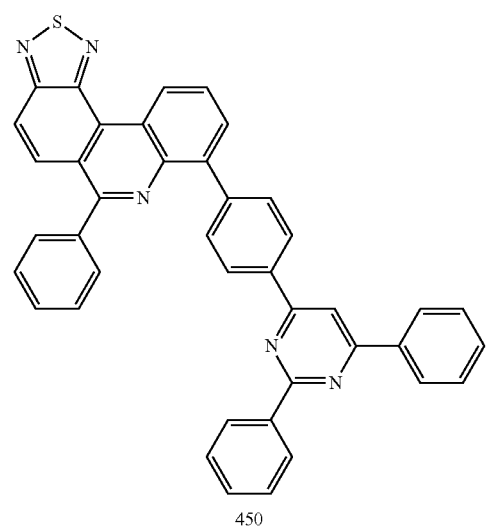
450

After adding 4-(4-bromophenyl)-2,6-diphenylpyrimidine (7.51 g, 19.4 mmol), Pd(PPh₃)₄ (1.12 g, 0.97 mmol), K₂CO₃ (8.04 g, 58.2 mmol) and toluene/ethanol/H₂O to Compound 11-4 (10.0 g, 19.4 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 450 (10.4 g, yield 77%).

[Preparation Example 44] Preparation of Compound 473

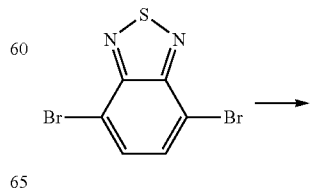

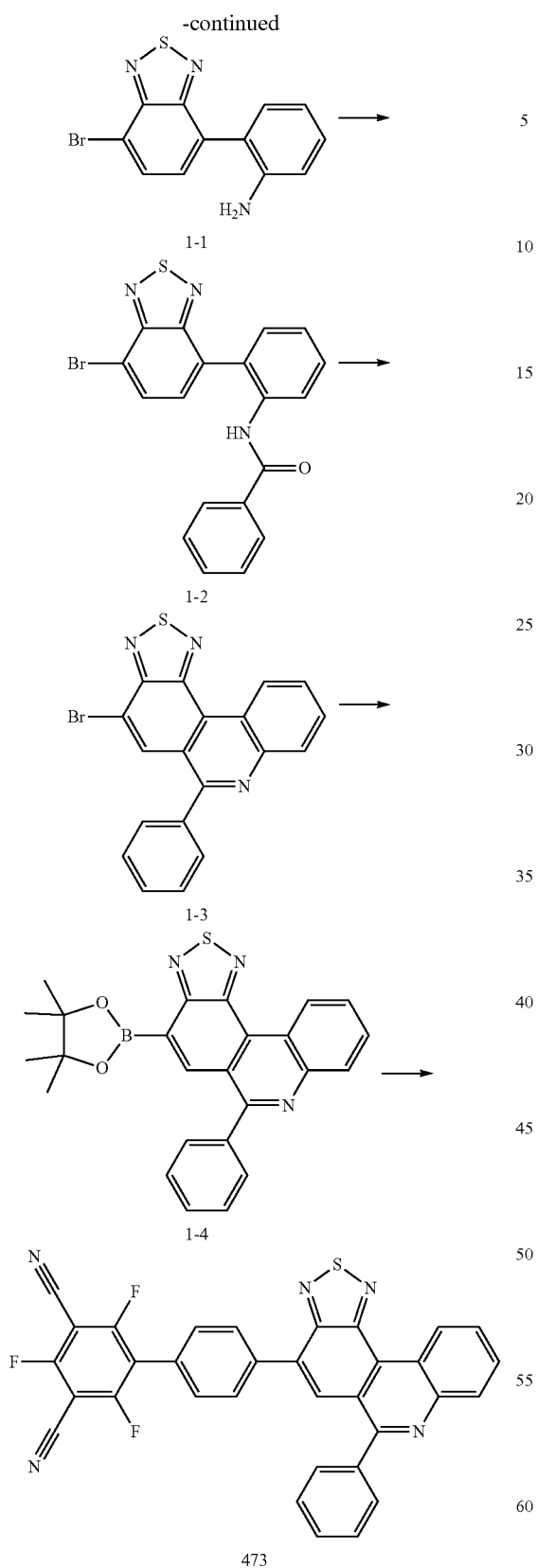

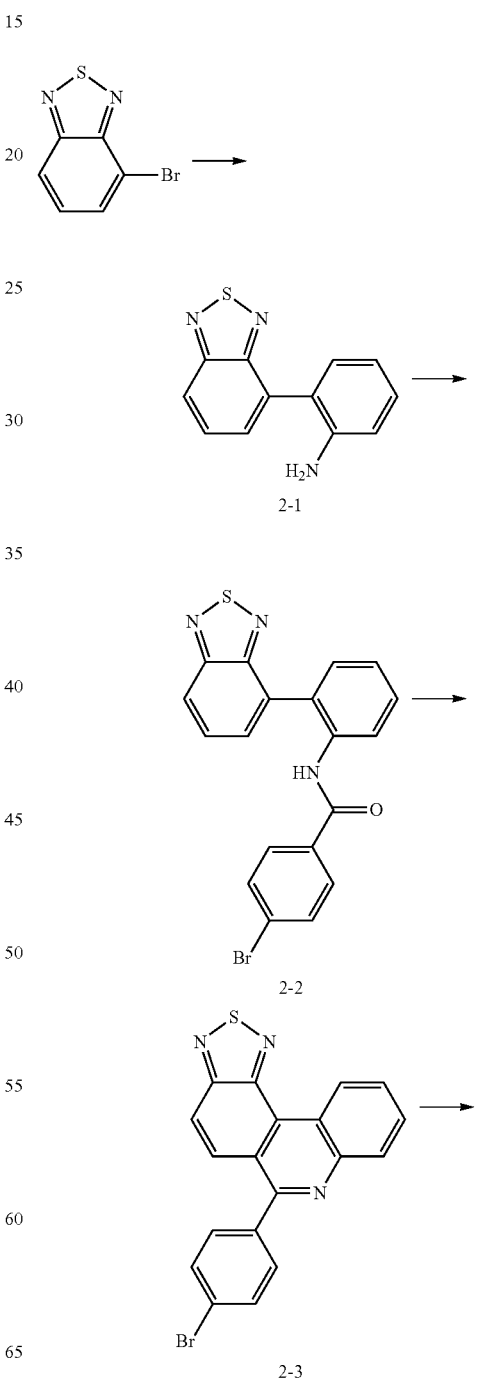

ethanol/H₂O to Compound 1-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 473 (9.7 g, yield 74%).

[Preparation Example 45] Preparation of Compound 485

After adding 4'-bromo-2,4,6-trifluoro-[1,1'-biphenyl]-3,5-dicarbonitrile (7.67 g, 22.76 mmol), Pd(PPh₃)₄ (1.25 g, 1.09 mmol), K₂CO₃ (25.0 g, 65.4 mmol) and toluene/

-continued

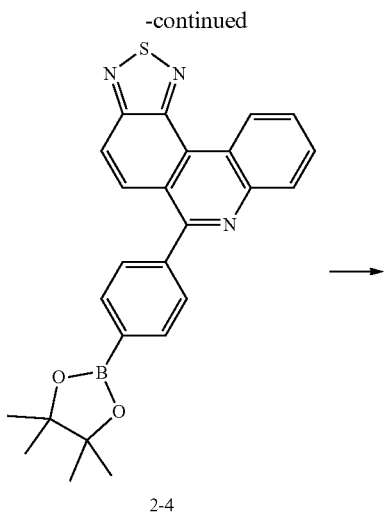

2-4

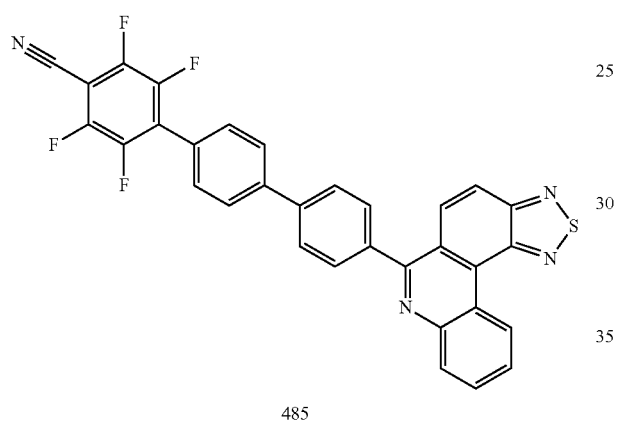

485

After adding 4'-bromo-2,3,5,6-tetrafluoro-[1,1'-biphenyl]-4-carbonitrile (7.5 g, 22.76 mmol), Pd(PPh₃)₄ (1.25 g, 1.09 mmol), K₂CO₃ (25.0 g, 65.4 mmol) and toluene/ethanol/H₂O to Compound 2-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 485 (10.1 g, yield 79%).

[Preparation Example 46] Preparation of Compound 505

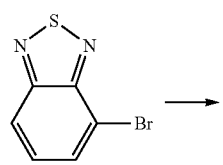

-continued

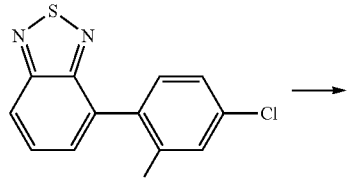

3-1

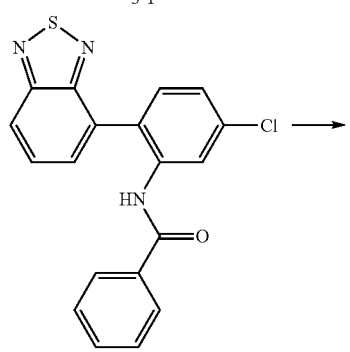

3-2

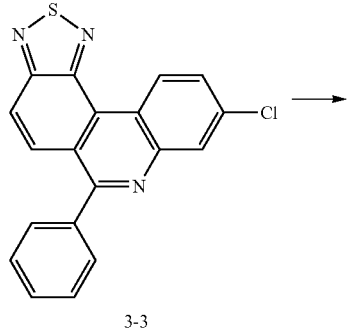

3-3

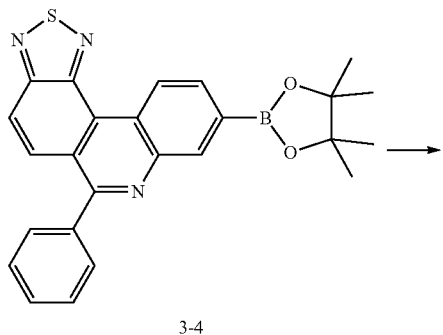

3-4

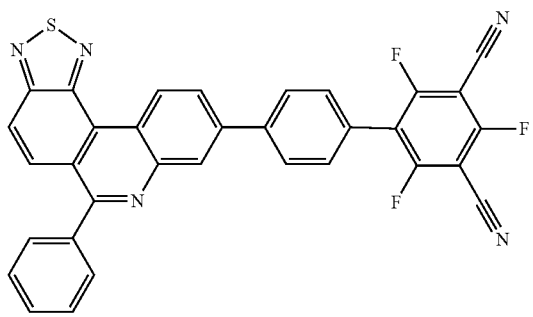

505

After adding 4'-bromo-2,4,6-trifluoro-[1,1'-biphenyl]-3,5-dicarbonitrile (7.6 g, 22.76 mmol), Pd(PPh₃)₄ (1.25 g, 1.09 mmol), K₂CO₃ (25.0 g, 65.4 mmol) and toluene/ethanol/

H₂O to Compound 3-4 (10.0 g, 22.76 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 505 (9.5 g, yield 73%).

[Preparation Example 47] Preparation of Compound 527

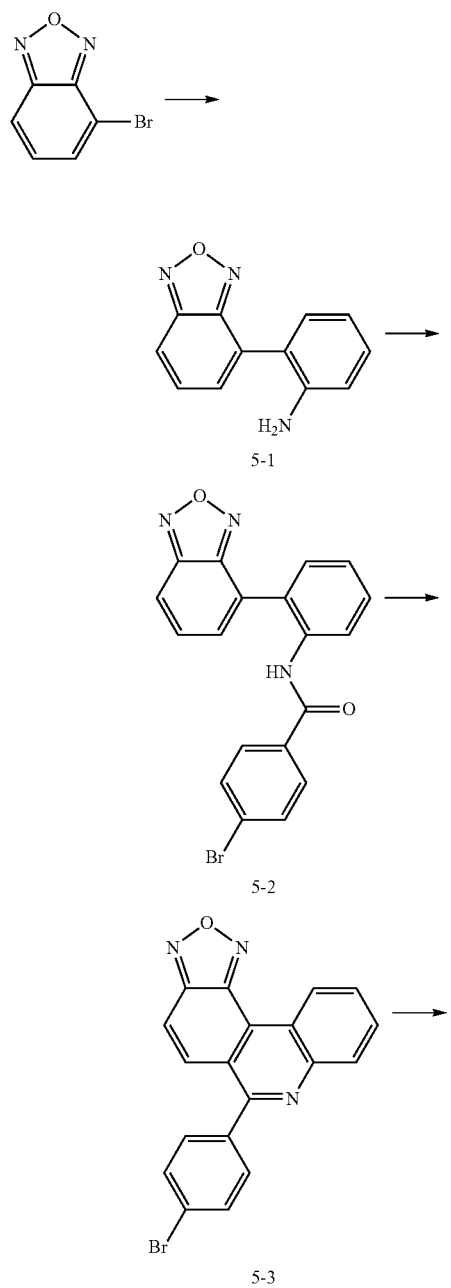

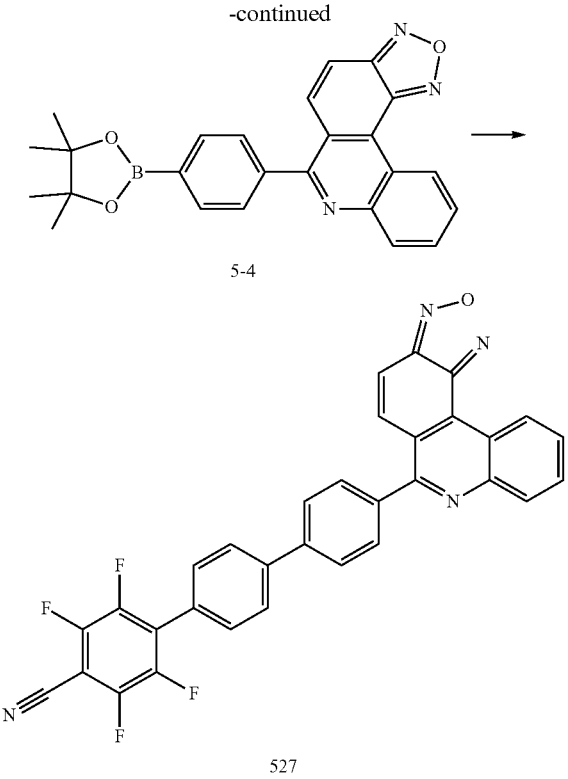

After adding 4'-bromo-2,3,5,6-tetrafluoro-[1,1'-biphenyl]-4-carbonitrile (7.5 g, 23.62 mmol), Pd(PPh₃)₄ (1.25 g, 1.09 mmol), K₂CO₃ (25.0 g, 65.4 mmol), and toluene/ethanol/H₂O to Compound 3-4 (10.0 g, 23.61 mmol), the result was stirred for 6 hours at 110° C. After the reaction was completed, the result was cooled to room temperature, and extracted with distilled water and dichloromethane. The organic layer was dried with anhydrous MgSO₄, and after removing the solvent using a rotary evaporator, the result was purified by column chromatography using dichloromethane and hexane as a developing solvent to obtain Compound 527 (9.4 g, yield 75%).

Compounds were prepared in the same manner as in the preparation examples, and the synthesis identification results are shown in the following Tables 1 and 2.

TABLE 1

| NO | ¹H NMR (CDCl₃, 300 Mz) |
|---|---|
| 1 | 8.36 (4H, d), 8.20-8.19 (4H, m), 7.94 (1H, d), 7.85 (1H, m), 7.70-7.65 (3H, m), 7.50-7.49 (7H, m) |
| 16 | 8.35 (2H, m), 8.23-8.19 (5H, m), 7.94-7.85 (4H, m), 7.70-7.49 (10H, m) |
| 31 | 8.36 (4H, d), 8.20-8.19 (3H, m), 8.07 (1H, s), 7.96-7.94 (3H, 3m), 7.85 (1H, m), 7.70-7.65 (3H, m), 7.50-7.49 (7H, m), 7.25 (2H, d) |
| 46 | 8.35-8.30 (4H, m), 8.23-8.19 (4H, m), 8.07 (1H, s), 7.94-7.85 (4H, m), 7.70-7.49 (10H, m), 7.25 (2H, d) |
| 61 | 8.38-8.36 (5H, m), 8.19 (2H, m), 8.07 (1H, s), 7.94 (2H, m), 7.85 (1H, m), 7.73-7.61 (5H, m), 7.50-7.49 (7H, m) |
| 76 | 8.35 (2H, d), 8.23-8.19 (4H, m), 8.07 (1H, s), 7.94-7.85 (6H, m), 7.73-7.49 (12H, m) |
| 91 | 9.18-9.14 (4H, m), 8.55 (1H, d), 8.20-8.19 (3H, m), 8.07 (1H, s), 7.94 (1H, m), 7.85 (1H, m), 7.74-7.65 (5H, m), 7.49 (1H, m), 7.25-7.23 (6H, m) |
| 107 | 8.71 (2H, d), 8.60 (1H, s), 8.33 (2H, m), 8.20-8.19 (4H, m), 7.94-7.85 (3H, m), 7.70-7.49 (7H, m), 7.29 (2H, d) |

TABLE 1-continued

| NO | ¹H NMR (CDCl₃, 300 Mz) |
|---|---|
| 109 | 8.69 (2H, d), 8.36 (4H, d), 8.20 (1H, d), 7.99-7.94 (4H, m), 7.85 (1H, m), 7.70 (1H, m), 7.50 (7H, m) |
| 139 | 8.69 (2H, d), 8.36 (4H, m), 8.20 (1H, d), 7.99-7.94 (4H, m), 7.85 (3H, m), 7.70 (1H, m), 7.50 (7H, m), 7.25 (2H, d) |
| 144 | 8.69 (2H, d), 8.55 (1H, d), 8.36 (2H, d), 8.20-8.19 (2H, m), 7.96-7.85 (12H, m), 7.70 (1H, m), 7.58-7.50 (6H, m), 7.35 (1H, m), 7.25-7.16 (4H, m) |
| 174 | 8.69 (2H, d), 8.55 (1H, d), 8.38-8.36 (3H, m), 8.20-8.19 (2H, m), 7.99-7.85 (11H, m), 7.73-7.70 (2H, m), 7.61-7.50 (7H, m), 7.35 (1H, m), 7.20-7.16 (2H, m) |
| 199 | 9.18-9.14 (4H, m), 8.69 (2H, d), 8.55 (2H, d), 8.20 (1H, d), 7.99-7.94 (2H, m), 7.85 (3H, m), 7.74-7.70 (3H, m), 7.50 (1H, d), 7.25-7.23 (6H, m) |
| 213 | 8.69 (2H, d), 8.20 (1H, d), 7.99-7.94 (6H, m), 7.85-7.70 (8H, m), 7.51-7.50 (7H, m) |
| 215 | 8.71-8.69 (6H, m), 8.33 (2H, d), 8.20 (2H, m), 7.99-7.85 (4H, m), 7.70 (1H, m) 7.55-7.49 (4H, m), 7.29 (2H, d) |
| 217 | 8.39-8.36 (6H, m), 8.24-8.19 (3H, m), 7.99 (1H, d), 7.65 (2H, m), 7.50-7.49 (8H, m) |
| 232 | 8.39-8.35 (4H, m), 8.24-8.19 (4H, m), 7.99-7.94 (3H, m), 7.65-7.49 (10H, m) |
| 247 | 8.45 (1H, d), 8.36 (4H, m), 8.23-8.19 (3H, m), 7.99-7.90 (4H, m), 7.65 (2H, m), 7.50-7.49 (8H, m), 7.25 (2H, d) |
| 253 | 8.55 (1H, d), 8.45 (1H, d), 8.36 (2H, d), 8.24-8.19 (6H, m), 7.99-7.90 (5H, m), 7.68-7.49 (11H, m), 7.35 (1H, m), 7.25-7.16 (4H, m) |
| 262 | 8.45 (1H, m), 8.35-8.19 (8H, m), 8.19-7.85 (6H, m), 7.65-7.49 (10H, m) |
| 268 | 8.55 (1H, d), 8.45 (1H, d), 8.35-8.19 (10H, m), 8.19-7.80 (6H, m), 7.68-7.49 (11H, m), 7.35 (1H, m), 7.20-7.16 (2H, m) |
| 283 | 8.55 (1H, d), 8.45-8.36 (4H, m), 8.24-8.19 (4H, m), 7.99-7.90 (4H, m), 7.73-7.49 (13H, m), 7.35 (1H, m), 7.20-7.16 (2H, m) |
| 298 | 8.55 (1H, d), 8.45 (1H, d), 8.35 (2H, d), 8.23-8.19 (6H, m), 7.99-7.90 (5H, m), 7.80-7.49 (14H, m), 7.35 (1H, m), 7.20-7.16 (2H, m) |
| 307 | 9.18-9.14 (4H, m), 8.55 (2H, d), 8.45 (1H, d), 8.23-8.19 (3H, m)7.99 (1H, d), 7.90 (1H, d), 7.74-7.65 (4H, m), 7.50-7.49 (2H, m), 7.25-7.23 (6H, m) |
| 323 | 8.76-8.63 (4H, m), 8.39-8.33 (3H, m), 8.19 (2H, d), 7.99 (1H, d), 7.90 (1H, d), 7.65-7.49 (7H, m), 7.29 (2H, d) |
| 325 | 8.36 (4H, m), 8.20-8.19 (3H, m), 8.07 (1H, s), 7.96-7.94 (3H, m), 7.85 (1H, m), 7.70-7.65 (3H, m), 7.50-7.49 (7H, m), 7.25 (2H, m) |
| 326 | 8.35-8.30 (4H, m), 8.23-8.19 (4H, m), 8.07 (1H, s), 7.94-7.85 (4H, m), 7.70-7.49 (10H, m), 7.25 (2H, m) |
| 337 | 8.69 (2H, d), 8.36 (4H, m), 8.20 (1H, d), 7.99-7.96 (4H, m), 7.85 (3H, m), 7.70 (1H, m), 7.50 (7H, m), 7.25 (2H, d) |
| 338 | 8.35 (2H, d), 8.23-8.19 (4H, m), 7.99-7.85 (7H, m), 7.70-7.49 (14H, m) |
| 353 | 8.69 (2H, d), 8.36 (4H, m), 8.20 (1H, d), 8.07 (1H, s), 7.96-7.94 (3H, m), 7.85 (3H, m), 7.70 (1H, m), 7.50-7.41 (7H, m), 7.41-7.19 (6H, m) |
| 354 | 8.69 (2H, d), 8.35-8.30 (4H, m), 8.23-8.20 (1H, m), 8.07 (1H, s), 7.94-7.85 (8H, m), 7.70 (1H, m), 7.55-7.41 (7H, m) |
| 361 | 8.69 (2H, d), 8.36 (4H, d), 8.20 (1H, d), 8.07 (1H, s), 7.96-7.94 (3H, m), 7.85 (3H, m), 7.70 (1H, m), 7.50-7.41 (7H, m), 7.25-7.19 (6H, m) |
| 362 | 8.69 (2H, d), 8.35-8.30 (4H, m), 8.23-8.20 (2H, m), 8.07 (1H, s), 7.94-7.85 (8H, m), 7.70 (1H, m), 7.55-7.41 (7H, m), 7.19 (4H, m) |
| 409 | 8.36-8.31 (5H, m), 8.19 (2H, d), 8.09-8.07 (2H, m), 7.96-7.94 (3H, m), 7.65 (2H, m), 7.50-7.41 (8H, m), 7.25-7.19 (6H, m) |
| 411 | 9.18-9.14 (4H, m), 8.55 (2H, d), 8.31 (1H, m), 8.19 (2H, m), 8.09-8.07 (2H, m), 7.94 (1H, s), 7.74-7.65 (4H, m), 7.49-7.41 (2H, m), 7.25-7.19 (10H, m) |
| 412 | 8.82 (1H, d), 8.71 (2H, d), 8.47 (1H, s), 8.33-8.19 (6H, m), 8.07 (1H, s), 7.90 (1H, d), 7.65-7.41 (7H, m), 7.29 (2H, d), 7.19 (4H, m) |
| 417 | 8.36-8.31 (5H, m), 8.19 (2H, m), 8.09-8.06 (4H, m), 7.96-7.94 (3H, m), 7.65-7.41 (13H, m), 7.25-7.19 (6H, m) |
| 425 | 8.45 (1H, d), 8.36 (4H, d), 8.23-8.19 (3H, m), 8.07 (1H, s), 7.96-7.90 (3H, m), 7.65 (2H, m), 7.50-7.41 (8H, m), 7.25-7.19 (6H, m) |
| 426 | 8.45 (1H, d), 8.35-8.19 (8H, m), 8.07 (1H, s), 7.94-7.85 (5H, m), 7.65-7.41 (10H, m) |
| 449 | 8.36 (4H, d), 8.19-8.14 (3H, m), 7.99-7.96 (4H, m), 7.65 (3H, m), 7.50-7.49 (8H, m), 7.25 (2H, d) |
| 450 | 8.35-8.30 (4H, m), 8.23-8.14 (4H, m), 7.99-7.94 (4H, m), 7.65-7.49 (11H, m), 7.25 (2H, d) |
| 473 | 8.20-8.19 (3H, m), 8.07 (1H, s), 7.94 (1H, d), 7.85 (1H, m), 7.70-7.65 (3H, m), 7.49 (1H, m), 7.25 (4H, s) |
| 485 | 8.69 (2H, d), 8.20 (1H, d)7.99-7.94 (2H, m), 7.85 (2H, d), 7.70 (1H, t), 7.50 (1H, d), 7.25 (4H, s) |
| 505 | 8.45 (1H, d), 8.23-8.19 (3H, m), 7.99 (1H, d), 7.65 (2H, m)7.50-7.49 (2H, m) |
| 527 | 8.69 (2H, d), 8.20 (1H, d), 7.99-7.94 (2H, m), 7.85 (3H, m), 7.70 (1H, t), 7.50 (1H, d), 7.25 (4H, s) |

TABLE 2

| Compound | FD-MS | Compound | FD-MS |
|---|---|---|---|
| 1 | m/z = 544.14 (C34H20N6S = 544.63) | 2 | m/z = 620.17 (C40H24N6S = 620.73) |
| 3 | m/z = 696.20 (C46H28N6S = 696.83) | 4 | m/z = 620.17 (C40H24N6S = 620.73) |
| 5 | m/z = 696.20 (C46H28N6S = 696.83) | 6 | m/z = 709.20 (C46H27N7S = 709.83) |
| 7 | m/z = 709.20 (C46H27N7S = 709.83) | 8 | m/z = 572.17 (C36H24N6S = 572.17) |
| 9 | m/z = 644.17 (C42H24N6S = 644.17) | 10 | m/z = 696.20 (C46H28N6S = 696.83) |
| 11 | m/z = 710.18 (C46H26N6OS = 710.81) | 12 | m/z = 726.16 (C46H26N6S2 = 726.87) |
| 13 | m/z = 744.18 (C46H29N6OPS = 744.81) | 14 | m/z = 736.24 (C49H32N6S = 736.89) |
| 15 | m/z = 744.20 (C50H28N6S = 744.87) | 16 | m/z = 543.15 (C35H21N5S = 543.64) |
| 17 | m/z = 619.18 (C41H25N5S = 619.74) | 18 | m/z = 695.21 (C47H29N5SS = 695.84) |
| 19 | m/z = 619.18 (C41H25N5S = 619.74) | 20 | m/z = 695.21 (C47H29N5S = 695.84) |
| 21 | m/z = 708.20 (C47H28N6S = 708.84) | 22 | m/z = 708.20 (C47H28N6S = 708.84) |
| 23 | m/z = 571.18 (C37H25N5S = 571.70) | 24 | m/z = 643.1S (C43H25N5S = 643.76) |
| 25 | m/z = 708.20 (C47H28N6S = 708.84) | 26 | m/z = 709.19 (C47H27N5OS = 709.82) |
| 27 | m/z = 725.17 (C47H27N5S2 = 725.88) | 28 | m/z = 743.19 (C47H30N5OPS = 743.82) |
| 29 | m/z = 735.24 (C50H33N5S = 735.90) | 30 | m/z = 743.21 (C51H29N5S = 743.88) |
| 31 | m/z = 620.17 (C40H24N6S = 620.73) | 32 | m/z = 696.20 (C46H28N6S = 696.83) |
| 33 | m/z = 772.24 (C52H32N6S = 772.93) | 34 | m/z = 696.20 (C46H28N6S = 696.83) |
| 35 | m/z = 772.24 (C52H32N6S = 772.93) | 36 | m/z = 785.23 (C52H31N7S = 785.92) |
| 37 | m/z = 785.23 (C52H31N7S = 785.92) | 38 | m/z = 648.20 (C42H28N6S = 648.78) |
| 39 | m/z = 720.20 (C48H28N6S = 720.85) | 40 | m/z = 772.24 (C52H32N6S = 772.93) |
| 41 | m/z = 786.22 (C52H30N6OS = 786.91) | 42 | m/z = 802.19 (C52H30N6S2 = 802.97) |
| 43 | m/z = 820.21 (C52H33N6OPS = 820.91) | 44 | m/z = 812.27 (C55H36N6S = 812.99) |
| 45 | m/z = 820.24 (C56H32N6S = 820.97) | 46 | m/z = 619.18 (C41H25N5S = 619.74) |
| 47 | m/z = 695.21 (C47H29N5S = 695.84) | 48 | m/z = 771.24 (C53H33N5S = 771.94) |
| 49 | m/z = 695.21 (C47H29N5S = 695.84) | 50 | m/z = 771.24 (C53H33N5S = 771.94) |
| 51 | m/z = 784.24 (C53H32N6S = 784.94) | 52 | m/z = 784.24 (C53H32N6S = 784.94) |
| 53 | m/z = 647.21 (C43H29N5S = 647.80) | 54 | m/z = 719.21 (C49H29N5S = 719.86) |

TABLE 2-continued

| Compound | FD-MS | Compound | FD-MS |
|---|---|---|---|
| 55 | m/z = 771.24 (C53H33N5S = 771.94) | 56 | m/z = 785.22 (C53H31N5OS = 785.92) |
| 57 | m/z = 801.20 (C53H31N5S2 = 801.98) | 58 | m/z = 819.20 (C53H34N5OPS = 819.92) |
| 59 | m/z = 811.27 (56H37N5S = 812.00) | 60 | m/z = 819.24 (C57H33N5S = 819.98) |
| 61 | m/z = 620.17 (C40H24N6S = 620.73) | 62 | m/z = 696.20 (C46H28N6S = 696.83) |
| 63 | m/z = 772.24 (C52H32N6S = 772.93) | 64 | m/z = 696.20 (C46H28N6S = 696.83) |
| 65 | m/z = 772.24 (C52H32N6S = 772.93) | 66 | m/z = 785.23 (C52H31N7S = 785.92) |
| 67 | m/z = 785.23 (C52H31N7S = 785.92) | 68 | m/z = 648.20 (C42H28N63 = 648.78) |
| 69 | m/z = 720.20 (C48H28N6S = 720.85) | 70 | m/z = 772.24 (C52H32N6S = 772.93) |
| 71 | m/z = 786.22 (C52H30N6OS = 786.91) | 72 | m/z = 802.19 (C52H30N6S2 = 802.97) |
| 73 | m/z = 820.21 (C52H33N6OPS = 820.91) | 74 | m/z = 812.27 (C55H36N6S = 812.99) |
| 75 | m/z = 820.24 (C56H32N6S = 820.97) | 76 | m/z = 619.18 (C41H25N5S = 619.74) |
| 77 | m/z = 695.21 (C47H29N5S = 695.84) | 78 | m/z = 771.24 (C53H33N5S = 771.94) |
| 79 | m/z = 695.21 (C47H29N5S = 695.84) | 80 | m/z = 771.24 (C53H33N5S = 771.94) |
| 81 | m/z = 784.24 (C53H32N6S = 784.94) | 82 | m/z = 784.24 (C53H32N6S = 784.94) |
| 83 | m/z = 647.21 (C43H29N5S = 647.80) | 84 | m/z = 719.21 (C49H29N5S = 719.86) |
| 85 | m/z = 771.24 (C53H33N5S = 771.94) | 86 | m/z = 785.22 (C53H31N5OS = 785.92) |
| 87 | m/z = 801.20 (C53H31N5S2 = 801.98) | 88 | m/z = 819.22 (C53H34N5OPS = 819.92) |
| 89 | m/z = 811.27 (56H37N5S = 812.00) | 90 | m/z = 819.24 (C57H33N5S = 819.98) |
| 91 | m/z = 620.17 (C40H24N6S = 620.73) | 92 | m/z = 719.21 (C49H29N5S = 719.86) |
| 93 | m/z = 573.10 (C35H19N5S2 = 573.69) | 94 | m/z = 467.12 (C29H17N5S = 467.55) |
| 95 | m/z = 533.16 (C34H23N5S = 533.65) | 96 | m/z = 619.18 (C41H25N5S = 619.74) |
| 97 | m/z = 465.10 (C27H20N3OPS = 465.51) | 98 | m/z = 517.13 (C33H19N5S = 517.61) |
| 99 | m/z = 575.12 (C35H21N5S2 = 575.70) | 100 | m/z = 517.13 (C33H19N5S = 517.61) |
| 101 | m/z = 522.09 (C32H18N4S2 = 522.64) | 102 | m/z = 506.12 (C32H18N4OS = 506.58) |
| 103 | m/z = 581.16 (C38H23N5S = 581.69) | 104 | m/z = 581.16 (C38H23N5S = 581.69) |
| 105 | m/z = 589.13 (C37H24N3OPS = 589.65) | 106 | m/z = 589.13 (C37H24N3OPS = 589.65) |
| 107 | m/z = 567.15 (C37H21N5S = 567.67) | 108 | m/z = 491.13 (C31H17N5S = 491.57) |
| 109 | m/z = 544.14 (C34H20N6S = 544.63) | 110 | m/z = 620.17 (C40H24N6S = 620.73) |
| 111 | m/z = 696.20 (C46H28N6S = 696.83) | 112 | m/z = 620.17 (C40H24N6S = 620.73) |
| 113 | m/z = 696.20 (C46H28N6S = 696.83) | 114 | m/z = 709.20 (C46H27N7S = 709.83) |
| 115 | m/z = 709.20 (C46H27N7S = 709.83) | 116 | m/z = 572.17 (C36H24N6S = 572.17) |
| 117 | m/z = 644.17 (C42H24N6S = 644.17) | 118 | m/z = 696.20 (C46H28N6S = 696.83) |
| 119 | m/z = 710.18 (C46H26N6OS = 710.81) | 120 | m/z = 726.16 (C46H26N6S2 = 726.87) |
| 121 | m/z = 744.18 (C46H29N6OPS = 744.81) | 122 | m/z = 736.24 (C49H32N6S = 736.89) |
| 123 | m/z = 744.20 (C50H28N6S = 744.87) | 124 | m/z = 543.15 (C35H21N5S = 543.64) |
| 125 | m/z = 619.18 (C41H25N5S = 619.74) | 126 | m/z = 695.21 (C47H29N5S = 695.84) |
| 127 | m/z = 619.18 (C41H25N5S = 619.74) | 128 | m/z = 695.21 (C47H29N5S = 695.84) |
| 129 | m/z = 708.20 (C47H28N6S = 708.84) | 130 | m/z = 708.20 (C47H28N6S = 708.84) |
| 131 | m/z = 571.18 (C37H25N5S = 571.70) | 132 | m/z = 643.18 (C43H25N5S = 643.76) |
| 133 | m/z = 708.20 (C47H28N6S = 708.84) | 134 | m/z = 709.19 (C47H27N5OS = 709.82) |
| 135 | m/z = 725.17 (C47H27N5S2 = 725.88) | 136 | m/z = 743.19 (C47H30N5OPS = 743.82) |
| 137 | m/z = 735.24 (C50H33N5S = 735.90) | 138 | m/z = 743.21 (C51H29N5S = 743.88) |
| 139 | m/z = 620.17 (C40H24N6S = 620.73) | 140 | m/z = 696.20 (C46H28N6S = 696.83) |
| 141 | m/z = 772.24 (C52H32N6S = 772.93) | 142 | m/z = 696.20 (C46H28N6SN6S = 696.93) |
| 143 | m/z = 772.24 (C52H32N6S = 772.93) | 144 | m/z = 785.23 (C52H31N7S = 785.92) |
| 145 | m/z = 785.23 (C52H31N7S = 785.92) | 146 | m/z = 648.20 (C42H28N6S = 648.78) |
| 147 | m/z = 720.20 (C48H28N6S = 720.85) | 148 | m/z = 772.24 (C52H32N6S = 772.93) |
| 149 | m/z = 786.22 (C52H30N6OS = 786.91) | 150 | m/z = 802.19 (C52H30N6S2 = 802.97) |
| 151 | m/z = 820.21 (C52H33N6OPS = 820.91) | 152 | m/z = 812.27 (C55H36N6S = 812.99) |
| 153 | m/z = 820.24 (C56H32N6S = 820.97) | 154 | m/z = 619.18 (C41H25N5S = 619.74) |
| 155 | m/z = 695.21 (C47H29N5S = 695.84) | 156 | m/z = 771.24 (C53H33N5S = 771.94) |
| 157 | m/z = 695.21 (C47H29N5S = 695.84) | 158 | m/z = 771.24 (C53H33N5S = 771.94) |
| 159 | m/z = 784.24 (C53H32N6S = 784.94) | 160 | m/z = 784.24 (C53H32N6S = 784.94) |
| 161 | m/z = 647.21 (C43H29N5S = 647.80) | 162 | m/z = 719.21 (C49H29N5S = 719.86) |
| 163 | m/z = 771.24 (C53H33N5S = 771.94) | 164 | m/z = 785.22 (C53H31N5OS = 785.92) |
| 165 | m/z = 801.20 (C53H31N5S2 = 801.98) | 166 | m/z = 819.22 (C53H34N5OPS = 819.92) |
| 167 | m/z = 811.27 (56H37N5S = 812.00) | 168 | m/z = 819.24 (C57H33N5S = 819.98) |
| 169 | m/z = 620.17 (C40H24N6S = 620.73) | 170 | m/z = 696.20 (C46H28N6S = 696.83) |
| 171 | m/z = 772.24 (C52H32N6S = 772.93) | 172 | m/z = 696.20 (C46H28N6S = 696.83) |
| 173 | m/z = 772.24 (C52H32N6S = 772.93) | 174 | m/z = 785.23 (C52H31N7S = 785.92) |
| 175 | m/z = 785.23 (C52H31N7S = 785.92) | 176 | m/z = 648.20 (C42H28N6S = 648.78) |
| 177 | m/z = 720.20 (C48H28N6S = 720.85) | 178 | m/z = 772.24 (C52H32N6S = 772.93) |
| 179 | m/z = 786.22 (C52H30N6OS = 786.91) | 180 | m/z = 802.19 (C52H30N6S2 = 802.97) |
| 181 | m/z = 820.21 (C52H33N6OPS = 820.91) | 182 | m/z = 812.27 (C55H36N6S = 812.99) |
| 183 | m/z = 820.24 (C56H32N6S = 820.97) | 184 | m/z = 619.18 (C41H25N5S = 619.74) |
| 185 | m/z = 695.21 (C47H29N5S = 695.84) | 186 | m/z = 771.24 (C53H33N5S = 771.94) |
| 187 | m/z = 695.21 (C47H29N5S = 695.84) | 188 | m/z = 771.24 (C53H33N5S = 771.94) |
| 189 | m/z = 784.24 (C53H32N6S = 784.94) | 190 | m/z = 784.24 (C53H32N6S = 784.94) |
| 191 | m/z = 647.21 (C43H29N5S = 647.80) | 192 | m/z = 719.21 (C49H29N5S = 719.86) |
| 193 | m/z = 771.24 (C53H33N5S = 771.94) | 194 | m/z = 785.22 (C53H31N5OS = 785.92) |
| 195 | m/z = 801.20 (C53H31N5S2 = 801.98) | 196 | m/z = 819.22 (C53H34N5OPS = 819.92) |
| 197 | m/z = 811.27 (56H37N5S = 812.00) | 198 | m/z = 819.24 (C57H33N5S = 819.98) |
| 199 | m/z = 620.17 (C40H24N6S = 620.73) | 200 | m/z = 719.21 (C49H29N5S = 719.86) |
| 201 | m/z = 573.10 (C35H19N5S2 = 573.69) | 202 | m/z = 467.12 (C29H17N5S = 467.55) |
| 203 | m/z = 533.16 (C34H23N5S = 533.65) | 204 | m/z = 619.18 (C41H25N5S = 619.74) |
| 205 | m/z = 465.10 (C27H20N3OPS = 465.51) | 206 | m/z = 517.13 (C33H19N5S = 517.61) |
| 207 | m/z = 575.12 (C35H21N5S2 = 575.70) | 208 | m/z = 517.13 (C33H191N5S = 517.61) |
| 209 | m/z = 522.09 (C32H18N4S2 = 522.64) | 210 | m/z = 506.12 (C32H18N4OS = 506.58) |

TABLE 2-continued

| Compound | FD-MS | Compound | FD-MS |
|---|---|---|---|
| 211 | m/z = 581.16 (C38H23N5S = 581.69) | 212 | m/z = 581.16 (C38H23N5S = 581.69) |
| 213 | m/z = 589.13 (C37H24N3OPS = 589.65) | 214 | m/z = 589.13 (C37H24N3OPS = 589.65) |
| 215 | m/z = 567.15 (C37H21N5S = 567.67) | 216 | m/z = 491.12 (C31H17N5S = 491.57) |
| 217 | m/z = 544.14 (C34H20N6S = 544.63) | 218 | m/z = 620.17 (C40H24N6S = 620.73) |
| 219 | m/z = 696.20 (C46H28N6S = 696.83) | 220 | m/z = 620.17 (C40H24N6S = 620.73) |
| 221 | m/z = 696.20 (C46H28N6S = 696.83) | 222 | m/z = 709.20 (C46H27N7S = 709.83) |
| 223 | m/z = 709.20 (C46H27N7S = 709.83) | 224 | m/z = 572.17 (C36H24N6S = 572.17) |
| 225 | m/z = 644.17 (C42H24N6S = 644.17) | 226 | m/z = 696.20 (C46H28N6S = 696.83) |
| 227 | m/z = 710.18 (C46H26N6OS = 710.81) | 228 | m/z = 726.16 (C46H26N6S2 = 726.87) |
| 229 | m/z = 744.18 (C46H29N6OPS = 744.81) | 230 | m/z = 736.24 (C49H32N6S = 736.89) |
| 231 | m/z = 744.20 (C50H28N6S = 744.87) | 232 | m/z = 543.15 (C35H21N5S = 543.64) |
| 233 | m/z = 619.18 (C41H25N5S = 619.74) | 234 | m/z = 695.21 (C47H29N5SS = 695.84) |
| 235 | m/z = 619.18 (C41H25N5S = 619.74) | 236 | m/z = 695.21 (C47H29N5S = 695.84) |
| 237 | m/z = 708.20 (C47H28N6S = 708.84) | 238 | m/z = 708.20 (C47H28N6S = 708.84) |
| 239 | m/z = 571.18 (C37H25N5S = 571.70) | 240 | m/z = 643.18 (C43H25N5S = 643.76) |
| 241 | m/z = 708.20 (C47H28N6S = 708.84) | 242 | m/z = 709.19 (C47H27N5OS = 709.82) |
| 243 | m/z = 725.17 (C47H27N5S2 = 725.88) | 244 | m/z = 743.19 (C47H30N5OPS = 743.82) |
| 245 | m/z = 735.24 (C50H33N5S = 735.90) | 246 | m/z = 743.21 (C51H29N5S = 743.88) |
| 247 | m/z = 620.17 (C40H24N6S = 620.73) | 248 | m/z = 696.20 (C46H28N6S = 696.83) |
| 249 | m/z = 772.24 (C52H32N6S = 772.93) | 250 | m/z = 696.20 (C46H28N6S = 696.83) |
| 251 | m/z = 772.24 (C52H32N6S = 772.93) | 252 | m/z = 785.23 (C52H31N7S = 785.92) |
| 253 | m/z = 785.23 (C52H31N7S = 785.92) | 254 | m/z = 648.20 (C42H28N6S = 648.78) |
| 255 | m/z = 720.20 (C48H28N6S = 720.85) | 256 | m/z = 772.24 (C52H32N6S = 772.93) |
| 257 | m/z = 786.22 (C52H30N6OS = 786.91) | 258 | m/z = 802.19 (C52H30N6S2 = 802.97) |
| 259 | m/z = 820.21 (C52H33N6OPS = 820.91) | 260 | m/z = 812.27 (C55H36N6S = 812.99) |
| 261 | m/z = 820.24 (C56H32N6S = 820.97) | 262 | m/z = 619.18 (C41H25N5S = 619.74) |
| 263 | m/z = 695.21 (C47H29N5S = 695.84) | 264 | m/z = 771.24 (C53H33N5S = 771.94) |
| 265 | m/z = 695.21 (C47H29N5S = 695.84) | 266 | m/z = 771.24 (C53H33N5S = 771.94) |
| 267 | m/z = 784.24 (C53H32N6S = 784.94) | 268 | m/z = 784.24 (C53H32N6S = 784.94) |
| 269 | m/z = 647.21 (C43H29N5S = 647.80) | 270 | m/z = 719.21 (C49H29N5S = 719.86) |
| 271 | m/z = 771.24 (C53H33N5S = 771.94) | 272 | m/z = 785.22 (C53H31N5OS = 785.92) |
| 273 | m/z = 801.20 (C53H31N5S2 = 801.98) | 274 | m/z = 819.22 (C53H34N5OPS = 819.92) |
| 275 | m/z = 811.27 (56H37N5S = 812.00) | 276 | m/z = 819.24 (C57H33N5S = 819.98) |
| 277 | m/z = 620.17 (C40H24N6S = 620.73) | 278 | m/z = 696.20 (C46H28N6S = 696.83) |
| 279 | m/z = 772.24 (C52H32N6S = 772.93) | 280 | m/z = 696.20 (C46H28N6S = 696.83) |
| 281 | m/z = 772.24 (C52H32N6S = 772.93) | 282 | m/z = 785.23 (C52H31N7S = 785.92) |
| 283 | m/z = 785.23 (C52H31N7S = 785.92) | 284 | m/z = 648.20 (C42H28N6S = 648.78) |
| 285 | m/z = 720.20 (C48H28N6S = 720.85) | 286 | m/z = 772.24 (C52H32N6S = 772.93) |
| 287 | m/z = 786.22 (C52H30N6OS = 786.91) | 288 | m/z = 802.19 (C52H30N6S2 = 802.97) |
| 289 | m/z = 820.21 (C52H33N6OPS = 820.91) | 290 | m/z = 812.27 (C55H36N6S = 812.99) |
| 291 | m/z = 820.24 (C56H32N6S = 820.97) | 292 | m/z = 619.18 (C41H25N5S = 619.74) |
| 293 | m/z = 695.21 (C47H29N5S = 695.34) | 294 | m/z = 771.24 (C53H33N5S = 771.94) |
| 295 | m/z = 695.21 (C47H29N5S = 695.84) | 296 | m/z = 771.24 (C53H33N5S = 771.94) |
| 297 | m/z = 784.24 (C53H32N6S = 784.94) | 298 | m/z = 784.24 (C53H32N6S = 784.94) |
| 299 | m/z = 647.21 (C43H29N5S = 647.80) | 300 | m/z = 719.21 (C49H29N5S = 719.86) |
| 301 | m/z = 771.24 (C53H33N5S = 771.94) | 302 | m/z = 785.22 (C53H31N5OS = 785.92) |
| 303 | m/z = 801.20 (C53H31N5S2 = 801.98) | 304 | m/z = 819.22 (C53H34N5OPS = 819.92) |
| 305 | m/z = 811.27 (56H37N5S = 812.00) | 306 | m/z = 819.24 (C57H33N5S = 819.98) |
| 307 | m/z = 620.17 (C40H24N6S = 620.73) | 308 | m/z = 719.21 (C49H29N5S = 719.86) |
| 309 | m/z = 573.10 (C35H19N5S2 = 573.69) | 310 | m/z = 467.12 (C29H17N5S = 467.55) |
| 311 | m/z = 533.16 (C34H23N5S = 533.65) | 312 | m/z = 619.18 (C41H25N5S = 619.74) |
| 313 | m/z = 465.10 (C27H20N3OPS = 465.51) | 314 | m/z = 517.13 (C33H19N5S = 517.61) |
| 315 | m/z = 575.12 (C35H21N5S2 = 575.70) | 316 | m/z = 517.13 (C33H19N5S = 517.61) |
| 317 | m/z = 522.09 (C32H18N4S2 = 522.64) | 318 | m/z = 506.12 (C32H18N4OS = 506.58) |
| 319 | m/z = 581.16 (C38H23N5S = 581.69) | 320 | m/z = 581.16 (C38H23N5S = 581.69) |
| 321 | m/z = 589.13 (C37H24N3OPS = 589.65) | 322 | m/z = 589.13 (C37H24N3OPS = 589.65) |
| 323 | m/z = 567.15 (C37H21N5S = 567.67) | 324 | m/z = 491.12 (C31H17N5S = 491.57) |
| 325 | m/z = 604.20 (C40H24N6O = 604.67) | 326 | m/z = 603.20 (C41H25N5O = 603.68) |
| 327 | m/z = 604.20 (C40H24N6O = 604.67) | 328 | m/z = 551.17 (C37H21N5O = 551.60) |
| 329 | m/z = 679.24 (C46H29N7 = 679.78) | 330 | m/z = 678.25 (C47H30N6 = 678.79) |
| 331 | m/z = 679.24 (C46H29N7 = 679.78) | 332 | m/z = 626.22 (C43H26N6 = 626.72) |
| 333 | m/z = 620.17 (C40H24N6S = 620.73) | 334 | m/z = 619.18 (C41H25N5S = 619.74) |
| 335 | m/z = 620.17 (C40H24N6S = 620.73) | 336 | m/z = 567.15 (C37H21N5S = 567.67) |
| 337 | m/z = 604.20 (C40H24N6O = 604.67) | 338 | m/z = 603.20 (C41H25N5O = 603.68) |
| 339 | m/z = 604.20 (C40H24N6O = 604.67) | 340 | m/z = 551.17 (C37H21N5O = 551.60) |
| 341 | m/z = 604.20 (C40H24N6O = 604.67) | 342 | m/z = 603.20 (C41H25N5O = 603.68) |
| 343 | m/z = 604.20 (C40H24N6O = 604.67) | 344 | m/z = 551.17 (C37H21N5O = 551.60) |
| 345 | m/z = 679.24 (C46H29N7 = 679.78) | 346 | m/z = 678.25 (C47H30N6 = 678.79) |
| 347 | m/z = 679.24 (C46H29N7 = 679.78) | 348 | m/z = 626.22 (C43H26N6 = 626.72) |
| 349 | m/z = 679.24 (C46H29N7 = 679.78) | 350 | m/z = 678.25 (C47H30N6 = 678.79) |
| 351 | m/z = 679.24 (C46H29N7 = 679.78) | 352 | m/z = 626.22 (C43H26N6 = 626.72) |
| 353 | m/z = 696.20 (C46H28N6S = 696.83) | 354 | m/z = 695.21 (C47H29N5S = 695.84) |
| 355 | m/z = 696.20 (C46H28N6S = 696.83) | 356 | m/z = 643.18 (C43H25N5S = 643.76) |
| 357 | m/z = 696.20 (C46H28N6S = 696.83) | 358 | m/z = 695.21 (C47H29N5S = 695.84) |
| 359 | m/z = 696.20 (C46H28N6S = 696.83) | 360 | m/z = 643.18 (C43H25N5S = 643.76) |
| 361 | m/z = 680.23 (C46H28N6O = 680.77) | 362 | m/z = 679.23 (C47H29N5O = 679.78) |
| 363 | m/z = 680.23 (C46H28N6O = 680.77) | 364 | m/z = 627.20 (C43H25N5O = 627.70) |
| 365 | m/z = 680.23 (C46H28N6O = 680.77) | 366 | m/z = 679.23 (C47H29N5O = 679.78) |

TABLE 2-continued

| Compound | FD-MS | Compound | FD-MS |
|---|---|---|---|
| 367 | m/z = 680.23 (C46H28N6O = 680.77) | 368 | m/z = 627.20 (C43H25N5O = 627.70) |
| 369 | m/z = 755.27 (C52H33N7 = 755.88) | 370 | m/z = 754.28 (C53H34N6 = 754.89) |
| 371 | m/z = 755.27 (C52H33N7 = 755.88) | 372 | m/z = 702.25 (C49H30N6 = 702.82) |
| 373 | m/z = 755.27 (C52H33N7 = 755.88) | 374 | m/z = 754.28 (C53H34N6 = 754.89) |
| 375 | m/z = 755.27 (C52H33N7 = 755.88) | 376 | m/z = 702.25 (C49H30N6 = 702.82) |
| 377 | m/z = 696.20 (C46H28N6S = 696.83) | 378 | m/z = 695.21 (C47H29N5S = 695.84) |
| 379 | m/z = 696.20 (C46H28N6S = 696.83) | 380 | m/z = 643.18 (C43H25N5S = 643.76) |
| 381 | m/z = 620.17 (C40H24N6S = 620.73) | 382 | m/z = 619.18 (C41H25N5S = 619.74) |
| 383 | m/z = 620.17 (C40H24N6S = 620.73) | 384 | m/z = 567.15 (C37H21N5S = 567.67) |
| 385 | m/z = 680.23 (C46H28N6O = 680.77) | 386 | m/z = 679.23 (C47H29N5O = 679.78) |
| 387 | m/z = 680.23 (C46H28N6O = 680.77) | 388 | m/z = 627.20 (C43H25N5O = 627.70) |
| 389 | m/z = 604.20 (C40H24N6O = 604.67) | 390 | m/z = 603.20 (C41H25N5O = 603.68) |
| 391 | m/z = 604.20 (C40H24N6O = 604.67) | 392 | m/z = 551.17 (C37H21N5O = 551.60) |
| 393 | m/z = 755.27 (C52H33N7 = 755.88) | 394 | m/z = 754.28 (C53H34N6 = 754.89) |
| 395 | m/z = 755.27 (C52H33N7 = 755.88) | 396 | m/z = 702.25 (C49H30N6 = 702.82) |
| 397 | m/z = 679.24 (C46H29N7 = 679.78) | 398 | m/z = 678.25 (C47H30N6 = 678.79) |
| 399 | m/z = 679.24 (C46H29N7 = 679.78) | 400 | m/z = 626.22 (C43H26N6 = 626.72) |
| 401 | m/z = 696.20 (C46H28N6S = 696.83) | 402 | m/z = 695.21 (C47H29N5S = 695.84) |
| 403 | m/z = 696.20 (C46H28N6S = 696.83) | 404 | m/z = 643.18 (C43H25N5S = 643.76) |
| 405 | m/z = 620.17 (C40H24N6S = 620.73) | 406 | m/z = 619.18 (C41H25N5S = 619.74) |
| 407 | m/z = 620.17 (C40H24N6S = 620.73) | 408 | m/z = 567.15 (C37H21N5S = 567.67) |
| 409 | m/z = 680.23 (C46H28N6O = 680.77) | 410 | m/z = 679.23 (C47H29N5O = 679.78) |
| 411 | m/z = 680.23 (C46H28N6O = 680.77) | 412 | m/z = 627.20 (C43H25N5O = 627.70) |
| 413 | m/z = 604.20 (C40H24N6O = 604.67) | 414 | m/z = 603.20 (C41H25N5O = 603.68) |
| 415 | m/z = 604.20 (C40H24N6O = 604.67) | 416 | m/z = 551.17 (C37H21N5O = 551.60) |
| 417 | m/z = 755.27 (C52H33N7 = 755.88) | 418 | m/z = 754.28 (C53H34N6 = 754.89) |
| 419 | m/z = 755.27 (C52H33N7 = 755.88) | 420 | m/z = 702.25 (C49H30N6 = 702.82) |
| 421 | m/z = 679.24 (C46H29N7 = 679.78) | 422 | m/z = 678.25 (C47H30N6 = 678.79) |
| 423 | m/z = 679.24 (C46H29N7 = 679.78) | 424 | m/z = 626.22 (C43H26N6 = 626.72) |
| 425 | m/z = 696.20 (C46H28N6S = 696.83) | 426 | m/z = 695.21 (C47H29N5S = 695.84) |
| 427 | m/z = 696.20 (C46H28N6S = 696.83) | 428 | m/z = 643.18 (C43H25N5S = 643.76) |
| 429 | m/z = 680.23 (C46H28N6O = 680.77) | 430 | m/z = 679.23 (C47H29N5O = 679.78) |
| 431 | m/z = 680.23 (C46H28N6O = 680.77) | 432 | m/z = 627.20 (C43H25N5O = 627.70) |
| 433 | m/z = 604.20 (C40H24N6O = 604.67) | 434 | m/z = 603.20 (C41H25N5O = 603.68) |
| 435 | m/z = 604.20 (C40H24N6O = 604.67) | 436 | m/z = 551.17 (C37H21N5O = 551.60) |
| 437 | m/z = 755.27 (C52H33N7 = 755.88) | 438 | m/z = 754.28 (C53H34N6 = 754.89) |
| 439 | m/z = 755.27 (C52H33N7 = 755.88) | 440 | m/z = 702.25 (C49H30N6 = 702.82) |
| 441 | m/z = 679.24 (C46H29N7 = 679.78) | 442 | m/z = 678.25 (C47H30N6 = 678.79) |
| 443 | m/z = 679.24 (C46H29N7 = 679.78) | 444 | m/z = 626.22 (C43H26N6 = 626.72) |
| 445 | m/z = 696.20 (C46H28N6S = 696.83) | 446 | m/z = 695.21 (C47H29N5S = 695.84) |
| 447 | m/z = 696.20 (C46H28N6S = 696.83) | 448 | m/z = 643.18 (C43H25N5S = 643.76) |
| 449 | m/z = 620.17 (C40H24N6S = 620.73) | 450 | m/z = 619.18 (C41H25N5S = 619.74) |
| 451 | m/z = 620.17 (C40H24N6S = 620.73) | 452 | m/z = 567.15 (C37H21N5S = 567.67) |
| 453 | m/z = 680.23 (C46H28N6O = 680.77) | 454 | m/z = 679.23 (C47H29N5O = 679.78) |
| 455 | m/z = 680.23 (C46H28N6O = 680.77) | 456 | m/z = 627.20 (C43H25N5O = 627.70) |
| 457 | m/z = 604.20 (C40H24N6O = 604.67) | 458 | m/z = 603.20 (C41H25N5O = 603.68) |
| 459 | m/z = 604.20 (C40H24N6O = 604.67) | 460 | m/z = 551.17 (C37H21N5O = 551.60) |
| 461 | m/z = 755.27 (C52H33N7 = 755.88) | 462 | m/z = 754.28 (C53H34N6 = 754.89) |
| 463 | m/z = 755.27 (C52H33N7 = 755.88) | 464 | m/z = 702.25 (C49H30N6 = 702.82) |
| 465 | m/z = 679.24 (C46H29N7 = 679.78) | 466 | m/z = 678.25 (C47H30N6 = 678.79) |
| 467 | m/z = 679.24 (C46H29N7 = 679.78) | 468 | m/z = 626.22 (C43H26N6 = 626.72) |
| 469 | m/z = 562.08 (C32H14F4N4S = 562.54) | 470 | m/z = 544.09 (C32H15F3N4S = 544.55) |
| 471 | m/z = 544.09 (C32H15F3N4S = 544.55) | 472 | m/z = 526.10 (C32H16F2N4S = 526.56) |
| 473 | m/z = 569.09 (C33H14F3N5S = 569.56) | 474 | m/z = 551.10 (C33H15F2N5S = 551.57) |
| 475 | m/z = 544.09 (C32H15F3N4S = 544.55) | 476 | m/z = 551.10 (C33H15F2N5S = 551.57) |
| 477 | m/z = 555.08 (C31H14F5N3S = 555.52) | 478 | m/z = 562.08 (C32H14F4N4S = 562.54) |
| 479 | m/z = 526.10 (C32H16F2N4S = 526.56) | 480 | m/z = 544.09 (C32H15F3N4S = 544.55) |
| 481 | m/z = 540.11 (C34H16N6S = 540.60) | 482 | m/z = 515.12 (C33H7N5S = 515.59) |
| 483 | m/z = 515.12 (C33H7N5S = 515.59) | 484 | m/z = 490.12 (C32H18N4S = 490.58) |
| 485 | m/z = 562.08 (C32H14F4N4S = 562.54) | 486 | m/z = 544.09 (C32H15F3N4S = 544.55) |
| 487 | m/z = 544.09 (C32H15F3N4S = 544.55) | 488 | m/z = 526.10 (C32H16F2N4S = 526.56) |
| 489 | m/z = 569.09 (C33H14F3N5S = 569.56) | 490 | m/z = 551.10 (C33H15F2N5S = 551.57) |
| 491 | m/z = 544.09 (C32H15F3N4S = 544.55) | 492 | m/z = 551.10 (C33H15F2N5S = 551.57) |
| 493 | m/z = 555.08 (C31H14F5N3S = 555.52) | 494 | m/z = 562.08 (C32H14F4N4S = 562.54) |
| 495 | m/z = 526.10 (C32H16F2N4S = 526.56) | 496 | m/z = 544.09 (C32H15F3N4S = 544.55) |
| 497 | m/z = 540.11 (C34H16N6S = 540.60) | 498 | m/z = 515.12 (C33H7N5S = 515.59) |
| 499 | m/z = 515.12 (C33H7N5S = 515.59) | 500 | m/z = 490.12 (C32H18N4S = 490.58) |
| 501 | m/z = 562.08 (C32H14F4N4S = 562.54) | 502 | m/z = 544.09 (C32H15F3N4S = 544.55) |
| 503 | m/z = 544.09 (C32H15F3N4S = 544.55) | 504 | m/z = 526.10 (C32H16F2N4S = 526.56) |
| 505 | m/z = 569.09 (C33H14F3N5S = 569.56) | 506 | m/z = 551.10 (C33H15F2N5S = 551.57) |
| 507 | m/z = 544.09 (C32H15F3N4S = 544.55) | 508 | m/z = 551.10 (C33H15F2N5S = 551.57) |
| 509 | m/z = 555.08 (C31H14F5N3S = 555.52) | 510 | m/z = 562.08 (C32H14F4N4S = 562.54) |
| 511 | m/z = 526.10 (C32H16F2N4S = 526.56) | 512 | m/z = 544.09 (C32H15F3N4S = 544.55) |
| 513 | m/z = 540.11 (C34H16N6S = 540.60) | 514 | m/z = 515.12 (C33H7N5S = 515.59) |
| 515 | m/z = 515.12 (C33H7N5S = 515.59) | 516 | m/z = 490.12 (C32H18N4S = 490.58) |
| 517 | m/z = 524.13 (C34H16N6O = 524.54) | 518 | m/z = 553.11 (C33H14F3N5O = 553.50) |
| 519 | m/z = 546.11 (C32H4F4N4O = 546.48) | 520 | m/z = 510.12 (C32H16F2N4O = 510.50) |
| 521 | m/z = 524.13 (C34H16N6O = 524.54) | 522 | m/z = 553.11 (C33H14F3N5O = 553.50) |

TABLE 2-continued

| Compound | FD-MS | Compound | FD-MS |
|---|---|---|---|
| 523 | m/z = 546.11 (C32H4F4N4O = 546.48) | 524 | m/z = 510.12 (C32H16F2N4O = 510.50) |
| 525 | m/z = 524.13 (C34H16N6O = 524.54) | 526 | m/z = 553.11 (C33H14F3N5O = 553.50) |
| 527 | m/z = 546.11 (C32H4F4N4O = 546.48) | 528 | m/z = 510.12 (C32H16F2N4O = 510.50) |
| 529 | m/z = 599.18 (C40H21N7 = 599.65) | 530 | m/z = 628.16 (C39H19F3N6 = 628.61) |
| 531 | m/z = 621.15 (C38H19F4N5 = 621.59) | 532 | m/z = 585.17 (C38H21F2N5 = 585.61) |
| 533 | m/z = 599.18 (C40H21N7 = 599.65) | 534 | m/z = 628.16 (C39H19F3N6 = 628.61) |
| 535 | m/z = 621.15 (C38H19F4N5 = 621.59) | 536 | m/z = 585.17 (C38H21F2N5 = 585.61) |
| 537 | m/z = 599.18 (C40H21N7 = 599.65) | 538 | m/z = 628.16 (C39H19F3N6 = 628.61) |
| 539 | m/z = 621.15 (C38H19F4N5 = 621.59) | 540 | m/z = 585.17 (C38H21F2N5 = 585.61) |
| 541 | m/z = 565.11 (C35H15N7S = 565.61) | 542 | m/z = 594.08 (C34H13F3N6S = 594.57) |
| 543 | m/z = 587.08 (C33H13F4N5S = 587.55) | 544 | m/z = 551.10 (C33H15F2N5S = 551.57) |
| 545 | m/z = 565.11 (C35H15N7S = 565.61) | 546 | m/z = 594.08 (C34H13F3N6S = 594.57) |
| 547 | m/z = 587.08 (C33H13F4N5S = 587.55) | 548 | m/z = 551.10 (C33H15F2N5S = 551.57) |
| 549 | m/z = 565.11 (C35H15N7S = 565.61) | 550 | m/z = 594.08 (C34H13F3N6S = 594.57) |
| 551 | m/z = 587.08 (C33H13F4N5S = 587.55) | 552 | m/z = 551.10 (C33H15F2N5S = 551.57) |
| 553 | m/z = 565.11 (C35H15N7S = 565.61) | 554 | m/z = 594.08 (C34H13F3N6S = 594.57) |
| 555 | m/z = 587.08 (C33H13F4N5S = 587.55) | 556 | m/z = 551.10 (C33H15F2N5S = 551.57) |
| 557 | m/z = 565.11 (C35H15N7S = 565.61) | 558 | m/z = 594.08 (C34H13F3N6S = 594.57) |
| 559 | m/z = 587.08 (C33H13F4N5S = 587.55) | 560 | m/z = 551.10 (C33H15F2N5S = 551.57) |
| 561 | m/z = 565.11 (C35H15N7S = 565.61) | 562 | m/z = 594.08 (C34H13F3N6S = 594.57) |
| 563 | m/z = 587.08 (C33H13F4N5S = 587.55) | 564 | m/z = 551.10 (C33H15F2N5S = 551.57) |
| 565 | m/z = 565.11 (C35H15N7S = 565.61) | 566 | m/z = 594.08 (C34H13F3N6S = 594.57) |
| 567 | m/z = 587.08 (C33H13F4N5S = 587.55) | 568 | m/z = 551.10 (C33H15F2N5S = 551.57) |
| 569 | m/z = 565.11 (C35H15N7S = 565.61) | 570 | m/z = 594.08 (C34H13F3N6S = 594.57) |
| 571 | m/z = 587.08 (C33H13F4N5S = 587.55) | 572 | m/z = 551.10 (C33H15F2N5S = 551.57) |
| 573 | m/z = 565.11 (C35H15N7S = 565.61) | 574 | m/z = 594.08 (C34H13F3N6S = 594.57) |
| 575 | m/z = 587.08 (C33H13F4N5S = 587.55) | 576 | m/z = 551.10 (C33H15F2N5S = 551.57) |
| 577 | m/z = 565.11 (C35H15N7S = 565.61) | 578 | m/z = 594.08 (C34H13F3N6S = 594.57) |
| 579 | m/z = 587.08 (C33H13F4N5S = 587.55) | 580 | m/z = 551.10 (C33H15F2N5S = 551.57) |
| 581 | m/z = 565.11 (C35H15N7S = 565.61) | 582 | m/z = 594.08 (C34H13F3N6S = 594.57) |
| 583 | m/z = 587.08 (C33H13F4N5S = 587.55) | 584 | m/z = 551.10 (C33H15F2N5S = 551.57) |
| 585 | m/z = 565.11 (C35H15N7S = 565.61) | 586 | m/z = 594.08 (C34H13F3N6S = 594.57) |
| 587 | m/z = 587.08 (C33H13F4N5S = 587.55) | 588 | m/z = 551.10 (C33H15F2N5S = 551.57) |
| 589 | m/z = 565.11 (C35H15N7S = 565.61) | 590 | m/z = 594.08 (C34H13F3N6S = 594.57) |
| 591 | m/z = 587.08 (C33H13F4N5S = 587.55) | 592 | m/z = 551.10 (C33H15F2N5S = 551.57) |
| 593 | m/z = 565.11 (C35H15N7S = 565.61) | 594 | m/z = 594.08 (C34H13F3N6S = 594.57) |
| 595 | m/z = 587.08 (C33H13F4N5S = 587.55) | 596 | m/z = 551.10 (C33H15F2N5S = 551.57) |
| 597 | m/z = 565.11 (C35H15N7S = 565.61) | 598 | m/z = 594.08 (C34H13F3N6S = 594.57) |
| 599 | m/z = 587.08 (C33H13F4N5S = 587.55) | 600 | m/z = 551.10 (C33H15F2N5S = 551.57) |
| 601 | m/z = 565.11 (C35H15N7S = 565.61) | 602 | m/z = 594.08 (C34H13F3N6S = 594.57) |
| 603 | m/z = 587.08 (C33H13F4N5S = 587.55) | 604 | m/z = 551.10 (C33H15F2N5S = 551.57) |
| 605 | m/z = 565.11 (C35H15N7S = 565.61) | 606 | m/z = 594.08 (C34H13F3N6S = 594.57) |
| 607 | m/z = 587.08 (C33H13F4N5S = 587.55) | 608 | m/z = 551.10 (C33H15F2N5S = 551.57) |
| 609 | m/z = 565.11 (C35H15N7S = 565.61) | 610 | m/z = 594.08 (C34H13F3N6S = 594.57) |
| 611 | m/z = 587.08 (C33H13F4N5S = 587.55) | 612 | m/z = 551.10 (C33H15F2N5S = 551.57) |
| 613 | m/z = 549.13 (C35H15N7O = 549.55) | 614 | m/z = 578.11 (C34H13F3N6O = 578.51) |
| 615 | m/z = 571.10 (C33H13F4N5O = 571.49) | 616 | m/z = 535.12 (C33H15F2N5O = 535.51) |
| 617 | m/z = 549.13 (C35H15N7O = 549.55) | 618 | m/z = 578.11 (C34H13F3N6O = 578.51) |
| 619 | m/z = 571.10 (C33H13F4N5O = 571.49) | 620 | m/z = 535.12 (C33H15F2N5O = 535.51) |
| 621 | m/z = 549.13 (C35H15N7O = 549.55) | 622 | m/z = 578.11 (C34H13F3N6O = 578.51) |
| 623 | m/z = 571.10 (C33H13F4N5O = 571.49) | 624 | m/z = 535.12 (C33H15F2N5O = 535.51) |
| 625 | m/z = 549.13 (C35H15N7O = 549.55) | 626 | m/z = 578.11 (C34H13F3N6O = 578.51) |
| 627 | m/z = 571.10 (C33H13F4N5O = 571.49) | 628 | m/z = 535.12 (C33H15F2N5O = 535.51) |
| 629 | m/z = 549.13 (C35H15N7O = 549.55) | 630 | m/z = 578.11 (C34H13F3N6O = 578.51) |
| 631 | m/z = 571.10 (C33H13F4N5O = 571.49) | 632 | m/z = 535.12 (C33H15F2N5O = 535.51) |
| 633 | m/z = 549.13 (C35H15N7O = 549.55) | 634 | m/z = 578.11 (C34H13F3N6O = 578.51) |
| 635 | m/z = 571.10 (C33H13F4N5O = 571.49) | 636 | m/z = 535.12 (C33H15F2N5O = 535.51) |
| 637 | m/z = 624.18 (C41H20N8 = 624.66) | 638 | m/z = 653.15 (C40H18F3N7 = 353.62) |
| 639 | m/z = 646.15 (C39H18F4N6 = 646.60) | 640 | m/z = 610.17 (C39H20F2N6 = 610.62) |
| 641 | m/z = 624.18 (C41H20N8 = 624.66) | 642 | m/z = 653.15 (C40H18F3N7 = 353.62) |
| 643 | m/z = 646.15 (C39H18F4N6 = 646.60) | 644 | m/z = 610.17 (C39H20F2N6 = 610.62) |
| 645 | m/z = 624.18 (C41H20N8 = 624.66) | 646 | m/z = 653.15 (C40H18F3N7 = 353.62) |
| 647 | m/z = 646.15 (C39H18F4N6 = 646.60) | 648 | m/z = 610.17 (C39H20F2N6 = 610.62) |
| 649 | m/z = 624.18 (C41H20N8 = 624.66) | 650 | m/z = 653.15 (C40H18F3N7 = 353.62) |
| 651 | m/z = 646.15 (C39H18F4N6 = 646.60) | 652 | m/z = 610.17 (C39H20F2N6 = 610.62) |
| 653 | m/z = 548.14 (C35H16N8 = 548.56) | 654 | m/z = 577.12 (C34H14F3N7 = 577.53) |
| 655 | m/z = 570.12 (C33H14F4N6 = 570.51) | 656 | m/z = 534.14 (C33H16F2N6 = 534.52) |
| 657 | m/z = 624.18 (C41H20N8 = 624.66) | 658 | m/z = 653.15 (C40H18F3N7 = 353.62) |
| 659 | m/z = 646.15 (C39H18F4N6 = 646.60) | 660 | m/z = 610.17 (C39H20F2N6 = 610.62) |
| 661 | m/z = 619.08 (C35H12F3N7S = 619.58) | 662 | m/z = 619.08 (C35H12F3N7S = 619.58) |
| 663 | m/z = 619.08 (C35H12F3N7S = 619.58) | 664 | m/z = 619.08 (C35H12F3N7S = 619.58) |

<Experimental Example 1-1> Manufacture of Organic Light Emitting Device

Comparative Example 1-1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

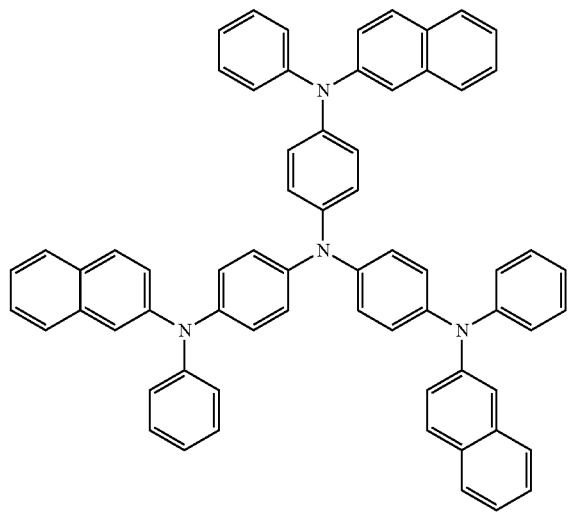

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

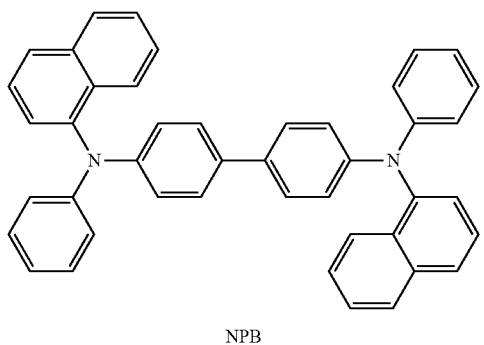 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

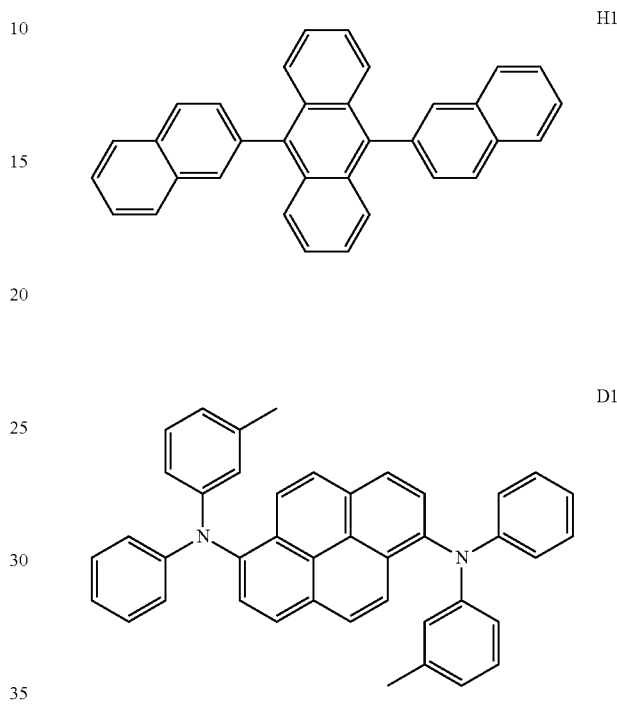

Subsequently, a compound of the following Structural Formula E1 was deposited to a thickness of 300 Å on the light emitting layer to form an electron transfer layer. As an electron injection layer, lithium fluoride (LiF) was deposited to a thickness of 10 Å, and an Al cathode was employed to a thickness of 1,000 Å, and as a result, an OLED device was manufactured.

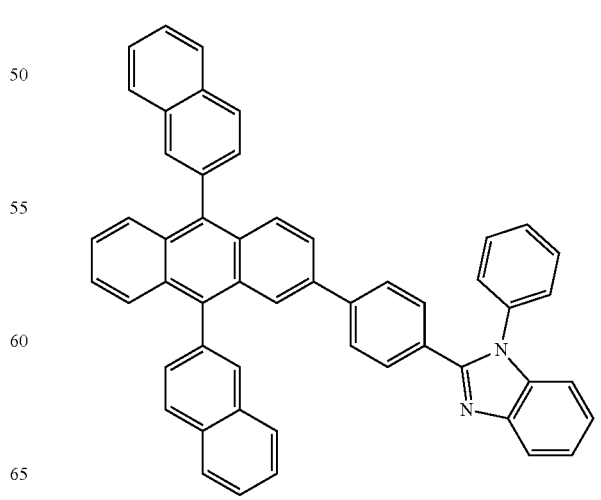

-continued

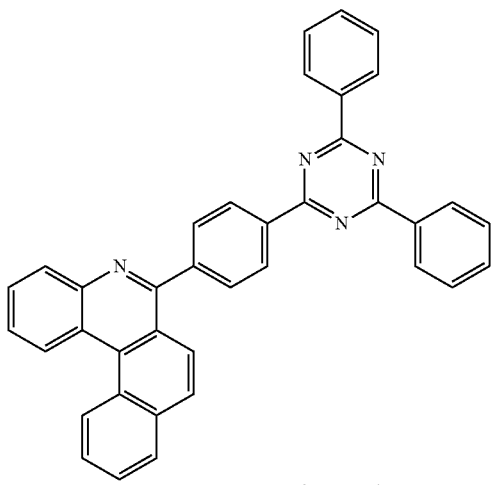

E2

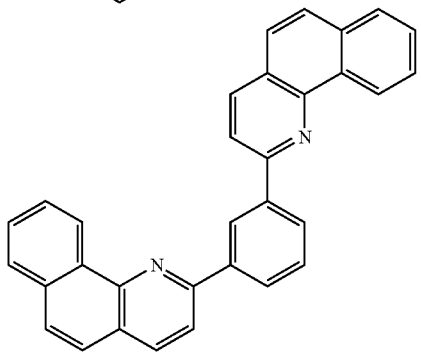

BBQB

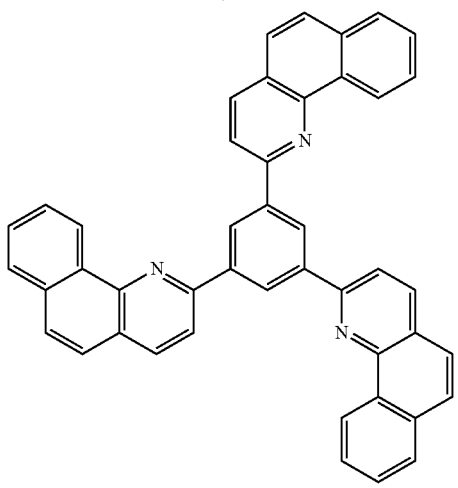

TBQB

Meanwhile, all the organic compounds required to manufacture the OLED device were vacuum sublimation purified under $10^{-8}$ torr to $10^{-6}$ torr by each material to be used in the OLED manufacture.

Example 1-1 to Example 1-41 and Comparative Examples 1-2 to 1-4

Organic electroluminescent devices were manufactured in the same manner as in Comparative Example 1-1 except that, in Example 1-1 to Example 1-41 and Comparative Examples 1-2 to 1-4, compounds of the following Table 3 prepared in the preparation examples were used instead of E1 used when forming the electron transfer layer in Comparative Example 1-1.

<Experimental Example 1-2> Evaluation on Organic Electroluminescent Device

For each of the organic light emitting devices manufactured in Comparative Example 1-1 to Comparative Example 1-4 and Example 1-1 to Example 1-41, electroluminescent (EL) properties were measured using M7000 manufactured by McScience Inc., and with the measurement results, $T_{95}$ was measured when standard luminance was 700 cd/m² through a lifetime measurement system (M6000) manufactured by McScience Inc. Results of measuring driving voltage, light emission efficiency, color coordinate (CIE) and lifetime of the blue organic light emitting devices manufactured according to the present disclosure are as shown in Table 3.

TABLE 3

| | Compound | Driving Voltage (V) | Light Emission Efficiency (cd/A) | CIE (x, y) | Lifetime ($T_{95}$) |
|---|---|---|---|---|---|
| Example 1-1 | 1 | 5.03 | 6.68 | (0.134, 0.101) | 65 |
| Example 1-2 | 16 | 4.92 | 6.83 | (0.134, 0.102) | 43 |
| Example 1-3 | 31 | 4.90 | 6.76 | (0.134, 0.101) | 42 |
| Example 1-4 | 46 | 4.84 | 6.98 | (0.134, 0.103) | 43 |
| Example 1-5 | 61 | 5.05 | 6.32 | (0.134, 0.102) | 37 |
| Example 1-6 | 76 | 4.81 | 6.97 | (0.134, 0.101) | 42 |
| Example 1-7 | 91 | 4.79 | 7.10 | (0.134, 0.102) | 42 |
| Example 1-8 | 107 | 4.78 | 7.11 | (0.134, 0.101) | 42 |
| Example 1-9 | 109 | 4.81 | 7.01 | (0.134, 0.101) | 41 |
| Example 1-10 | 139 | 4.90 | 6.88 | (0.134, 0.100) | 44 |
| Example 1-11 | 144 | 4.85 | 6.89 | (0.134, 0.101) | 54 |
| Example 1-12 | 174 | 4.78 | 7.05 | (0.134, 0.100) | 50 |
| Example 1-13 | 199 | 5.01 | 6.67 | (0.134, 0.100) | 41 |
| Example 1-14 | 213 | 4.78 | 7.17 | (0.134, 0.100) | 43 |
| Example 1-15 | 215 | 4.85 | 6.81 | (0.134, 0.100) | 44 |
| Example 1-16 | 217 | 4.80 | 6.90 | (0.134, 0.100) | 44 |
| Example 1-17 | 232 | 4.81 | 6.96 | (0.134, 0.102) | 43 |
| Example 1-18 | 247 | 4.76 | 7.00 | (0.134, 0.101) | 39 |
| Example 1-19 | 253 | 4.74 | 7.05 | (0.134, 0.102) | 40 |
| Example 1-20 | 262 | 4.77 | 7.02 | (0.134, 0.100) | 39 |
| Example 1-21 | 268 | 4.85 | 6.83 | (0.134, 0.103) | 43 |
| Example 1-22 | 283 | 4.85 | 6.86 | (0.134, 0.100) | 55 |
| Example 1-23 | 298 | 4.79 | 6.88 | (0.134, 0.102) | 41 |
| Example 1-24 | 307 | 4.79 | 6.99 | (0.134, 0.101) | 56 |
| Example 1-25 | 323 | 4.85 | 6.89 | (0.134, 0.100) | 37 |
| Example 1-26 | 325 | 4.82 | 6.90 | (0.134, 0.102) | 40 |
| Example 1-27 | 326 | 4.83 | 6.98 | (0.134, 0.103) | 44 |
| Example 1-28 | 337 | 4.83 | 6.91 | (0.134, 0.100) | 39 |
| Example 1-29 | 338 | 4.77 | 7.00 | (0.134, 0.103) | 54 |
| Example 1-30 | 353 | 4.98 | 6.62 | (0.134, 0.102) | 43 |
| Example 1-31 | 354 | 4.92 | 6.71 | (0.134, 0.100) | 45 |
| Example 1-32 | 361 | 4.99 | 6.71 | (0.134, 0.099) | 44 |
| Example 1-33 | 362 | 4.85 | 6.88 | (0.134, 0.102) | 45 |
| Example 1-34 | 409 | 4.85 | 6.91 | (0.134, 0.100) | 46 |
| Example 1-35 | 411 | 4.85 | 6.91 | (0.134, 0.103) | 43 |
| Example 1-36 | 412 | 4.92 | 6.65 | (0.134, 0.102) | 45 |
| Example 1-37 | 417 | 4.79 | 6.72 | (0.134, 0.101) | 40 |
| Example 1-38 | 425 | 4.85 | 6.62 | (0.134, 0.102) | 43 |
| Example 1-39 | 426 | 4.70 | 6.92 | (0.134, 0.102) | 45 |
| Example 1-40 | 449 | 4.98 | 6.70 | (0.134, 0.099) | 43 |
| Example 1-41 | 450 | 4.96 | 6.71 | (0.134, 0.100) | 42 |
| Comparative Example 1-1 | E1 | 5.56 | 5.91 | (0.134, 0.100) | 28 |
| Comparative Example 1-2 | E2 | 5.52 | 6.09 | (0.134, 0.101) | 28 |
| Comparative Example 1-3 | BBQB | 5.50 | 6.10 | (0.134, 0.101) | 30 |
| Comparative Example 1-4 | TBQB | 5.51 | 6.15 | (0.134, 0.102) | 29 |

As seen from the results of Table 3, the organic light emitting device using the electron transfer layer material of the blue organic light emitting device of the present disclosure had lower driving voltage and significantly improved light emission efficiency and lifetime compared to the comparative examples. Particularly, it was identified that Compounds 91, 107, 213, 253, 262 and 338 were superior in all aspects of driving, efficiency and lifetime.

Such a result is considered to be due to the fact that, when using the disclosed compound having proper length and strength, and flatness as an electron transfer layer, a compound in an excited state is made by receiving electrons under a specific condition, and particularly when an excited state is formed in the hetero-skeleton site of the compound, excited energy moves to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2-1> Manufacture of Organic Light Emitting Device

Comparative Example 2-1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

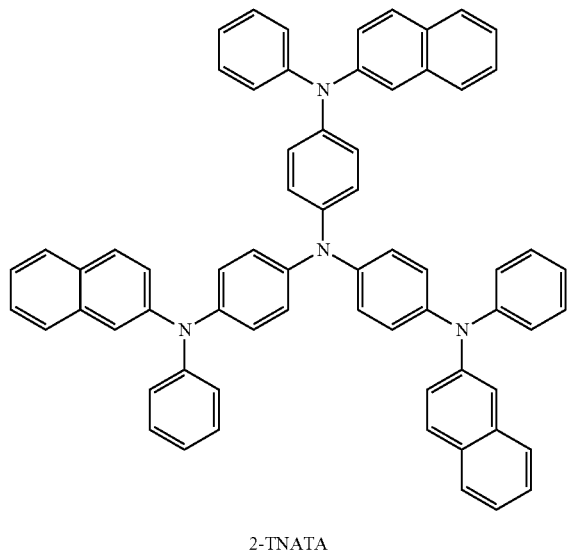 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N, N'-diphenyl-4, 4'-diamine (NPB) was introduced, and evaporated by applying a current to the cell to deposit a hole transfer layer having a thickness of 300 Å on the hole injection layer.

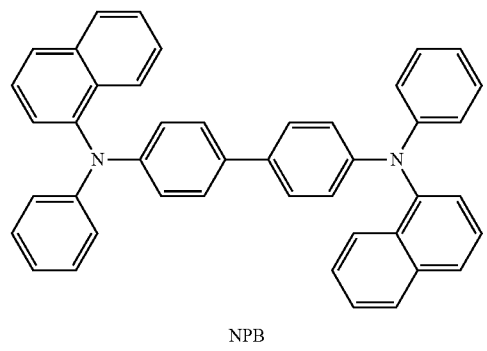 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

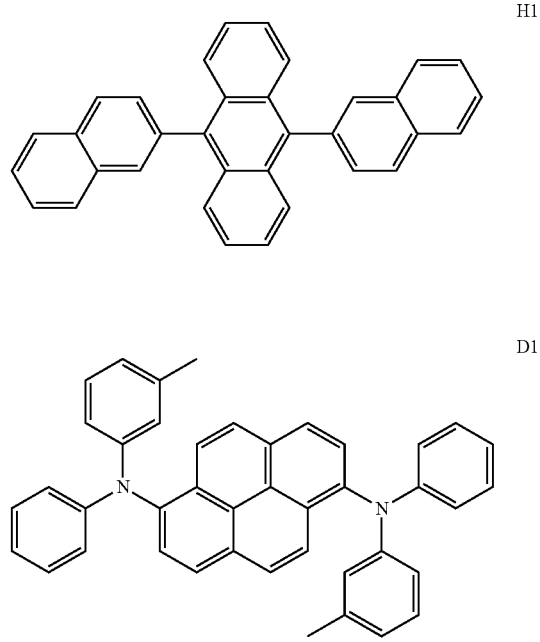

Subsequently, as a hole blocking layer, a compound of the following Structural Formula E2 was deposited to a thickness of 50 Å.

Subsequently, as an electron transfer layer, a compound of the following Structural Formula E1 was deposited to a thickness of 300 Å.

E1

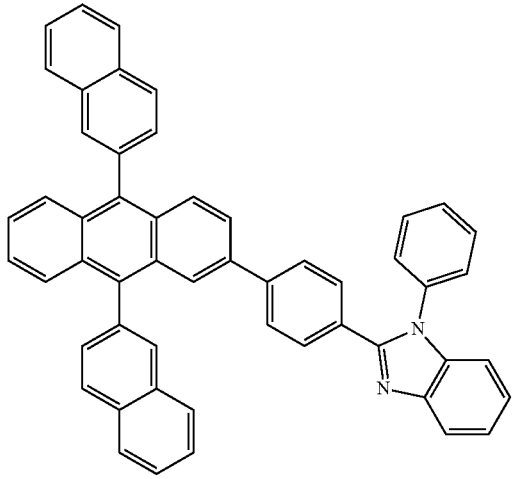

E2

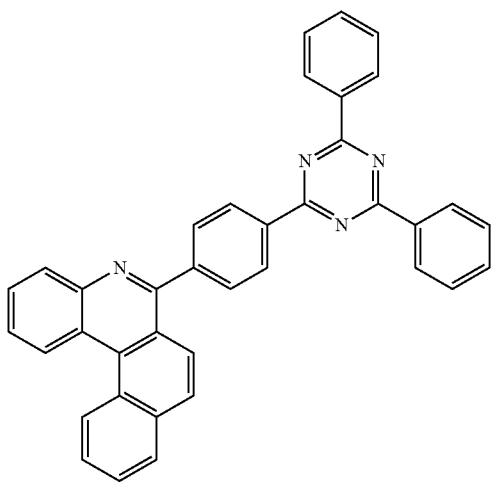

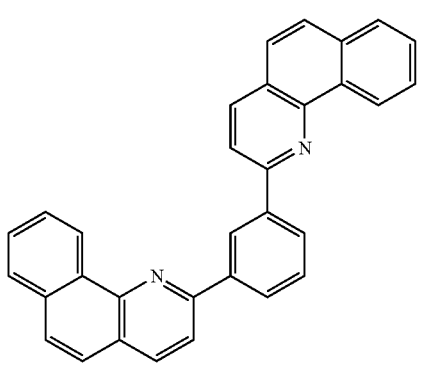

BBQB

-continued

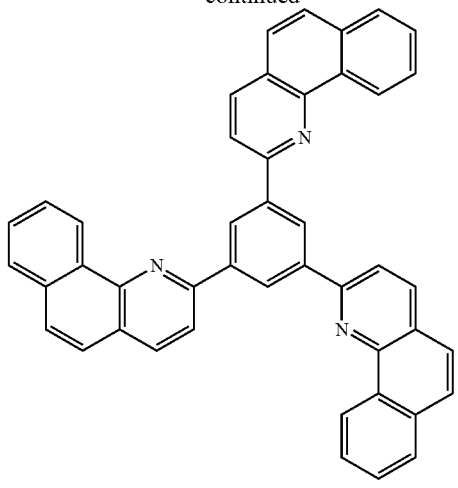

TBQB

As an electron injection layer, lithium fluoride (LiF) was deposited to a thickness of 10 Å, and an Al cathode was employed to a thickness of 1,000 Å, and as a result, an OLED device was manufactured. Meanwhile, all the organic compounds required to manufacture the OLED device were vacuum sublimation purified under $10^{-8}$ torr to $10^{-6}$ torr by each material to be used in the OLED manufacture.

Example 2-1 to Example 2-41, Comparative Example 2-2 and Comparative Example 2-3

Organic electroluminescent devices were manufactured in the same manner as in Comparative Example 2-1 except that, in Example 2-1 to Example 2-41, Comparative Example 2-2 and Comparative Example 2-3, compounds of the following Table 4 prepared in the preparation examples were used instead of E2 used when forming the hole blocking layer in Comparative Example 2-1.

<Experimental Example 2-2> Evaluation on Organic Electroluminescent Device

For each of the organic light emitting devices manufactured in Comparative Example 2-1 to Comparative Example 2-3 and Example 2-1 to Example 2-41, electroluminescent (EL) properties were measured using M7000 manufactured by McScience Inc., and with the measurement results, $T_{95}$ was measured when standard luminance was 700 cd/m$^2$ through a lifetime measurement system (M6000) manufactured by McScience Inc. Results of measuring driving voltage, light emission efficiency, color coordinate (CIE) and lifetime of the blue organic light emitting devices manufactured according to the present disclosure are as shown in Table 4.

TABLE 4

| | Compound | Driving Voltage (V) | Light Emission Efficiency (cd/A) | CIE (x, y) | Lifetime ($T_{95}$) |
|---|---|---|---|---|---|
| Example 2-1 | 1 | 4.96 | 6.77 | (0.134, 0.101) | 56 |
| Example 2-2 | 16 | 5.07 | 6.83 | (0.134, 0.102) | 55 |
| Example 2-3 | 31 | 5.05 | 6.81 | (0.134, 0.101) | 70 |
| Example 2-4 | 46 | 4.98 | 6.75 | (0.134, 0.103) | 55 |

TABLE 4-continued

| Com-pound | Driving Voltage (V) | Light Emission Efficiency (cd/A) | CIE (x, y) | Lifetime ($T_{95}$) |
|---|---|---|---|---|
| Example 2-5 | 61 | 4.95 | 6.95 | (0.134, 0.102) | 51 |
| Example 2-6 | 76 | 4.89 | 6.94 | (0.134, 0.101) | 52 |
| Example 2-7 | 91 | 4.93 | 6.88 | (0.134, 0.102) | 58 |
| Example 2-8 | 107 | 5.05 | 6.65 | (0.134, 0.101) | 57 |
| Example 2-9 | 109 | 5.04 | 6.75 | (0.134, 0.101) | 58 |
| Example 2-10 | 139 | 5.10 | 6.58 | (0.134, 0.100) | 73 |
| Example 2-11 | 144 | 4.85 | 7.14 | (0.134, 0.101) | 49 |
| Example 2-12 | 174 | 5.08 | 7.02 | (0.134, 0.100) | 43 |
| Example 2-13 | 199 | 4.90 | 6.71 | (0.134, 0.100) | 48 |
| Example 2-14 | 213 | 4.93 | 6.71 | (0.134, 0.100) | 45 |
| Example 2-15 | 215 | 5.01 | 6.95 | (0.134, 0.100) | 53 |
| Example 2-16 | 217 | 4.86 | 6.86 | (0.134, 0.100) | 56 |
| Example 2-17 | 232 | 4.85 | 6.89 | (0.134, 0.102) | 46 |
| Example 2-18 | 247 | 5.04 | 7.06 | (0.134, 0.101) | 50 |
| Example 2-19 | 253 | 5.10 | 6.97 | (0.134, 0.102) | 51 |
| Example 2-20 | 262 | 4.84 | 7.14 | (0.134, 0.100) | 44 |
| Example 2-21 | 268 | 4.88 | 7.02 | (0.134, 0.103) | 42 |
| Example 2-22 | 283 | 5.06 | 6.65 | (0.134, 0.100) | 51 |
| Example 2-23 | 298 | 5.05 | 6.78 | (0.134, 0.102) | 41 |
| Example 2-24 | 307 | 5.05 | 6.77 | (0.134, 0.101) | 48 |
| Example 2-25 | 323 | 4.90 | 6.95 | (0.134, 0.100) | 58 |
| Example 2-26 | 325 | 5.11 | 6.46 | (0.134, 0.102) | 73 |
| Example 2-27 | 326 | 4.78 | 7.20 | (0.134, 0.103) | 57 |
| Example 2-28 | 337 | 5.07 | 6.53 | (0.134, 0.100) | 71 |
| Example 2-29 | 338 | 4.85 | 7.19 | (0.134, 0.103) | 41 |
| Example 2-30 | 353 | 4.91 | 6.65 | (0.134, 0.102) | 47 |
| Example 2-31 | 354 | 5.05 | 6.71 | (0.134, 0.100) | 55 |
| Example 2-32 | 361 | 5.00 | 6.77 | (0.134, 0.099) | 58 |
| Example 2-33 | 362 | 4.96 | 6.87 | (0.134, 0.102) | 53 |
| Example 2-34 | 409 | 4.99 | 6.74 | (0.134, 0.100) | 46 |
| Example 2-35 | 411 | 4.96 | 6.80 | (0.134, 0.103) | 43 |
| Example 2-36 | 412 | 5.03 | 6.69 | (0.134, 0.102) | 50 |
| Example 2-37 | 417 | 4.84 | 7.13 | (0.134, 0.101) | 55 |
| Example 2-38 | 425 | 4.80 | 7.14 | (0.134, 0.102) | 52 |
| Example 2-39 | 426 | 4.82 | 7.14 | (0.134, 0.102) | 50 |
| Example 2-40 | 449 | 4.79 | 7.15 | (0.134, 0.099) | 48 |
| Example 2-41 | 450 | 5.04 | 6.85 | (0.134, 0.100) | 49 |
| Comparative Example 2-1 | E2 | 5.52 | 6.09 | (0.134, 0.101) | 28 |
| Comparative Example 2-2 | BBQB | 5.50 | 6.10 | (0.134, 0.101) | 30 |
| Comparative Example 2-3 | TBQB | 5.51 | 6.15 | (0.134, 0.102) | 29 |

As seen from the results of Table 4, the organic light emitting device using the hole blocking layer material of the blue organic light emitting device of the present disclosure had lower driving voltage and significantly improved light emission efficiency and lifetime compared to the comparative examples. Particularly, it was identified that Compounds 144, 262, 268, 326, 338, 417, 425, 426 and 449 were significantly superior in all aspects of driving, efficiency and lifetime.

Such results are due to the fact that the compound is a bipolar type having both a p-type and an n-type, and therefore, hole leakage is prevented and excitons are effectively trapped in the light emitting layer.

<Experimental Example 3-1> Manufacture of Organic Light Emitting Device

Comparative Example 3-1

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a 2-stack white organic light emitting device (WOLED) structure. As for the first stack, the following TAPC was thermal vacuum deposited first to a thickness of 300 Å to form a hole transfer layer. After forming the hole transfer layer, a light emitting layer was thermal vacuum deposited thereon as follows. As the light emitting layer, the following TCz1, a host, was 8% doped with the following FIrpic, a blue phosphorescent dopant, and deposited to 300 Å. After forming an electron transfer layer to 400 Å using the following TmPyPB, the following BBQB compound was 20% doped with $Cs_2CO_3$ to form as a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to the following TAPC, and then depositing the following TAPC to 300 Å. A light emitting layer was formed thereon by 8% doping the following Ir(ppy)$_3$, a green phosphorescent dopant, to TCz1, a host, and depositing the result to 300 Å, and then an electron transfer layer was formed to 600 Å using the following TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the organic light emitting diode (OLED) device were vacuum sublimation purified under $10^{-8}$ torr to $10^{-6}$ torr for each material to be used in the OLED manufacture.

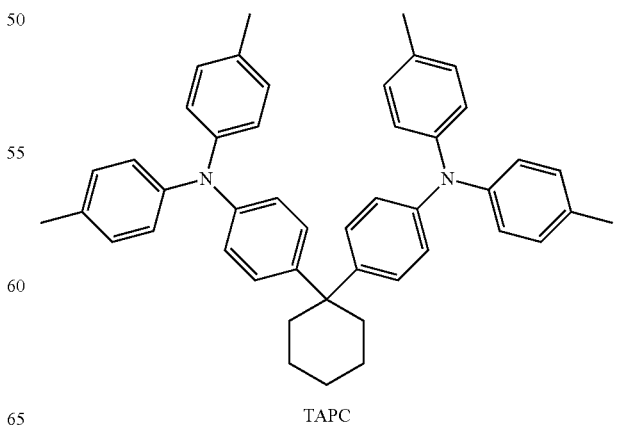

TAPC

-continued

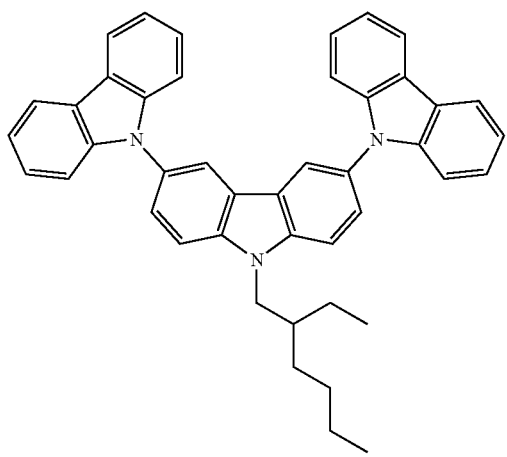

TCz1

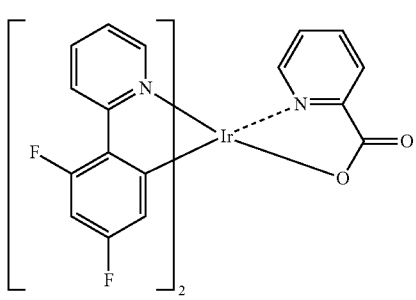

FIrpic

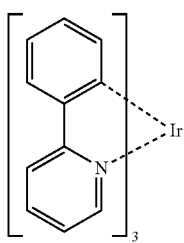

Ir(ppy)3

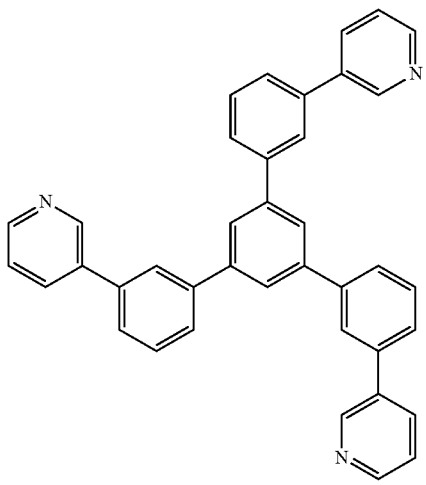

TmPyPB

-continued

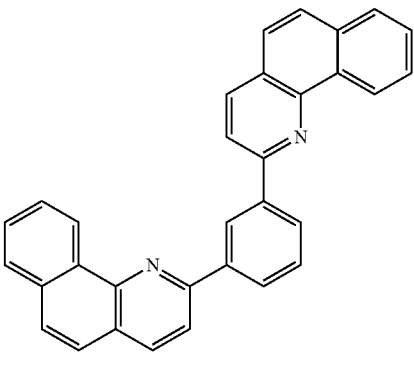

BBQB

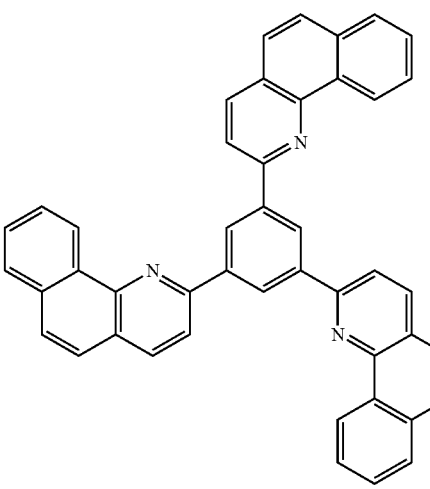

TBQB

E2

Example 3-1 to Example 3-41, Comparative Example 3-2 and Comparative Example 3-3

Organic electroluminescent devices were manufactured in the same manner as in Comparative Example 3-1 except that, in Example 3-1 to Example 3-41, Comparative Example 3-2 and Comparative Example 3-3, compounds of the following Table 5 were used instead of BBQB used when forming the charge generation layer in Comparative Example 3-1.

<Experimental Example 3-2> Evaluation an Organic Electroluminescent Device

For each of the organic light emitting devices manufactured as above, electroluminescent (EL) properties were measured using M7000 manufactured by McScience Inc., and with the measurement results, $T_{95}$ was measured when standard luminance was 3,500 cd/m² through a lifetime measurement system (M6000) manufactured by McScience Inc. Results of measuring driving voltage, light emission efficiency, color coordinate (CIE) and lifetime of the white organic light emitting devices manufactured according to the present disclosure are as shown in Table 5.

TABLE 5

| | Compound | Driving Voltage (V) | Light Emission Efficiency (cd/A) | CIE (x, y) | Lifetime ($T_{95}$) |
|---|---|---|---|---|---|
| Example 3-1 | 1 | 7.78 | 63.95 | (0.218, 0.427) | 61 |
| Example 3-2 | 16 | 7.60 | 65.45 | (0.220, 0.431) | 40 |
| Example 3-3 | 31 | 7.57 | 64.75 | (0.220, 0.431) | 39 |
| Example 3-4 | 46 | 7.48 | 66.88 | (0.200, 0.421) | 40 |
| Example 3-5 | 61 | 7.81 | 60.55 | (0.228, 0.436) | 35 |
| Example 3-6 | 76 | 7.44 | 66.74 | (0.243, 0.442) | 39 |
| Example 3-7 | 91 | 7.41 | 67.99 | (0.221, 0.433) | 39 |
| Example 3-8 | 107 | 7.39 | 68.12 | (0,208, 0.415) | 39 |
| Example 3-9 | 109 | 7.44 | 67.13 | (0.233, 0.433) | 38 |
| Example 3-10 | 139 | 7.57 | 65.89 | (0.238, 0.438) | 41 |
| Example 3-11 | 144 | 7.50 | 66.01 | (0.225, 0.429) | 50 |
| Example 3-12 | 174 | 7.39 | 67.56 | (0.209, 0.415) | 47 |
| Example 3-13 | 199 | 7.74 | 63.89 | (0.231, 0.440) | 38 |
| Example 3-14 | 213 | 7.39 | 68.71 | (0.211, 0.419) | 40 |
| Example 3-15 | 215 | 7.49 | 65.26 | (0.209, 0.419) | 41 |
| Example 3-16 | 217 | 7.42 | 66.11 | (0.207, 0.409) | 41 |
| Example 3-17 | 232 | 7.43 | 66.66 | (0,208, 0.415) | 40 |
| Example 3-18 | 247 | 7.35 | 67.06 | (0.214, 0.420) | 36 |
| Example 3-19 | 253 | 7.33 | 67.56 | (0.224, 0.429) | 37 |
| Example 3-20 | 262 | 7.37 | 67.21 | (0.221, 0.434) | 36 |
| Example 3-21 | 268 | 7.50 | 65.45 | (0.212, 0.422) | 40 |
| Example 3-22 | 283 | 7.49 | 65.70 | (0.228, 0.418) | 51 |
| Example 3-23 | 298 | 7.40 | 65.89 | (0.231, 0.420) | 38 |
| Example 3-24 | 307 | 7.41 | 66.98 | (0.219, 0.411) | 52 |
| Example 3-25 | 323 | 7.50 | 65.98 | (0.219, 0.411) | 35 |
| Example 3-26 | 325 | 7.45 | 66.11 | (0.210, 0.412) | 37 |
| Example 3-27 | 326 | 7.47 | 66.84 | (0.218, 0.421) | 41 |
| Example 3-28 | 337 | 7.46 | 66.21 | (0.209, 0.432) | 36 |
| Example 3-29 | 338 | 7.38 | 67.04 | (0.231, 0.418) | 50 |
| Example 3-30 | 353 | 7.69 | 63.38 | (0.243, 0.442) | 40 |
| Example 3-31 | 354 | 7.61 | 64.23 | (0.205, 0.411) | 42 |
| Example 3-32 | 361 | 7.72 | 64.22 | (0.243, 0.442) | 41 |
| Example 3-33 | 362 | 7.50 | 65.88 | (0.209, 0.419) | 42 |
| Example 3-34 | 409 | 7.49 | 66.18 | (0.210, 0.420) | 43 |
| Example 3-35 | 411 | 7.50 | 66.20 | (0.231, 0.419) | 40 |
| Example 3-36 | 412 | 7.49 | 66.24 | (0.229, 0.420) | 40 |
| Example 3-37 | 417 | 7.31 | 66.80 | (0.224, 0.423) | 35 |
| Example 3-38 | 425 | 7.45 | 66.27 | (0.220, 0.424) | 37 |
| Example 3-39 | 426 | 7.29 | 67.57 | (0.221, 0.430) | 40 |
| Example 3-40 | 449 | 7.56 | 65.46 | (0.205, 0.411) | 39 |
| Example 3-41 | 450 | 7.54 | 65.64 | (0.231, 0.418) | 39 |
| Comparative Example 3-1 | BBQB | 8.43 | 58.11 | (0.220, 0.429) | 27 |
| Comparative Example 3-2 | TBQB | 8.47 | 58.90 | (0.222, 0.430) | 28 |
| Comparative Example 3-3 | E2 | 8.45 | 58.05 | (0.221, 0.431) | 25 |

As seen from the results of Table 5, the organic light emitting device using the charge generation layer material of the 2-stack white organic light emitting device of the present disclosure had lower driving voltage and improved light emission efficiency compared to the comparative examples. Particularly, it was identified that Compounds 91, 107, 213, 253, 262 and 338 were significantly superior in all aspects of driving, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal thereto, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

In addition, by the core structure of the present application having a substituent at two places and thereby combining an electron-deficient substituent and an aryl or acene-based substituent, the electron-deficient substituent readily receives electrons from the electron injection layer, and the aryl or acene-based substituent stabilizes the molecule itself and transfers the supplied electrons to the light emitting layer, which may enhance device properties. Accordingly, higher molecular stability and device properties may be obtained compared to the materials in which phenanthridine is single substituted as in the comparative examples.

<Experimental Example 4-1> Manufacture of Organic Light Emitting Device

Comparative Example 4-1

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition. On the transparent ITO electrode (anode), organic materials were formed in a 2-stack white organic light emitting device (WOLED) structure. As for the first stack, the following TAPC was thermal vacuum deposited first to a thickness of 300 Å to form a hole transfer layer. After forming the hole transfer layer, a light emitting layer was thermal vacuum deposited thereon as follows. As the light emitting layer, the following TCz1, a host, was 8% doped with the following FIrpic, a blue phosphorescent dopant, and deposited to 300 Å. After forming an electron transfer layer to 400 Å using the following TmPyPB, the following Bphen was 20% doped with $Cs_2CO_3$ to form as a charge generation layer to 100 Å. As for the second stack, $MoO_3$ was thermal vacuum deposited first to a thickness of 50 Å to form a hole injection layer. A hole transfer layer, a common layer, was formed to 100 Å by 20% doping $MoO_3$ to the following TAPC, and then depositing the following TAPC to 300 Å. A light emitting layer was formed thereon by 8% doping the following Ir(ppy)$_3$, a green phosphorescent dopant, to the following TCz1, a host, and depositing the result to 300 Å, and then an electron transfer layer was formed to 600 Å using the following TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured. Meanwhile, all the organic compounds required to manufacture the OLED device were vacuum sublimation purified under $10^{-8}$ torr to $10^{-6}$ torr for each material to be used in the OLED manufacture.

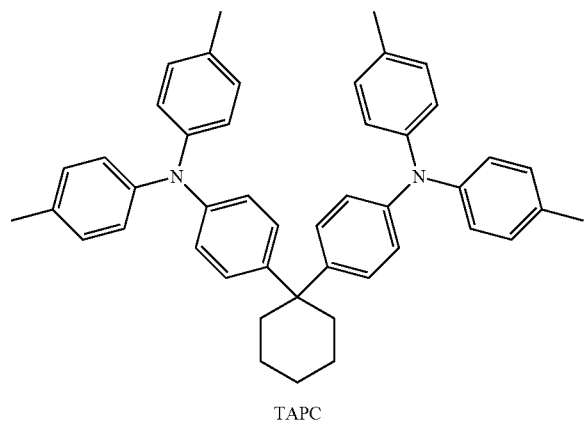

TAPC

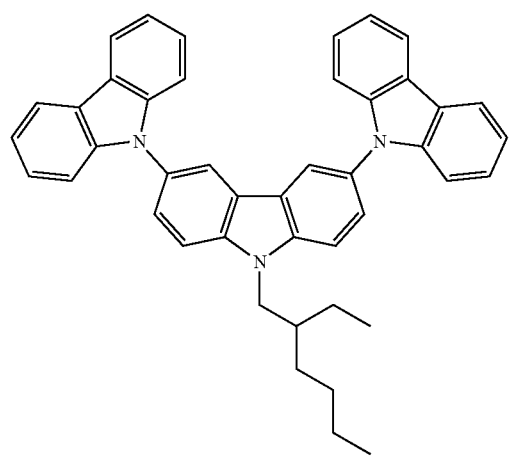

TCz1

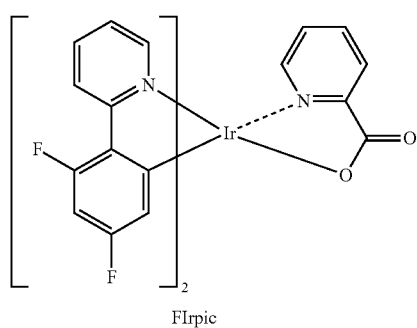

FIrpic

-continued

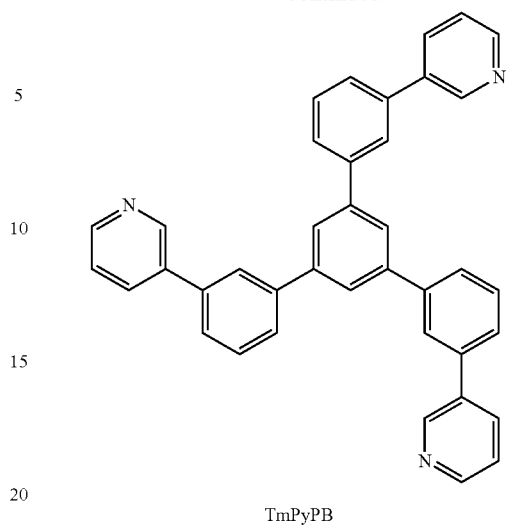

TmPyPB

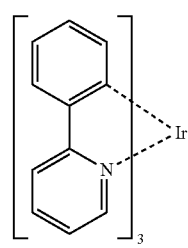

Ir(ppy)3

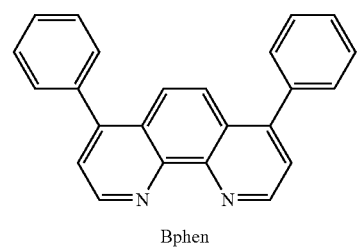

Bphen

Example 4-1 to Example 4-4

Organic electroluminescent devices were manufactured in the same manner as in Comparative Example 4-1 except that, in Example 4-1 to Example 4-4, compounds presented in Table 6 were used instead of $MoO_3$ used when forming the hole injection layer in Comparative Example 4-1.

<Experimental Example 4-2> Evaluation on Organic Electroluminescent Device

For each of the organic electroluminescent devices manufactured as above, electroluminescent (EL) properties were measured using M7000 manufactured by McScience Inc., and with the measurement results, $T_{95}$ was measured when standard luminance was 3,500 cd/m$^2$ through a lifetime measurement system (M6000) manufactured by McScience Inc. Results of measuring driving voltage, light emission efficiency, color coordinate (CIE) and lifetime of the white organic electroluminescent device manufactured according to the present disclosure are as shown in Table 6.

TABLE 6

| | Compound | Driving Voltage (V) | Light Emission Efficiency (cd/A) | CIE (x, y) | Lifetime ($T_{95}$) |
|---|---|---|---|---|---|
| Example 4-1 | 473 | 5.12 | 6.61 | (0.134, 0.100) | 52 |
| Example 4-2 | 485 | 5.14 | 6.65 | (0.134, 0.101) | 53 |
| Example 4-3 | 505 | 5.17 | 6.72 | (0.134, 0.100) | 55 |
| Example 4-4 | 527 | 5.24 | 6.71 | (0.134, 0.101) | 55 |
| Comparative Example 4-1 | $MoO_3$ | 5.45 | 6.06 | (0.134, 0.101) | 44 |

As seen from the results of Table 6, the organic electroluminescent device using the hole injection layer material of the 2-stack white organic electroluminescent device of the present disclosure had lower driving voltage and improved light emission efficiency compared to Comparative Example 4-1.

Such a result is considered to be due to the fact that holes may be smoothly injected by being formed with materials having an energy level similar to the energy level of the hole transfer layer receiving holes from a P-type charge generation layer, and, by having a low LUMO energy level, electrons produced from the P-type charge generation layer, which are in a stable state due to anionization, are readily injected through a gap state produced in an N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

The invention claimed is:

1. A heterocyclic compound represented by the following Chemical Formula 1:

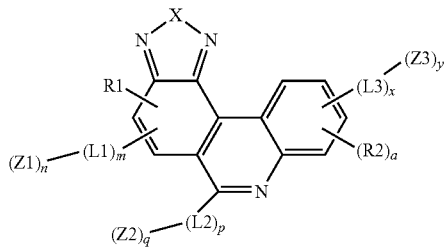

[Chemical Formula 1]

wherein, in Chemical Formula 1,

X is O; S; or NR;

L1 to L3 are the same as or different from each other, and each independently a direct bond; a substituted or unsubstituted arylene group having 6 to 60 carbon atoms; or a substituted or unsubstituted heteroarylene group having 2 to 60 carbon atoms;

Z1 to Z3 are the same as or different from each other, and each independently selected from the group consisting of hydrogen; deuterium; a halogen group; a cyano group; —P(=O)(R104)(R105); —N(R106)(R107); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms;

R1 and R2 are the same as or different from each other, and each independently selected from the group consisting of hydrogen; deuterium; a halogen group; a cyano group; —P(=O)(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; and a substituted or unsubstituted heteroaryl group having 2 to 60 carbon atoms, or adjacent two or more groups bond to each other to form a substituted or unsubstituted aliphatic hydrocarbon ring; a substituted or unsubstituted aromatic hydrocarbon ring; a substituted or unsubstituted aliphatic heteroring; or a substituted or unsubstituted aromatic heteroring;

R is hydrogen; deuterium; a halogen group; a cyano group; a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; a substituted or unsubstituted heterocycloalkyl group having 2 to 60 carbon atoms; a substituted or unsubstituted aryl group having 6 to 60 carbon atoms; or a substituted or unsubstituted heteroaryl group having 2 to 60 carbon atoms;

R104 to R107 and R104' to R107' are each independently hydrogen; deuterium; a halogen group; an alkyl group; an alkenyl group; an alkoxy group; a cycloalkyl group; an aryl group; or a heteroaryl group;

m, p, x, n, q and y are each an integer of 1 to 5;

a is an integer of 1 to 3; and when m, p, x, n, q, y and a are each an integer of 2 or greater, substituents in the parentheses are the same as or different from each other.

2. The heterocyclic compound of claim 1, wherein Chemical Formula 1 is represented by one of the following Chemical Formulae 2 to 5:

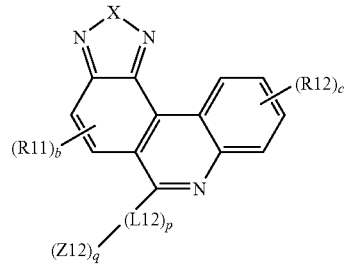

[Chemical Formula 2]

-continued

[Chemical Formula 3]

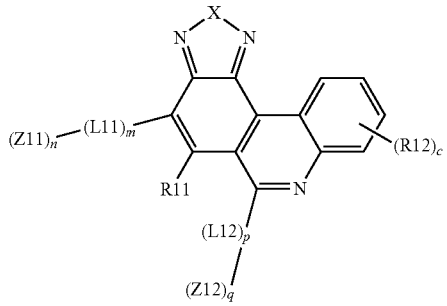

[Chemical Formula 4]

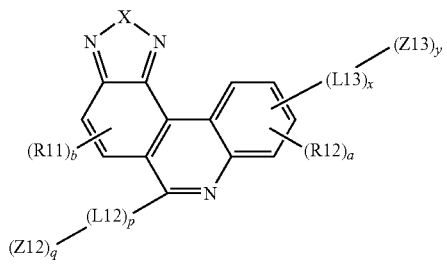

[Chemical Formula 5]

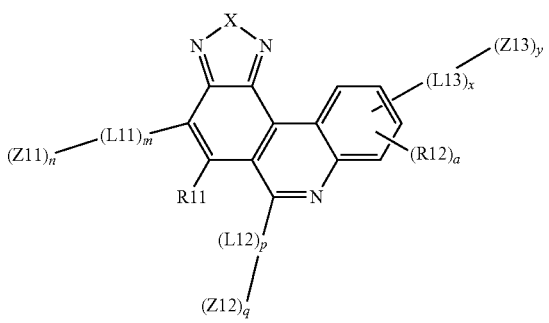

in Chemical Formula 2 to Chemical Formula 5,
X, m, p, x, n, q, y, a and R have the same definitions as in Chemical Formula 1,
L11 to L13 are the same as or different from each other, and each independently a direct bond; a substituted or unsubstituted arylene group having 6 to 60 carbon atoms; or a substituted or unsubstituted heteroarylene group having 2 to 60 carbon atoms,
Z11 to Z13 are the same as or different from each other, and each independently selected from the group consisting of a cyano group; —P(=O)(R104)(R105); a substituted or unsubstituted aryl group having 6 to 60 carbon atoms; and a substituted or unsubstituted heteroaryl group having 2 to 60 carbon atoms,
R11 and R12 are the same as or different from each other, and each independently selected from the group consisting of hydrogen; deuterium; a halogen group; a cyano group; —P(=O)(R104')(R105'); —N(R106')(R107'); a substituted or unsubstituted alkyl group having 1 to 60 carbon atoms; a substituted or unsubstituted alkenyl group having 2 to 60 carbon atoms; a substituted or unsubstituted alkynyl group having 2 to 60 carbon atoms; a substituted or unsubstituted alkoxy group having 1 to 60 carbon atoms; a substituted or unsubstituted cycloalkyl group having 3 to 60 carbon atoms; and a substituted or unsubstituted heterocycloalkyl group having 2 to 60 carbon atoms, R104, R105 and R104' to R107' are each independently hydrogen; deuterium; a halogen group; an alkyl group; an alkenyl group; an alkoxy group; a cycloalkyl group; an aryl group; or a heteroaryl group, b is 1 or 2, c is an integer of 1 to 4, when b is 2, two R11s are the same as or different from each other, and when c is 2 or greater, a plurality of R12s are the same as or different from each other.

3. The heterocyclic compound of claim 1, wherein R1 and R2 are hydrogen.

4. The heterocyclic compound of claim 1, wherein L1 to L3 are the same as or different from each other, and each independently a direct bond; a phenylene group unsubstituted or substituted with a halogen group; a biphenylene group; or a terphenylene group.

5. The heterocyclic compound of claim 1, wherein R is a substituted or unsubstituted aryl group having 6 to 60 carbon atoms.

6. The heterocyclic compound of claim 1, wherein Z1 to Z3 are the same as or different from each other, and each independently hydrogen; deuterium; a cyano group; —P(=O)(R104)(R105); a substituted or unsubstituted aryl group having 6 to 40 carbon atoms; or a substituted or unsubstituted heteroaryl group having 2 to 40 carbon atoms.

7. The heterocyclic compound of claim 1, wherein Chemical Formula 1 is represented by any one of the following compounds:

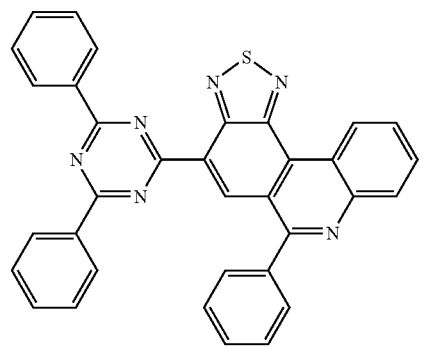

1

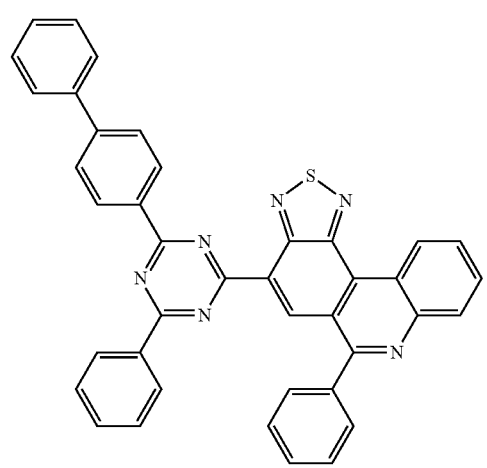

2

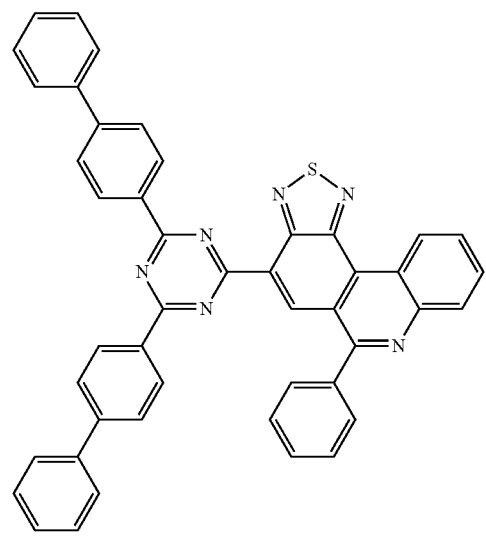
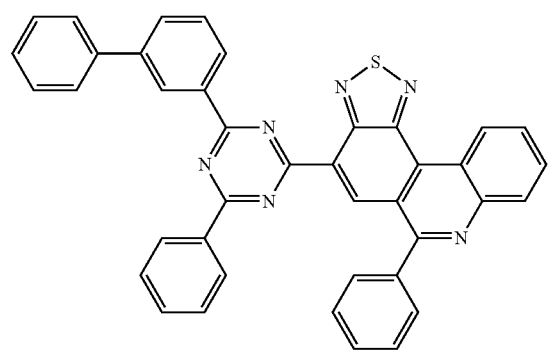
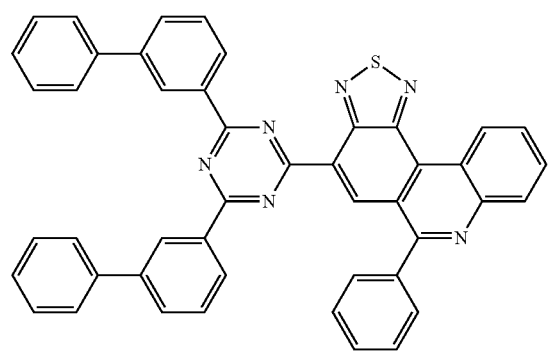
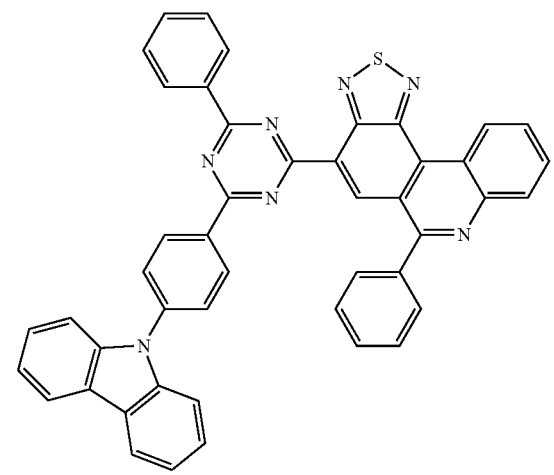

385
-continued
10
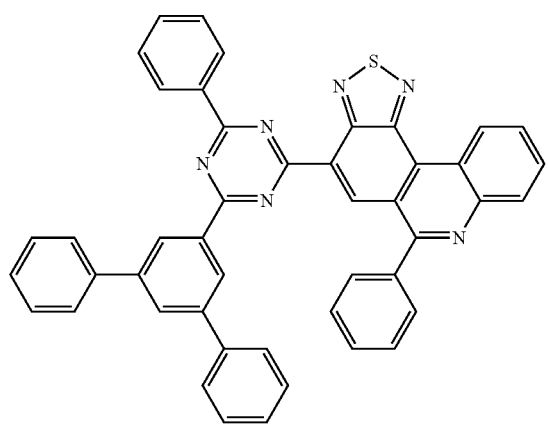
11
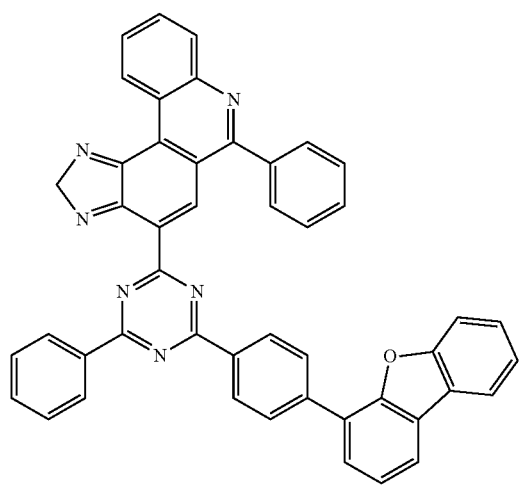
12
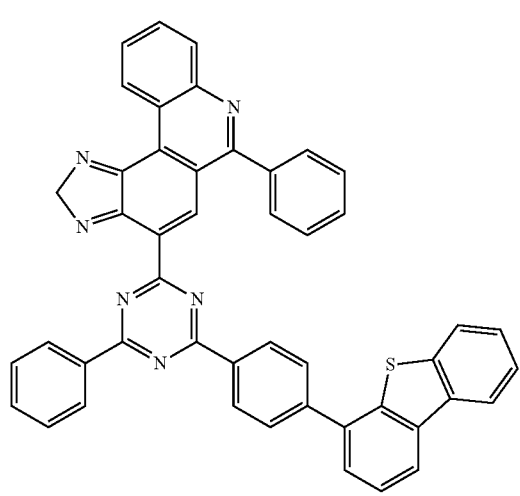
386
-continued
13
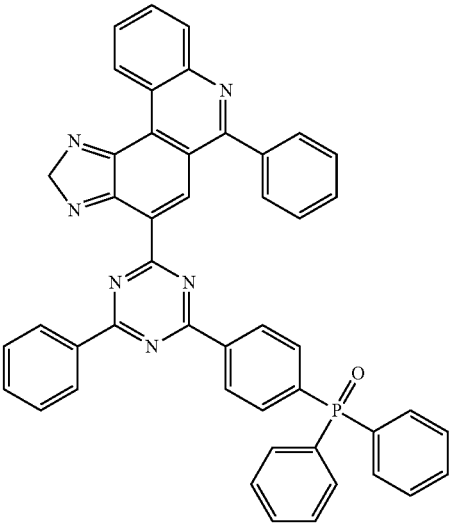
14
15

387
-continued
16
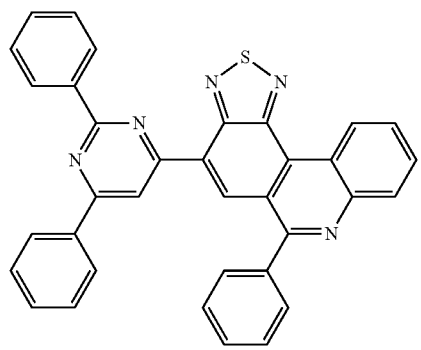
17
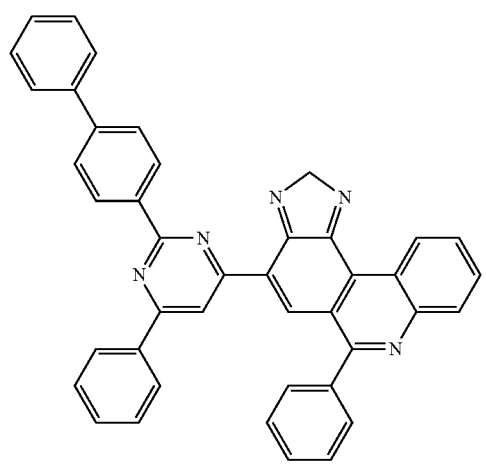
18
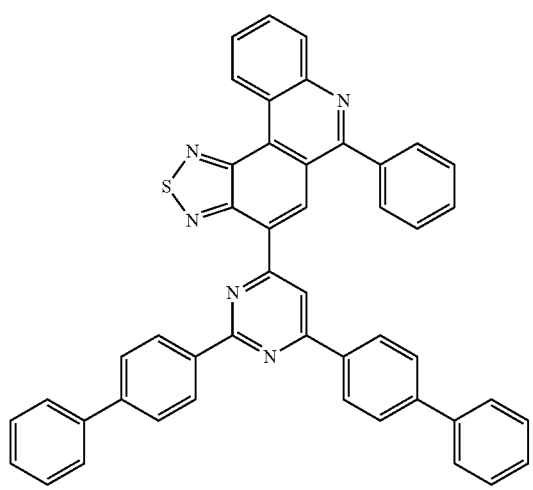
388
-continued
19
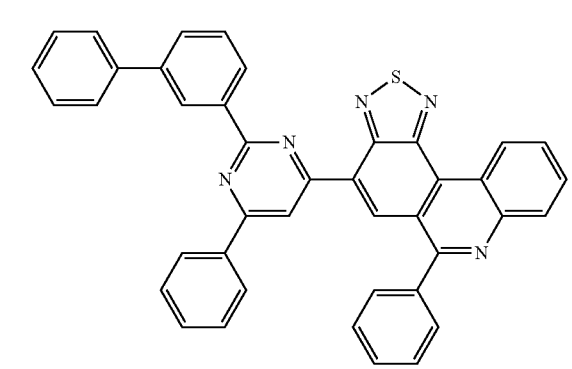
20
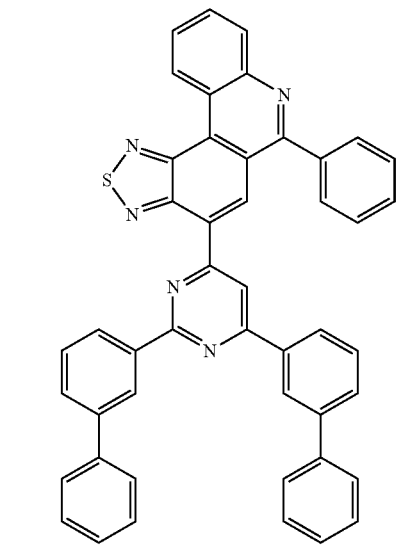
21
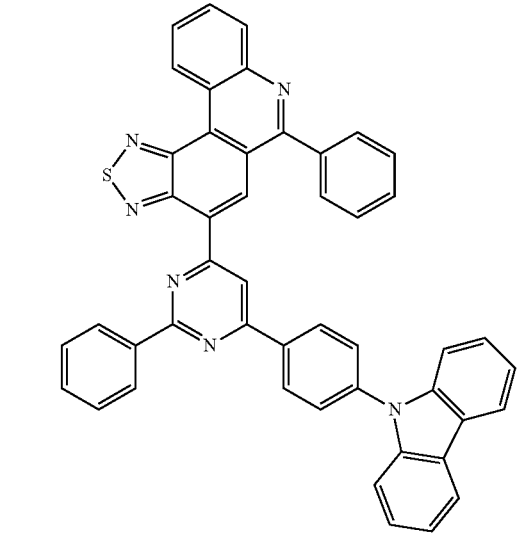

389
-continued
22
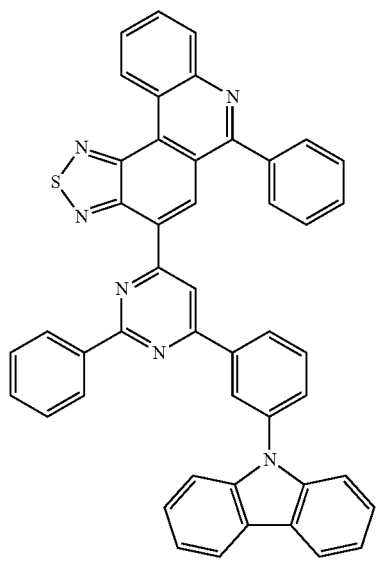
23
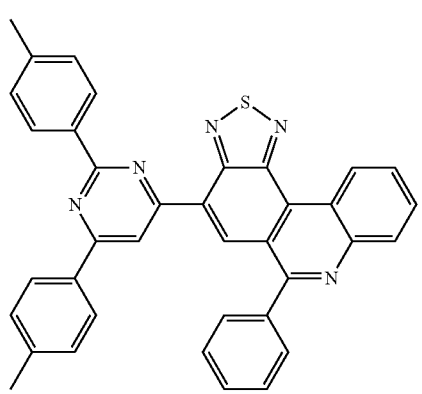
24
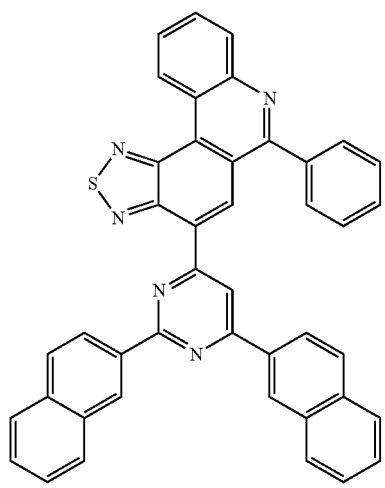
390
-continued
25
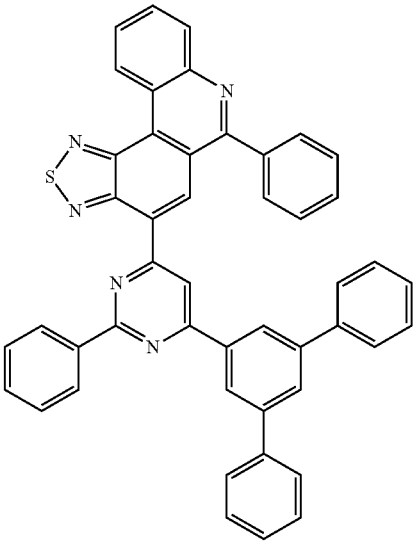
26
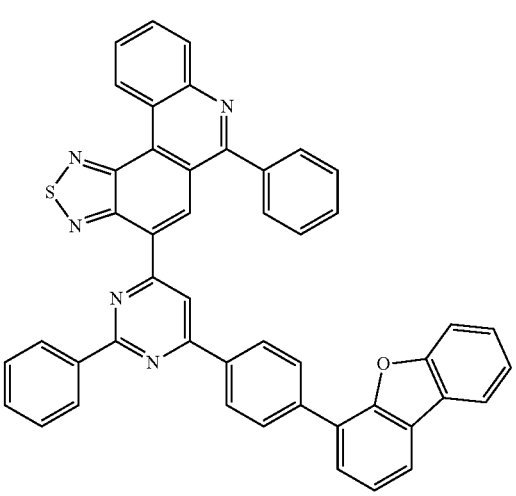
27
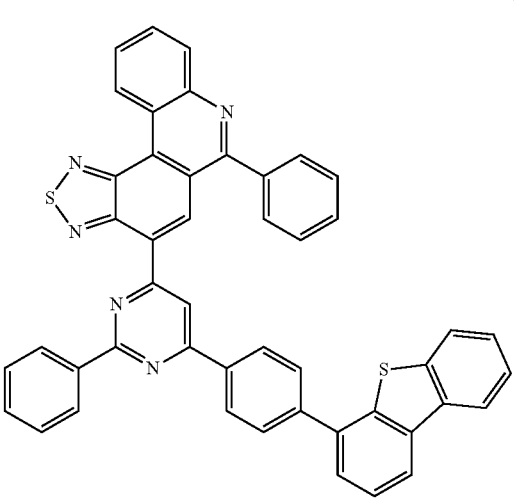

391
-continued
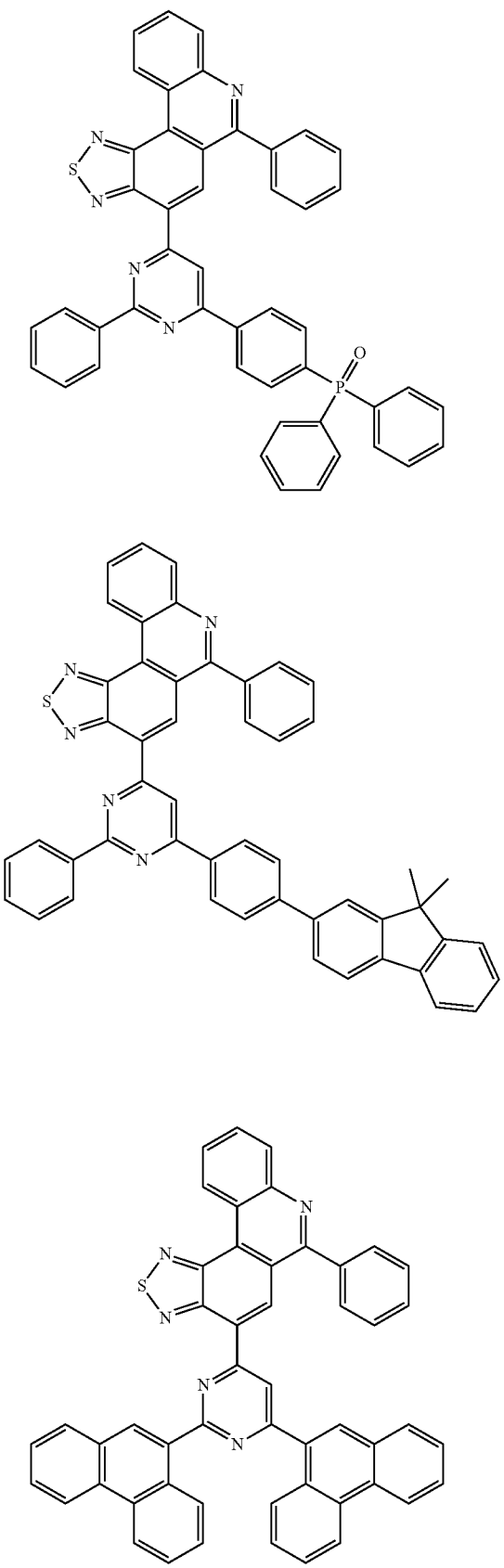
28
29
30
392
-continued
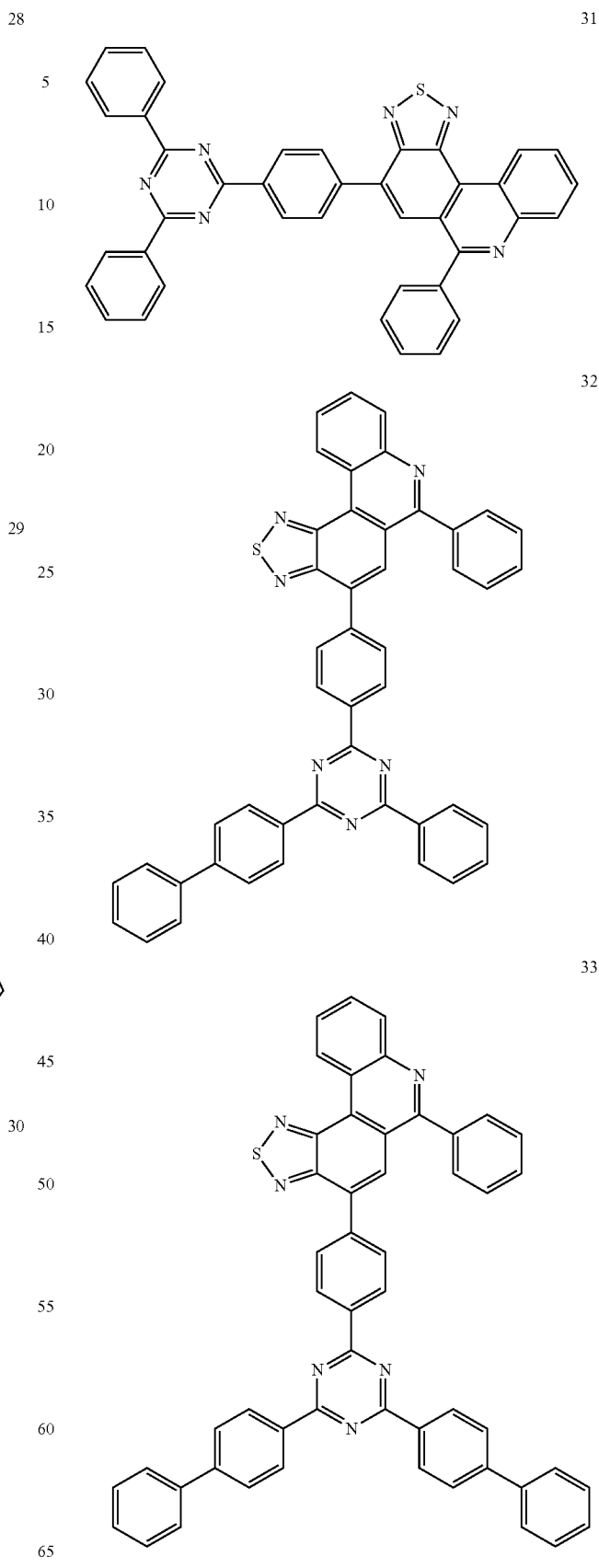
31
32
33

393
-continued
34
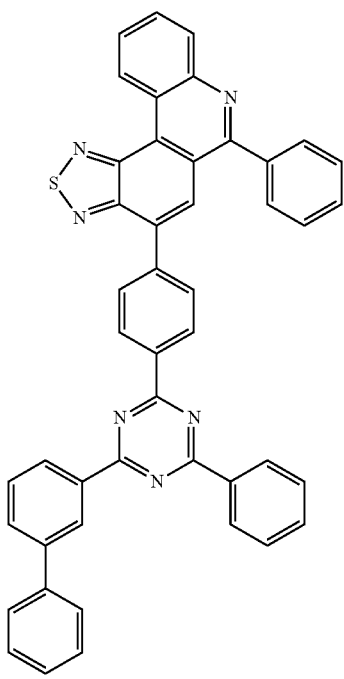
36
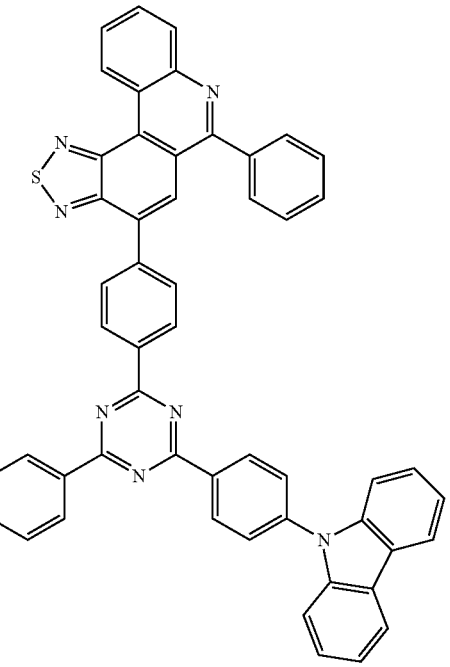
394
-continued
35
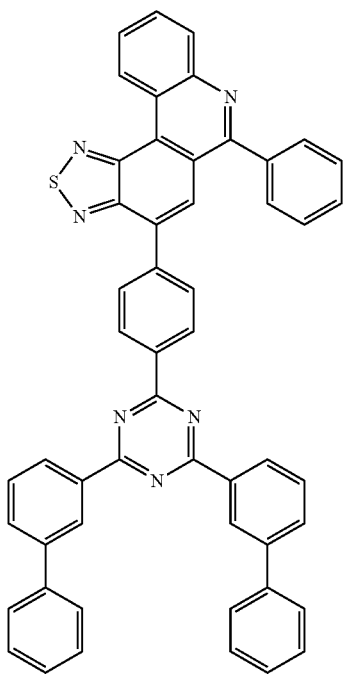
37
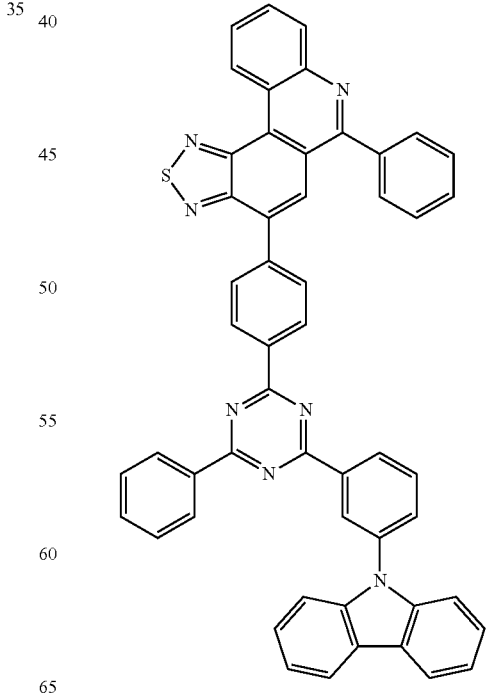

38
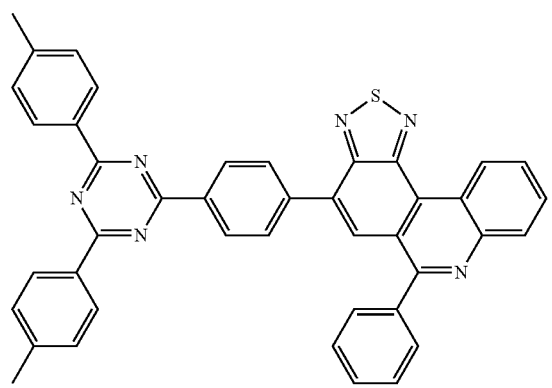
40
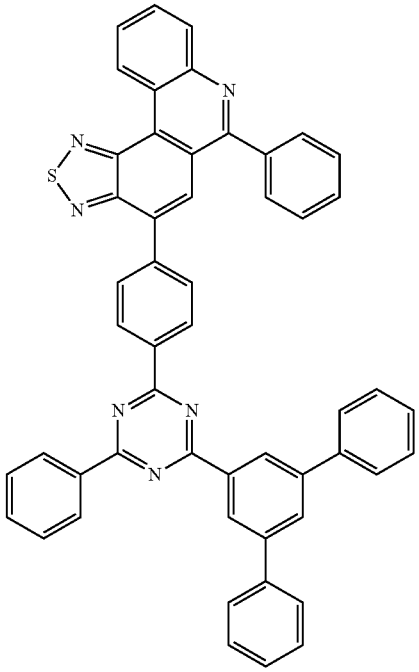
39
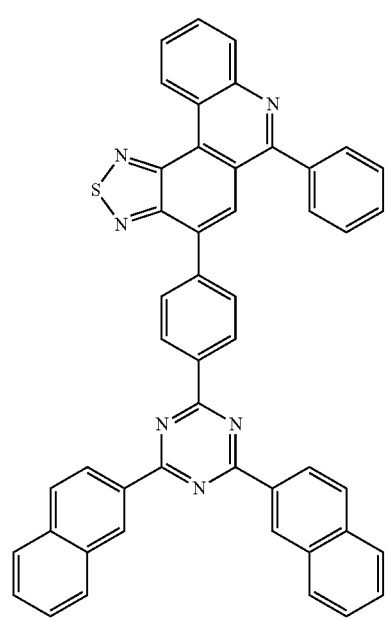
41
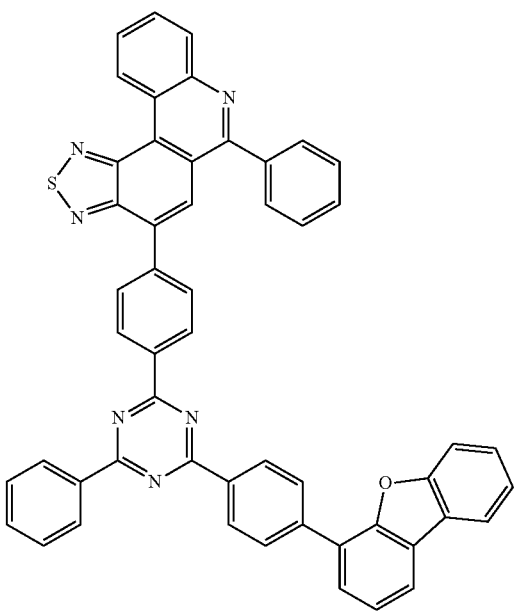

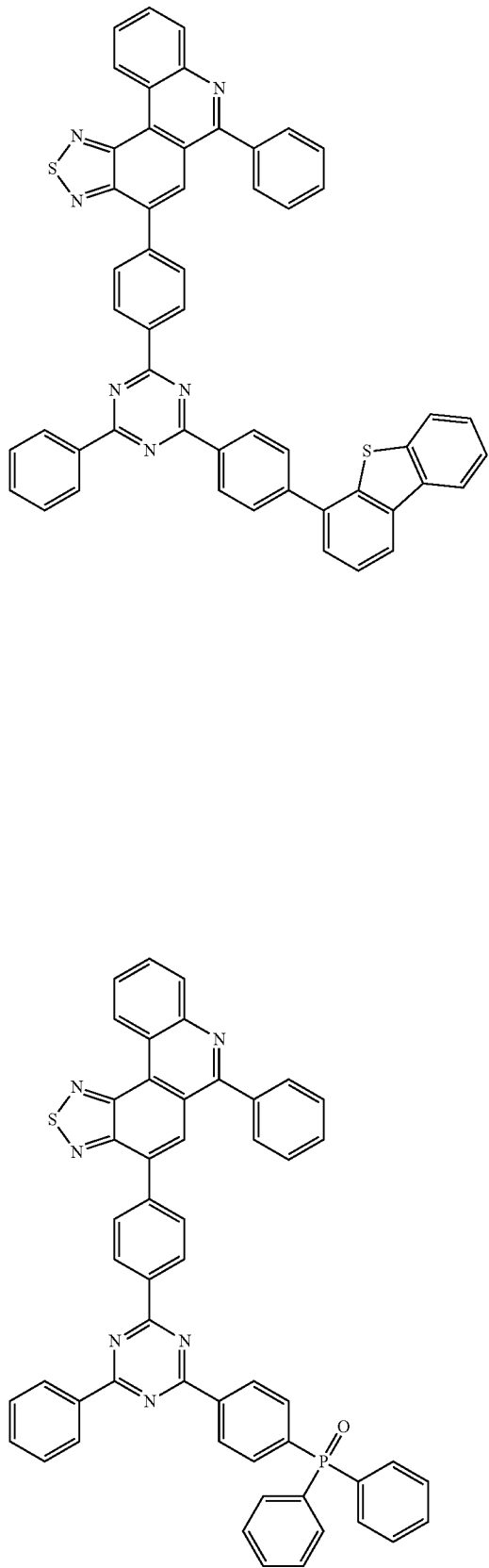
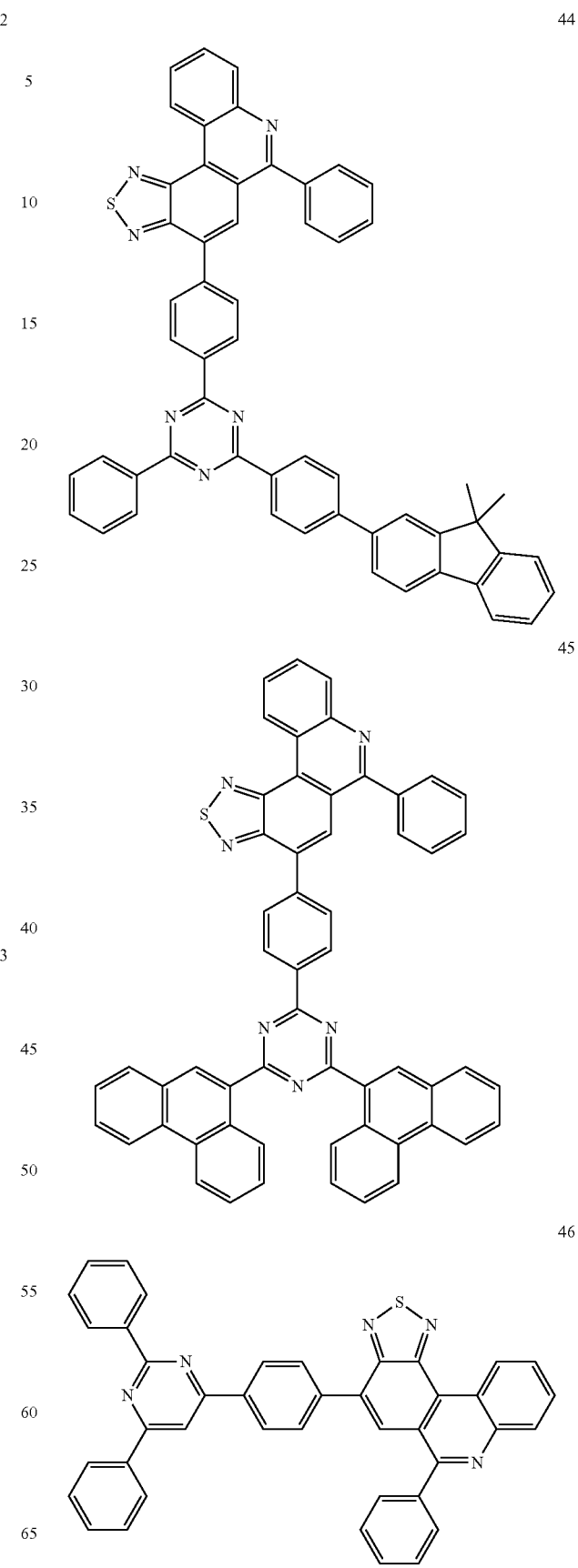

399
-continued
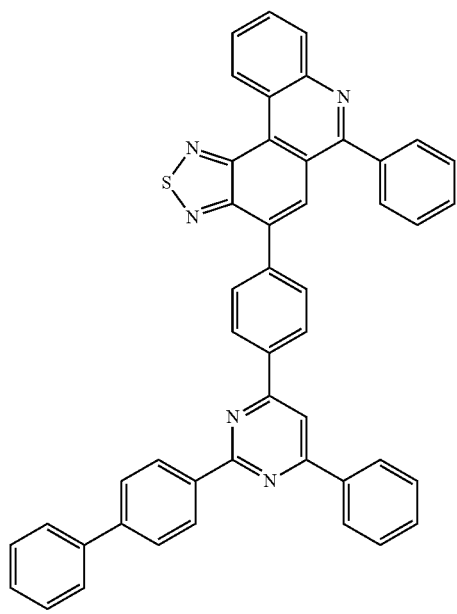
47
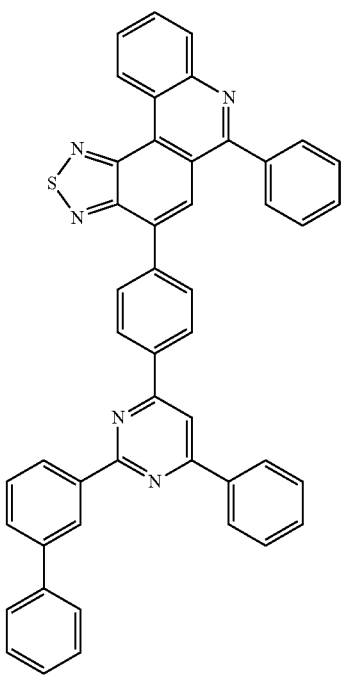
49
48
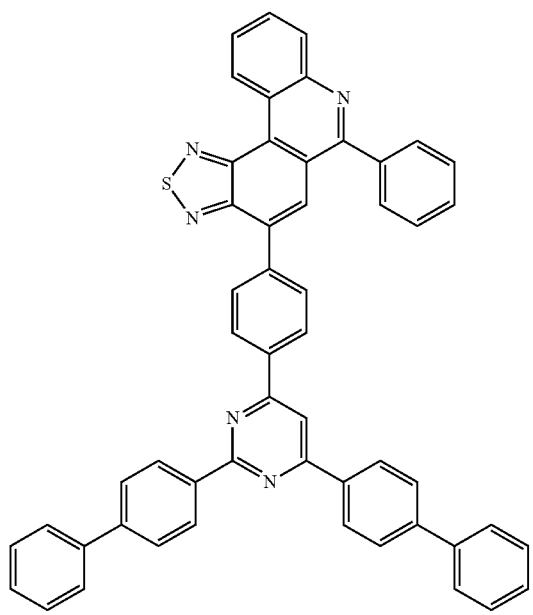
400
-continued
50
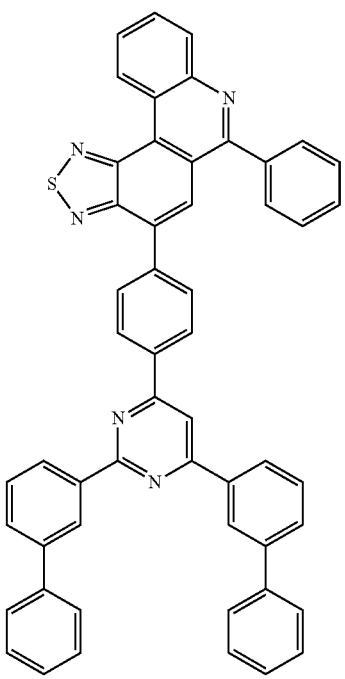

51
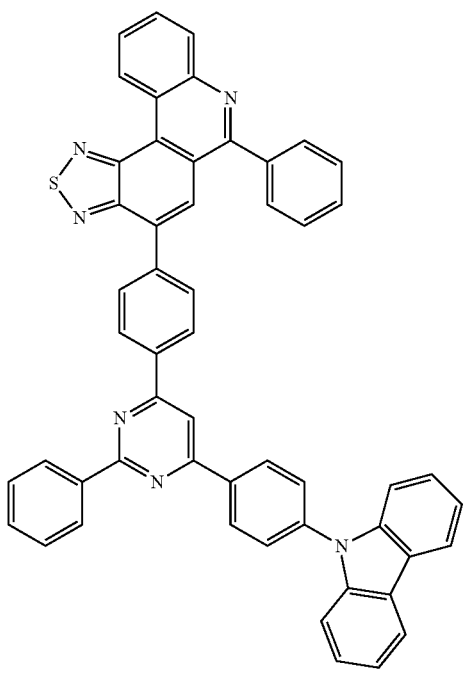
52
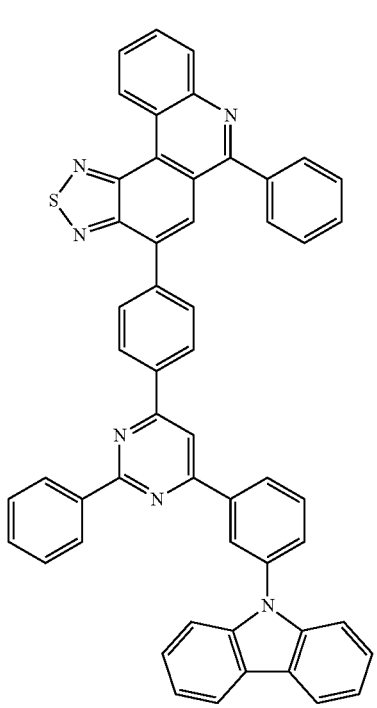
53
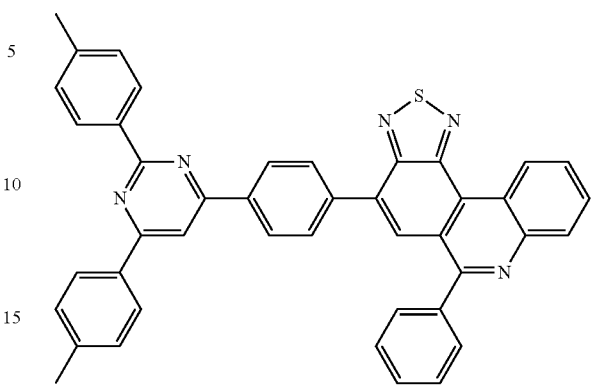
54
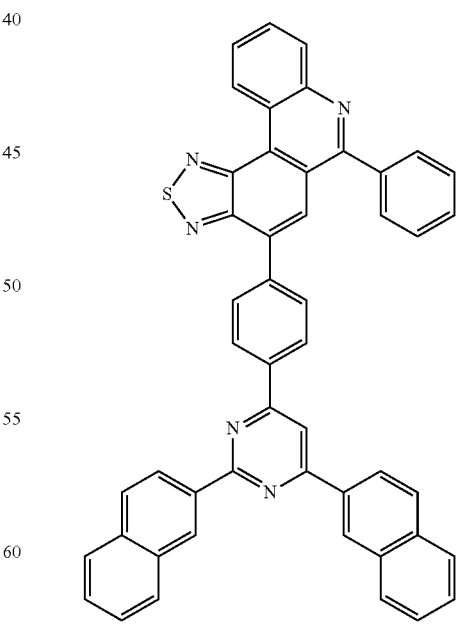

403
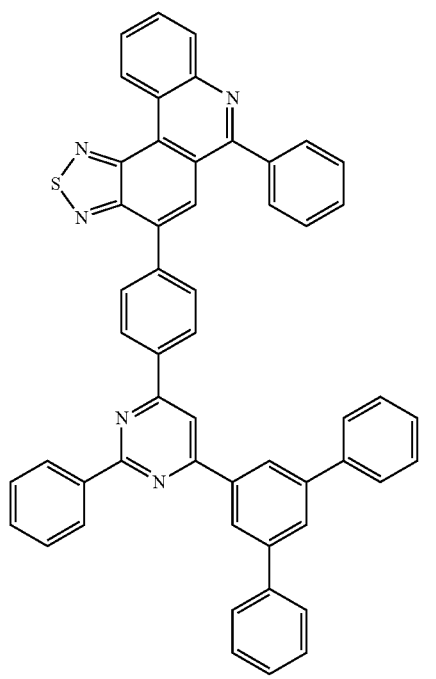
56
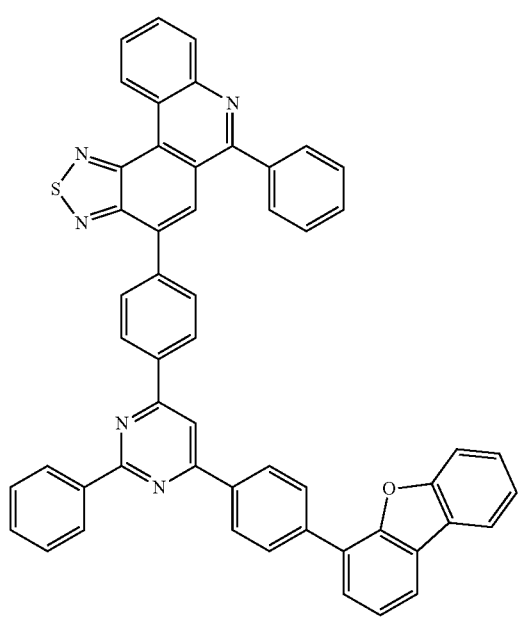
404
57
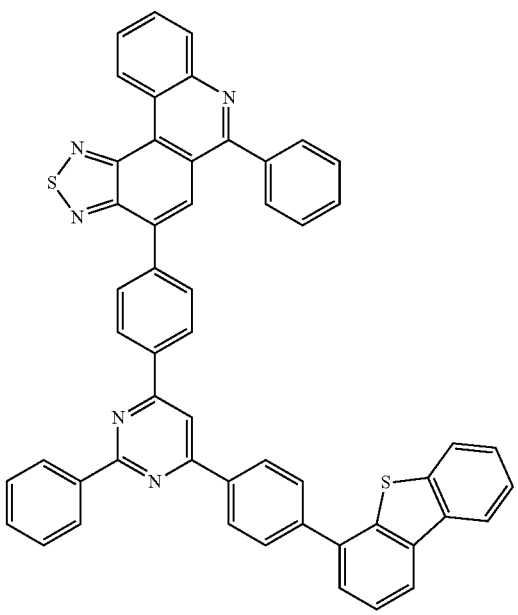
58
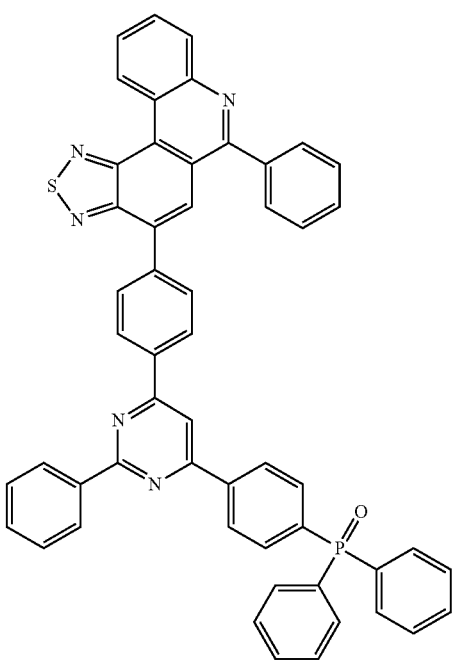

59
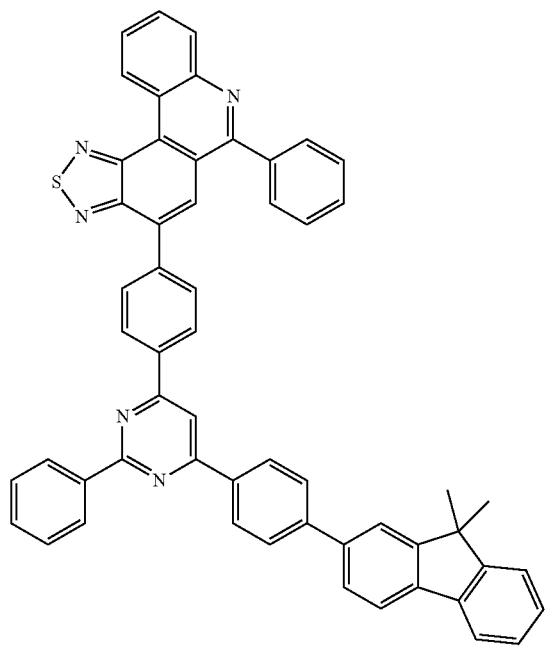
60
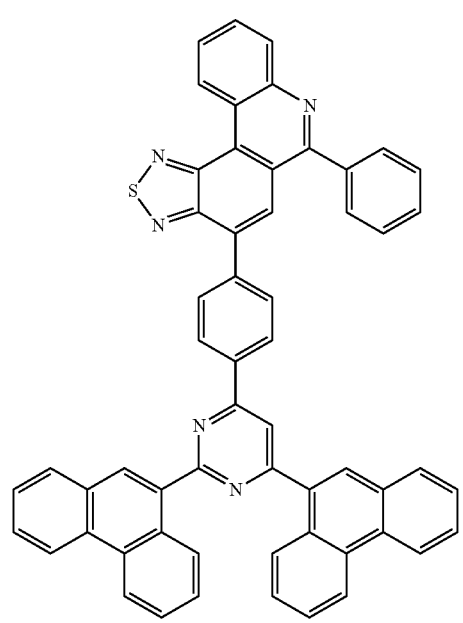
61
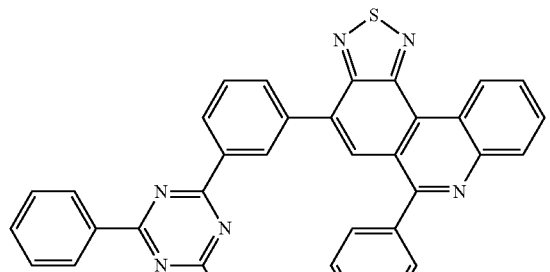
62
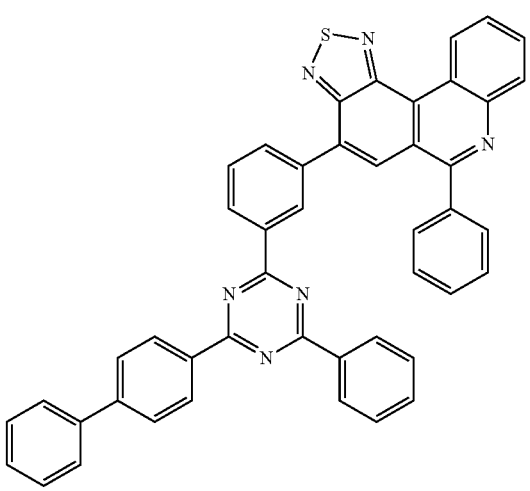
63
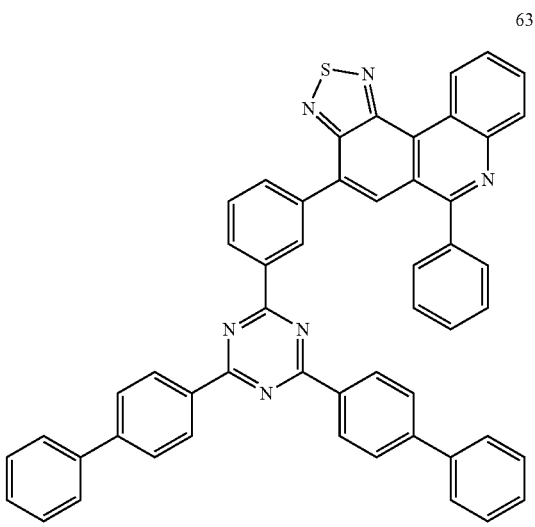

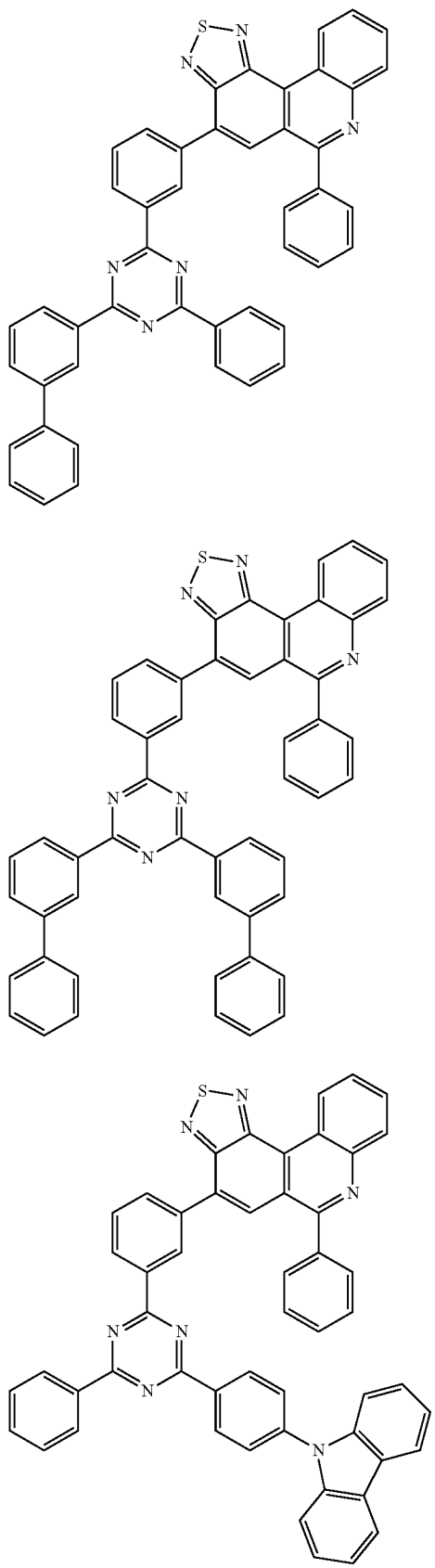
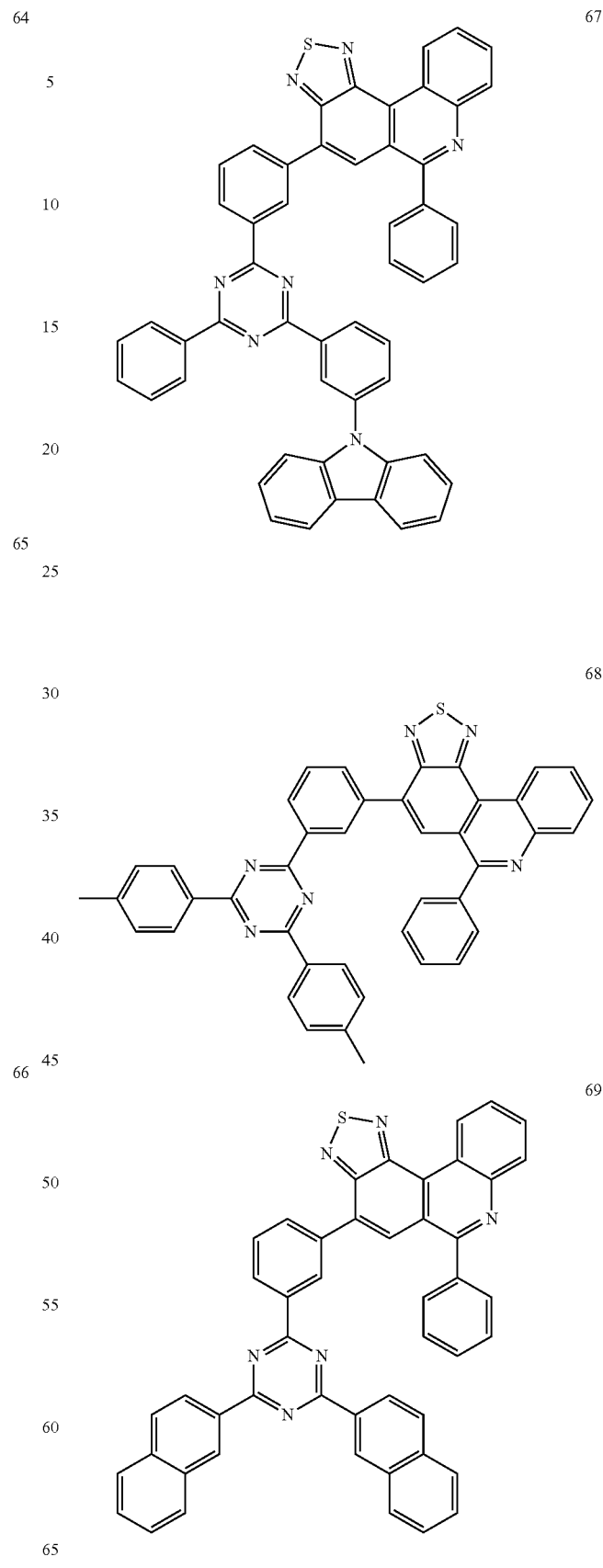

409
-continued
410
-continued
70
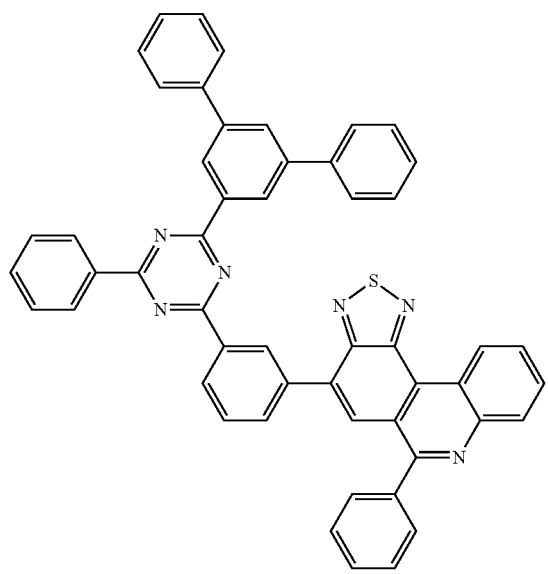
71
73
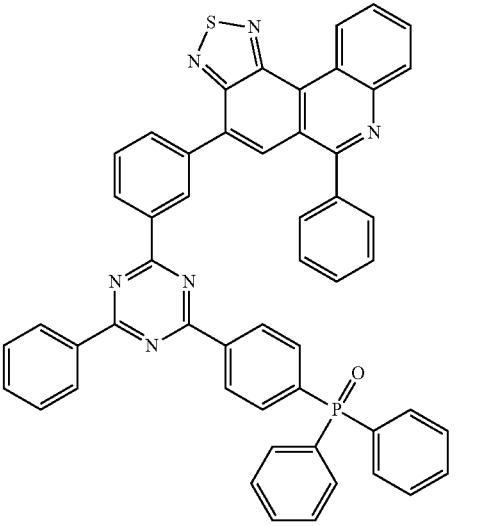
74
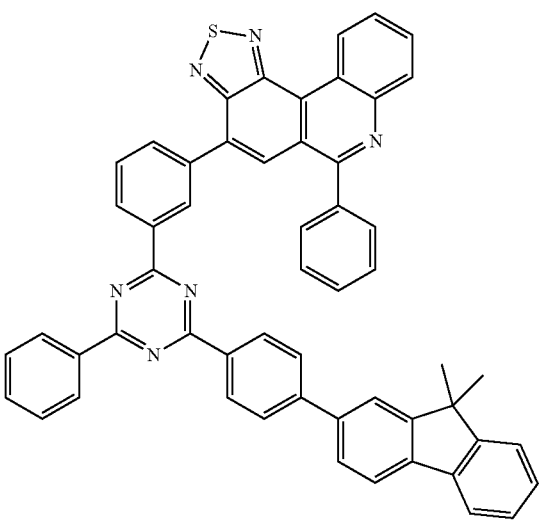
72
75
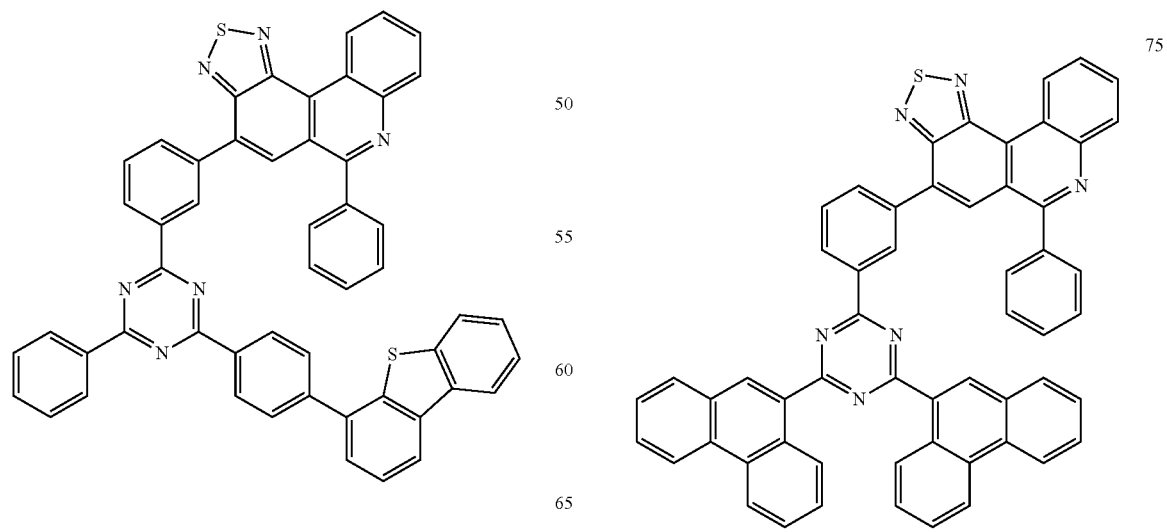

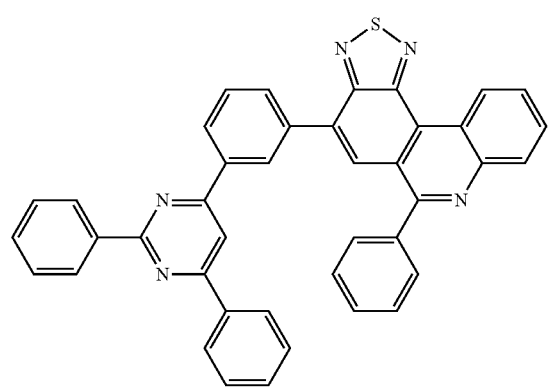
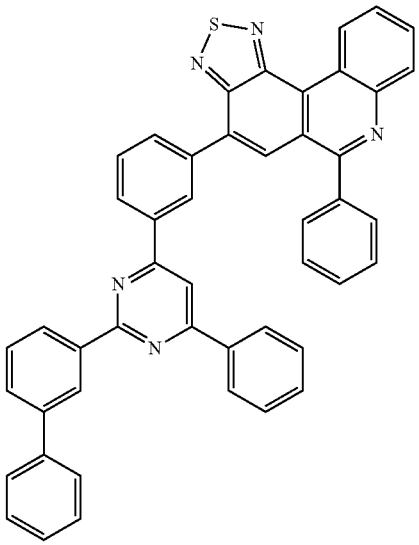

82
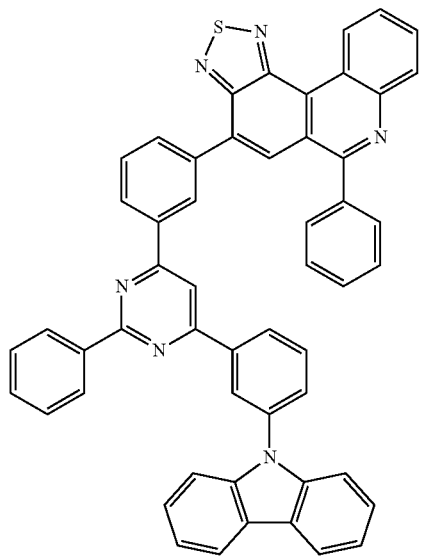
83
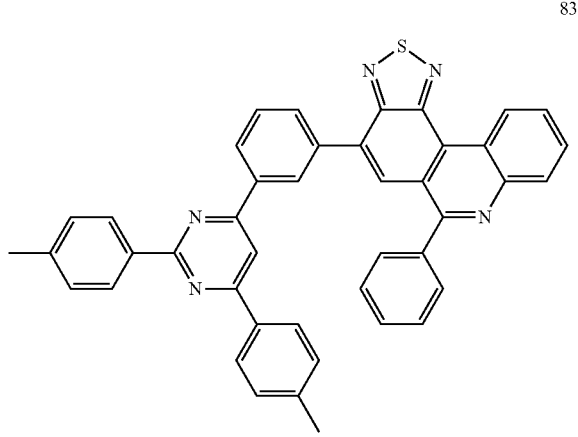
84
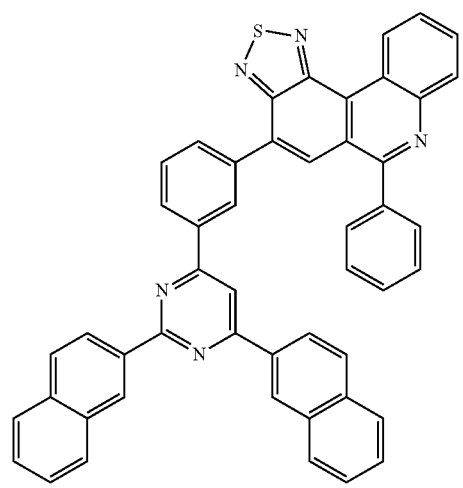
85
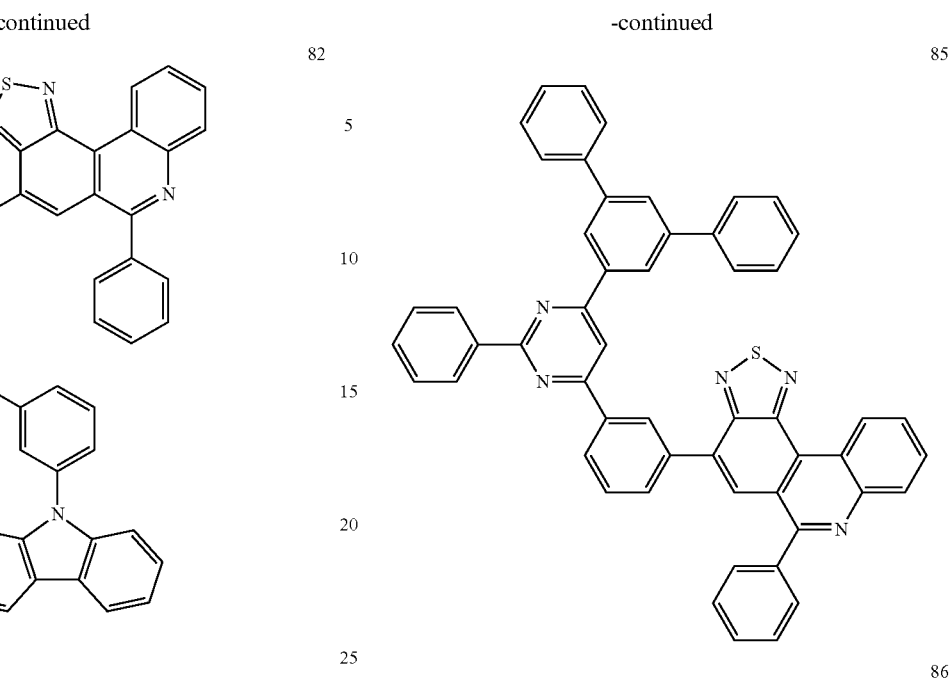
86
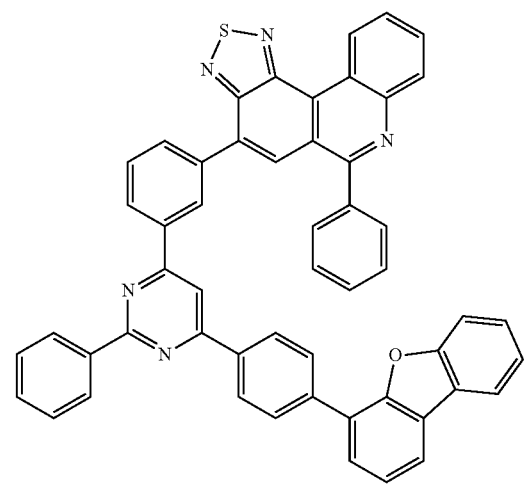
87
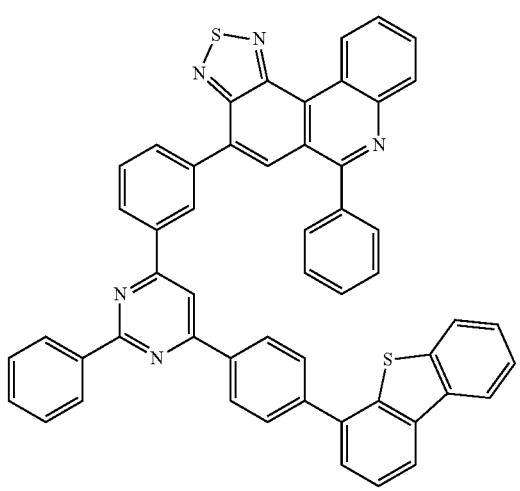

88
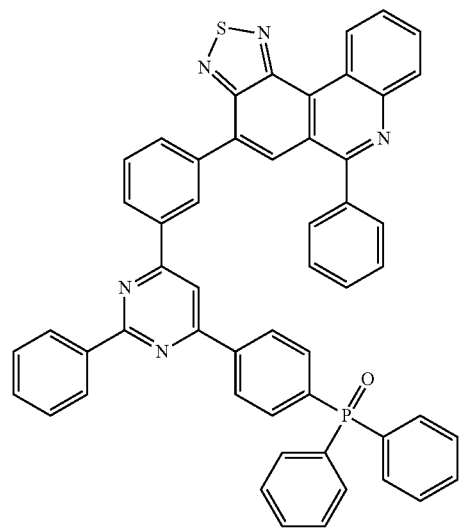
89
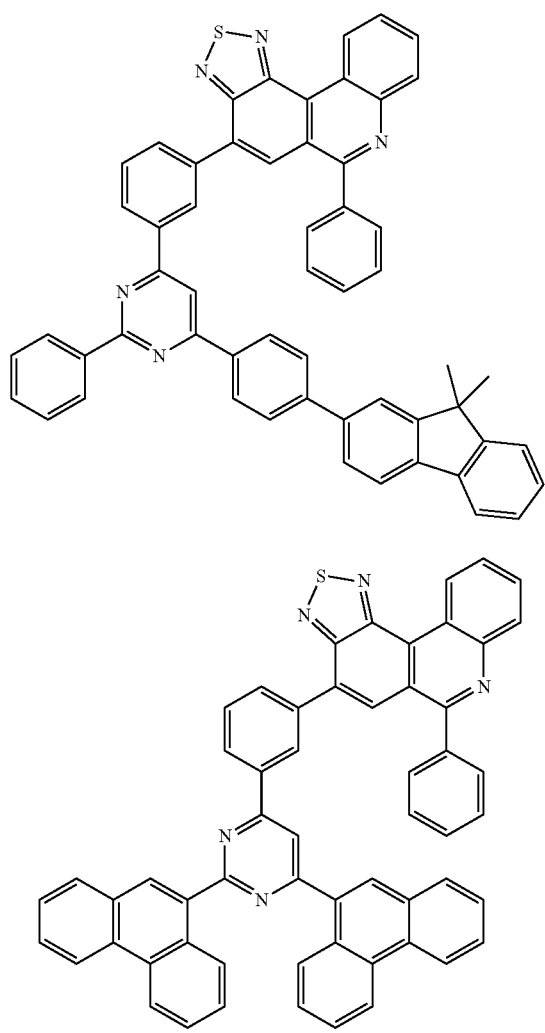
90
91
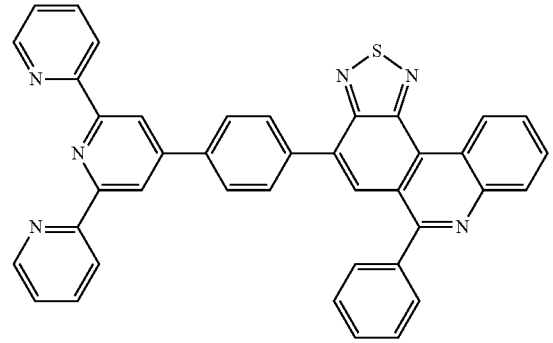
92
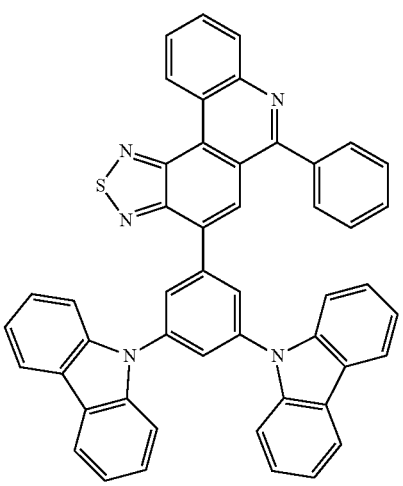
93
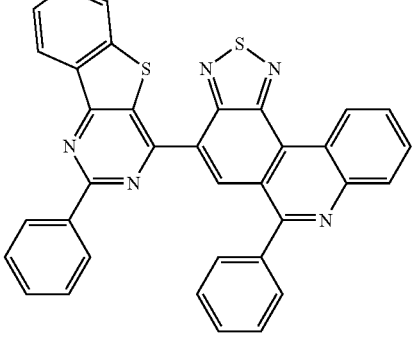
94
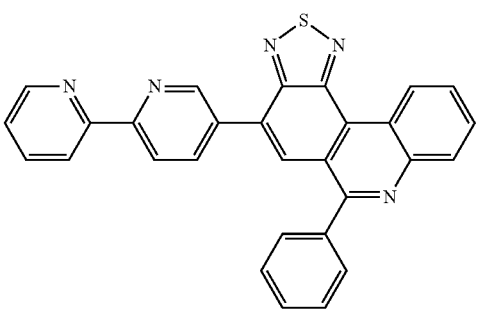

95
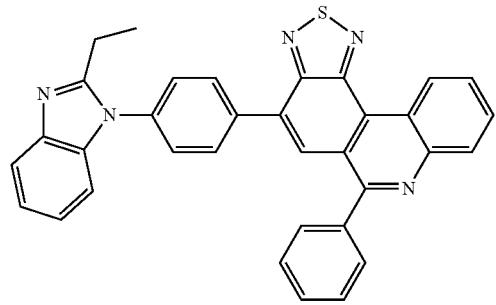
96
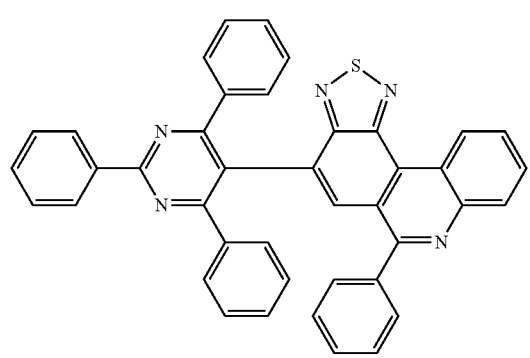
97
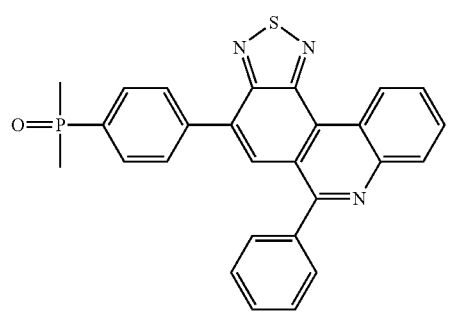
98
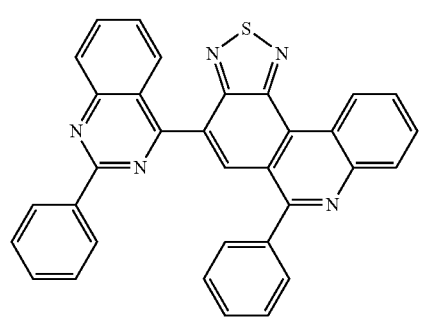
99
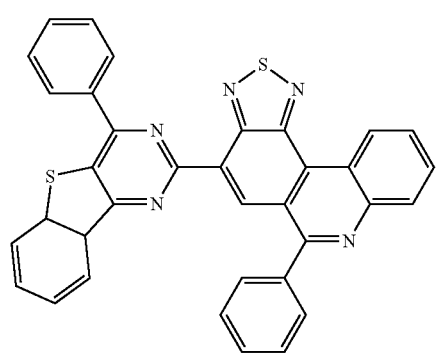
100
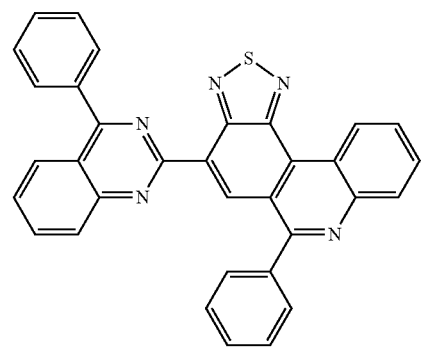
101
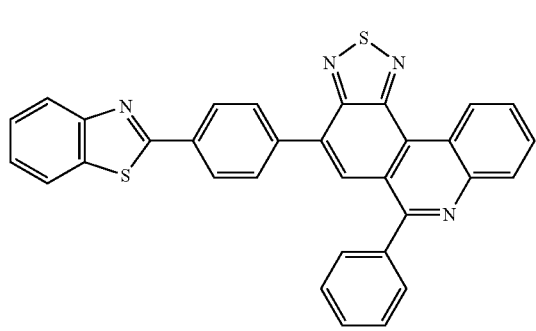
102
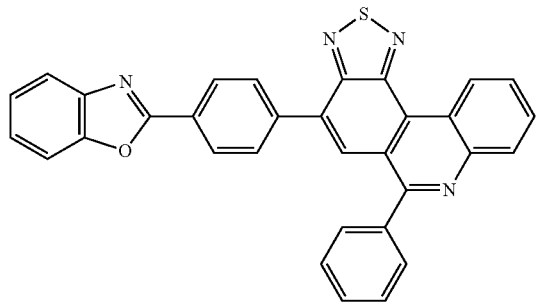
103
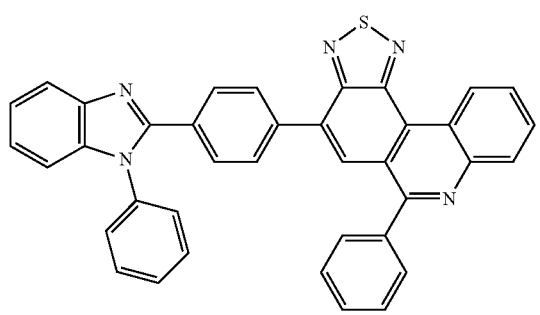

-continued
104
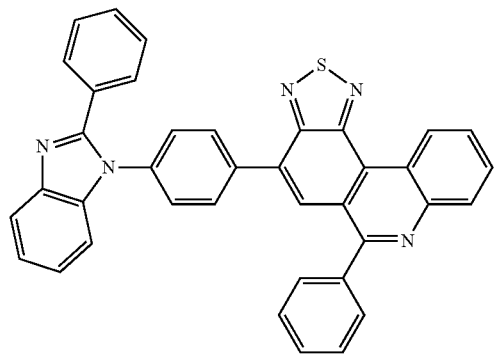
105
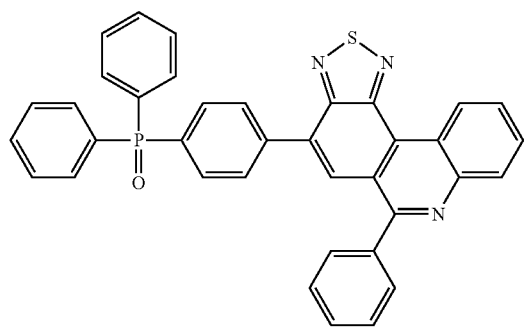
106
107
-continued
108
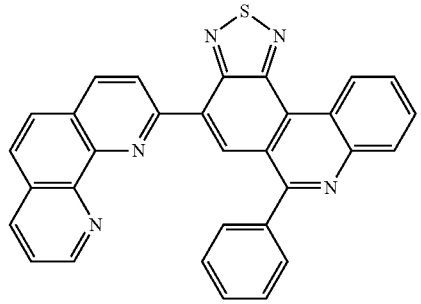
109
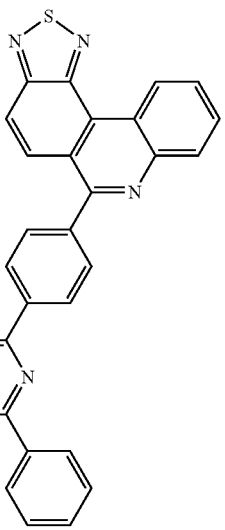
110
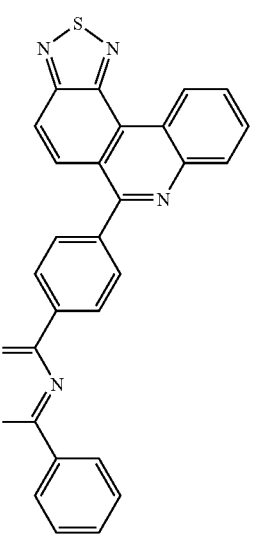

-continued
111
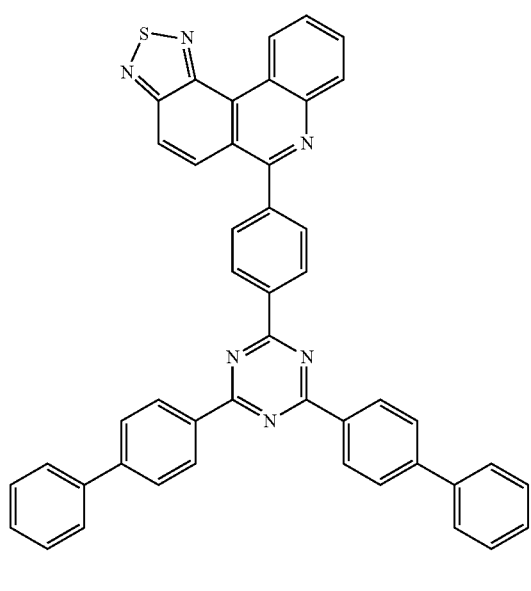
112
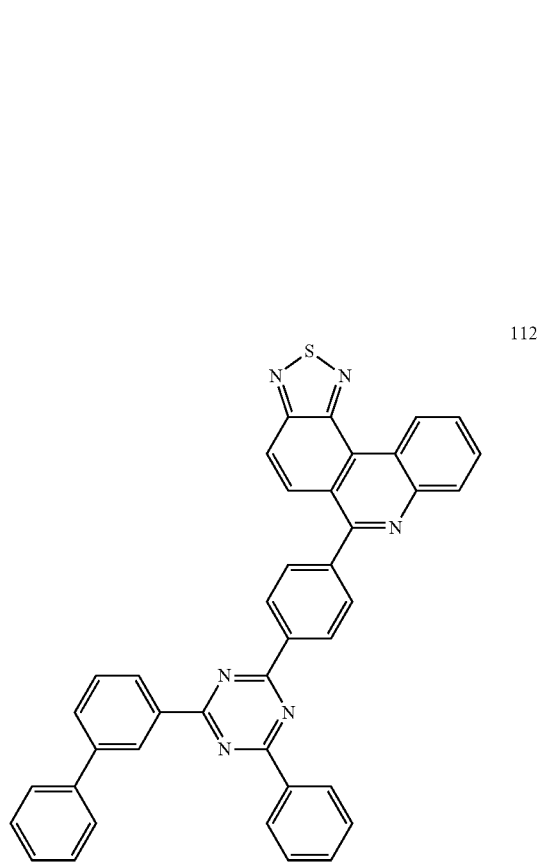
-continued
113
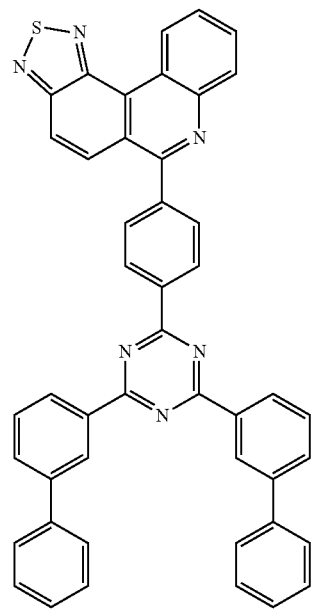
114
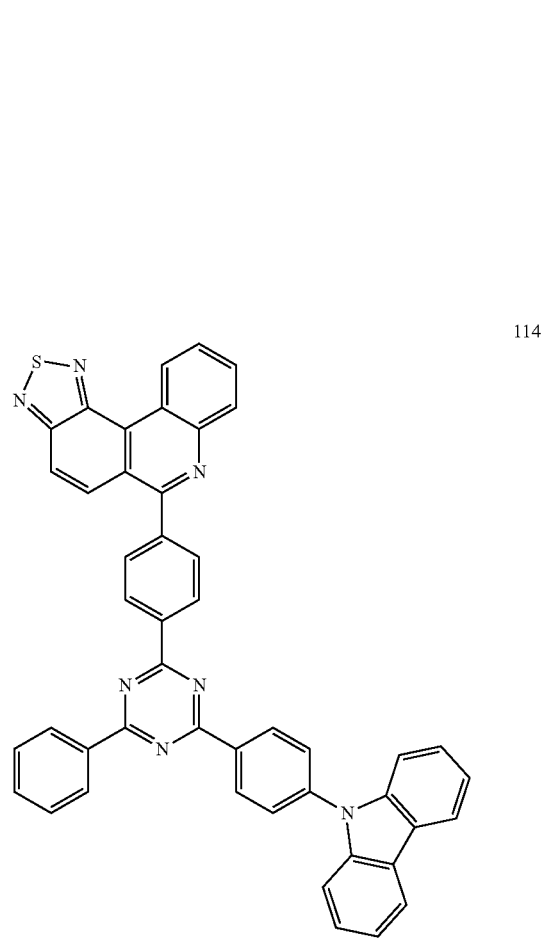

423
-continued
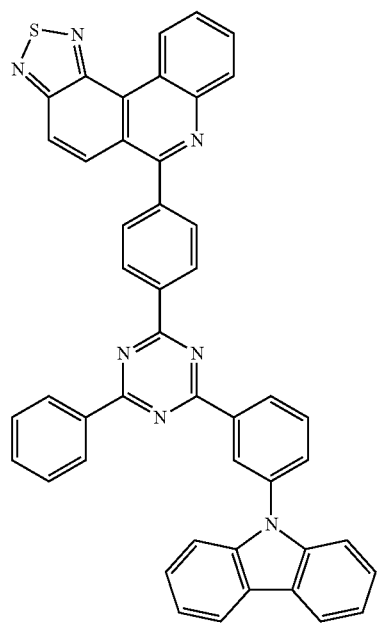
115
424
-continued
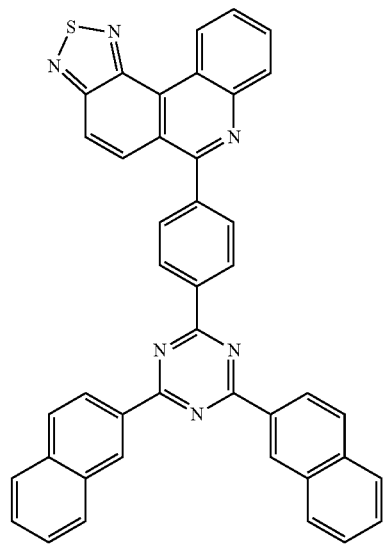
117
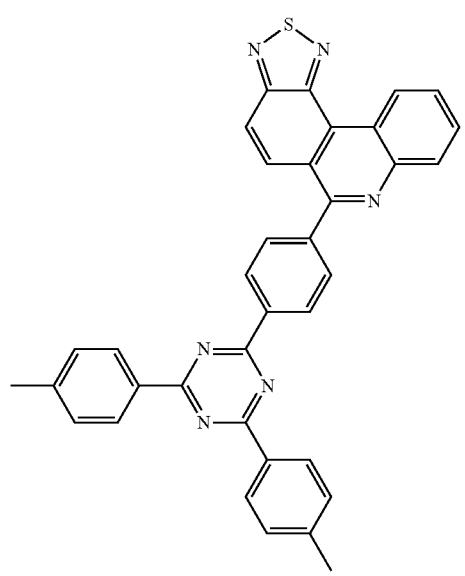
116
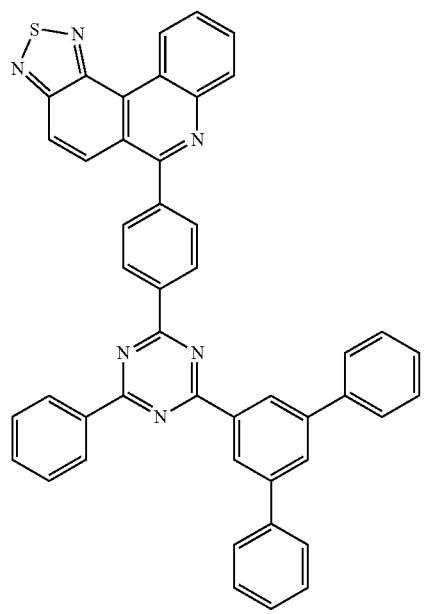
118

119
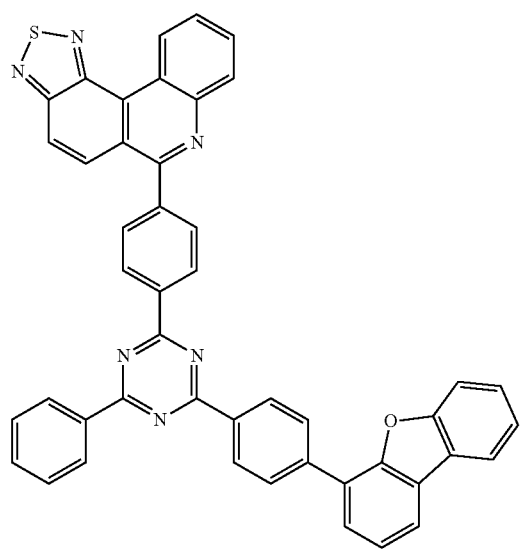
121
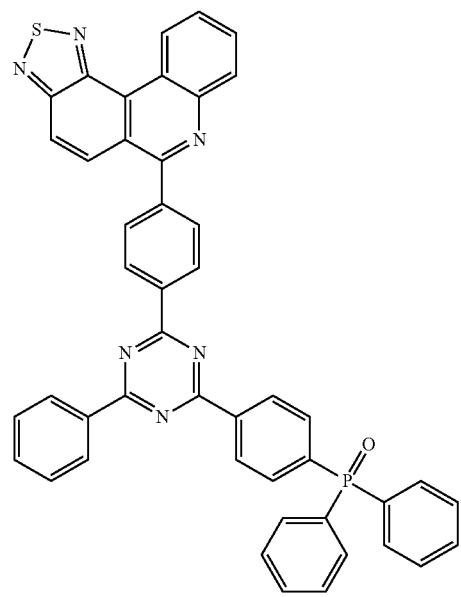
120
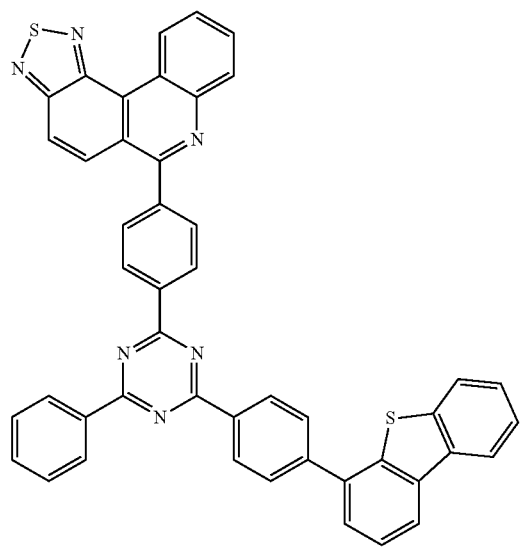
122
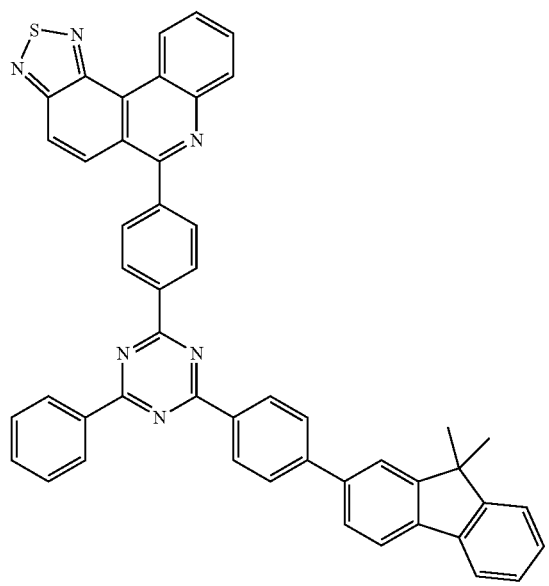

427
-continued
428
-continued
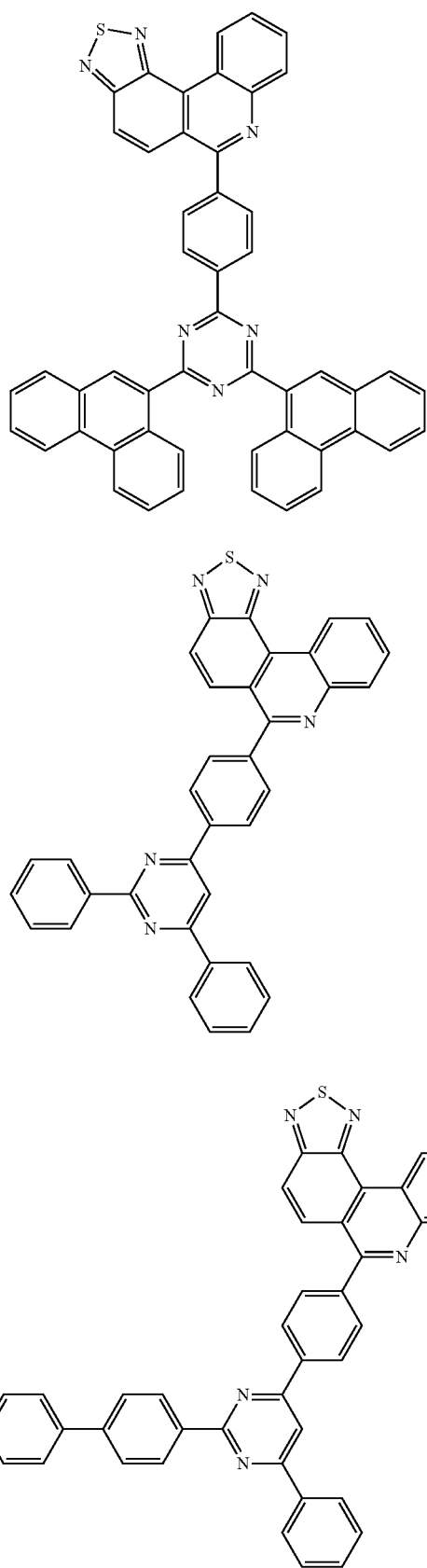
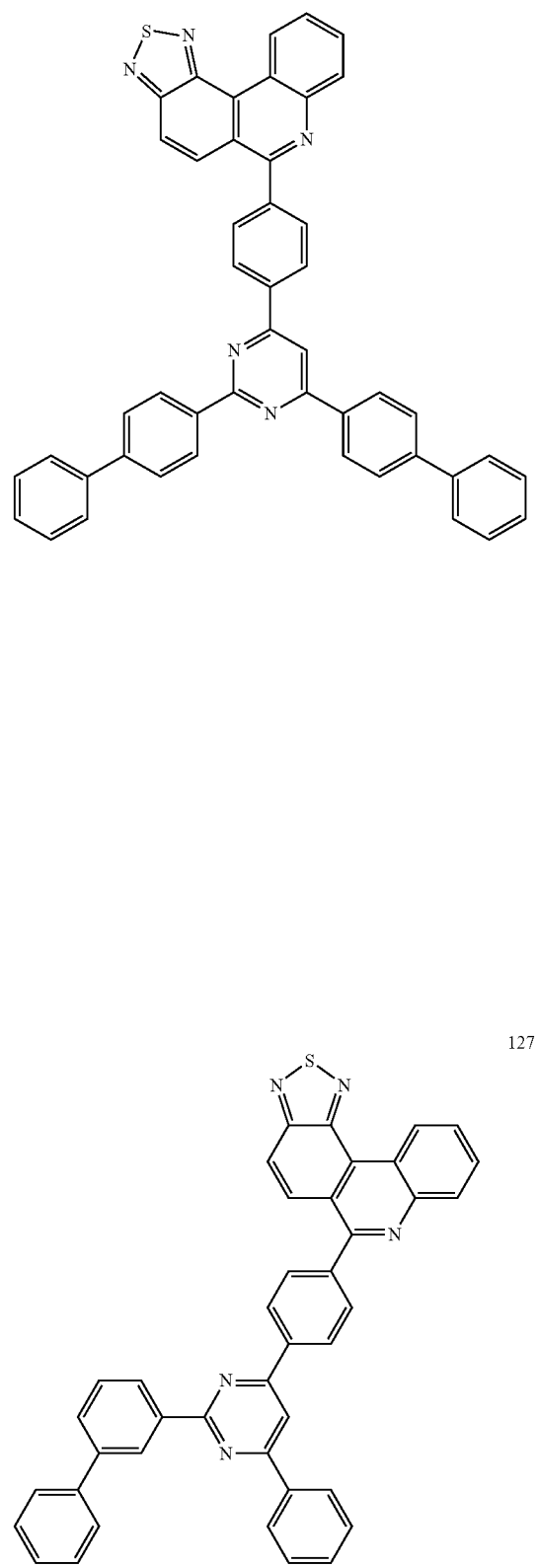

429
-continued
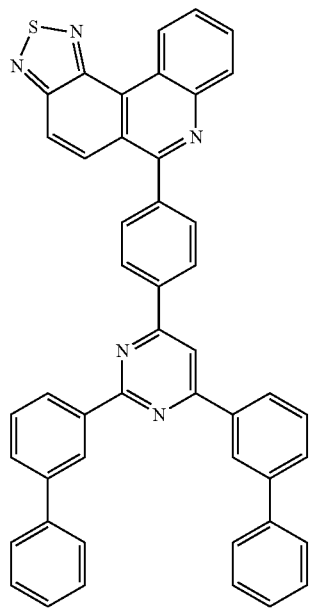
128
430
-continued
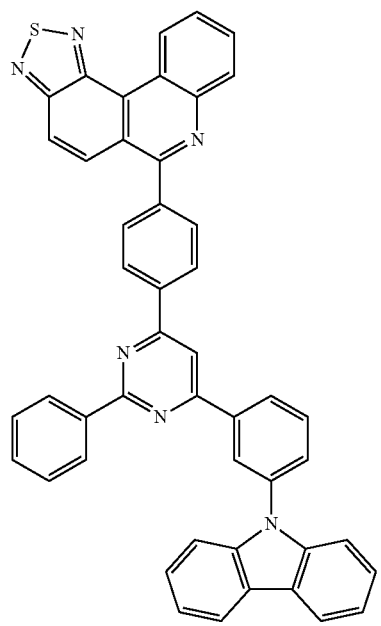
130
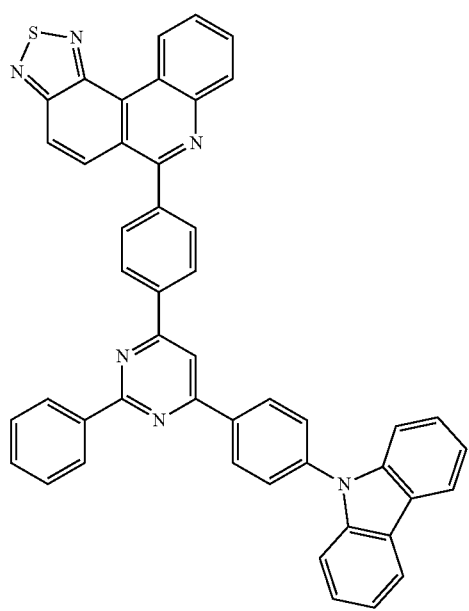
129
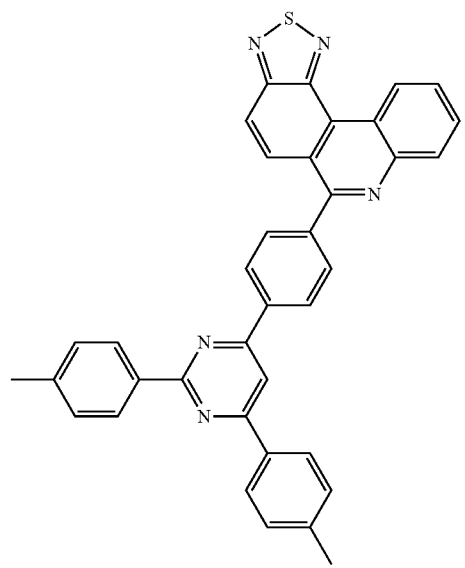
131

431
-continued
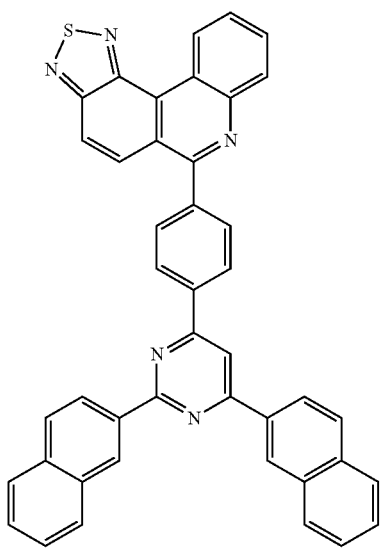
132
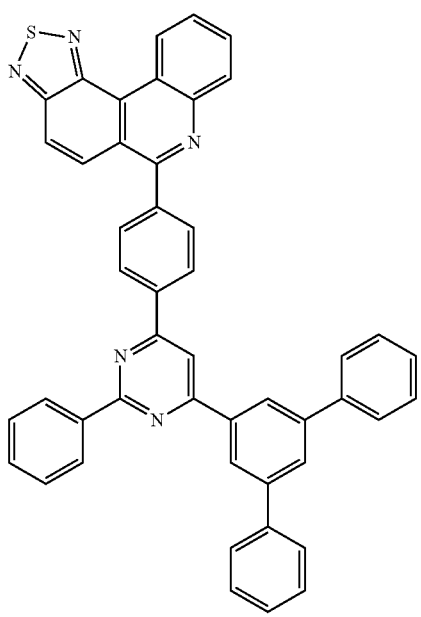
133
432
-continued
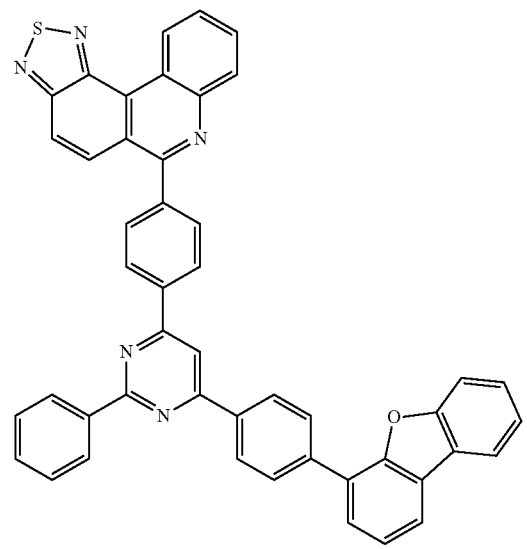
134
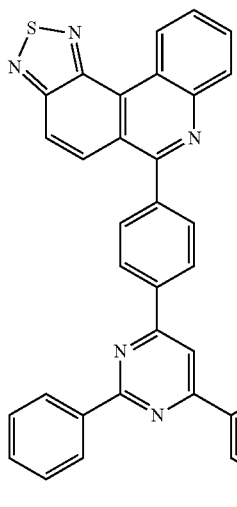
135

433
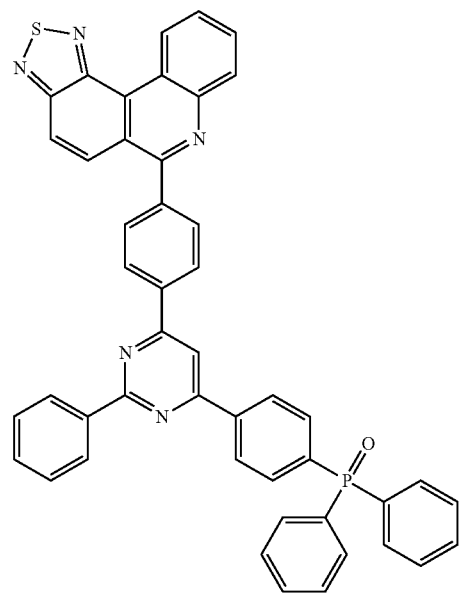
136
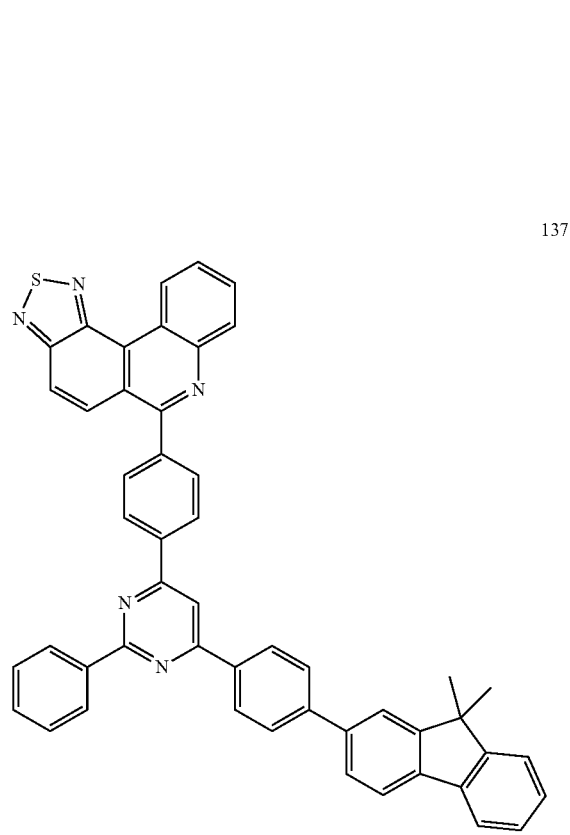
137
434
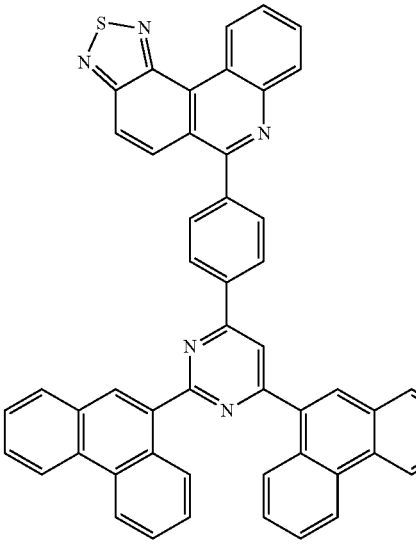
138
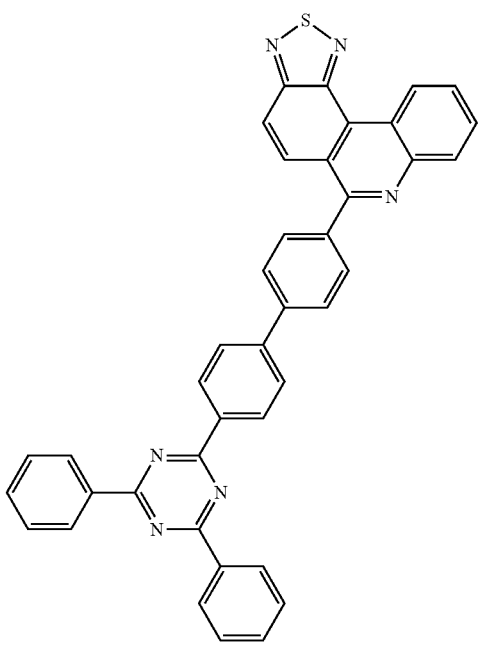
139

435
-continued
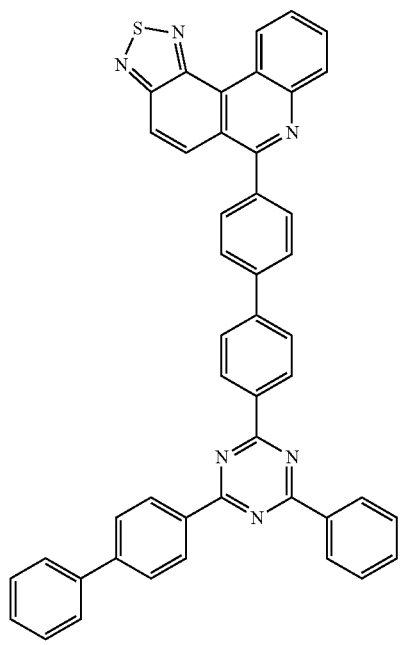
140
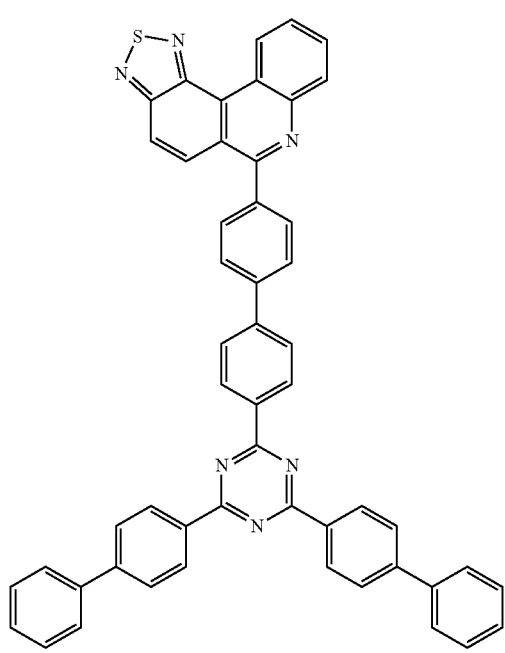
141
436
-continued
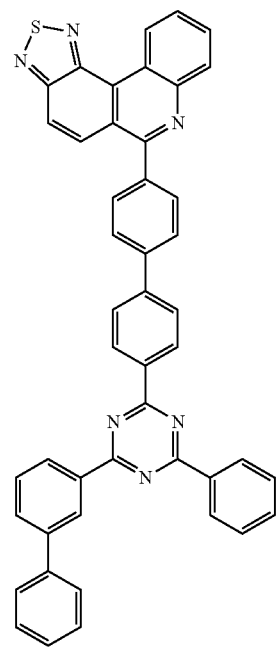
142
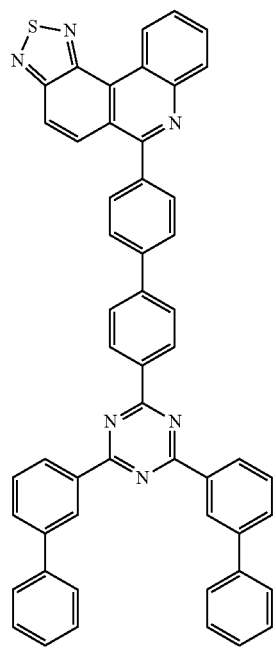
143

144
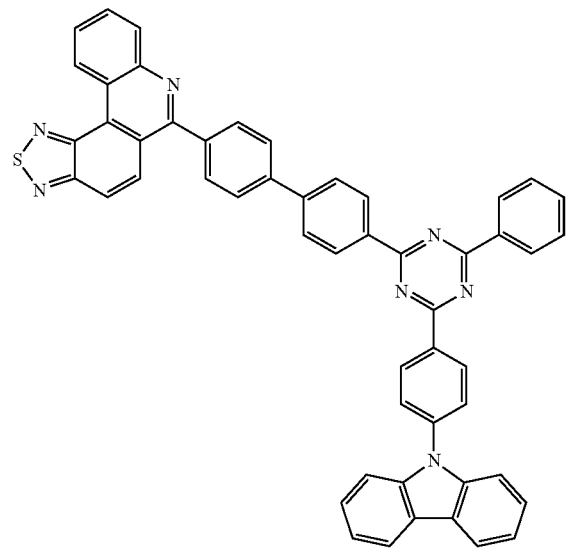
145
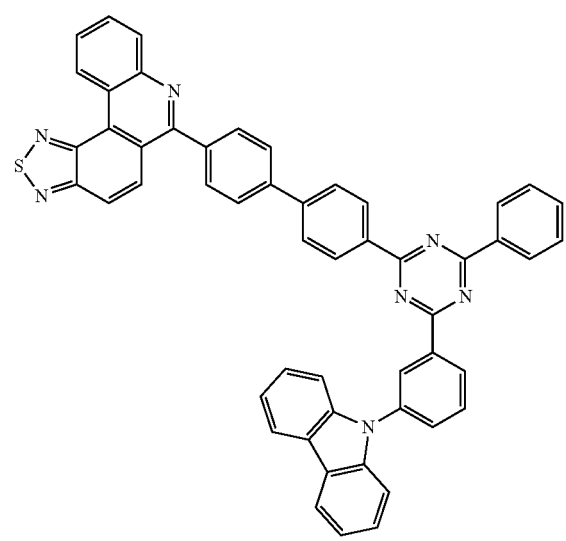
146
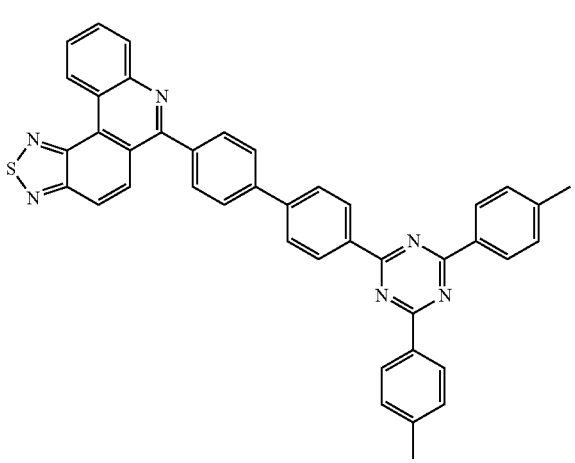
147
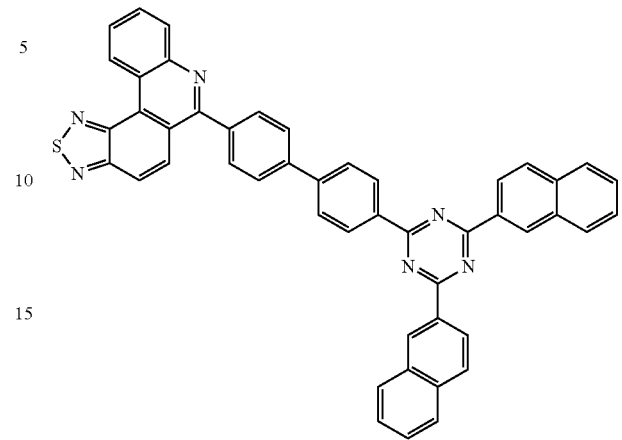
148
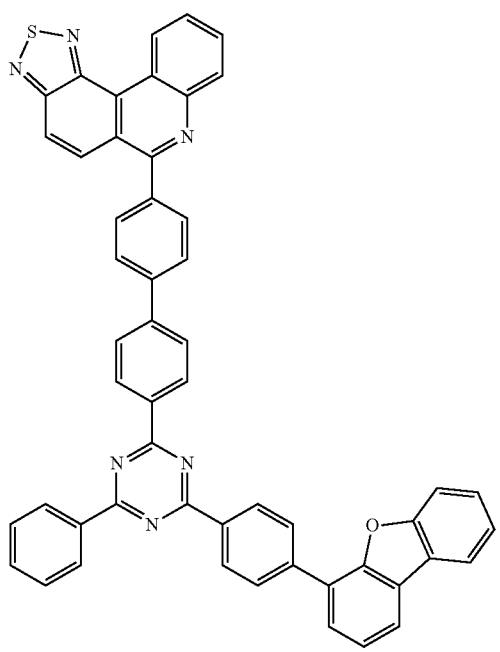
149

150
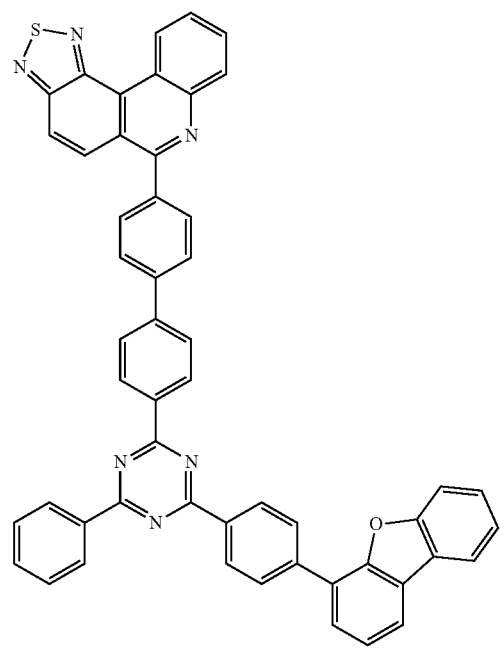
151
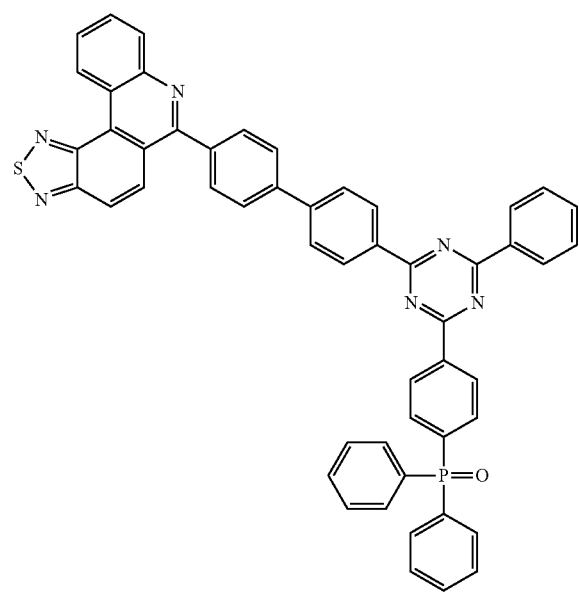
152
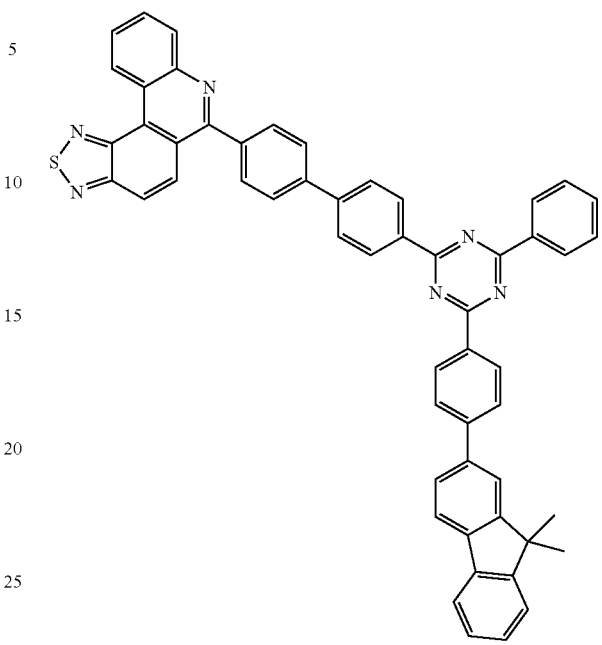
153
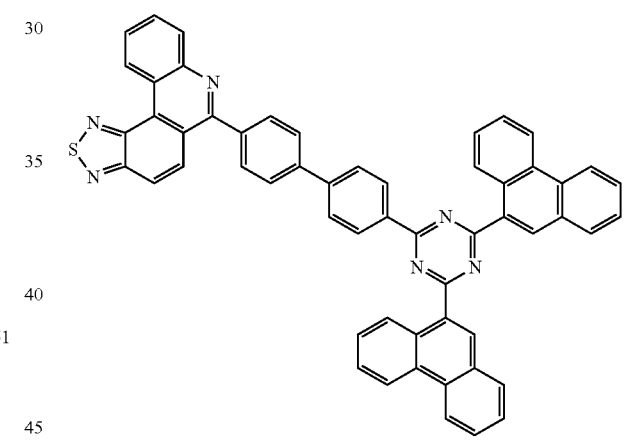
154
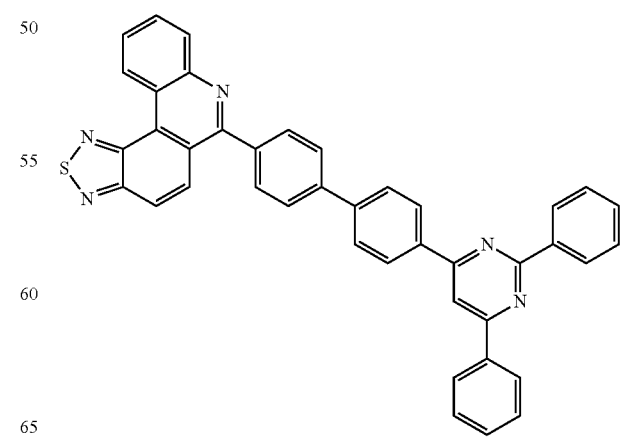

155
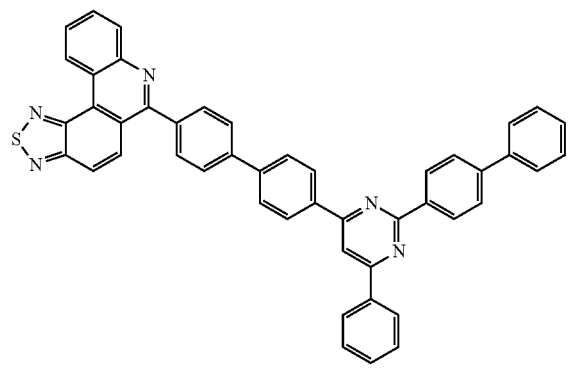
158
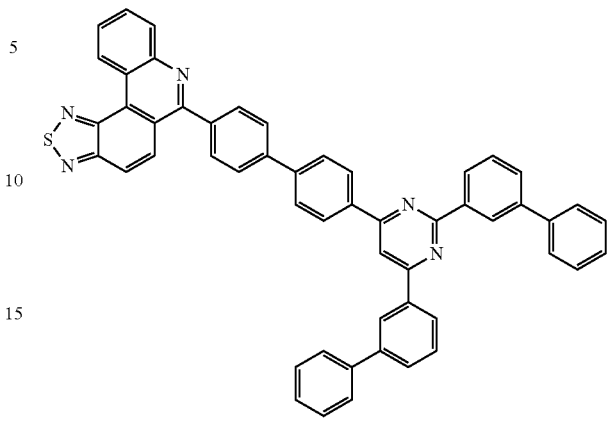
156
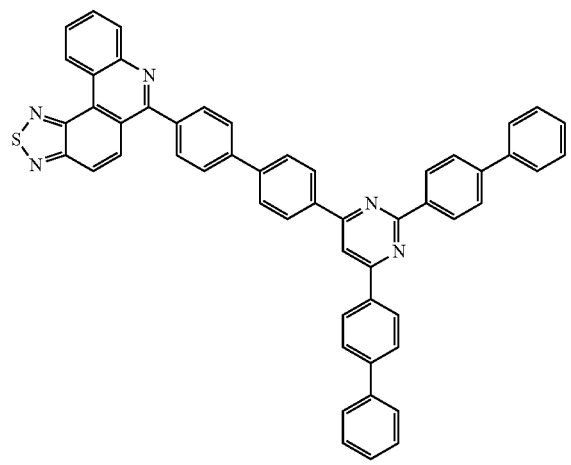
159
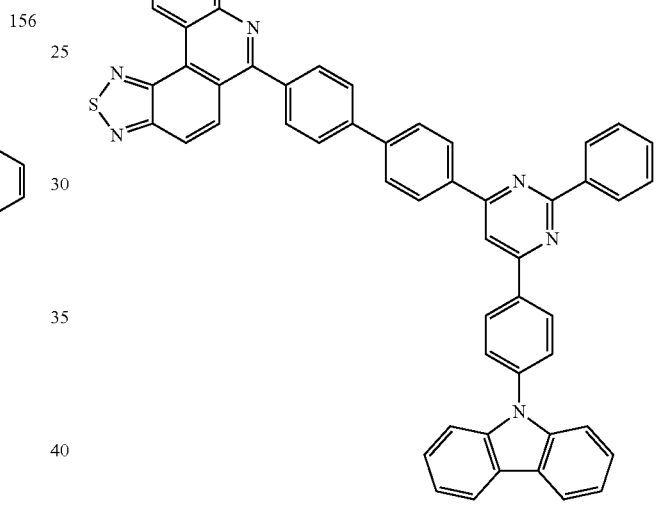
157
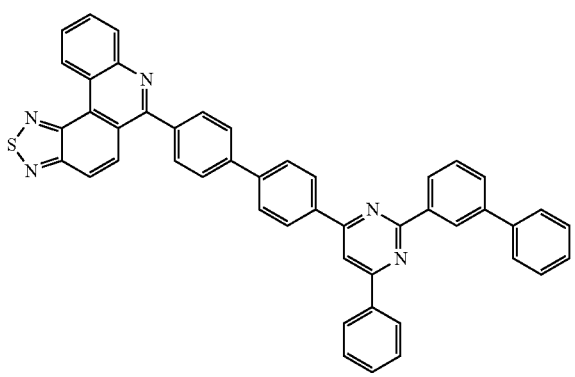
160
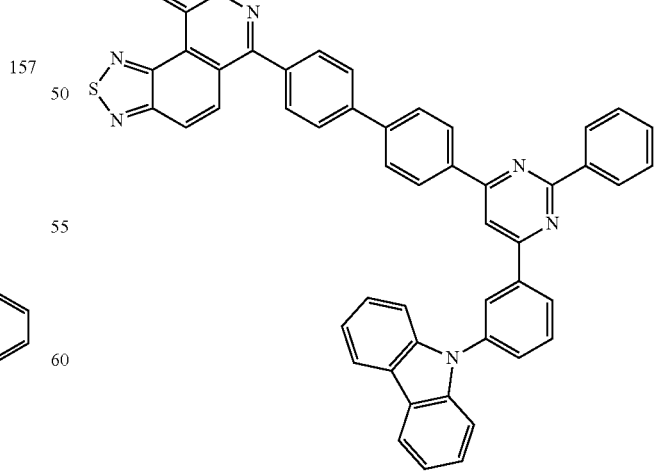

161
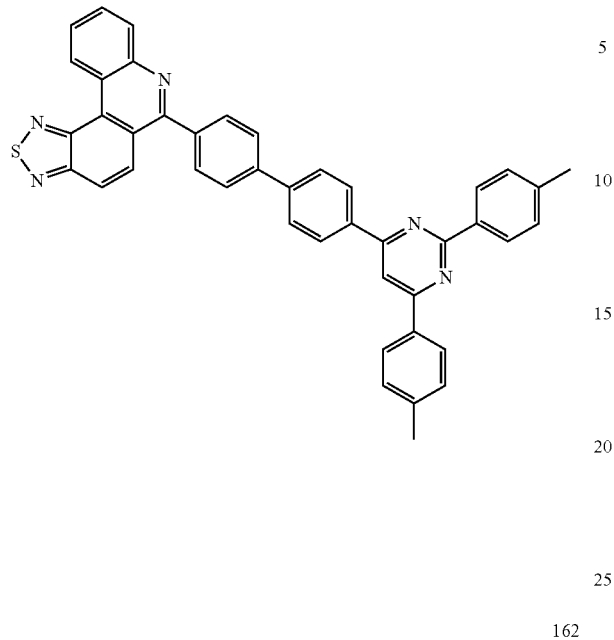
162
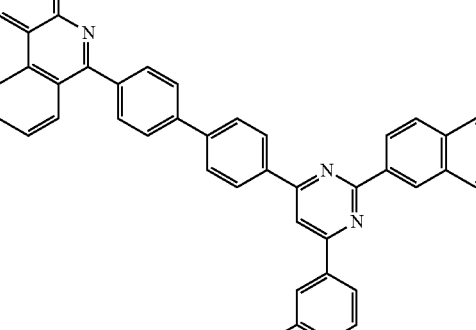
163
164
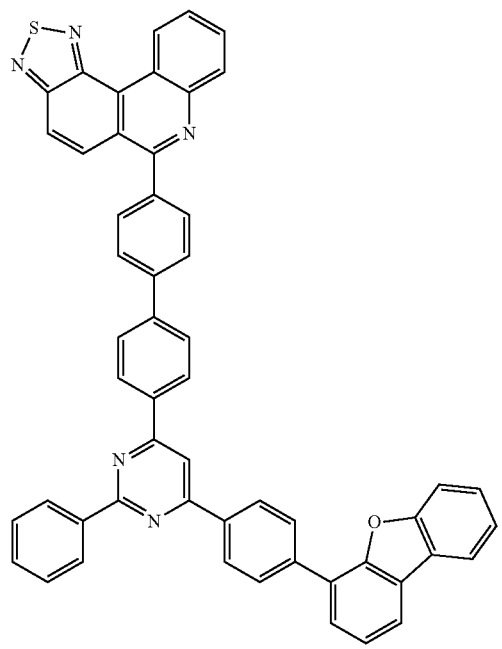
165
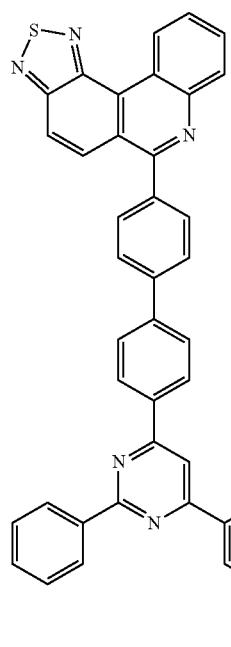

445
-continued
166
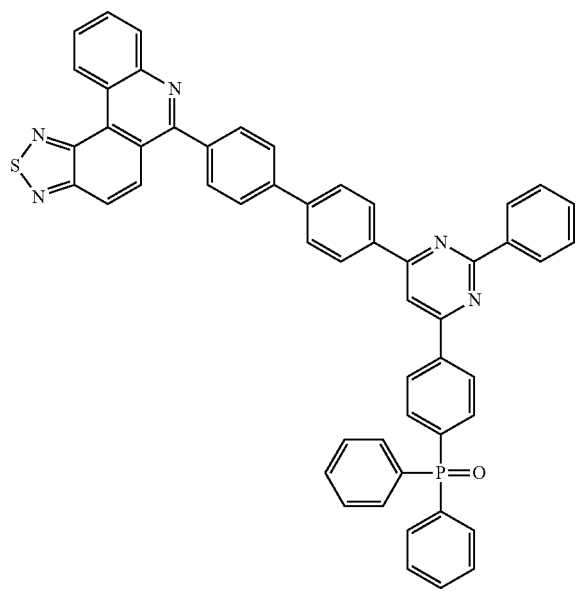
167
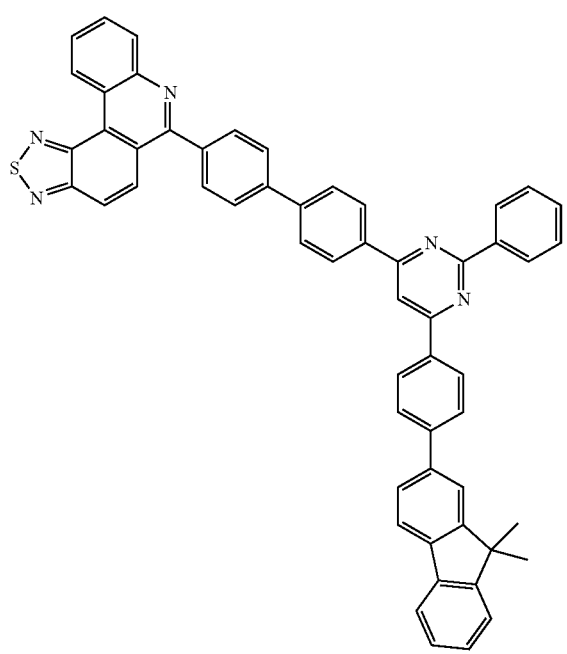
446
-continued
168
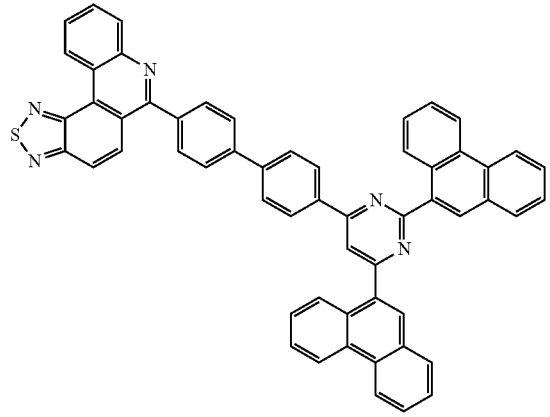
169
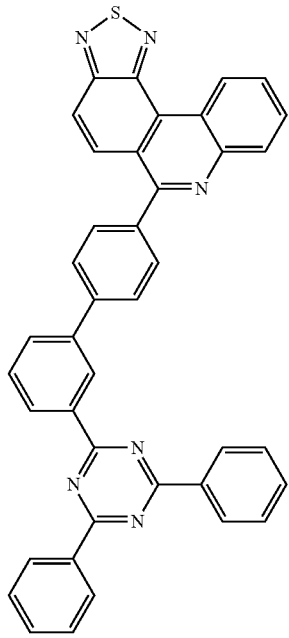
170
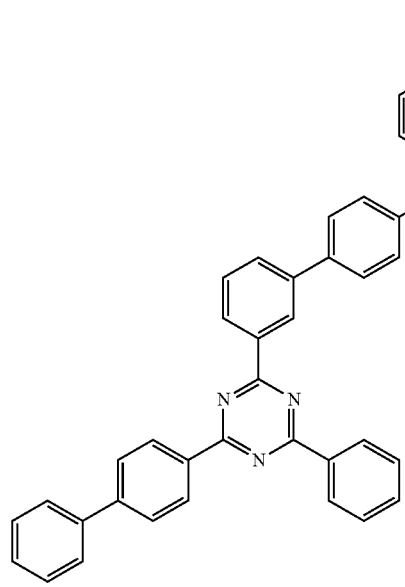

447
-continued
171
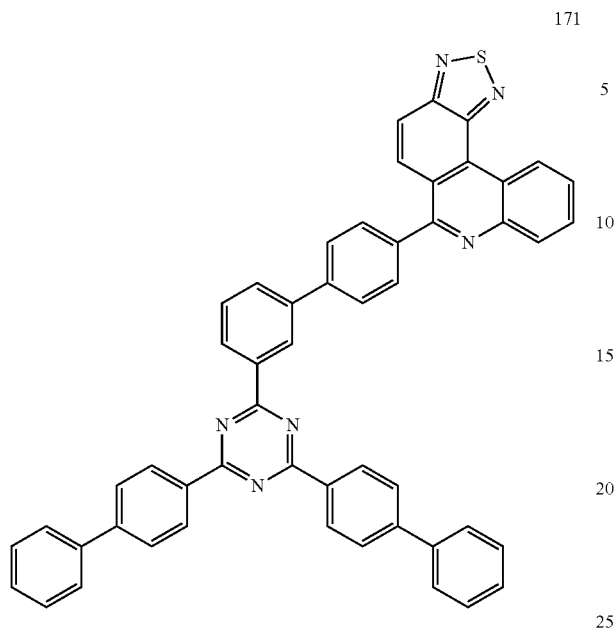
173
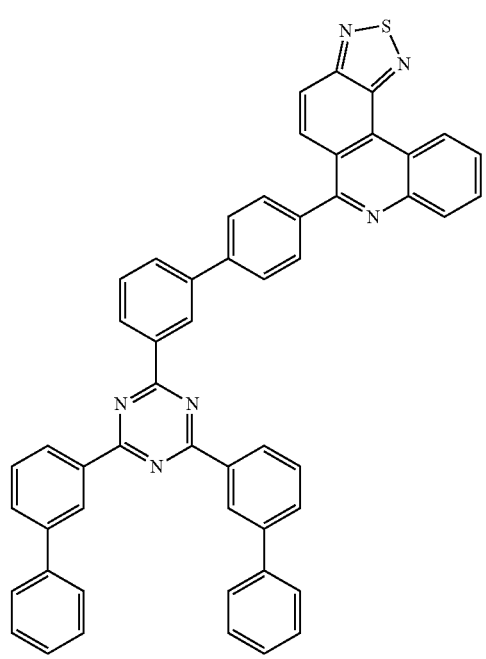
172
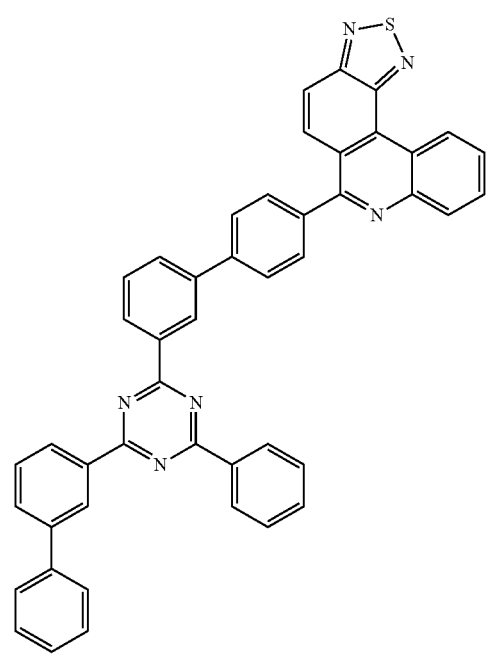
448
-continued
174
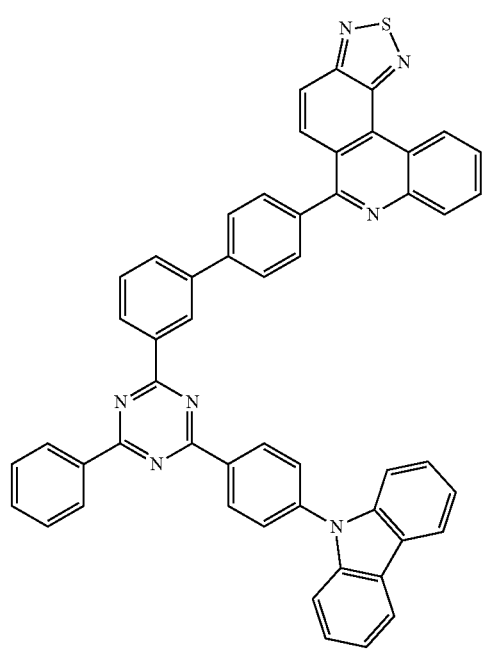

449
-continued
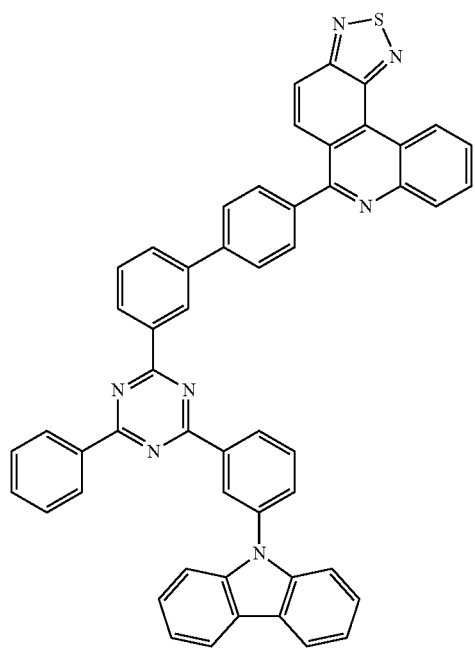
175
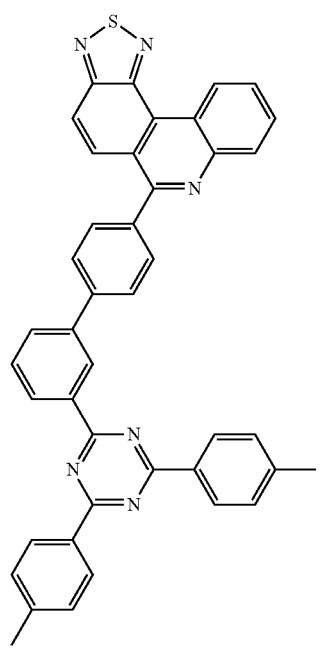
176
450
-continued
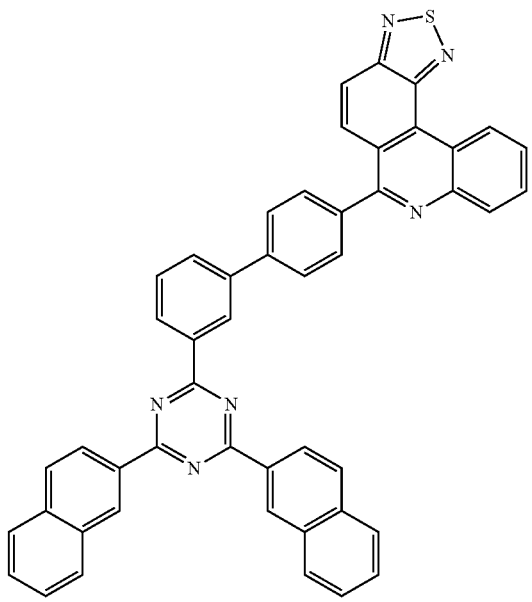
177
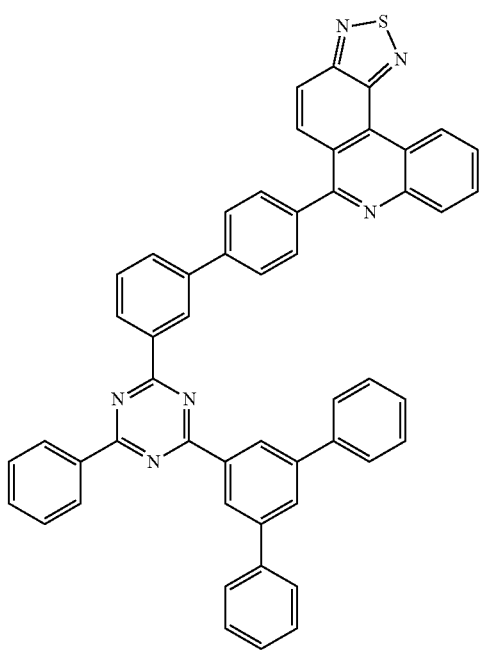
178

451
-continued
179
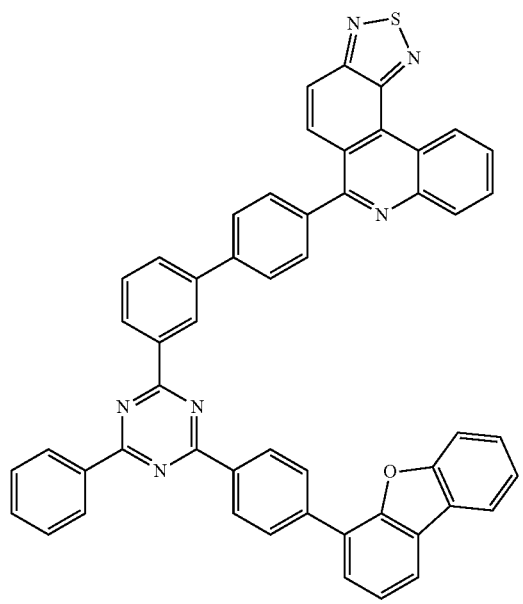
180
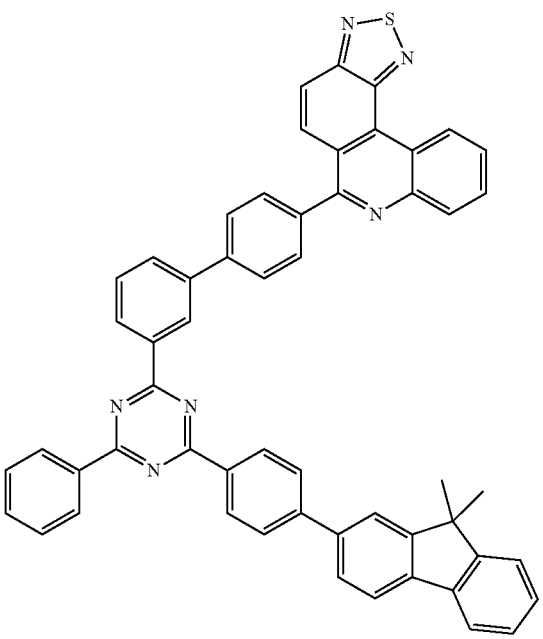
452
-continued
181
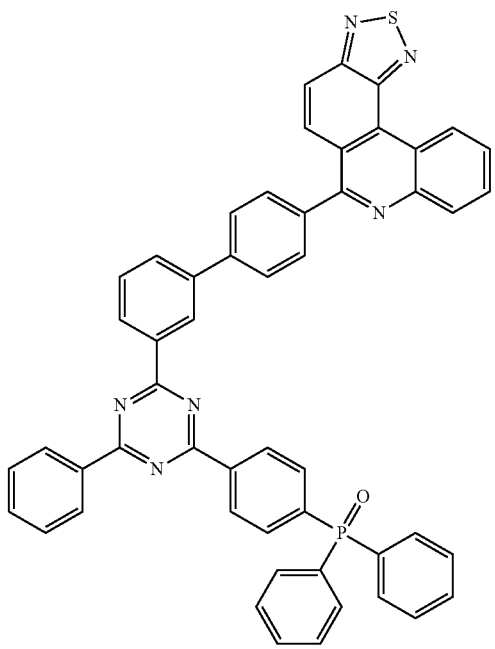
182
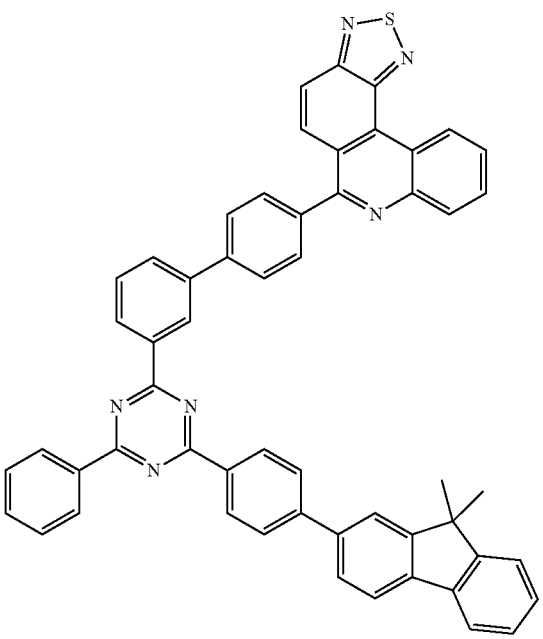

453
-continued
454
-continued
183
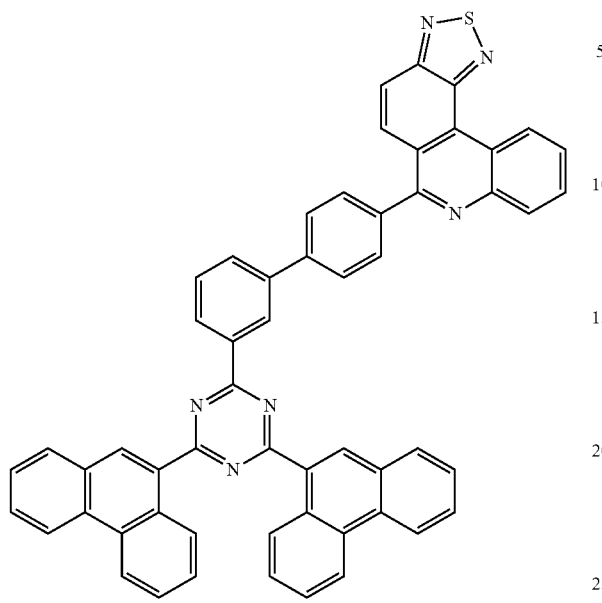
185
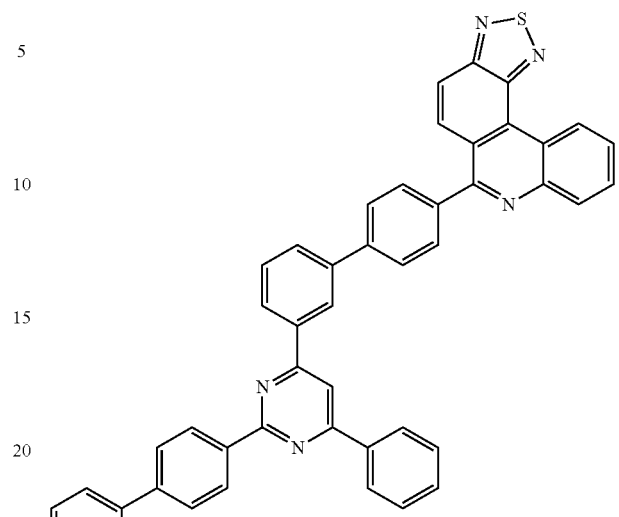
184
186
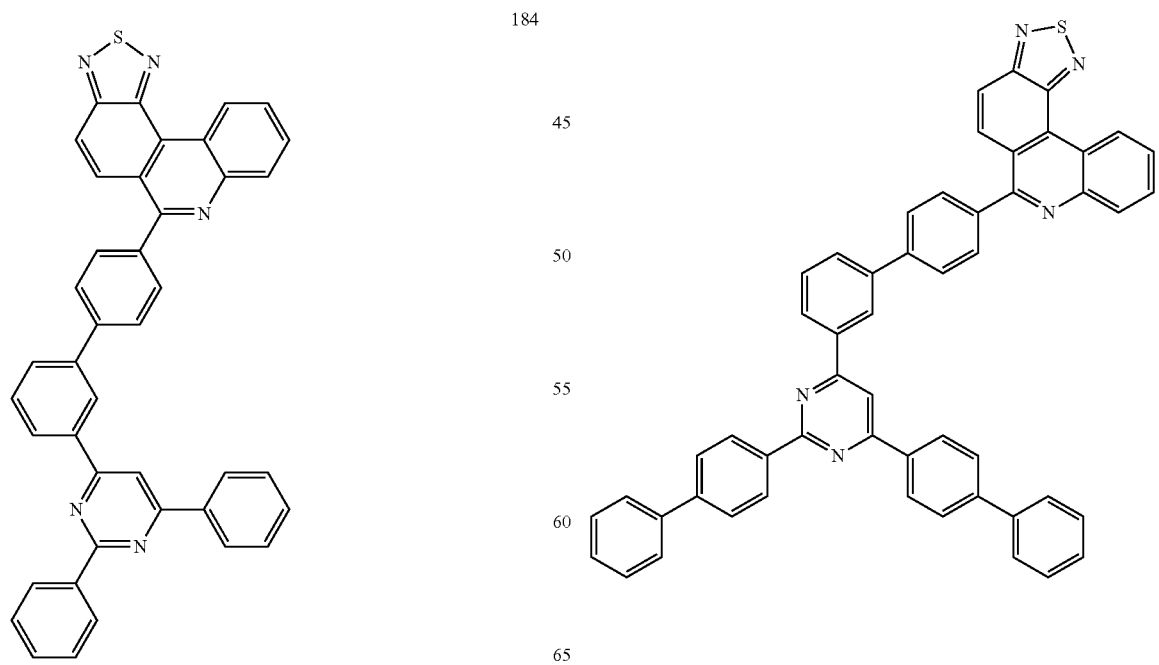

187
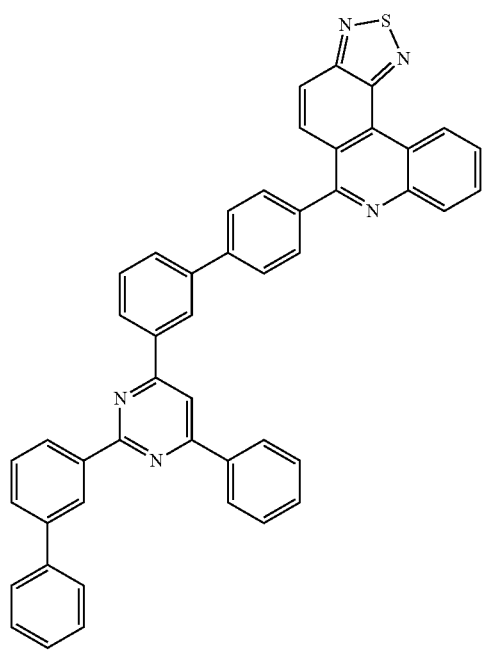
188
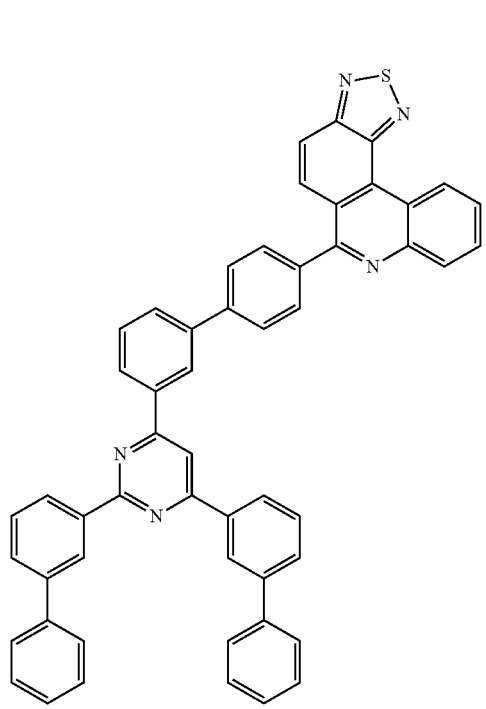
189
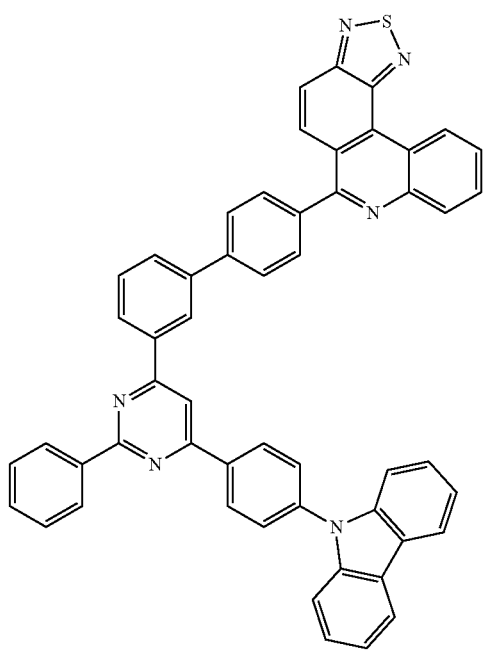
190
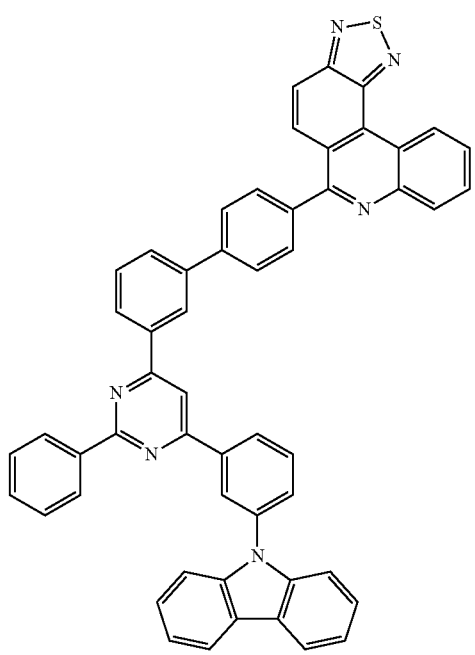

457
-continued
458
-continued
191
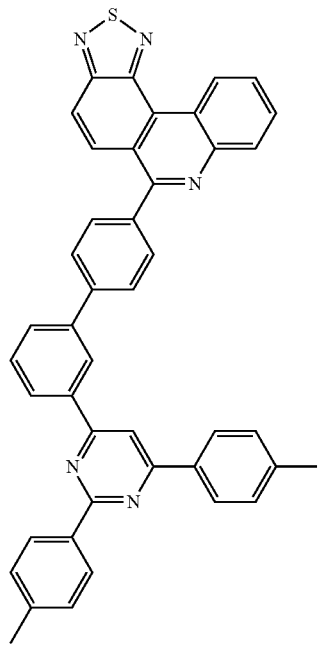
193
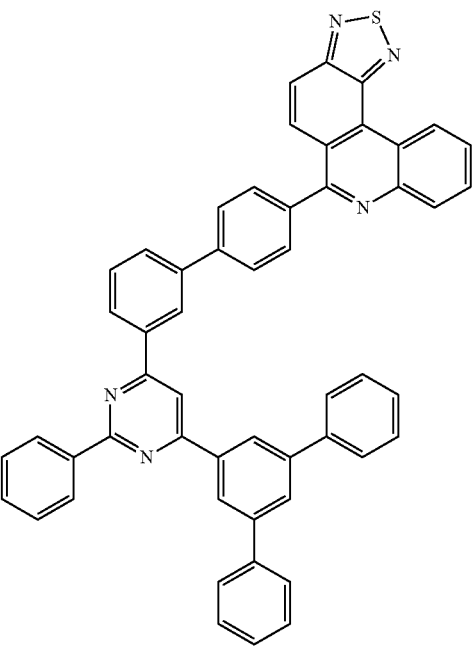
192
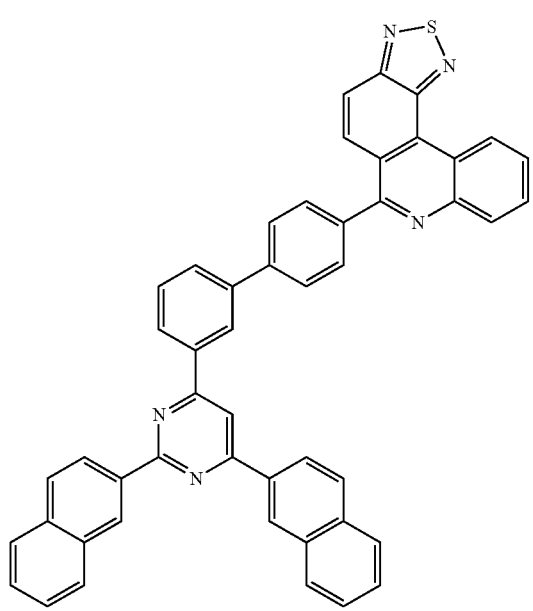
194
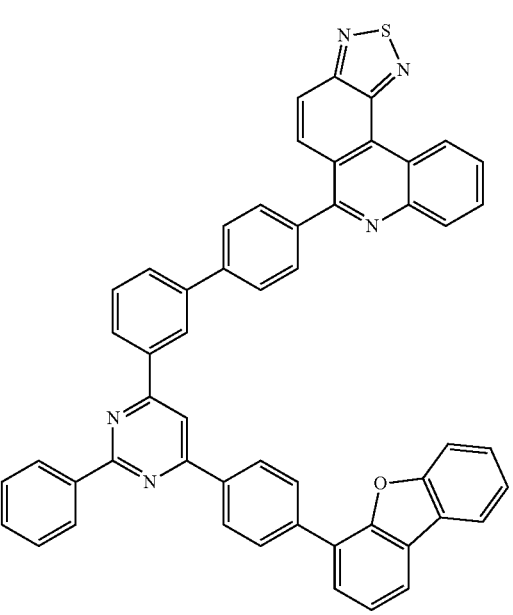

195
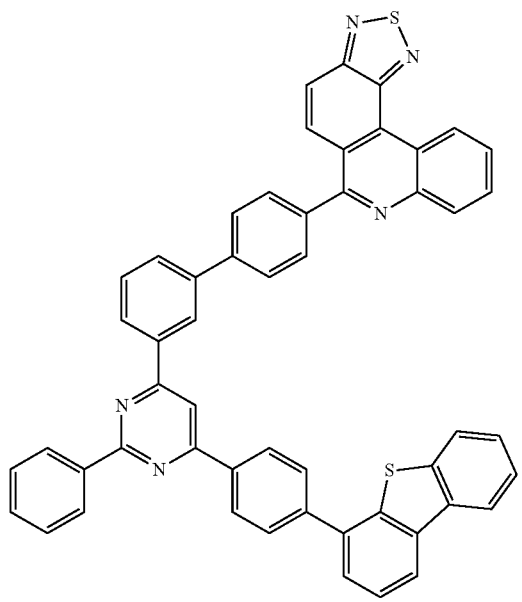
197
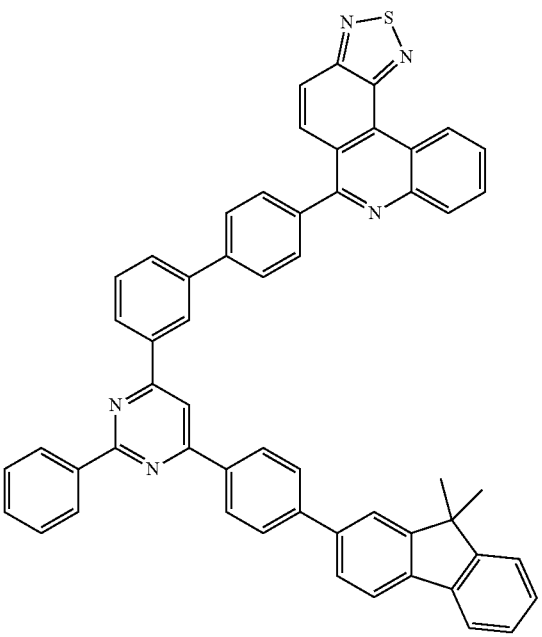
196
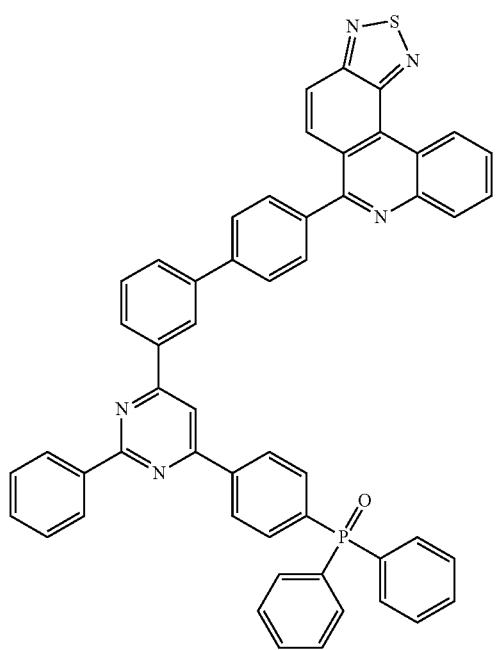
198
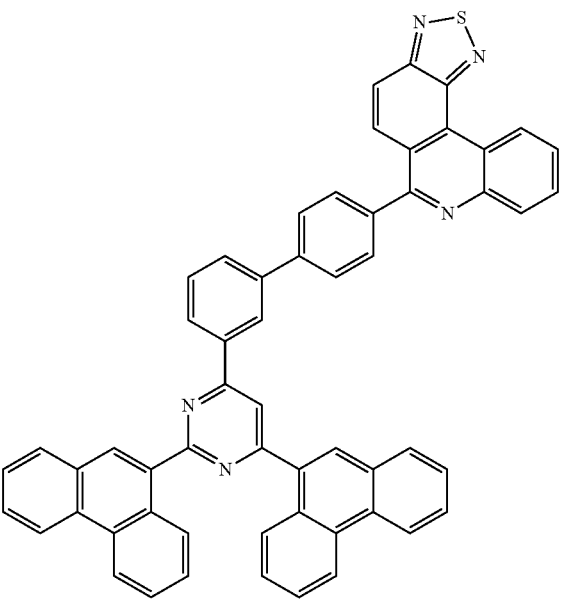

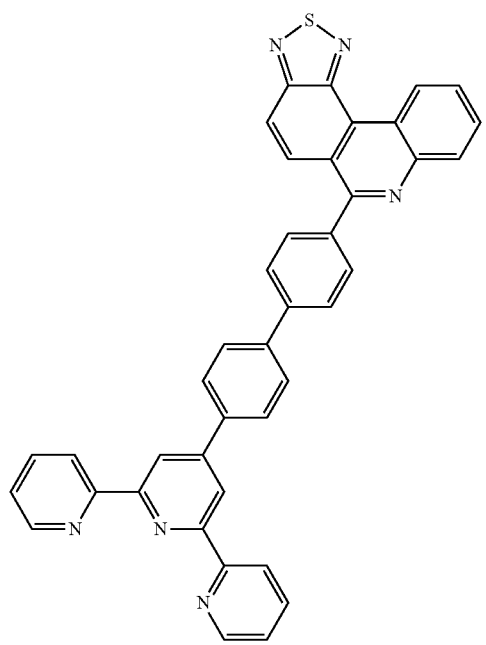
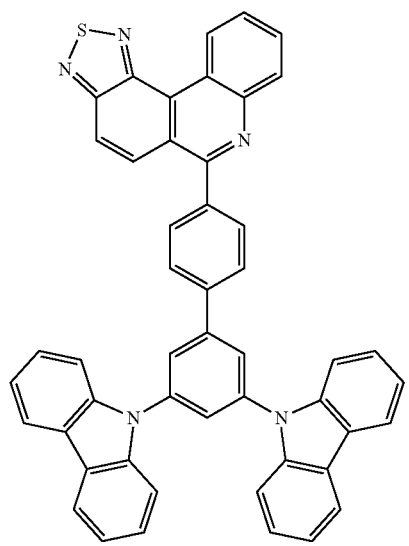
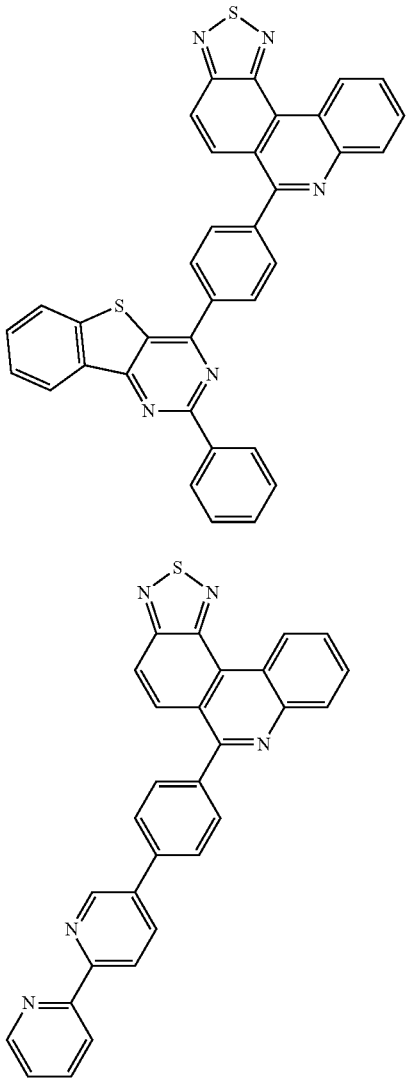

-continued
204
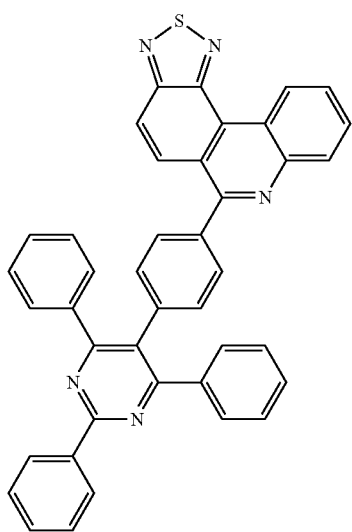
207
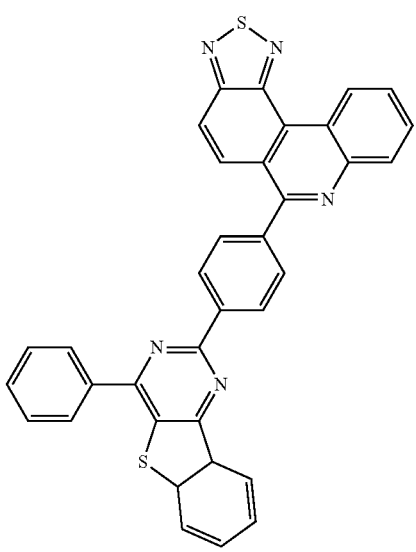
205
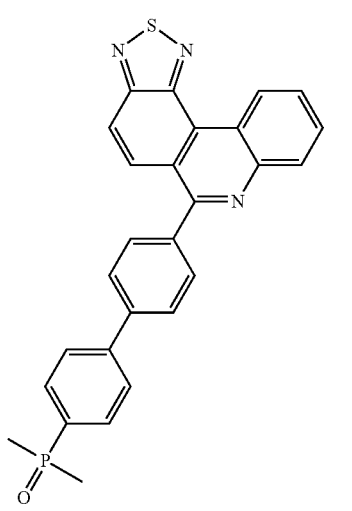
208
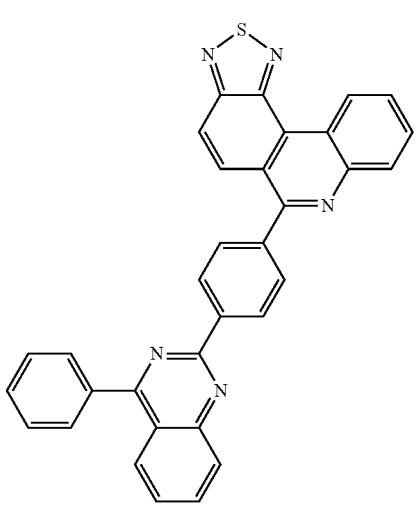
206
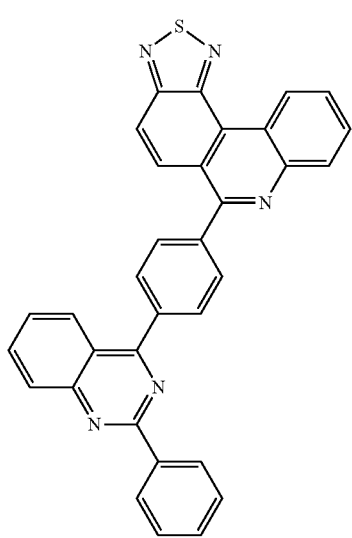
209
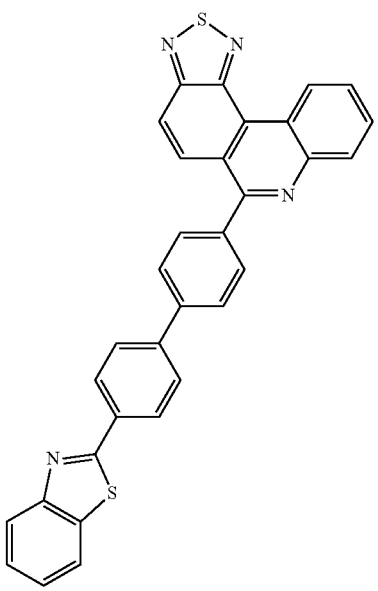

465
-continued
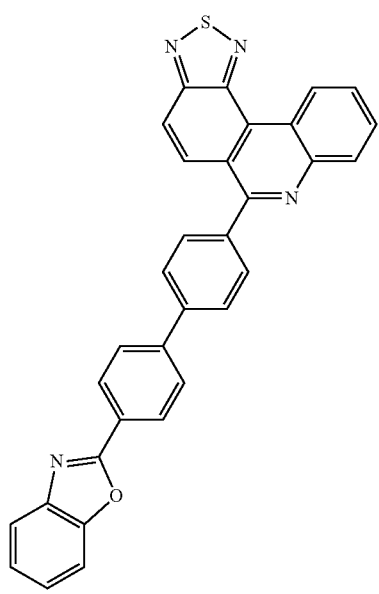
210
466
-continued
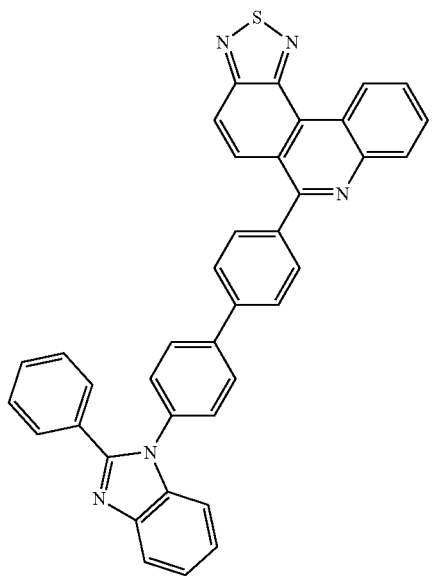
212
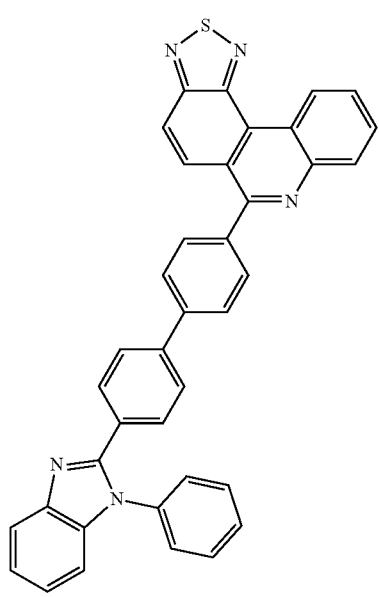
211
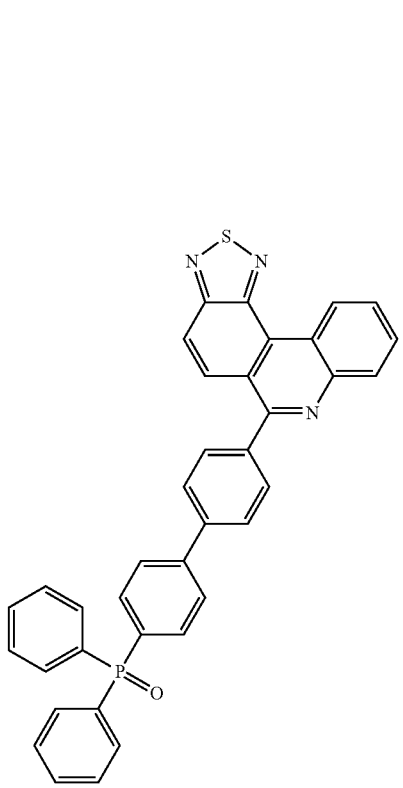
213

214 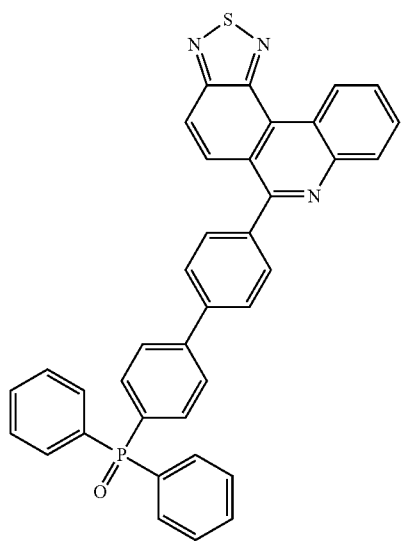
215 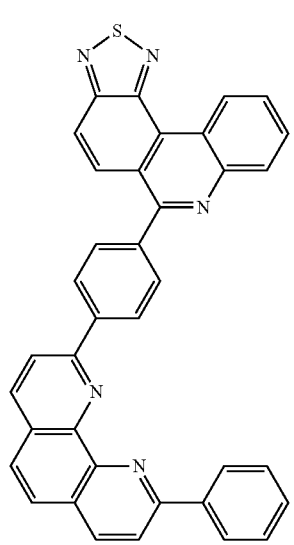
216 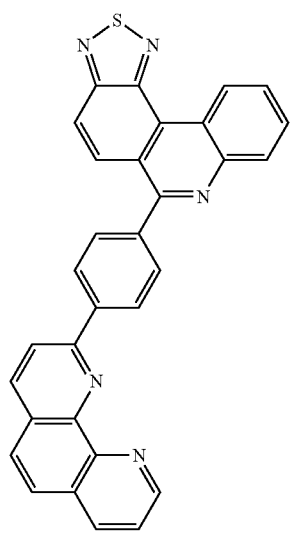
217 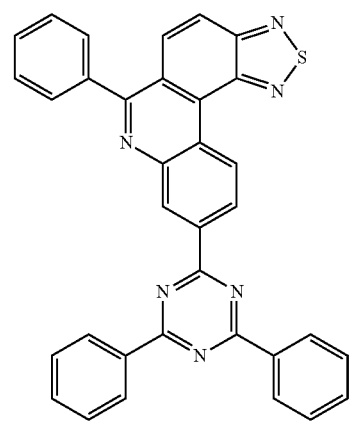
218
219 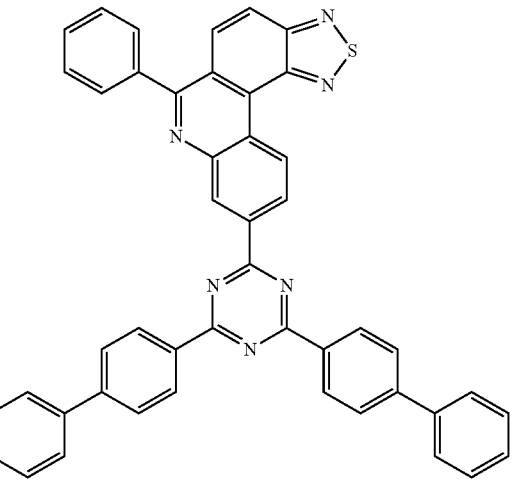

469
-continued
220
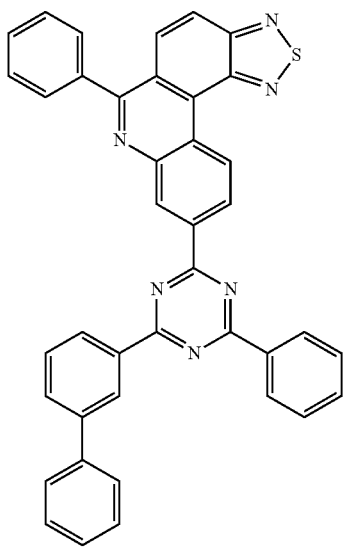
221
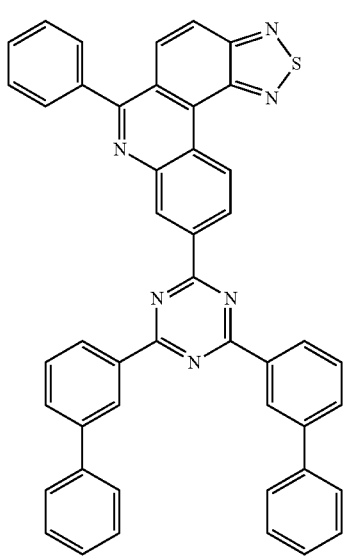
222
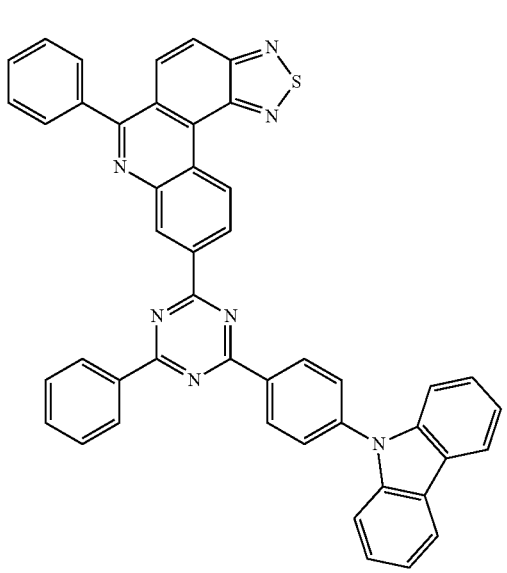
470
-continued
223
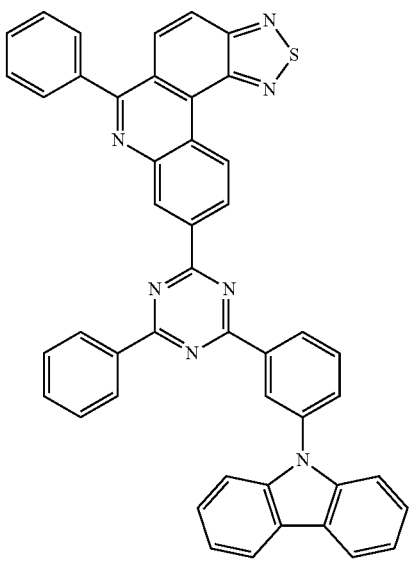
224
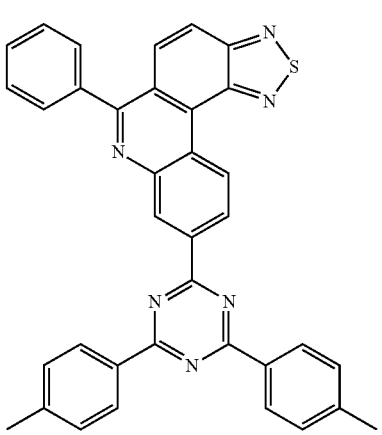
225
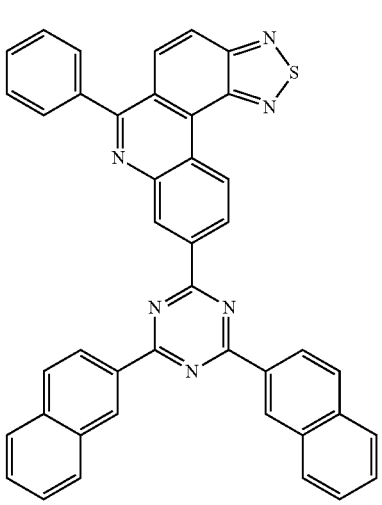

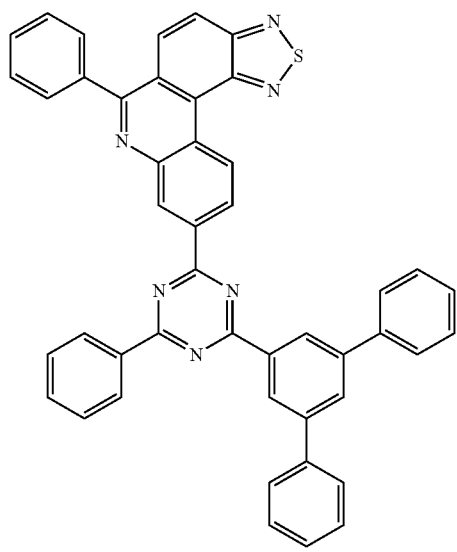

473
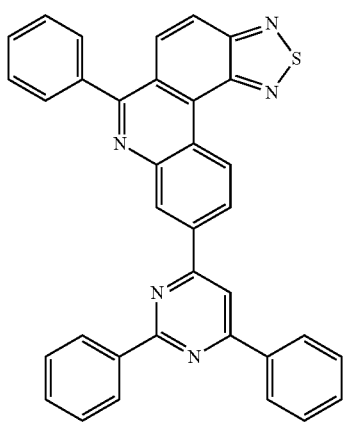
232
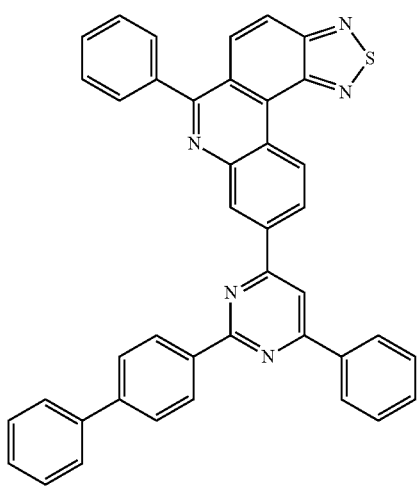
233
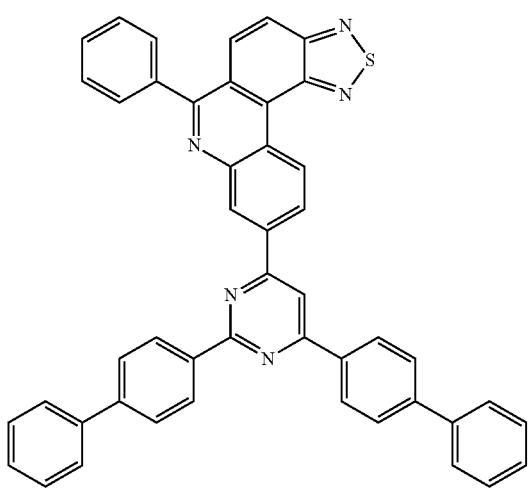
234
474
-continued
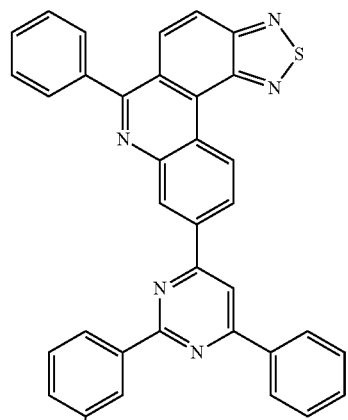
235
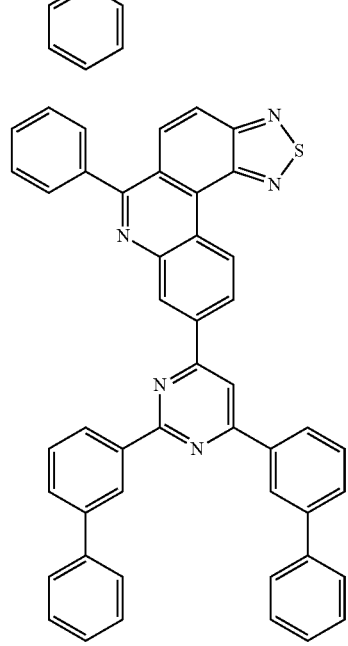
236
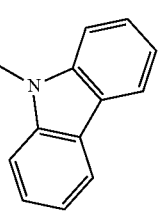
237

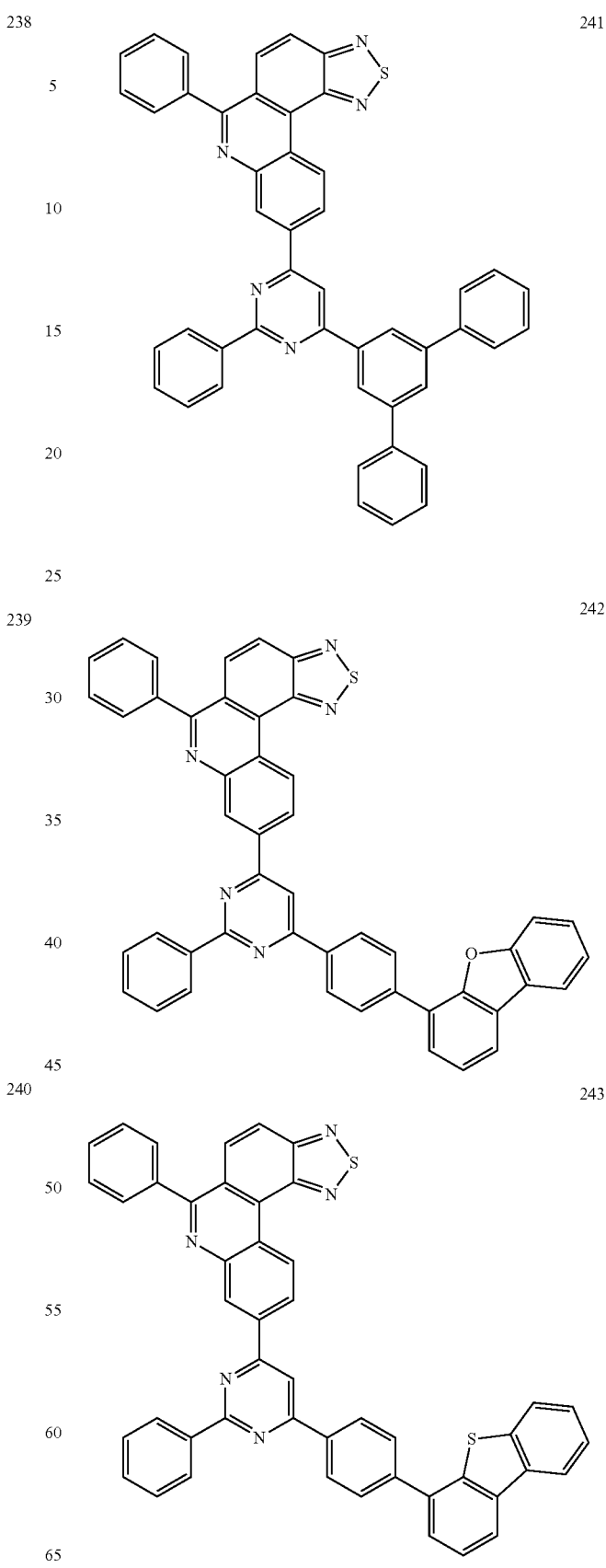

477
-continued
244
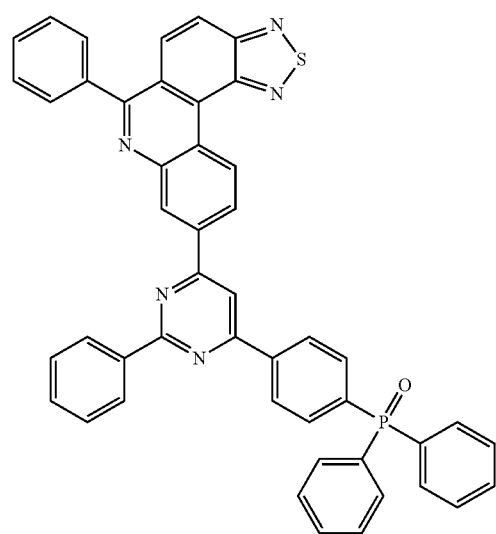
245
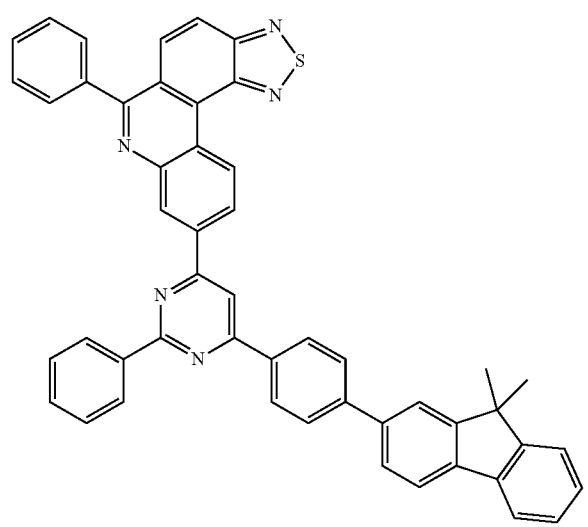
246
478
-continued
247
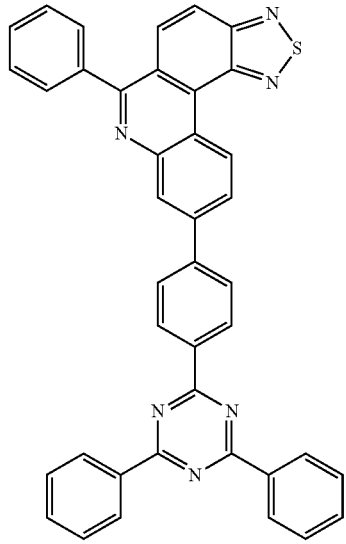
248
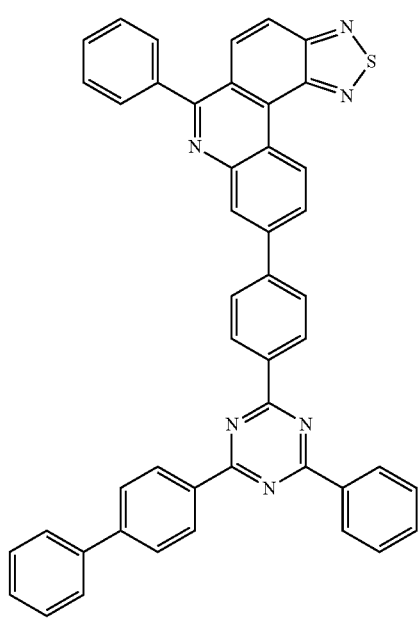

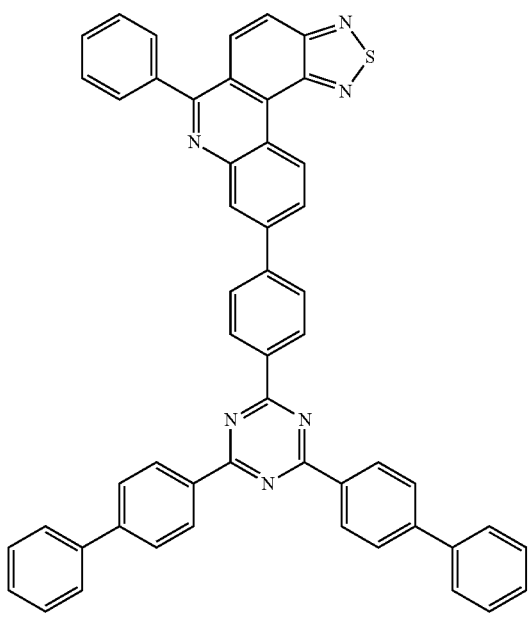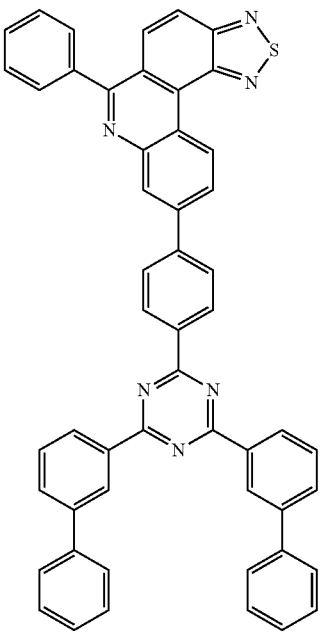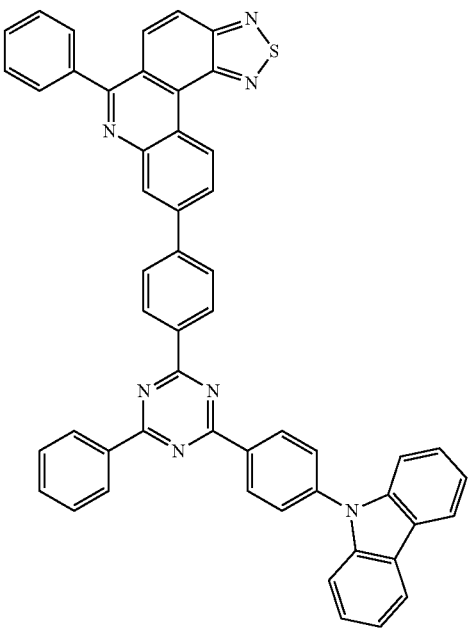

253
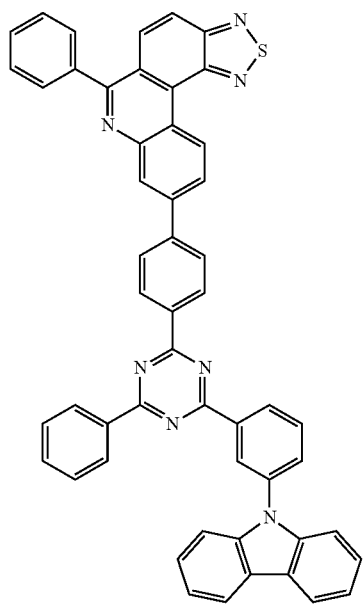
481
-continued
255
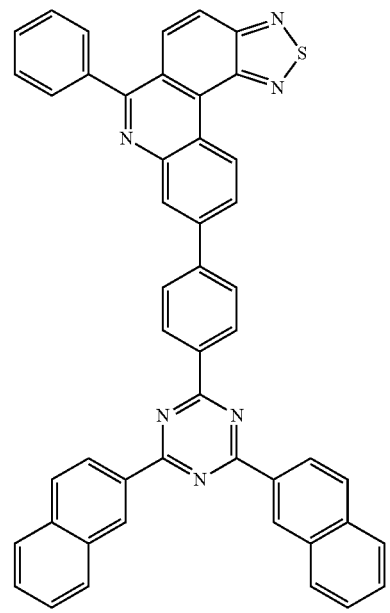
254
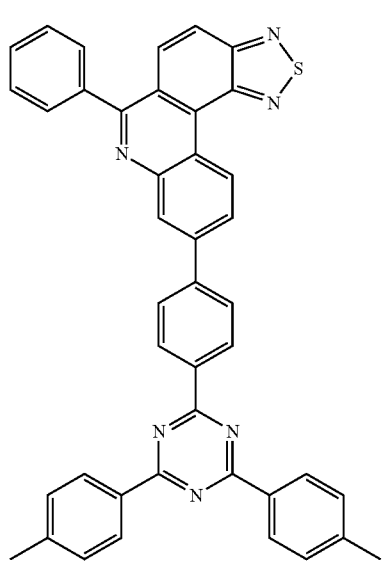
256
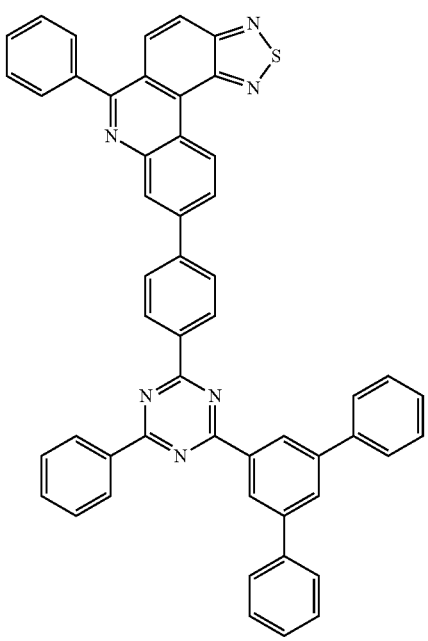

483
-continued
257
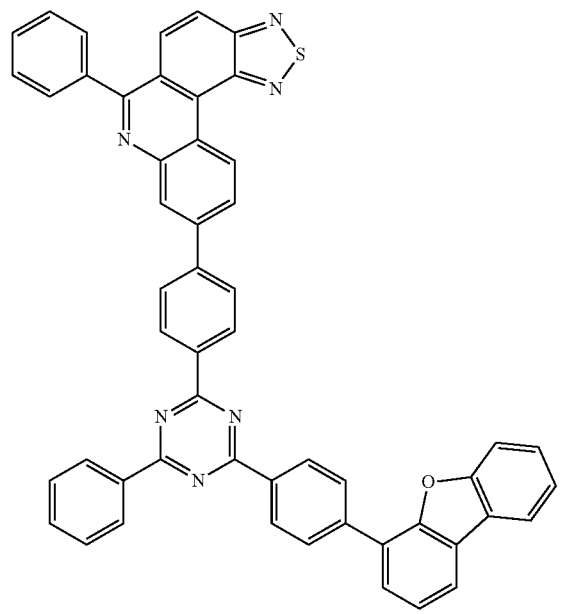
258
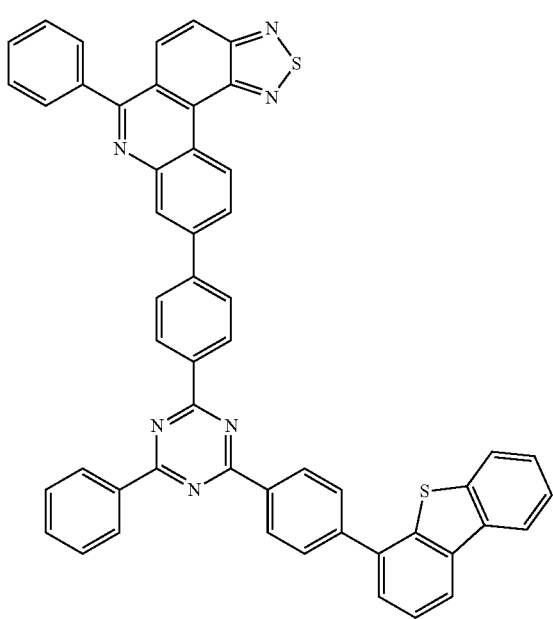
484
-continued
259
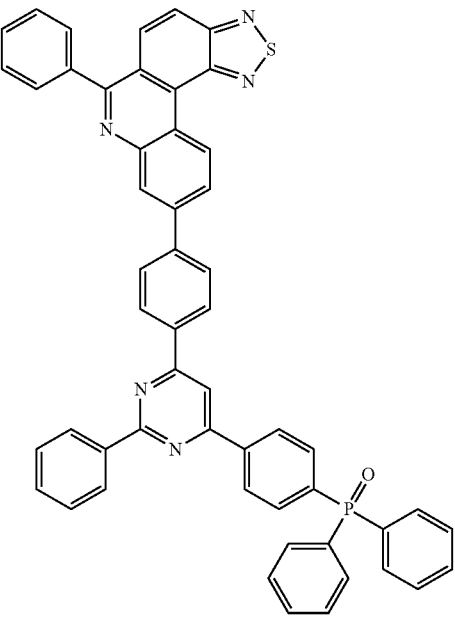
260
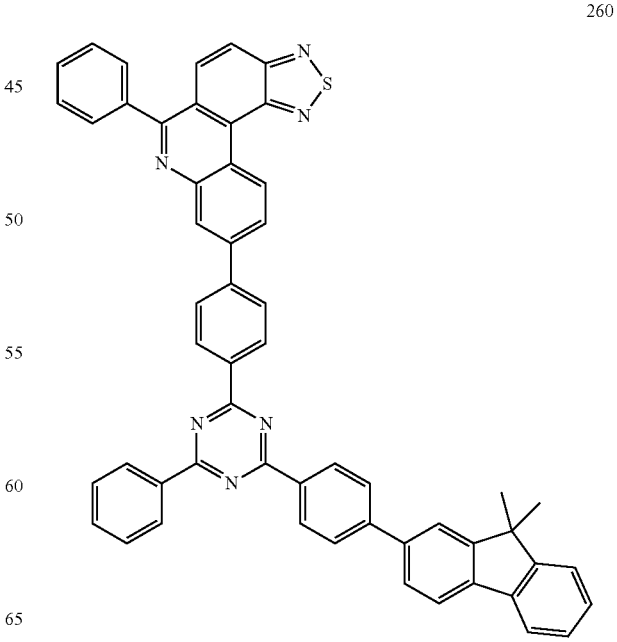

485
-continued
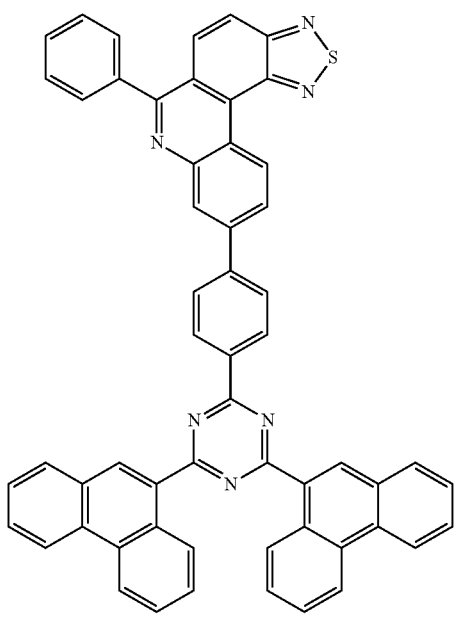
261
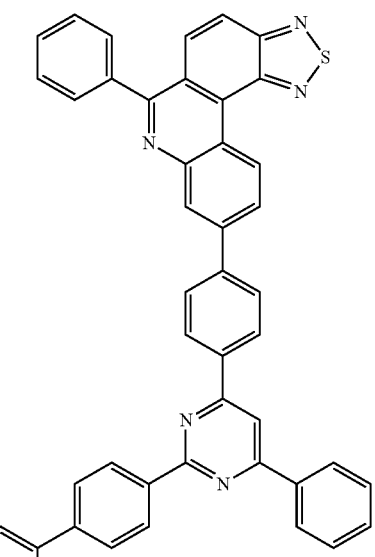
263
486
-continued
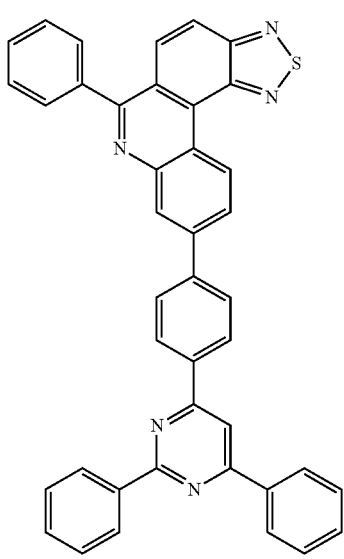
262
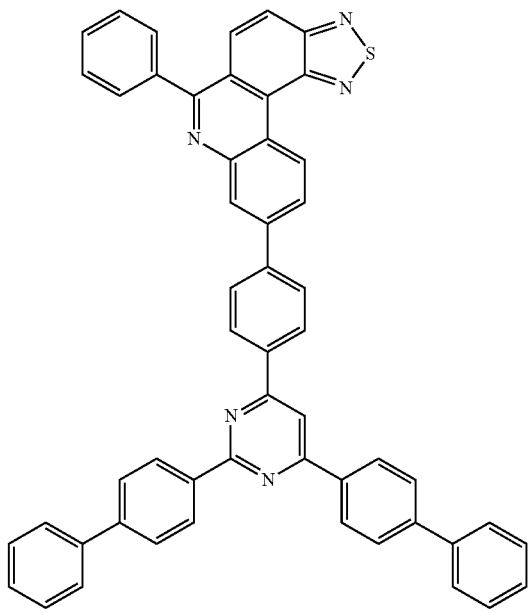
264

487
-continued
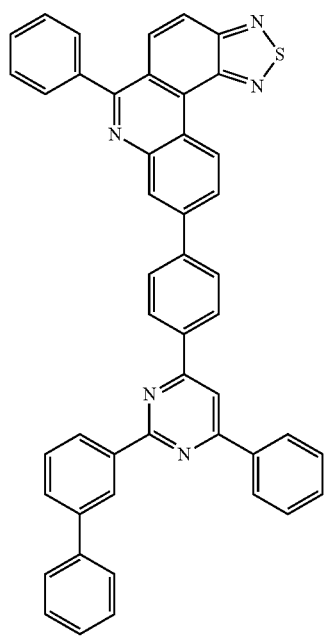
265
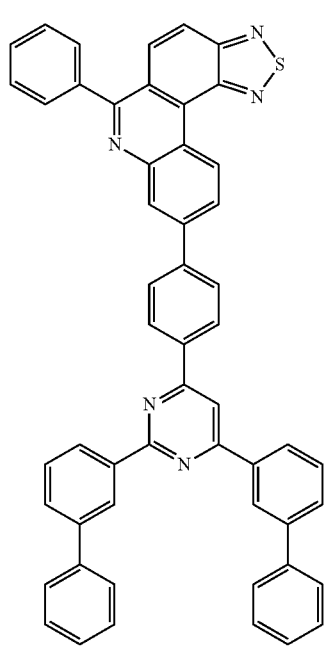
266
488
-continued
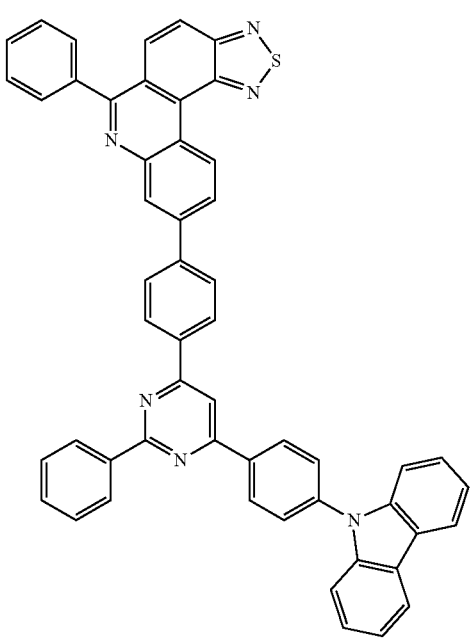
267
268

489
-continued
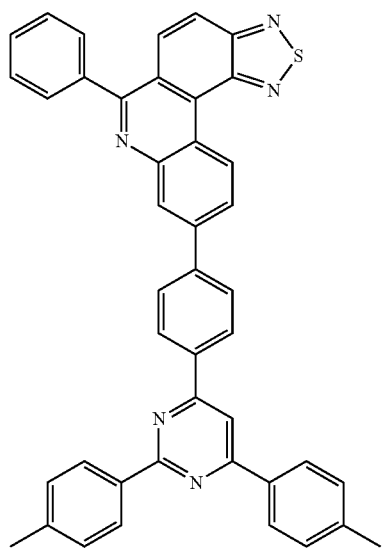
269
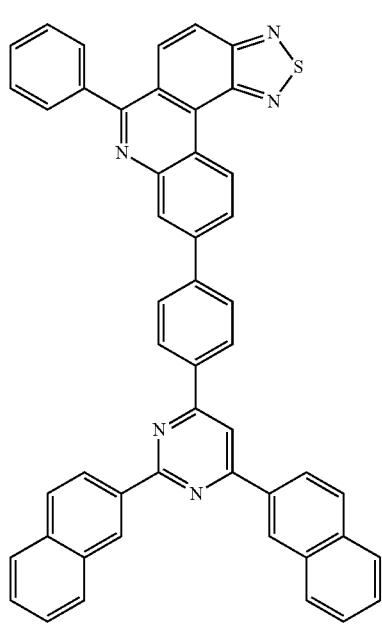
270
490
-continued
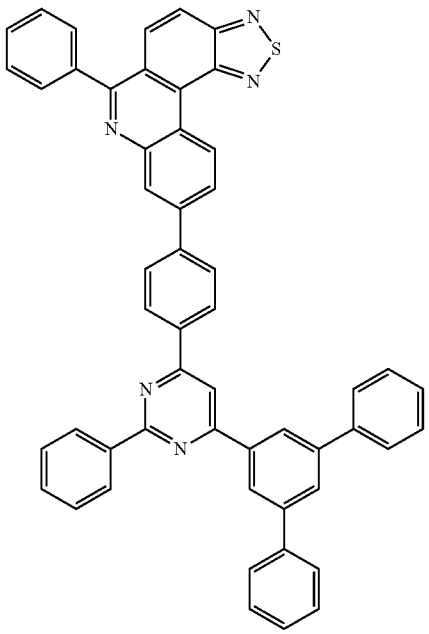
271
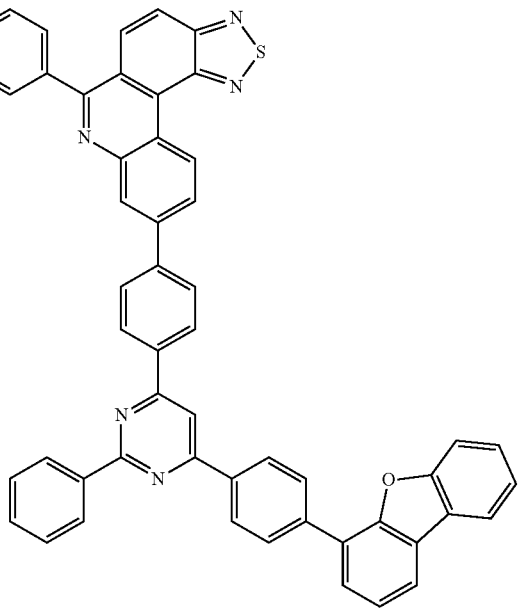
272

491
-continued
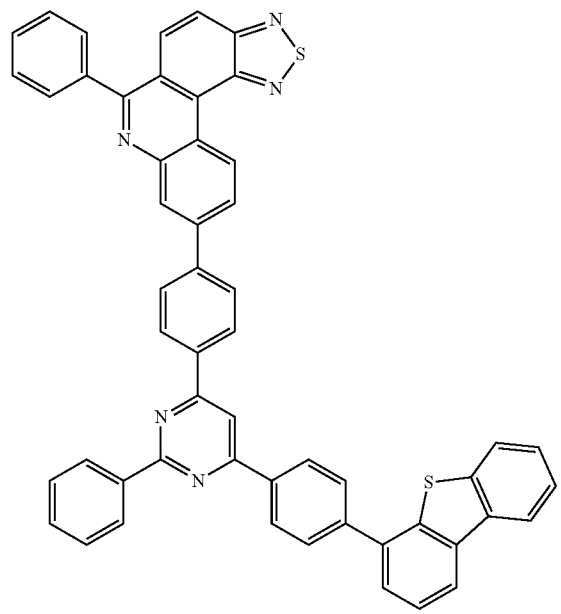
273
492
-continued
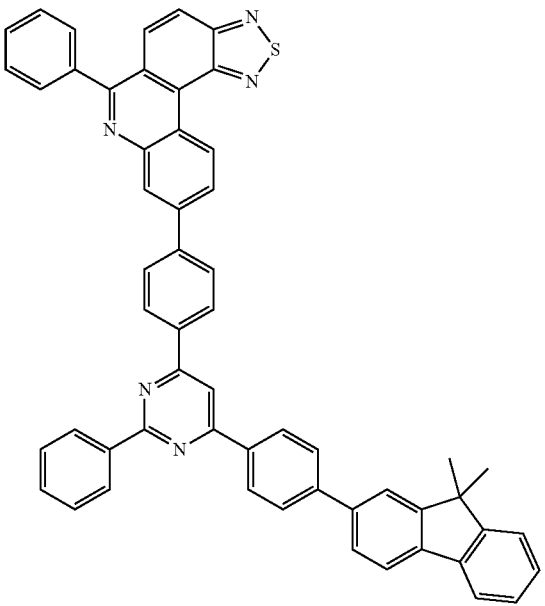
275
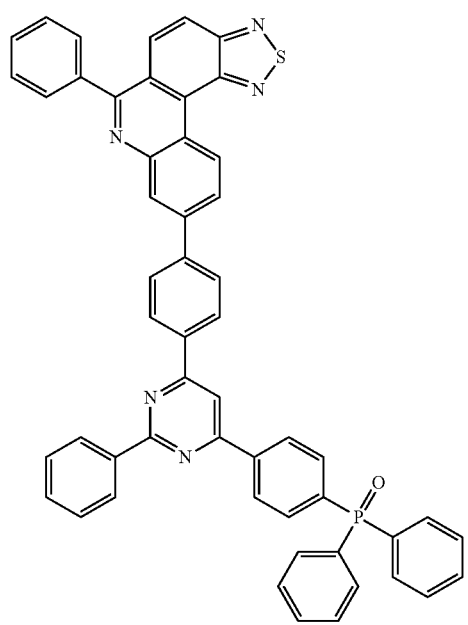
274
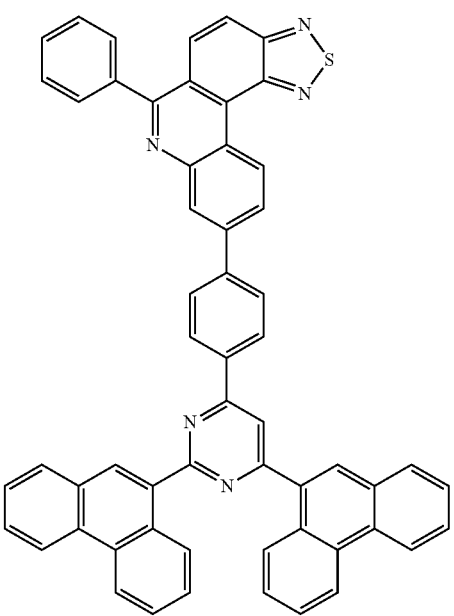
276

493
-continued
277
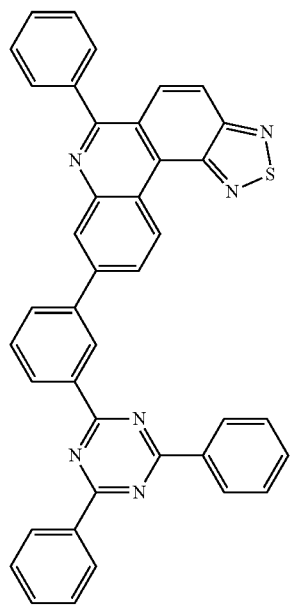
494
-continued
279
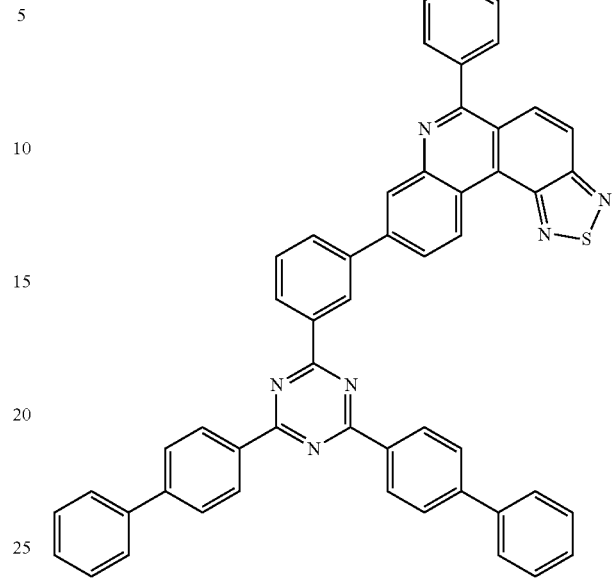
278
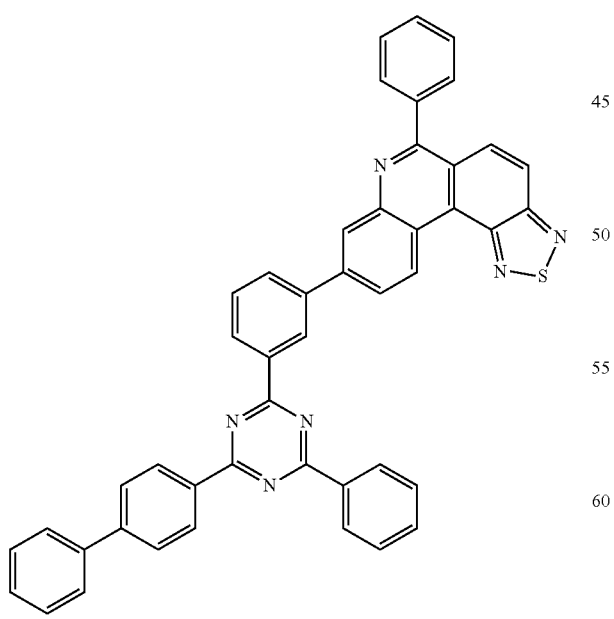
280
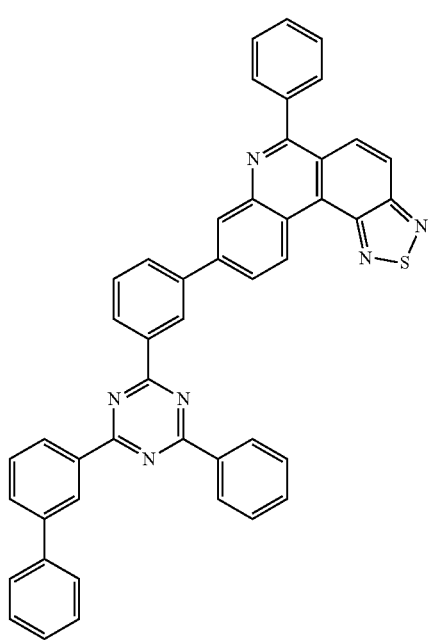

281
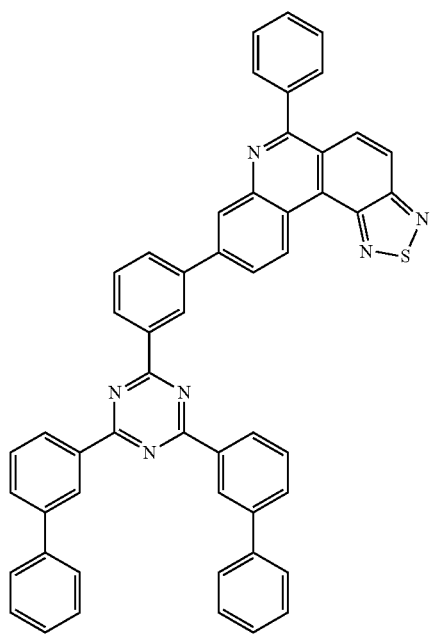
283
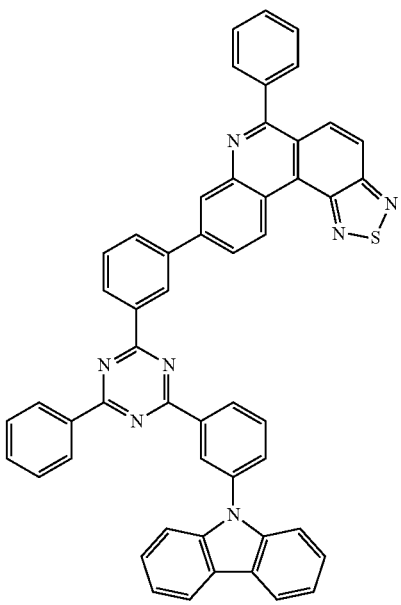
282
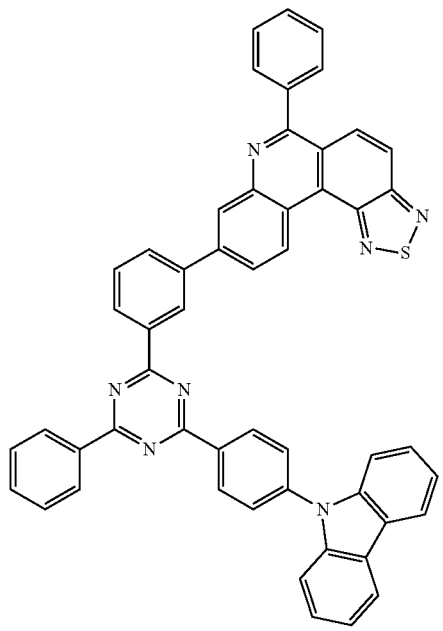
284
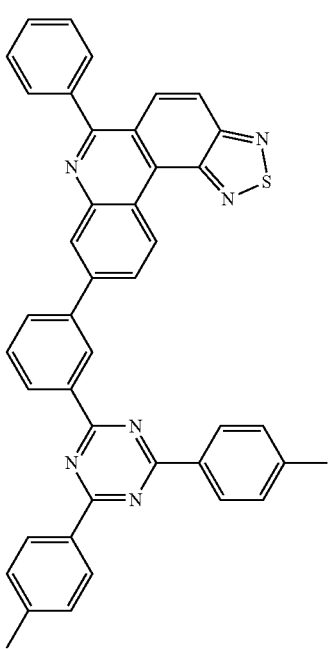

285
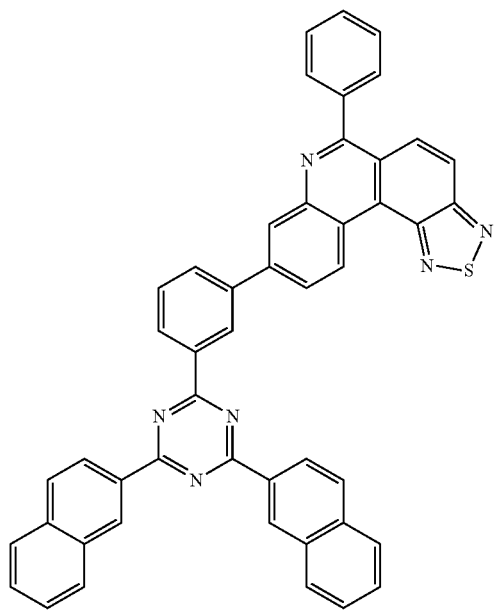
287
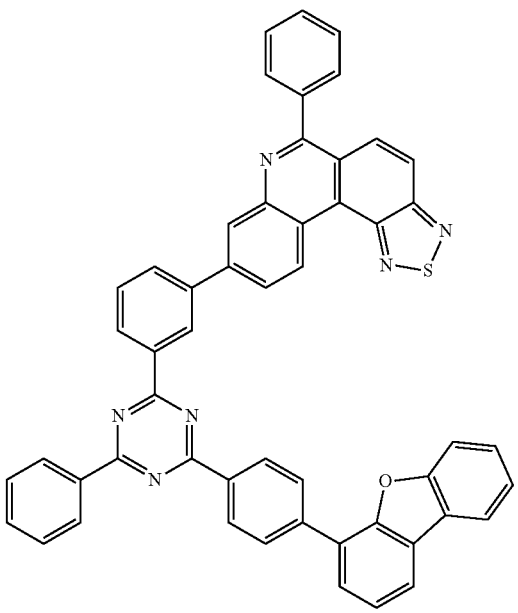
286
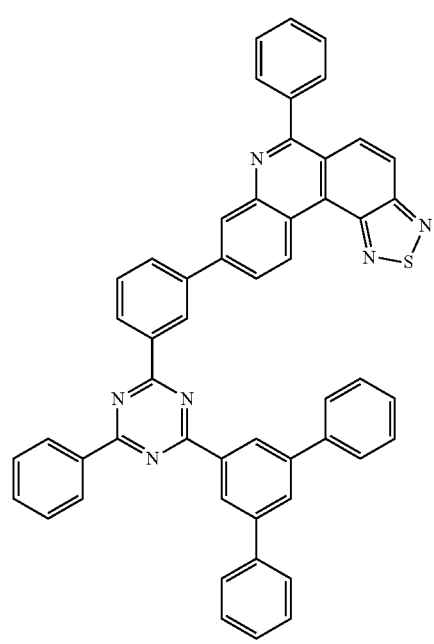
288
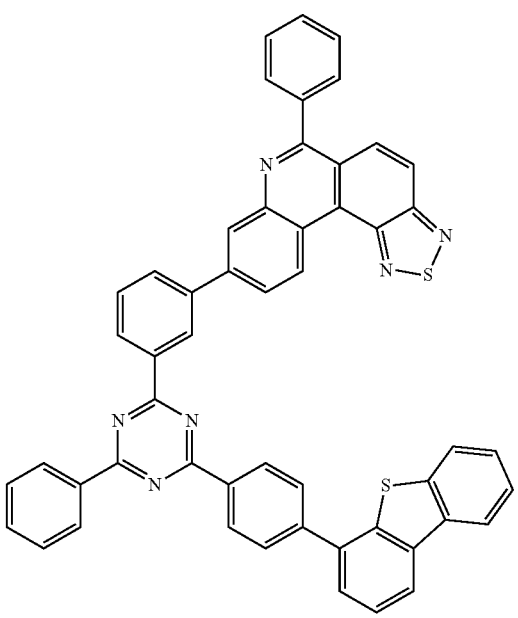

499
-continued
289
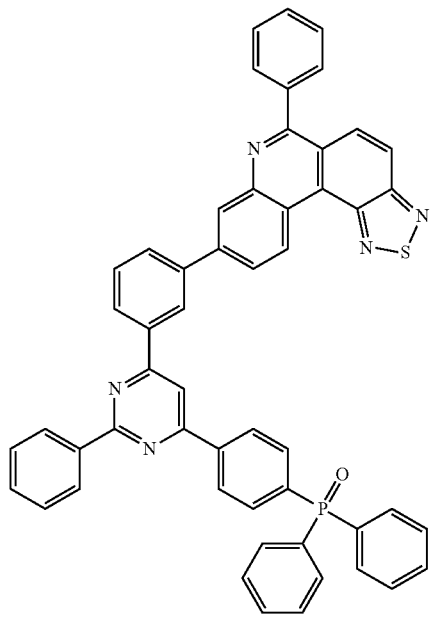
291
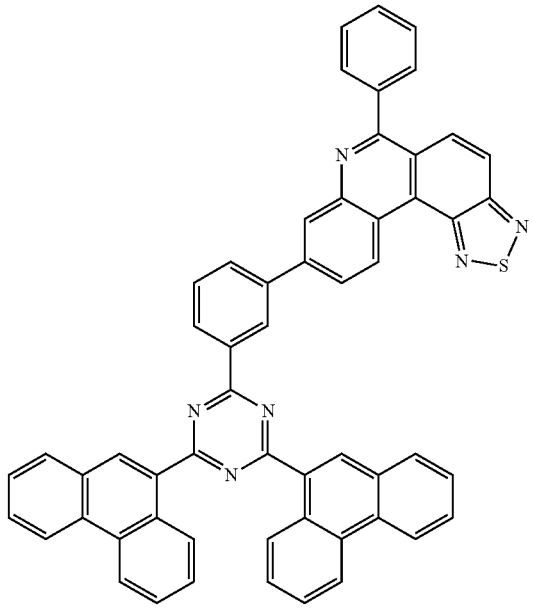
290
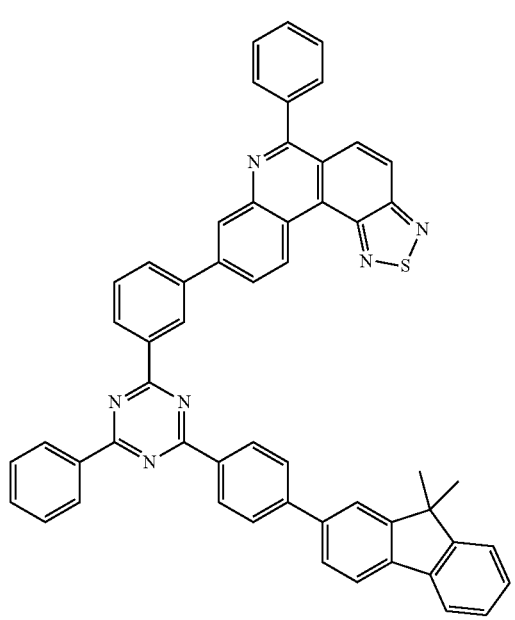
500
-continued
292
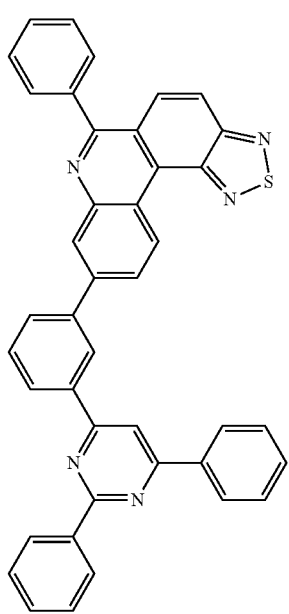

-continued
293
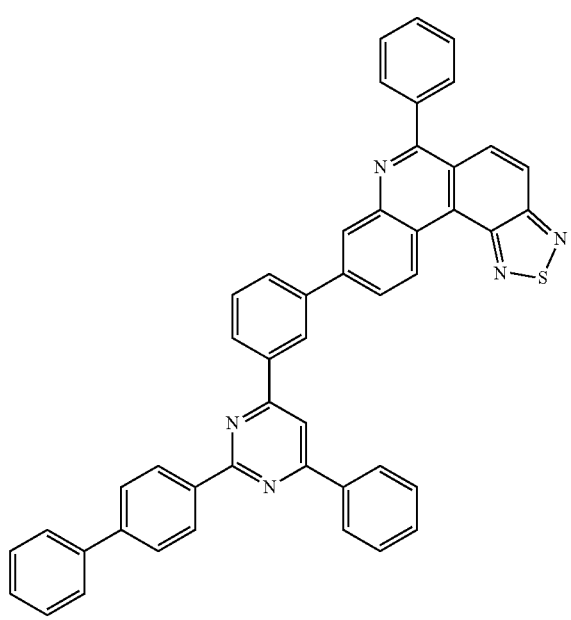
294
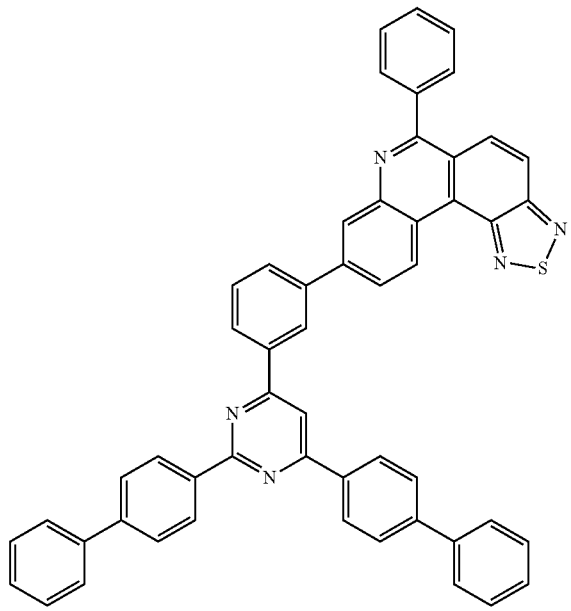
-continued
295
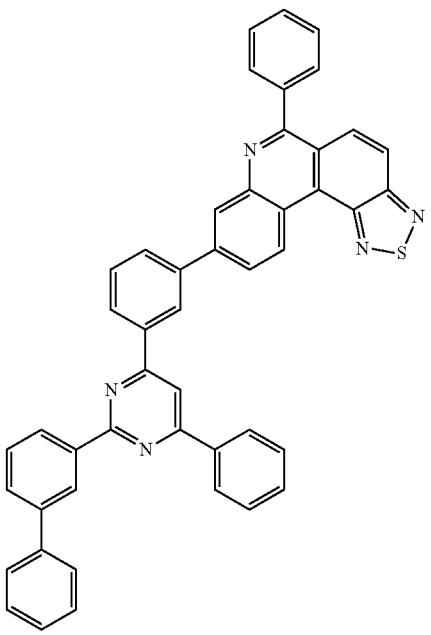
296
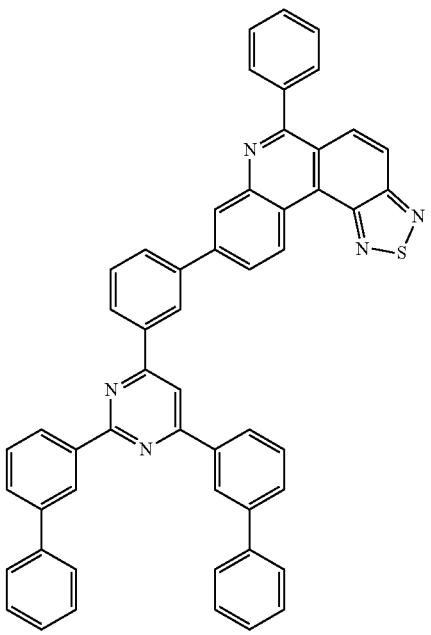

503
-continued
297
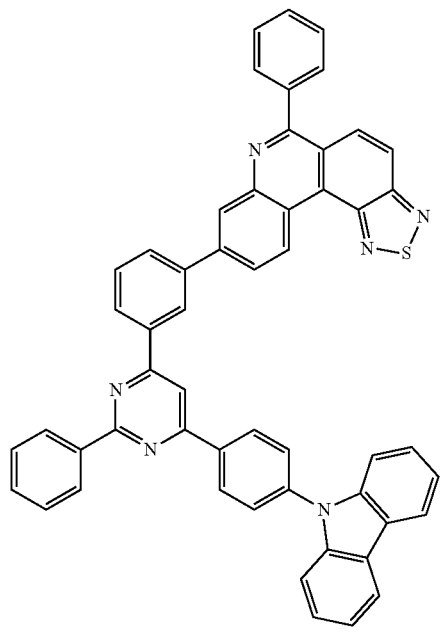
298
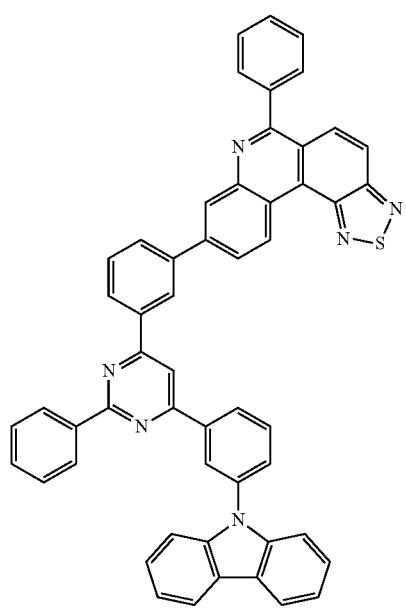
504
-continued
299
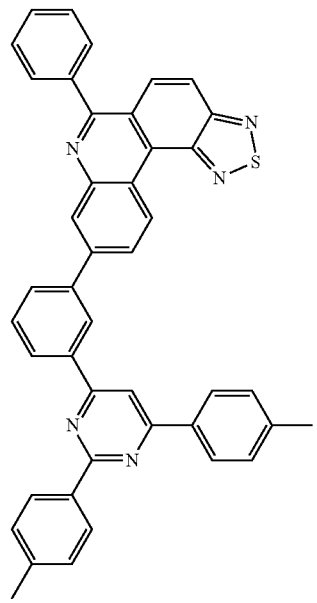
300
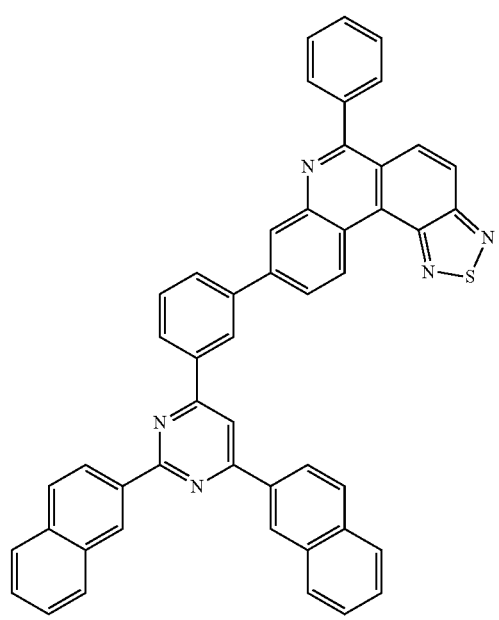

505
-continued
301
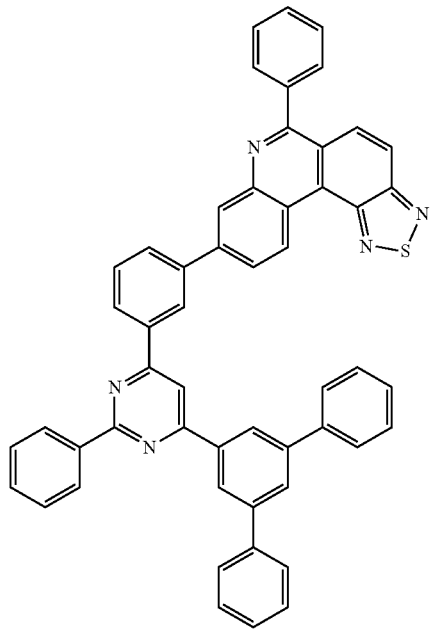
302
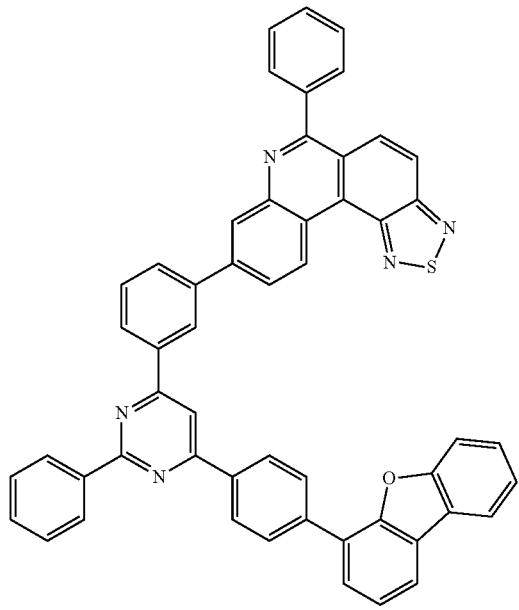
506
-continued
303
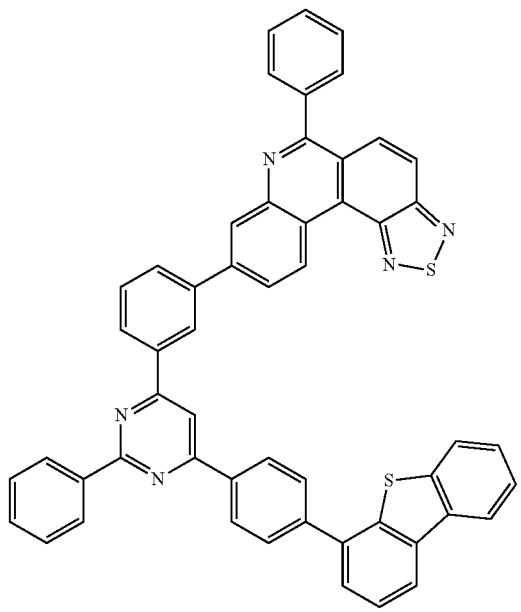
304
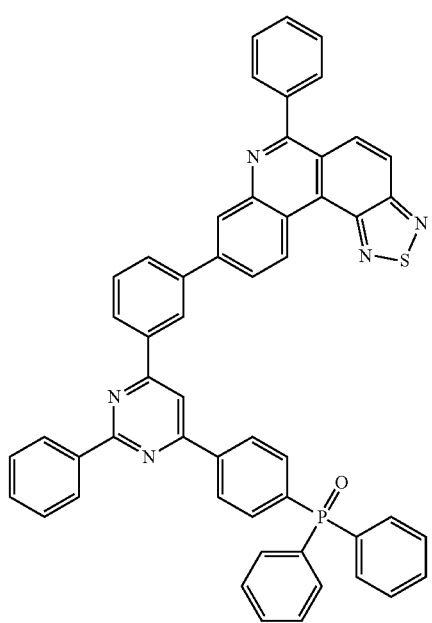

305
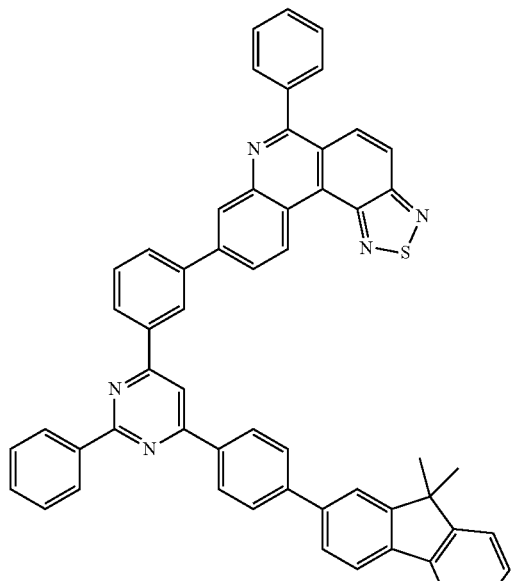
306
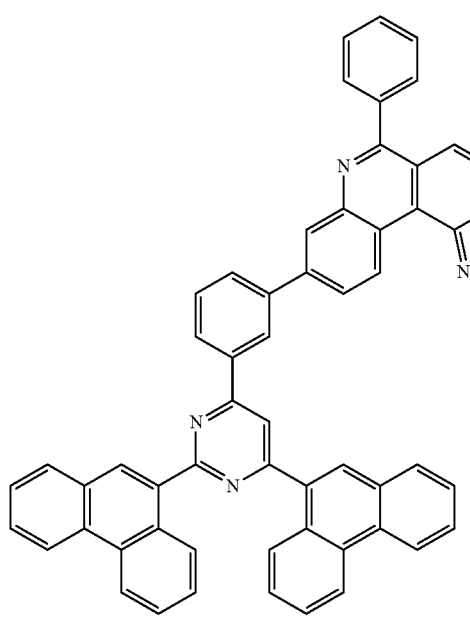
307
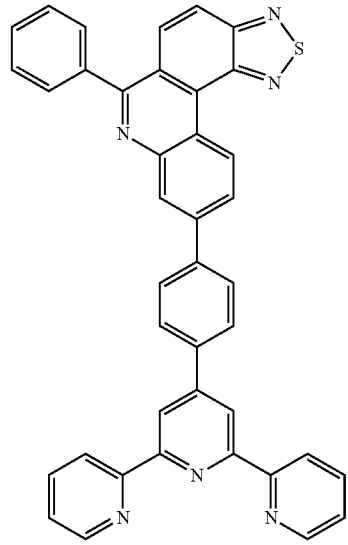
308
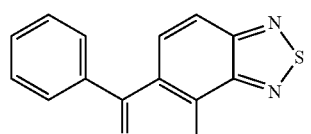
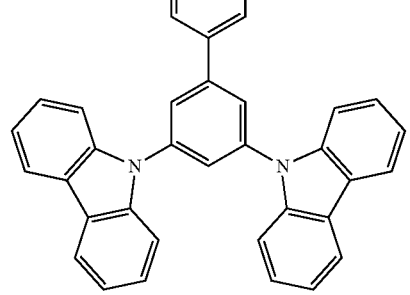
309
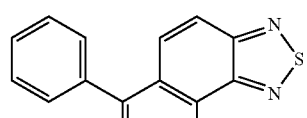
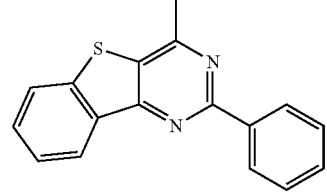

509
-continued
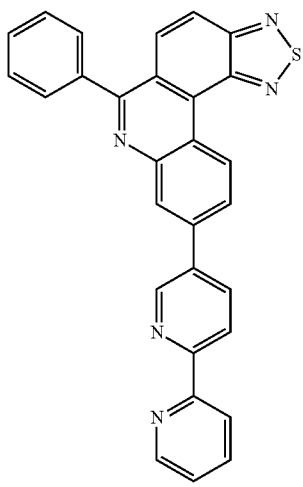
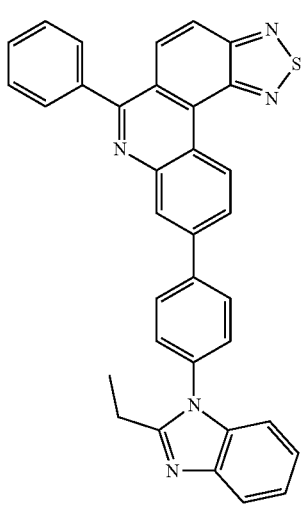
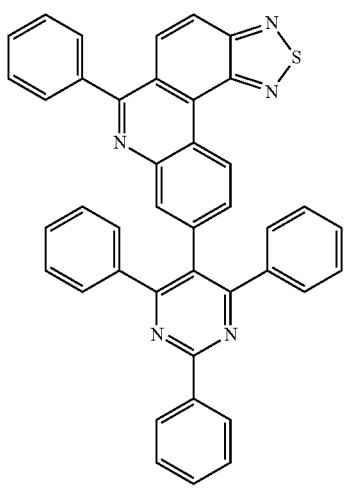
510
-continued
310
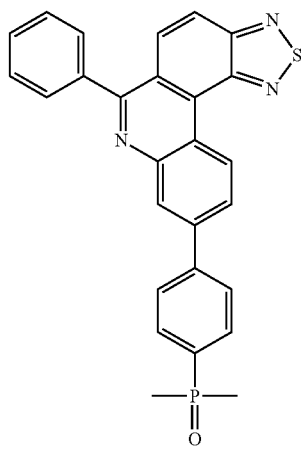
311
313
314
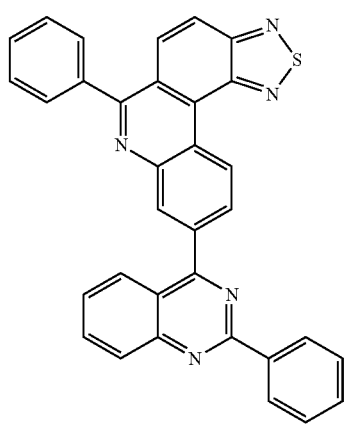
312
315
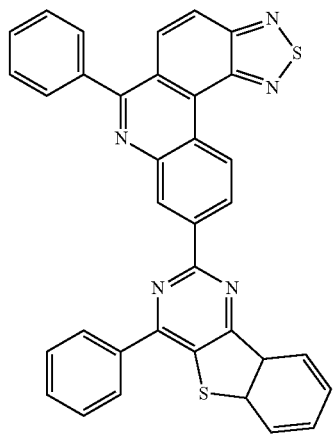

511
-continued
512
-continued
316
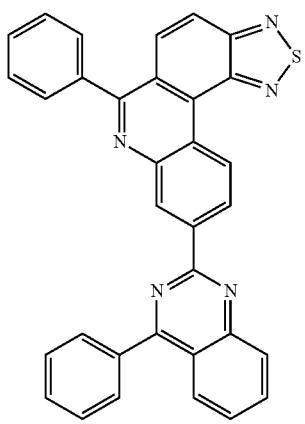
319
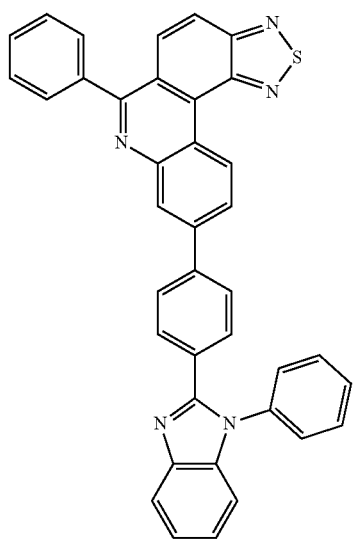
317
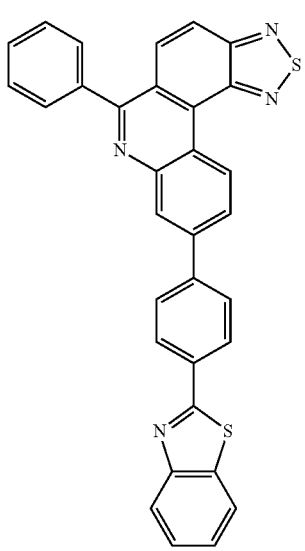
320
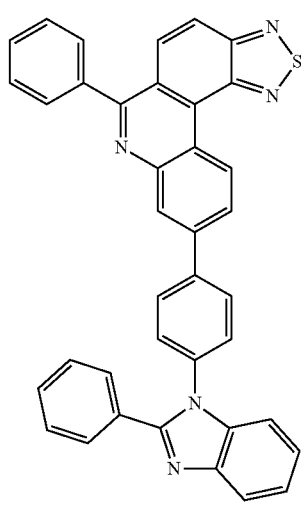
318
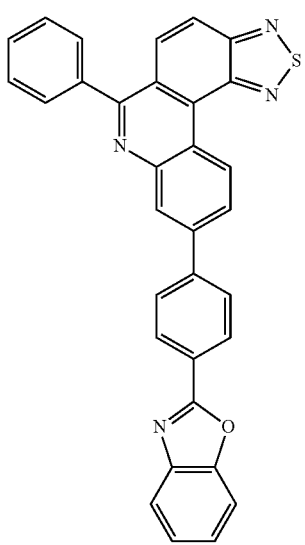
321
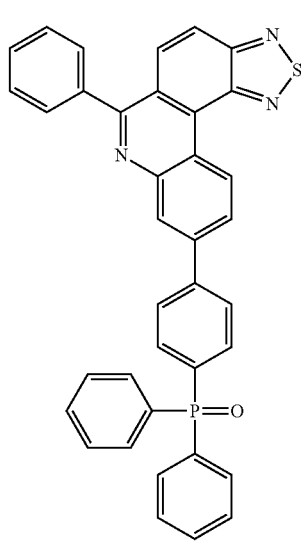

322
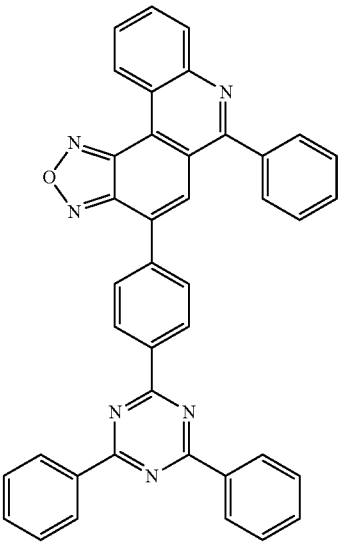
323
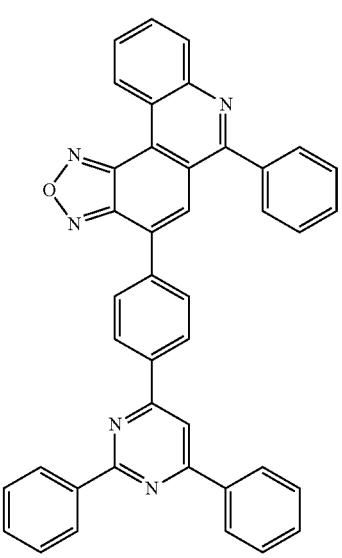
324
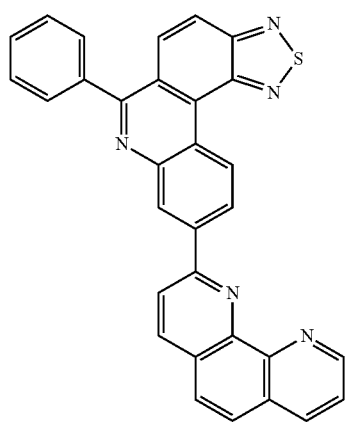
325
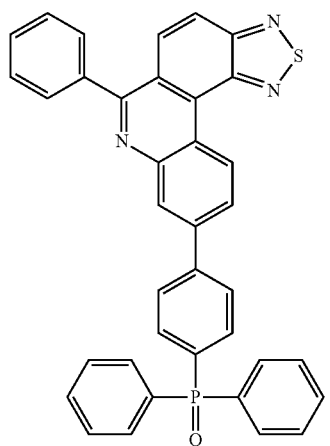
326
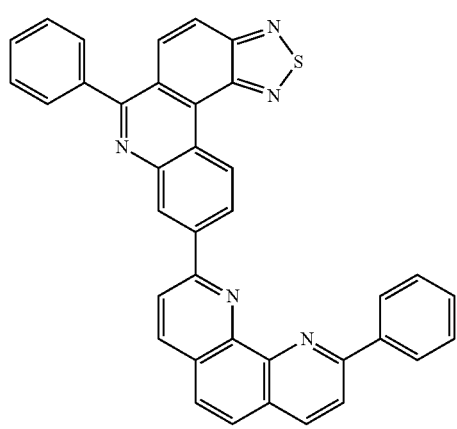
327
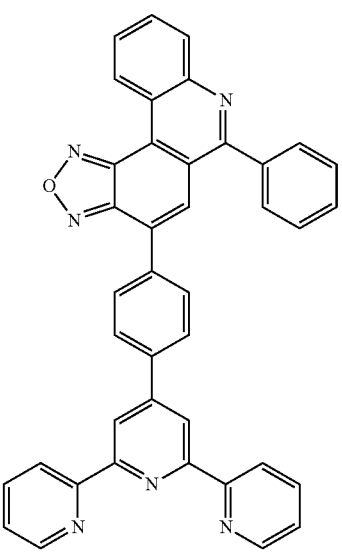

328
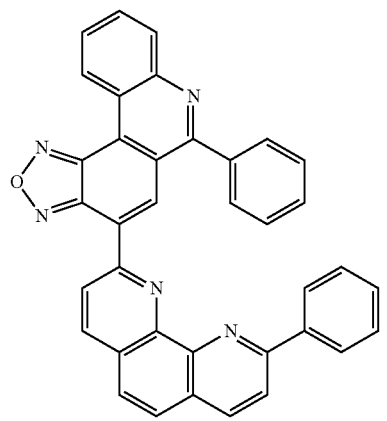
329
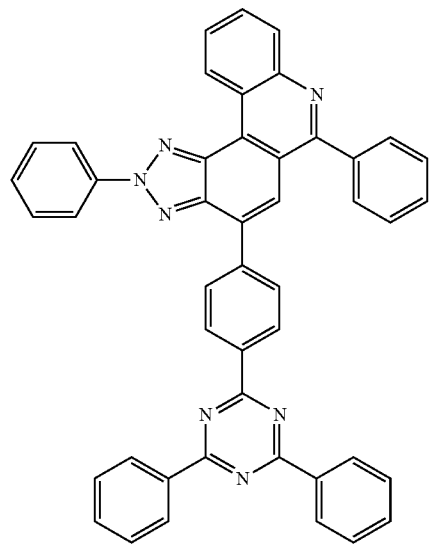
330
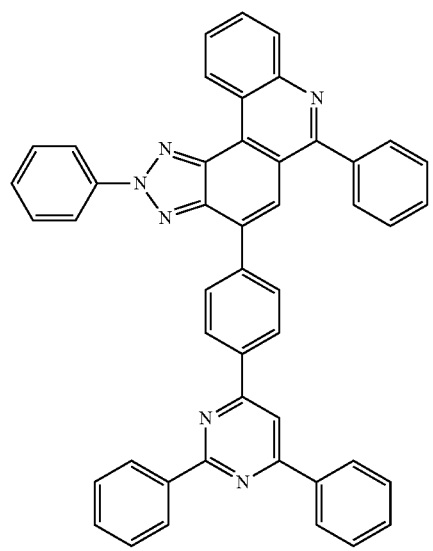
331
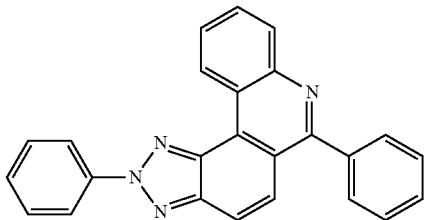
332
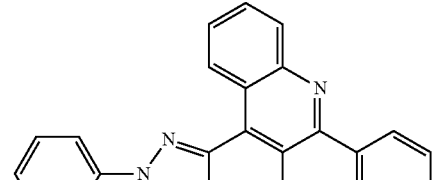
333
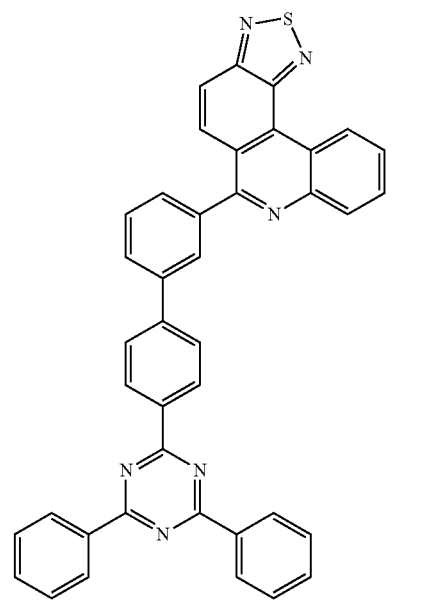

517
-continued
518
-continued
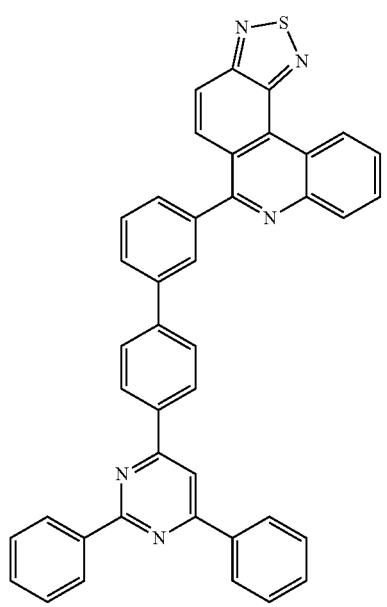
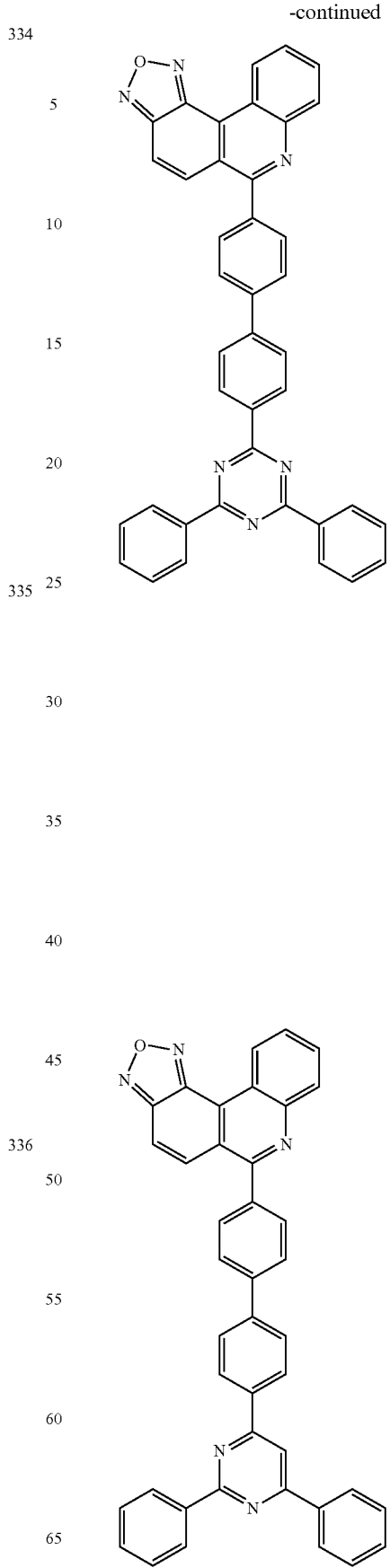

519
-continued
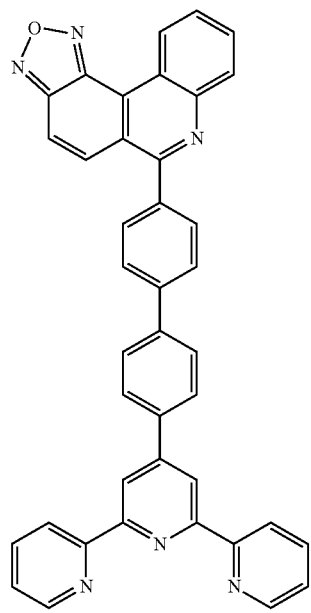
520
-continued
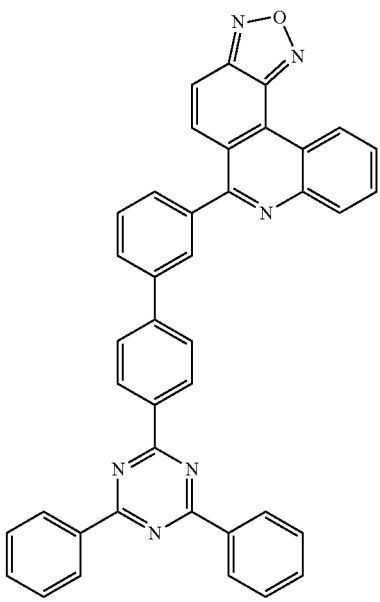
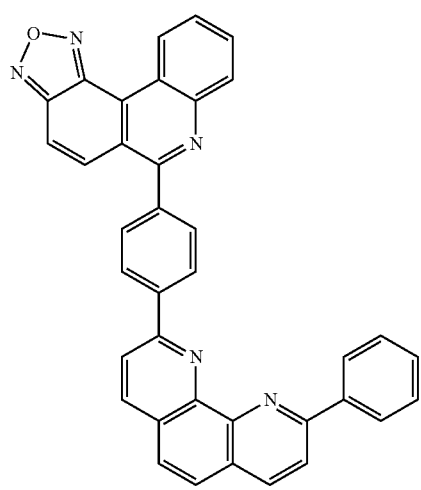
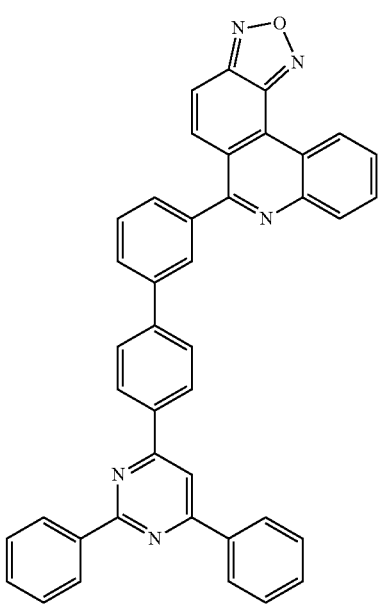

521
-continued
522
-continued
343
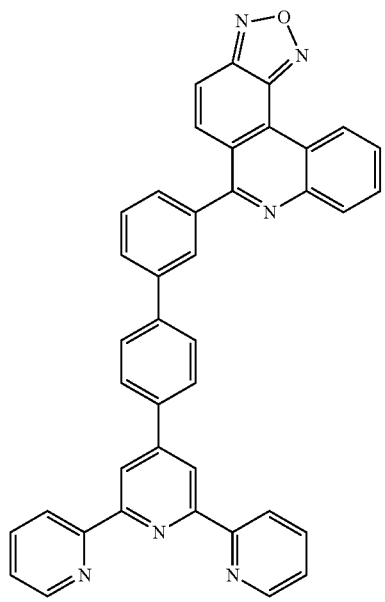
346
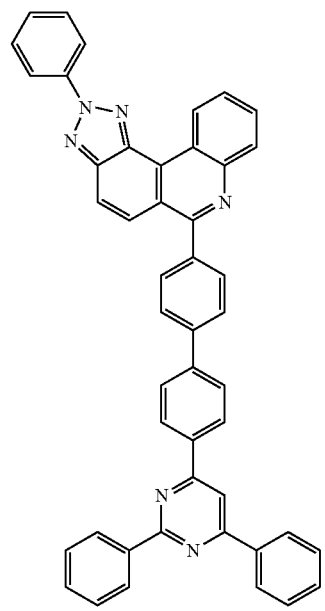
344
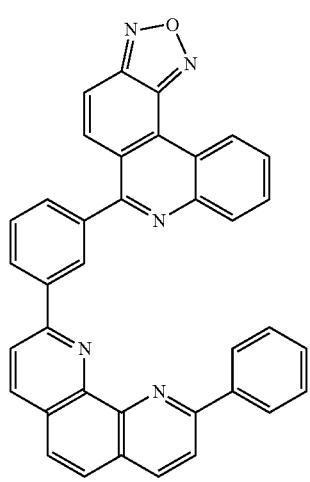
345
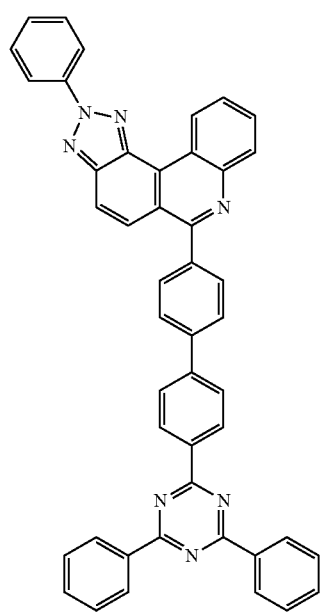
347
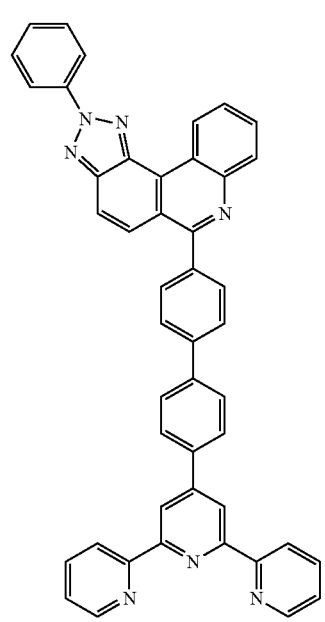

523
-continued
348
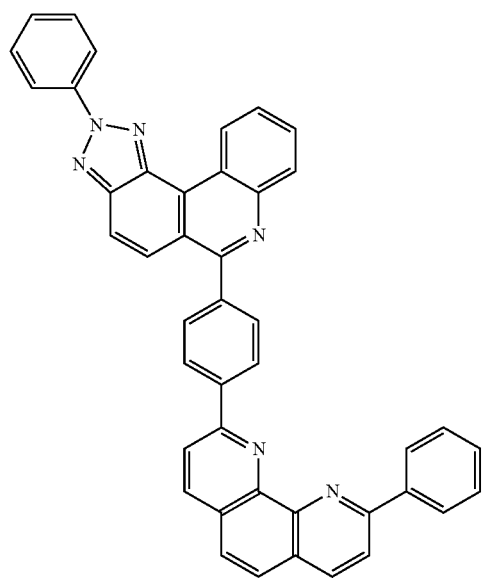
349
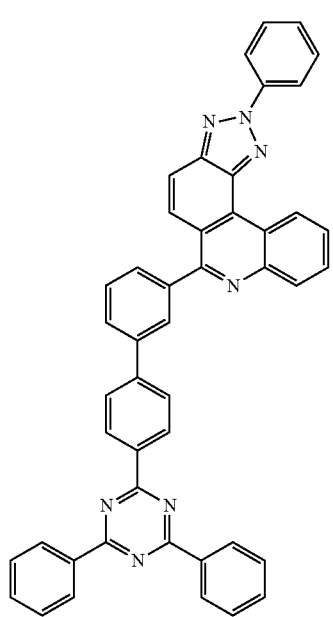
524
-continued
350
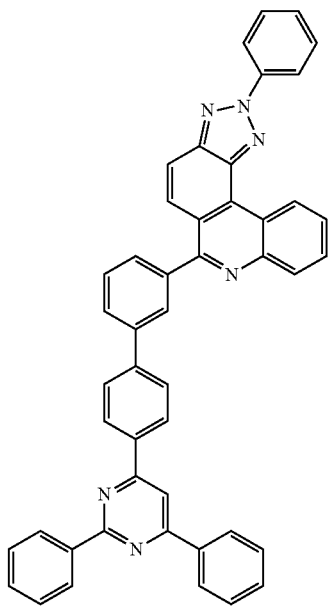
351
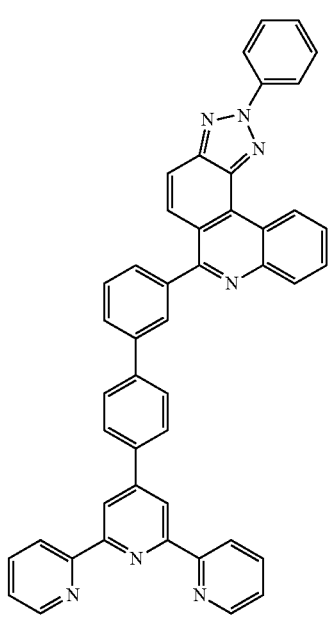

525
-continued
352
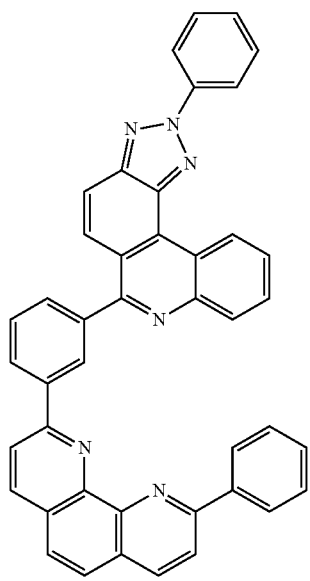
526
-continued
354
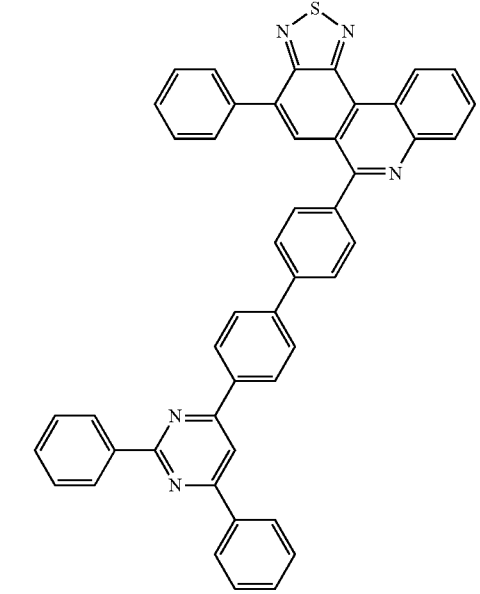
353
355
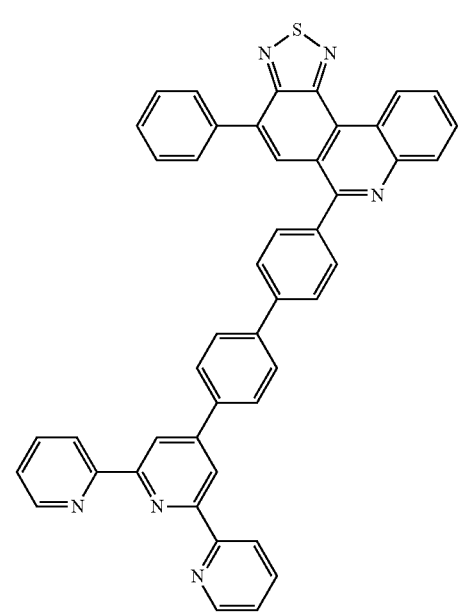

527
-continued
356
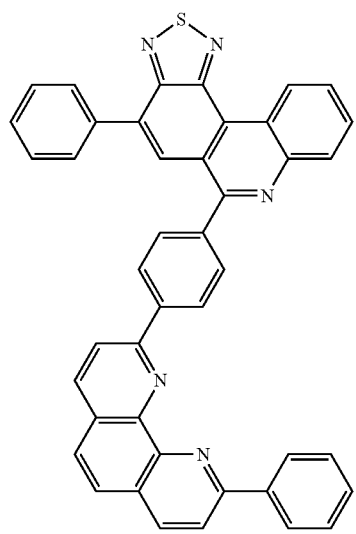
528
-continued
358
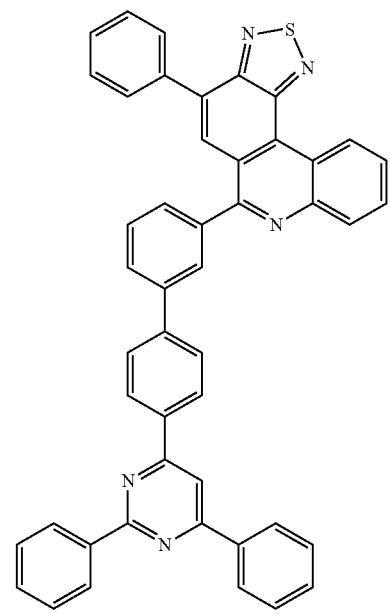
357
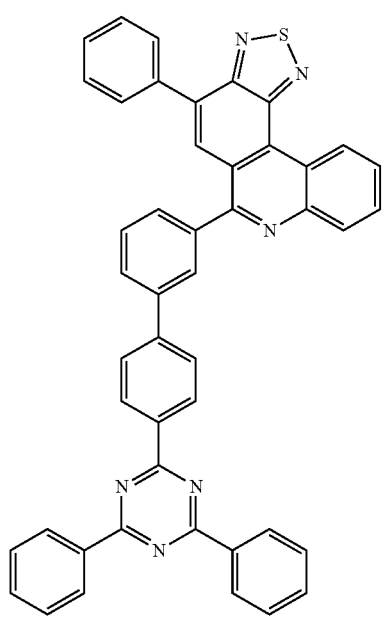
359
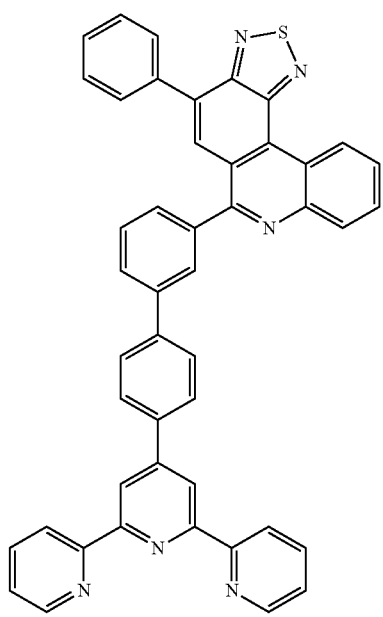

529
-continued
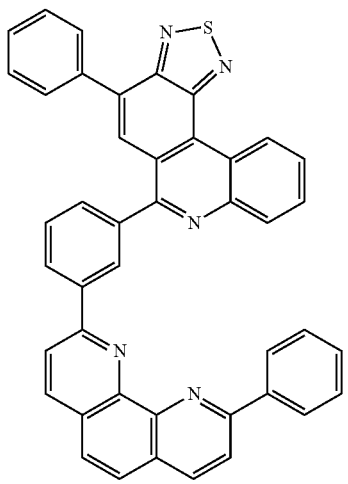
361
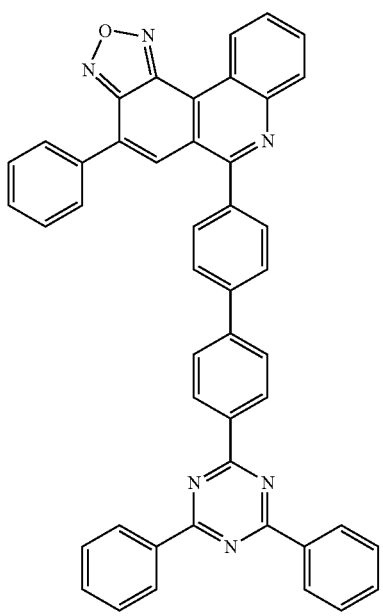
530
-continued
360
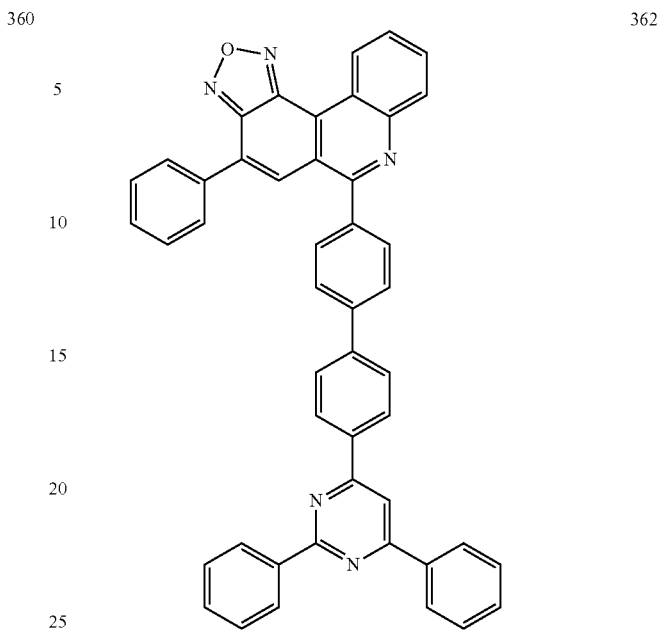
362
363
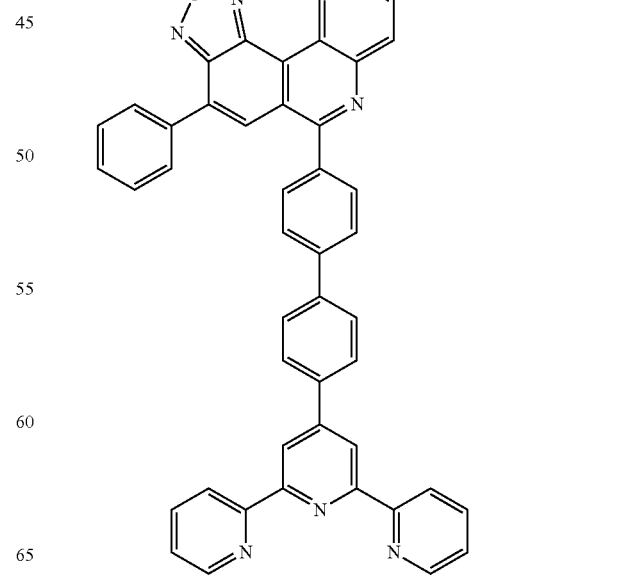

-continued
531
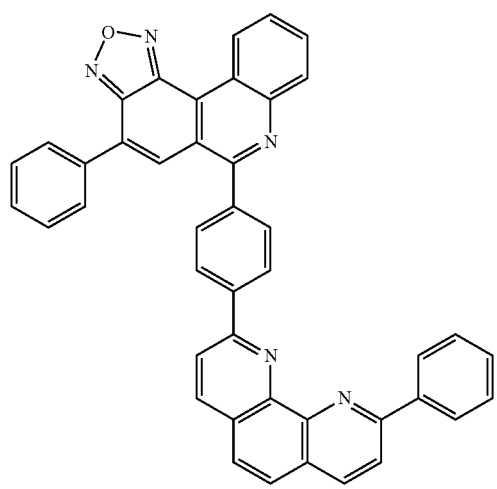
364
532
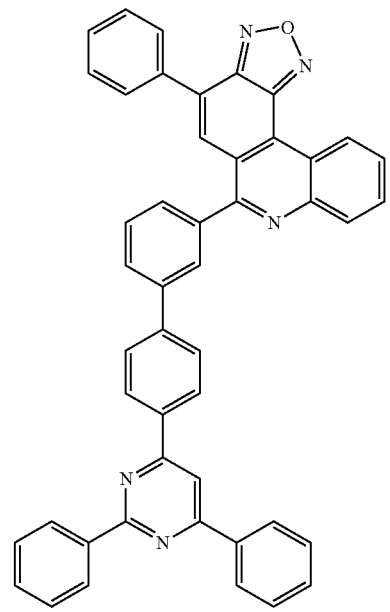
366
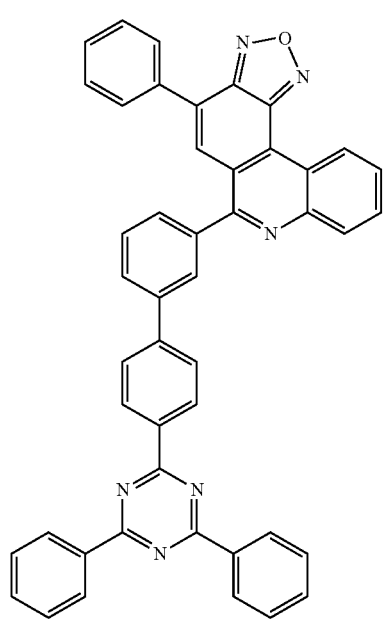
365
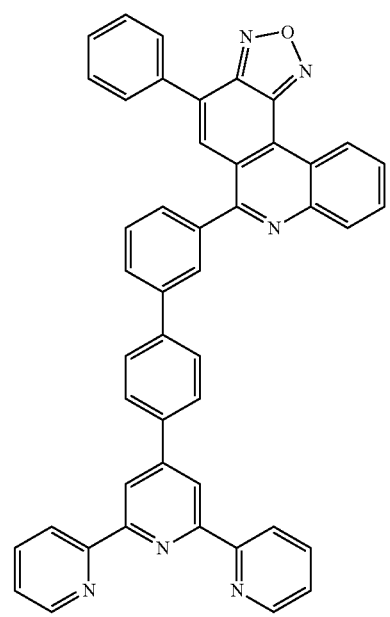
367

533
-continued
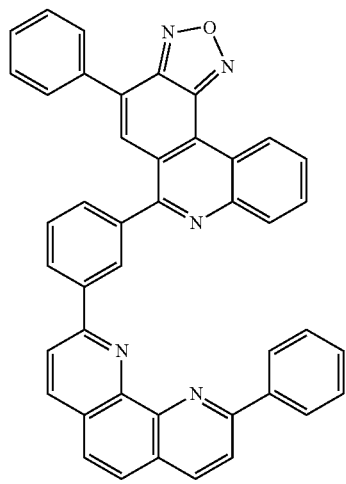
368
534
-continued
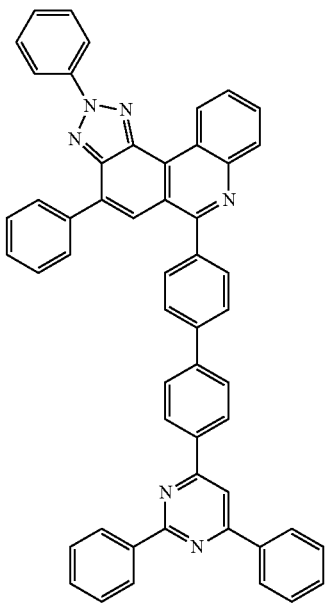
370
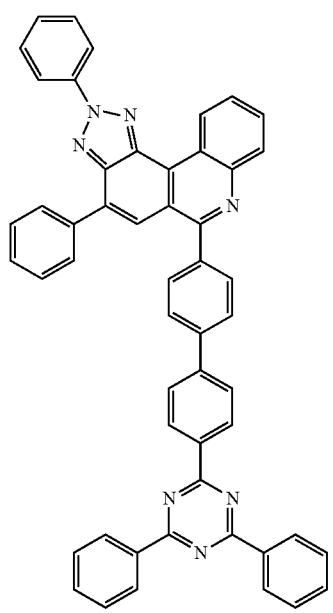
369
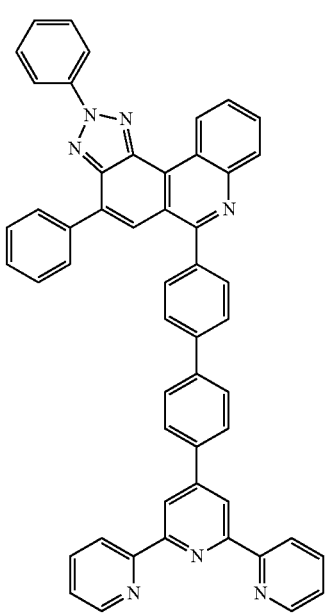
371

535
-continued
372
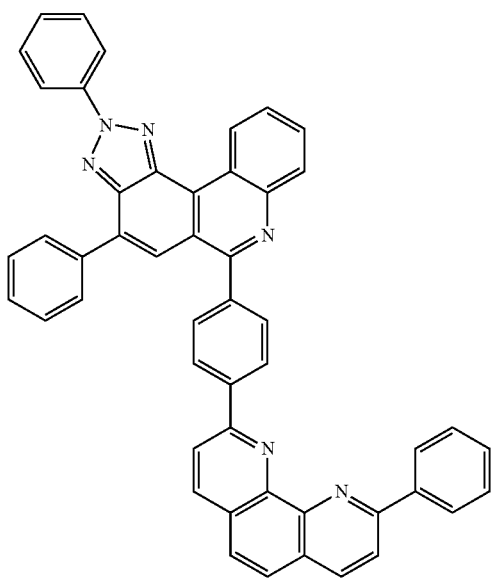
373
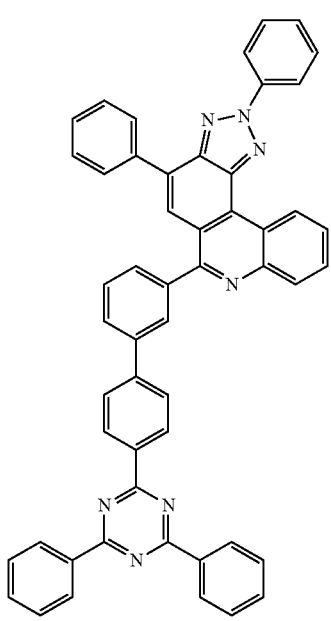
536
-continued
374
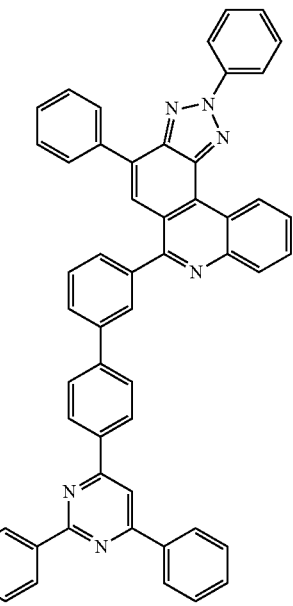
375
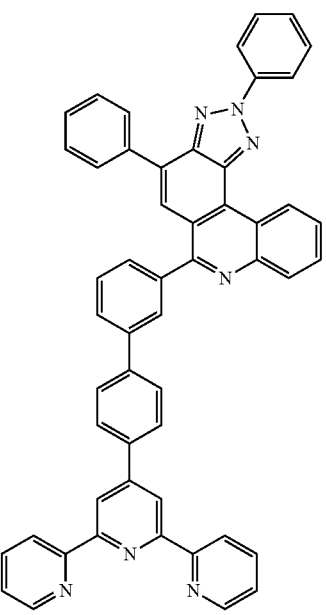

537
-continued
376
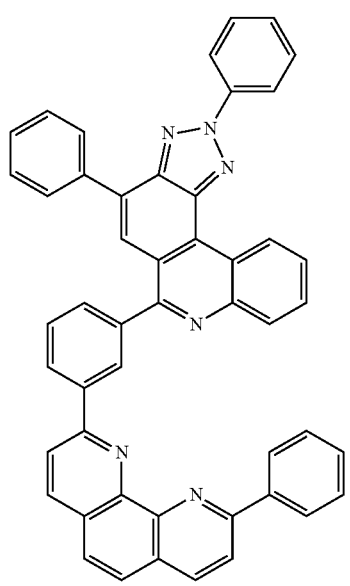
378
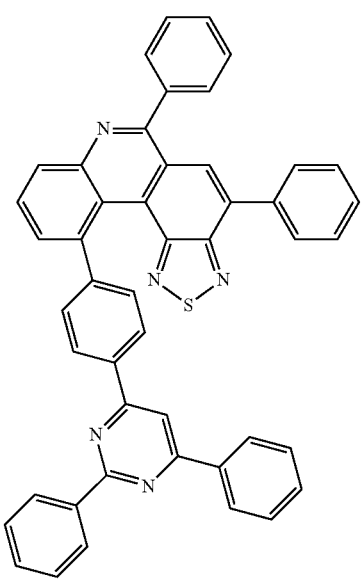
379
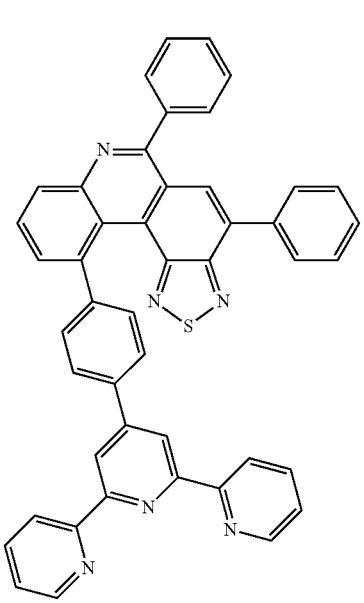
377
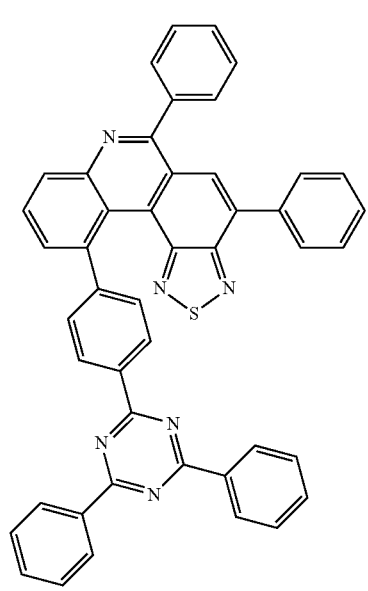
380
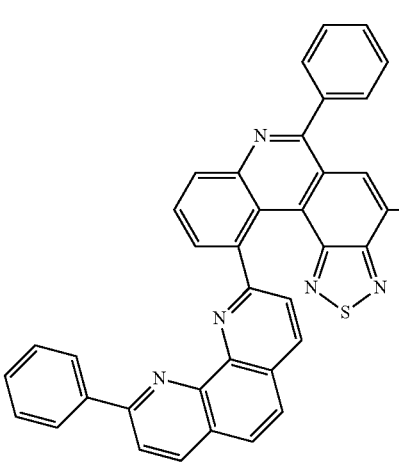

539
-continued
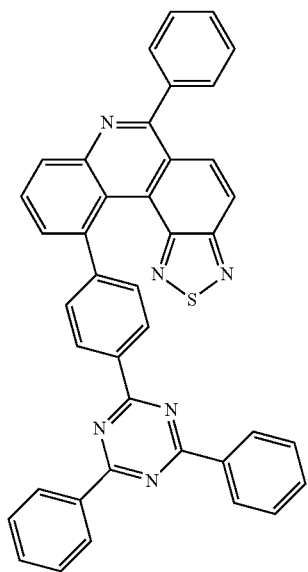
381
540
-continued
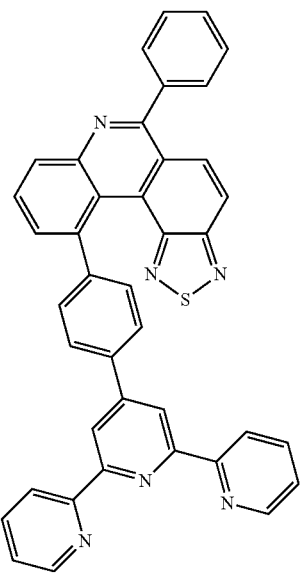
383
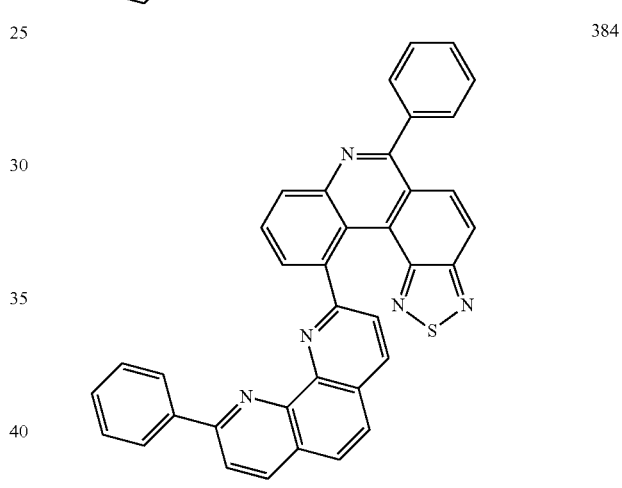
384
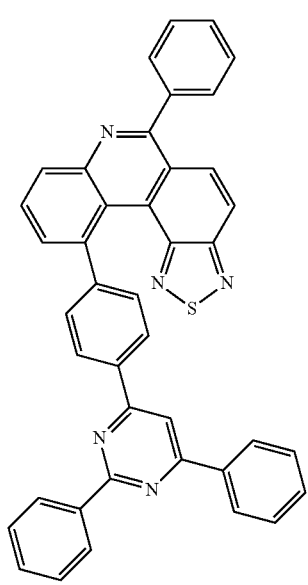
382
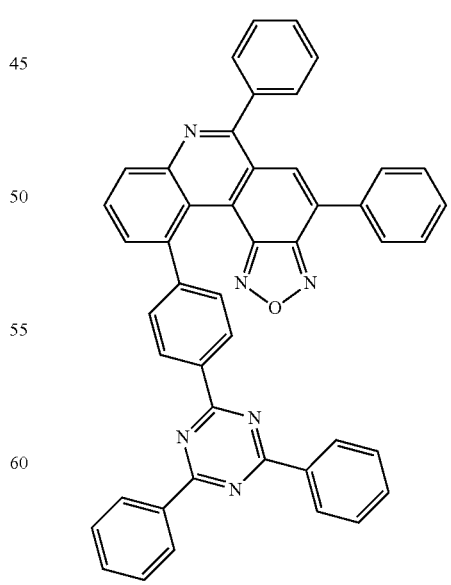
385

541
-continued
386
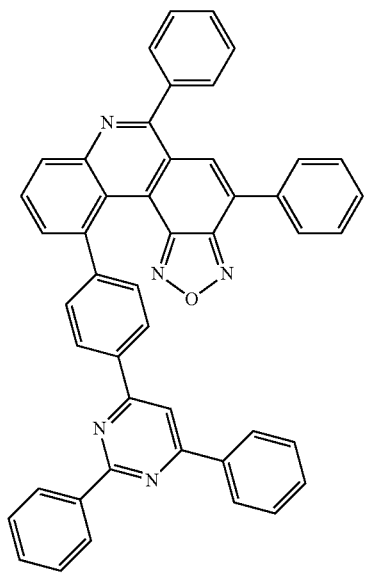
387
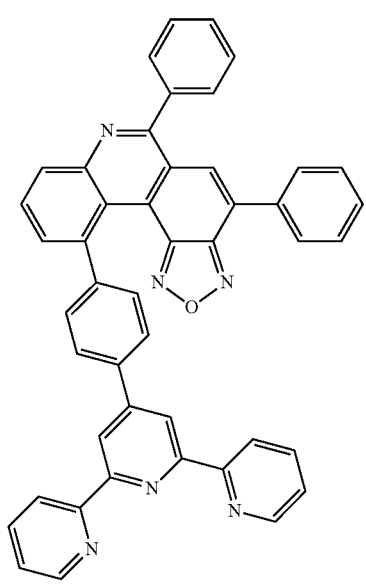
388
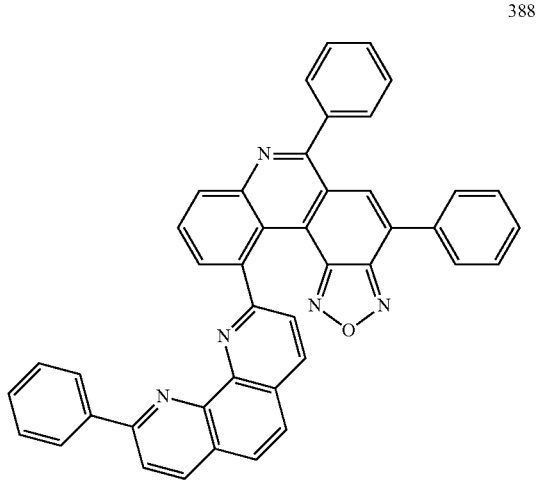 [SMILES: c1ccc(-c2ccc3ccc4ccc(-c5cccc6nc(-c7ccccc7)c7cc(-c8ccccc8)c8nn(-c9ccccc9)nc8c7c56)nc4c3n2)cc1]
542
-continued
389
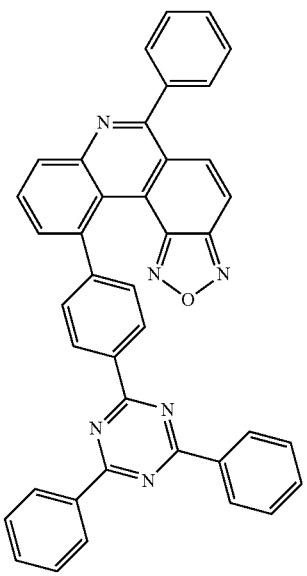
390
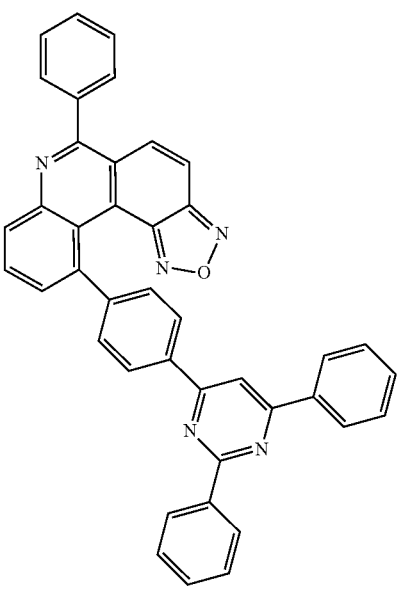

-continued
391
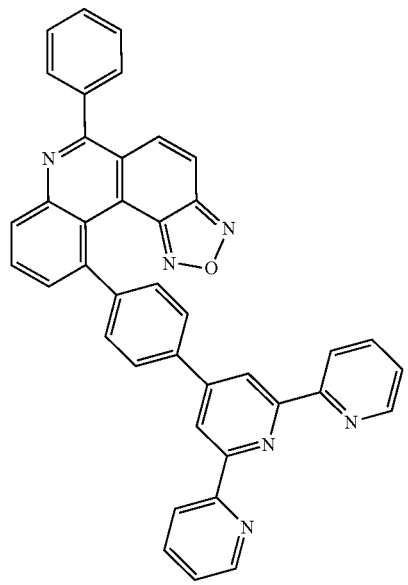
392
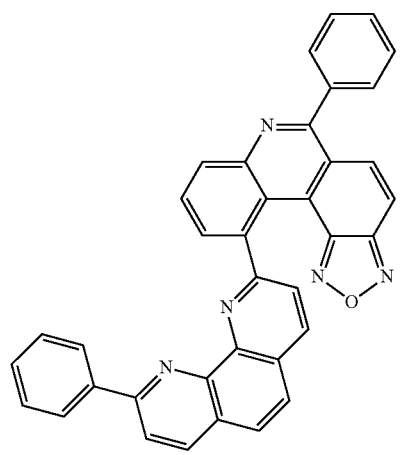
393
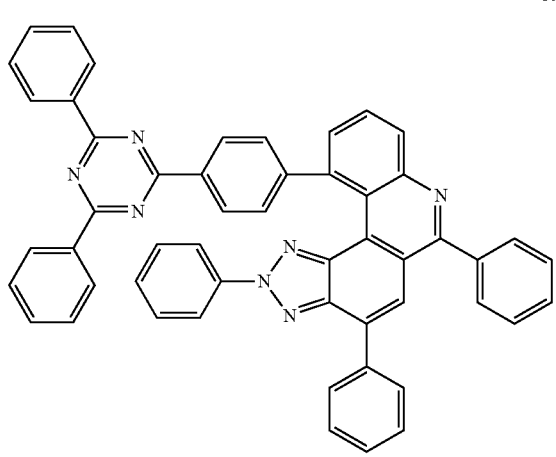
-continued
394
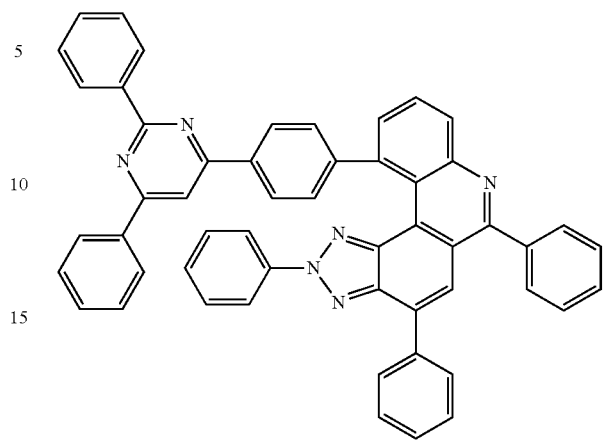
395
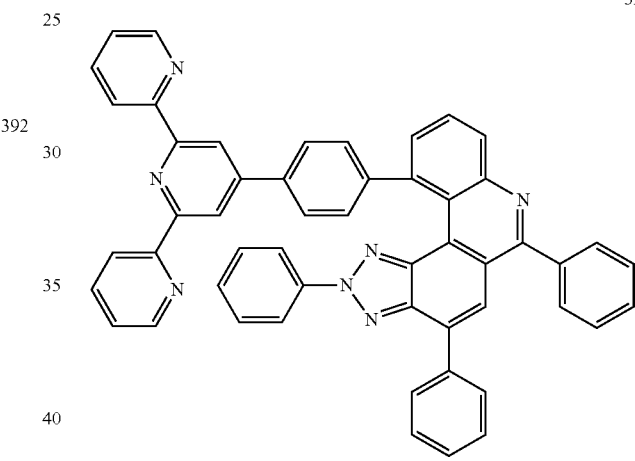
396
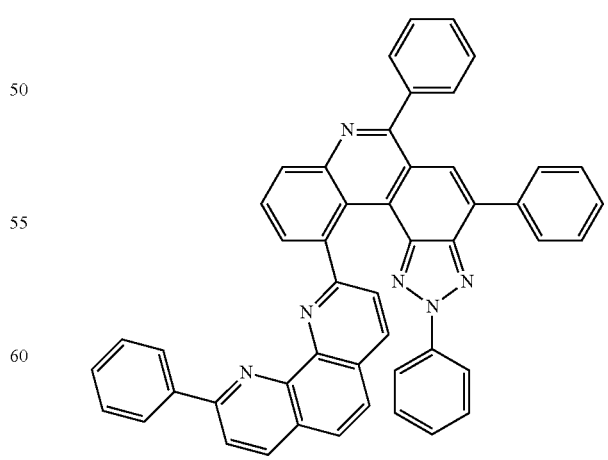

-continued
397
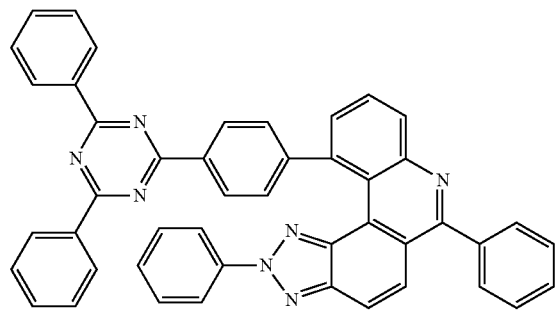
398
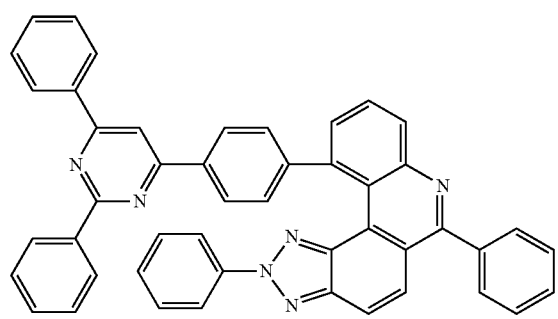
399
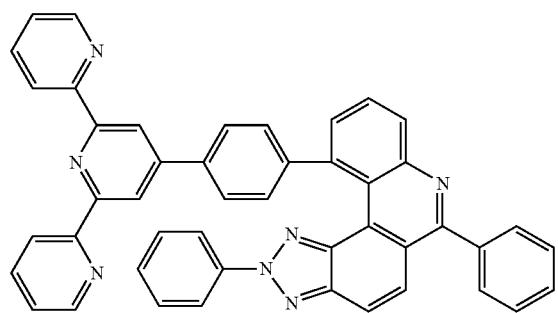
400
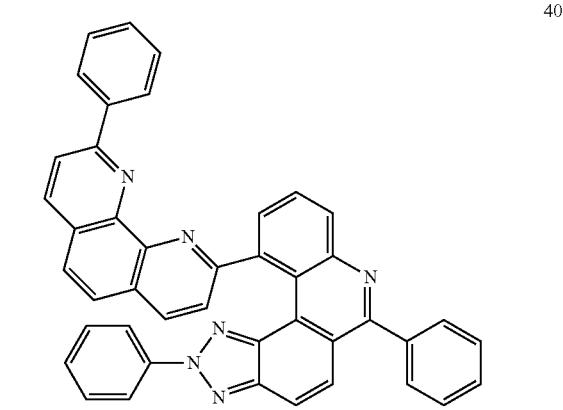
-continued
401
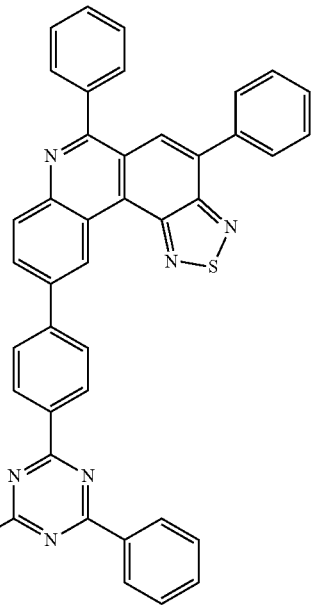
402
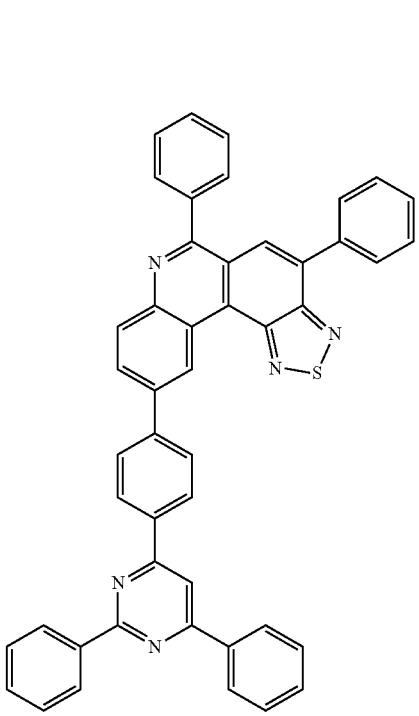

547
-continued
548
-continued
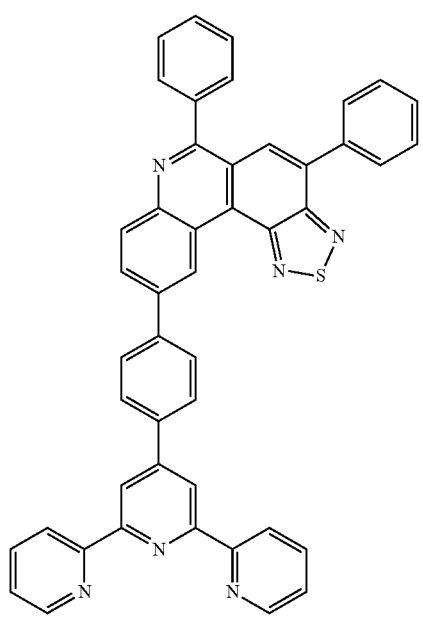
403
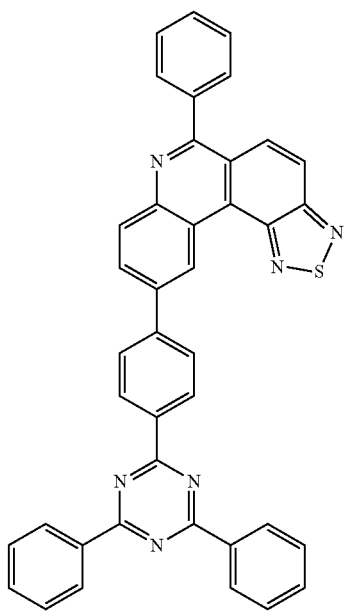
405
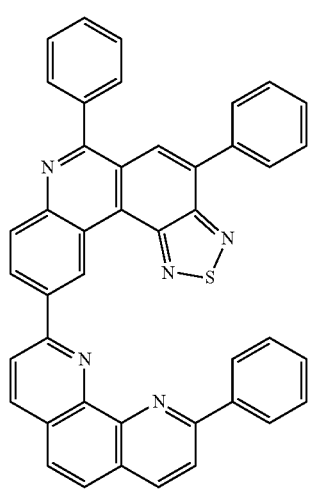
404
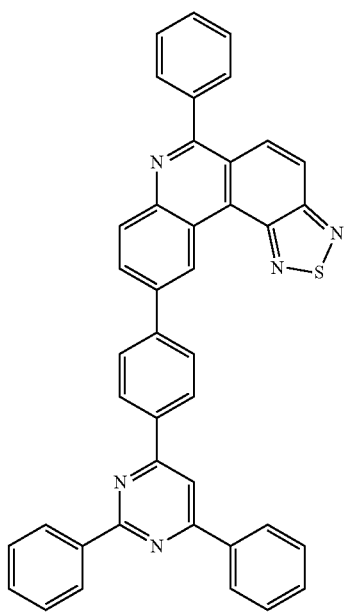
406

549
-continued
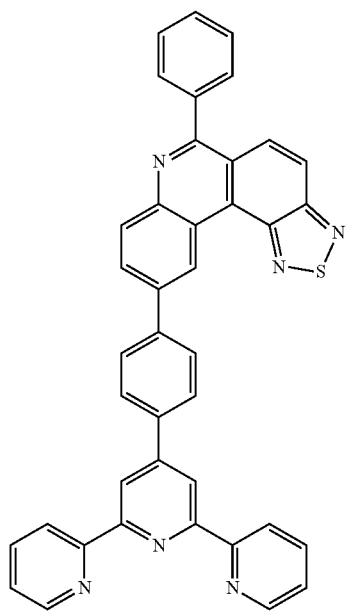
407
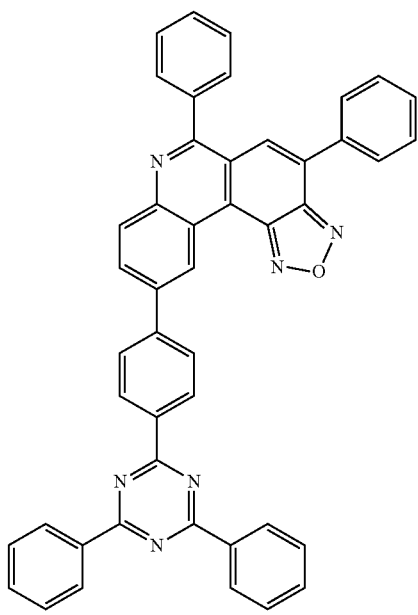
550
-continued
409
408
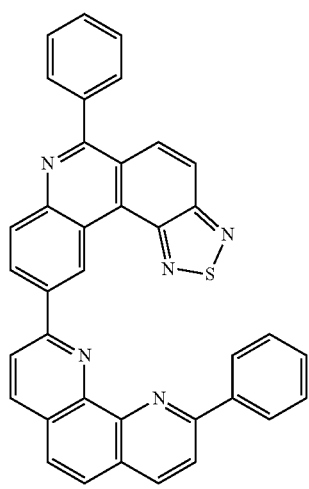
410
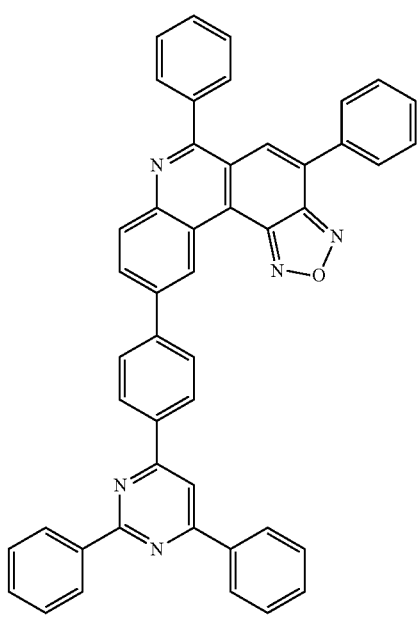

411
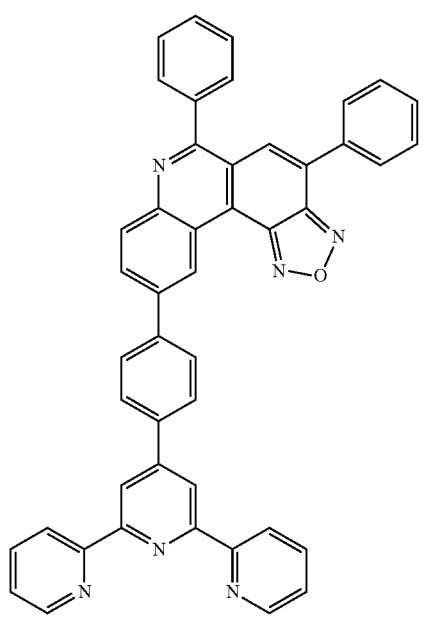
412
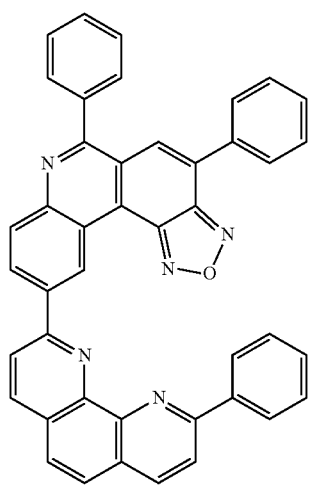
413
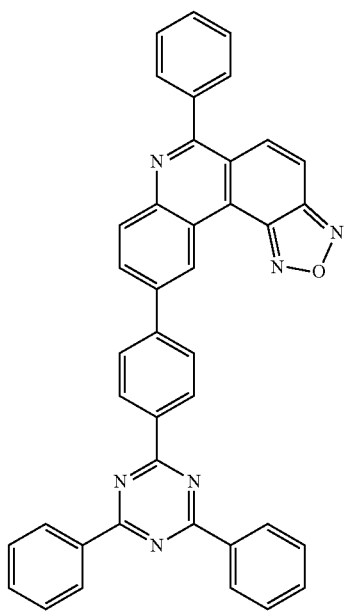
414
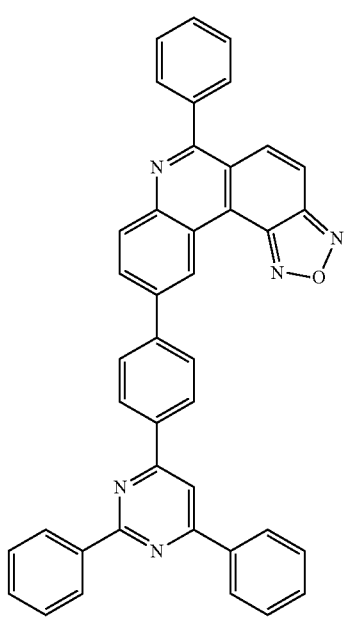

553
-continued
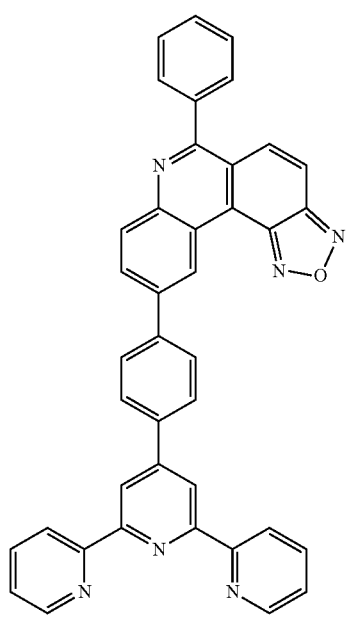
415
554
-continued
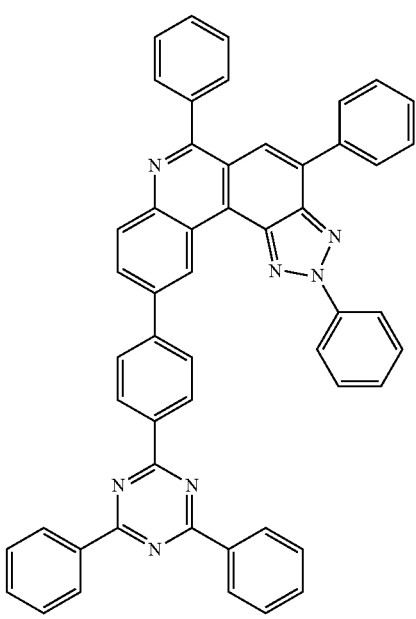
417
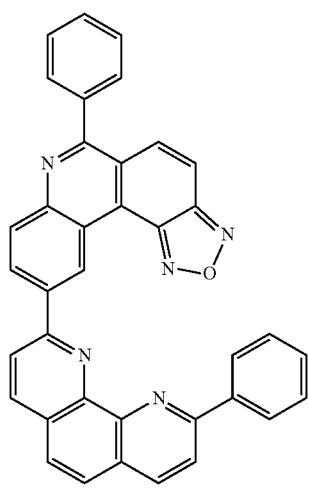
416
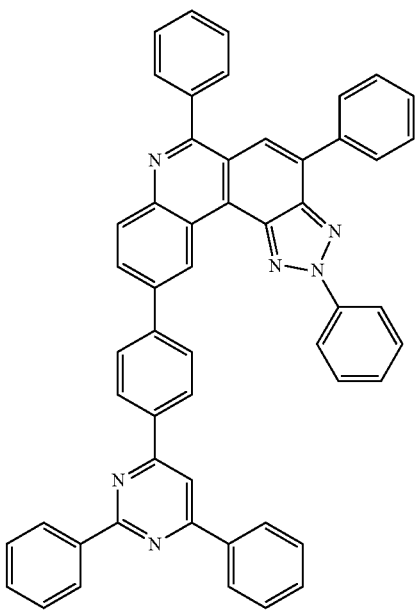
418

555
-continued
419
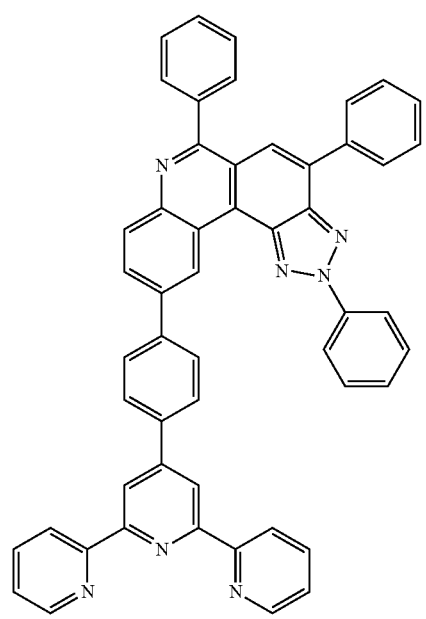
421
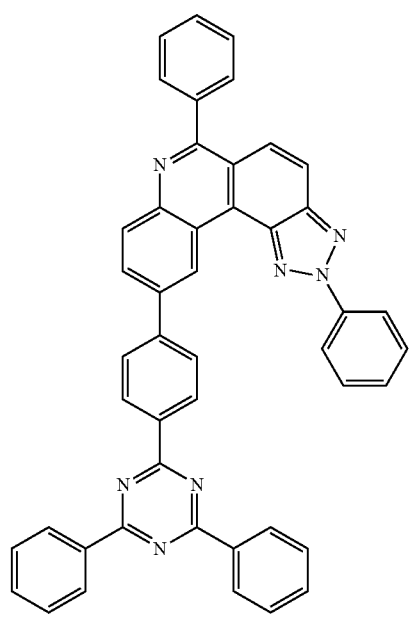
420
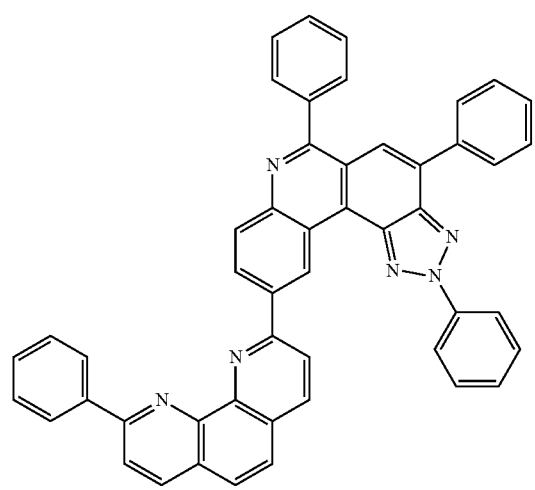
422
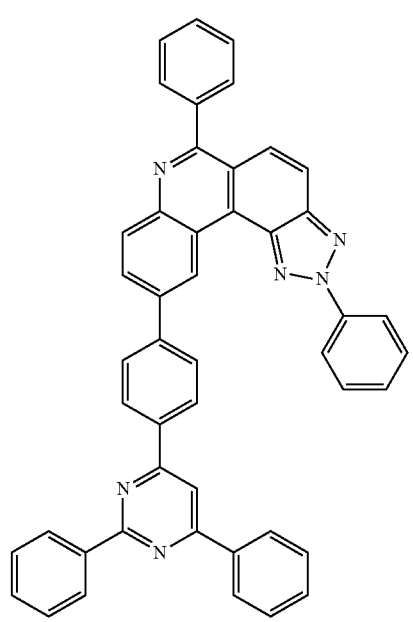

-continued
423
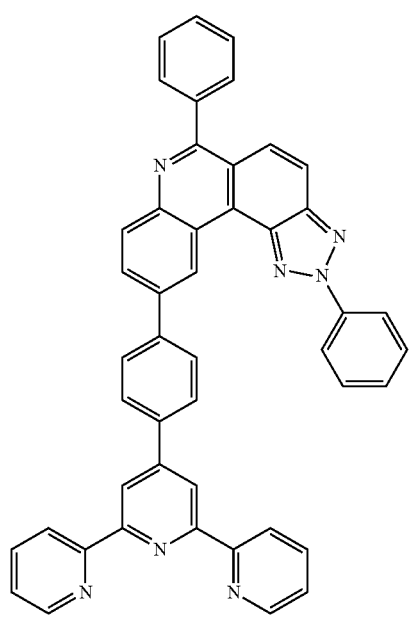
424
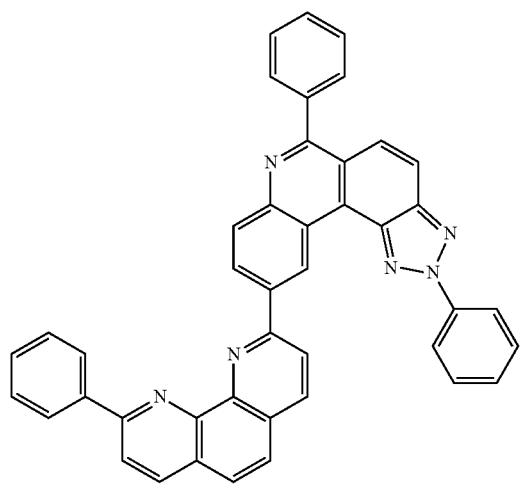
-continued
425
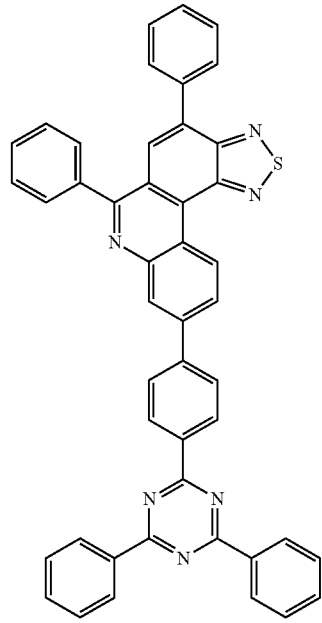
426
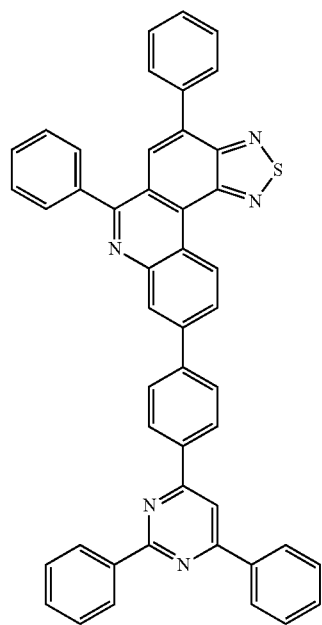

559
-continued
560
-continued
427
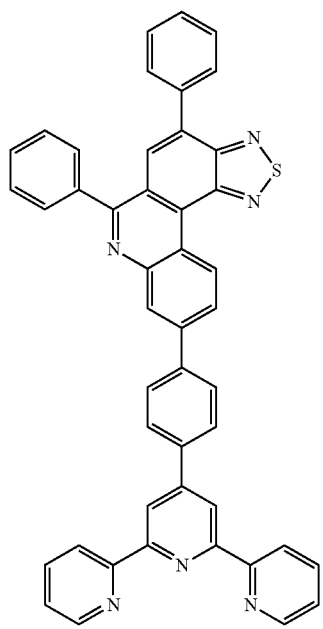
429
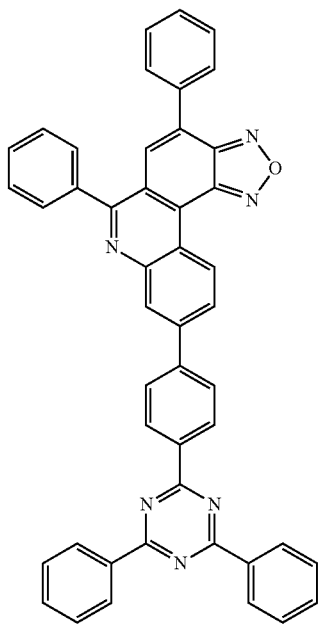
428
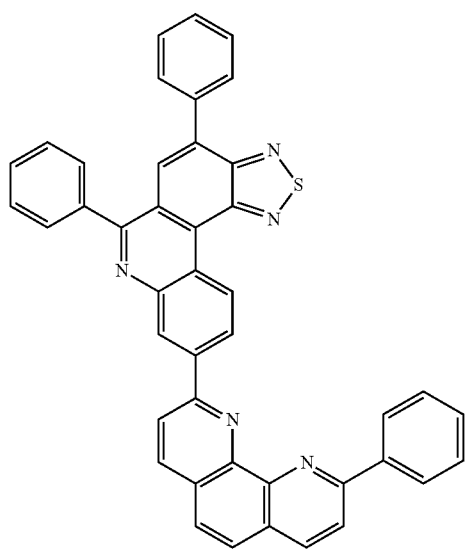
430
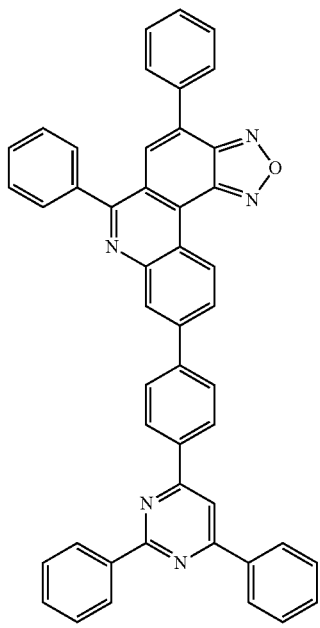

561
-continued
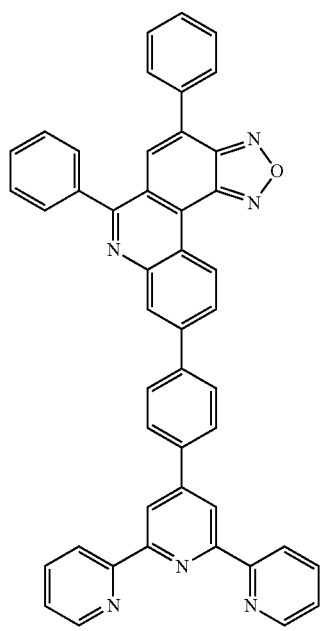
431
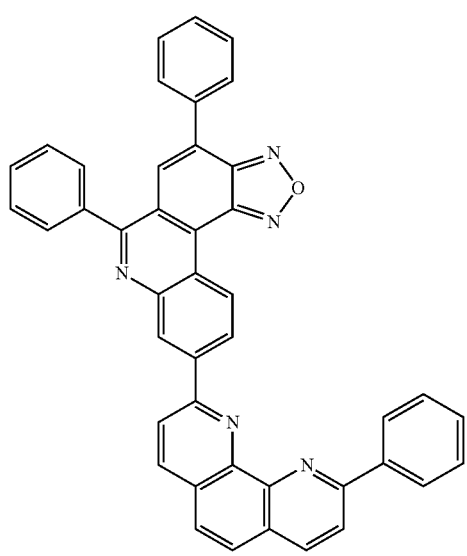
432
562
-continued
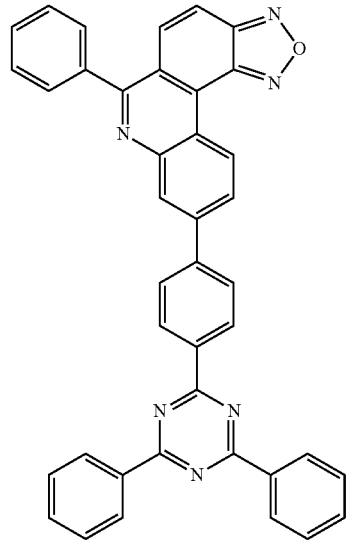
433
434
435
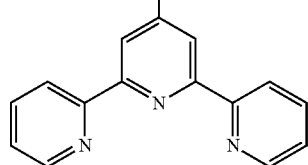

563
-continued
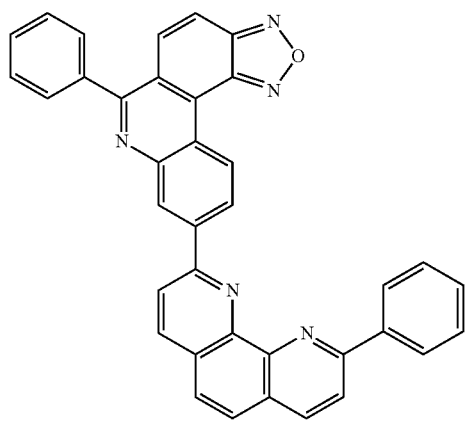
436
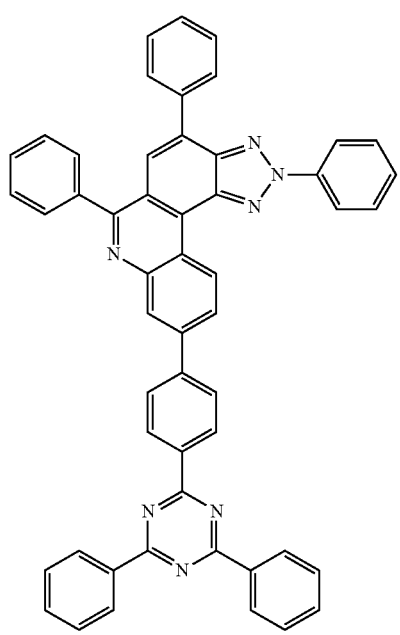
437
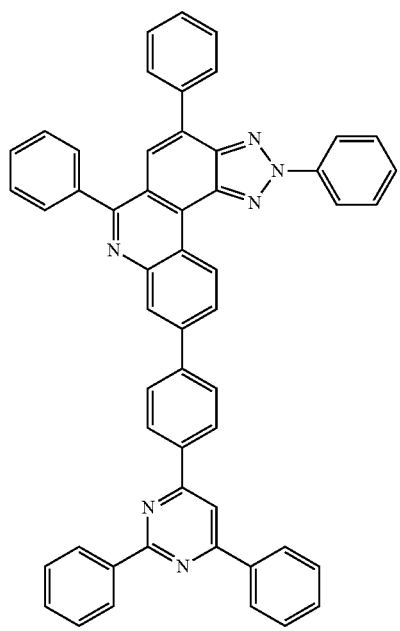
438
564
-continued
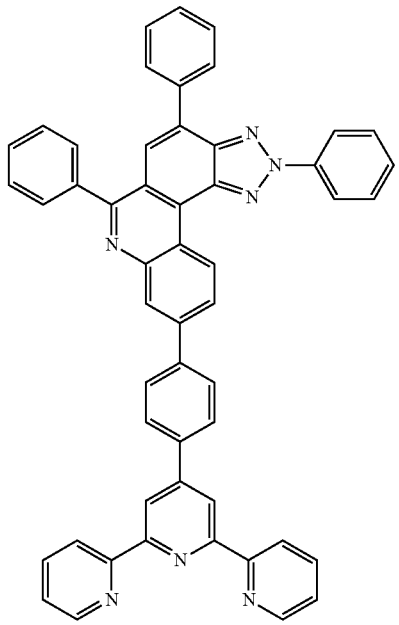
439
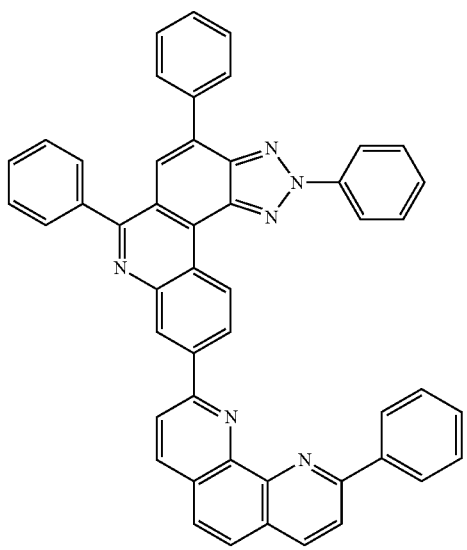
440

565
-continued
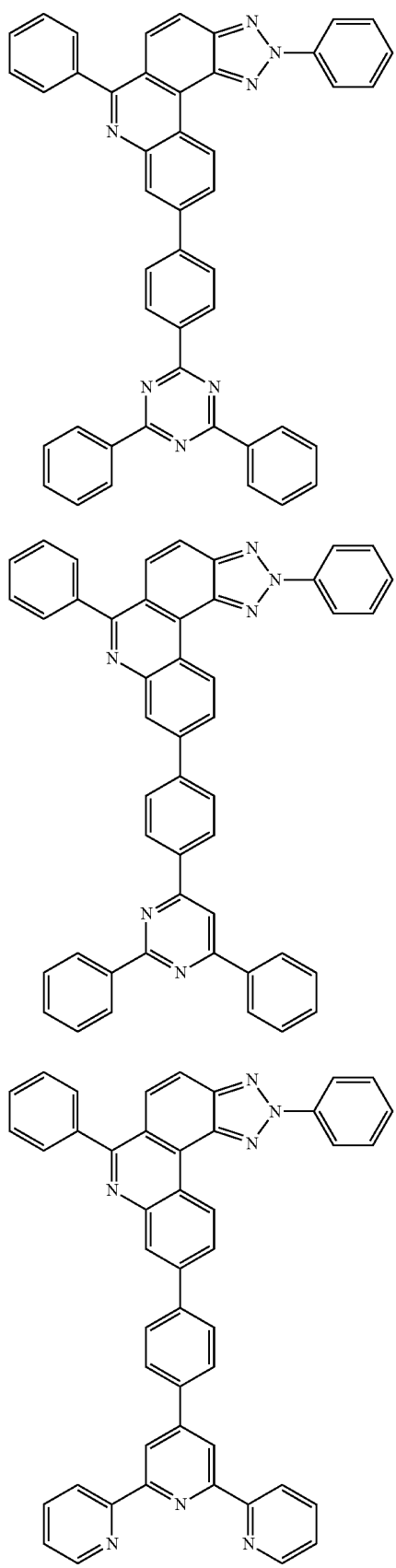
566
-continued
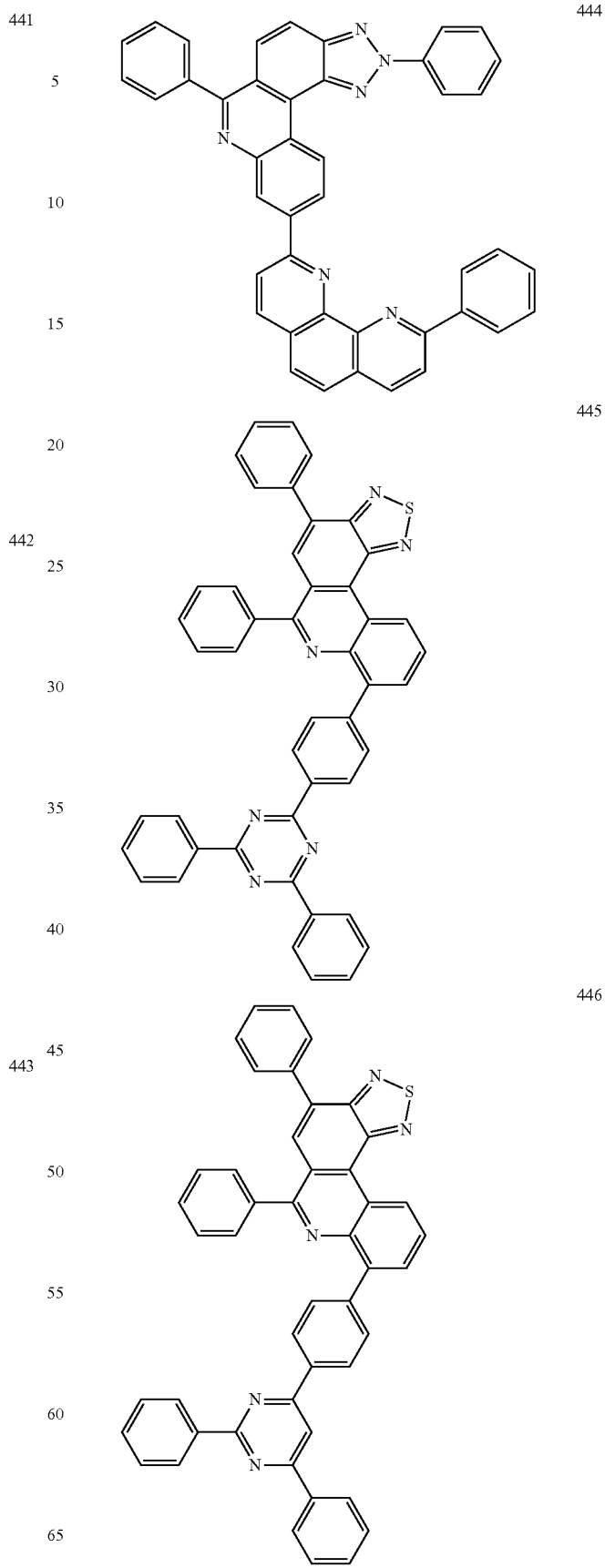

567
-continued
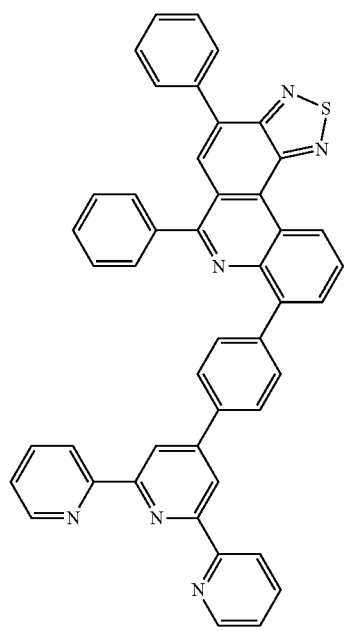
568
-continued
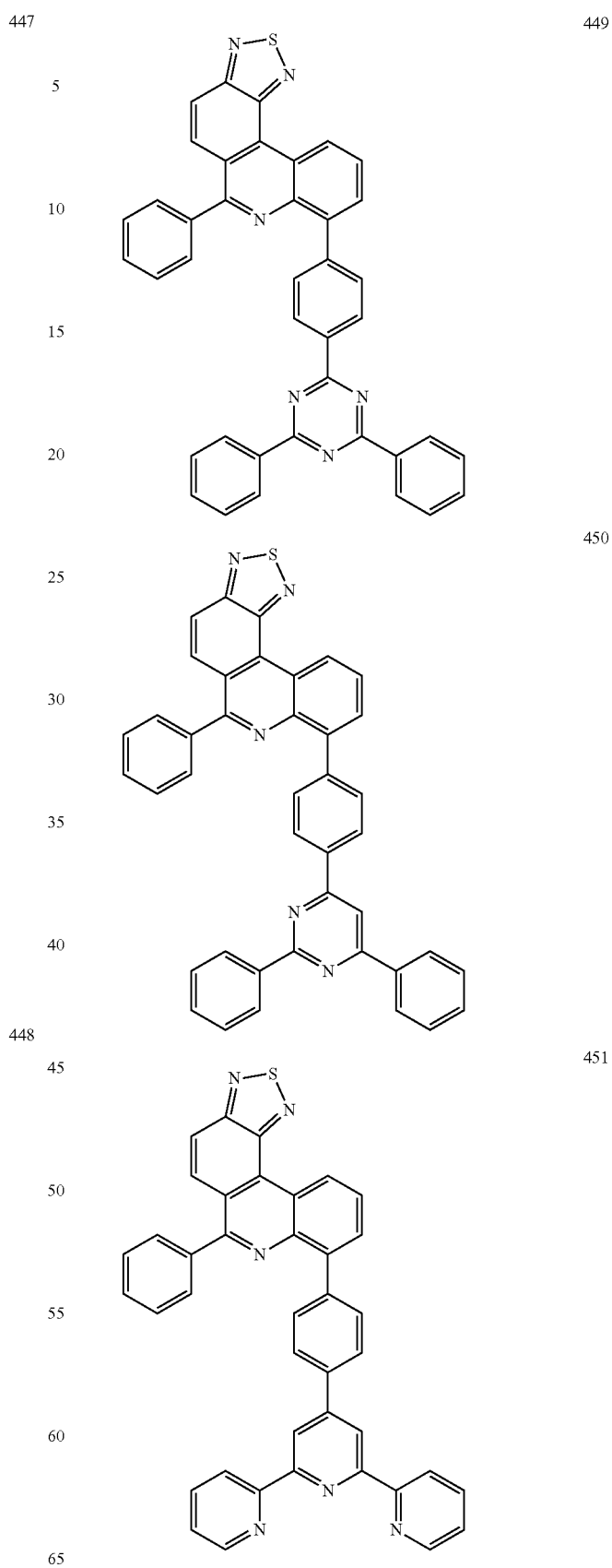

569
-continued
452
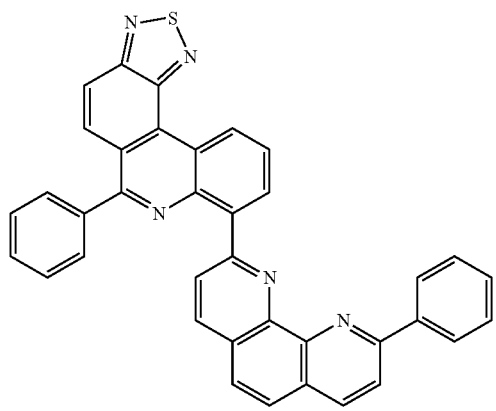
453
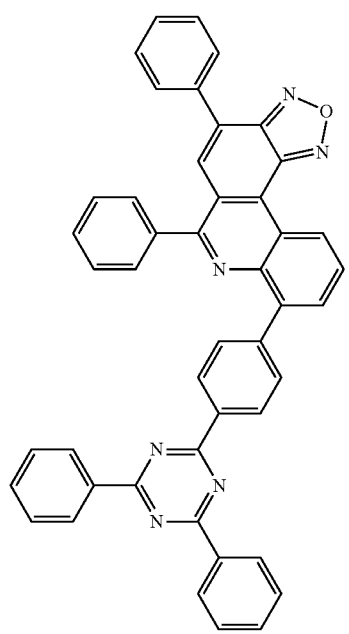
454
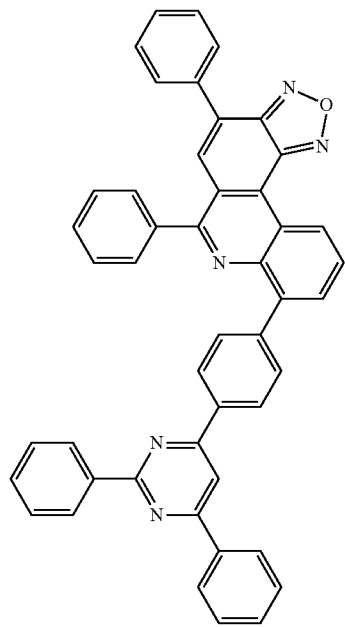
570
-continued
455
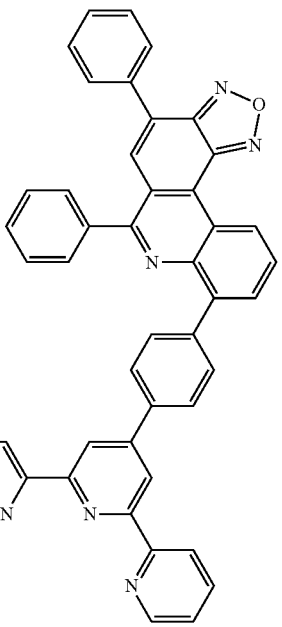
456
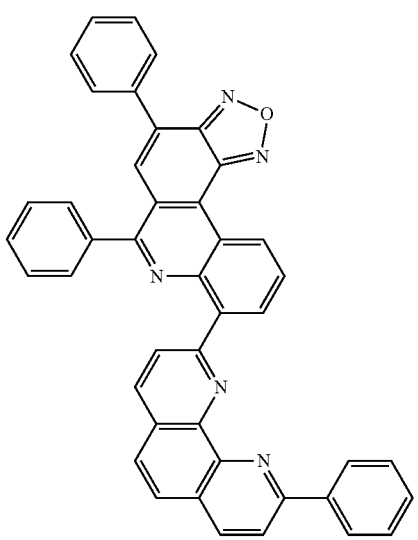

571
-continued
572
-continued
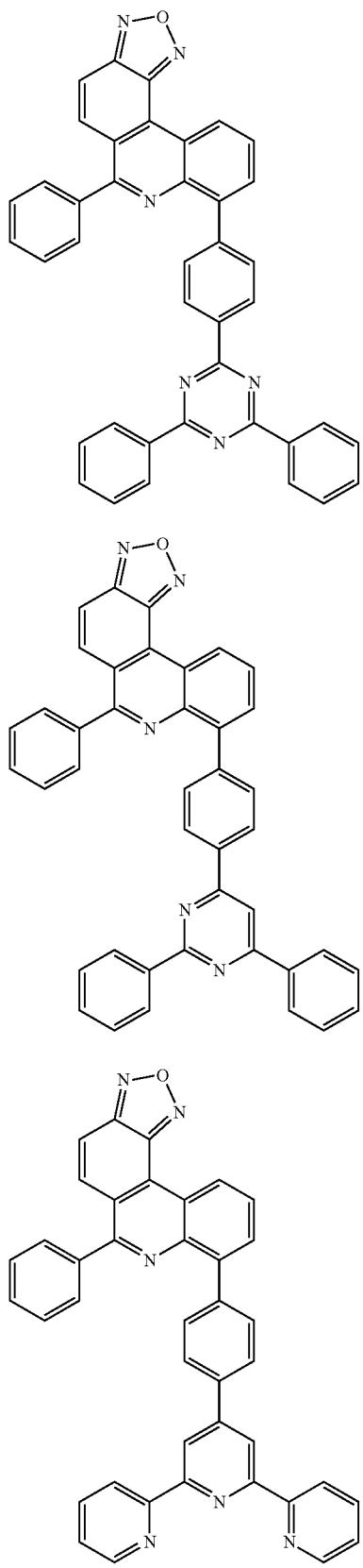
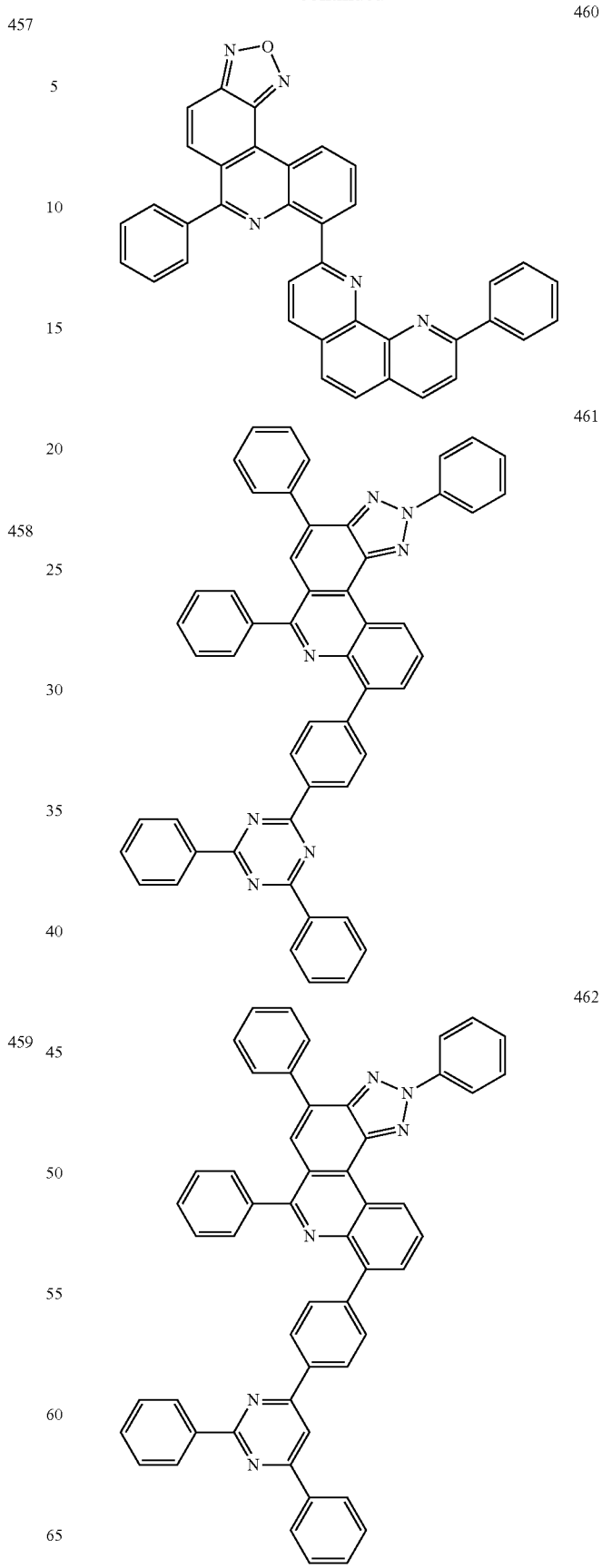

573
-continued
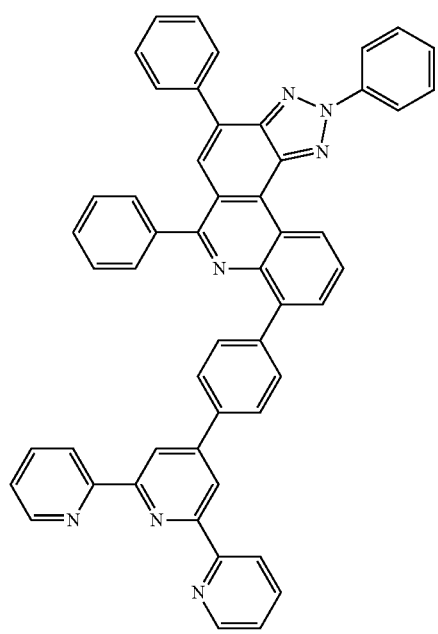
463
574
-continued
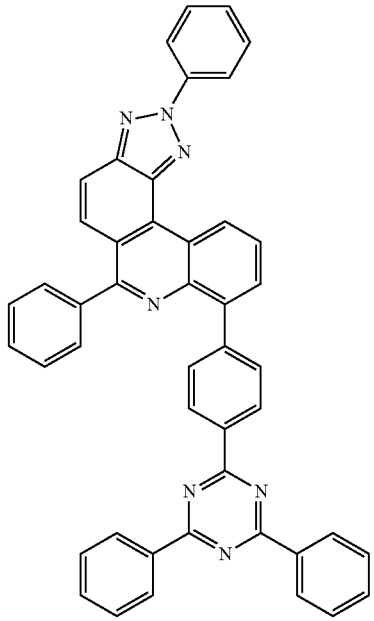
465
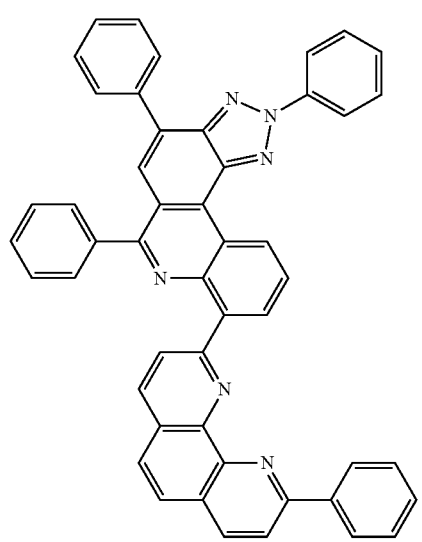
464
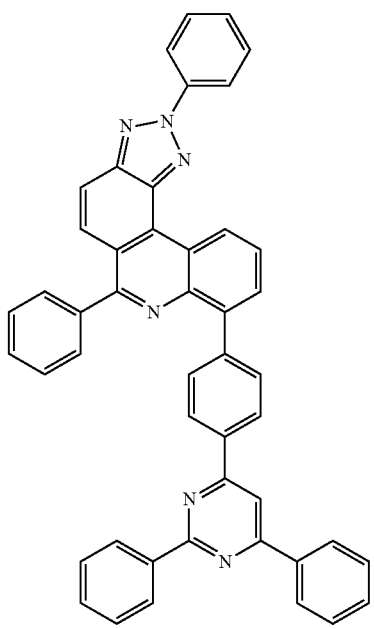
466

575
-continued
467
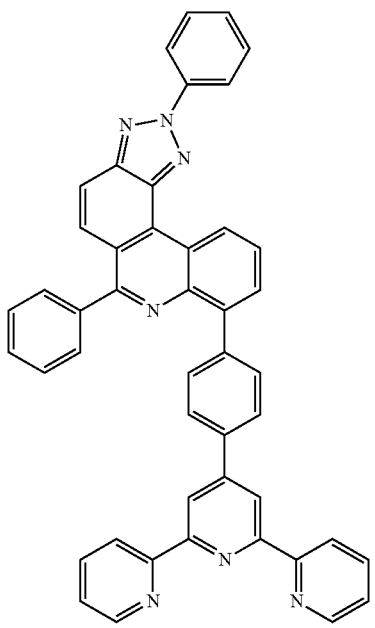
468
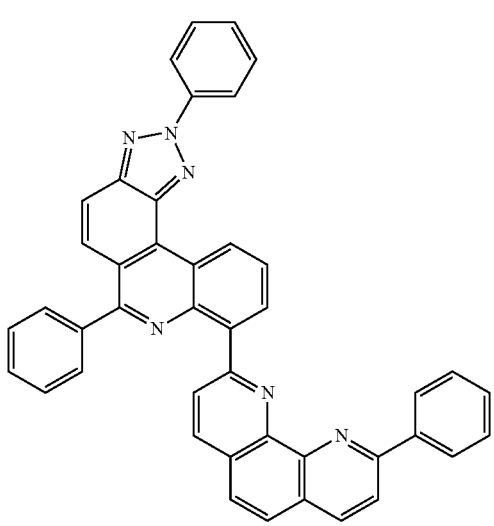
576
-continued
469
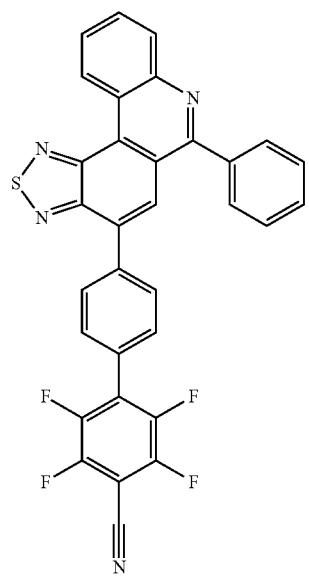
470
471
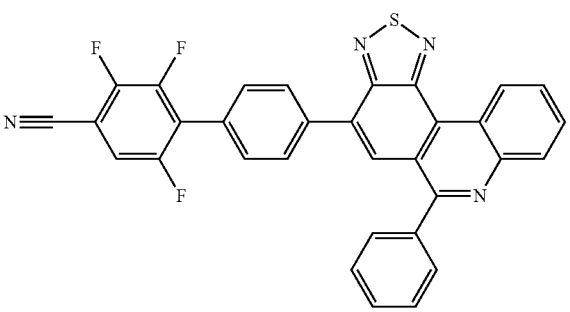

577 -continued
472
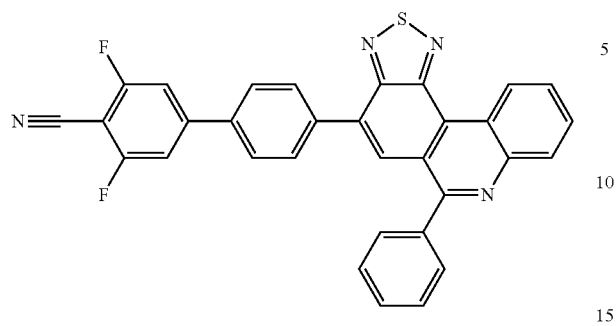
473
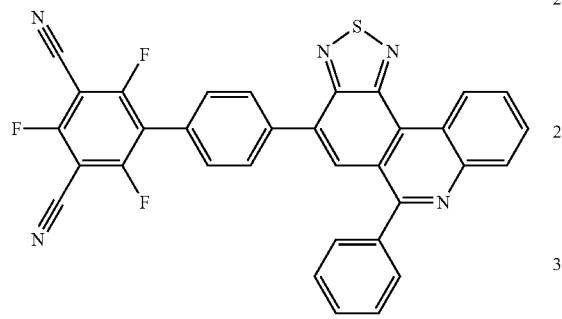
474
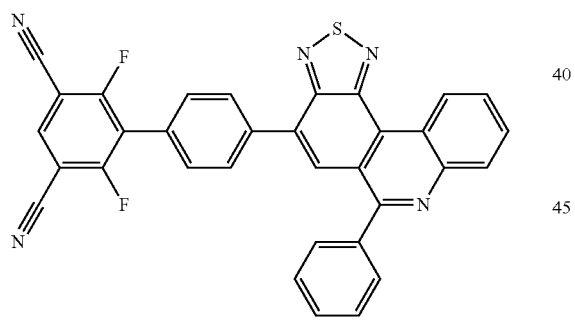
475
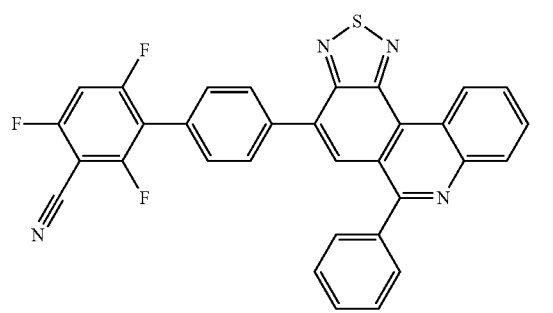
578 -continued
476
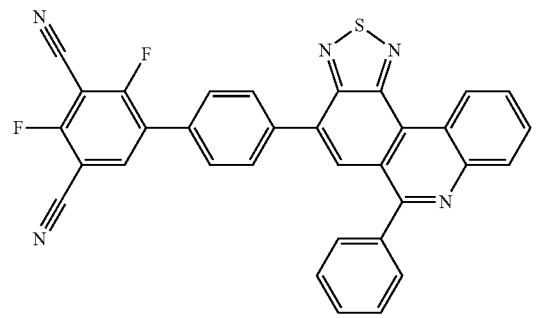
477
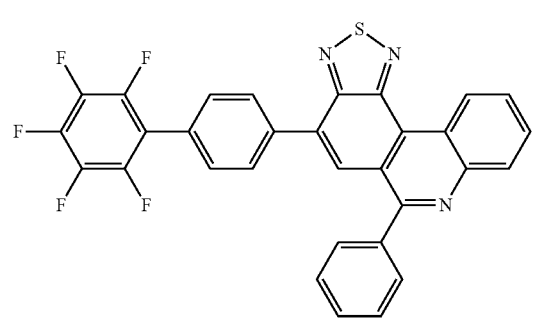
478
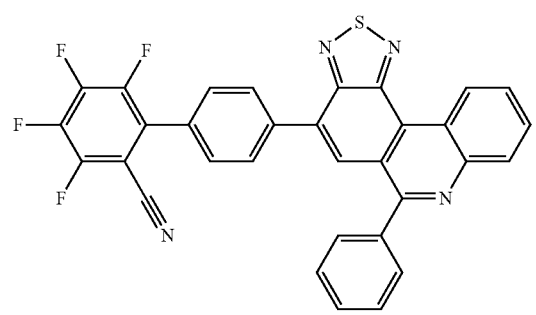
479
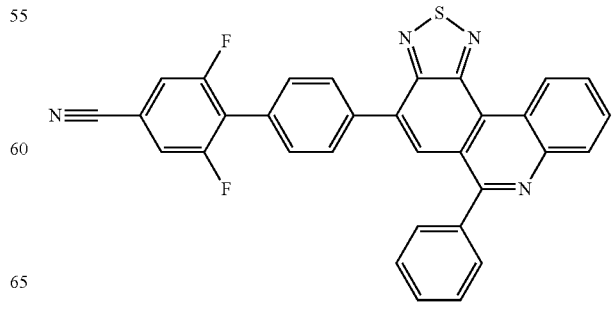

-continued
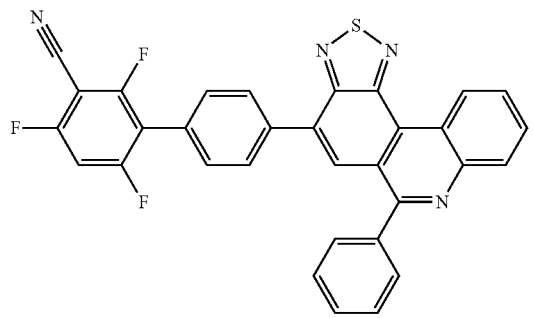
480
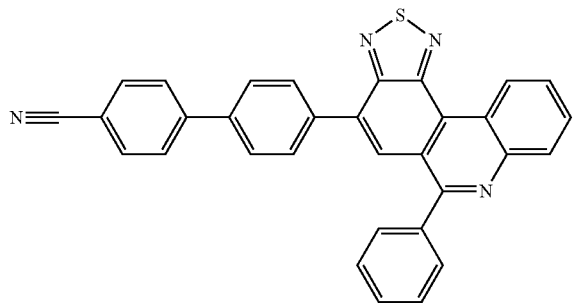
484
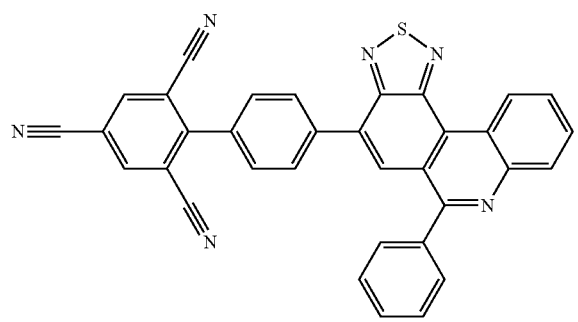
481
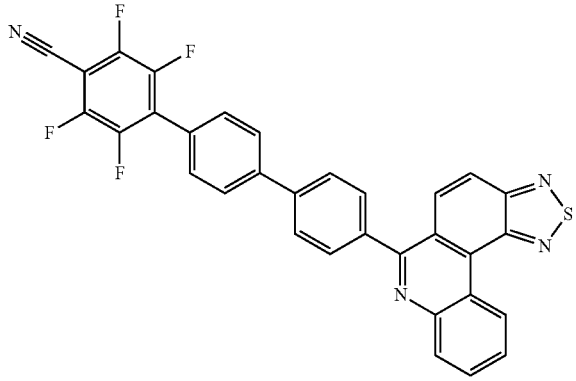
485
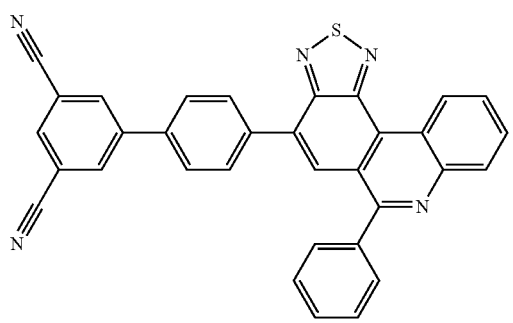
482
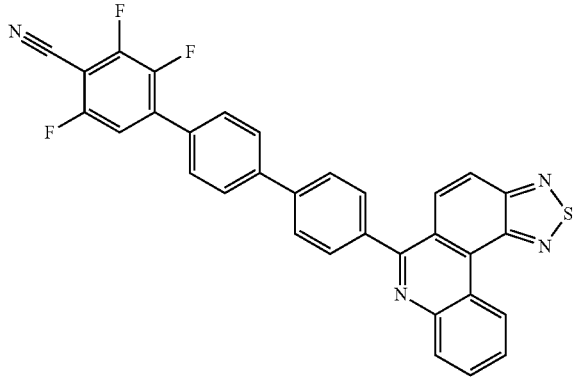
486
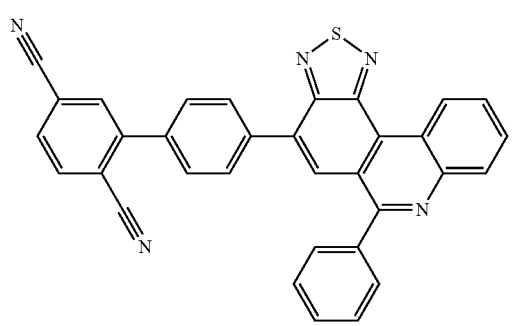
483
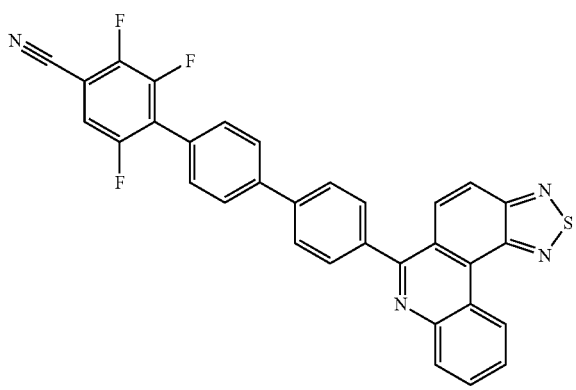
487

581
-continued
488
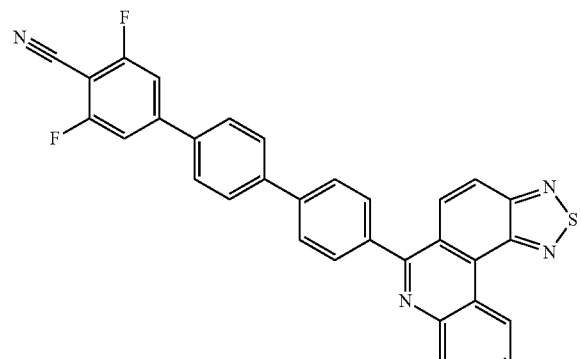
489
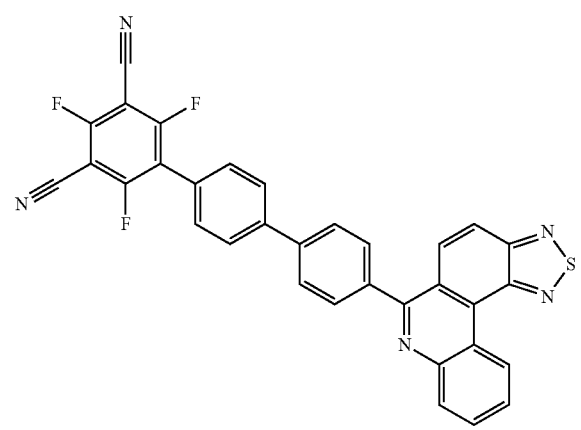
490
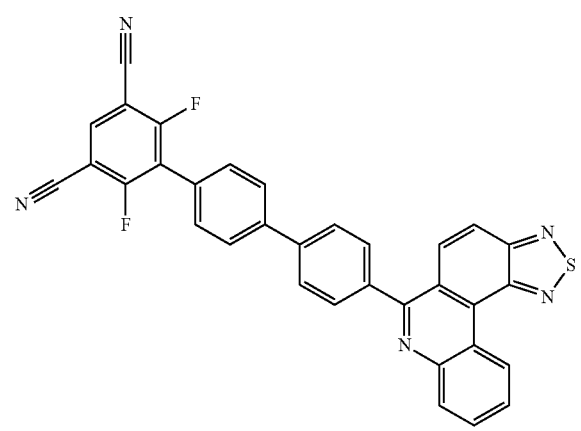
491
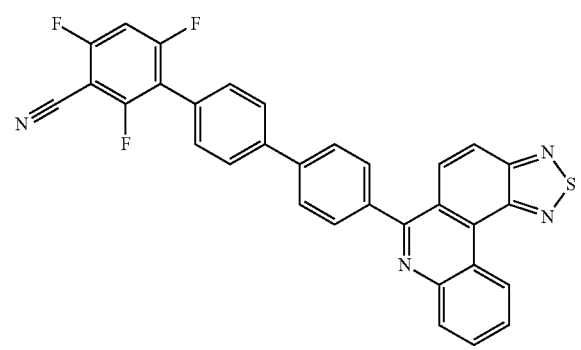
582
-continued
492
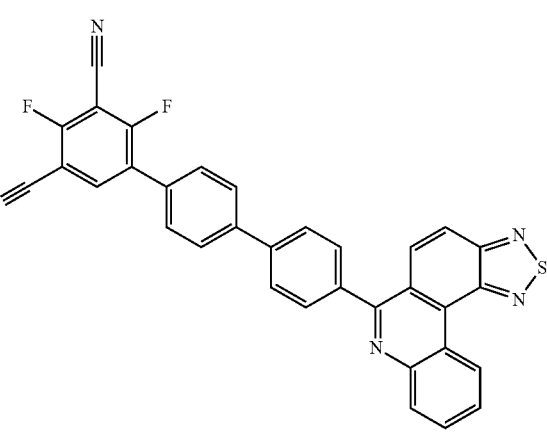
493
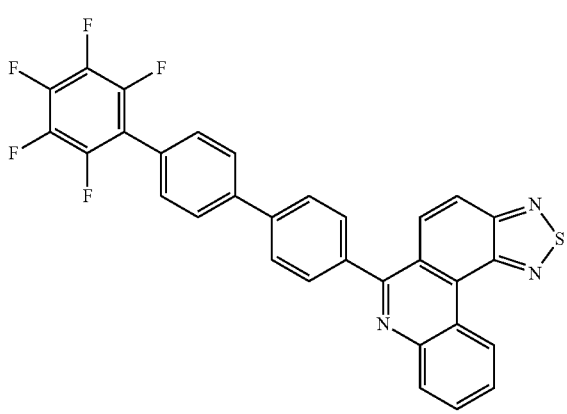
494
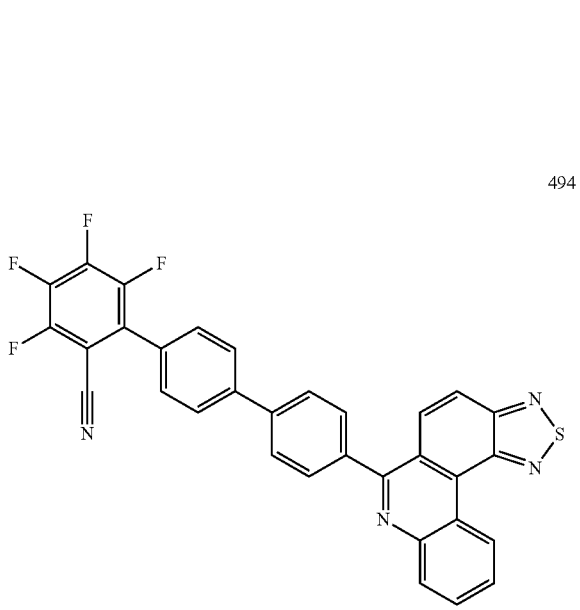

495
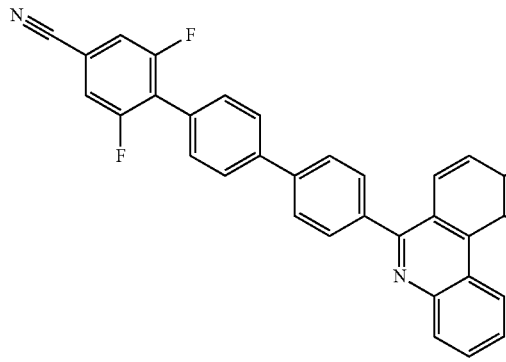
498
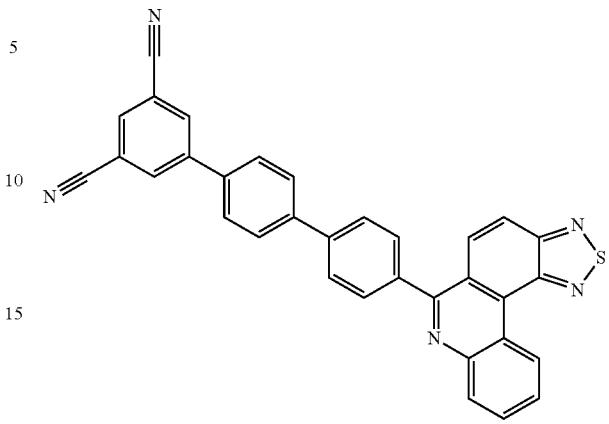
496
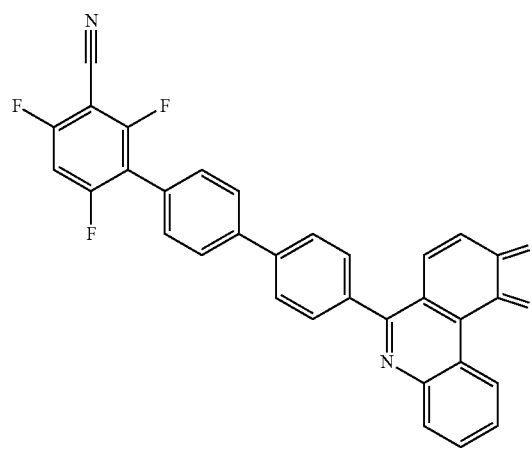
499
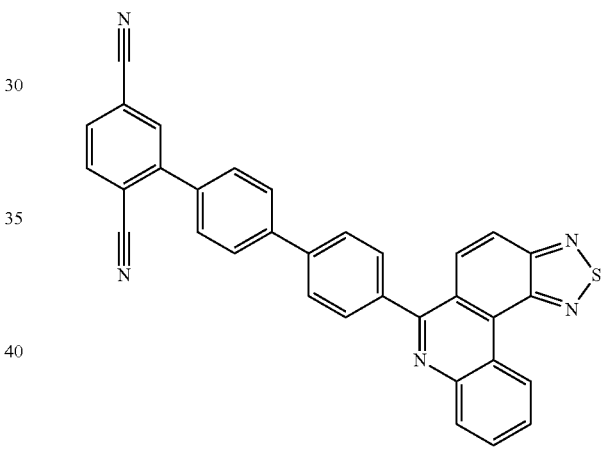
497
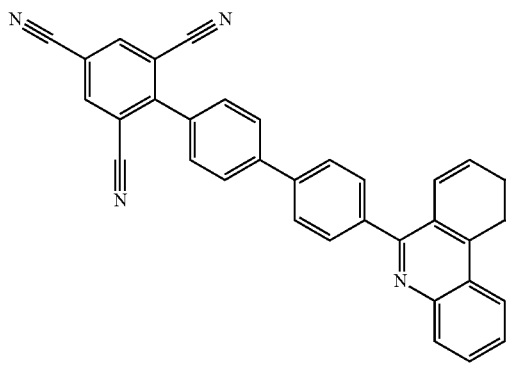
500
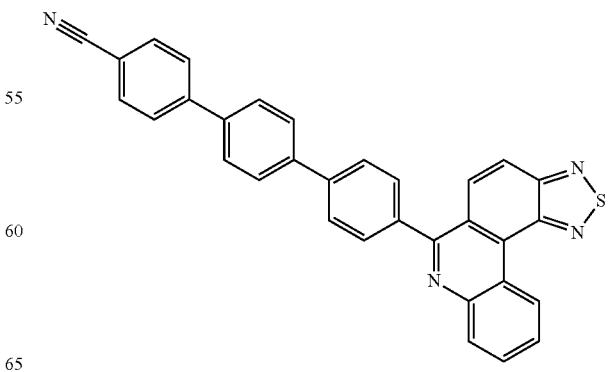

585
-continued
586
-continued
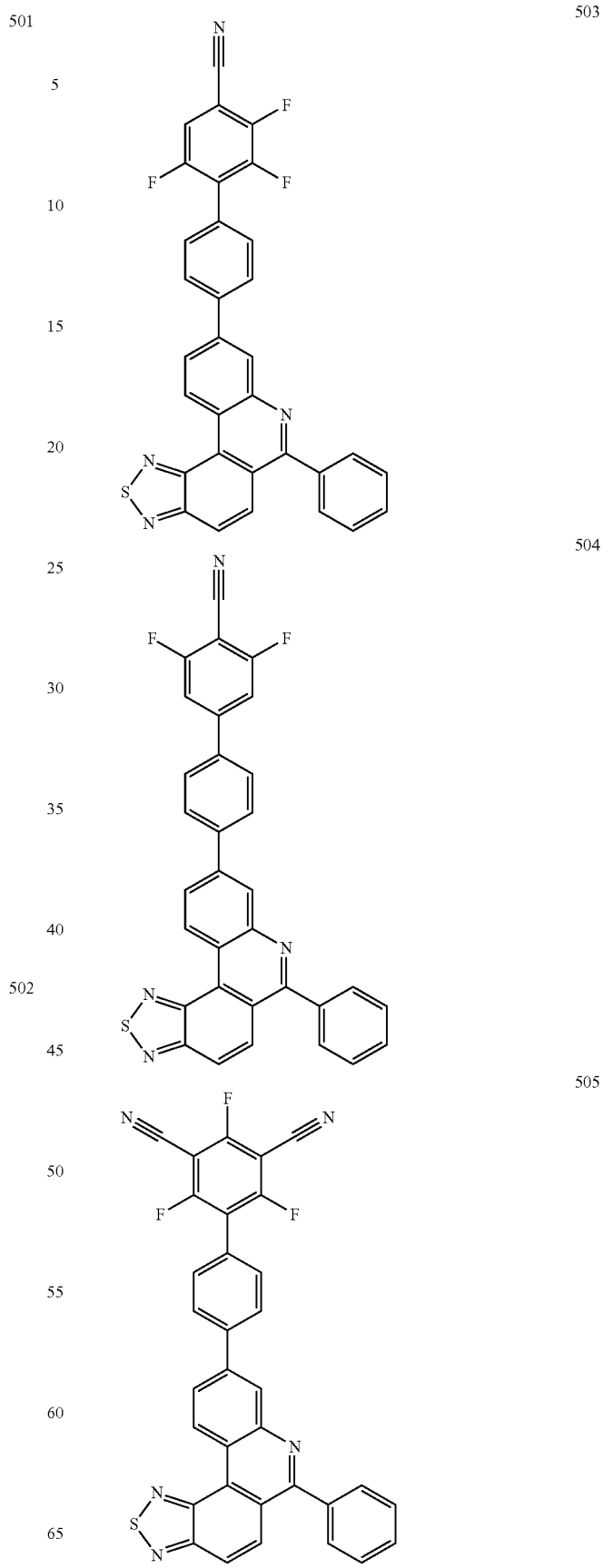

587
-continued
| 587 | 588 |
|---|---|
| 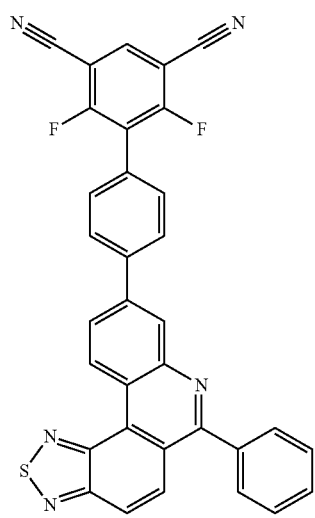 | 506 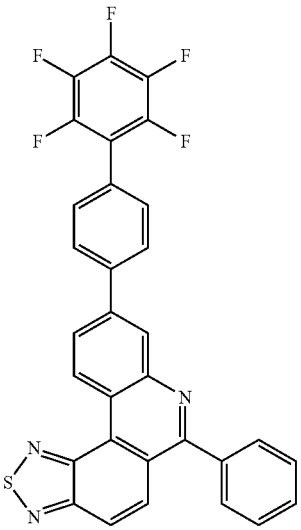 509 |
| 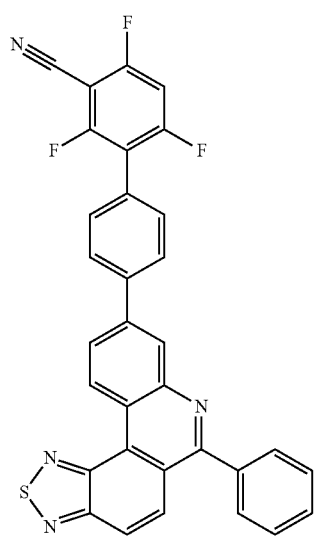 | 507 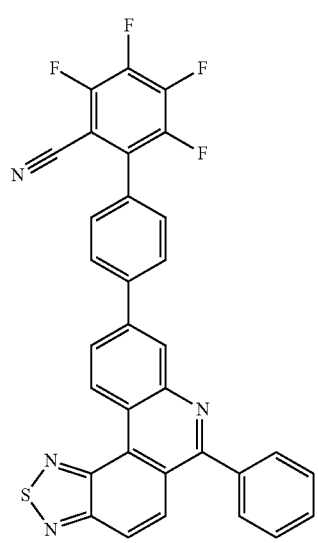 510 |
| 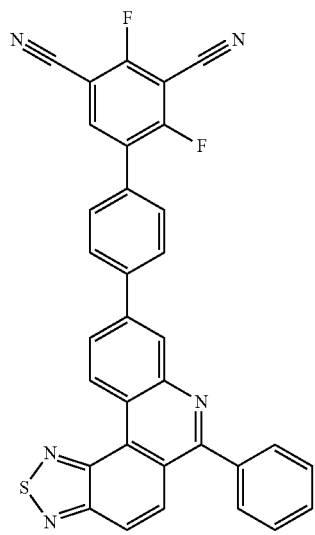 | 508 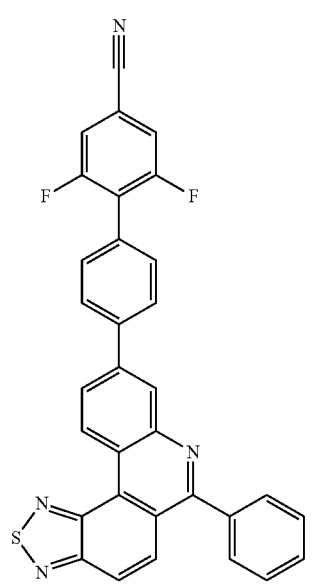 511 |

589
-continued
590
-continued
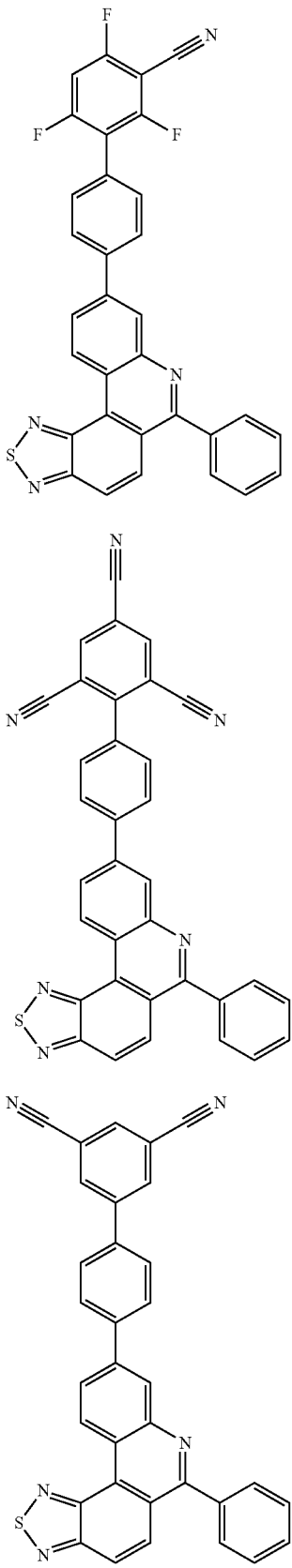
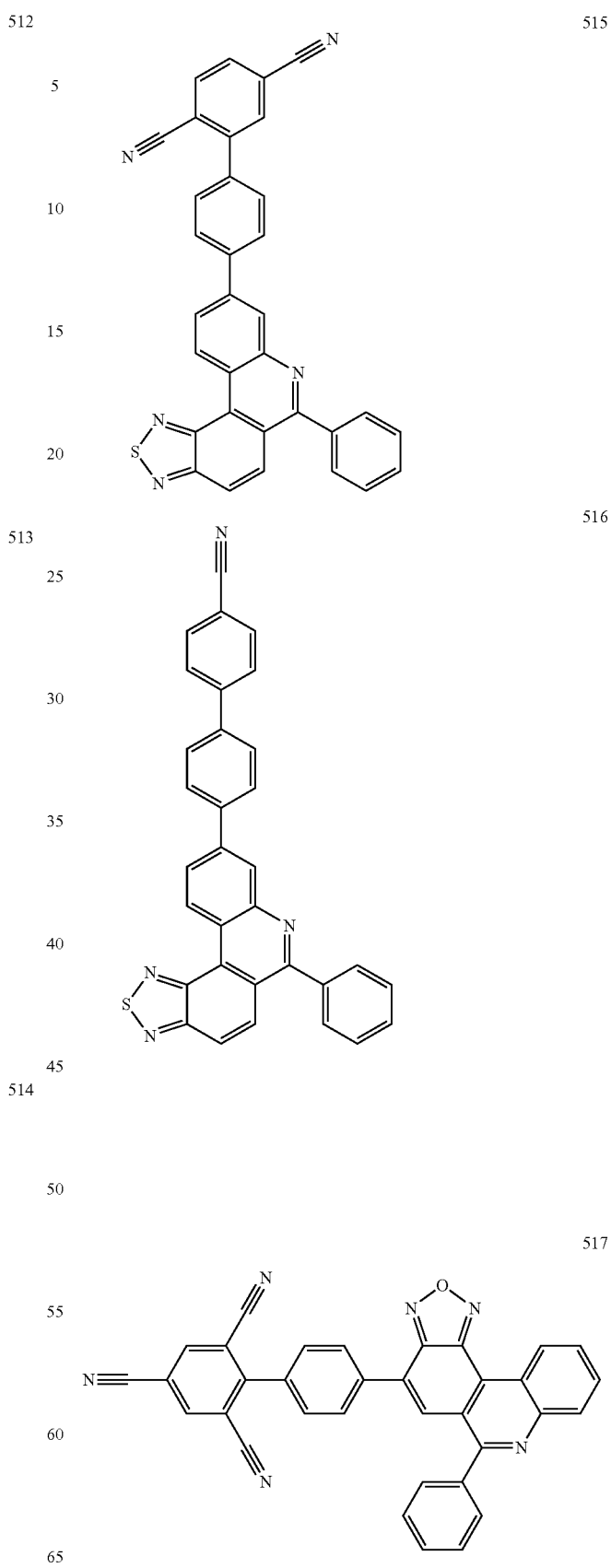

518
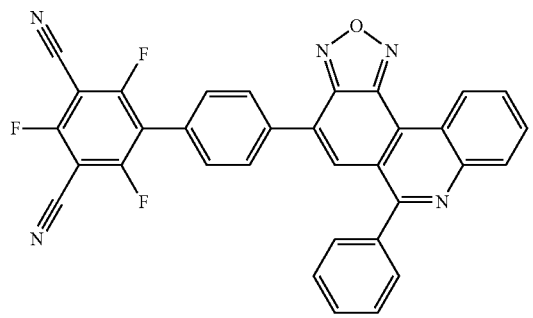
519
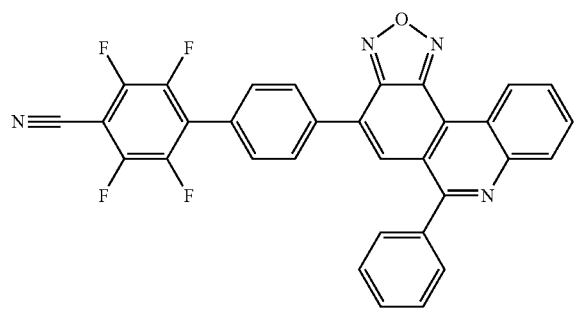
520
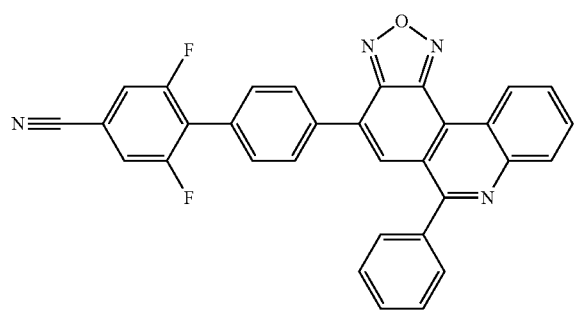
521
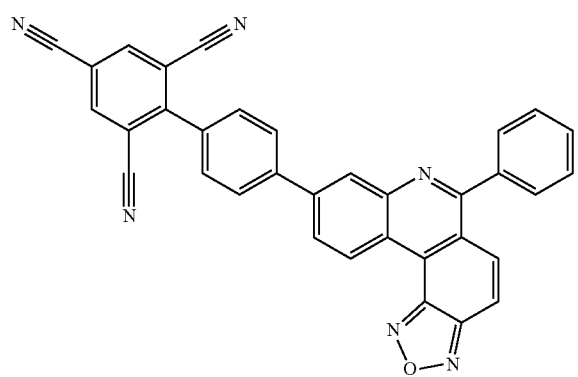
522
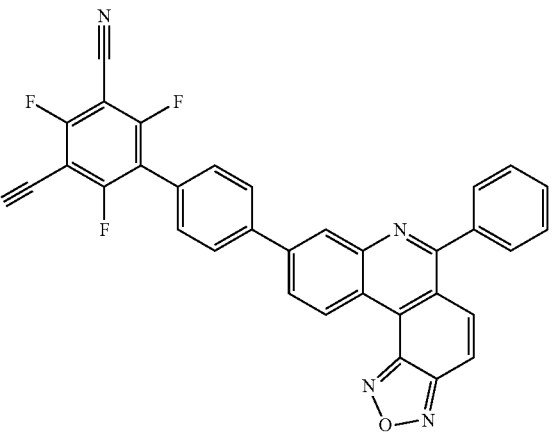
523
524
525
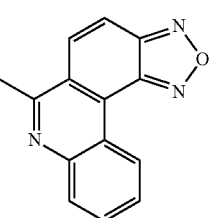

593
-continued
526
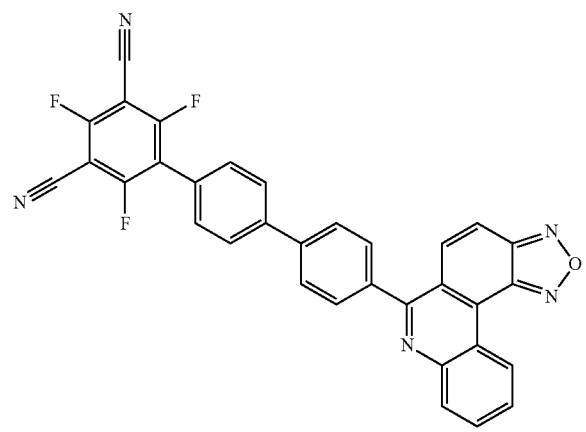
527
594
-continued
529
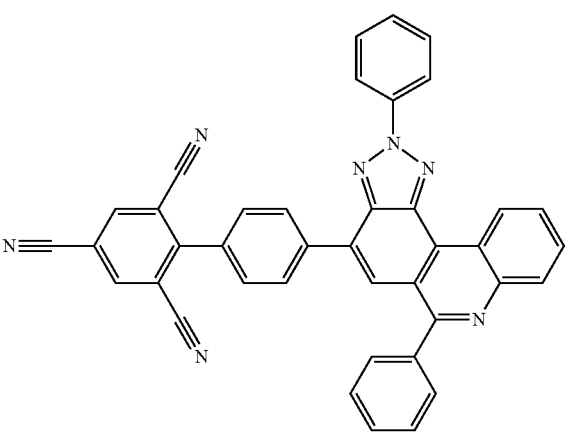
530
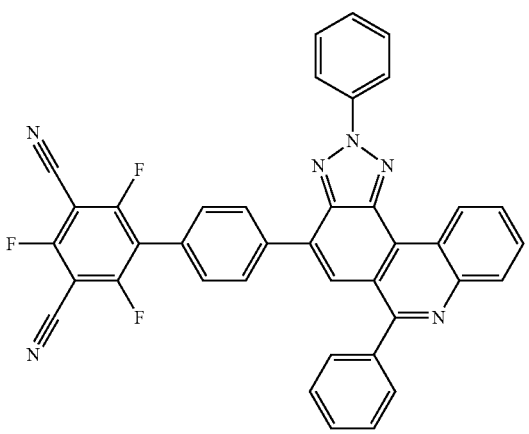
528
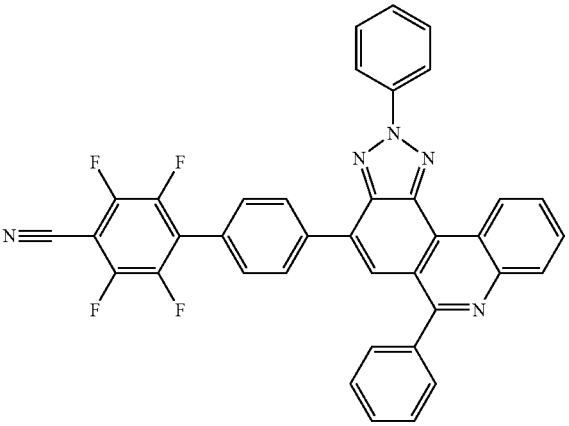
531

-continued
532
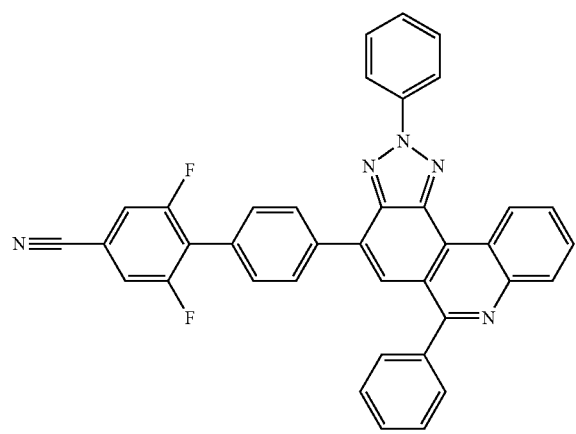
533
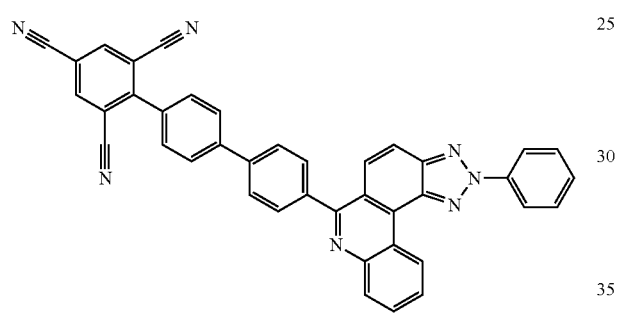
534
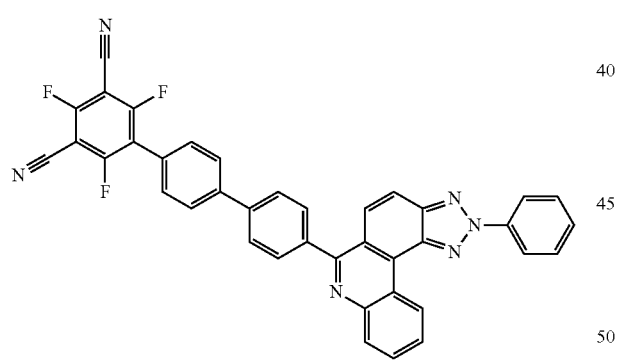
535
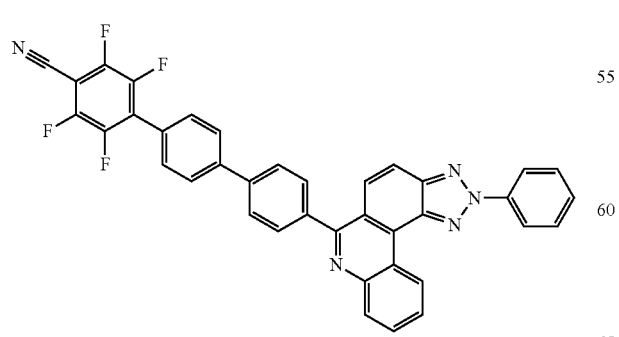
-continued
536
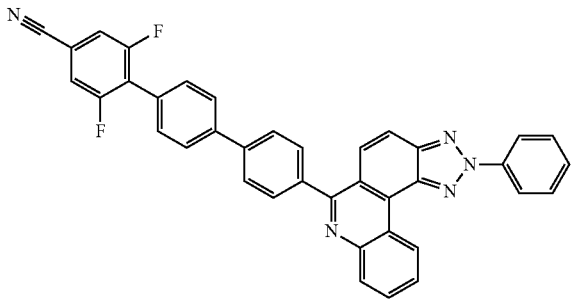
537
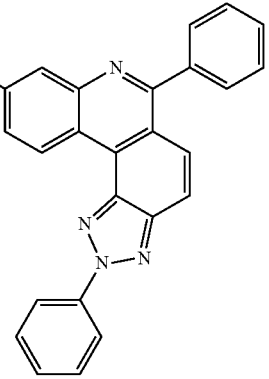
538
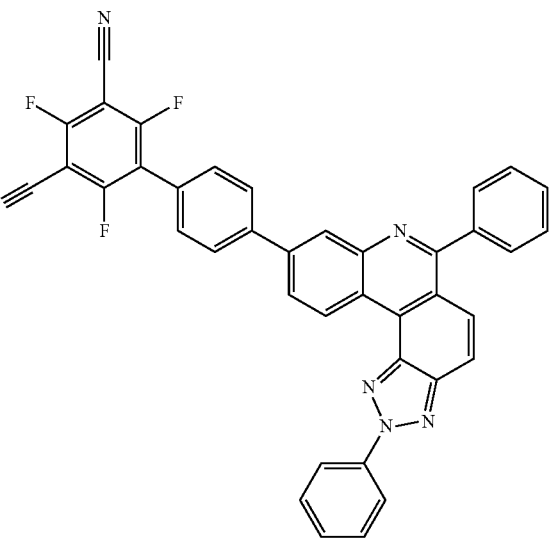

597
-continued
539
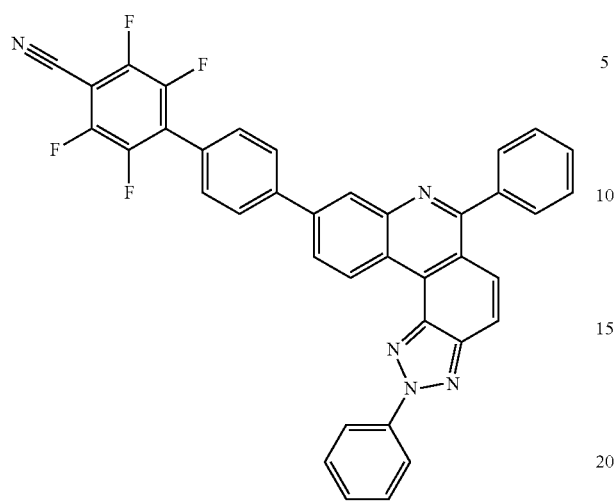
540
541
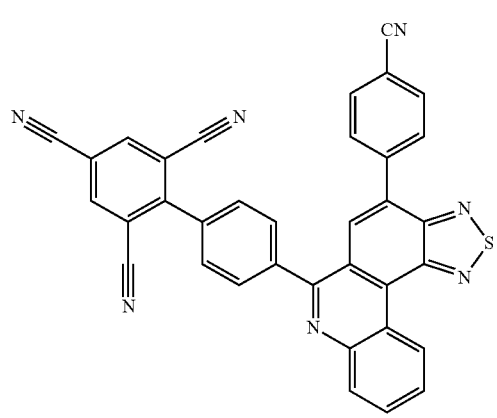
598
-continued
542
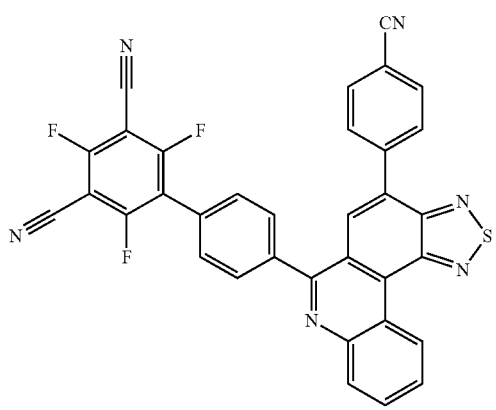
543
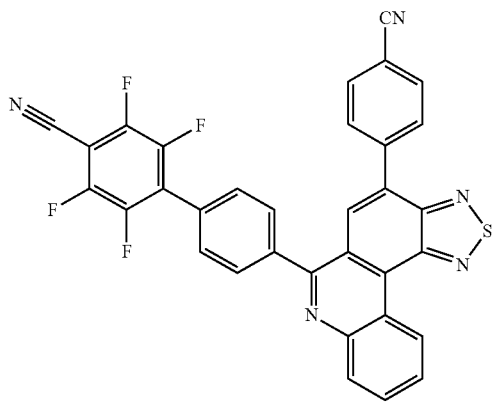
544
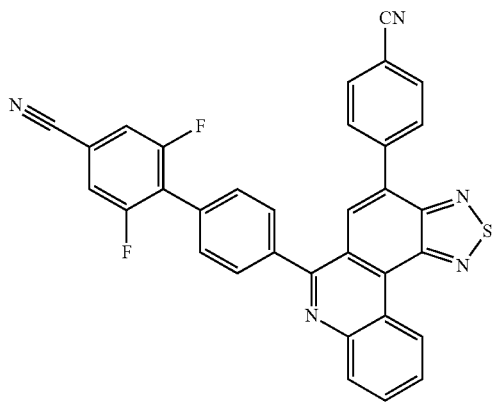
545

546 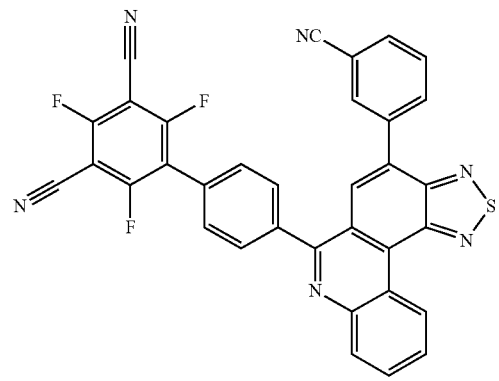
547 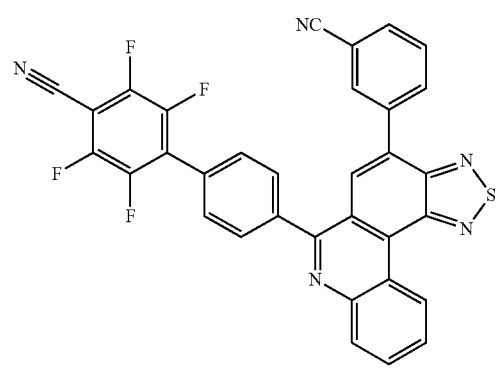
548 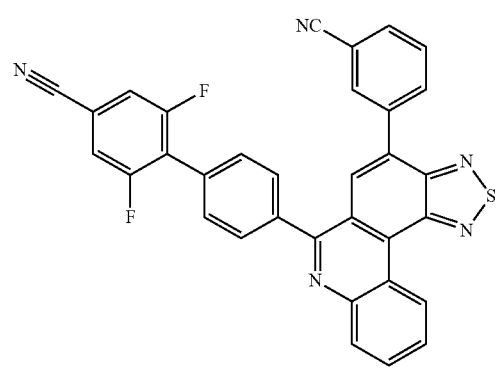
549 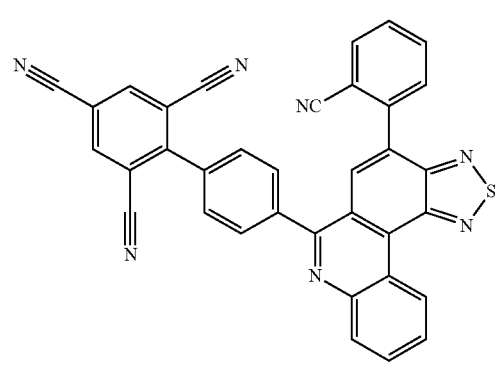
550 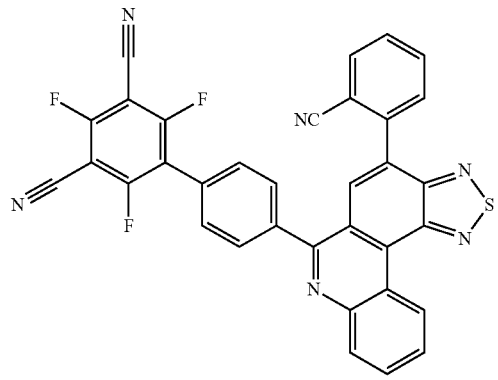
551 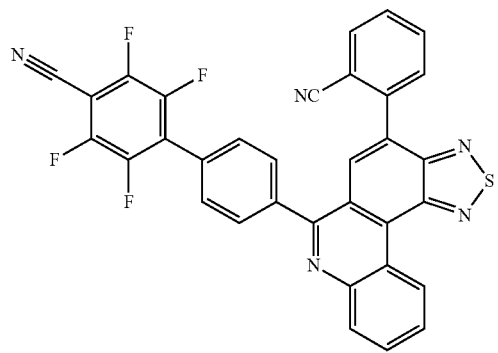
552 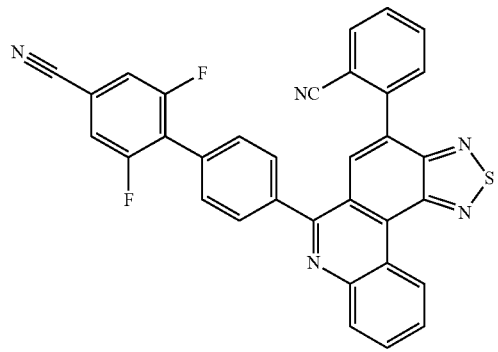
553 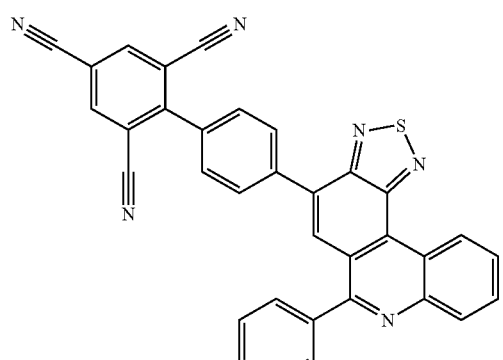

554
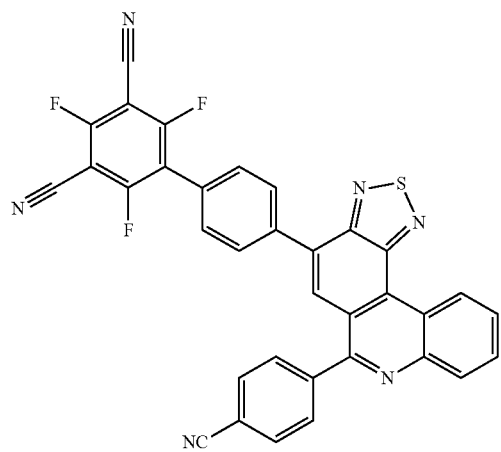
557
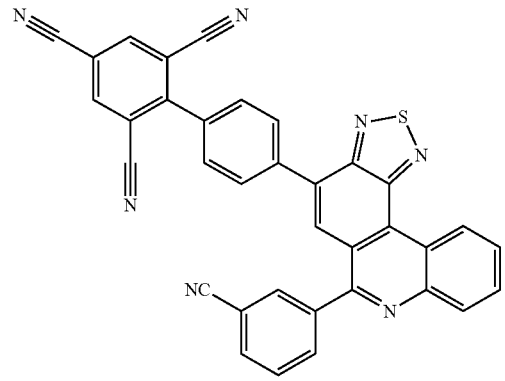
555
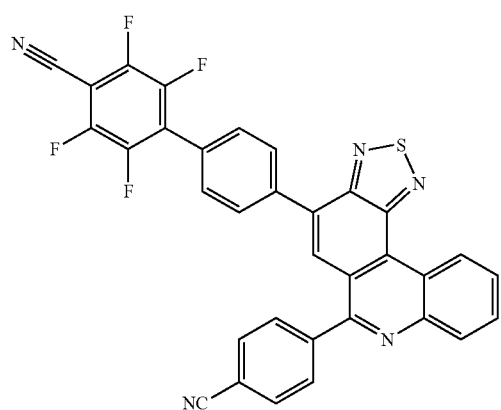
558
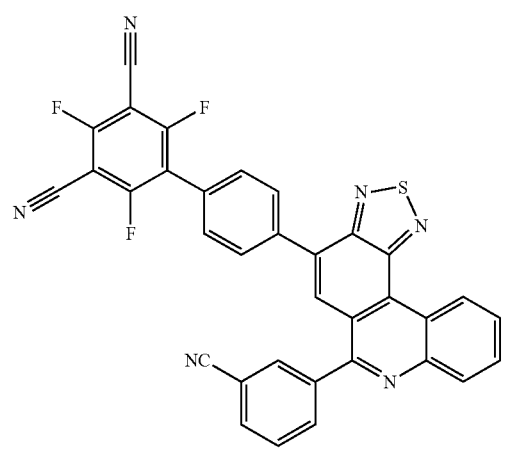
556
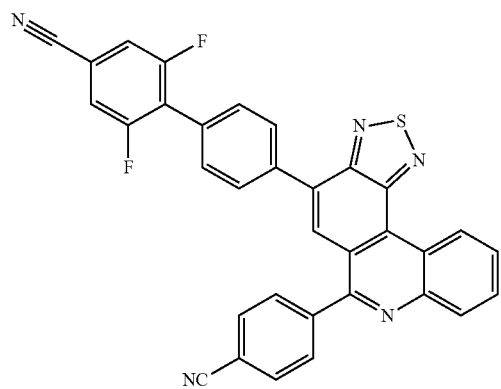
559
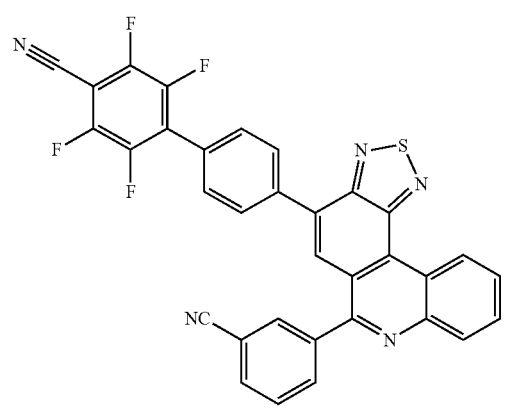

560
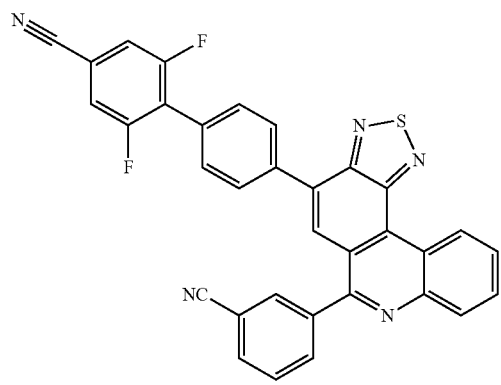
563
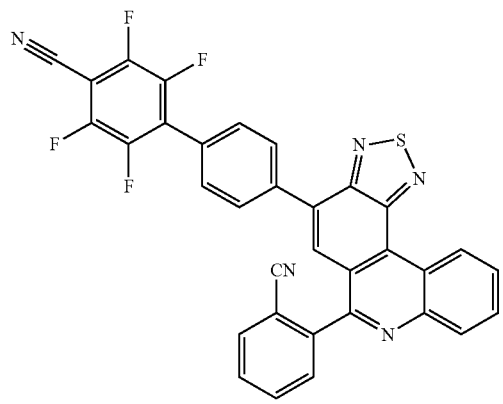
561
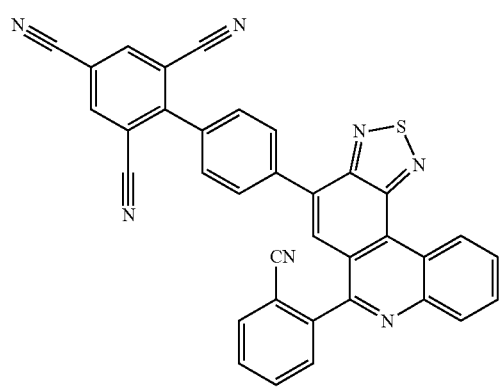
564
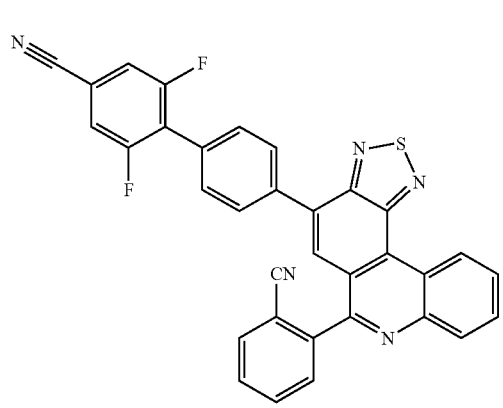
562
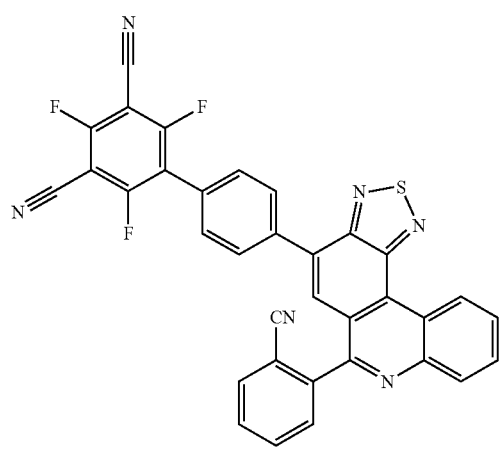
565
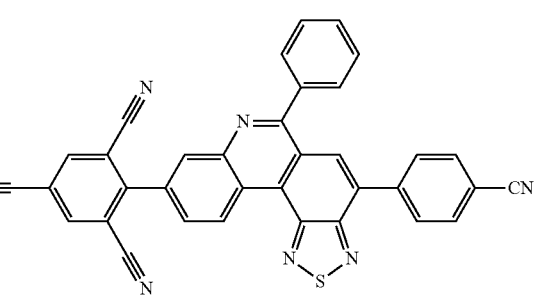
566
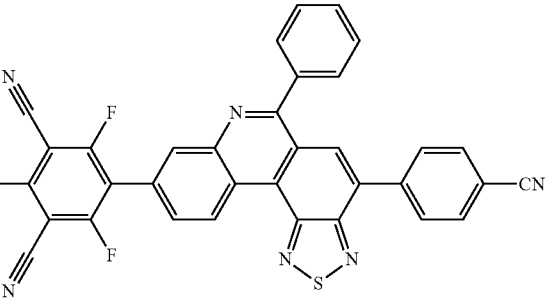

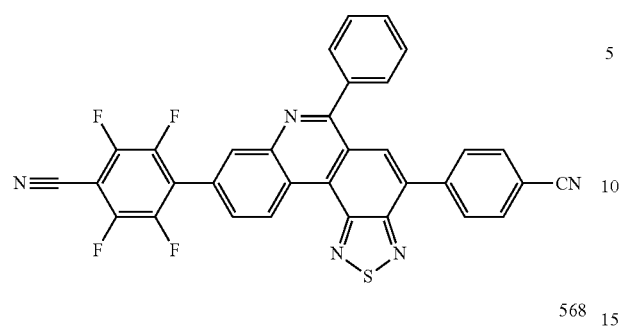
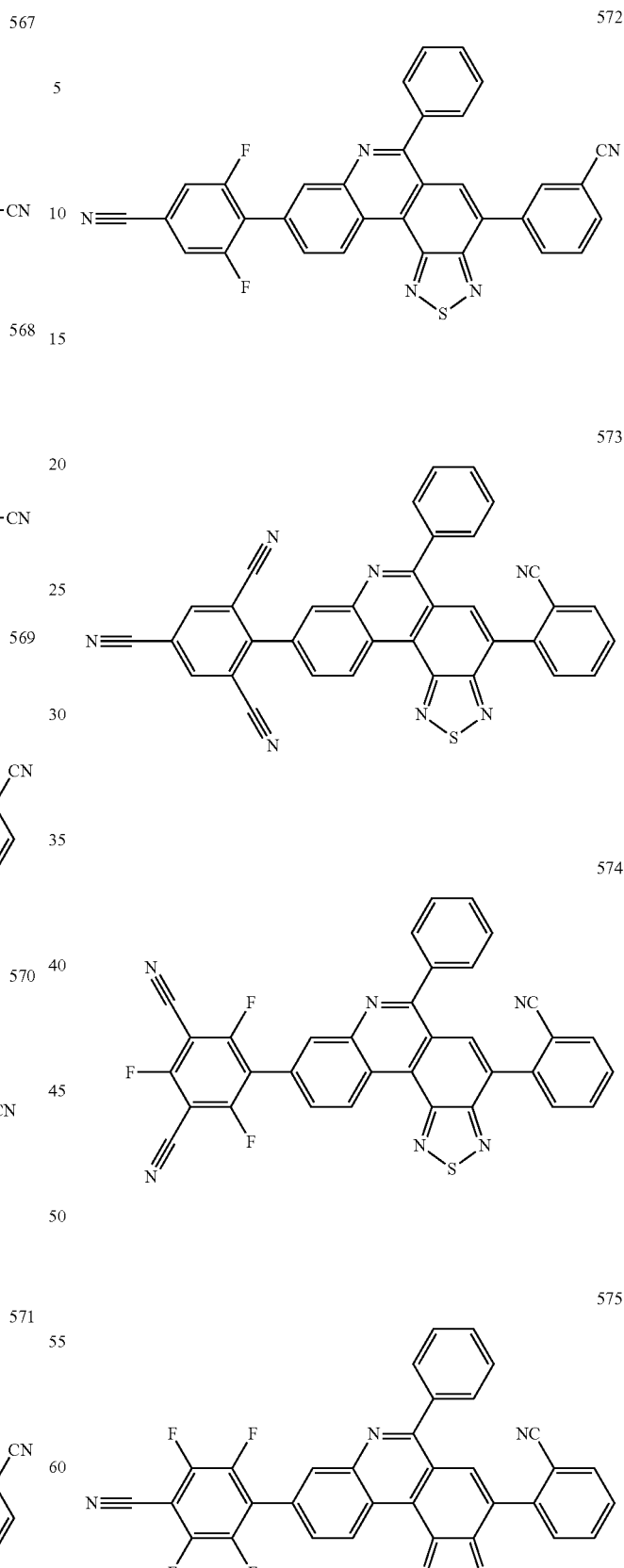

576
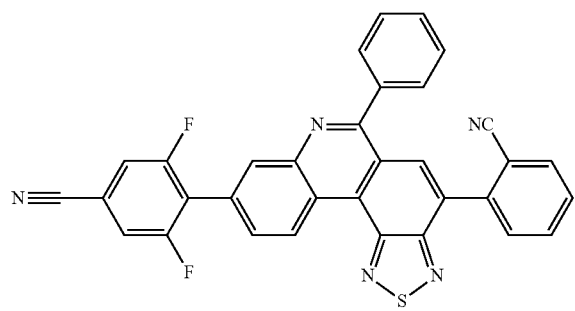
577
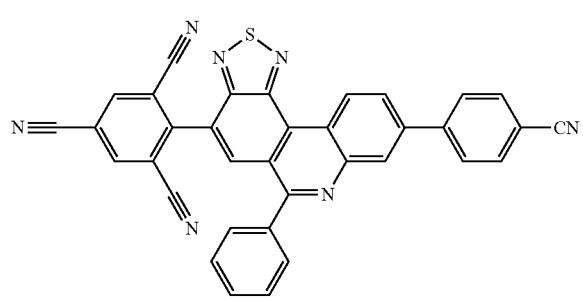
578
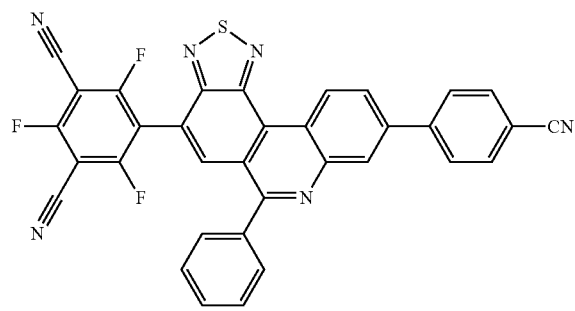
579
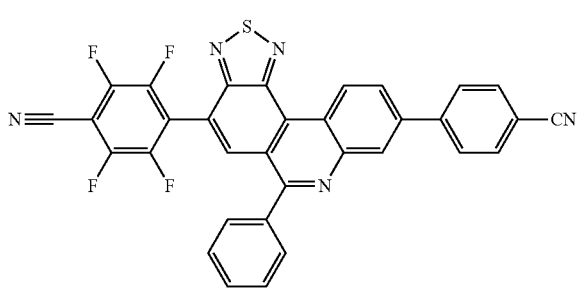
580
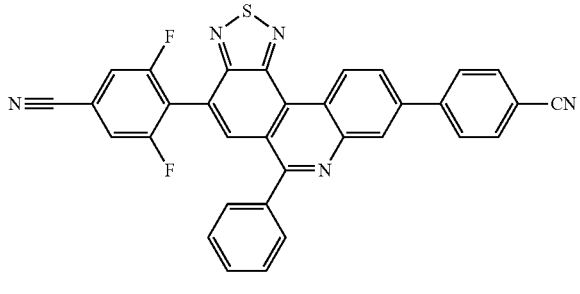
581
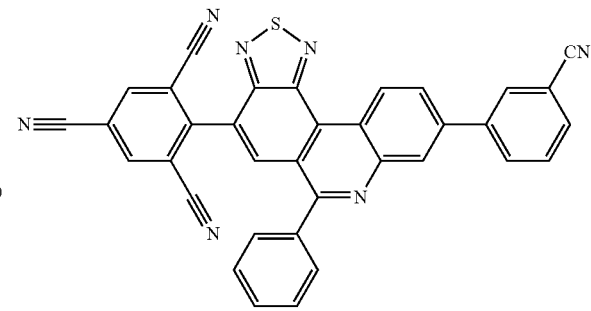
582
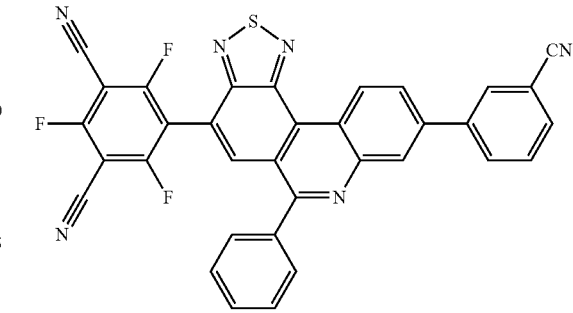
583
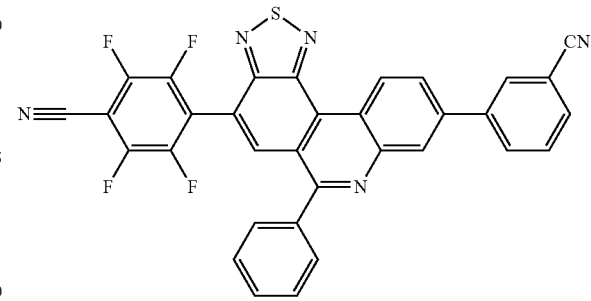
584
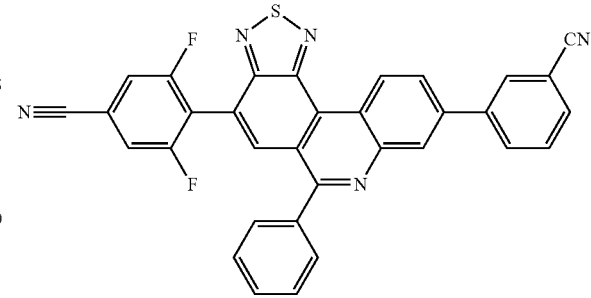
585
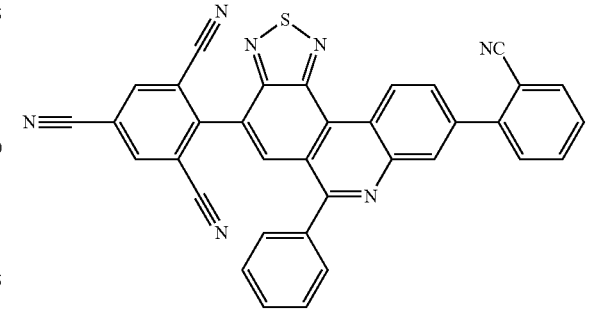

586
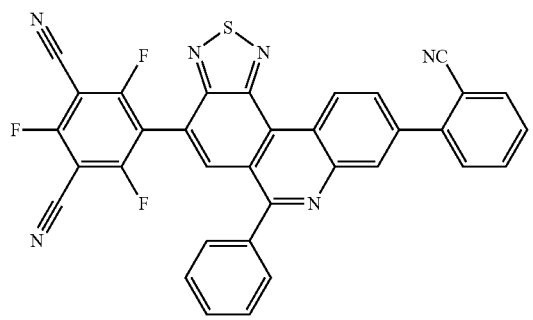
587
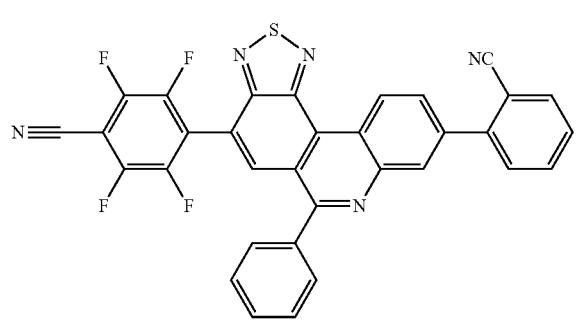
588
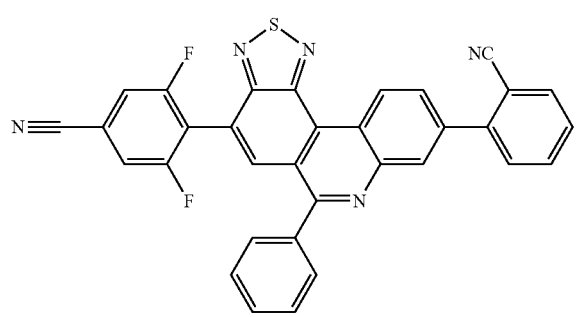
589
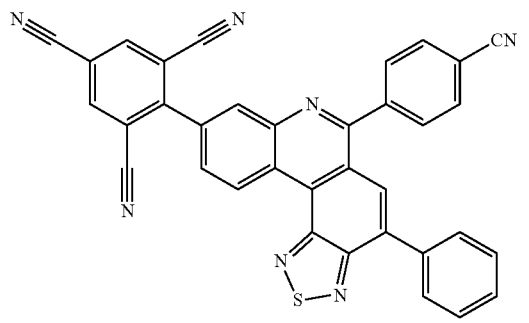
590
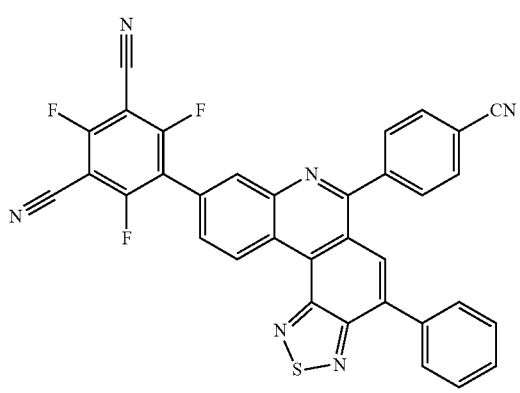
591
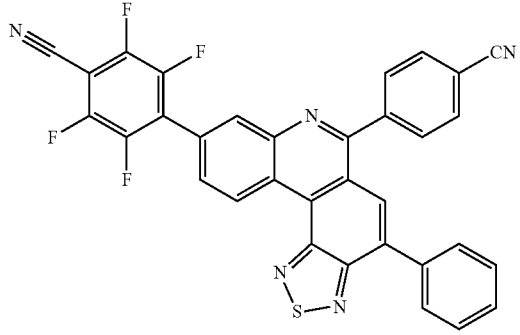
592
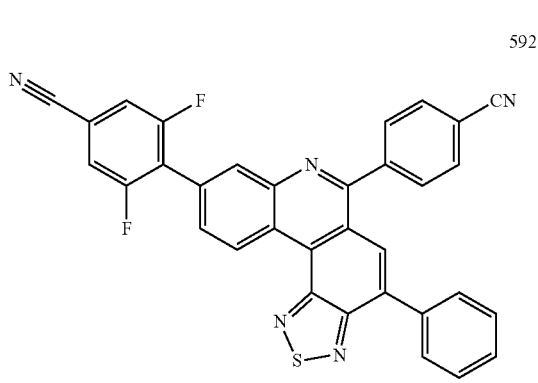
593
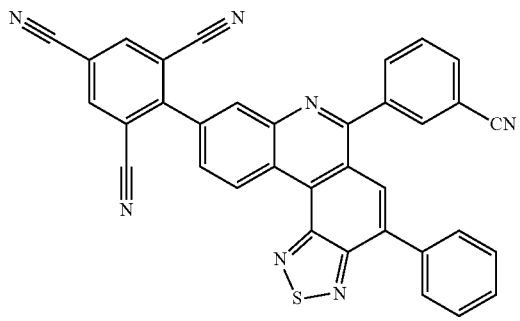

594
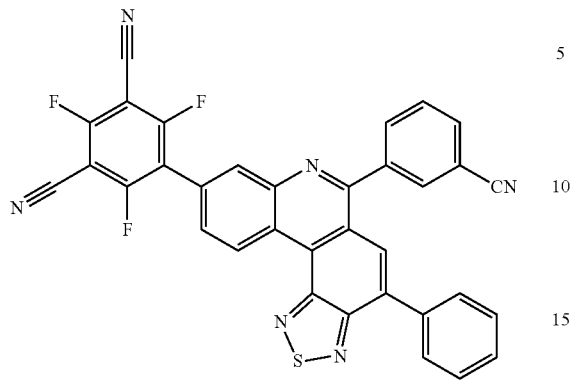
595
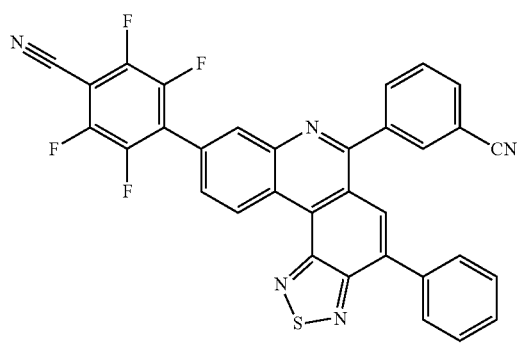
596
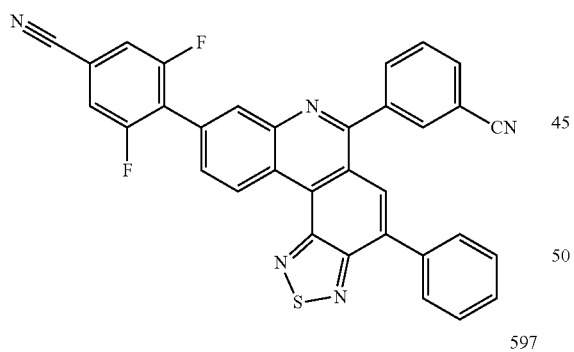
597
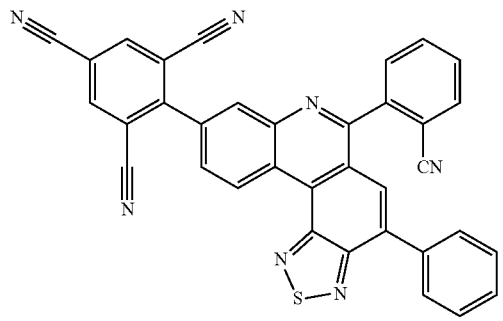
598
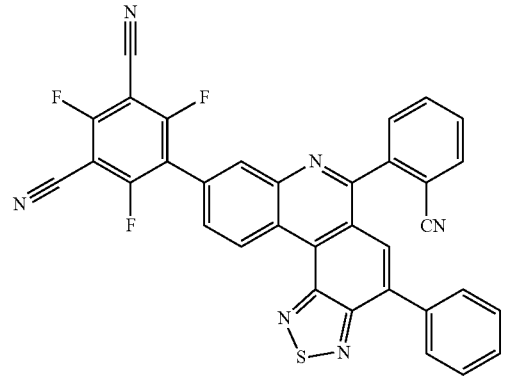
599
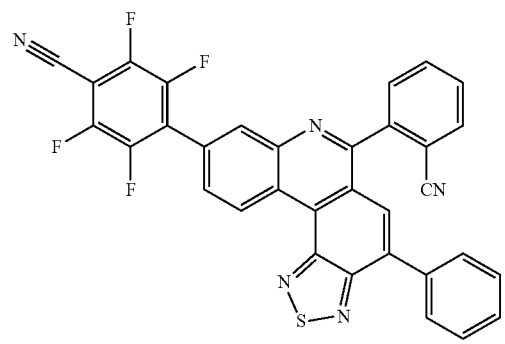
600
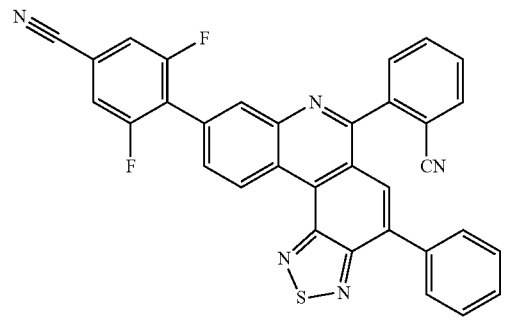
601
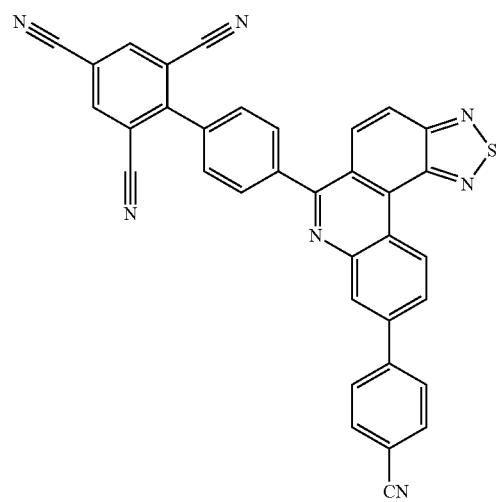

602
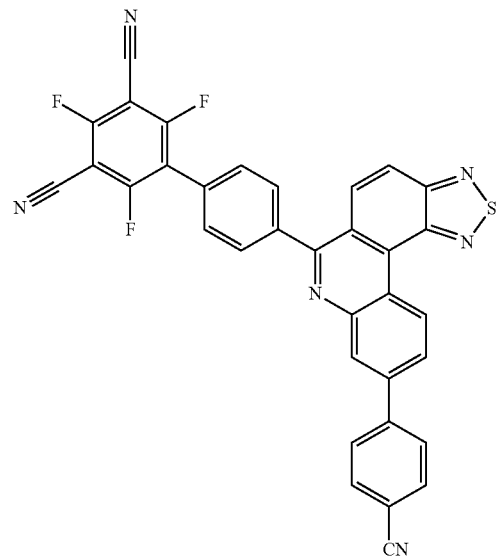
603
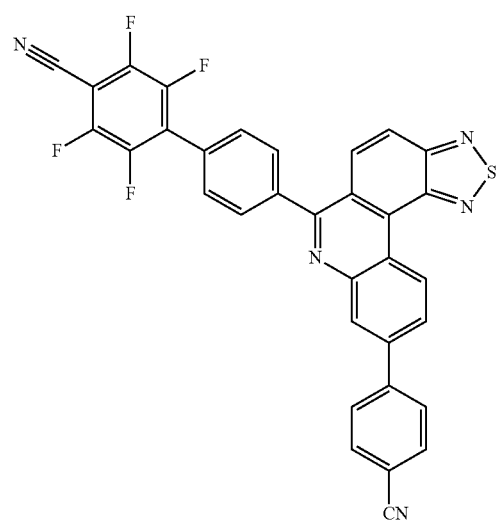
604
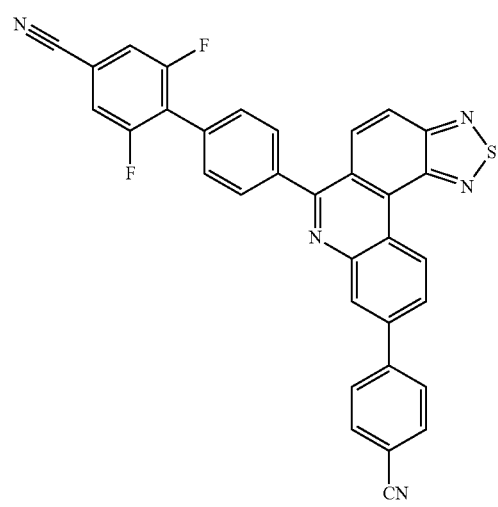
605
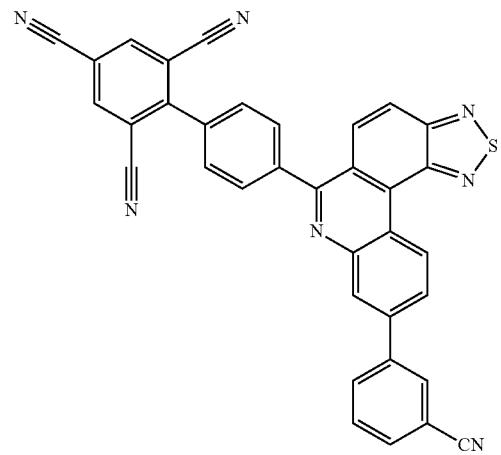
606
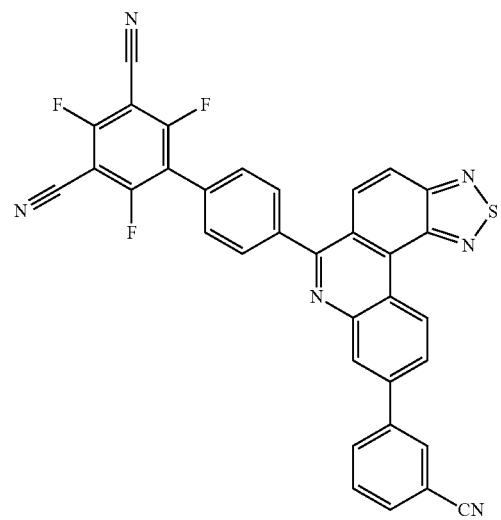
607
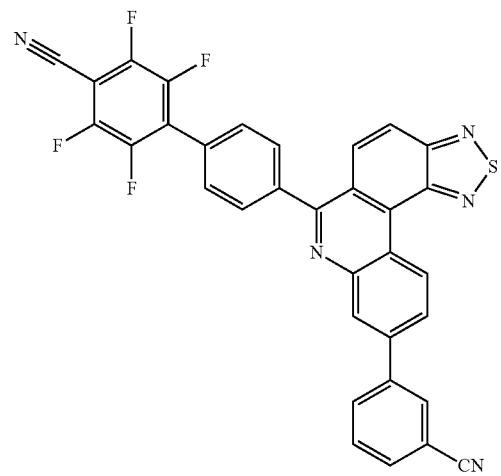

615
-continued
608
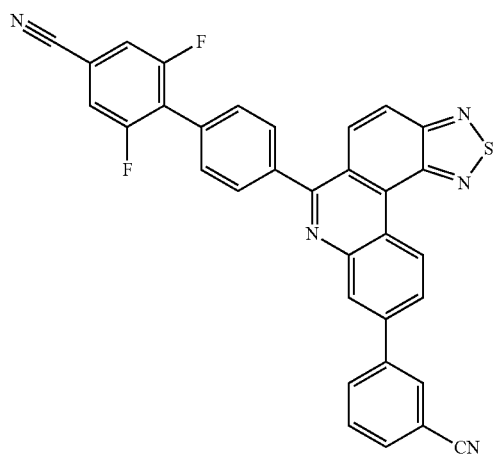
609
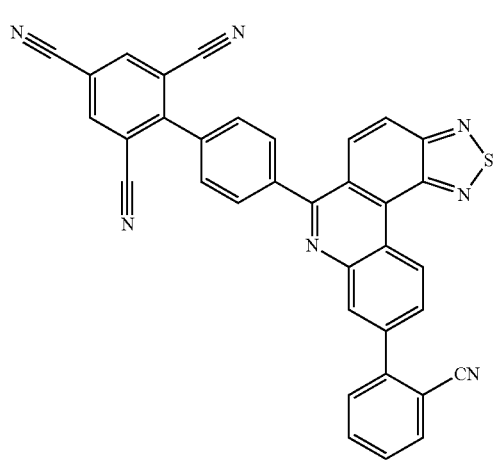
610
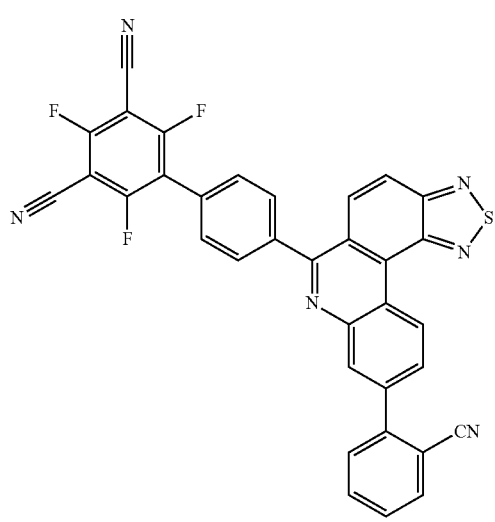
616
-continued
611
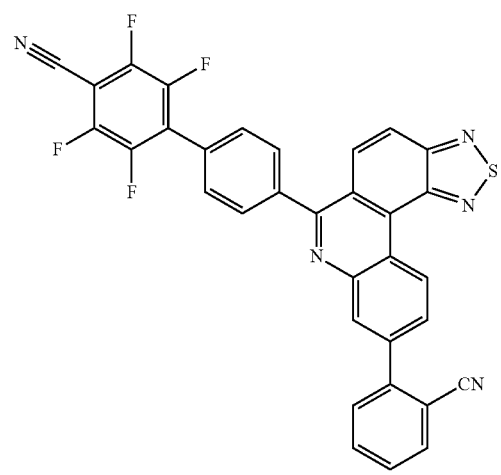
612
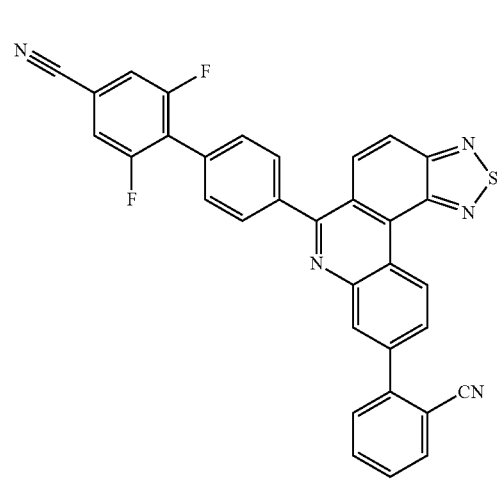
613
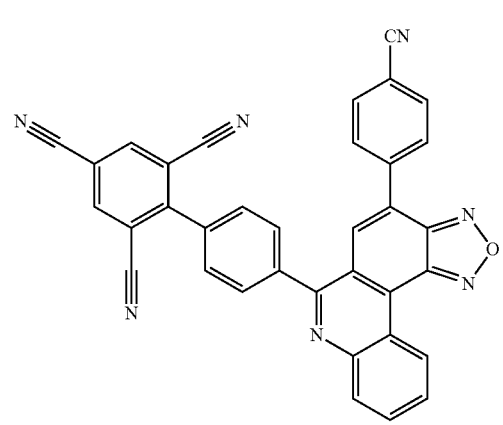

614
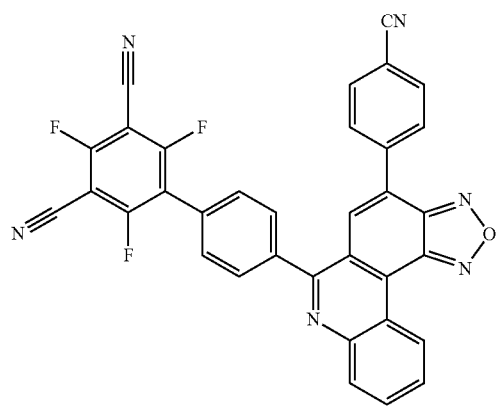
615
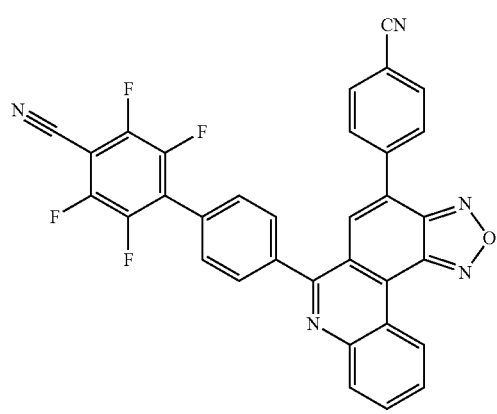
616
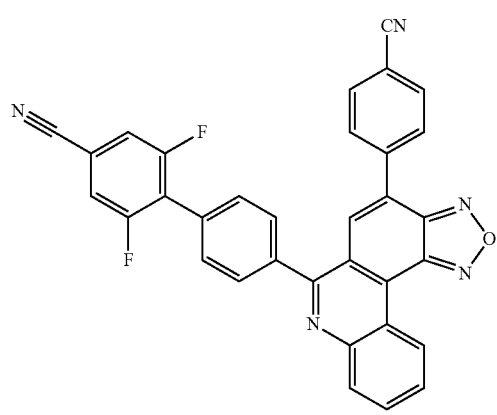
617
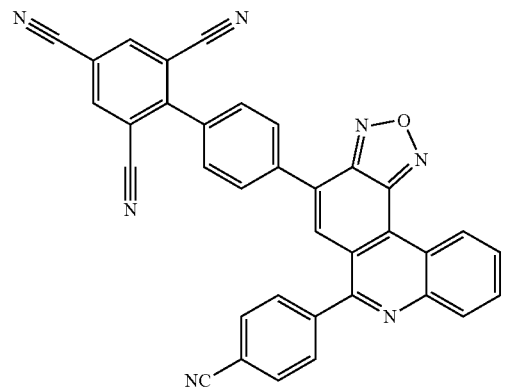
618
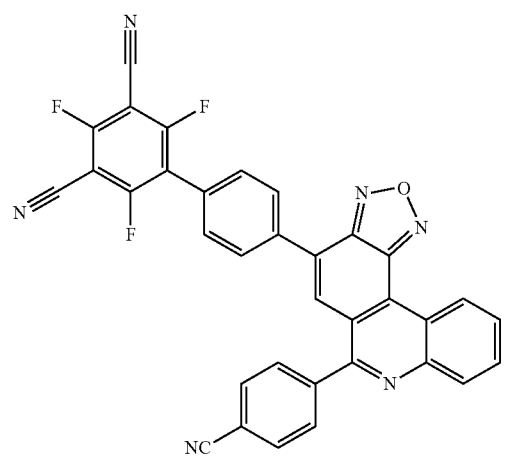
619
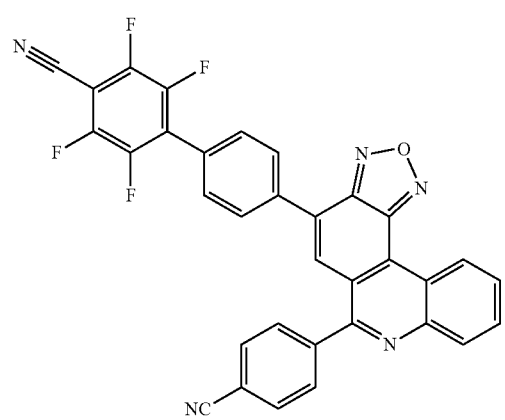

619
-continued
620
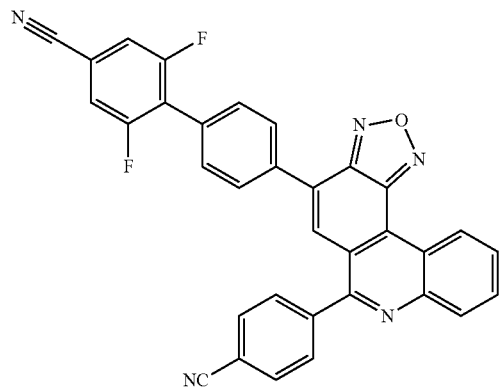
620
-continued
624
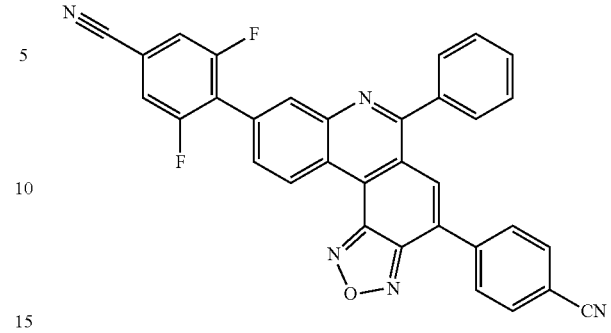
621
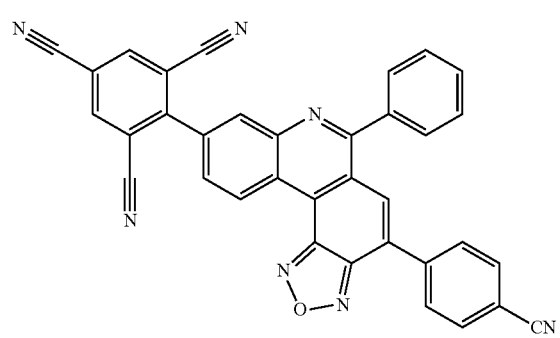
625
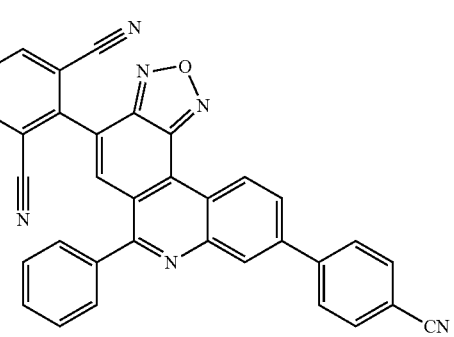
622
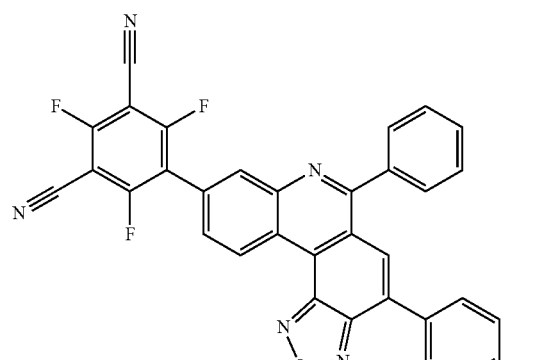
626
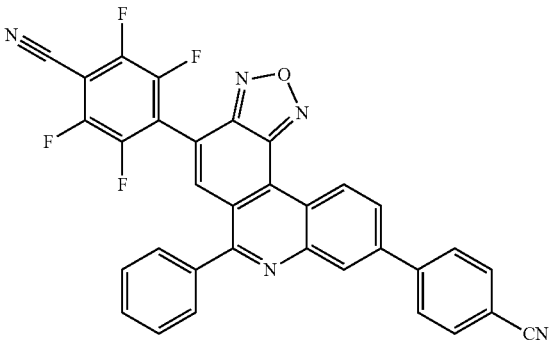
623
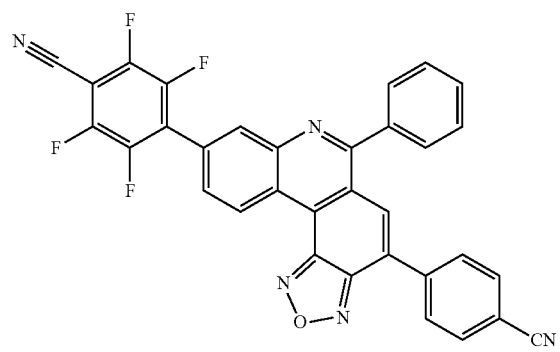

-continued
628
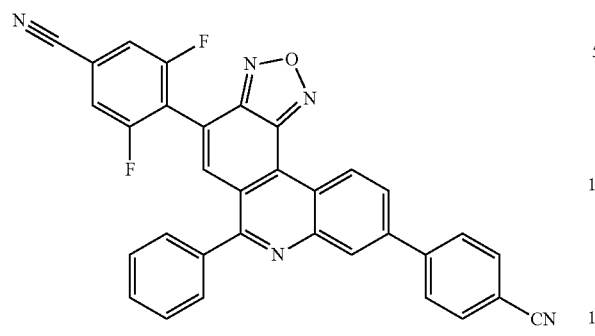
629
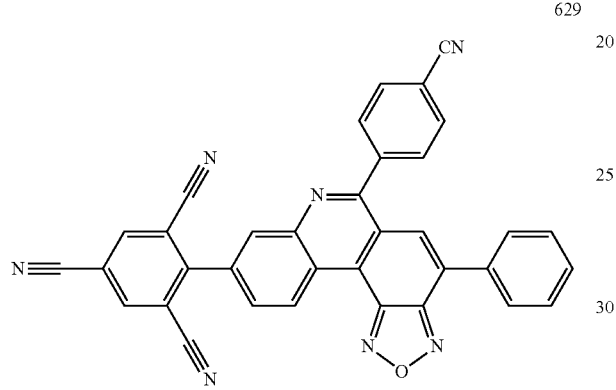
630
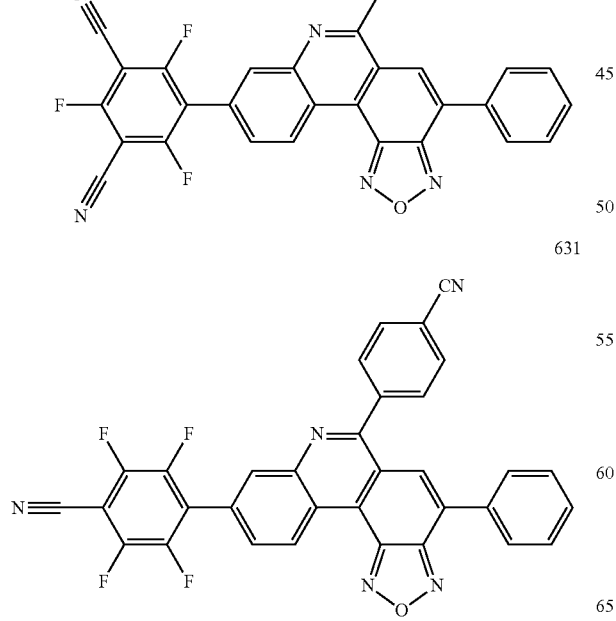
631
-continued
632
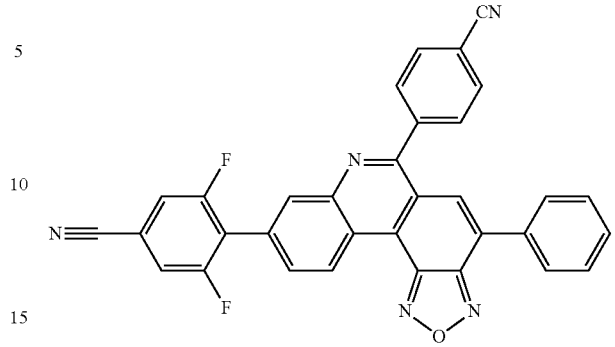
633
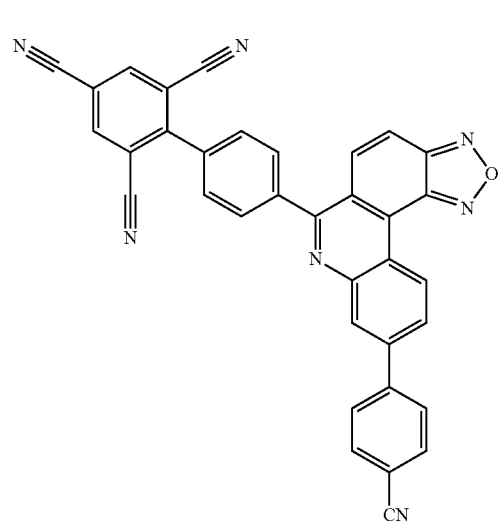
634
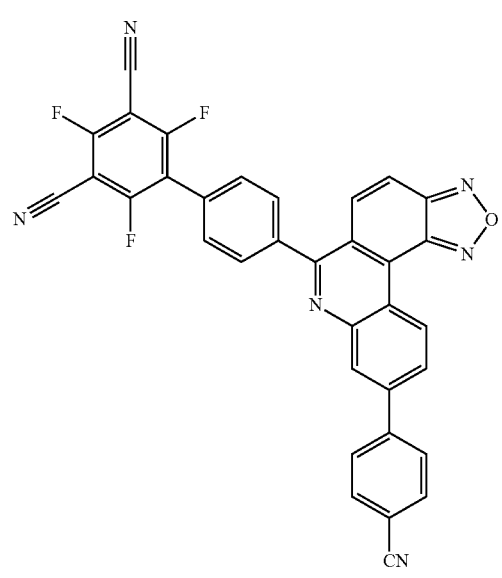

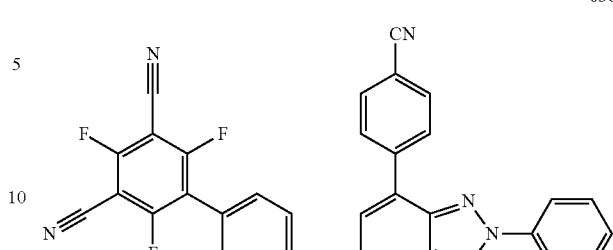
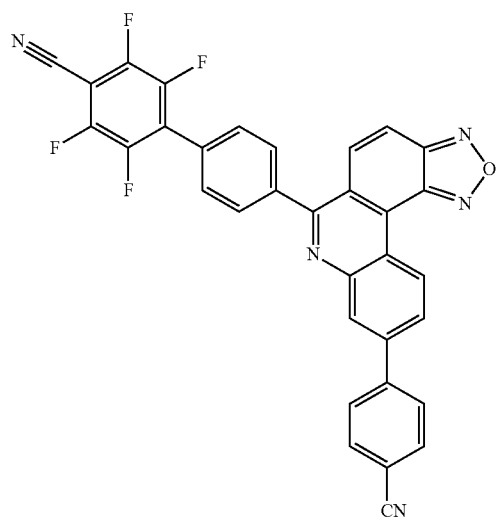
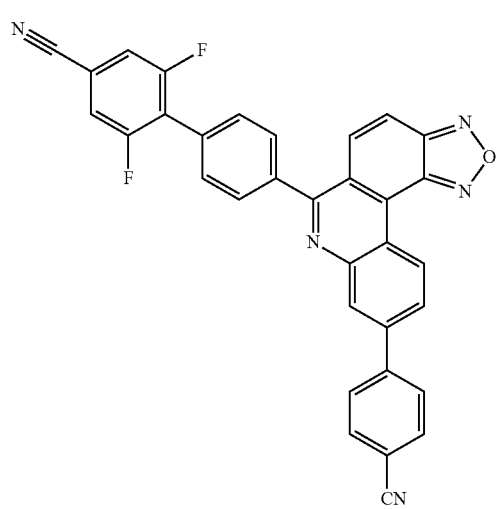
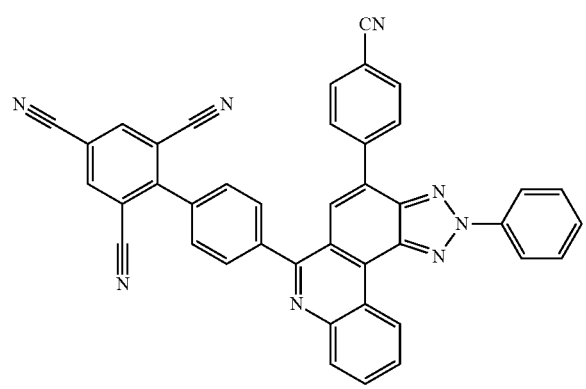
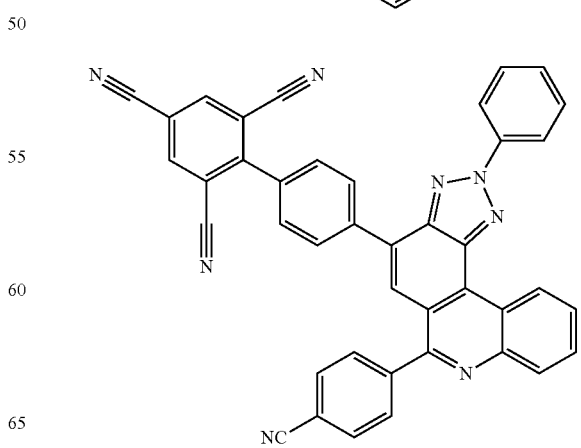

-continued
642
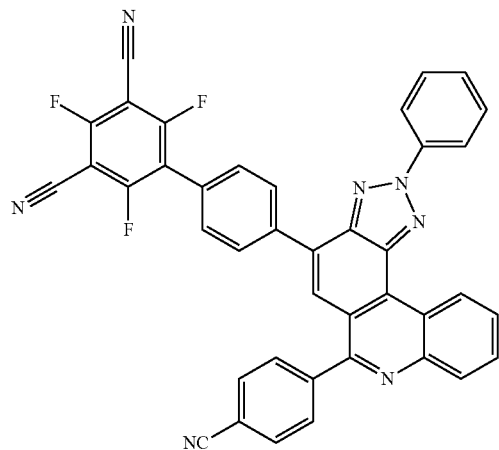
643
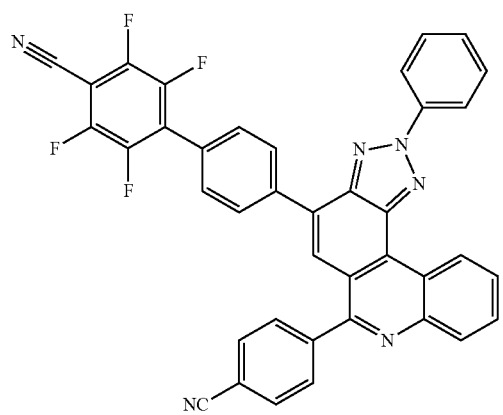
644
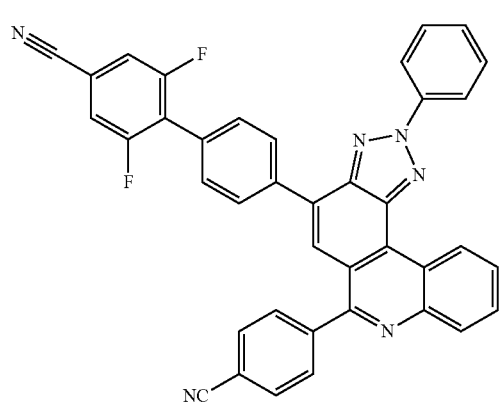
-continued
645
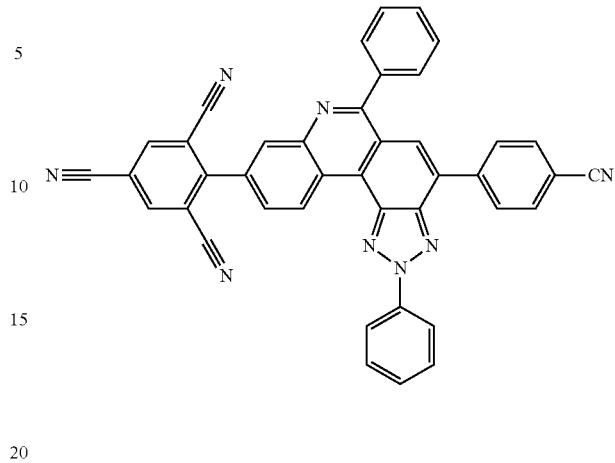
646
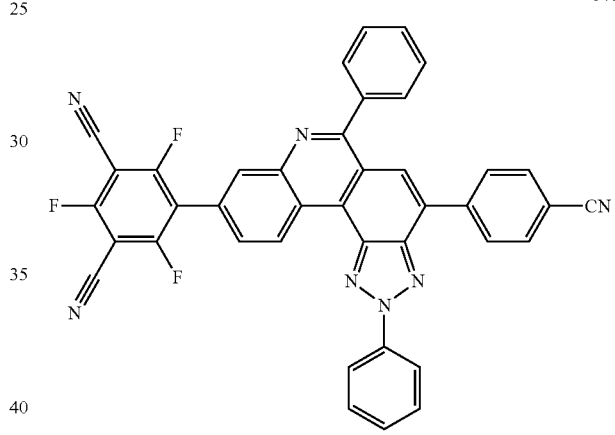
647
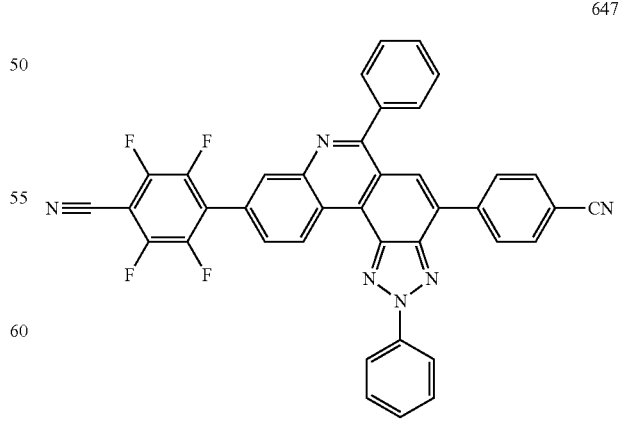

-continued
648
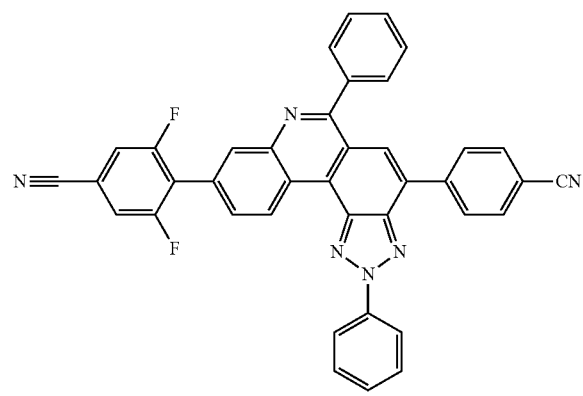
649
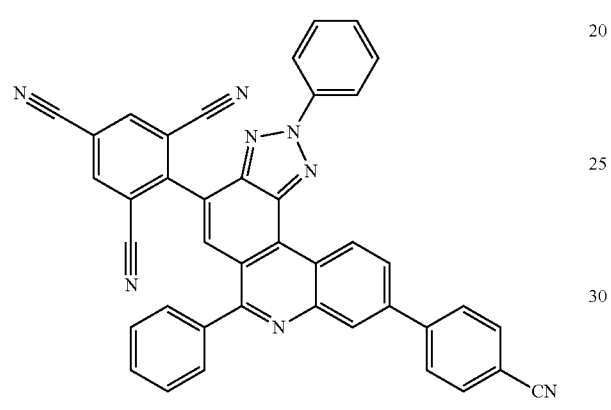
650
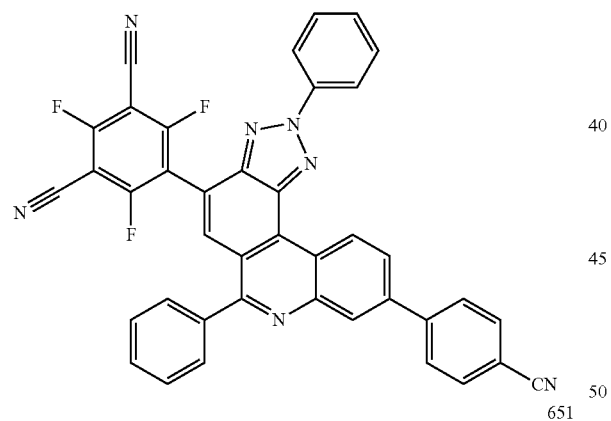
651
-continued
652
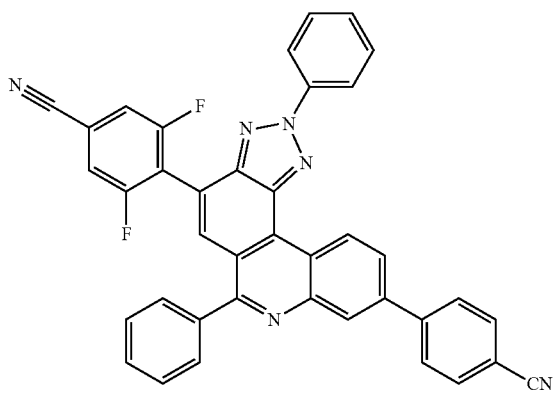
653
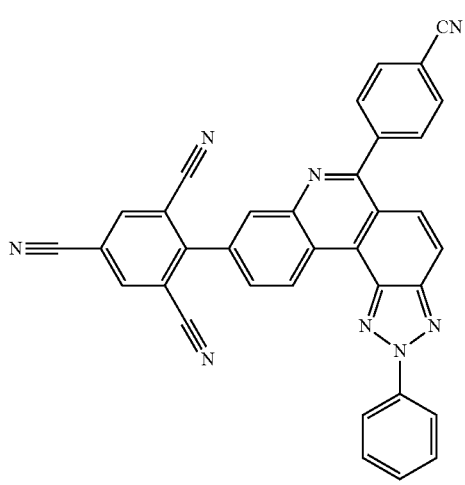
654
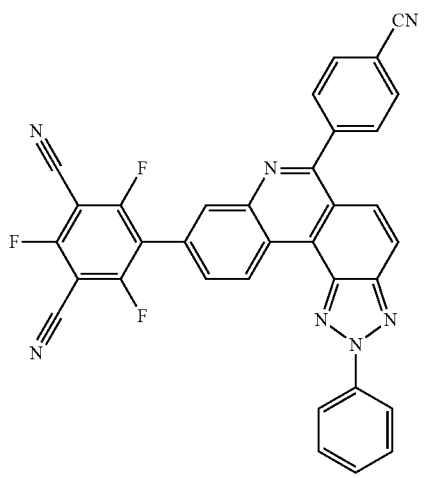

629
-continued
630
-continued
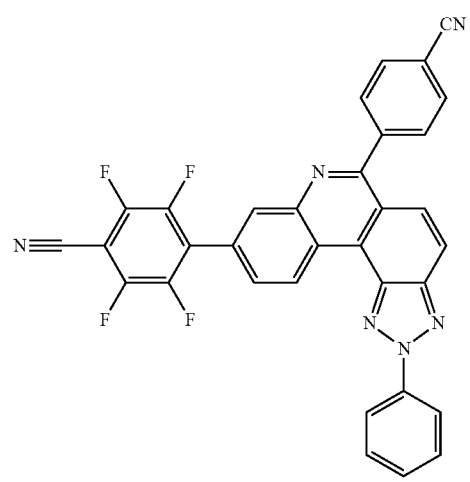
655
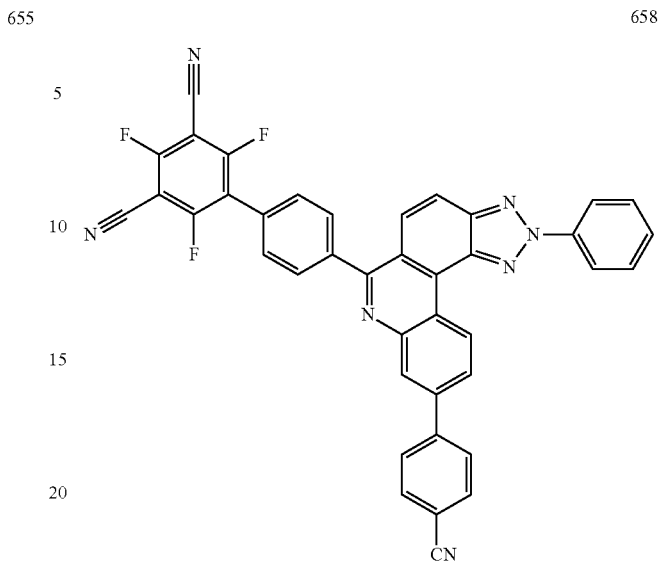
658
656
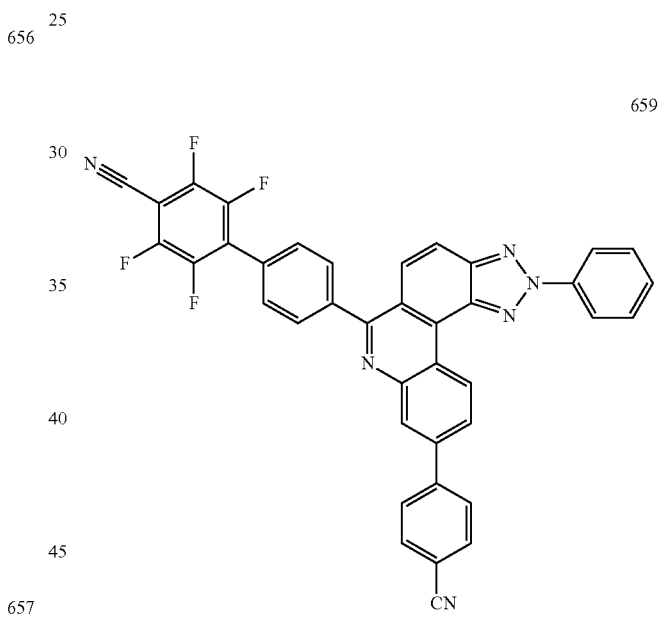
659
657
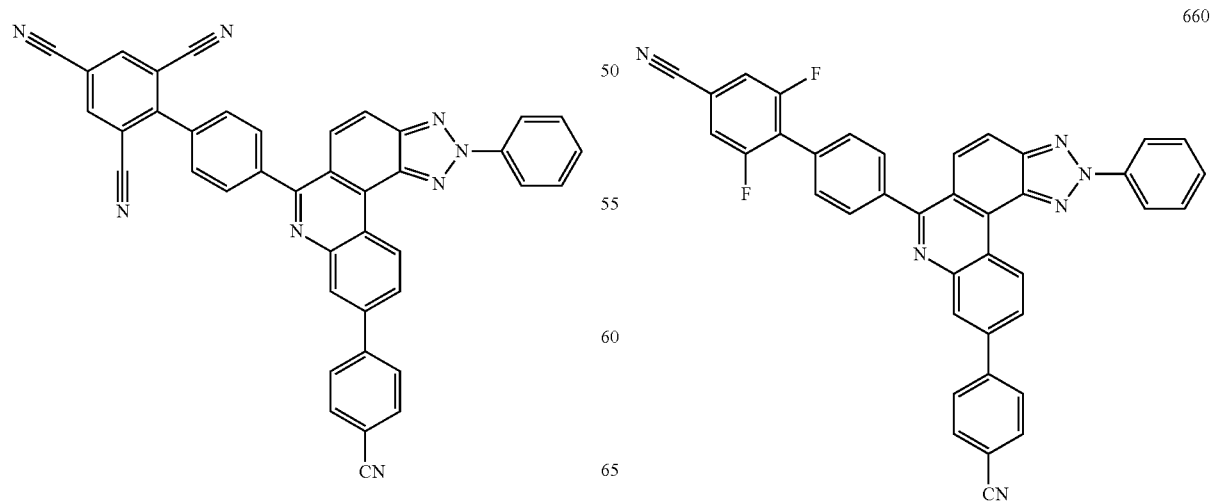
660

631
-continued

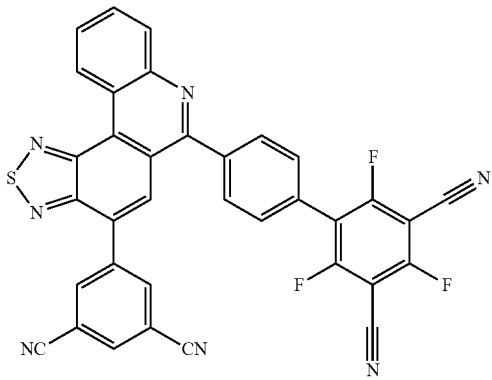

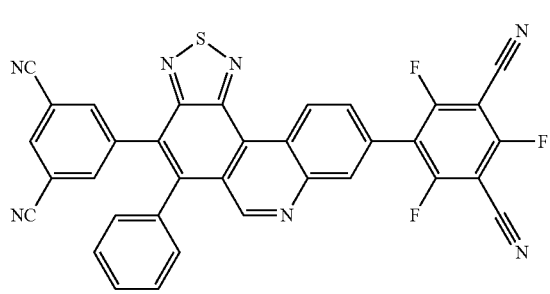

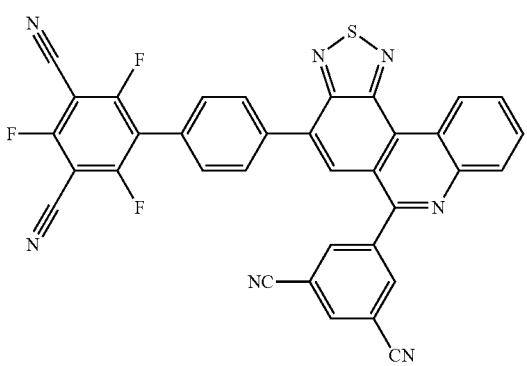

632
-continued

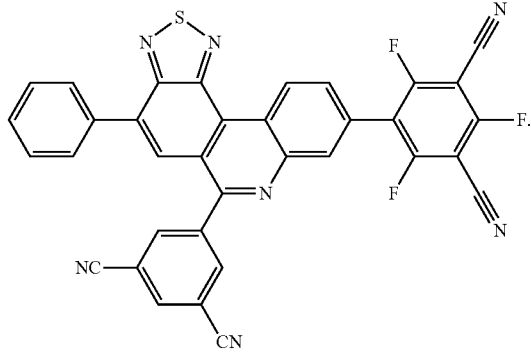

8. An organic light emitting device comprising:
a first electrode;
a second electrode; and
one or more organic material layers provided between the first electrode and the second electrode,
wherein one or more layers of the organic material layers include the heterocyclic compound of claim 1.

9. The organic light emitting device of claim 8, wherein the organic material layer includes an electron transfer layer, and the electron transfer layer includes the heterocyclic compound.

10. The organic light emitting device of claim 8, wherein the organic material layer includes a hole blocking layer, and the hole blocking layer includes the heterocyclic compound.

11. The organic light emitting device of claim 8, further comprising one, two or more layers selected from the group consisting of a light emitting layer, a hole injection layer, a hole transfer layer, an electron injection layer, an electron transfer layer, an electron blocking layer and a hole blocking layer.

12. The organic light emitting device of claim 8 comprising:
a first stack provided on the first electrode and including a first light emitting layer;
a charge generation layer provided on the first stack;
a second stack provided on the charge generation layer and including a second light emitting layer; and
the second electrode provided on the second stack.

13. The organic light emitting device of claim 12, wherein the charge generation layer includes the heterocyclic compound.

14. The organic light emitting device of claim 12, wherein the charge generation layer includes an N-type charge generation layer, and the N-type charge generation layer includes the heterocyclic compound.

15. The organic light emitting device of claim 12, wherein the second stack further includes a hole injection layer, and the hole injection layer includes the heterocyclic compound.

* * * * *